US007625932B2

(12) United States Patent
Albaugh et al.

(10) Patent No.: US 7,625,932 B2
(45) Date of Patent: Dec. 1, 2009

(54) PYRROLE AND PYRAZOLE DERIVATIVES AS POTENTIATORS OF GLUTAMATE RECEPTORS

(75) Inventors: Pamela Ann Albaugh, Carlsbad, CA (US); Esteban Dominguez-Manzanares, Alcobendas (ES); Jian Eric Hong, Carmel, IN (US); William Joseph Hornback, Fishers, IN (US); Delu Jiang, Carmel, IN (US); Paul Leslie Ornstein, Carmel, IN (US); Michelle Lee Thompson, Greenwood, IN (US); Eric George Tromiczak, Carmel, IN (US); Zhipei Wu, Noblesville, IN (US); Hamideh Zarrinmayeh, Carmel, IN (US); Dennis Michael Zimmerman, Zionsville, IN (US); Ana Maria Castano Mansanet, Alcobendas (ES); Larry Gene Huffman, Indianapolis, IN (US); William David Miller, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 544 days.

(21) Appl. No.: 10/570,985

(22) PCT Filed: Aug. 27, 2004

(86) PCT No.: PCT/US2004/028815

§ 371 (c)(1),
(2), (4) Date: Mar. 8, 2006

(87) PCT Pub. No.: WO2005/040110

PCT Pub. Date: May 6, 2005

(65) Prior Publication Data

US 2007/0066573 A1 Mar. 22, 2007

Related U.S. Application Data

(60) Provisional application No. 60/537,794, filed on Jan. 20, 2004.

(30) Foreign Application Priority Data

Oct. 8, 2003 (EP) .................................... 3380224

(51) Int. Cl.

| | |
|---|---|
| *A61K 31/675* | (2006.01) |
| *A61K 31/433* | (2006.01) |
| *C07D 417/02* | (2006.01) |
| *C07D 413/02* | (2006.01) |

(52) U.S. Cl. ....................... 514/363; 514/372; 514/378; 514/381; 514/383; 514/406; 548/253; 548/364.1; 548/517; 548/530

(58) Field of Classification Search ....................... None
See application file for complete search history.

(56) References Cited

U.S. PATENT DOCUMENTS 5,776,954 A 7/1998 De Laszlo et al.

FOREIGN PATENT DOCUMENTS

| | | | |
|---|---|---|---|
| EP | 0273602 | A1 | 12/1987 |
| EP | 0976744 | A1 | 2/2000 |
| WO | WO 98/33496 | | 8/1998 |

OTHER PUBLICATIONS

Abdelhamid, Abdou O. et al., Synthesis of Pyridazine, Pyridazin-3-One, 2-Amino Pyrrole and 2,5-Diamino-Pyridine Derivatives From Propanedinitrile, Rev. Port. Quim., 1985, 500-504, 27, 500.

Abdelhamid, Abdou O. et al., Synthesis of Pyridazine, Pyridazin-3-One, 2-Aminopyrrole and 2,5-Diaminopyridine Derivatives From Dicyanomethylene Compounds, Heterocycles, 1986, 101-107, 24, 1.

Ito, I. et al., Allosteric Potentiation of Quisqualate Receptors By A Nootropic Drug Aniracetam, Journal of Physiology, 1990, 533-543, 424.

Ornstein, Paul L. et al., Biarylpropylsulfonamides as Novel, Potent Potntiators of 2-Amino-3-(5-methyl-3-hydroxyisoxazol-4-yl)-propanoic Acid (AMPA) Receptors, J. Med Chem, 2000, 4354-4358, 43.

*Primary Examiner*—Kamal A Saeed
(74) *Attorney, Agent, or Firm*—Tonya L. Combs

(57) ABSTRACT

The present invention relates to pyrrole and pyrazole compounds of formula (I) and their pharmaceutically acceptable salts, and further relates to their use in treating schizophrenia, cognitive deficits associated with schizophrenia, Alzheimer's disease, dementia of the Alzheimer's type, mild cognitive impairment, or depression. The compounds act as potentiators on glutamate receptors, in particular AMPA and the GluR family.

10 Claims, No Drawings

PYRROLE AND PYRAZOLE DERIVATIVES AS POTENTIATORS OF GLUTAMATE RECEPTORS

This application is a United States national phase entry, pursuant to 35 U.S.C. 371, of PCT/US2004/028815, filed Sep. 9, 2004, which claims the benefit of European provisional patent application serial number 03380224.0 filed Oct. 8, 2003, and U.S. provisional patent application Ser. No. 60/537,794 filed Jan. 20, 2004.

BACKGROUND OF THE INVENTION

Glutamate is the major excitatory neurotransmitter in the central nervous system. Three glutamate receptor ion channel subtypes have been identified based on their sensitivity to the selective activators (agonists) N-methyl-D-aspartate (NMDA), α-amino-3-hydroxy-5-methyl-4-isoxazole propionic acid (AMPA), and kainate.

AMPA receptors mediate cellular responses to glutamate by direct and indirect mechanisms. When activated by glutamate or AMPA, AMPA receptor ion channels allow sodium ions ($Na^+$) and calcium ions ($Ca^{2+}$) to pass directly through the channel pore. In addition, AMPA receptor ion channels can facilitate the activation of NMDA receptors by initiating cellular depolarization that relieves magnesium ion ($Mg^{2+}$)-dependent block of NMDA receptors.

Multiple AMPA receptor subtypes have been identified and cloned: $GluR^1$, $GluR^2$, $GluR^3$, and $GluR^4$ as disclosed by Hollmann and Heinemann, *Ann. Rev. Neurosci.*, 17, 31-108 (1994). Each subunit consists of a sequence of approximately 900 amino acids. Four subunits are thought to assemble to form a tetrameric ion channel complex with the functional properties of this ion channel most likely being determined by its subunit composition.

Ion channel currents activated by glutamate via AMPA receptors are transient. The time course of currents is modified by refractory states caused during glutamate binding which is referred to as desensitization and by the rate of glutamate removal from the ion channel binding site which results in deactivation. Ion influx through AMPA receptors may be enhanced by compounds that either prevent desensitization or by compounds that slow deactivation rates. Compounds that enhance glutamate-stimulated ion influx at AMPA receptors are known as positive AMPA receptor allosteric modulators or AMPA receptor potentiators. One such compound, which selectively potentiates AMPA receptor function, is cyclothiazide. Since AMPA receptors play a pivotal role in mediating fast excitatory transmission in the central nervous system, molecules that enhance AMPA receptor function have multiple therapeutic targets.

Compounds that allosterically potentiate AMPA receptors have been shown to enhance synaptic activity in vitro and in vivo as disclosed, for example, by I. Ito, et al., *J. Physiol.*, 424, 533-543 (1990) and A. Copani, et al., *Journal of Neurochemistry*, 58, 1199-1204 (1992). Such compounds have also been shown to enhance learning and memory in rats, monkeys, and humans, and are reviewed by Gouliaev and Senning, *Brain Research Reviews,* 19, 180-222 (1994).

International Patent Application Publication WO 98/33496 published Aug. 6, 1998 discloses certain sulfonamide derivatives which are useful, for example, for treating psychiatric and neurological disorders, for example cognitive disorders, Alzheimer's disease, age-related dementias, age-induced memory impairment, tardive dyskinesia, Huntington's chorea, myoclonus, Parkinson's disease, reversal of drug-induced states (such as cocaine, amphetamines, alcohol-induced states), depression, attention deficit disorder, attention deficit hyperactivity disorder, psychosis, cognitive deficits associated with psychosis, and drug-induced psychosis. P. L. Ornstein, et al. *J. Med. Chem.,* 43, 4354 (2000) further disclose biarylpropylsulfonamides which are potent potentiators of AMPA receptors. In addition, X. Li, et al., *Neuropharmacology,* 40, 1028 (2001) disclose antidepressant-like actions of AMPA receptor potentiators. D. D. Schoepp, et al. and Tizzano, et al., *Society for Neuroscience Abstracts,* 26(1-2), 528.19 and 528.20, 30th Annual Meeting, New Orleans, (Nov. 4-9, 2000) disclose an orally active AMPA receptor potentiator that enhances spatial learning and memory performance in rats, and reverses both pharmacologically and age-associated learning and memory deficit in rats.

European Patent No. 0 273 602 discloses substituted 3-cyanothiophenes which are useful as herbicides. In addition, Abdelhamid and Abed disclose in *Rev. Port. Quim,* 27, 500 (1985) and Heterocycles, 24(1), 101 (1986) various 2-amino pyrroles.

SUMMARY OF THE INVENTION

The present invention provides compounds of Formula I:

Formula I

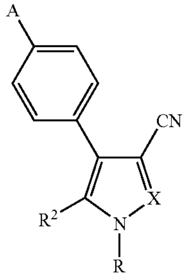

wherein

X represents N or $CR^1$;

R represents hydrogen, methyl, ethyl, n-propyl, or $—SO_2$(1-4C)alkyl;

$R^1$ represents hydrogen, F, Cl, Br, I, CHO, —CN, —S(phenyl), $CF_3$, -(1-4C)alkyl, -(1-4C)alkoxy, —S(1-4C)alkyl, —SO(1-4C)alkyl, $—SO_2$(1-4C)alkyl, —C(=O)(1-3C) alkyl, $NH_2$, —NH(1-4C)alkyl, —N[(1-4C)alkyl]$_2$, or —NH(4-7C)cycloalkyl;

$R^2$ represents $—CO_2H$, $—C(=O)NHR^{13}$; —C(=O)NHOH, —C(=O)NHCN, $—SO_2OH$, $—SO_2NH$(1-4C)alkyl, $—C(=O)NHSO_2$(1-4C)alkyl, —PH(=O)(OH), $—P(=O)(OH)_2$, $—P(=O)(OH)NH_2$, —P(=O)(OH)CH[(1-4C)alkoxy]$_2$,

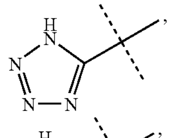,

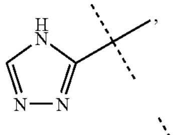,

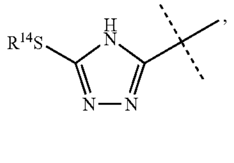,

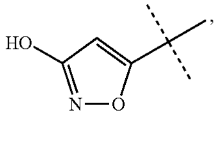,

-continued

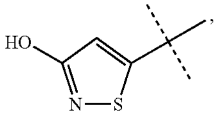,

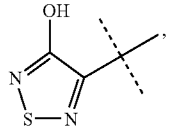, or

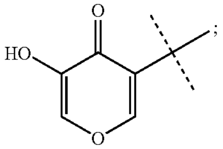;

$R^4$ represents hydrogen, OH, —$CH_2OH$, —$CH_2O$(1-4C)alkyl, F, Cl, $CF_3$, $OCF_3$, —CN, $NO_2$, $NH_2$, -(1-4C)alkyl, -(1-4C)alkoxy, —C(=O)NH(1-4C)alkyl, —C(=O)$NH_2$, —NHC(=O)(1-4C)alkyl, —$(CH_2)_m$$NHSO_2R^{10}$, —$(CH_2)_n$CN, —$(CH_2)_m$$CO_2H$, —$(CH_2)_m$$CO_2$(1-6C)alkyl, —C(=O)H, —C(=O)(1-4C)alkyl, —NH(1-4C)alkyl, —N[(1-4C)alkyl]$_2$, —$SR^{10}$, —$SOR^{10}$, —$SO_2R^{10}$, or SH;

$R^5$ represents hydrogen; F, Cl, —CN, $NO_2$, $NH_2$, —$(CH_2)_m$$NHSO_2R^{10}$, -(1-4C)alkyl, or -(1-4C)alkoxy;

$R^6$ represents hydrogen, -(1-4C)alkyl, —$SO_2R^{11}$, or —C(=O)(1-4C)alkyl;

$R^7$ represents hydrogen or -(1-4C)alkyl;

$R^8$ represents hydrogen, F, Cl, Br, -(1-4C)alkyl, -(1-4C)alkoxy, $NO_2$, $NH_2$, —CN, —$NHSO_2R^{11}$, or —C(=O)(1-4C)alkyl;

$R^{8a}$ represents hydrogen, F, Cl, Br, -(1-4C)alkyl, $NO_2$, $NH_2$, NH(1-6C)alkyl, N[(1-6C)alkyl]$_2$, —C(=O)$NH_2$, —CN, —$CO_2H$, —S(1-4C)alkyl, —$NHCO_2$(1-4C)alkyl, or —C(=O)(1-4C)alkyl;

$R^{10}$, $R^{11}$, and $R^{12}$ each independently represent -(1-4C)alkyl, $CF_3$, N[(1-4C)alkyl]$_2$, —$(CH_2)_3$Cl, thienyl, phenyl, —$CH_2$phenyl, or —$(CH_2)_2$phenyl, wherein phenyl, as used in substituent $R^{10}$, $R^{11}$ or $R^{12}$, is unsubstituted or substituted with F, Cl, Br, , —CN, $CF_3$, -(1-4C)alkyl, -(1-4)alkoxy, or acetyl;

$R^{13}$ represents hydrogen, -(1-4C)alkyl, —$CH_2CF_3$, triazole, or tetrazole;

$R^{14}$ represents -(1-4C)alkyl;

$R^{15}$ represents hydrogen or -(1-4C)alkyl;

m represents 0, 1, 2, or 3;

n represents 1, 2, 3, or 4;

p represents 1 or 2; and

A is selected from the group consisting of —OH, Br, I, —$(CH_2)_m$CN, —C$(CH_3)_2$CN, $NO_2$, —$NH_2$, —O$(CH_2)_n$$NH_2$, —O$(CH_2)_n$$NHSO_2$(1-4C)alkyl, —O$(CH_2)_n$$NHSO_2$aryl, —NH$(CH_2)_n$$NHSO_2$(1-4C)alkyl, —N$(CH_3)$$(CH_2)_n$$NHSO_2$(1-4C)alkyl, —NH$(CH_2)_n$$NHSO_2$aryl, —S$(CH_2)_n$$NHSO_2$(1-4C)alkyl, —S$(CH_2)_n$$NHSO_2$aryl, —S(1-4C)alkyl, -(1-6C)alkyl, -(1-4C)alkoxy, -(2-4C)alkenyl, -(2-4C)alkenyloxy, —$CO_2H$, —$CO_2$(1-4C)alkyl, —CHO, —C(=O)(1-4C)alkyl, —C(=O)$NH_2$, —C(=O)NH(1-6C)alkyl, —C(=O)$NR^{15}$$(CH_2)_m$phenyl wherein phenyl is unsubstituted or substituted with one or two substituents independently selected from the group consisting of OH, F, Cl, Br, I, $NO_2$, $NH_2$, —$NHSO_2$(1-4C)alkyl, —CN, -(1-4C)alkyl, and -1-4C)alkoxy; —$OSO_2CF_3$, —O$(CH_2)_n$CN, $(CH_2)_m$$NHSO_2R^{12}$, —CH$(CH_3)$$(CH_2)_p$$NHSO_2R^{12}$, —$(CH_2)_p$CH$(CH_3)$$NHSO_2R^{12}$, —NH$(CH_2)_m$phenyl wherein phenyl is unsubstituted or substituted with one or two substituents independently selected from the group consisting of OH, F, Cl, Br, I, $NO_2$, $NH_2$, CN, -(1-4C)alkyl, and -(1-4C)alkoxy; —NH(1-4C)alkyl, —N[(1-4C)alkyl]$_2$, —C(=O)NH(3-6C)cycloalkyl, —C(=O)NH$(CH_2)_n$N[(1-4C)alkyl]$_2$, —C(=O)NH$(CH_2)_n$NH(1-4C)alkyl, —$(CH_2)_n$$NH_2$, —O$(CH_2)_n$$SR^4$, —O$(CH_2)_n$$OR^{14}$, —$(CH_2)_n$$NHR^{12}$, —$(CH_2)_n$NH(3-6C)cycloalkyl, —$(CH_2)_n$N[(1-4C)alkyl]$_2$, —NHC(=O)N[(1-4C)alkyl]$_2$,

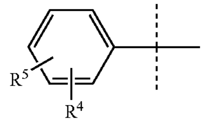, 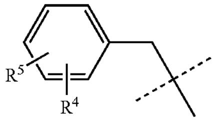,

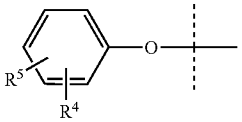, 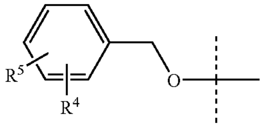,

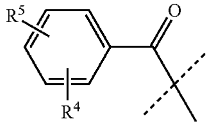 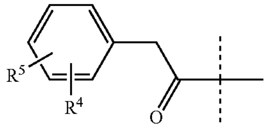,

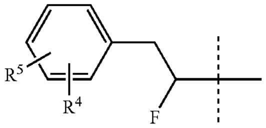, 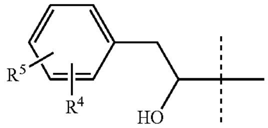,

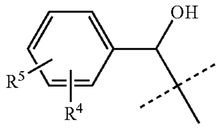, 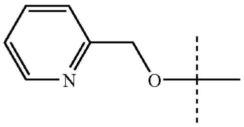,

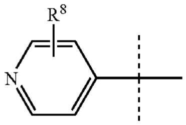, 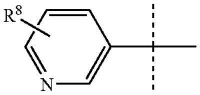,

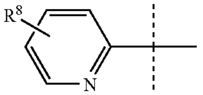, 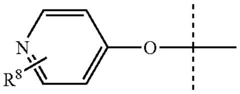,

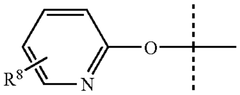, 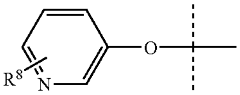,

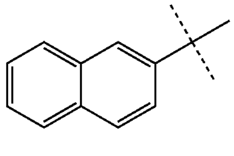, 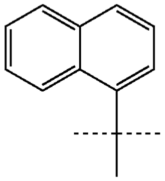,

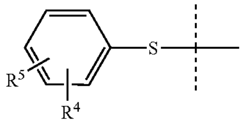 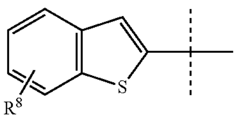,

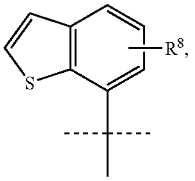 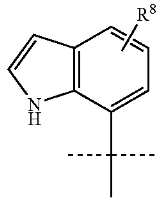,

-continued
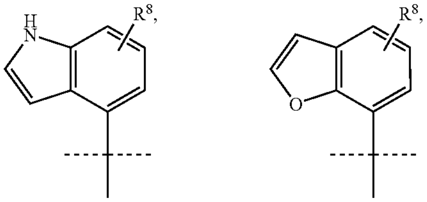
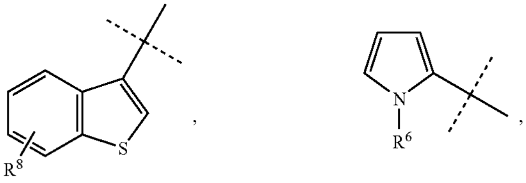
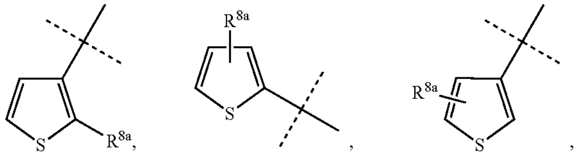
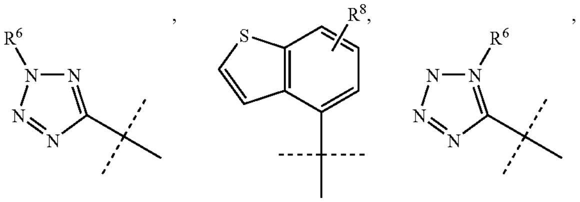
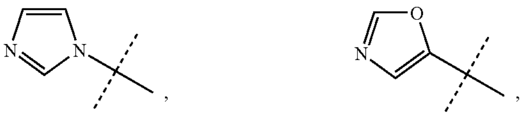
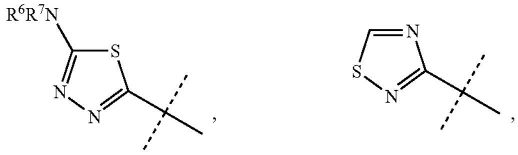
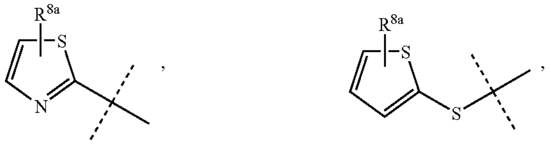
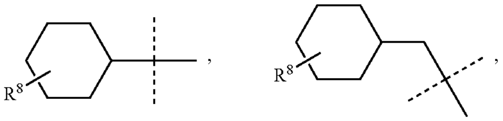
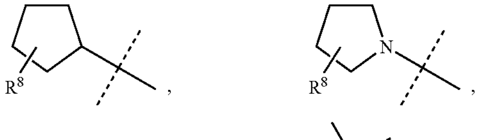
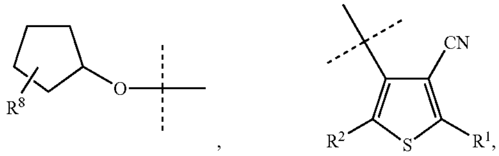
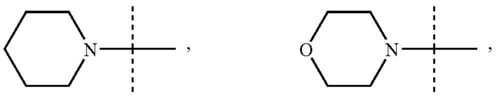
-continued
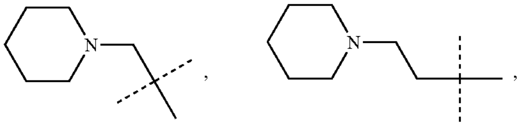
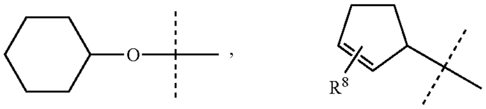
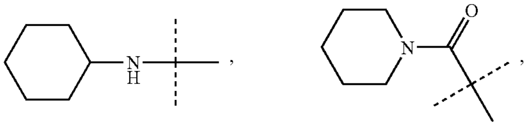
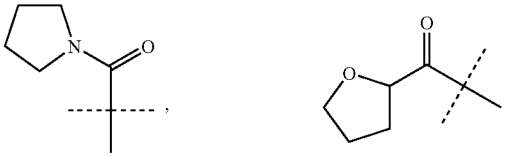
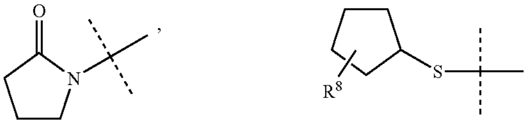
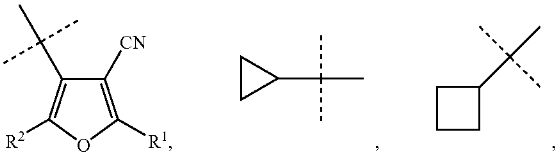
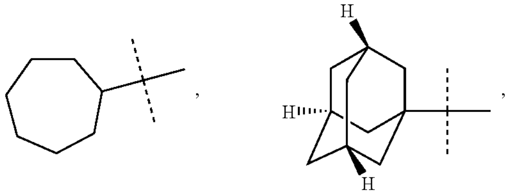
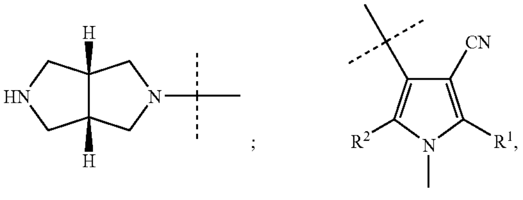
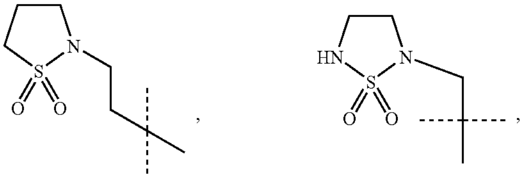
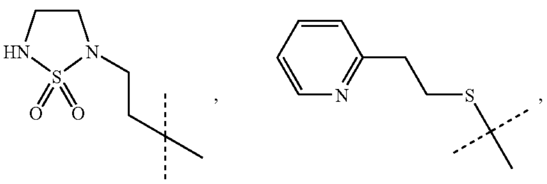
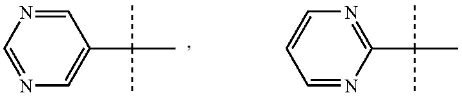
and -continued

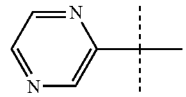

and the pharmaceutically acceptable salts thereof, with the proviso that when R is methyl, $R^1$ is $SCH_3$, and $R^2$ is $CO_2H$, A is other than 4-tert-butyl-phenyl; and provided that when R is methyl, $R^1$ is hydrogen, and $R^2$ is $CO_2H$, A is other than 2,6-dimethylphenyl; and further provided that when R is methyl, $R^1$ is ethyl, and $R^2$ is —C(═O)$NHSO_2CH_3$, A is other than

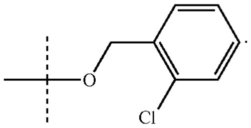

.

In addition, the present invention provides compounds of Formula II:

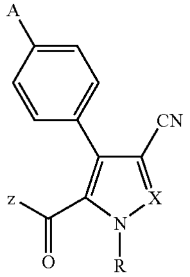

Formula II wherein

X represents N or $CR^1$;

R represents hydrogen, methyl, ethyl, n-propyl, or $SO_2$(1-4C) alkyl;

$R^1$ represents hydrogen, F, Cl, Br, I, CHO, —CN, —S(phenyl), $CF_3$, -(1-4C)alkyl, -(1-4C)alkoxy, —S(1-4C)alkyl, —SO(1-4C)alkyl, —$SO_2$(1-4C)alkyl, —C(═O)(1-3C) alkyl, $NH_2$, —NH(1-4C)alkyl, —N[(1-4C)alkyl]$_2$, or —NH(4-7C)cycloalkyl;

Z represents —O-(1-6C)alkyl, —O-(2-4C)alkenyl, —O-(1-6C)alkylaryl, —O-(1-6C)alkyl(3-6C)cycloalkyl, —O-(1-6C)alkyl-N,N-(1-6C)dialkylamine, —O-(1-6C)alkyl-pyrrolidine, —O-(1-6C)alkyl-piperidine, —O-(1-6C)alkyl-morpholine, or N—H(1-6C)alkyl;

$R^4$ represents hydrogen, OH, —$CH_2OH$, —$CH_2O$(1-4C) alkyl, F, Cl, $CF_3$, $OCF_3$, —CN, $NO_2$, $NH_2$, -(1-4C) alkyl, -(1-4C)alkoxy, —C(═O)NH(1-4C)alkyl, —C(═O)$NH_2$, —NHC(═O)(1-4C)alkyl, —$(CH_2)_m$ $NHSO_2R^{10}$, —$(CH_2)_n$CN, —$(CH_2)_mCO_2H$, —$(CH_2)_m$ $CO_2$(1-6C)alkyl, —C(═O)H, —C(═O)(1-4C)alkyl, —NH(1-4C)alkyl, —N[(1-4C)alkyl]$_2$, —$SR^{10}$, —$SOR^{10}$, —$SO_2R^{10}$, or SH;

$R^5$ represents hydrogen; F, Cl, —CN, $NO_2$, $NH_2$, —$(CH_2)_m$ $NHSO_2R^{10}$, -(1-4C)alkyl, or -(1-4C)alkoxy;

$R^6$ represents hydrogen, -(1-4C)alkyl, —$SO_2R^{11}$, or —C(═O)(1-4C)alkyl;

$R^7$ represents hydrogen or -(1-4C)alkyl;

$R^8$ represents hydrogen, F, Cl, Br, -(1-4C)alkyl, -(1-4C) alkoxy, $NO_2$, $NH_2$, —CN, —$NHSO_2R^{11}$, or —C(═O)(1-4C)alkyl;

$R^{8a}$ represents hydrogen, F, Cl, Br, -(1-4C)alkyl, $NO_2$, $NH_2$, NH(1-6C)alkyl, N[(1-6C)alkyl]$_2$, —C(═O)$NH_2$, —CN, —$CO_2H$, —S(1-4C)alkyl, —$NHCO_2$(1-4C)alkyl, or —C(═O)(1-4C)alkyl;

$R^{10}$, $R^{11}$, and $R^{12}$ each independently represent -(1-4C)alkyl, $CF_3$, N[(1-4C)alkyl]$_2$, —$(CH_2)_3Cl$, thienyl, phenyl, —$CH_2$phenyl, or —$(CH_2)_2$phenyl, wherein phenyl, as used in substituent $R^{10}$, $R^{11}$ or $R^{12}$, is unsubstituted or substituted with F, Cl, Br, , —CN, $CF_3$, -(1-4C)alkyl, -(1-4)alkoxy, or acetyl;

$R^{13}$ represents hydrogen, -(1-4C)alkyl, —$CH_2CF_3$, triazole, or tetrazole;

$R^{14}$ represents -(1-4C)alkyl;

$R^{15}$ represents hydrogen or -(1-4C)alkyl;

m represents 0, 1, 2, or 3;

n represents 1, 2, 3, or 4;

p represents 1 or 2; and

A is selected from the group consisting of —H, Br, I, —$(CH_2)_m$ CN, —C$(CH_3)_2$CN, $NO_2$, $NH_2$, —O$(CH_2)_n$ $NH_2$, —O$(CH_2)_n NHSO_2$(1-4C)alkyl, —O$(CH_2)_n$ $NHSO_2$aryl, —NH$(CH_2)_n NHSO_2$(1-4C)alkyl, —N$(CH_3)$ $(CH_2)_n NHSO_2$(1-4C)alkyl, —NH$(CH_2)_n NHSO_2$aryl, —S$(CH_2)_n NHSO_2$(1-4C)alkyl, —S$(CH_2)_n NHSO_2$aryl, —S(1-4C)alkyl, -(1-6C)alkyl, -(14C)alkoxy, -(2-4C)alkenyl, -(2-4C)alkenyloxy, —$CO_2H$, —$CO_2$(1-4C)alkyl, —CHO, —C(═O)(1-4C)alkyl, —C(═O)$NH_2$, —C(═O) NH(1-6C)alkyl, —C(═O)$NR^{15}(CH_2)_m$phenyl wherein phenyl is unsubstituted or substituted with one or two substituents independently selected from the group consisting of OH, F, Cl, Br, I, $NO_2$, $NH_2$, —$NHSO_2$(1-4C) alkyl, —CN, -(1-4C)alkyl, and -1-4C)alkoxy; —$OSO_2CF_3$, —O$(CH_2)_n$CN, $(CH_2)_m NHSO_2R^{12}$, —CH $(CH_3)(CH_2)_p NHSO_2R^{12}$, —$(CH_2)_p$CH$(CH_3)NHSO_2R^{12}$, —NH$(CH_2)_m$phenyl wherein phenyl is unsubstituted or substituted with one or two substituents independently selected from the group consisting of OH, F, Cl, Br, I, $NO_2$, $NH_2$, CN, -(1-4C)alkyl, and -1-4C)alkoxy; —NH(1-4C) alkyl, —N[(1-4C)alkyl]$_2$, —C(═O)NH(3-6C)cycloalkyl, —C(═O)NH$(CH_2)_n$N[(1-4C)alkyl]$_2$, —C(═O)NH $(CH_2)_n$NH(1-4C)alkyl, —$(CH_2)_n NH_2$, —O$(CH_2)_n SR^{14}$, —O$(CH_2)_n OR^{14}$, —$(CH_2)NHR^2$, —$(CH_2)_n$NH(3-6C)cycloalkyl, —$(CH_2)_n$N[(1-4C)alkyl]$_2$, —NHC(═O)N[(1-4C)alkyl]$_2$,

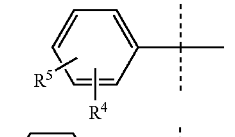

,

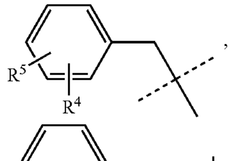

,

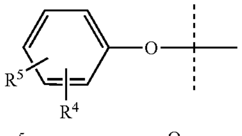

,

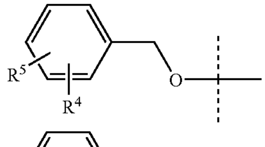

,

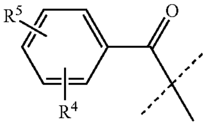

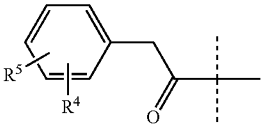

,

-continued
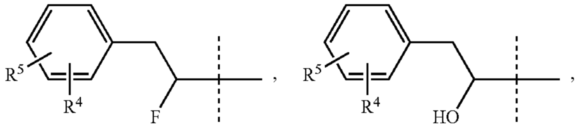
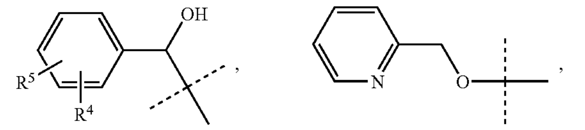
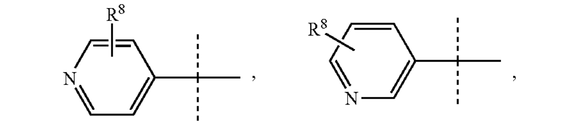
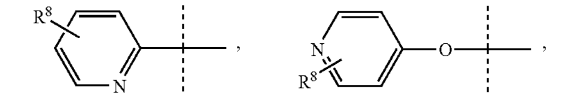
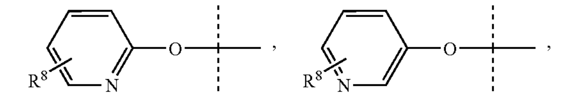
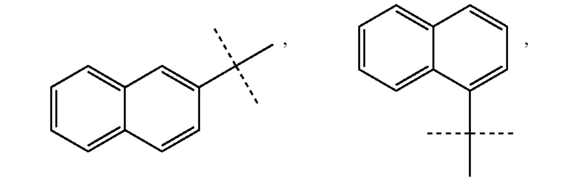
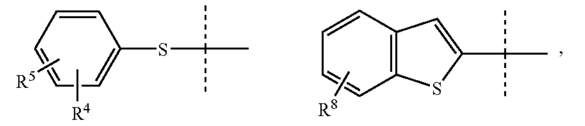
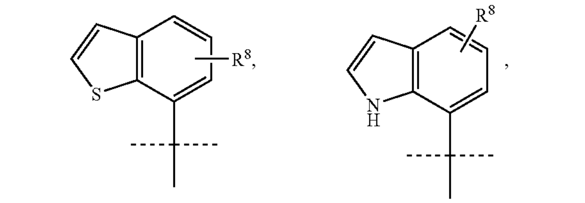
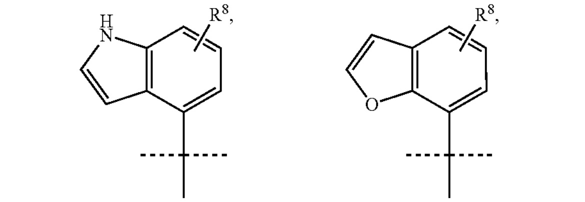
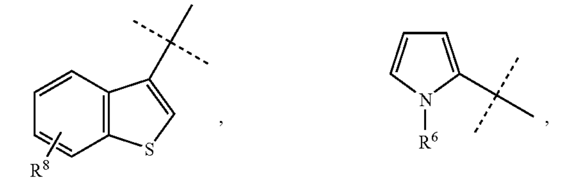
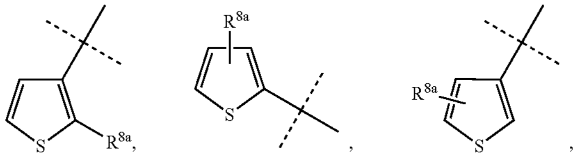
-continued
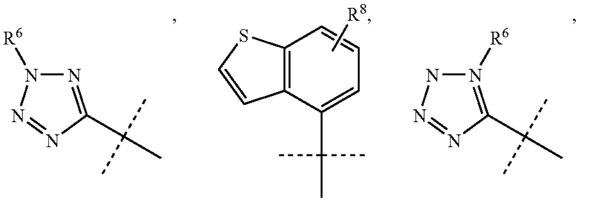
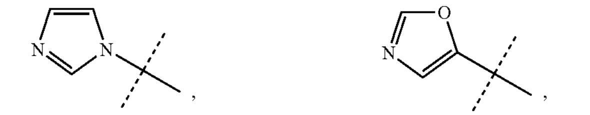
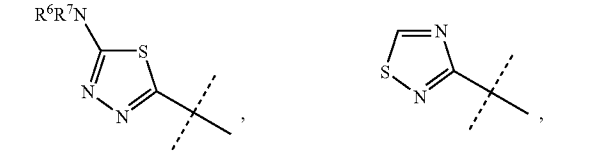
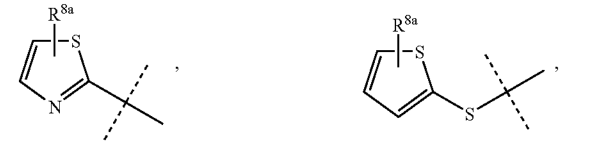
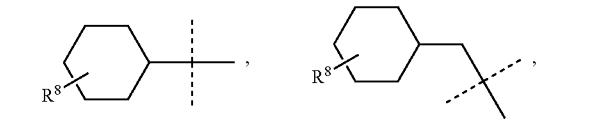
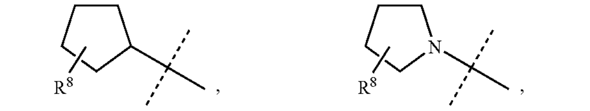
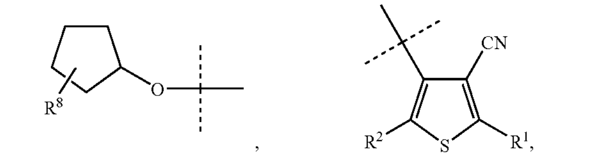
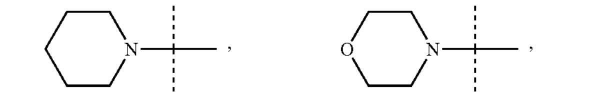
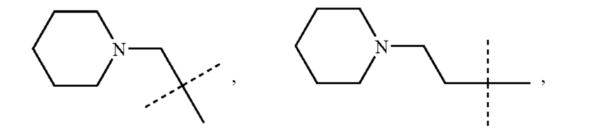
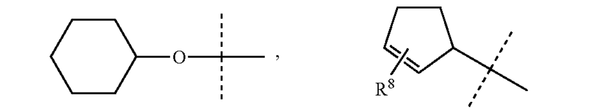
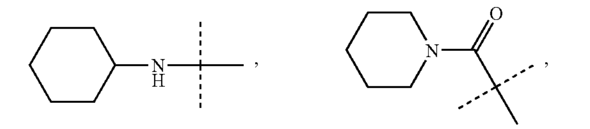
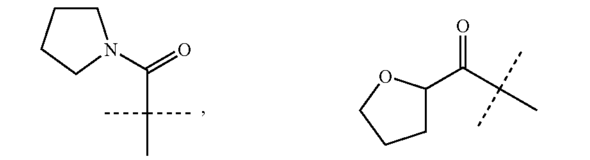

-continued

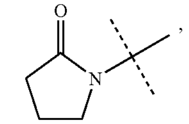,
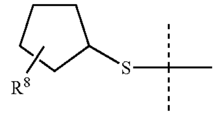
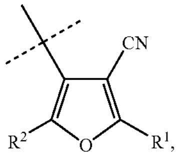
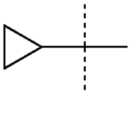,
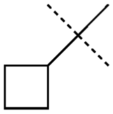,
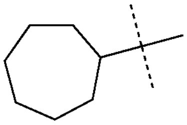,
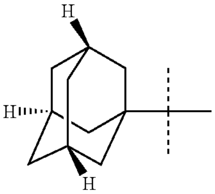,
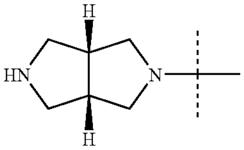;
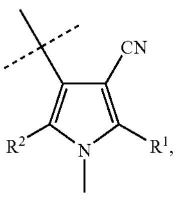
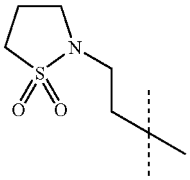,
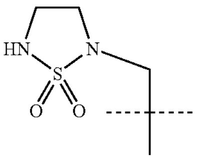,
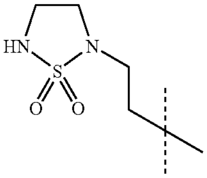,
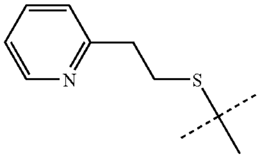,
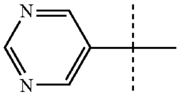,
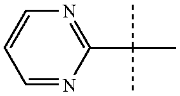
and
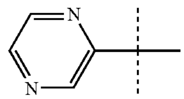

and the pharmaceutically acceptable salts thereof, with the proviso that when R is methyl and $R^1$ is $SCH_3$, A is other than 4-tert-butyl-phenyl; and further provided that when R is methyl and $R^1$ is hydrogen, A is other than 2,6-dimethylphenyl.

It is appreciated by one of ordinary skill in the art that compounds of Formula II include useful intermediates for the preparation of compounds of Formula I and also prodrugs of Formula I.

In addition, the present invention provides compounds of Formula I':

Formula I'

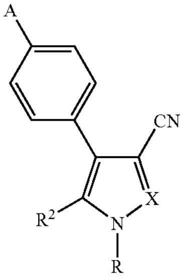

wherein

X represents N or $CR^1$;

R represents hydrogen, methyl, ethyl, n-propyl, or $—SO_2$(1-4C)alkyl, $R^1$ represents hydrogen, F, Cl, Br, I, CHO, —CN, —S(phenyl), $CF_3$, -(1-4C)alkyl, -(1-4C)alkoxy, —S(1-4C)alkyl, —SO(1-4C)alkyl, $—SO_2$(1-4C)alkyl, —C(═O)(1-3C) alkyl, $NH_2$, —NH(1-4C)alkyl, $—N[(1\text{-}4C)alkyl]_2$, or —NH(4-7C)cycloalkyl;

$R^2$ represents $CO_2H$, $—C(═O)NHR^{13}$; —C(═O)NHOH, —C(═O)NHCN, $—SO_2OH$, $—SO_2NH$(1-4C)alkyl, $—C(═O)NHSO_2$(1-4C)alkyl, —PH(═O)(OH), $—P(═O)(OH)_2$, $—P(═O)(OH)NH_2$, —P(═O)(OH)CH$[(1\text{-}4C)alkoxy]_2$,

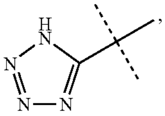,
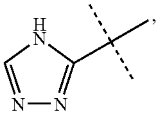,
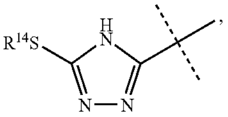,
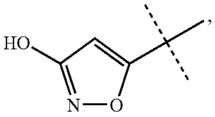,
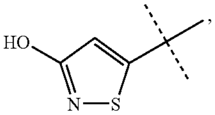,
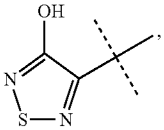, or
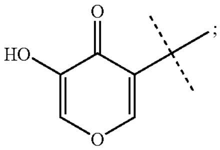;

$R^4$ represents hydrogen, OH, $—CH_2OH$, $—CH_2O$(1-4C) alkyl, F, Cl, $CF_3$, $OCF_3$, —CN, $NO_2$, $NH_2$, -(1-4C) alkyl, -(1-4C)alkoxy, —C(═O)NH(1-4C)alkyl, —NHC (═O)(1-4C)alkyl, $—(CH_2)_mNHSO_2R^{10}$, $—(CH_2)_nCN$, $—(CH_2)_mCO_2H$, $—(CH_2)_mCO_2$(1-6C)alkyl, —C(═O)H, —C(═O)(1-4C)alkyl, —NH(1-4C)alkyl, $—N[(1\text{-}4C)alkyl]_2$, $—SR^{10}$, $—SOR^{10}$, $—SO_2R^{10}$, SH, phenyl, or phenyl substituted with one or two substituents independently selected from the group consisting of F, Cl, Br, I, —CN, -(1-4C)alkyl, and -(1-4C)alkoxy, $R^5$ represents hydrogen; F, Cl, —CN, $NO_2$, $NH_2$, $—(CH_2)_mNHSO_2R^{10}$, -(1-4C)alkyl, or -(1-4C)alkoxy;

$R^6$ represents hydrogen, -(1-4C)alkyl, $—SO_2R^{11}$, —C(═O)(1-4C)alkyl;

$R^7$ represents hydrogen or -(1-4C)alkyl;

$R^8$ represents hydrogen, P, Cl, Br, -(1-4C)alkyl, $NO_2$, $NH_2$, —CN, —$NHSO_2R^{11}$, and —C(=O)(1-4C)alkyl;

$R^{8a}$ represents hydrogen, F, Cl, Br, -(1-4C)alkyl, $NO_2$, $NH_2$, —CN, —S(1-4C)alkyl, and —C(=O)(1-4C)alkyl;

$R^{10}$, $R^{11}$, and $R^{12}$ each independently represent -(1-4C) alkyl, phenyl, —$CH_2$phenyl, or —$(CH_2)_2$phenyl, wherein phenyl, as used in substituent $R^{10}$, $R^{11}$ or $R^{12}$, is unsubstituted or substituted with F, Cl, Br, $CF_3$, (1-4C)alkyl, or -(1-4) alkoxy;

$R^{13}$ represents hydrogen, -(1-4C)alkyl, triazole, or tetrazole;

$R^{14}$ represents -(1-4C)alkyl;

$R^{15}$ represents hydrogen or -(1-4C)alkyl;

m represents 0, 1, 2, or 3;

n represents 1, 2, 3, or 4;

p represents 1 or 2; and

A is selected from the group consisting of I, —$(CH_2)_m$CN, —$C(CH_3)_2$CN, $NO_2$, $NH_2$, -(1-6C)alkyl, -(1-4C) alkoxy, -(24C)alkenyl, -(24C)alkenyloxy, —$CO_2$H, —$CO_2$(1-4C)alkyl, —CHO, —C(=O)(1-4C)alkyl, —C(=O)$NH_2$, —C(=O)NH(1-6C)alkyl, —C(=O)$NR^{15}(CH_2)_m$phenyl wherein phenyl is unsubstituted or substituted with one or two substituents independently selected from the group consisting of OH, F, Cl, Br, I, $NO_2$, $NH_2$, —$NHSO_2$(1-4C)alkyl, —CN, -(1-4C)alkyl, and -(1-4C)alkoxy, —$OSO_2CF_3$, —$O(CH_2)_n$CN, —NHC(=O)(1-4C)alkyl, —NHC(=O)$(CH_2)_m$phenyl wherein phenyl is unsubstituted or substituted with one or two substituents independently selected from the group consisting of OH, F, Cl, Br, I, $NO_2$, $NH_2$, CN, -(1-4C) alkyl and -(1-4C)alkoxy; —$(CH_2)_m NHSO_2R^{12}$, —$CH(CH_3)(CH_2)_p NHSO_2R^{12}$, —$(CH_2)_p CH(CH_3)NHSO_2R^{12}$, —NH$(CH_2)_m$phenyl wherein phenyl is unsubstituted or substituted with one or two substituents independently selected from the group consisting of OH, F, Cl, Br, I, $NO_2$, $NH_2$, CN, -(1-4C) alkyl, and -(1-4C)alkoxy; —NH(1-4C)alkyl, —N[(1-4C) alkyl]$_2$, —C(=O)NH(3-6C)cycloalkyl, —C(=O)NH$(CH_2)_n$N[(1-4C)alkyl]$_2$, —C(=O)NH$(CH_2)_n$NH(1-4C) alkyl, —$(CH_2)_n NH_2$, —$(CH_2)_n NHR^{12}$, —$(CH_2)_n$NH(3-6C) cycloalkyl, —$(CH_2)_n$N[(1-4C)alkyl]$_2$, —NHC(=O)$NHR^{12}$, —NHC(=O)N[(1-4C)alkyl]$_2$,

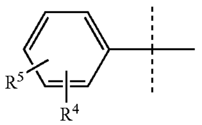,
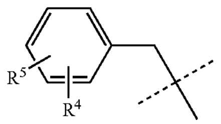,
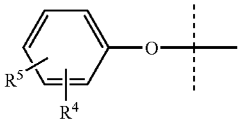,
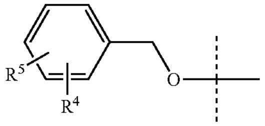,
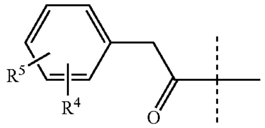,
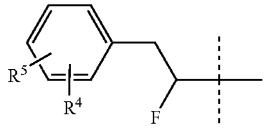,
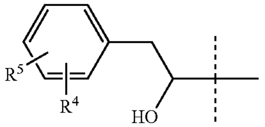,
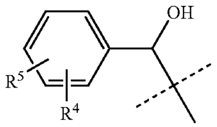,
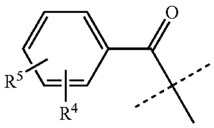,
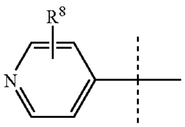, -continued

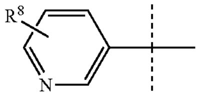,
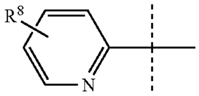,
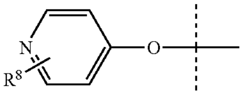,
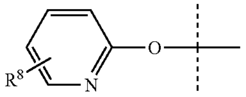,
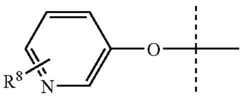,
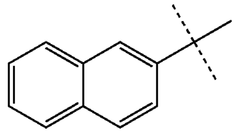,
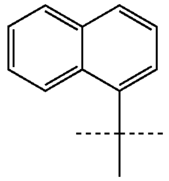,
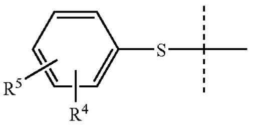
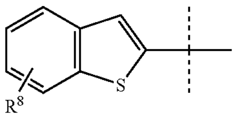,
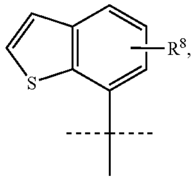
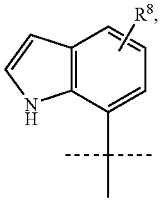
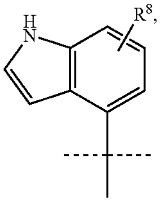
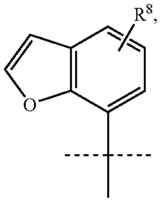
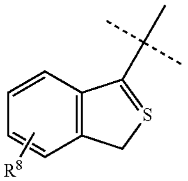,
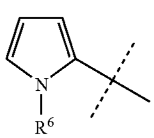,
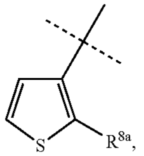
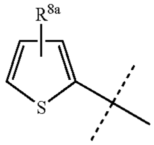,
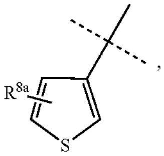,
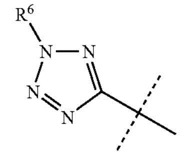,
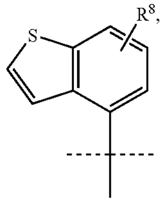
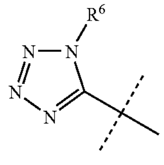, -continued

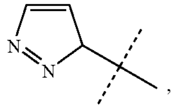 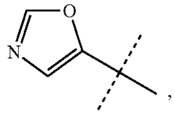

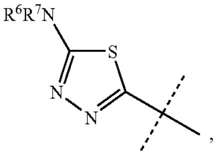 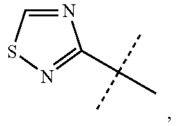

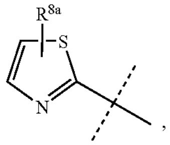 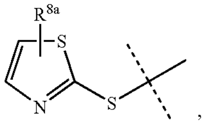

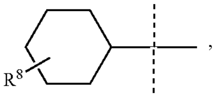 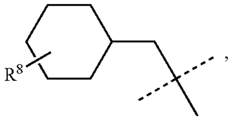

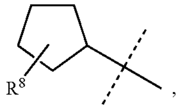 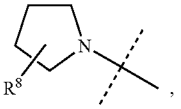

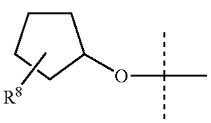 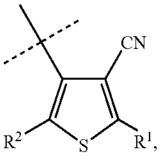

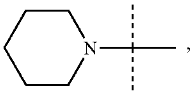 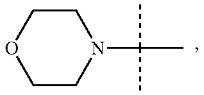

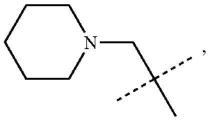 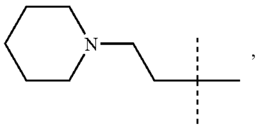

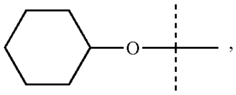 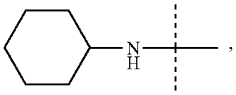

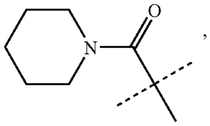 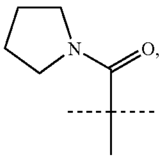

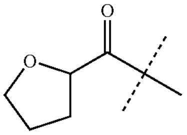 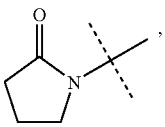

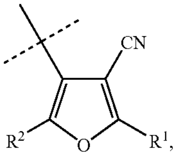 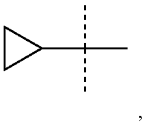

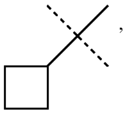 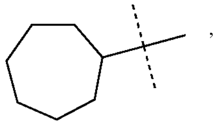

-continued

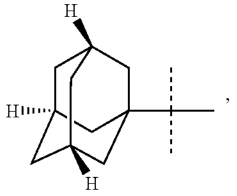 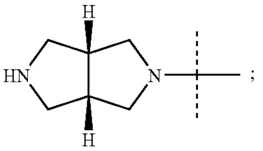

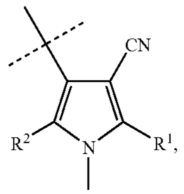 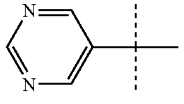

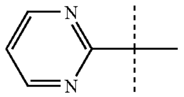

and

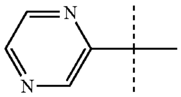

and the pharmaceutically acceptable salts thereof, with the proviso that when R is methyl, $R^1$ is $SCH_3$, and $R^2$ is $CO_2H$, A is other than 4-tert-butyl-phenyl; and provided that when R is methyl, $R^1$ is hydrogen, and $R^2$ is $CO_2H$, A is other than 2,6-dimethylphenyl; and further provided that when R is methyl, $R^1$ is ethyl, and $R^2$ is $—C(=O)NHSO_2CH_3$, A is other than

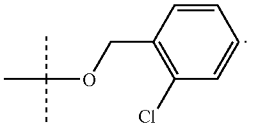

The present invention further provides a method of potentiating glutamate receptor function in a patient, which comprises administering to said patient an effective amount of a compound of Formula I.

In addition, the present invention further provides a method of treating schizophrenia, cognitive deficits associated with schizophrenia, Alzheimer's disease, dementia of the Alzheimer's type, mild cognitive impairment, Parkinson's disease, or depression, in a patient, which comprises administering to said patient an effective amount of a compound of Formula I or Formula II, or a pharmaceutically acceptable salt thereof.

According to another aspect, the present invention provides the use of a compound of Formula I or Formula II, or a pharmaceutically acceptable salt thereof, for the manufacture of a medicament for treating schizophrenia, cognitive deficits associated with schizophrenia, Alzheimer's disease, dementia of the Alzheimer's type, mild cognitive impairment, Parkinson's disease, or depression.

In addition, the present invention provides a compound of Formula I or Formula II, or a pharmaceutically acceptable salt thereof, for use as a pharmaceutical, in particular for treating schizophrenia, cognitive deficits associated with schizophrenia, Alzheimer's disease, dementia of the Alzheimer's type, mild cognitive impairment, Parkinson's disease, or depression.

The invention further provides pharmaceutical compositions comprising, a compound of Formula I, or a pharmaceutically acceptable salt thereof, and a pharmaceutically acceptable carrier, diluent, or excipient.

The invention further provides pharmaceutical compositions comprising, a compound of Formula II, or a pharmaceutically acceptable salt thereof, and a pharmaceutically acceptable diluent or carrier.

In addition, this invention also encompasses novel intermediates used in the preparation of compounds of Formula I and Formula II, prodrugs of the compounds of Formula I, and processes for the synthesis of the compounds of Formula I and Formula II.

In addition, the present invention provides a pharmaceutical composition which comprises a first component which is a compound of Formula I or Formula II, or a pharmaceutically acceptable salt thereof, and a second component which is an antipsychotic.

The present invention provides a pharmaceutical composition which comprises a first component which is a compound of Formula I or Formula II, or a pharmaceutically acceptable salt thereof, and a second component which is an antidepressant.

In addition, the present invention provides a pharmaceutical composition which comprises a first component which is a compound of Formula I or Formula II, or a pharmaceutically acceptable salt thereof, and a second component which is a drug useful in treating a cognitive disorder.

The invention further provides a method for treating a patient suffering from or susceptible to schizophrenia or cognitive deficits associated with schizophrenia comprising administering to said patient an effective amount of a first component which is a compound of Formula I or Formula II, or a pharmaceutically acceptable salt thereof, in combination with an effective amount of a second component which is an antipsychotic.

The invention further provides a method for treating a patient suffering from or susceptible to depression, comprising administering to said patient an effective amount of a first component which is a compound of Formula I or Formula II, or a pharmaceutically acceptable salt thereof, in combination with an effective amount of a second component which is an antidepressant.

The invention further provides a method for treating a patient suffering from or susceptible to a cognitive disorder, comprising administering to said patient an effective amount of a first component which is a compound of Formula I or Formula II, or a pharmaceutically acceptable salt thereof, in combination with an effective amount of a second component which is a drug useful in treating a cognitive disorder.

DETAILED DESCRIPTION OF THE INVENTION

As used herein the term "potentiating glutamate receptor function" refers to any increased responsiveness of glutamate receptors, for example AMPA receptors, to glutamate or an agonist, and includes but is not limited to inhibition of rapid desensitization or deactivation of AMPA receptors to glutamate.

A wide variety of conditions may be treated or prevented by compounds of Formula I or Formula II, and their pharmaceutically acceptable salts through their action as potentiators of glutamate receptor function. Such conditions include those associated with glutamate hypofunction, such as psychiatric and neurological disorders, for example cognitive disorders and neuro-degenerative disorders such as Alzheimer's disease; dementia of the Alzheimer's type, age-related dementias; age-induced memory impairment; cognitive deficits due to autism, Down's syndrome and other central nervous system disorders with childhood onset, cognitive deficits post electroconvulsive therapy, movement disorders such as tardive dyskinesia, Huntington's chorea, myoclonus, dystonia, spasticity, Parkinson's disease; reversal of drug-induced states (such as cocaine, amphetamines, alcohol-induced states); depression, including major depressive disorder and treatment resistant depression; attention deficit disorder; attention deficit hyperactivity disorder; psychosis such as schizophrenia; cognitive deficits associated with psychosis such as schizophrenia, drug-induced psychosis, stroke, and sexual dysfunction. Compounds of Formula I or Formula II may also be useful for improving memory (both short term and long term) and learning ability. The present invention provides the use of compounds of Formula I or Formula II for the treatment of each of these conditions.

It is understood by one of ordinary skill in the art that cognition includes various "domains". These domains include short-term memory, long term memory, working memory, executive function, and attention. As used herein the term "cognitive disorder" is meant to encompass any disorder characterized by a deficit in one or more of the cognitive domains, including but not limited to short term memory, long term memory, working memory, executive function, and attention. It is further understood that the term "cognitive disorder" includes, but is not limited to the following specific disorders: age-related cognitive decline, mild cognitive impairment, Alzheimer's disease, dementia, dementia of the Alzheimer's type, Parkinson's dementia, Lewy Body dementia, substance-induced persisting dementia, alcohol-induced persisting dementia, alcohol-induced cognitive impairment, AIDS-induced dementia, learning disorders, cognitive deficits subsequent to cardiac bypass surgery and grafting, stroke, cerebral ischemia, spinal cord trauma, head trauma, perinatal hypoxia, cardiac arrest, and hypoglycemic neuronal damage, vascular dementia, multi-infarct dementia, cognitive deficits associated with amylotrophic lateral sclerosis, and cognitive deficits associated with multiple sclerosis.

The fourth edition of the Diagnostic and Statistical Manual of Mental Disorders (DSM-IV) (1994, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV and that terminology and classification systems evolve with medical scientific progress.

As used herein the term "a drug useful in treating a cognitive disorder" includes, but is not limited to acetylcholinesterase inhibitors, NMDA receptor antagonists, 5-$HT_6$ antagonists, M1 agonists, serotonin reuptake inhibitors, norepinephrine reuptake inhibitors, combined serotonin-norepinephrine reuptake inhibitors, monoamine oxidase inhibitors, phosphodiesterase-4 inhibitors, tricyclic antidepressants, and AMPA receptor potentiators. More specifically, the term "a drug useful in treating a cognitive disorder" includes, but is not limited to the following compounds which are well known and readily available to one of ordinary skill in the art: donepezil, rivastigmine, galantamine, memantine, tacrine, phenserine, physostigmine, xanomeline, CX516, milameline, aniracetam, piracetam, oxiracetam, suritozole, fluoxetine, sertraline, citalopram, duloxetine, atomoxetine, venlafaxine, milnacipran, fluvoxamine, paroxetine, buproprion, reboxetine, imipramine, and rolipram.

As used herein the term "antidepressant" includes serotonin reuptake inhibitors, norepinephrine-serotonin reuptake inhibitors, selective norepinephrine reuptake inhibitors, and the like. For example, "antidepressant" includes fluoxetine, venlafaxine, citalopram, fluvoxamine, paroxetine, sertraline, milnacipran, reboxetine, and duloxetine. Fluoxetine and duloxetine are preferred antidepressants.

As used herein the term “antipsychotic” includes typical and atypical antipsychotics. Thus, the term “antipsychotic” includes, for example, haloperidol, chlorpromazine, clozapine, risperidone, olanzapine, aripiprazole, ziprasidone, sertindole, amisulpride, zotepine, sulpiride, and quitiapine. Olanzapine is the preferred antipsychotic.

As used herein “fluoxetine” will be used to mean any acid addition salt or the free base, and to include either the racemic mixture or either of the R and S enantiomers. Fluoxetine hydrochloride is a preferred salt.

The following specific combinations are preferred:

Formula I/fluoxetine
Formula I/duloxetine
Formula I/paroxetine
Formula I/olanzapine
Formula I/risperidone
Formula I/aripiprazole
Formula I/sertindole
Formula I/quetiapine
Formula I/ziprasidone
Formula I/zotepine
Formula I/memantine
Formula I/donepezil
Formula I/rivastigmine
Formula I/galantalmine,
Formula I/tacrine
Formula I/CX516
Formula I/atomoxetine
Formula II/fluoxetine
Formula II/duloxetine
Formula II/paroxetine
Formula II/olanzapine
Formula II/risperidone
Formula II/aripiprazole
Formula II/sertindole
Formula II/quetiapine
Formula II/ziprasidone
Formula II/zotepine
Formula II/memantine
Formula II/donepezil
Formula II/galantamine,
Formula II/tacrine
Formula II/CX516
Formula II/atomoxetine The following combinations are especially preferred:

| First Component | Second Component |
| --- | --- |
| 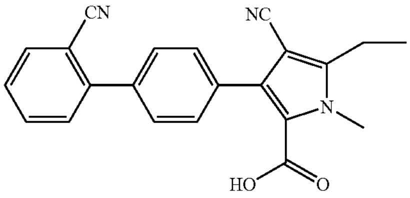 | fluoxetine |

-continued

| First Component | Second Component |
| --- | --- |
| 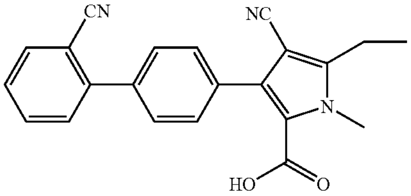 | duloxetine |
| 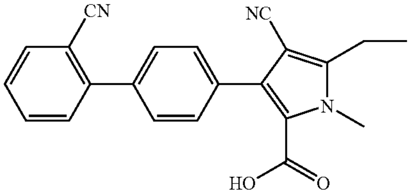 | atomoxetine |
| 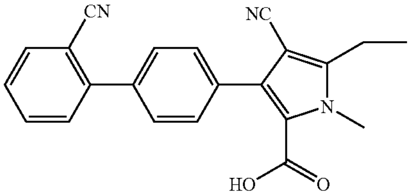 | olanzapine |
| 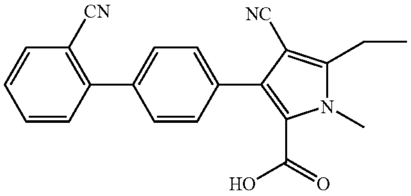 | donepezil |
| 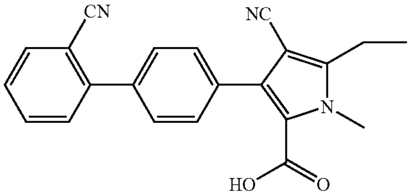 | memantine |
| 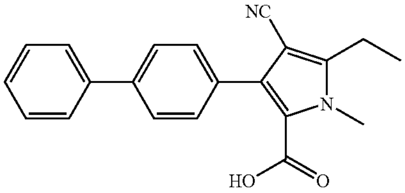 | fluoxetine |
| 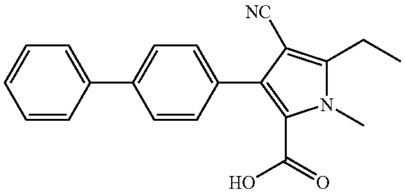 | duloxetine |

-continued
| First Component | Second Component |
|---|---|
| 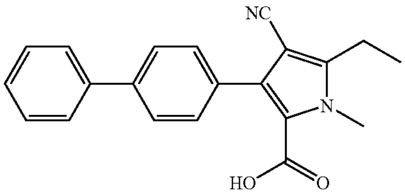 | atomoxetine |
| 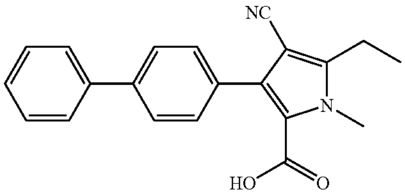 | olanzapine |
| 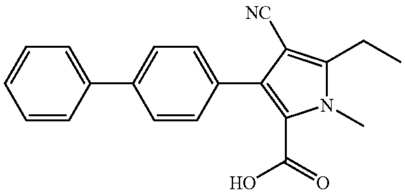 | donepezil |
| 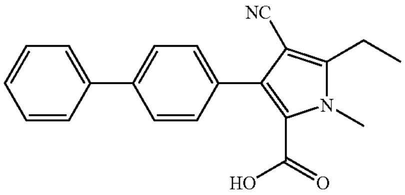 | memantine |
| 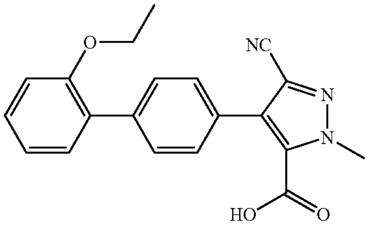 | fluoxetine |
| 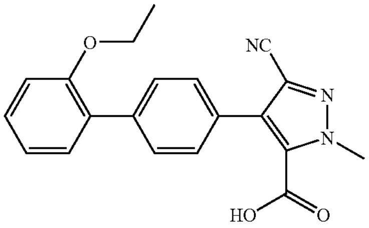 | duloxetine |
| 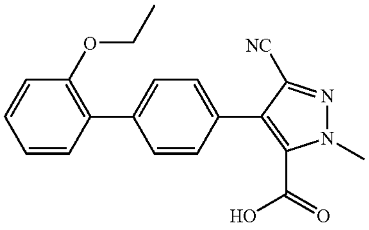 | atomoxetine |
-continued
| First Component | Second Component |
|---|---|
| 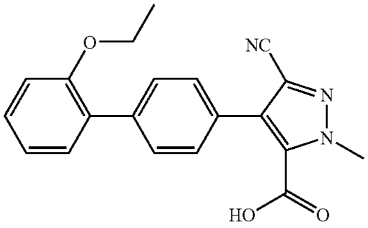 | olanzapine |
| 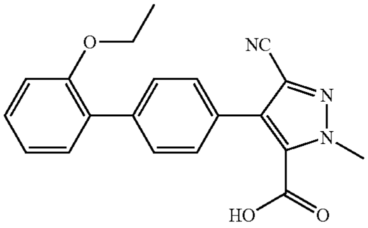 | donepezil |
| 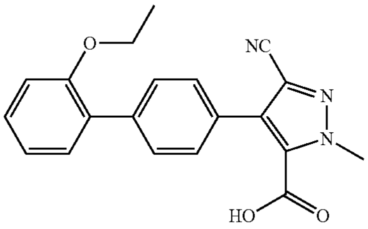 | memantine |
| 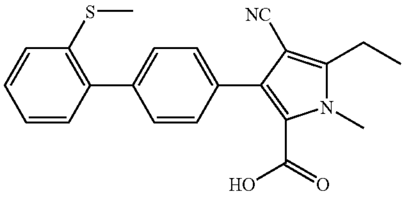 | fluoxetine |
| 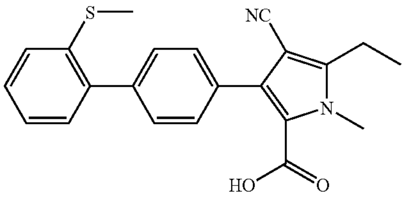 | duloxetine |
| 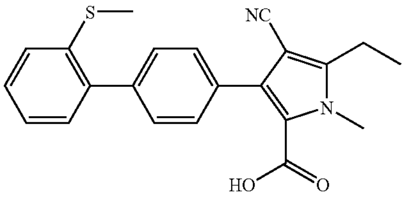 | atomoxetine |
| 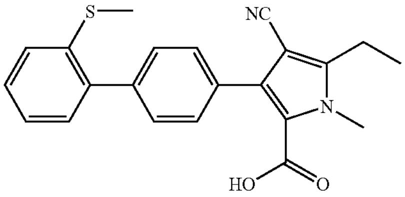 | olanzapine |

-continued

| First Component | Second Component |
|---|---|
| 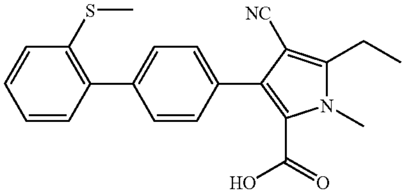 | donepezil |
| 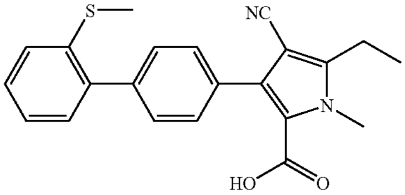 | memantine |
| 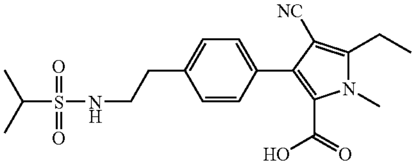 | fluoxetine |
| 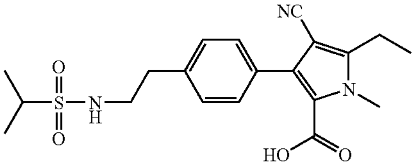 | duloxetine |
| 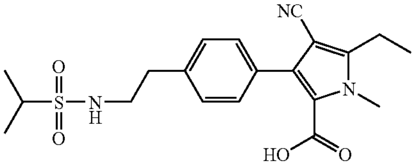 | atomoxetine |
| 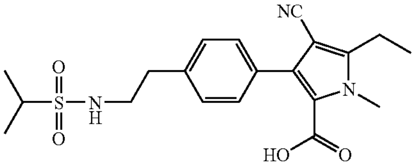 | olanzapine |
| 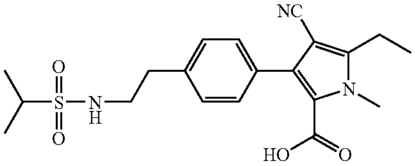 | donepezil |
| 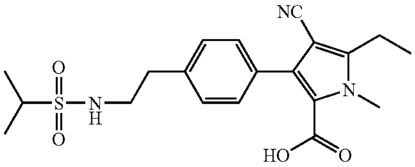 | memantine |

The present invention includes solvates of compounds of Formula I, such as DMF and DMSO solvates. In addition, the present invention includes the pharmaceutically acceptable salts of the compounds defined by Formula I and Formula II. A compound of this invention can possess a sufficiently acidic group, a sufficiently basic group, or both functional groups, and accordingly react with any of a number of organic and inorganic bases, and inorganic and organic acids, to form a pharmaceutically acceptable salt.

The term "pharmaceutically acceptable salt" as used herein, refers to salts of the compounds of the above Formulas which are substantially non-toxic to living organisms. Typical pharmaceutically acceptable salts include those salts prepared by reaction of the compounds of the present invention with a pharmaceutically acceptable mineral or organic acid or an organic or inorganic base. Such salts are known as acid addition and base addition salts. Such salts include the pharmaceutically acceptable salts listed in *Journal of Pharmaceutical Science,* 66, 2-19 (1977), which are known to the skilled artisan. Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, 1-naphthalenesulfonate, 2-napththalenesulfonate, 1,5-naphthalenedisulfonate, mandelate, tararate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid. The HCl salt is most preferred.

Base addition salts include those derived from organic bases or inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, calcium acetate, diethylamine, diethanolamine, and the like. The potassium, sodium, calcium, diethylamine, and diethanolamine salt forms are particularly preferred.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that the above salts may form hydrates, solvates, or exist in a substantially anhydrous form.

As used herein the term "prodrug" refers to compounds that are drug precursors, which following administration, release the drug in vivo via a chemical or physiological process. For example, a prodrug, on being brought to the physiological pH or through enzyme action, is converted to the desired drug form in vivo by enzymatic and/or chemical hydrolytic cleavage of an ester to provide the corresponding carboxylic acid drug.

Various forms of prodrugs are known to one of ordinary skill in the art. For examples of such prodrug derivatives, see Design of Prodrugs, edited by H. Bundgaard, (Elsevier, 1985); D. Fleisher, et al., Advanced Drug Delivery Reviews, 19, 115, (1996); H. Bundgaard, Advanced Drug Delivery Reviews, 8, 1-38 (1992); H. Bundgaard, et al., Journal of Pharmaceutical Sciences, 77, 285 (1988); and N. Kakeya, et al., Chem Pharm Bull, 32, 692 (1984).

Examples of prodrugs of Formula I are those that form in vivo cleavable esters or amides. An in vivo cleavable ester or amide is, for example, an ester or amide which is cleaved in the human or animal body to produce the parent acid of Formula Ia. The amide and ester moieties may incorporate other functional groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

As used herein, the term "stereoisomer" refers to a compound made up of the same atoms bonded by the same bonds but having different three-dimensional-1 structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the specific stereoisomers and enantiomers of compounds of Formula I and Formula II can be prepared by one of ordinary skill in the art utilizing well known techniques and processes, such as those disclosed by J. Jacques, et al., "*Enantiomers, Racemates, and Resolutions*", John Wiley and Sons, Inc., 1981, and E. L. Eliel and S. H. Wilen, "*Stereochemistry of Organic Compounds*", (Wiley-Interscience 1994), and European Patent Application No. EP-A-838448, published Apr. 29, 1998. Examples of resolutions include recrystallization techniques or chiral chromatography.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103-120

As used herein the term "substantially pure" refers to pure crystalline form of the compound comprising greater than about 95% of the desired crystalline form, and preferably, greater than about 98% of the desired crystalline form.

As used herein, $R^a$ represents -(1-4C)alkyl or —$SO_2$(1-4C) alkyl.

As used herein, the terms "Halo", "Halide" or "Hal" refers to a chlorine, bromine, iodine or fluorine atom, unless otherwise specified herein.

As used herein, the term "Me" refers to a methyl group, the term "Et" refers to an ethyl group, the term "Pr" refers to a propyl group, the term "iPr" refers to an isopropyl group and the term "Ph" refers to a phenyl group.

As used herein the term "-(1-6C)alkyl" refers to a straight or branched, monovalent, saturated aliphatic chain of 1 to 6 carbon atoms and includes, but is not limited to, methyl, ethyl, propyl, isopropyl, butyl, isobutyl, t-butyl, pentyl, isopentyl, and hexyl. The term "-(1-6C)alkyl" includes within its definition the terms "-(1-4C)alkyl" and "-(1-3C)alkyl".

As used herein the term "-(1-6C)alkoxy" refers to a straight or branched alkyl chain having from one to six carbon atoms attached to an oxygen atom. Typical -(1-6C)alkoxy groups include methoxy, ethoxy, propoxy, isopropoxy, butoxy, t-butoxy, pentoxy and the like. The term "-(1-6C)alkoxy" includes within its definition the term "-(1-4C)alkoxy".

As used herein the term "-(2-4C)alkenyl" refers to a straight or branched, monovalent, unsaturated aliphatic chain having from two to four carbon atoms. Typical (2-4C)alkenyl groups include ethenyl (also known as vinyl), 1-methylethenyl, 1-methyl-1-propenyl, 1-butenyl, 2-methyl-2-propenyl, 1-propenyl, 2-propenyl, 2-butenyl, and the like.

As used herein the term "-(2-4C)alkenyloxy" refers to a straight or branched, monovalent, unsaturated aliphatic chain having from two to four carbon atoms attached to an oxygen atom. Typical -(2-4C)alkenyl groups include ethenyloxy, 1-methylethenyloxy, 1-methyl-1-propenyloxy, 1-butenyloxy, 2-methyl-2-propenyloxy, 1-propenyloxy, 2-propenyloxy, 2-butenyloxy, and the like.

As used herein the term "-(3-6C)cycloalkyl" refers to a saturated hydrocarbon ring structure containing from three to six carbon atoms. Typical -(3-6C)cycloalkyl groups include cyclopropyl, cyclobutyl, cyclopentyl, cyclohexyl, and the like.

As used herein the term "-(4-7C)cycloalkyl" refers to a saturated hydrocarbon ring structure containing from four to seven carbon atoms. Typical -(4-7C)cycloalkyl groups include cyclobutyl, cyclopentyl, cyclohexyl, cycloheptyl, and the like.

As used herein, the terms "aryl" or "Ar" refer to a carbocyclic or heterocyclic group which may contain one or more fused or non-fused phenyl rings and includes, for example, phenyl, biphenyl, 1- or 2-naphthyl, 1,2-dihydronaphthyl, 1,2,3,4-tetrahydronaphthyl, and the like. In addition, the aryl group may be substituted or unsubstituted as set forth herein. The terms "aryl" or "Ar" may further include the following:

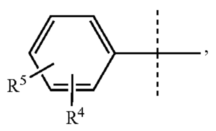
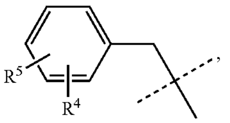
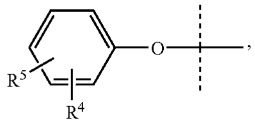
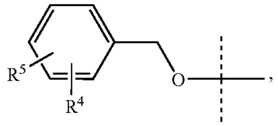
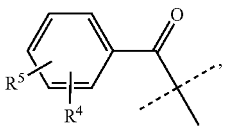
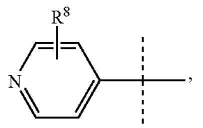
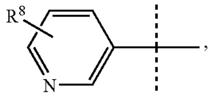
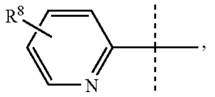
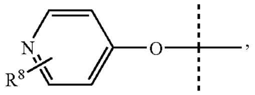
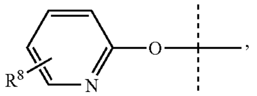
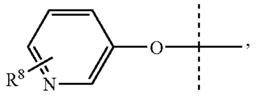
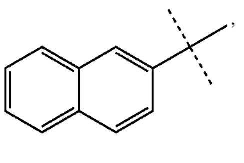

-continued

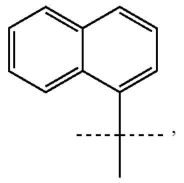
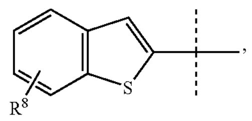
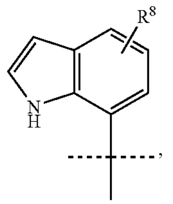
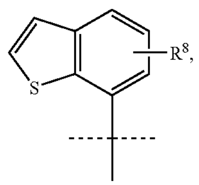
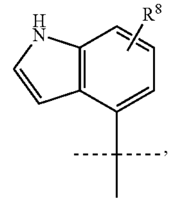
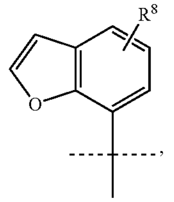
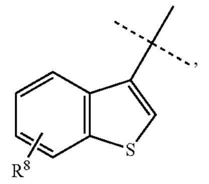
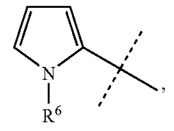
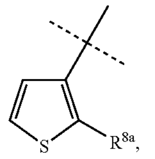
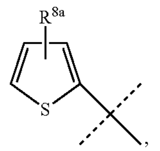
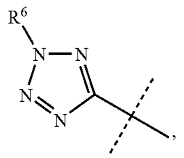
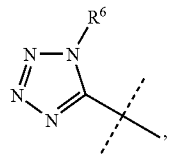
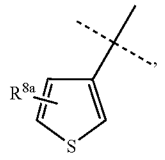
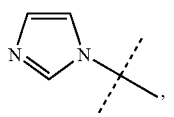
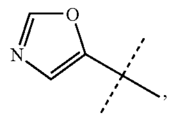
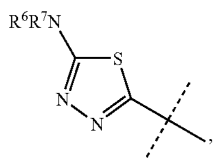
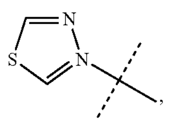
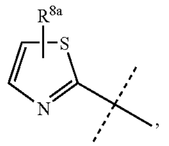

-continued
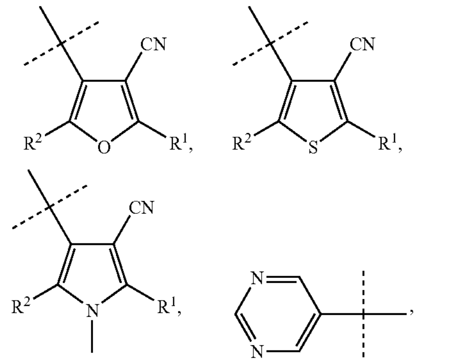
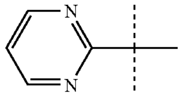
and
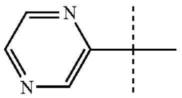
wherein the substituents are as defined herein.
As used herein, the term "(1-6C)alkylaryl" includes the following:
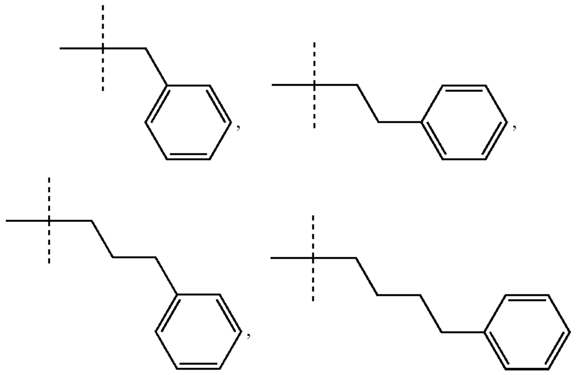
and the like.
As used herein, the term "(1-6C)alkyl(3-6C)cycloalkyl" includes the following:
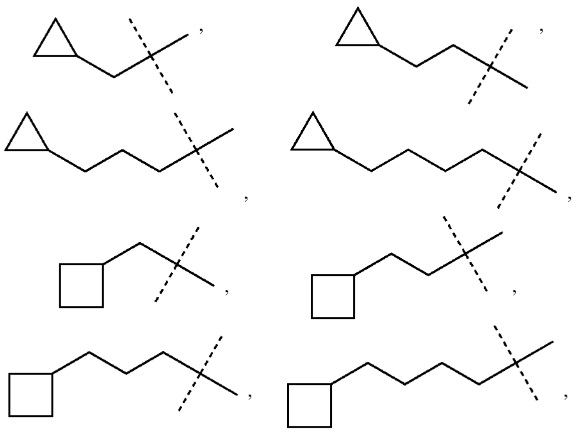
-continued
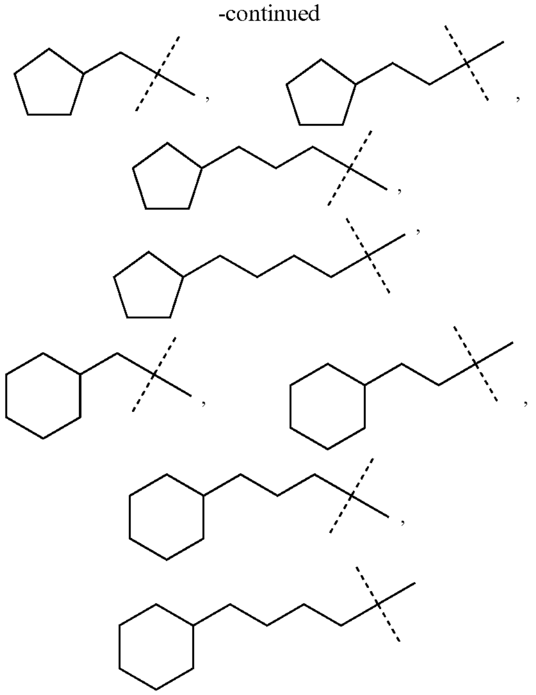
and the like.
As used herein the term "(1-6C)alkyl-N,N-(1-6C)dialkylamine" includes the following:
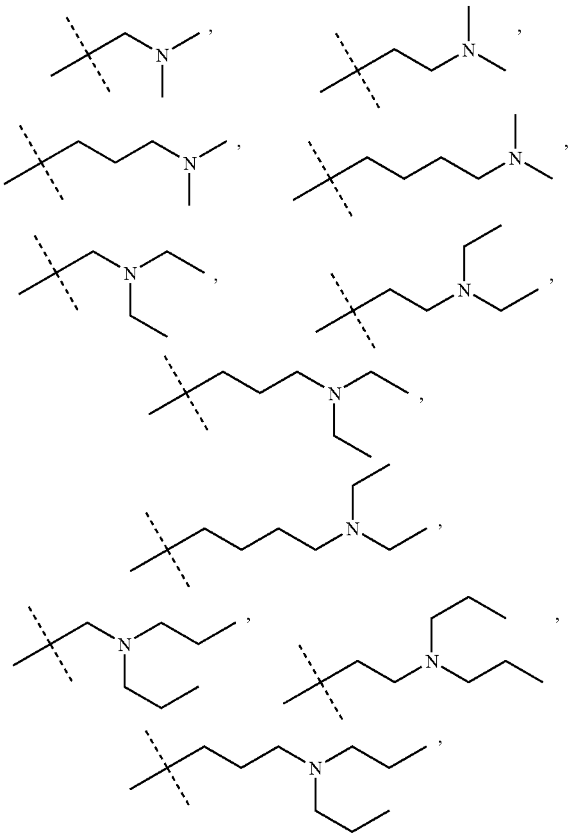

-continued

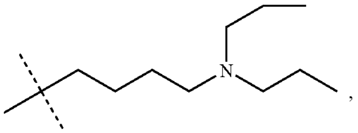

and the like.

As used herein the term "(1-6C)alkyl-pyrrolidine" includes the following:

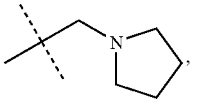

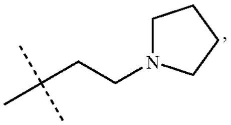

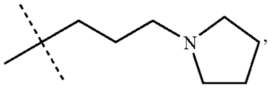

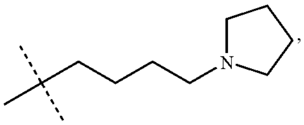

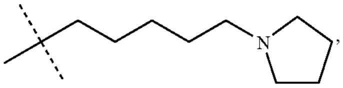

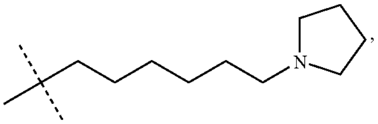

and the like.

As used herein the term "(1-6C)alkyl-piperidine" includes the following:

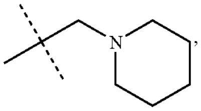

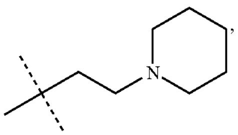

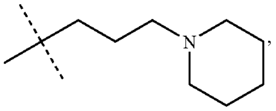

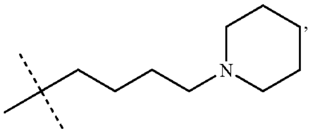

-continued

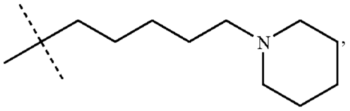

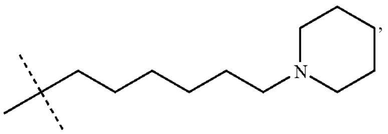

and the like.

As used herein the term "(1-6C)alkyl-morpholine" includes the following:

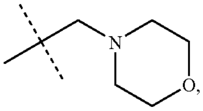

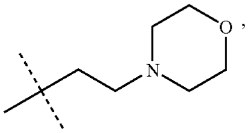

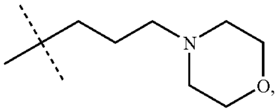

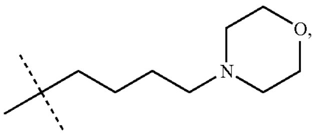

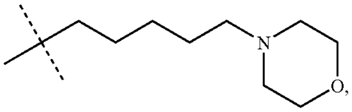

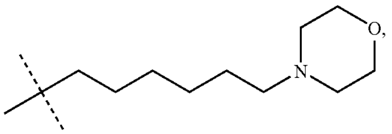

and the like.

As used herein the term "bis(pinacolato)diboron" refers to the following structure:

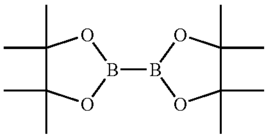

As used herein, the term "Hartwig's Ligand" refers to the following compound:

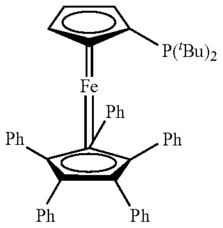

As used herein, "BINAP" refers to the following compound:

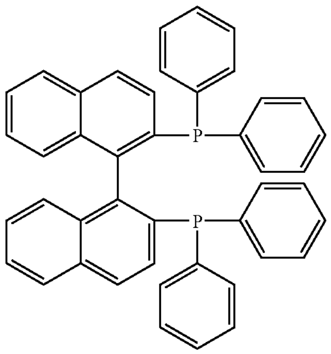

The compounds of Formula I and Formula II can be prepared by one of ordinary skill in the art following art recognized techniques and procedures. More specifically, compounds of Formula I and Formula II can be prepared as set forth in the schemes, methods, and examples set forth below. The reagents and starting materials are readily available to one of ordinary skill in the art. All substituents, unless otherwise specified, are as previously defined.

Scheme I

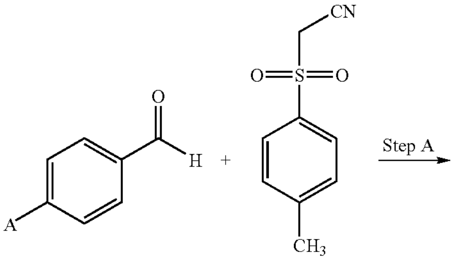

(1) (2)

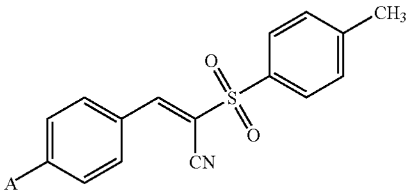

(3)

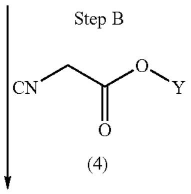

(4)

-continued

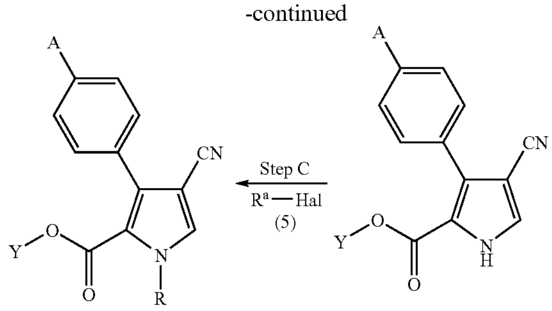

Formula IIb Formula IIa

For example, in Scheme I, step A, the benzaldehyde of structure (1) is combined with the toluenesulfonylacetonitrile of structure (2) under conditions well known in the art to provide the acrylonitrile of structure (3) wherein A is as defined herein. See *Synthesis,* 806 (1980) for general synthetic technique. More specifically, the benzaldehyde (1) is combined with about one equivalent of the toluenesulfonylacetonitrile (2) in a suitable organic solvent, such as toluene. Examples of suitable benzaldehydes (1) include, 4-phenylbenzaldehyde, 4-bromobenzaldehyde, 4-(trifluoromethyl)-benzaldehyde, 4-(2-pyridyl)benzaldehyde, 4-(3-pyridyl)benzaldehyde, 4-(4-pyridyl)benzaldehyde, 4-(2,6-dimethylphenyl)-benzaldehyde, 4-(4-chlorophenyl)benzaldehyde, 4-(3,5-dichlorophenyl)benzaldehyde, 4-(3,4-dichlorophenyl)benzaldehyde, 4-(4-fluorophenyl)benzaldehyde, 4-(4-methylphenyl)benzaldehyde, 4-[4-(trifluoromethyl)phenyl]benzaldehyde, 4-(2-methoxyphenyl)benzaldehyde, 4-(2-chlorophenyl)benzaldehyde, 4-(2-methylphenyl)benzaldehyde, 4-[2-(trifluoromethyl)phenyl]benzaldehyde, 4-(2-nitrophenyl)benzaldehyde, 4-benzyloxybenzaldehyde, 4-phenoxybenzaldehyde, 4-(pyridin-2-yloxy)benzaldehyde, 4-(pyridin-3-yloxy)benzaldehyde, 4-(pyridin-4-yloxy)benzaldehyde, 4-(4-chlorophenoxy)benzaldehyde, 4-(4-fluorophenoxy)benzaldehyde, and the like. A catalytic amount of a suitable base, such as piperidine is added with about 0.2 equivalents of acetic acid and the reaction mixture is heated to about 110° C. for about 1 to 18 hours. The reaction is then cooled and the acrylonitrile of structure (3) is isolated using techniques well known in the art, for example, collection of resulting solids by filtration, rinsing the solids with a suitable organic solvent, such as toluene, and drying under vacuum to provide acrylonitrile (3).

In Scheme I, step B, acrylonitrile (3) is combined with an alkylisocyanoacetate of structure (4) under conditions well known in the art to provide the compound of Formula IIa wherein Y represents (1-6C)alkyl. See *Synthesis,* 471 (1999) for general synthetic technique. More specifically, acrylonitrile (3) is dissolved in a suitable organic solvent, such as THF and treated with about 4 equivalents of a suitable base, such as DBU at room temperature. After about 10 to 30 minutes of stirring, about 2 equivalents of an alkylisocyanoacetate (4) is added, wherein Y represents (1-6C)alkyl, and the reaction is stirred for about 3 to 18 hours. Examples of suitable alkylisocyanoacetates (4) include, methyl isocyanoacetate, ethyl cyanoacetate, and the like. The pyrrole (5) is then isolated using techniques well known in the art, for example, water is added to the reaction mixture which is then extracted with a suitable organic solvent, such as ethyl acetate. The organic extracts are combined, washed with aqueous HCl, water, brine, dried over anhydrous magnesium sulfate, filtered, and concentrated under vacuum to provide the crude compound of Formula IIa. The crude compound of Formula IIa can be purified by techniques well known in the art, such as silica gel chromatography or recrystallization from a suitable solvent or solvent mixture, such as ethyl acetate:hexanes.

In Scheme I, step C, the compound of Formula IIa is alkylated under standard alkylating conditions well known in the art with a suitable alkylating agent of structure (5) wherein Hal represents Cl, Br, or I and $R^a$ represents (1-4C)alkyl or $SO_2$(1-4C)alkyl, to provide the compound of Formula IIb. More specifically, the compound of Formula IIa is dissolved in a suitable organic solvent, such as dimethylsulfoxide and treated with about 1.1 equivalents of a suitable base, such as potassium carbonate at room temperature. The mixture is allowed to stir for about 10 to 30 minutes and about 1.2 equivalents of the alkylating agent (5) is added to the reaction. Examples of suitable alkylating agents include methyl iodide, ethyl iodide, propyl iodide, isopropyl iodide, ethyl bromide, propyl bromide, butyl bromide, butyl chloride, tert-butyl bromide, methanesulfonyl chloride, ethanesulfonyl chloride, propanesulfonyl chloride, isopropylsulfonyl chloride, and the like. The reaction mixture is allowed to stir for about 6 to 18 hours. The compound of Formula IIb is then isolated and purified using techniques well known in the art, such as extraction followed by recrystallization from a suitable solvent or solvent system. For example, the reaction mixture is diluted with water, extracted with a suitable organic solvent, such as ethyl acetate, the organic extracts are combined, washed with aqueous acid, water, and brine and dried over anhydrous magnesium sulfate. After filtering and concentrating the filtrate under vacuum, the residue is then recrystallized from a suitable organic solvent mixture, such as ethyl acetate:hexanes to provide the compound of Formula IIb.

Scheme II

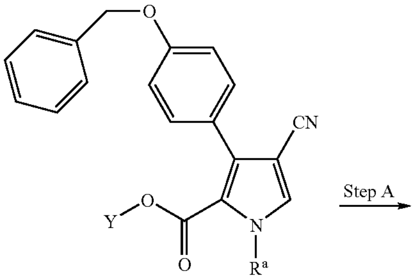

Formula IIc

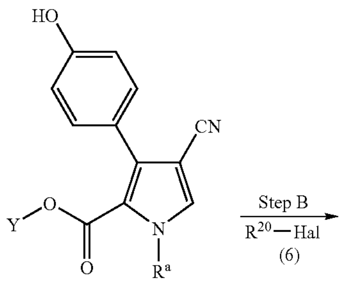

Formula IId

-continued

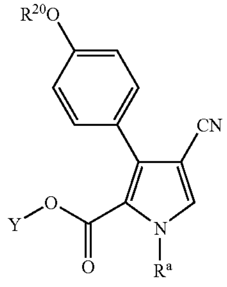

Formula IIe

In Scheme II, step A, the compound of Formula IIc is deprotected under conditions well known in the art to provide the compound of Formula IId. More specifically, compound of Formula IIc is dissolved in a suitable organic solvent or solvent mixture, such as ethanol:THF and treated with a catalytic amount of a suitable hydrogenation catalyst, such as palladium hydroxide on carbon. The mixture is placed under hydrogen gas at about 344 kPa for about 12 to 24 hours and then filtered. The filtrate is concentrated under vacuum and the residue is purified using techniques well know in the art, such as chromatography on silica gel eluting with a suitable organic solvent or solvent mixture, such as ethyl acetate: hexanes to provide the purified compound of Formula IId.

In Scheme II, step B, the compound of Formula IId is alkylated under conditions well known in the art with an alkylating agent (6) wherein $R^{20}$ represents -(1-4C)alkyl, -(2-4C)alkenyl, $—(CH_2)_nCN$, $(CH_2)_nNHSO_2R^{12}$,

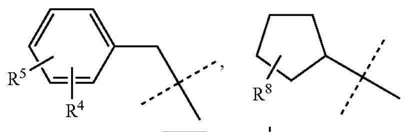

and

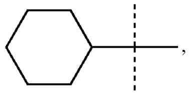

and Hal represents Cl, Br, or I to provide the compound of Formula IIe. Examples of suitable alkylating agents (6) are methyl iodide, ethyl iodide, propyl iodide, isopropyl iodide, ethyl bromide, propyl bromide, butyl bromide, butyl chloride, tert-butyl bromide, cyclopropyl bromide, cylcohexyl bromide, bromoacetonitrile, 3-bromopropionitrile, 4-bromobutyronitrile, 2-cyanobenzyl bromide, 3-cyanobenzyl bromide, 4-cyanobenzyl bromide, 2-fluorobenzyl bromide, 3-fluorobenzyl bromide, 4-fluorobenzyl bromide, and the like. More specifically, the compound of Formula IId is dissolved in a suitable organic solvent, such as dry DMF and treated with about 1.1 to 1.3 equivalents of a suitable base, such as sodium hydride under an inert atmosphere, such as nitrogen. The reaction mixture is then stirred at room temperature for about 15 minutes to 1 hour and then treated with about 1.5 equivalents of the suitable alkylating agent (6). The reaction mixture is allowed to stir at room temperature for about 1 to 24 hours and then quenched with water. The product is then isolated and purified by techniques well known in the art, such as extraction and chromatography. For example, the quenched reaction mixture is extracted with a suitable organic solvent, such as ethyl acetate, the organic extracts are combined, washed with water, brine, dried over anhydrous magnesium sulfate, and filtered. The filtrate is concentrated under vacuum to provide the compound of Formula IIe which is then purified by flash chromatography on silica gel with a suitable eluent, such as ethyl acetate:hexanes to provide the compound of Formula IIe.

Scheme III

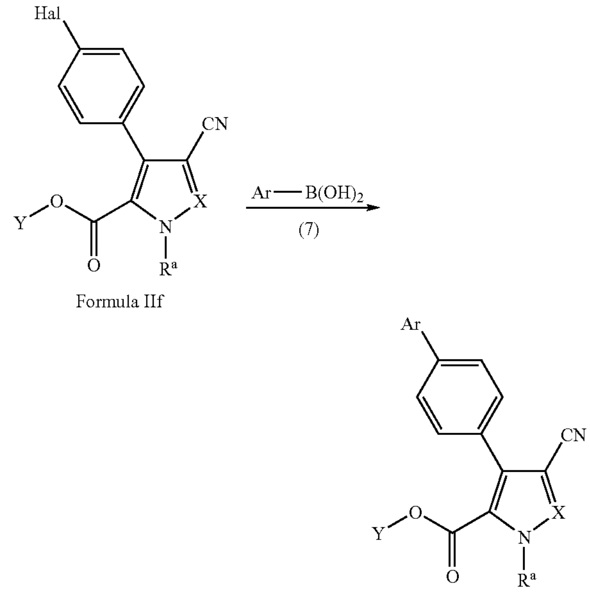

Formula IIf

Formula IIg

In Scheme III, the compound of Formula IIf, wherein Hal is iodo or bromo, is coupled to a suitable aryl boronic acid of structure (7), wherein Ar represents a suitable aryl group, under standard palladium catalyzed cross-coupling reaction conditions well known to one of ordinary skill in the art to provide the compound of Formula IIg. See Suzuki, A., *Journal of Organometallic Chemistry,* 576, 147-168 (1999), and Miyaura and Suzuki, *Chemical Reviews,* 95, 2457-2483 (1995) for examples of general cross-coupling techniques and for methods for preparing suitable starting materials and reagents. Examples of suitable aryl boronic acids (7) include, but are not limited to the following;

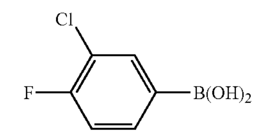
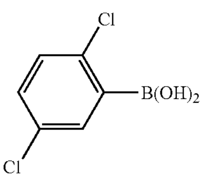
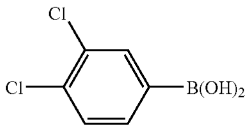
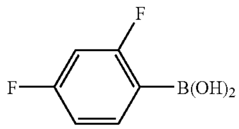
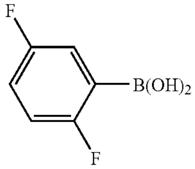
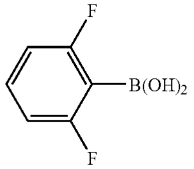

-continued

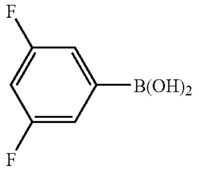
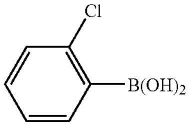
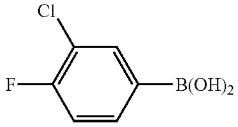
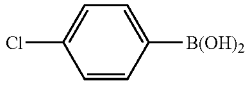
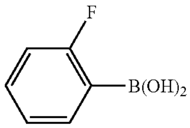
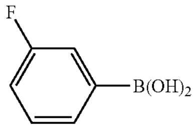
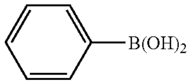
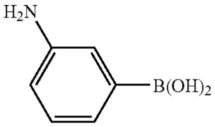
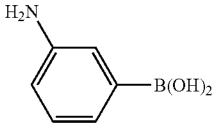
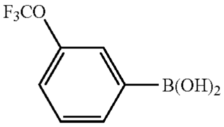
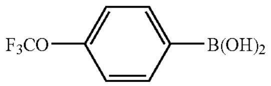
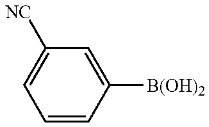
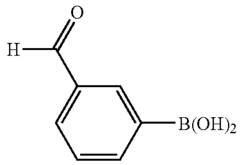
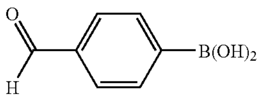
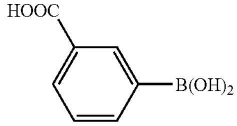
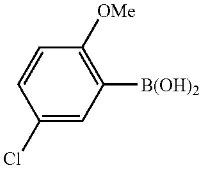
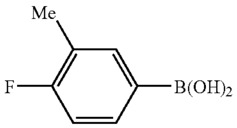
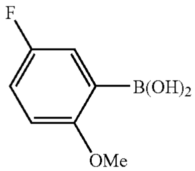
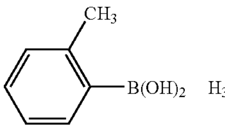
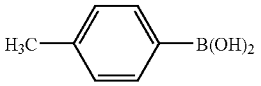
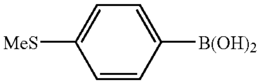
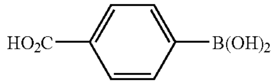
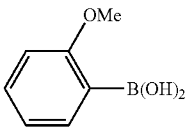
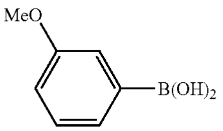

-continued

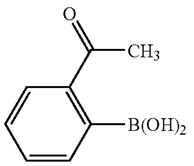
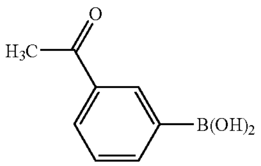
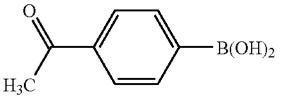
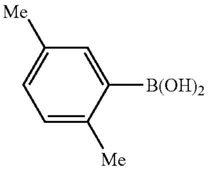
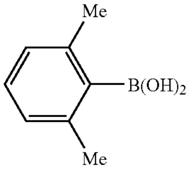
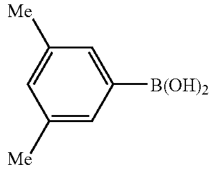
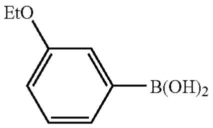
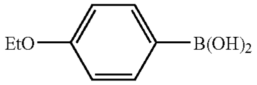
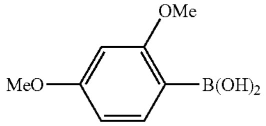
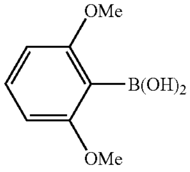
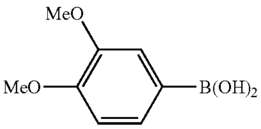
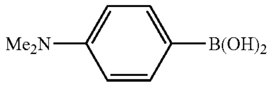
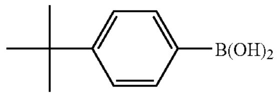
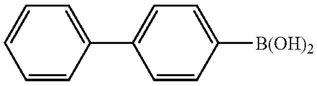
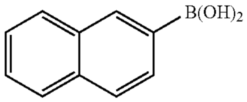
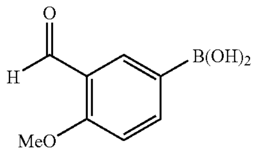
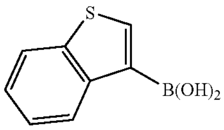
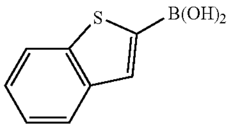
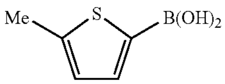
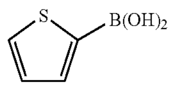
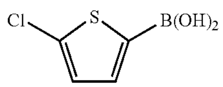
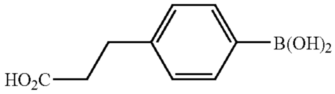
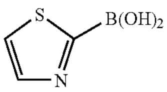

-continued

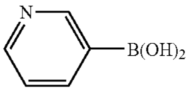
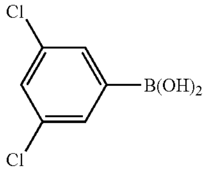
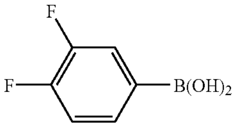
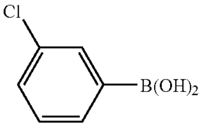
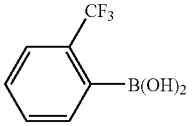
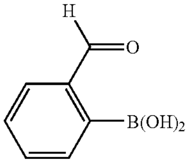
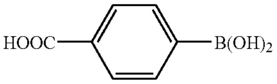
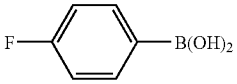
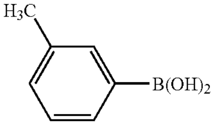
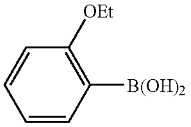
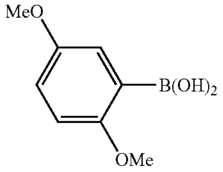
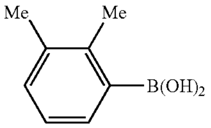
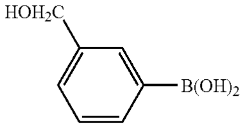
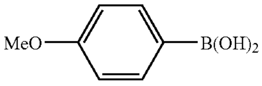
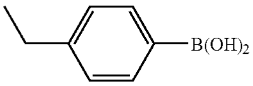
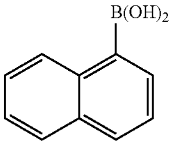
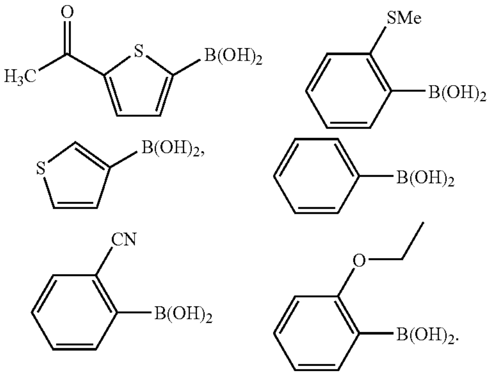

More specifically, the compound of Formula IIf is combined with about 1.1 to 1.5 equivalents of the boronic acid (7) in a suitable organic solvent. Examples of suitable organic solvents include 1,4-dioxane, 1,2-dimethoxyethane, benzene, toluene, acetone, and the like. About 0.03 to 0.10 equivalents of a suitable catalyst, such as tetrakis(triphenylphosphine)palladium or [1,1-bis(diphenylphosphino) ferrocene] dichloro-palladium(II) and about 3 to 5 equivalents of a suitable base are added to the reaction mixture with stirring. Examples of suitable bases include 2M $Na_2CO_3$, $NaHCO_3$, $Cs_2CO_3$, $Tl_2CO_3$, $K_3PO_4$, CsF, triethylamine, and the like. The reaction is heated to about 60 to 100° C. for about 1 to 18 hours, then cooled to room temperature, and quenched with water. The product is then isolated and purified by techniques well known in the art, such as extraction and chromatography. For example, the quenched reaction mixture is extracted with a suitable organic solvent, such as ethyl acetate, the organic extracts are combined, washed with water, brine, dried over anhydrous magnesium sulfate, filtered, and concentrated under vacuum to provide the crude compound of Formula IIg. This crude material can then be purified by flash chromatography on silica gel with a suitable eluent, such as ethyl acetate:hexane to provide the compound of Formula IIg.

Scheme IIIa

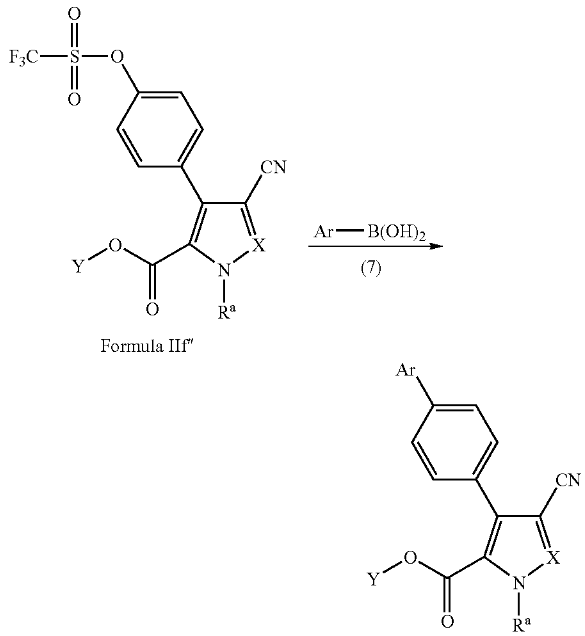

Formula IIf''

Formula IIg

In Scheme IIIa, the compound of Formula IIf'' is coupled to a suitable aryl boronic acid of structure (7), wherein Ar represents a suitable aryl group, in a manner analogous to the procedure set forth in Scheme III to provide the compound of Formula IIg.

Scheme IV

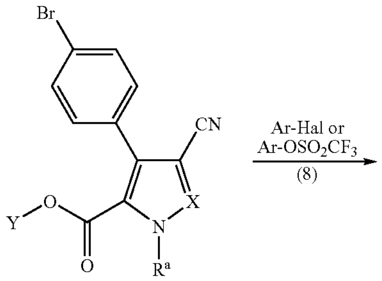

Formula IIf'

-continued

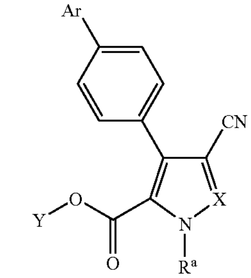

Formula IIg

In Scheme IV, the compound of Formula IIf' is coupled to an aryl halide or triflate of structure (8), wherein Ar represents a suitable aryl group, under standard palladium catalyzed cross-coupling reaction conditions well known to one of ordinary skill in the art to provide the compound of Formula IIg. See Suzuki, A., *Journal of Organometallic Chemistry,* 576, 147-168 (1999), Miyaura and Suzuki, *Chemical Reviews,* 95, 2457-2483 (1995), Ishiyama, T, et al., *J. Org. Chem.,* 60, 7508 (1995, Ishiyama, T, et al., *Tetrahedron Lett.,* 38, 3447 (1997), and *Tetrahedron Lett.,* 38(22), 3841 (1997) for general synthetic techniques. More specifically, about 1.1 equivalents of the corresponding aryl halide or aryl triflate (8) is combined with about 1.2 equivalents of bis(pinacolato)diboron, about 0.03 equivalents of a suitable catalyst, such as $PdCl_2$(dppf), and about 3.0 equivalents of potassium acetate, in suitable organic solvent, such as DMF, dioxane, or DMSO, and the reaction mixture is heated to about 80° C. for about 1 to 4 hours with stirring. The reaction is then cooled to room temperature and about one equivalent of the compound of Formula IIf' is added with an additional 0.3 equivalents of $PdCl_2$ (dppf) and about 5 equivalents of a suitable base, such as 2M sodium carbonate, cesium fluoride, or $K_3PO_4$. The reaction mixture is then heated to about 80° C. for about 1 to 18 hours, cooled to room temperature, and quenched with water. The compound of Formula IIg is then isolated and purified by techniques well known in the art such as those set forth in Scheme III above.

Scheme V

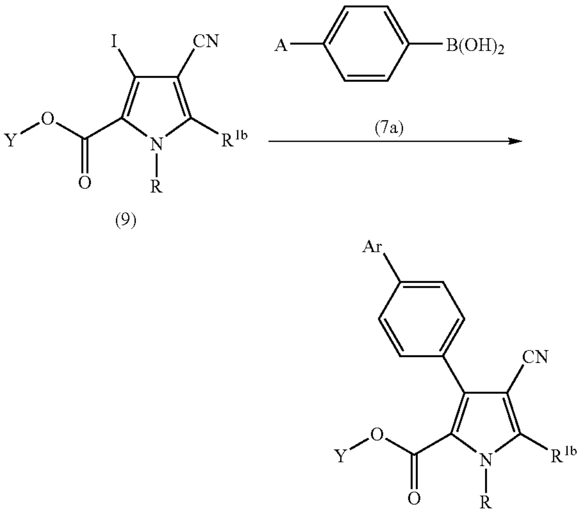

(9)

Formula IIg'

In Scheme V, the compound of structure (9), wherein $R^{1b}$ represents hydrogen or (1-4C)alkyl is coupled to a suitable boronic acid of structure (7a), under standard palladium catalyzed cross-coupling reaction conditions analogous to the procedure set forth in Scheme III to provide the compound of Formula IIg'. It is also understood by one of ordinary skill in the art, that in general, a boronic ester can be used in place of the boronic acid of structure (7) or (7a) in the palladium catalyzed cross-coupling reactions described herein.

Scheme VI

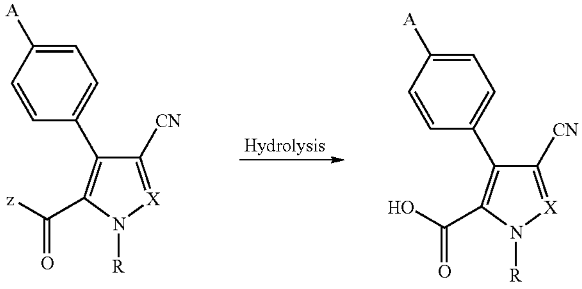

Formula II

Formula Ia

In Scheme VI, the compound of Formula II is converted to the carboxylic acid of Formula Ia under conditions well known in the art by treatment with a suitable hydrolysis agent, such as a suitable base or enzyme. For example, the compound of Formula II is dissolved in a suitable organic solvent or solvent mixture, such as THF, methanol, ethanol, and the like. The mixture is treated with water and a slight excess of a suitable base, such as lithium hydroxide, sodium hydroxide, potassium hydroxide, and the like, and stirred for about 1 to 18 hours at a temperature of about 25° C. to about 60° C. The product of Formula Ia is then isolated and purified by techniques well known in the art, such as extraction techniques and recrystallization. For example, the reaction mixture is acidified with a suitable acid, such as 1N HCl and the product of Formula Ia is then extracted from the mixture with a suitable organic solvent, such as methylene chloride. The organic extracts are then combined, dried over anhydrous magnesium sulfate, filtered, and concentrated under vacuum. The residue can then be purified by recrystallization from a suitable organic solvent such as ethyl acetate to provide purified compound of Formula Ia.

Scheme VIa

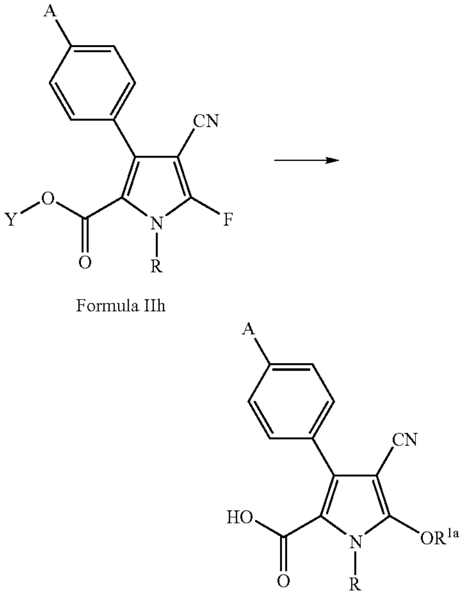

Formula IIh

Formula Ib $R^{1a}$ represents (1-4C)alkyl

In Scheme VIa, the compound of Formula IIh (see Scheme XVIa) is converted to the carboxylic acid of Formula Ib under conditions well known in the art. For example, the compound of Formula IIh is combined with an excess of lithium hydroxide in a suitable solvent mixture, such as THF:water (2:1). To this mixture is added an excess of (1-4C)alkanol, such as methanol, ethanol, propanol, or n-butanol, and the reaction is stirred at room temperature for about 10 to 24 hours. The product of Formula Ib is then isolated and purified by techniques well known in the art, such as extraction techniques. For example, the reaction mixture concentrated under vacuum and the residue dissolved in water and washed with methylene chloride. The aqueous is then acidified with a suitable acid, such as 1N HCl and the product of Formula Ib is then extracted with suitable organic solvents, such as methylene chloride and diethyl ether. The organic extracts are then combined, dried over anhydrous magnesium sulfate, filtered, and concentrated under vacuum to provide the compound of Formula Ib.

Scheme VII

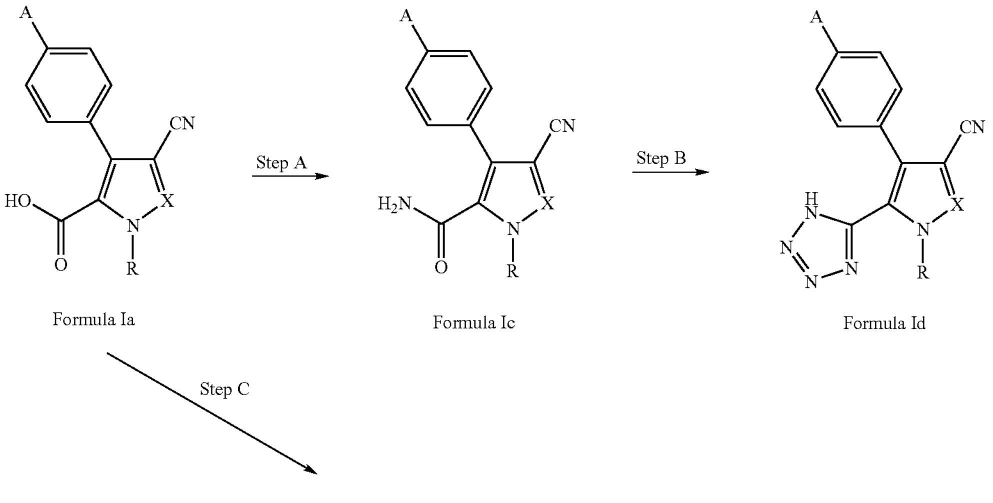

Formula Ia

Formula Ic

Formula Id

-continued

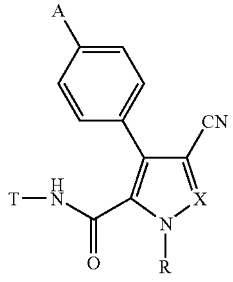

Formula Ie

Wherein T represents

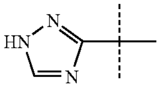

or

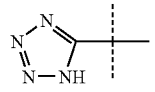

In Scheme VII, step A, the carboxylic acid of Formula Ia is converted to the primary amide of Formula Ic under conditions well known in the art. For example, Formula Ia is dissolved in a suitable organic solvent, such as THF and treated with about 1.1 to 1.3 equivalents of oxalyl chloride at temperature of about 0° C. to 25° C. followed by addition of a catalytic amount of DMF with stirring. The reaction mixture is allowed to stir for about 1 to 8 hours and then it is concentrated under reduced vacuum. The residue is then dissolved in THF and treated with a slight excess of an ammonia/methanol solution at room temperature with stirring. The reaction mixture is allowed to stir for about 1 to 4 hours and then it is concentrated under vacuum. The product of Formula Ic is then purified by techniques well known in the art, such as chromatography on silica gel with a suitable eluent, such as methanol/methylene chloride to provide the purified primary amide of Formula Ic.

In Scheme VII, step B, the primary amide of Formula Ic is the converted to the tetrazole of Formula Id under standard conditions. For example, about 2 equivalents silicon tetrachloride and about 12 equivalents of sodium azide are combined in a suitable organic solvent, such as acetonitrile and stirred at room temperature for about 20 minutes. About 1 equivalent of the primary amide of Formula Ic is added to the stirring mixture and the reaction mixture is heated at about 100° C. for about 8 to 24 hours. Saturated aqueous potassium carbonate is then added to the reaction after cooling, followed by addition of a suitable organic solvent, such as methylene chloride. The reaction mixture is rinsed with methylene chloride and the aqueous layer is then acidified to a pH of about 3-4 with a suitable acid, such as 1M HCl. The tetrazole of Formula Id is then extracted from the aqueous with a suitable organic solvent, such as methylene chloride, the organic extracts are combined, dried over anhydrous magnesium sulfate, filtered and concentrated to provide the tetrazole of Formula Id.

In Scheme VII, step C, the primary amide of Formula Ia is converted to the compound of formula Ie under conditions well known in the art. For example, the primary amide of Formula Ia is dissolved in a suitable organic solvent, such as THF and treated with about 1.1 to 1.3 equivalents of oxalyl chloride at temperature of about 0° C. to 25° C. followed by addition of a catalytic amount of DMF with stirring. The reaction mixture is allowed to stir for about 1 to 8 hours and then it is concentrated under reduced vacuum to provide the corresponding acid chloride. This acid chloride is then dissolved in a suitable organic solvent, such as pyridine and treated with an excess of 2-amino-1,3,4-triazole or 5-aminotetrazole and the mixture is stirred at room temperature for about 12 to 24 hours. The product of Formula Ie is then isolated and purified using techniques well known to one of ordinary skill in the art, such as extraction techniques and chromatography. For example, the reaction is treated with water and extracted with a suitable organic solvent, such as methylene chloride. The organic extracts are combined, dried over anhydrous magnesium sulfate, filtered, and concentrated under vacuum. The crude residue is then purified by chromatography on silica gel with a suitable eluent, such as toluene/ethyl acetate, to provide the purified compound of Formula Ie.

Scheme VIII

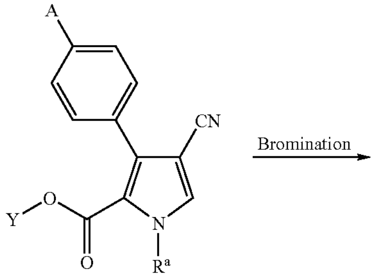

Formula IIb

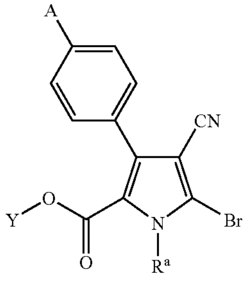

Formula IIj

In Scheme VIII, the compound of Formula IIb is converted to the bromo derivative of Formula IIj under conditions well known in the art. For example, the compound of Formula IIb is dissolved in a suitable organic solvent, such as THF or a mixture of THF and DMF, and treated with about 1.5 to 3 equivalents of a suitable brominating reagent, such as N-bromosuccinimde with stirring at room temperature. The reaction mixture is stirred for about 10 to 24 hours and then quenched with water. The compound of Formula IIj is isolated and purified using techniques well known in the art, such as extraction techniques and chromatography. For example, the reaction mixture is extracted with a suitable organic solvent, such as ethyl acetate or methylene chloride, the organic extracts are combined, dried over anhydrous magnesium sulfate, filtered, and concentrated under vacuum. The crude residue is then purified by flash chromatography on silica gel with a suitable eluent, such as ethyl acetate:hexanes to provide the purified compound of Formula IIj.

Scheme IX

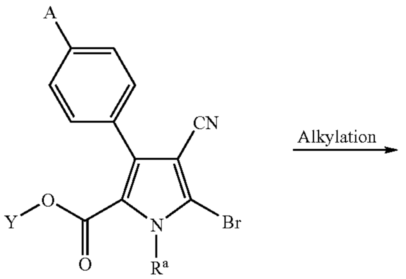

Formula IIj

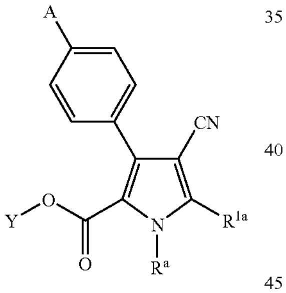

Formula IIk

In Scheme IX, the compound of Formula IIj is alkylated under standard conditions to provide the compound of Formula IIk. For example, the compound of Formula IIj is dissolved in a suitable organic solvent such as HMPA and treated with a catalytic amount of a suitable catalyst, such as tetrakis(triphenylphosphine)-palladium(0), and about 2 equivalents of a tin reagent of formula $[(1\text{-}4C)alkyl]_4Sn$, such as tetraethyltin. The reaction mixture is then heated at about 100° C. with stirring for about 12 to 24 hours. After cooling, the reaction is quenched with water. The resulting product of Formula IIk is then isolated and purified by techniques well known in the art, such as extraction and chromatography. For example, the reaction mixture is extracted with a suitable organic solvent, such as ethyl acetate, the organic extracts are combined, dried over anhydrous magnesium sulfate, filtered, and concentrated under vacuum. The crude residue is then purified by flash chromatography on silica gel with a suitable eluent, such as ethyl acetate:hexanes to provide the purified compound of Formula IIk.

Scheme X

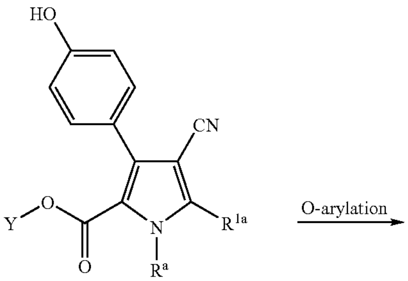

Formula IIm

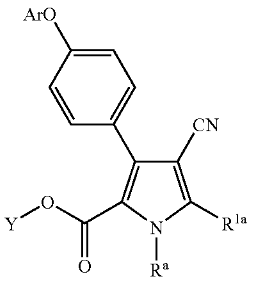

Formula IIn $R^{1a}$ represents (1-4C)alkyl

In Scheme X, the compound of Formula IIm is O-alkylated or O-arylated under conditions well known in the art to provide the compound of Formula IIn. See for example, *Tetrahedron,* 56, 5045 (2000) for general synthetic techniques. For example, the compound of Formula IIm is dissolved in a suitable organic solvent, such as methylene chloride and is treated with about 2 equivalents of a boronic acid, such as an aryl boronic acid (7), and about 2 equivalents of copper(II) acetate. The reaction mixture is stirred at room temperature for about 12 to 24 hours and then poured through diatomaceous earth and into water. The resulting product of Formula IIn is then isolated and purified by techniques well known in the art, such as extraction and chromatography. For example, the reaction mixture is extracted with a suitable organic solvent, such as methylene chloride, the organic extracts are combined, washed with 1N HCl, water, brine, dried over anhydrous magnesium sulfate, filtered, and concentrated under vacuum. The crude residue is then purified by flash chromatography on silica gel with a suitable eluent, such as ethyl acetate:hexanes to provide the purified compound of Formula IIn.

In an alternative procedure according to Scheme X, the compound of Formula IIm is dissolved in a suitable organic solvent, such as acetonitrile and treated with about 5 equivalents of potassium fluoride on alumina, a catalytic amount of a crown ether, such as 18-crown-6, and a suitable fluorosubstituted aryl derivative, such as 2-fluorobenzonitrile, 3-fluorobenzonitrile, 4-fluorobenzonitrile, 1-fluoro-2-nitrobenzene, 1-fluoro-3-nitrobenzene, 1-fluoro-4-nitrobenzene, and the like. The reaction mixture is heated at reflux for about 12 to 24 hours and then poured into water. The resulting product of Formula IIn is then isolated and purified by techniques well known in the art, such as extraction and chromatography. For example, the reaction mixture is extracted with a suitable organic solvent, such as ethyl acetate, the organic extracts are combined, washed with water, brine, dried over anhydrous magnesium sulfate, filtered, and concentrated under vacuum. The crude residue is then purified by flash chromatography on silica gel with a suitable eluent, such as ethyl acetate:hexanes to provide the purified compound of Formula IIn.

Scheme XI

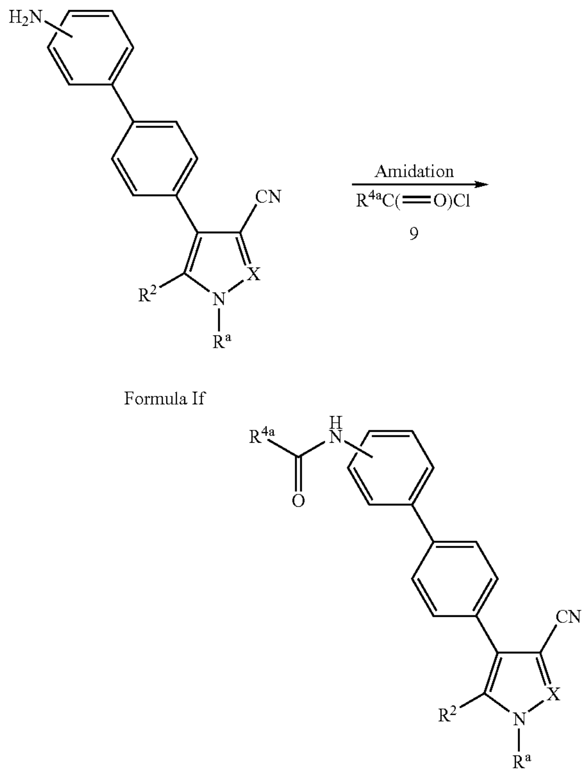

Formula If

Formula Ig $R^{4a}$ represents (1-4C)alkyl

In Scheme XI, the compound of Formula If is amidated under conditions well known in the art to provide the compound of Formula Ig. For example, compound of Formula If is dissolved in a suitable organic solvent, such as THF and treated with about 3 equivalents of a suitable base, such as triethylamine, and about 1.1 to 1.4 equivalents of the acid chloride of structure 21, such as acetyl chloride, propionyl chloride, butyryl chloride, isobutyryl chloride, and the like. The reaction mixture is stirred at room temperature for about 2 to 8 hours. The resulting compound of Formula Ig is then isolated and purified by techniques well known in the art, such as extraction and chromatography. For example, the reaction mixture is poured into water and extracted with a suitable organic solvent, such as ethyl acetate. The organic extracts are combined, washed with water, brine, dried over anhydrous magnesium sulfate, filtered, and concentrated under vacuum. The crude residue is then purified by flash chromatography on silica gel with a suitable eluent, such as ethyl acetate:hexanes to provide the compound of Formula Ig.

In addition, it is appreciated by one of ordinary skill in the art that the compound of Formula If can be converted to the corresponding sulfonamide under analogous conditions using, for example, methanesulfonyl chloride, ethylsulfonyl chloride, isopropylsulfonyl chloride, and the like.

Scheme XII

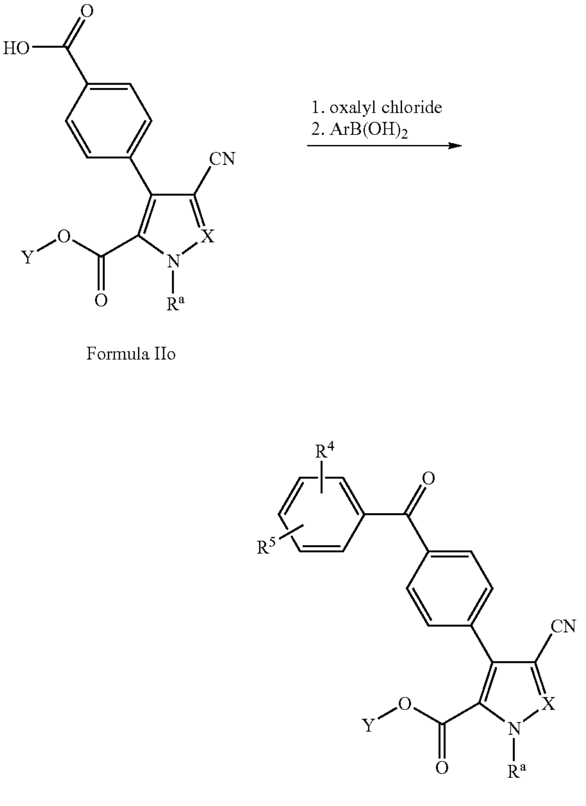

Formula IIo

Formula IIp

In Scheme XII the carboxylic acid of Formula IIo is converted to the ketone of Formula IIp under conditions well known in the art. For example, the carboxylic acid of Formula IIo is dissolved in a suitable organic solvent, such as THF and treated with about 1.1 to 1.3 equivalents of oxalyl chloride. To this solution is added a catalytic amount of DMF and the reaction is stirred at room temperature for about 2 hours. The reaction mixture is then concentrated under vacuum to provide the corresponding acid chloride. This acid chloride is then dissolved in THF and added to a stirring mixture of about 1.2 equivalents of the corresponding boronic acid (structure 7), a catalytic amount of a suitable palladium catalyst, such as tetrakis(triphenylphosphine)-palladium(0), and a suitable base, such as cesium carbonate in a suitable organic solvent, such as toluene. The reaction mixture is then heated at reflux for about 12 to 24 hours, cooled, and poured into water.

The resulting ketone of Formula IIp is then isolated and purified by techniques well known in the art, such as extraction and chromatography. For example, the reaction mixture is poured into water and extracted with a suitable organic solvent, such as ethyl acetate. The organic extracts are combined, washed with water, brine, dried over anhydrous magnesium sulfate, filtered, and concentrated under vacuum. The crude residue is then purified by flash chromatography on silica gel with a suitable eluent, such as ethyl acetate:hexanes to provide the compound of Formula IIp.

Scheme XIII

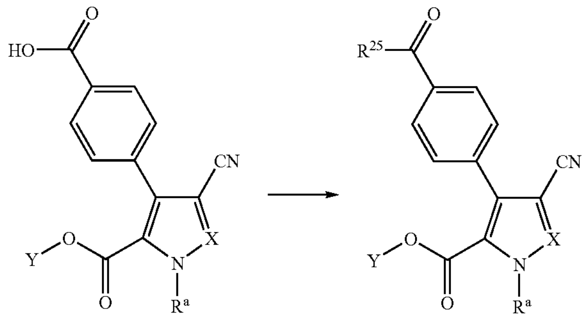

Formula IIo Formula IIq $R^{25}$ represents (1-4C)alkyl

In Scheme XIII the compound of Formula IIo is converted to the ketone of Formula IIq under conditions well known in the art. For example, the compound of Formula IIo is dissolved in a suitable organic solvent, such as THF and treated with about 1.1 to 1.3 equivalents of oxalyl chloride. To this solution is added a catalytic amount of DMF and the reaction is stirred at room temperature for about 2 hours. The reaction mixture is then concentrated under vacuum to provide the corresponding acid chloride. This acid chloride is then dissolved in a suitable organic solvent, such as THF and added to about 0.14 equivalents of copper cyanide, about 0.14 equivalents lithium bromide, and about 1.4 equivalents of a filtered reagent of formula $R^{25}ZnBr$ in THF at about 30° C. with stirring. The reaction mixture is allowed to warm to room temperature and stir for about 4 hours, and poured into water.

The resulting ketone of Formula IIq is then isolated and purified by techniques well known in the art, such as extraction and chromatography. For example, the reaction mixture is poured into water and extracted with a suitable organic solvent, such as ethyl acetate. The organic extracts are combined, washed with water, brine, dried over anhydrous magnesium sulfate, filtered, and concentrated under vacuum. The crude residue is then purified by flash chromatography on silica gel with a suitable eluent, such as ethyl acetate:hexanes to provide the amide of Formula IIq.

-continued

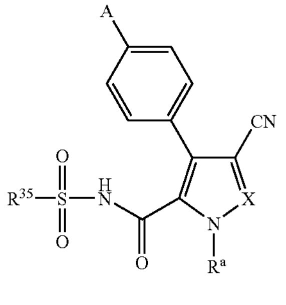

Formula Ih

X represents N or $CR^{1a}$ wherein $R^{1a}$ represents hydrogen, F, Cl, Br, $CF_3$, -(1-4C)alkyl, —S(1-4C)alkyl, —SO(1-4C)alkyl, —$SO_2$(1-4C)alkyl, —C(═O)(1-3C)alkyl, or —N[(1-4C)alkyl]$_2$; and $R^{35}$ represents (1-4C)alkyl.

In Scheme XIV, the compound of Formula Ia' is converted to the sulfonamide of Formula Ih under conditions well known in the art. For example, the compound of Formula Ia' is dissolved in a suitable organic solvent, such as methylene chloride followed by addition of about 1.1 equivalents of a suitable base, such as N,N-dimethylaminopyridine and about 1.2 equivalents of EDCI. To this stirring mixture at room temperature is added about 1.1 equivalents of the sulfonamide of structure 25, $R^{35}SO_2NH_2$, and the reaction mixture is allowed to stir for about 3 to 18 hours. The resulting sulfonamide of Formula Ih is then isolated and purified by one of ordinary skill in the art using extraction techniques and chromatography. For example, the reaction mixture is poured into 1N HCl and extracted with a suitable organic solvent, such as methylene chloride. The organic extracts are combined, washed with water and brine, dried over anhydrous magnesium sulfate, filtered, and concentrated under vacuum. The crude residue is then purified by flash chromatography on silica gel with a suitable eluent, such as methylene chloride: methanol to provide the purified sulfonamide of Formula Ih.

Scheme XIV

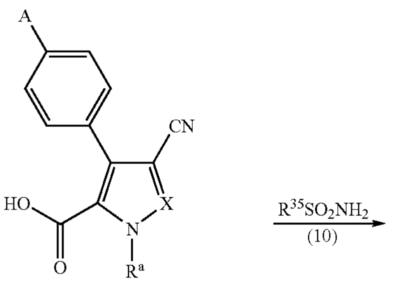

Formula Ia'

Scheme XV

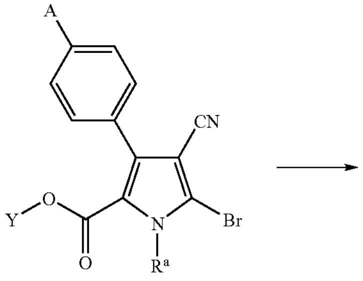

Formula IIj

-continued

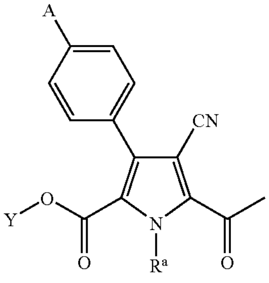

Formula IIr

In Scheme XV, the compound of Formula IIj is converted to the methyl ketone of Formula IIr under standard conditions well known in the art. For example, about 1.5 equivalents of tributyl(1-ethoxyvinyl)tin and a catalytic amount of a suitable palladium catalyst, such as dichlorobis(triphenylphosphine) palladium(II), is added to the compound of Formula Ig dissolved in a suitable organic solvent, such as THF. The reaction mixture is heated at reflux with stirring for about 12 to 24 hours and then quenched with 5N HCl. The compound of Formula IIr is then isolated and purified using techniques well known in the art. For example, the quenched reaction is extracted with a suitable organic solvent, such as ethyl acetate, the organic extracts are combined, washed with water and brine, dried over anhydrous magnesium sulfate, filtered, and concentrated under vacuum. The crude residue is then purified by flash chromatography on silica gel with a suitable eluent, such as ethyl acetate:hexanes to provide the purified methyl ketone of Formula Ir.

Scheme XVI

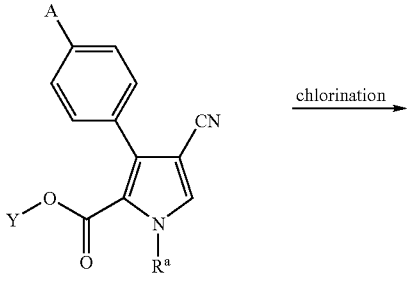

Formula IIb

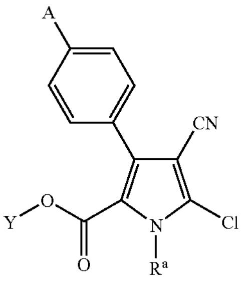

Formula IIs

In Scheme XVI, the compound of Formula IIb is converted to the compound of Formula IIs using N-chlorosuccinamide, a manner analogous to the procedure set forth in Scheme VIII.

Scheme XVIa

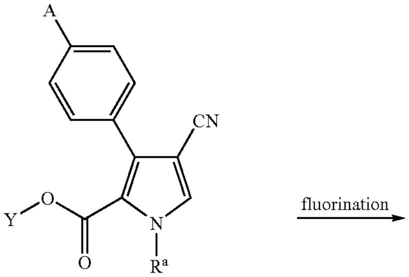

Formula IIb

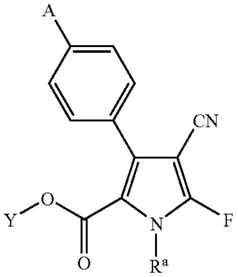

Formula IIh'

In Scheme XVIa, the compound of Formula IIb is converted to the compound of Formula IIh'. For example, dissolve the compound of Formula IIb and about 1.5 equivalents of SELECTFLUOR® (1-chloromethyl-4-fluoro-1,4-diazoniabicyclo[2.2.2]octane bis-(tetrafluoroborate)) in a suitable organic solvent, such as acetonitrile and heat the mixture at about 80° C. for about 8 to 24 hours. The product is then isolated using standard techniques, such as extraction. For example, water is added to the reaction mixture which is then extracted with a suitable organic solvent, such as methylene chloride. The organic extracts are combined, dried over anhydrous magnesium sulfate, filtered, and concentrated under vacuum. The crude material can then be purified by chromatography on silica gel with a suitable eluent, such as ethyl acetate/hexane to provide the purified compound of Formula IIh'.

Scheme XVII

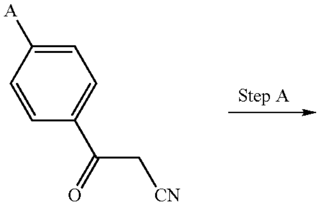

(11)

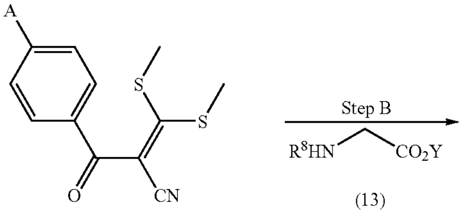

(12) (13)

-continued

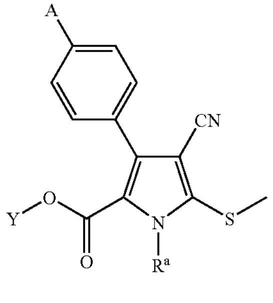

Formula IIt

In Scheme XVII, step A, the compound of structure 11 is converted to the compound of structure 12 under standard conditions. For example, the compound of structure 11 is dissolved in a suitable organic solvent, such as DMSO and about 1 equivalent of carbon disulfide is added. The stirring mixture is cooled to about −15° C. and about 2.4 equivalents of a suitable base, such as sodium hydride is added. The reaction mixture is allowed to stir for about 2.5 hours while warming to room temperature. The reaction mixture is then cooled to about −15° C. and treated with about 2 equivalents of iodomethane. The reaction mixture is then allowed to warm to room temperature and stir for about 12 to 24 hours, and quenched with water. The product of structure 12 is then isolated and purified by techniques well known in the art. For example, the quenched reaction mixture is extracted with a suitable organic solvent, such as ethyl acetate, the organic extracts are combined, washed with water and brine, dried over anhydrous magnesium sulfate, filtered, and concentrated under vacuum. The crude residue is then purified by flash chromatography on silica gel with a suitable eluent, such as ethyl acetate:hexanes to provide the purified compound of structure 12.

In Scheme XVII, step B, the compound of structure 12 is converted to the cyclized compound of Formula IIt under standard conditions. For example, the compound of structure 12 is dissolved in a suitable organic solvent, such as ethanol, and treated with about 1.1 equivalents of a compound of structure 13, such as sarcosine ethyl ester HCl, and about 3 equivalents of a suitable base, such as triethylamine. The reaction mixture is heated at reflux for about 0.5 to 2 hours, then cooled, and poured into water. The compound of Formula IIt is then isolated and purified by techniques well known in the art For example, the quenched reaction mixture is extracted with a suitable organic solvent, such as ethyl acetate, the organic extracts are combined, washed with water and brine, dried over anhydrous magnesium sulfate, filtered, and concentrated under vacuum. The crude residue is then purified by flash chromatography on silica gel with a suitable eluent, such as ethyl acetate:hexanes to provide the purified compound of Formula IIt.

Scheme XVIII

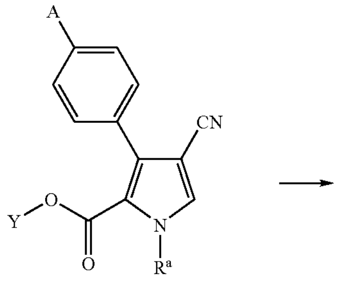

Formula IIb

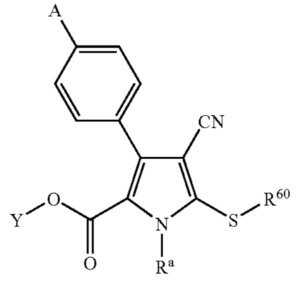

Formula IIu $R^{50}$ represents -(1-4C)alkyl

In Scheme XVIII, the compound of Formula IIb is converted to the compound of Formula IIu under standard conditions. For example, the compound of Formula IIb is dissolved in a suitable organic solvent, such as THF and cooled to about −78° C. About 1.1 equivalents of lithium bis(trimethylsilyl)amide is added and the solution is allowed to stir for about 0.5 to 1 hour. Then about 1.2 equivalents of a suitable (1-4C)alkyl disulfide is added to the reaction mixture which is allowed to warm to room temperature and stir for about 2 to 6 hours before quenching with water. The compound of Formula IIu is then isolated and purified by techniques well known in the art, such as extraction and chromatography.

Scheme XIX

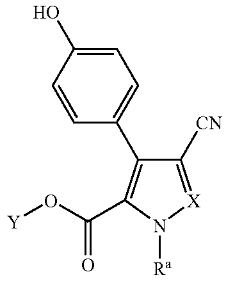

Formula IIw

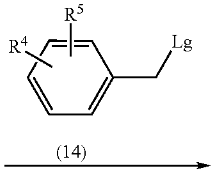

-continued

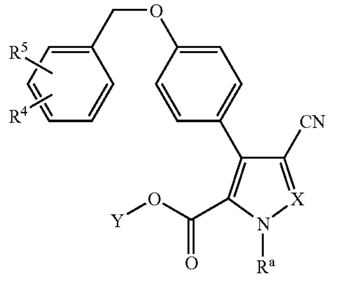

Formula IIx

Lg represents a suitable leaving group

In Scheme XIX, the compound of Formula IIw is converted to the compound of Formula IIx under conditions well known in the art. For example, the compound of Formula IIw is dissolved in a suitable organic solvent, such as acetone and treated with about 1.2 equivalents of a compound of structure (14) wherein Lg represents a suitable leaving group, such as F or Br, and about 1.5 equivalents of a suitable base, such as potassium carbonate. The reaction mixture is allowed to stir at room temperature for about 8 to 24 hours. The product is then isolated and purified by techniques well known in the art. For example, the reaction mixture is concentrated under vacuum and the residue is purified by flash chromatography on silica gel with a suitable eluent to provide the purified compound of formula IIx.

Scheme XX

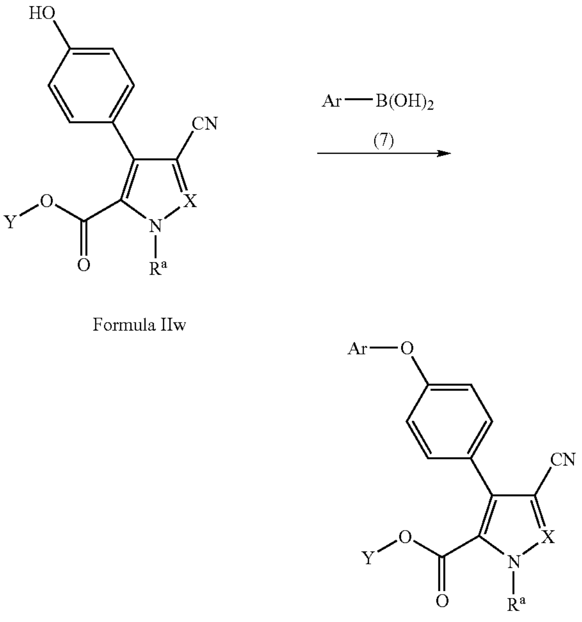

Formula IIw

Formula IIy

In Scheme XX, the compound of Formula IIw is converted to the compound of Formula IIy under conditions well known in the art such as the conditions set forth in Scheme X. For example, the compound of Formula IIw is dissolved in a suitable organic solvent, such as methylene chloride and treated with about 1.4 equivalents of a suitable boronic acid of structure (7), as described hereinabove at Scheme III, about 1 equivalent of copper (II) acetate, and about 5 equivalents of a suitable base, such as triethylamine. The reaction mixture is allowed to stir for about 18 to 36 hours at room temperature and then filtered through diatomaceous earth. The organic filtrate is washed with water, dried over anhydrous potassium carbonate, filtered and concentrated under vacuum to provide the crude product of Formula IIy. The crude material can be purified by techniques well known in the art, such as flash chromatography on silica gel with a suitable eluent, such as methylene chloride to provide the purified compound of Formula IIy.

Scheme XXI

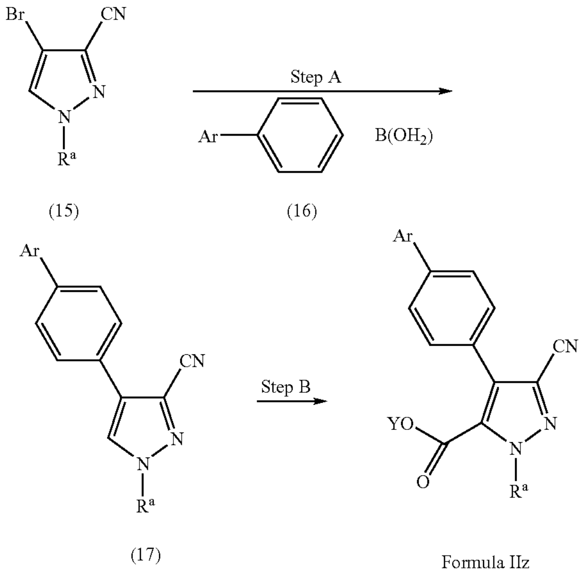

(15) (16)

(17)

Formula IIz

In Scheme XXI, Step A, the compound of structure (15) is converted to the compound of structure (17) in a manner analogous to the procedure set forth in Scheme III utilizing standard palladium cross-coupling reaction conditions well known to one of ordinary skill in the art. The compound of structure (15) is prepared under standard alkylating conditions of 4-bromo-1H-pyrazole-3-carbonitrile using an alkylating agent, such as methyl iodide.

In Scheme XXI, Step B, the compound of structure (17) is converted to the compound of Formula IIz under standard conditions. For example, the compound of structure (17) is dissolved in a suitable organic solvent, such as THF and cooled to about −70° C. The solution is then treated with about 0.9 equivalents of a suitable base, such as n-butyllithium and then stirred for about 0.5 to 1 hour at −70° C. To this solution is then added about 3 equivalents of a suitable chloroformate, such as ethyl chloroformate and the reaction mixture is allowed to warm to room temperature over about one hour. The reaction is then quenched with saturated ammonium chloride and extracted with a suitable organic solvent, such as ethyl acetate. The organic extracts are combined, washed with water, brine, dried over anhydrous sodium sulfate, filtered and concentrated under vacuum. The crude product can then be purified by chromatography on silica gel with a suitable eluent, such as toluene:ethyl acetate to provide the purified compound of Formula IIz.

Scheme XXII

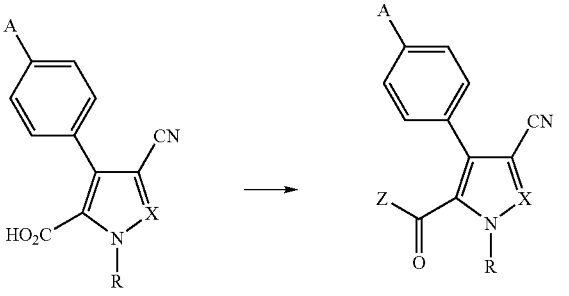

Formula Ia

Formula II

In Scheme XXII, the compound of Formula Ia is readily converted to the compound of Formula II under esterification or amidation conditions well known in the art. See for example Theodora Greene, "Protective Groups in Organic Synthesis," John Wiley & Sons, Inc, pages 154-184 and pages 249-265, (1981). More specifically, for example, the compound of Formula Ia is dissolved in a suitable organic solvent and treated with a suitable acid, such as hydrochloric acid. Examples of suitable organic solvents include, methyl alcohol, ethyl alcohol, propyl alcohol, isopropyl alcohol, n-butyl alcohol, isobutyl alcohol, t-butyl alcohol, pentyl alcohol, isopentyl alcohol, hexyl alcohol, 3-methylpentyl alcohol, 2-ethylbutyl alcohol, and the like. The reaction is heated at about 30° C. to about 60° C. for about 1 hour to about 16 hours. The product is then isolated and purified using techniques well known to one of ordinary skill in the art, such as extraction techniques and chromatography. For example, the above reaction is cooled, diluted with a suitable organic solvent, such as ethyl acetate, washed with saturated sodium bicarbonate, brine, dried over anhydrous magnesium sulfate, filtered and concentrated under vacuum to provide the compound of Formula II. This material may be further purified by flash chromatography on silica gel with a suitable eluent such as ethyl acetate/hexane.

Alternatively, the compound of Formula Ia is dissolved in a suitable organic solvent and treated with an excess of thionyl chloride. Examples of suitable organic solvents are anhydrous methyl alcohol, ethyl alcohol, propyl alcohol, isopropyl alcohol, butyl alcohol, isobutyl alcohol, t-butyl alcohol, pentyl alcohol, isopentyl alcohol, hexyl alcohol, 3-methylpentyl alcohol, 2-ethylbutyl alcohol, and the like. The solution is stirred at reflux for about 1 to 3 hours, and at room temperature for about 8 to 16 hours. The mixture is then concentrated under vacuum, and the residue is purified in a manner analogous to the procedures described above to provide the compound of Formula II.

Scheme XXIII

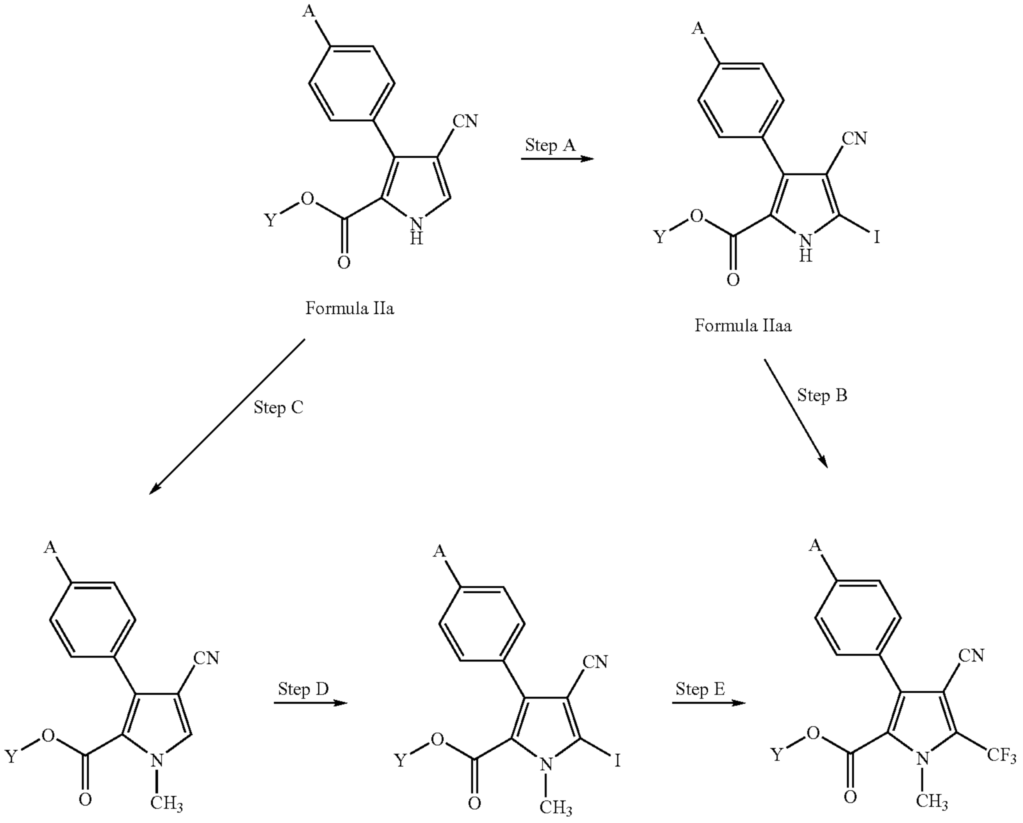

Formula IIa

Formula IIaa

Formula IIbb

Formula IIcc

Formula IIdd

In Scheme XXIII, step A, the compound of Formula IIa is converted to the compound of Formula IIaa using N-iodosuccinamide, in a manner analogous to the procedure set forth in Scheme VIII.

In Scheme XXIII, step B, the compound of Formula IIaa is converted to the compound of Formula IIdd under standard conditions wherein a trifluoromethyl group replaces the iodo functionality. Additionally, the pyrrole nitrogen is methylated via methyl iodide that is generated in the reaction mixture. For example, see Chen and Wu, *J Chem. Soc., Chem. Comm.*, 1989, page 705 for general synthetic techniques. More specifically, the compound of Formula IIaa is combined with a catalytic amount of copper iodide or copper bromide, such as about 0.2 equivalents of copper bromide, and about 2 equivalents of methyl 2,2-difluoro-2-(fluorosulfonyl)acetate in a suitable organic solvent, such as DMF or DMSO. The reaction mixture is heated at reflux for about 30 minutes to about 6 hours and the resulting compound of Formula IIdd is isolated and purified by techniques well known in the art. For example, the reaction mixture is diluted with water and extracted with a suitable organic solvent, such as ethyl acetate. The organic extracts are combined, dried over anhydrous sodium sulfate, filtered, and concentrated under vacuum to provide the crude material. This material can then be purified by radial chromatography on silica gel with a suitable eluent, such as ethyl acetate:hexanes to provide the purified compound of Formula IIdd.

In Scheme XXIII, step C, the compound of Formula IIa is converted to the compound of Formula IIbb in a manner analogous to the procedure set forth in Scheme I, step C, with methyl iodide.

In Scheme XXIII, step D, the compound of Formula IIbb is converted to the compound of Formula IIcc in a manner analogous to the procedure set forth in Scheme VIII using N-Iodosuccinamide.

In Scheme XXIII, step E, the compound of Formula IIcc is converted to the compound of Formula IIdd in a manner analogous to the procedure set forth above, in Scheme XXIII, step B.

The examples set forth herein represent typical syntheses of the compounds of the present invention. The following examples have been labeled as follows for ease of reference: "Example E-1" refers for example to compounds wherein $R^2$ represents an ester group; "Example A-1" refers for example to pyrrole compounds wherein $R^1$ is a carboxylic acid group; "Example Am-1" refers for example to compounds wherein $R^2$ is an amide group; "Example S-1" refers for example to compounds wherein $R^2$ is a sulfonamide group; "Example Pz-1" refers for example to pyrazole compounds wherein X represents nitrogen in Formulas I or II; and "Example T-1" refers for example to compounds wherein $R^2$ is a triazole or tetrazole group. The reagents and starting materials are readily available to one of ordinary skill in the art.

As used herein, the terms listed in the following table have the corresponding meanings as indicated:

| Term | Meaning |
|---|---|
| Ex. | Example |
| MS(FIA) | Flow injection analysis mass spectrometry |
| MS(FD) | Field distortion mass spectrometry |
| MS(IS) | Ion spray mass spectrometry |
| MS(FAB) | Fast atom bombardment mass spectrometry |
| MS(ES) | Electron spray mass spectrometry |
| HRMS | High resolution mass spectrometry |
| $^1$H NMR | Proton nuclear magnetic resonance spectrometry |

-continued

| Term | Meaning |
|---|---|
| ss NMR | Solid state nuclear magnetic resonance spectrometry |
| XRD | X-Ray Diffraction |
| XRPD | X-Ray Powder Diffraction |
| eq. | equivalents |
| g | grams |
| mg | milligrams |
| L | liters |
| mL | milliliters |
| μL | microliters |
| mol | moles |
| mmol | millimoles |
| psi | pounds per square inch |
| m.p. | melting point |
| DSC | differential scanning calorimetry |
| J/g | joules per gram |
| min | minutes |
| h or hr | hours |
| ° C. | degrees Celsius |
| TLC | thin layer chromatography |
| HPLC | high performance liquid chromatography |
| $R_f$ | retention factor |
| $R_t$ | retention time |
| δ | parts per million down-field from tetramethylsilane |
| aq. | aqueous |
| Celite ® | diatomaceous earth filtering agent |
| HMPA | hexamethylphosphoramide |
| RT or rt | room temperature |
| DMF | N,N-dimethylformamide |
| DMSO | methyl sulfoxide |
| LDA | lithium diisopropylamide |
| EtOAc | ethyl acetate |
| THF | tetrahydrofuran |
| iPrOAc | isopropyl acetate |
| HOBt | 1-hydroxybenzotriazole |
| methyl DAST | dimethylaminosulfur trifluoride |
| DMAP | dimethylaminopyridine |
| DAST | diethylaminosulfur triflouride |
| TFA | trifluoroacetic acid |
| MTBE | tert-butyl methyl ether |
| DBU | 1,8-diazabicyclo[5.4.0]undec-7-ene |
| TEA | triethylamine |
| TBDMS | tert-butyldimethylsilyl |
| NBS | N-bromosuccinimide |
| MIPK | methyl isopropyl ketone |
| $Et_3N$ | triethylamine |
| $(Boc)_2O$ | di-tert-butyl dicarbonate |
| DME | 1,2-dimethoxyethane |
| EtOH | ethanol |
| MeOH | methanol |
| MeCN | acetonitrile |
| BuLi | butyllithium |
| BuMgCl | Butylmagnesium chloride |
| Triflate | $-SO_3CF_3$ functional group |
| (dppf) | 1,1'-bis(diphenylphosphino)ferrocene |
| $C_6$PyCl | 1-hexylpyridinium chloride |
| S.M. | starting material |
| DCC | dicyclohexylcarbodiimide |
| $Pd_2(dba)_3$ | tris(dibenzylideneacetone)-dipalladium(0) |
| EDCI | 1-ethyl-3-[3-(dimethylamino)propyl]-carbodiimide HCl |
| SELECTFLUOR ® | 1-chloromethyl-4-fluoro-1,4-diazoniabicyclo[2.2.2]octane bis-(tetrafluoroborate) |

Preparation 1

Preparation of 3-methylthiothiophene

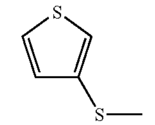

To a solution of 3-bromothiophene (15 g, 92 mmol) in hexane (135 ml) at -40° C. is added dropwise a solution of n-BuLi (63.2 ml, 1.6 M). Then THF (45 ml) is added to the flask and the 3-lithiothiophene precipitates as a white solid. More hexane is added (45 ml) and the reaction mixture is warmed to room temperature. Methyl disulfide (9.1 ml, 101.2 mmol) is added dropwise to the resulting solution and the reaction mixture is stirred for 12 hours at room temperature. Water (aprox. 100 mL) is added to the flask, the organic layer separated, dried with magnesium sulphate, filtered, and the solvent is evaporated yielding 13 g (95%) of title compound as a colorless oil. See also Wu, X.; Chen, T.-A.; Zhu, L.; Rieke, R. D. *Tetrahedron Letters* 1994, 35, 3673-3674.

Preparation 2

Preparation of 2-iodo-3-methylthiothiophene

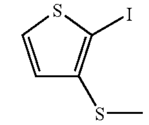

To a solution of 3-methylthiothiophene (16 g, 123 mmol, preparation 1) in methylene chloride (300 ml) is added dropwise a solution of bis(pyridine)iodonium(I) tetrafluoroborate (46 g, 123 mmol, see J. Org. Chem., 55, 3104, (1990) for preparation of this reagent) in methylene chloride (500 ml) at room temperature. After 10 minutes water is added, the organic layer separated, dried with magnesium sulphate, filtered, and the solvent evaporated. The crude product is dissolved in ethyl acetate (200 ml) and washed with a solution of $NaHSO_3$ 10% (3×100 ml). The organic layer is separated, dried with magnesium sulphate, filtered, and the solvent evaporated yielding 23 g (74%) of title compound as a slightly colored oil. NOTE: The product is light sensitive and gets darker over a period of hours.

Preparation 3

Preparation of 2-(4-bromophenyl)-3-methylthiothiophene

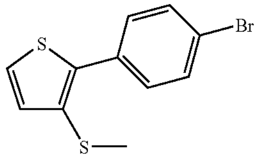

A solution of 2-iodo-3-methylthiothiophene (18 g, 70.3 mmol, preparation 2), 4 bromobenzeneboronic acid (14.1 g, 70.3 mmol), potassium carbonate (21.4 g, 155 mmol), tetrakis (triphenylphosphine)-palladium (0) (8.1 g, 7.02 mmol) in a mixture of anhydrous dimethoxyethane (300 ml) and absolute ethanol (150 ml) is degassed with Ar or $N_2$ for 15 min and stirred for 12 hours at 80° C. The reaction mixture is cooled to room temperature, water (100 ml) is then added and the crude product is extracted with methylene chloride (3×150 ml). The crude product is purified by column chromatography using hexane as eluent solvent yielding 12 g (60%) of title compound as a white solid. NOTE: This product is also light sensitive and should be used immediately.

Preparation 4

Preparation of 3-methylthio-2-[4-(4,4,5,5-tetramethyl(1,3,2-dioxaborolan-2-yl))phenyl]thiophene

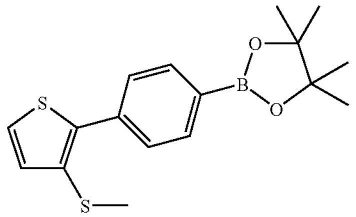

A solution of 2-(4-bromophenyl)-3-methylthiothiophene (12 g, 42 mmol, preparation 3), bis(pinacolato)diboron (11.8 g, 46.2 mmol), potassium acetate (13.6 g, 138.9 mmol), $PdCl_2$ (dppf) (3.42 g, 4.2 mmol) in anhydrous DMSO (150 ml) is stirred at 80° C. for 12 hours. The reaction mixture is then cooled to room temperature diluted with ethyl acetate (200 ml) and washed with water (3×100 ml). The organic layer is separated and dried with magnesium sulphate. To this solution, 10 g of silica is added and the solvent is evaporated. The resulting mixture is placed in a sintered glass funnel and eluted with a 10:1 mixture of Hexane/EtOAc. The catalyst remains in the silica The solvent is evaporated and the obtained solid is disaggregated with hexane (to eliminate most of the bis(pinacolato)diboron which is the major impurity) yielding 6 g (50%) of the title compound. NOTE: Several attempts to purify the product by column chromatography were performed but in all cases some bis(pinacolato)diboron is obtained as an impurity.

Preparation 5

Preparation of (tert-butoxy)-N-(3-thienyl)carboxamide

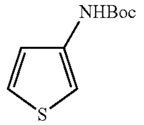

In a manner analogous to the method of Barker, J. M.; et al., *Synthetic Communications,* 25(23), 3729-3734 (1995), methyl-3-aminothiophene-2-carboxylate (42.8 g, 0.27 mol), is refluxed (120° C.) with 2M sodium hydroxide aqueous solution (270 mL) for 30 min. The reaction mixture is then cooled to 0° C. and acidified to pH 5.0 (Congo red) with concentrated hydrochloric acid. The thick precipitate is filtered off. The solid is dried and is then dissolved in acetone (300 mL) and the resulting solution is dried ($MgSO_4$), filtered, and evaporated at 20° C. (This acid decomposes quite rapidly, therefore this operation must be performed as soon as possible.) The resulting thick oil, is instantly treated with oxalic acid dihydrate (26.7 g) in 2-propanol (100 mL) at 38° C. for 45 min. The mixture is allowed to reach room temperature and diluted with ether (40 mL). The solid is filtered off and washed with ether. The resulting white solid (33.1 g) becomes pale lilac on exposure to light and air. (The salt is more stable than the acid and it is possible to keep it in a brown bottle under argon or nitrogen atmosphere for 2 days.) The resulting salt (33.1 g) is dissolved in water (400 mL) and basified with concentrated $NH_3$. The mixture is extracted with methylene chloride (3×200 mL) and the combined extracts are dried ($MgSO_4$), filtered, and evaporated to give a brown oil (15 g, 56%). (From 6.4 g of methyl-3-aminothiophene-2-carboxylate, is obtained 4.6 g of salt and from 2.0 g of this, 1.1 g (63%) of desired product.) This material (15 g, 0.15 mol) is dissolved in methylene chloride (300 mL) and $Et_3N$ (42.2 mL, 0.3 mol) is added at 0° C. Then, a solution of $(Boc)_2O$ (39.3 g, 0.18 mol) in methylene chloride (100 mL) is added dropwise at 0° C. and the mixture is stirred overnight at room temperature. TLC (Hexane/AcOEt 9:1) shows complete disappearance of starting material. The reaction is quenched by addition of water (200 mL). The mixture is extracted with methylene chloride (2×200 mL) and the combined extracts are dried ($MgSO_4$), filtered, and evaporated. The crude mixture is purified by flash chromatography (Silica gel-Hexane/EtOAc 9:1) to obtain 20.1 g (67%) of title compound as a white solid. NOTE: The complete sequence has to be done as fast as possible due to the instability of the amino acid intermediate. When scaled to 100 g of starting material, almost total decomposition of this starting amino acid is observed.

Preparation 6

Preparation of (tert-butoxy)-N-(2-iodo(3-thienyl))carboxamide

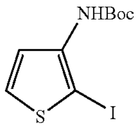

In a manner analogous to Campaigne, E. and Monroe, P. A. *J.A.C.S.*, 76, 2447-2450 (1954), to a boiling solution of (tert-butoxy)-N-(3-thienyl)carboxamide (21.0 g, 0.1 mol, preparation 5) in methylene chloride (400 mL) is added N-iodosuccinimide (23.7 g, 0.1 mol) in small portions. The heating bath is then set to 65° C. for 20 min. TLC (Hexane/AcOEt 9:1) shows complete consumption of starting material. The reaction is taken to room temperature, the solvent is evaporated and the crude is purified by flash chromatography (Silica gel-Hexane/EtOAc 9:1) to obtain 30.0 g (88%) of title compound as a white solid.

Preparation 7

Preparation of (tert-butoxy-N-[2-(4-bromophenyl(3-thienyl)]carboxamide

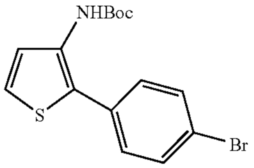

(tert-Butoxy)-N-(2-iodo(3-thienyl))carboxamide (16.88 g, 0.52 mol, preparation 6), 4-bromophenylboronic acid (15.65 g, 0.78 mol), $Na_2CO_3$ (1.01 g, 1.04 mol) and $Pd(Ph_3)_4$ (5.79 g, 0.052 mol) in 375 ml of an anhydrous and deoxygenated 2:1 DME/EtOH mixture is heated to 80° C. under nitrogen atmosphere for 24 h. TLC analysis (Hexane/EtOAc 9:1) shows complete disappearance of starting material. The organic solvents are evaporated, prior to the addition of water (200 mL). The mixture is then extracted with methylene chloride (3×150 mL) and the combined organic phases are dried (anhydrous $MgSO_4$), filtered, and concentrated to furnish a crude mixture as a yellowish solid. Purification by flash chromatography (Silica gel-Hexane/EtOAc 49:1) yields 10.8 g (60%) of title compound as a pale yellow solid.

Preparation 8

Preparation of 2-(4-bromophenyl)-3-thienylamine

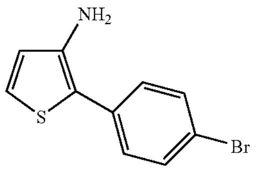

A solution of (tert-butoxy)-N-[2-(4-bromophenyl)(3-thienyl)]carboxamide (10.8 g, 0.3 mmol, preparation 7) in ethyl acetate (75 mL) at 0° C., is treated dropwise with 244 mL (8 mL/mmol) of freshly prepared 1N HCl in ethyl acetate and the mixture is stirred at room temperature overnight. The white precipitate is dissolved with $H_2O$ (100 mL) and neutralized with a $NaHCO_3$ saturated solution. The mixture is then extracted with ethyl acetate (3×100 mL) and the combined organics are dried and concentrated to give a slightly colored solid. Purification of the crude material by flash chromatography (Silica gel-Hexane/AcOEt 49:1 then 9:1) furnishes 5.7 g (74%) of title compound as a pale yellow solid.

Preparation 9

Preparation of 4-(2-nitrophenyl)benzaldehyde

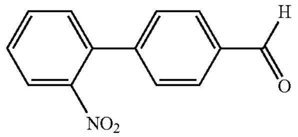

Add 1-bromo-2-nitrobenzene (13.30 g, 65.83 mmol), 4-formylphenylboronic acid (10.89 g, 72.41 mmol), [1,1-bis(diphenylphosphino)ferrocene]dichloropalladium(II) (1.61 g, 1.97 mmol) and 2M aqueous sodium carbonate (164.57 mL, 329.15 mmol) in DMF, and heat to 80° C. with stirring. After 18 hours, cool and pour into water. Extract the mixture with ethyl acetate. Combine the organic extracts, and wash with water and brine, dry over anhydrous magnesium sulfate, filter, and concentrate under reduced pressure. Purify by flash chromatography eluting with methylene chloride to provide the title compound. $^1H$ NMR (400 MHz; $CDCl_3$) δ-10.02(s, 1H), 7.92-7.99(m, 3H), 7.65(t, 1H), 7.58(t, 1H), 7.44-7.49(m, 3H).

Preparation 10

Preparation of 1-bromo-2-ethylsulfanyl-benzene

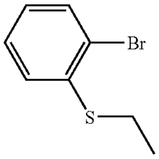

Add potassium carbonate (2.20 g, 15.92 mmol) to 2-bromobenzenethiol (2.00 g, 10.58 mmol) in acetone and stir at room temperature. After 10 minutes, add iodoethane (1.82 g, 11.67 mmol) with stirring. After 18 hours, add water and extract with ethyl acetate. Combine the organic extracts, wash with water and brine, dry over anhydrous magnesium sulfate, filter, and concentrate under reduced pressure. Purify the residue by flash chromatography eluting with ethyl acetate: hexanes to provide the title compound.

$^1$H NMR (400 MHz; $CDCl_3$) δ 7.55(d, 1H), 7.24-7.30(m, 2H), 6.99-7.02(m, 1H), 2.97(q, 2H), 1.38(t, 3H).

Preparation 11

Preparation of 2-(4-bromophenyl)-3-chlorothiophene

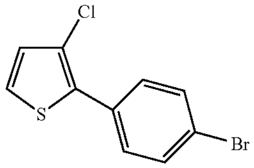

A solution of 2-(4-bromophenyl)-3-thienylamine (1.0 g, 3.94 mmol, preparation 8) in dry acetonitrile (7 mL) is added dropwise to a mixture of t-BuONO (1.87 mL, 15.76 mmol) and $CuCl_2$ (1.06 g, 7.87 mmol) in dry acetonitrile (15 mL) at 0° C. The reaction is stirred for 2 h. TLC (Hexane) shows complete consumption of starting material. Water (20 mL) is added and the mixture is extracted with ethyl acetate (2×20 mL). The combined organics are dried and concentrated to give a crude solid. Purification of the crude solid by flash chromatography (Silica gel-Hexane) provides 0.75 g (70%) of title compound as a pale yellow oil.

Preparation 12

Preparation of 3-chloro-2-[4-(4,4,5,5-tetramethyl(1,3,2-dioxaborolan-2-yl))phenyl]thiophene

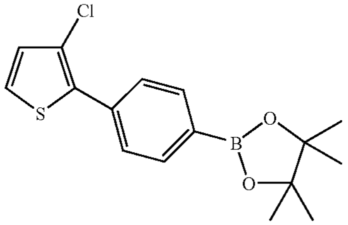

A mixture of 2-(4-bromophenyl)-3-chlorothiophene (1.0 g, 3.66 mmol, preparation 11), bis(pinacolato)diboron (1.39 g, 5.48 mmol), KOAc (1.18 g, 12.08 mmol) and $Pd(dppf)_2Cl_2$ catalyst (0.3 g, 0.37 mmol) in dry DMF (20 mL) deoxygenated by purging with nitrogen is heated at 80° C. overnight. TLC(Hexane/EtOAC 4:1) shows complete consumption of starting material. Water (20 mL) is added and extracted with ether (3×20 mL). The combined organic are washed with water and then dried and concentrated to give a crude solid. Purification of the crude solid by flash chromatography (Silica gel-Hexane/EtOAc 99:1) provides pure 1.05 g (89%) title compound as a pale yellow solid.

Preparation 13

Preparation of trifluoro-methanesulfonic acid 2-propyl-phenyl ester

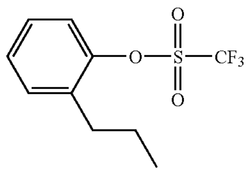

Add pyridine (1.74 g, 22.00 mmol) to 2-propylphenol (2.00 g, 14.68 mmol) in methylene chloride and stir at room temperature. After 10 minutes, cool to 0° C. Add trifluoromethanesulfonic anhydride (5.00 g, 17.72 mmol) and gradually allow the reaction to warm to ambient temperature. After 2 hours, add water to the reaction mixture and extract with methylene chloride. Combine the organic extracts, wash with 1N HCl, water and brine, dry over anhydrous magnesium sulfate, filter and concentrate under reduced pressure to provide the title compound. $^1$H NMR (400 MHz; $CDCl_3$) δ-7.24-7.32(m, 4H), 2.67(t, 2H), 1.65(m, 2H), 0.97(t, 3H).

Preparation 14

Preparation of trifluoro-methanesulfonic acid 4-tert-amylphenyl ester

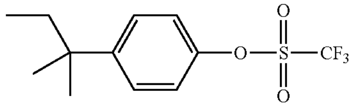

Prepare the title compound in a manner analogous to the procedure set forth in preparation 13 from 4-tert-amylphenol. $^1$H NMR (400 MHz, DMSO) δ 7.5 (d, d, J=2.20, 7.05 Hz, 2H), 7.38 (dd, J=2.20, 6.61 Hz, 2H), 3.30 (s, 3H), 1.61 (q, J=7.49 Hz, 2H), 1.24 (s, 6H), 0.59 (t, J=7.49 Hz, 3H).

Preparation 15

Preparation of 4,4,5,5-tetramethyl-2-(tert-amylphenyl)-4-yl-[1,3,2]dioxaborolane

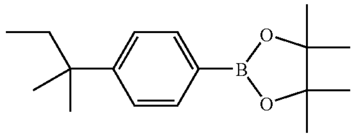

Prepare the title compound in a manner analogous to the procedure set forth in preparation 42 using trifluoro-methanesulfonic acid 4-tert-amylphenyl ester prepared in preparation 14. $^1$H NMR (400 MHz, CDCL3) δ 7.75 (d, J=7.93 Hz, 2H)7.34 (d, J=7.93 Hz, 2H), 1.65 (q, J=7.49 Hz, 2H), 1.34 (s, 6H), 1.28 (s, 3H), 1.24 (s, 3H), 0.67 (t, J=7.49 Hz, 3H).

Preparation 16

Preparation of 1-phenyl-adamantane

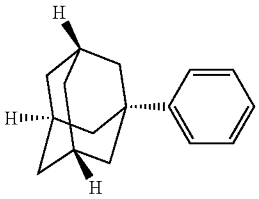

Add 1-bromoadamantane (10 g, 46.5 mmols), potassium carbonate (7.7 g, 55.8 mmols) and palladium on carbon (250 mg, catalytic) in benzene and heat to 120° C. for 1 week. Cool the reaction to room temperature and filter over Celite® rinsing with EtOAc. Concentrate under reduce pressure to provide the title compound. $^{1}H$ NMR (400 MHz; $CDCl_3$) δ 7.2-7.4(m, 5H), 2.10(s, 3H), 1.92(s, 6H), 1.77(s, 6H).

Preparation 17

Preparation of 4-adamanan-1-yl-benzaldehyde

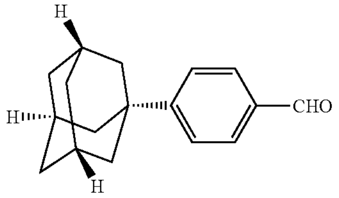

Add titanium(IV)chloride (2.4 mL, 21.6 mmol) to 1-phenyl-adamantane (2.7 g, 12.7 mmol, preparation 16) in methylene chloride at 0° C. After 15 minutes, add dichloromethyl methyl ether (1.15 mL, 12.7 mmol) and allow the reaction to stir at 0° C. for 1 hour, and then gradually allow to warm to ambient temperature. After 3 hours, pour the reaction mixture into ice-water and extract with methylene chloride. Combine the organic extracts, wash with water and brine, dry over anhydrous magnesium sulfate, filter, and concentrate under reduced pressure to provide the title compound. $^{1}H$ NMR (400 MHz; DMSO) δ 9.95 (s, 1H), 7.83 (d, 2H), 7.60(d, 2H), 2.05 (s, 3H), 1.85(s, 6H), 1.70(s, 6H).

Preparation 18

Preparation of 3-bromo-4-ethoxy-benzonitrile

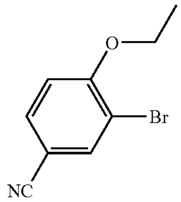

Add potassium carbonate (5.2 g, 37.9 mmol) to 3-bromo-4-hydroxy-benzonitrile (5.0 g, 25.2 mmol) in acetone with stirring at room temperature. After 15 minutes, add iodoethane (2.4 mL, 130.3 mmol) and continue stirring at room temperature. After 18 hours, pour the reaction mixture into water and extract with EtOAc. Combine the organic extracts, wash with water and brine, dry over anhydrous magnesium sulfate, filter, and concentrate under reduced pressure. Purify the residue by flash chromatography eluting with ethyl acetate:hexanes to provide the title compound.

Preparation 19

Preparation of
3-(3-bromo-4-hydroxy-phenyl)-propionic acid methyl ester

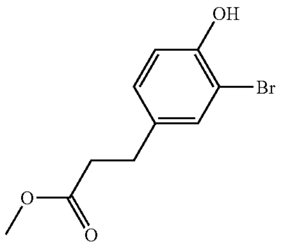

Add $HBF_4$-$Et_2O$ (4.4 mL, 27.7 mmol) to methyl-3-(4-hydroxyphenyl)-propionate (5.0 g, 27.7 mmol) in acetonitrile with stirring at 0° C. After 10 minutes, add N-bromosuccinimide (5.4 g, 30.5 mmol) and gradually allow to warm to room temperature. After 18 hours, pour into 38% $NaHSO_4$ and extract with diethyl ether. Combine the organic extracts, wash with water and brine, dry over anhydrous magnesium sulfate, filter, and concentrate under reduced pressure to provide the title compound.

Preparation 20

Preparation of
3-(3-bromo-4-ethoxy-phenyl)-propionic acid methyl ester

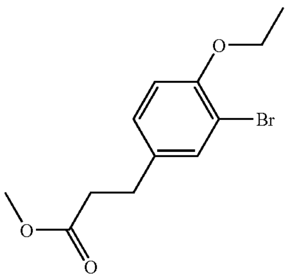

Prepare the title compound in a manner analogous to the procedure set forth in preparation 18 using 3-(3-bromo-4-hydroxy-phenyl)-propionic acid methyl ester prepared in preparation 19.

Preparation 21

Preparation of
(3-bromo-4-hydroxy-phenyl)-acetonitrile

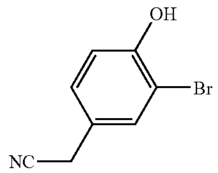

Prepare the title compound in a manner analogous to the procedure set forth in preparation 19 using (4-hydroxy-phenyl)-acetonitrile.

Preparation 22

Preparation of
(3-bromo-4-ethoxy-phenyl)-acetonitrile

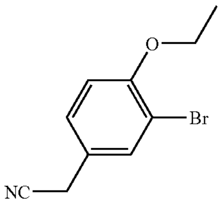

Prepare the title compound in a manner analogous to the procedure set forth in preparation 18 using (3-bromo-4-hydroxy-phenyl)-acetonitrile prepared in preparation 21.

Preparation 23

Preparation of 2-iodothiophene-3-carbonitrile

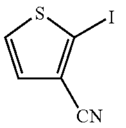

To a solution of diisopropylamine (32.1 mL, 229 mmol) in THF (1 L) at 40° C. is dropwise added n-BuLi (143 mL, 229 mmol) and the solution is stirred for 30 minutes. The reaction mixture is cooled to −78° C. and 25 g (229 mmol) of 3-cyanothiophene are then added. After stirring for 15 minutes, a solution of N-iodosuccinimide (52 g, 229 mmol) in THF (250 mL) is added and the reaction mixture is warmed to room temperature. Water (aprox. 200 mL) is added to the flask, the organic layer separated, dried with magnesium sulphate, filtered, and the solvent is evaporated. Purification by column chromatography (hexane-methyl butyl ether 100/1) provides the title compound as a white solid. $^{1}$H NMR ($CDCl_3$): 7.10 (d, J=5.6 Hz, 1H), 7.47 (d, J=5.6 Hz, 1H. $^{13}$C NMR($CDCl_3$): 87.1, 115.8, 120.8, 130.6, 133.

Preparation 24

Preparation of 2-(4-bromophenyl)thiophene-3-carbonitrile

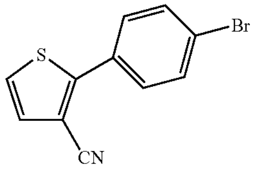

A solution of 2-iodothiophene-3-carbonitrile (20 g, 85 mmol, preparation 23), 4 bromobenzeneboronic acid (18.8 g. 94 mmol), potassium carbonate (26 g, 187 mmol) and tetrakis (triphenylphosphine)-palladium (0) (10 g, 8.5 mmol) in a mixture of anhydrous dimethoxyethane (300 mL) and absolute ethanol (150 mL) is degassed with Ar or $N_2$ for 15 min and stirred for 12 hours at 80° C. The reaction mixture is cooled to room temperature, water (100 ml) is then added and the crude product is extracted with methylene chloride (3×150 mL). The crude material is purified by column chromatography (hexane-ethyl acetate 10/1) to provide the title compound as a white solid. $^{1}$H NMR ($CDCl_3$): 7.32 (m, 2H), 7.62 (m, 4H).

Preparation 25

Preparation of 2-[4-(4,4,5,5-tetramethyl-1,3,2-dioxaborolan-2-yl)-phenyl]thiophene-3-carbonitrile

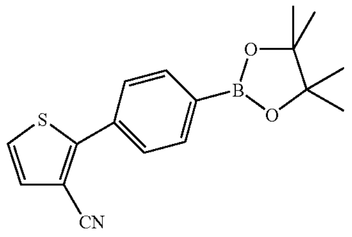

A solution of 2-(4-bromophenyl)thiophene-3-carbonitrile (16.3 g, 62 mmol, preparation 24), bis(pinacolato)diboron (17.2 g, 68 mmol), potassium acetate (20 g, 204 mmol), $PdCl_2$(dppf) (5 g, 6.1 mmol) in anhydrous DMSO (200 mL) is stirred at 80° C. for 12 hours. The reaction mixture is cooled to room temperature diluted with ethyl acetate (250 mL) and washed with water (3×100 mL). The organic layer is separated and dried with magnesium sulphate, filtered, and the solvent evaporated. The crude product is purified by column chromatography using a mixture of hexane ethyl acetate (8/1) of eluent solvent to provide the title compound. $^{1}$H NMR ($CDCl_3$): 1.37 (s, 12H), 7.32 (m, 2H), 7.76 (d, J=8.3 Hz, 2H). 7.91 (d, J=8.3 Hz, 2H). $^{13}$C NMR ($CDCl_3$): 25.2, 84.5, 106.8, 116.1, 126.2, 127.3, 131.0, 134.1, 135.9, 154.0.

Preparation 26

Preparation of 4-(2-cyanoethyl)phenyl(trifluoromethyl)sulfonate

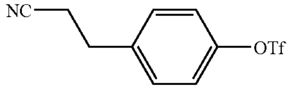

Add NaH 95% (90 mg, 3.74 mmol) to a −20° C. solution of 3-(4-hydroxy-phenyl)-propionitrile (3.4 mmol) in dry THF (25 ml) under nitrogen atmosphere and stir at this temperature for 1 hour. Then, add N-phenyltrifluorometheane-sulphonimide (3.74 mmol, 1.1 eq) in one portion and stir overnight at room temperature. Evaporate solvents to dryness and partition the crude between diethyl ether and water. Wash the organic phase with sodium carbonate 10% solution and NaCl sat. solution, dry over $MgSO_4$, filter, and remove the solvent in vacuo. Purification by flash chromatography (hexane:ethyl acetate, 4:1) provides the title compound.

Preparation 27

Preparation of 3-[4-(4,4,5,5-tetramethyl-1,3,2-dioxaborolan-2-yl)phenyl]propanenitrile

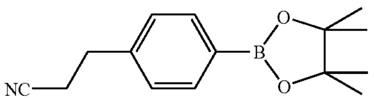

Heat at 80° C. a mixture of 4-(2-cyanoethyl)phenyl(trifluoromethyl)sulfonate (2.63 mmol, preparation 26), $PdCl_2$ (dppf) (0.5 mmol, 0.2 eq), bis(pinacolato)diboron (3.156 mmol, 1.2 eq) and potassium acetate (774 mg, 7.89 mmol, 3 eq) in DMF (16 ml) under nitrogen atmosphere overnight. Partition the reaction mixture between ethyl acetate and ice-water. Wash the organic phase with HCl 10% solution and water, dry over $MgSO_4$, and filter over Celite® and remove the solvent in vacuo. Purification by flash chromatography provides the title compound.

Preparation 28

Preparation of 2-(4-bromophenyl)phenylamine

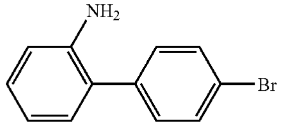

Add 4-bromophenyl boronic acid (5.0 g, 24.82 mmol), tetrakis(triphenylphosphine) palladium (0) (0.717 g, 0.620 mmol) and 2 M $Na_2CO_3$ (10 mL) to a solution of 2-iodoaniline (4.5 g, 20.69 mmol) in toluene (2 mL):ethanol (20 mL), degas and heat at 80° C. under nitrogen. After 4 h, add water and extract with ethyl acetate. Combine the organic layers, dry over sodium sulfate, filter, and concentrate under reduced pressure to give a residue. Purify the residue by flash chromatography (silica gel) eluting with ethyl acetate:hexane 1:12 to provide the title compound (3.53 g, 69%). Mass spectrum (m/e): 248 (M+1); 249 (M+2).

Preparation 29

Preparation of [2-(4-bromophenyl)phenyl][(methylethyl)sulfonyl]amine

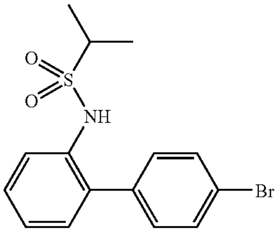

Add DBU drop wise (8.76 mL, 56.92 mmol) to a solution of 2-(4-bromophenyl)phenylamine (3.53 g, 14.23 mmol) in methylene chloride (50 ml) at 0° C., followed by isopropylsulfonyl chloride (3.29 mL, 28.46 mmol) also added drop wise and stir the reaction at room temperature for 24 h. Remove solvent under reduce pressure and purify the residue by silica gel chromatography eluting with ethyl acetate:hexane 1:4 to ethyl acetate to provide the title compound (4.93 g, 98%). Mass spectrum (m/e): 355 (M+1); 353 (M−1).

Preparation 30

Preparation of [(methylethyl sulfonyl]{2-[4-(4,4,5,5-tetramethyl(1,3,2-dioxaborolan-2-yl))phenyl]phenyl}amine

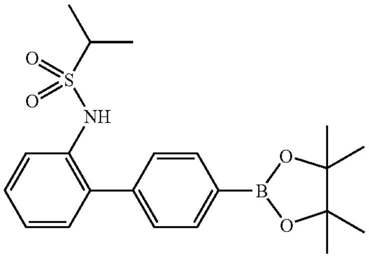

A mixture of [2-(4-bromophenyl)phenyl][(methylethyl)sulfonyl]amine (4.0 g, 11.22 mmol, preparation 29), bis(pinacolato)diboron (3.22 g, 12.34 mmol), [1,1'-bis(diphenylphosphino)ferrocene]-dichloropalladium(II) complex with methylene chloride (1:1) (0.276 g, 0.337 mmol) and potassium acetate (3.32 g, 33.87 mmol) in dry dimethyl sulfoxide (25 mL) is heated at 80° C. After 16 h add water and extract with ethyl acetate. Combine organic layers, dry over sodium sulfate and evaporate under reduce pressure. Dissolve the residue in methylene chloride and wash with a solution of 0.1N HCl. Combine the organic layers, dry over sodium sulfate, filter, and concentrate under reduced pressure. Purify the residue by flash chromatography (silica gel) eluting with ethyl acetate:hexane 1:3 to provide the title compound (4.07 g, 90%). Mass spectrum (m/e): 424 (M+23); 400 (M−1).

Preparation 31

Preparation of [(methylethyl)sulfonyl]{2-[4-(boronic acid)phenyl]phenyl}amine

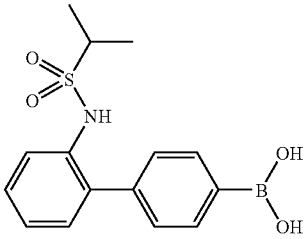

Add sodium periodate (1.12 g, 5.25 mmol) followed by a solution of 1 N ammonium acetate (8 mL) to a suspension of [(methylethyl)sulfonyl]{2-[4-(4,4,5,5-tetramethyl(1,3,2-dioxaborolan-2-yl))phenyl]phenyl}amine (0.7 g, 1.75 mmol, preparation 30) in acetone (16 mL)/water (0.8 mL). Stir the mixture at room temperature under nitrogen for 20 h. Filter the precipitate and evaporate organic layer. Extract aqueous layer with methylene chloride. Combine organic layers, dry over sodium sulfate, filter, and evaporate the solvent under reduced pressure. Add hexanes and tert-butylmethyl ether to the residue until a solid forms and then filter to provide the title compound (0.37 g, 67%). Mass spectrum (m/e): 337 (M+18); 318 (M−1).

Preparation 32

Preparation of 2-methylaminomethylene-malonitrile

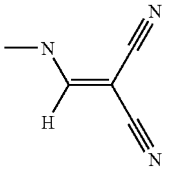

Add methylamine (2.0M, 800.00 mL, 1.6 mol) to ethoxymethylene-malonitrile (53.39 g, 0.437 mol) in diethylether with stirring at room temperature. After 18 hours, the reaction is concentrated under reduced pressure. Recrystallize the residue from ethanol to provide the title compound. $^1$H NMR (500 MHz; DMSO) δ-8.96(bs, 1H), 7.87(s, 1H), 2.94 (s, 3H).

Preparation 33

Preparation of 3-amino-4-cyano-1-methyl-1H-pyrrole-2-carboxylic acid ethyl ester

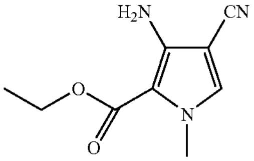

Add 2-methylaminomethylene-malonitrile (28.61 g, 0.267 mol, prepared in preparation 32), ethylbromoacetate (29.60 mL, 0.267 mol), and potassium carbonate (36.90 g, 0.267 mol) in DMF and heat to 80° C. with stirring. After 30 minutes, cool the reaction mixture to 50° C. Add sodium ethoxide in ethanol (20%, 130 mL, 0.347 mol) and heat to 90° C. After 30 minutes, allow the reaction mixture to cool to ambient temperature. After 18 hours, pour the reaction mixture into water and purify the resulting precipitate by vacuum filtration to afford the title compound. Mass spectrum (m/e): 194.0 (M+1).

Preparation 34

Preparation of 4-cyano-3-iodo-1-methyl-1H-pyrrole-2-carboxylic acid ethyl ester

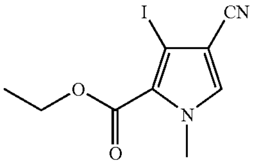

Add diiodomethane (22.15 mL, 274.97 mmol) to 3-amino-4-cyano-1-methyl-1H-pyrrole-2-carboxylic acid ethyl ester (14.75 g, 76.34 mmol, prepared in preparation 33) in acetonitrile with stirring at room temperature. Next, add isoamylnitrite (25.65 mL, 190.92 mmol) while heating the reaction to 35° C. After complete addition, the reaction is heated to 65° C. After 10 minutes; cool the reaction mixture to room temperature and concentrate under reduced pressure. Purify the residue by filtering over silica gel with methylene chloride and triturating the filtrate with hexane to afford the title compound.

Mass spectrum (m/e): 305.2 (M+1).

Preparation 35

Preparation of 2-(1-ethoxy-propylidene)-malononitrile

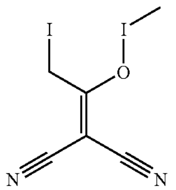

Add malononitrile (200.00 g, 3.03 mol) and triethylorthopropionate (61.00 mL, 3.03 mol) and heat to reflux with stirring. After 3 hours, cool the reaction to room temperature. After 18 hours, purify by vacuum distillation to afford the title compound.

$^1H$ NMR (500 MHz; $CDCl_3$) δ-4.42(q, 2H), 2.64(q, 2H), 1.43(t, 3H), 1.24(t, 3H).

Preparation 36

Preparation of 2-(1-methylamino-propylidene)-malononitrile

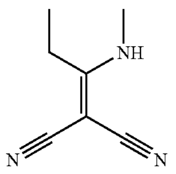

Prepare the title compound in a manner analogous to the procedure set forth in preparation 32 using 2-(1-ethoxy-propylidene)-malononitrile prepared in preparation 35.

$^1H$ NMR (500 MHz; DMSO) δ-8.84(bs, 1H), 3.06(d, 3H), 2.31(q, 2H), 1.11 (q, 3H), 1.24(q, 3H).

Preparation 37

Preparation of 3-amino-4-cyano-5-ethyl-1-methyl-1H-pyrrole-2-carboxylic acid ethyl ester

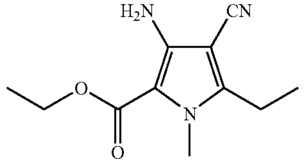

Prepare the title compound in a manner analogous to the procedure set forth in preparation 33 using 2-(1-methylamino-propylidene)-malononitrile prepared in preparation 36.

Alternatively the title compound may be prepared by the following procedure. Charge ethanol (3.40 L, denatured with 0.5% toluene) to a 22 L 3-neck reaction flask equipped with a mechanical stirrer, condenser, addition funnel and cooling bath. Cool the ethanol to 8° C. and add sodium ethoxide (805 grams, 11.35 mol) portion-wise over 20 minutes. In a separate flask, combine sarcosine ethyl ester hydrochloride (697 g, 4.54 mol), 2-(1-ethoxy-propylidene)-malononitrile (681 grams, 4.54 mol, prepared in preparation 35) and ethanol (3.0 L) and stir to dissolve the solids. Add the resulting solution to the 22 L flask over 33 minutes while maintaining about 11 C. Maintain the reaction mixture between 10-20° C. for 3.5 hours. Stir the mixture at room temperature overnight, then cool to 1° C. Adjust the pH to 7.0 by adding 1 N HCl (6.58 L) and stir the resulting suspension at 0-5° C. for 3 hours. Collect the precipitate by filtration, rinse the filter cake with deionized water (1.0 L) and vacuum-dry at 40° C., to afford the title compound in 66.7% yield. Mass spectrum (m/e): 222.4 (M+1).

Preparation 38

Preparation of 4-cyano-5-ethyl-3-iodo-1-methyl-1H-pyrrole-2-carboxylic acid ethyl ester

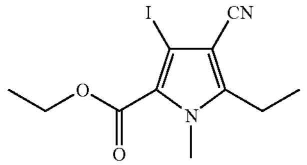

Prepare the title compound in a manner analogous to the procedure set forth in example 44 using 3-amino-4-cyano-5-ethyl-1-methyl-1H-pyrrole-2-carboxylic acid ethyl ester prepared in preparation 37.

Alternatively the title compound may be prepared by the following procedure. Charge the 3-amino-4-cyano-5-ethyl-1-methyl-1H-pyrrole-2-carboxylic acid ethyl ester prepared in preparation 37, diiodomethane, and acetonitrile to a 22 L round-bottom flask equipped with an addition funnel, thermocouple, overhead stirrer, and condenser. Dilute isoamyl nitrite with heptane and charge the resulting solution to the addition funnel. Warm the reaction mixture to 78° C. Add 0.65 L of the isoamyl nitrite solution over 1.75 hours, at which point vigorous evolution of nitrogen is observed. Suspend the addition of the isoamyl nitrite solution for about 20 minutes to allow the off-gassing to subside. Add the remainder of the isoamyl nitrite solution over 15 minutes. Stir the reaction mixture at reflux for an additional 2 hours, then cool to room temperature. Remove the solvent under reduced pressure and dilute the resulting concentrate with a mixture of 0.2 L pentane and 0.2 L methylene chloride. Pour the resulting mixture onto a 4 kg column of silica gel that is pre-wetted with cyclohexane. Elute the column with 5' gallons of cyclohexane, and discard the eluent. Next, elute the column with 6 gallons of a 1:1 mixture of cyclohexane:methylene chloride, followed by 5 gallons of 3:2 cyclohexane:methylene chloride. Combine these fractions and remove the solvent under reduced pressure. Suspend the resulting solid in 0.5 L of heptane and stir for 45 minutes. Collect the product by filtration, rinse with heptane, and vacuum-dry at 40° C. to afford the title compound (432.8 g) in 57.6% yield. Mass spectrum (m/e): 333.0 (M+1).

Preparation 39

Preparation of 4'-methoxy-2-propyl-biphenyl

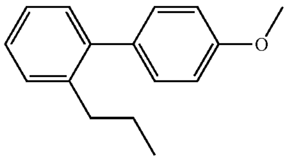

Prepare the title compound in a manner analogous to the procedure set forth in Method CII using trifluoro-methanesulfonic acid 2-propyl-phenyl ester and 4-methoxyphenylboronic acid. GC MS: 226

Preparation 40

Preparation of 4'-hydroxy-2-propyl-biphenyl

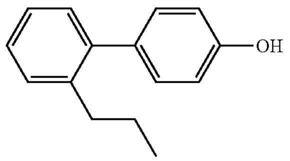

Prepare the title compound in a manner analogous to the procedures set forth in example E-49 using 4'-methoxy-2-propyl-biphenyl prepared in preparation 39. GC MS: 212

Preparation 41

Preparation of trifluoro-methanesulfonic acid 2'-propyl-biphenyl-4-yl ester

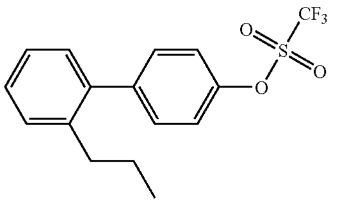

Prepare the title compound in a manner analogous to the procedures set forth in preparation 13 using 4'-hydroxy-2-propyl-biphenyl prepared in preparation 40. GC MS: 344.

Preparation 42

Preparation of 4,4,5,5-tetramethyl-2-(2'-propyl-biphenyl-4-yl)-[1,3,2]dioxaborolane

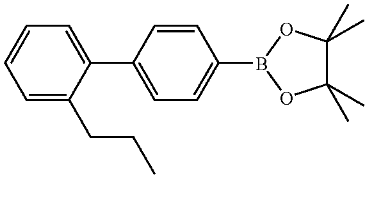

Add trifluoro-methanesulfonic acid 2'-propyl-bipheny-4-yl ester (1.06 g, 3.0 mmol, prepared in preparation 41), bis (pinacolato)diboron (1.4 g, 5.5 mmol), [1,1-bis(diphenylphospino)-ferrocene]dichloropalladium(II) (0.12 g, 0.15 mmol), and potassium acetate (1.4 g, 15.0 mmol) into DMF, and heat to 80° C. with stirring. After 4 hours, cool the reaction mixture and pour into water. Extract the quenched reaction with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the title compound. GC MS: 322.

Preparation 43

Preparation of 4-cyano-5-ethyl-3-[4-(methoxy-methyl-carbamoyl)-phenyl]-1H-methyl-1H-pyrrole-2-carboxylic acid ethyl ester

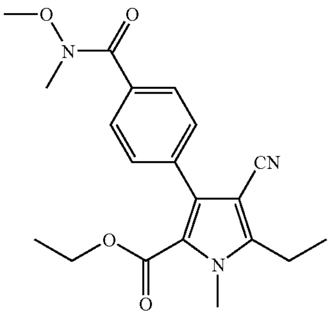

Add 3-(4-carboxy-phenyl)-4-cyano-5-ethyl-1-methyl-1H-pyrrole-2-carboxylic acid ethyl ester (1.0 g, 3.1 mmol, prepared in example E-157) in THF to oxalyl chloride (0.29 mL, 3.3 mmol) in THF followed by 1 drop of DMF and stir at room temperature. After 2 hours, concentrate to a residue. Next, add the residue to N,O-dimethylhydroxyamine hydrochloride (0.32 g, 3.3 mmol) and pyridine (0.75 mL, 9.3 mmol) in methylene chloride with stirring. After 2 hours, pour the reaction mixture into water and extract with methylene chloride. Combine the organic extracts, wash with water and brine, dry over anhydrous magnesium sulfate, filter, and concentrate under reduced pressure. Purify the residue by flash chromatography eluting with ethyl acetate:hexanes to provide the title compound. Mass spectrum (m/c): 370.1 (M+1).

Preparation 44

Preparation of 3-Amino-4-cyano-1,5-dimethyl-1H-pyrrole-2-carboxylic acid ethyl ester

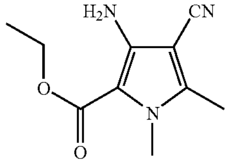

Preparation of 2-(1-Ethoxy-ethylidene)-malononitrile

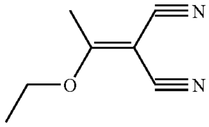

Combine malonitrile (50 g, 0.76 mol) and triethylorthoacetate (123.3 g, 0.76 mol) and heat at reflux for 3 hours while stirring under a nitrogen atmosphere. Cool to room temperature and concentrate under reduced vacuum to give 125 g of a solid. Purify the material by silica gel chromatography (Prep. 2000) eluting with methylene chloride to provide 116 g of the title compound as a solid. Mass spectrum (m/e): 136.0 (M*): (Bruker 300) [1]NMR (DMSO) 4.35-4.43 (2H, dd), 3.28-3.30 (3H, s), 1.27-1.34 (3H, t).

Preparation of 2-(1-Methylamino-ethylidene)-malononitrile

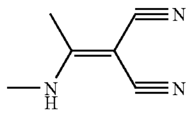

Add methylamine (1120 mL, 2.6 Eq.) to 2-(1-ethoxy-ethylidene)-malononitrile (115 g, 0.84 mol) in ether dropwise while stirring at room temperature under a nitrogen atmosphere. Stir at this temperature for 2 hours and then concentrate under reduced vacuum. Triturate the resulting solid in ethyl acetate (400 mL) and filter to produce 102 g of the title compound as a tan solid. Mass spectrum (m/e): 122.0 (M*+1): (Bruker 300)

$^1$H NMR (DMSO) 3.28-3.30 (3H, s), 2.14-2.16 (3H, s).

Preparation of Final Title Compound

Combine 2-(1-methylamino-ethylidene)-malononitrile (60 g, 0.49 mol), ethylbromoacetate (55 mL, 1 Eq.), and potassium carbonate (68.3 g, 1 eq.) in absolute ethanol (350 mL) and heat to reflux for 3 hours while stirring under a nitrogen atmosphere. Cool to room temperature and add dropwise 21 wt % solution of sodium ethoxide (280 mL, 1.2 eq.) and heat to reflux for 1 hour. Let cool to room temperature and stir overnight. Pour into water (500 mL) and collect the precipitate by filtration and dry thoroughly to give 36.41 g of a white solid. Purify the material by recrystallization from ethyl acetate to provide 32 g of the final title compound, 3-amino-4-cyano-1,5-dimethyl-1H-pyrrole-2-carboxylic acid ethyl ester, as crystals. Mass spectrum (m/e): 208.3 (M*+1): (Bruker 300) $^1$H NMR (DMSO) 4.14-4.22 (2H, dd), 3.59-3.62 (3H, s), 3.26-3.31 (3H, s), 1.21-1.26 (3H, t).

Preparation 45

Preparation of 4-cyano-3-iodo-1,5-dimethyl-1H-pyrrole-2-carboxylic acid ethyl ester

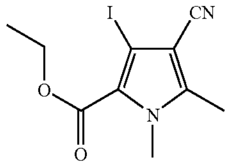

Add isoamylnitrite (2.5 Eq.) to 3-amino-4-cyano-1,5-dimethyl-1H-pyrrole-2-carboxylic acid ethyl ester (prepared in preparation 44) and diiodomethane (3.5 eq.) in acetonitrile (10 mL) with stirring at 55° C. under a nitrogen atmosphere. Slowly heat the reaction mixture to 75° C. and heat at this temperature for 3 hours. Cool to room temperature and pour into water, and extract the quenched reaction with ethyl acetate. Wash the organic extracts with water, dry over potassium carbonate, filter, and concentrate under reduced vacuum. Purify the residue by silica gel chromatography (Prep.2000) eluting with methylene chloride to provide a solid. Recrystallize from ethyl acetate to provide the title compound as crystals. Mass spectrum (m/e): 318.0 M*). (Bruker 300) $^1$H NMR ($CDCl_3$) 4.31-4.38 (2H, dd), 3.83-3.86 (3H, s), 2.41-2.44 (3H, s), 1.40-1.44 (3H, t).

Preparation 46

Preparation of 4-Bromo-1-methyl-1H-pyrazole-3-carbonitrile

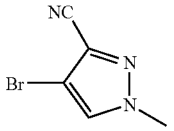

Add sodium hydride (60 wt % oil dispersion, 700 mg, 17.5 mmol) in several portions under a nitrogen purge to a solution of 4-bromo-1H-pyrazole-3-carbonitrile (2.0 g, 11.6 mmol) in 15 mL of anhydrous DMF at 0° C. Stir the reaction at 0° C. for one hour. Add methyl iodide (0.9 mL, 14.5 mmol) to the mixture and allow to stir and come to room temperature over 1 hour. Pour into 100 mL of ice-water and stir for 15 minutes. Filter off the resulting solid and rinse with 20 mL of water. Dry the solid overnight. Chromatograph (1/9-1/3 EtOAc/hexanes) over silica gel to give the title compound as a white solid (1.38 g, 63%), along with a small amount (100 mg) of the regioisomeric bromide.

Preparation 47

Preparation of 4-cyano-3-(2'-cyano-biphenyl-4-yl)-5-ethyl-1-methyl-1H-pyrrole-2-carboxylic acid dimethylaminomethyleneamide

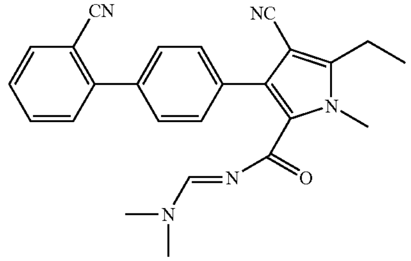

Prepare a solution of 4-cyano-3-(2'-cyano-biphenyl-4-yl)-5-ethyl-1-methyl-1H-pyrrole-2 carboxylic acid amide (167 mg, 0.47 mmol, prepared in example Am-3) in 2.5 mL of dry dimethoxymethyl-dimethyl-amine and heat to reflux under nitrogen. After 1 hour allow 1 mL of solvent to distill out of the reaction, then cool the mixture to room temperature. Dilute the slurry with 10 mL of hexanes, filter off the resulting product and wash with 5 mL hexanes. Vacuum-dry the solid overnight to give the title compound (183 mg, 95%). MS(ES+, m/e)=410 ($M^+$+1).

Preparation 48

Preparation of 4-Cyano-5-ethyl-1-methyl-3-[4-(4,4,5,5-tetramethyl-[1,3,2]dioxaborolan-2-yl)-phenyl]-1H-pyrrole-2-carboxylic acid ethyl ester

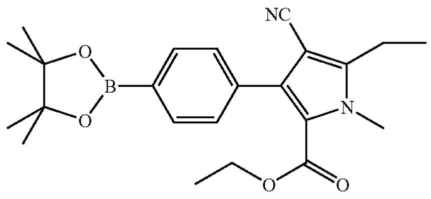

Add bispinacolato-diborane (3.52 mmol) and potassium acetate (7.04 mmol) into a solution of 3-(4-bromo-phenyl)-4-cyano-5-ethyl-1-methyl-1H-pyrrole-2-carboxylic acid ethyl ester (1.76 mmol, prepared in example E-247a, E-247b, or E-247c) in DMSO (17.6 mL). Degas the mixture at reduced pressure for 20 minutes until no bubbles are result. Recharge the atmosphere of the reaction with nitrogen. Add $PdCl_2$ (dppf) (0.352 mmol). Heat the reaction mixture at 90° C. for 18 hours. Then dilute with methylene chloride (30 mL) and wash with water (5×30 mL). Combine the organic layers, dry over anhydrous magnesium sulfate, filter, and concentrate under reduced pressure. Purify the residue by flash chromatography to provide the title compound. Mass spectrum (m/e): 409.1 (M+1). $R_f$=0.67 (50% EtOAc in hexanes)

Preparation 49

Preparation of ethyl 4-cyano-5-fluoro-3-iodo-1-methylpyrrole-2-carboxylate

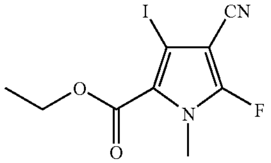

Dissolve 4-cyano-3-iodo-1-methyl-1H-pyrrole-2-carboxylic acid ethyl ester (2.69 mmol, prepared in preparation 34) and SELECTFLUOR® (4.04 mmol, 1-chloromethyl-4-fluoro-1,4-diazoniabicyclo[2.2.2]octane bis-(tetrafluoroborate)) in acetonitrile (27 mL). Heat the mixture at 80° C. for 16 h. Add $H_2O$ (30 mL) and methylene chloride (30 mL) into the reaction mixture. Extract with methylene chloride (3×30 mL). Combine the organic layers, dry over magnesium sulfate, filter, and concentrate under reduced pressure. Purify the residue by flash chromatography to provide the title compound. Mass spectrum (m/e): 318.9 (M−1). $R_f$=0.5 (50% $Et_2O$ in hexanes).

Preparation 50

Preparation of 4-cyano-5-ethyl-1-methyl-3-(4,4,5,5-tetramethyl-[1,3,2]dioxaborolan-2-yl)-1H-pyrrole-2-carboxylic acid ethyl ester

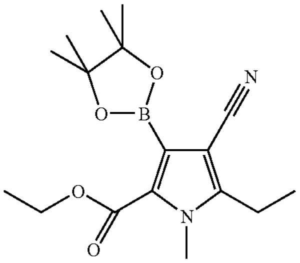

Add 4,4,5,5-tetramethyl-1,3,2-dioxaborolane (0.87 mL, 6.0 mmol) to 4-cyano-5-ethyl-3-iodo-1-methyl-1H-pyrrole-2-carboxylic acid ethyl ester (1.0 g, 3.0 mmol, prepared in prepared in Preparation 38), [1,1'-bis(diphenylphosphino) ferrocene]dichloro-palladium(II) complex with methylene chloride (1:1) (0.122 g, 0.15 mmol), and triethylamine (1.25 mL, 9.0 mmol) in acetonitrile and heat to reflux. After 3 hours, cool and pour into water. Extract with ethyl acetate. Wash the combined organics with water and brine, dry over magnesium sulfate, filter and concentrate under reduced pressure. Purify the residue by flash chromatography (silica gel), eluting with ethyl acetate:hexanes to provide the title compound. $^1$H NMR (400 MHz, $CDCl_3$) δ 4.33 (q, 2H), 3.84 (s, 3H), 2.80 (q, 2H), 1.40 (s, 12H), 1.46 (t, 3H), 1.22 (t, 3H).

Preparation 51

Preparation of propane-2-sulfonic acid{2-[4-(4,4,5,5-tetramethyl-[1,3,2]dioxaborolan-2-yl)-phenyl]-ethyl}-amide

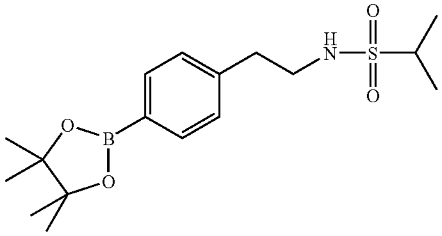

Add DBU (0.79 mL, 5.3 mmol) to 2-[4-(4,4,5,5-tetramethyl-[1,3,2]dioxaborolan-2-yl)-phenyl]-ethylamine (0.5 g, 1.8 mmol, can be prepared from 4-bromophenyl acetonitrile) in dichloromethane and stir at room temperature. After 10 minutes, cool to 0° C. and add isopropylsulfonylchloride (0.22 mL, 1.95 mmol). After 30 minutes, allow to warm to room temperature. After 3 hours, pour into water and extract with dichloromethane. Wash the combined organics with 1N HCl, water, and brine, dry over magnesium sulfate, filter and concentrate under reduced pressure. Purify the residue by flash chromatography (silica gel), eluting with ethyl acetate: hexanes to provide the title compound. Mass spectrum (ES−)=352.2 (M−1).

Preparation 52

Preparation of 4-(2-cyanophenyl) phenyl boronic acid

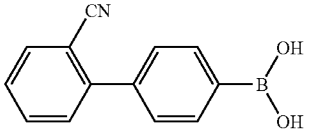

Dry THF (7 mL) is cooled to −3° C. under nitrogen. BuMgCl (1.1 mL, 2.2 mmol, 2M solution in THF) is added. n-BuLi (2.9 mL, 4.6 mmol, 1.6 M in hexanes) is then added dropwise over 20 min at −3° C. to 0° C. After addition, the solution is stirred at 0° C. for 45 min. The solution is cooled to −45° C. and treated dropwise over 20 min at −45 to −40° C. with a solution of 2-(4-bromophenyl)benzenecarbonitrile (1 g, 3.67 mmol) in a total of 6 mL THF. The resulting yellowish-orange solution is stirred 3 h at −40 to −35° C. An aliquot of the reaction mixture is periodically quenched with aq HCl/MTBE for HPLC analysis (Hitachi 7000 series, SB phenyl column, 218 nm, 65% MeCN /35% water with 0.05% TFA, 1 mL/min). After 3 h, the solution is cooled to −65° C. Trimethylborate (0.9 mL, 8.0 mmol) is added dropwise over 15 min at −65 to −60° C. The solution is stirred 1 h at −0° C. and then allowed to warm to 13° C. over 1 h. The reaction is cooled to 0° C. and quenched with 10 mL of 1N HCl, with vigorous stirring for 5 min. The mixture is extracted with 20 mL of ethyl acetate. The organic solution is washed with brine (25 mL), dried ($Na_2SO_4$) and concentrated to obtain 0.91 g of crude boronic acid (87.35% HPLC). This in 10 mL of toluene is heated to 90° C. with stirring during 10 min. Upon recooling to rt and then to 10° C., the solid is collected by filtration and rinsed three times with toluene to obtain 0.543 g of title compound (98.66% HPLC, Hitachi 7000 series, SB phenyl column, 218 nm, 65% MeCN/35% water with 0.05% TFA, 1 mL/min).

Additional Preparation of 4-(2-cyanophenyl)phenyl boronic acid

Dry THF (7 mL) is cooled to at −3° C. under nitrogen. BuMgCl (1.1 mL, 2.2 mmol, 2M in THF) is added. n-BuLi (2.9 mL, 4.6 mmol, 1.6 M in hexanes) is then added dropwise over 20 min at −3° C. to 0° C. After the addition, the solution is stirred at 0° C. for 45 min. The solution is cooled to −45° C. and treated dropwise over 20 min at −45 to −40° C. with a solution of 2-(4-bromophenyl)benzenecarbonitrile (1 g, 3.67 mmol) in a total of 6 mL THF. The resulting yellowish-orange solution is stirred 2 h at -40° C. After 2 h, the reaction is allowed to warm to −25° C. over 2.5 h. The reaction is allowed to warm to -8° C. over another 2 h (6 h total reaction time after the addition of 2-(4-bromophenyl)benzenecarbonitrile). The solution is cooled to −75° C. Trimethylborate (0.9 mL, 8.0 mmol) is added dropwise over 15 min at −75 to −70° C. The solution is stirred 1 h at −70° C. and then allowed to warm to 5° C. over 1 h. The reaction is cooled to 0° C. and quenched with 10 mL of water. The mixture is stirred for 2 min. It begins to turn dark as it warms. Hence, 10 mL of 1N HCl is added with vigorous stirring for 2 min. The mixture is extracted with 20 mL of ethyl acetate. The organic solution is washed with brine (25 mL), dried $Na_2SO_4$) and concentrated to obtain 0.92 g of crude boronic acid (83.10% HPLC, Hitachi 7000 series, SB phenyl column, 218 nm, 65% MeCN/35% water with 0.05% TFA, 1 mL/min). This in 10 mL of toluene is stirred 18 h at rt. The precipitated solid is collected by filtration and is rinsed three times with toluene to obtain 0.528 g of title compound (97.97% HPLC).

Additional Preparation of 4-(2-cyanophenyl)phenyl boronic acid

Dry THF (4 mL) is cooled to at −3° C. under nitrogen. BuMgCl (0.6 mL, 1.2 mmol, 2M in THF) is added. n-BuLi (1.5 mL, 2.4 mmol, 1.6 M in hexanes) is then added dropwise over 20 min at −3° C. to 0° C. After the addition, the solution is stirred at 0° C. for 45 min. The solution is cooled to −45° C. and treated dropwise over 20 min at −45 to −40° C. with a solution of 2-(4-bromophenyl)benzenecarbonitrile (0.5 g, 1.9 mmol) in a total of 4 mL THF. The resulting yellowish-orange solution is allowed to warm to −25° C. over 1 h. After 1 h, the solution is cooled to −73° C. Trimethylborate (0.43 mL, 3.87 mmol) is added dropwise over 15 min at −73° C. The solution is stirred 1 h at −73° C. The reaction is allowed to warm to −63° C. The reaction is quenched with 5 mL of 1N HCl and allowed to warm to 0° C. with stirring. The mixture is extracted with 10 mL ethyl acetate. The organic solution is shaken with brine, dried ($Na_2SO_4$).and concentrated to obtain 0.435 g of crude product. This in 5 mL of 1:1 toluene/heptane is heated to 95° C. with stirring for 10 min. Upon cooling to rt and then to 10° C., the solid is collected by filtration and rinsed three times 1:1 toluene/heptane. The solid is vacuum-dried to provide title compound (0.232 g, 95.65% HPLC, Hitachi 7000 series, SB phenyl column, 218 nm, 65% MeCN/35% water with 0.05% TFA, 1 mL/min).

Additional Preparation of 4-(2-cyanophenyl)phenyl boronic acid

Add 2-(4-bromophenyl)benzenecarbonitrile (1.29 g, 0.005 moles, preparation 61), tetrahydrofuran (52 mL), and triisopropyl borate (2.82 grams, 0.015 moles) to a 100 mL 3-neck round-bottom flask equipped with a magnetic stirrer, internal temperature probe, dry ice-acetone bath, and addition funnel. Stir the mixture under nitrogen and cool the contents of the 100 mL 3-neck round-bottom flask to −73° C. Transfer a solution of n-butyl lithium 1.6 M in hexanes (8.7 mL, 0.0139 moles) via cannula to the addition funnel. Add n-butyl lithium (4.7 mL, 0.0075 moles) to the reaction mixture over 7 minutes while maintaining −65 to −73° C. Slowly warm the reaction mixture to −15° C. Cool the reaction mixture to −70° C. Add n-butyl lithium (3.0 mL, 0.0048 moles) to the reaction mixture dropwise. Slowly warm the reaction mixture to −15° C. Cool the reaction mixture to −60° C. Add n-butyl lithium (1.0 mL, 0.0016 moles) to the reaction mixture dropwise. Slowly warm the reaction mixture to −15° C. Cool the reaction mixture to −30° C. Add 1.0 N hydrochloric acid (20 mL, 0.02 moles). Remove the dry ice-acetone bath, and allow the reaction mixture to warm to 23° C. Transfer the reaction m mixture to a separatory funnel. Separate the phases and concentrate the organic phase to a solid under reduced pressure (15-25 mm). Add water (50 mL), 5N NaOH until pH 11.5 is observed, dichloromethane (40 mL), and tetrahydrofuran (20 mL). Transfer the reaction mixture to a separatory funnel and separate the phases. Acidify the aqueous phase and concentrate the suspension under reduced pressure (15-25 mm) to remove residual organic solvents. Collect the precipitate by filtration. Vacuum (15-25 mm) dry the filter cake at 45° C. to provide the title compound (0.30 g, 0.0013 moles) in 26.9% yield. $^1H$ NMR (DMSO-$d_6$, 500.0 MHz): δ 8.21 (s, 2H); 7.98 (dd, 1H, J=1.5, 8); 7.95 (d, 2H, J=8); 7.82 (dt, 1H, J=1.5, 7.5); 7.66 (d, 1H, J=7); 7.61 (dt, 1H, J=1, 8); 7.57 (d, 2H, J=8).

Preparation 53

Preparation of 2-cyanophenylboronic acid

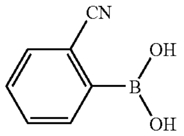

Dissolve 2-bromobenzonitrile (melt in water bath at 65° C. before use, 6.733 kg, 37.0 mol, 1 eq) in THF (52.5 L) in a cryogenic reactor and cool to −78° C. Add triisopropylborate (13.96 kg, 74 mol, 2 eq). Allow the mixture to cool to −78° C. again. Add hexyllithium (2.5M in hexane, 15.38 kg, 55.5 mol, 1.5 eq) over a period of 2 h (max internal temp=69° C.). After the addition, stir for 1 h at −75° C. Add the mixture (−74° C.) to water (48 L, 5° C.) over a period of 15 min with stirring to give a slightly yellow emulsion (−1° C.). Warm the mixture to 23° C. and stir at this temperature for 90 min. Separate the layers. Extract the aqueous layer with isopropyl acetate (24 L). Combine the organic layers and re-extract with brine (22 L). Combine the aqueous layers and acidify to pH 1 with 1M sulfuric acid (31 L). Extract the product twice with isopropyl acetate (41 L and 39 L). Combine the organic layers and stir overnight with brine (21 L) at 2° C. Collect the organic solution (90 L) and distill under reduced pressure at 50-60° C.

to reduce the volume to 10 L. Strip the suspension with isopropyl acetate (11 L). Add methylcyclohexane (20 L) at 25° C. Cool the suspension to -7° C. Collect the precipitated product by filtration. Wash the filter cake with a mixture of isopropyl acetate (2 L) and methylcyclohexane (4 L). Dry the filter cake on the rotovap at reduced pressure at 50° C. to obtain 2.997 kg of title compound as a white powder; 55% yield (poor yield due to some material sticking to the reactor wall). $^1$H NMR (solvent-$d_x$): § 7.53 (dt, 1H, J=1.5 Hz, 7.5 Hz), 7.62 (dt, 1H, J=1.5 Hz, 7.5 Hz), 7.73 (m, 2H).

Preparation 54

Preparation of 2-iodofluoren-9-one

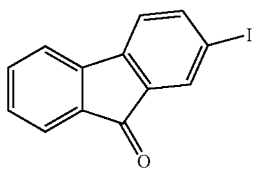

Add acetic acid (45 mL), concentrated sulfuric acid (5.4 grams, 0.055 moles), water (10 mL), 9-fluoreneone (9.01 grams, 0.05 moles), iodine (6.0 grams, 0.0237 moles), and periodic acid (2.85 grams, 0.0125 moles) to a 250 mL, 3-neck round-bottom flask equipped with a magnetic stirrer, internal temperature probe, heating mantle, and a glycol-cooled condenser fitted with a nitrogen inlet. Heat the reaction mixture to 45° C. and stir 1 hour, then warm to 50° C. and stir an additional 2.5 hrs. Warm the mixture to 60° C. and add additional acetic acid (45 mL). Stir the reaction mixture for an additional 10 hours, cool to room temperature and stir the reaction mixture at room temperature for about 8 hours. Collect the precipitate by filtration. Transfer the filter cake and acetic acid (40 mL) to a 250 mL, 3-neck round-bottom flask equipped with a magnetic stirrer, internal temperature probe, heating mantle, and a glycol-cooled condenser fitted with a nitrogen inlet. Heat the mixture to 70° C. and add additional acetic acid with continued warming until a clear solution is observed. Reduce the reaction mixture to 50° C. and stir at 50° C. for 2 hours. Slowly cool the reaction mixture to 25° C. and stir 1 hour. Recover the precipitate by vacuum filtration. Air-dried the resulting filter cake to provide the title compound (10.2 g, 66.6% yield). $^1$H NMR ($CDCl_3$, 500.0 MHz): δ 7.95 (d, 1H, J=1.5); 7.81 (dd, 1H, J=2, 8); 7.64 (d, 1H, J=7.5); 7.50 (m, 2H); 7.33-7.24 (m, 2H).

Preparation 55

Preparation of 2-(4-iodophenyl)benzoic acid

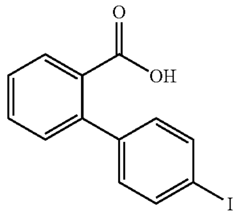

Add potassium tert-butoxide (5.61 g, 0.05 moles) and dimethoxyethane (67 mL) to a 250 mL 3-neck round-bottom flask equipped with a magnetic stirrer, internal temperature probe, and a nitrogen inlet. Stir the mixture at ambient temperature until the solid dissolves. Add 2-iodofluoren-9-one (1.5 grams, 0.005 moles, preparation 54) and stir until the solid dissolves. Add water (0.27 grams, 0.015 moles) and stir the reaction mixture at 23° C. for 1 hour. Add dichloromethane (70 mL) and concentrated hydrochloric acid to pH 1.0. Add water (50 mL) and separate the phases. Concentrate the organic phase under reduced pressure (15-25 mm) to a solid, and suspend the solid in a mixture of hexane (5 mL) and methyl-tert-butyl ether (5 mL) at ambient temperature for 3 hours. Isolate the solid by filtration and rinse the filter cake with pentane. Vacuum dry the solids to provide the title compound (1.25 grams, 0.0386 moles, 77.1% yield). 1H NMR (acetone-d6, 500.0 MHz): δ 7.94 (dd, 1H, J=1, 7.5); 7.82 (app. d, 2H, J=8); 7.66 (td, 1H, J=1, 7.5); 7.55 (td, 1H, J=1, 8); 7.44 (dd, 1H, J=1, 7.5); 7.22 (app. d, 2H, J=8).

Preparation 56

Preparation of 2-(4-iodophenyl)benzamide

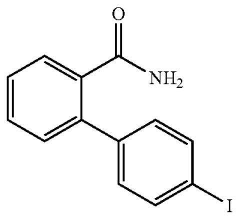

Add 2-(4-iodophenyl)benzoic acid (12.0 grams, 0.037 moles, preparation 55), dichloromethane (60 mL), dimethylformamide (0.5 mL, 0.0065 moles), and thionyl chloride (5.72 grams, 0.0481 moles) to a 250 mL 3-neck round-bottom flask equipped with a magnetic stirrer, internal temperature probe, heating mantle, condenser, and nitrogen inlet. Warm the reaction mixture to 36° C. for 45 minutes. Add thionyl chloride (1.7 grams, 0.0143 moles) and stir at 36° C. for 15 minutes. Add tetrahydrofuran (60 mL) dichloromethane (60 mL) and concentrated ammonium hydroxide (25 mL, 0.37 moles) to a 500 mL 3-neck round-bottom flask equipped with a magnetic stirrer, internal temperature probe, and cooling bath. Add the contents of the 250 mL flask to the 500 mL flask over 5 minutes while limiting the temperature to 30° C. Cool the reaction mixture to 18° C. and filter to collect the precipitate. Retain the filter cake. Transfer the filtrate to a separatory funnel and separate the phases. Concentrate the organic phase under reduced pressure (15-25 mm) to a solid, and suspend the solid in methyl-tert-butyl ether (25 mL). Isolate the solid by filtration and combine with the retained filter cake from above. Suspend the combined solids in methyl-tert-butyl ether (40 mL) at ambient temperature. Filter to isolate the solids. Suspend the solids in 50 mL water, and filter to recover the solids. Rinse the filter cake twice with water (20 mL). Dry the solids at 40° C. under reduced pressure (15-25 mm) to provide the title compound (9.7 grams, 0.030 moles, 81.1% yield). $^1$H NMR (acetone-$d_6$, 500.0 MHz): δ 7.82 (d, 2H), J=8.8; 7.58 (d, 1H, J=8.2); 7.54 (td, 1H), J=7.7, 1.6; 7.46 (td, 1H, J=7.7, 1.1); 7.42 (d, 1H, J=7.6); 7.30 (d, 2H, J=8.8); 6.91 (s, 1H); 6.62 (s, 1H).

Preparation 57

Preparation of 2-(4-iodophenyl)benzenecarbonitrile

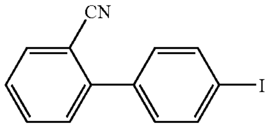

Add 2-(4-iodophenyl)benzamide (4.45 g, 0.0138 moles, preparation 56), acetonitrile (45 mL), and triethylamine (2.93 grams, 0.0289 moles) to a 100 mL 3-neck round-bottom flask equipped with a magnetic stirrer, internal temperature probe, ice-water bath, and addition funnel. Cool the contents of the 100 mL 3-neck round-bottom flask to 0° C. Add trifluoroacetic anhydride (3.04 grams, 0.0145 moles) to the reaction mixture via the addition funnel over 5 minutes. Observe a temperature increase to about 24° C., and cool the reaction mixture to 0° C. Stir the reaction mixture for 60 minutes. Add water (45 mL) and stir the suspension at ambient temperature for 60 minutes. Collect the precipitate by filtration and rinse the filter cake with water. Vacuum (15-25 mm) dry the filter cake at 50° C. to provide the title compound (4.03 g, 0.0132 moles) in 95.9% yield. $^1$H NMR($CDCl_3$, 500.0 MHz): δ 7.82 (app. d, 2H, J=9); 7.75 (dd, 1H, J=1.5, 8); 7.63 (dt, 1H, J=1.5, 7.5); 7.46 (d, 1H, J=8); 7.45 (dt, 1H, J=1.5, 7.5); 7.28 (app. d, 2H, J=8.5).

Preparation 58

Preparation of 2-[4-(4,4,5,5-tetramethyl-1,3,2-dioxaborolan-2-yl)phenyl]benzenecarbonitrile

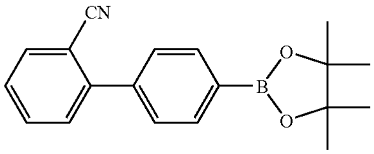

Add 2-(4-iodophenyl)benzenecarbonitrile (10.0 grams, 0.0328 moles, preparation 57), acetonitrile (100 mL), and triethylamine (8.50 grams, 0.084 moles) to a 250 mL 3-neck flask equipped with a condenser, internal temperature probe, septum, and heating mantle and stir under a nitrogen atmosphere. Add pinacol borane (6.7 grams, 0.0524 moles) and palladium black (0.174 grams, 0.00164 moles). Heat the reaction mixture to reflux and stir at reflux for 135 minutes. Cool the reaction mixture to ambient temperature and filter to remove palladium black Concentrate the filtrate to a solid under reduced pressure (15-25 mm) and dissolve the solid in isopropyl acetate (100 mL) and water (50 mL). Transfer the resulting mixture to a separatory funnel and separate phases. Discard the aqueous phase and dilute the organic phase with heptane (50 mL), water (50 mL) and dichloromethane (30 mL). Separate the phases and discard the aqueous phase. Add water (50 mL) and warm the mixture to 60° C. Stir at 60° C. for 5 minutes, then separate the phases. Extract the aqueous phase with methyl-tert-butyl ether (30 mL), separate the phases and discard the aqueous phase. Combine the organic phases and concentrate to an oil (12.5 grams) under reduced pressure. Dissolve the oil in a mixture of methyl-tert-butyl ether (1.5 mL) and dichloromethane (28.5 mL) and apply the solution to a 40 gram silica gel column. Elute the sample from the column using a mixture of methyl-tert-butyl ether (7.5 mL) and dichloromethane (142.5 mL). Concentrate the resulting solution to an oil (10.2 grams) under reduced pressure (15-25 mm). Observe that the oil spontaneously crystallizes upon standing at room temperature. Suspend the resulting solid in pentane (30 mL) and filter to recover the solid. Suspend the solids in a mixture of methyl-tert-butyl ether (3 mL) and pentane (70 mL), then filter the suspension to recover the solid product. Vacuum dry the solid at 25° C. under reduced pressure (15-25 mm). Suspend the solid again in a mixture of methyl-tert-butyl ether (3 mL) and pentane (50 mL), filter and dry the solid at 25° C. under reduced pressure (15-25 mm) to provide the title compound (5.8 g, 0.019 moles) in 57.9% yield. $^1$H NMR ($CDCl_3$, 500.0 MHz): δ 7.92 (app. d, 2H, J=8); 7.75 (dd, 1H, J=1, 7.5); 7.62 (td, 1H, J=1.5, 7.5); 7.55 (app. d, 211, J=8); 7.50 (dd, 1H, J=1, 7.5); 7.43 (td, 1H, 1, 7.5); 1.35 (s, 12H).

Preparation 59

Preparation of 2-(4-bromophenyl)benzoic acid

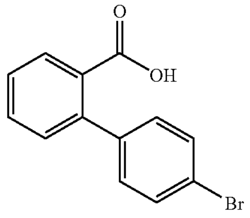

Add potassium tert-butoxide (90.0 g, 0.80 moles) and tetrahydrofuran (350 mL) to a 1000 mL 3-neck round-bottom flask equipped with an overhead stirrer, internal temperature probe, cooling bath, and nitrogen inlet. Stir the mixture at ambient temperature until the solid dissolves. Add 2-bromofluoren-9-one (20.8 grams, 0.08 moles) and stir for 10 minutes. Add water (4.32 grams, 0.24 moles) dropwise and stir the reaction mixture for 15 minutes. An exotherm to 39° C. is observed. Cool the reaction mixture to 25° C. and filter to recover the off-white precipitate. Cover the filter cake with rubber dam during the filtration. Retain the filter cake and transfer the filtrate back to the 1000 mL round-bottom flask. Add water (50 mL) and adjust the pH of the resulting mixture to pH 1.0 by slow addition of concentrated HCl (19 g, 0.193 moles) while cooling to maintain 15-20° C. Transfer the mixture to a separatory funnel and add water (30 mL). Separate the phases. Extract the aqueous phase with tetrahydrofuran (20 mL) and combine the organic phases. Transfer the aqueous phase to a 1000 mL beaker. Concentrate the organic phase under reduced pressure (15-25 mm) to a yellow solid (2.5 g). Retain the yellow solid.

Add tetrahydrofuran (50 mL) to the 1000 mL beaker containing the aqueous phase from above. Stir the mixture using a magnetic stirrer and maintain 15-20° C. using an ice-water bath and simultaneously add the off-white precipitate and concentrated HCl (61 g, 0.61 moles). This affords a biphasic mixture having pH 1.65. Transfer the biphasic mixture to a separatory funnel and separate the phases. Extract the aqueous phase with tetrahydrofuran (20 mL), then discard the aqueous phase and combine the organic solutions. Concentrate the combined solution under reduced pressure (15-25 mm) to a pale yellow solid (23 g). Dissolve the pale yellow solid in methyl-tert-butyl ether (50 mL) and tetrahydrofuran (20 mL). Extract the solution with water (20 mL). Separate the phases. Discard the aqueous phase. Concentrate the organic phase under reduced pressure (15-25 mm) to an off-white solid (20.7 g). Add pentane (40 mL) to the solid and stir the resulting suspension at ambient temperature until the solid is finely divided. Isolate the solid by filtration and rinse the filter cake three times with pentane (20 mL). Retain the filtrate. Air dry the solids to provide the title compound (16.7 grams, 0.060 moles, 75.3% yield). $^1$H NMR ($CDCl_3$, 500.0 MHz): δ 7.96 (dd, 1H, J=1.5, 8); 7.55 (td, 1H, J=1.5, 7.5); 7.50 (app. d, 2H, J=9); 7.43 (td, 1H, J=1, 8); 7.31 (dd, 1H, J=1.5, 8); 7.18 (app. d, 2H, J=9).

Preparation 60

Preparation of 2-(4-bromophenyl)benzamide

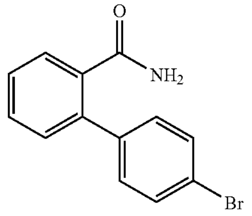

Add 2-(4-bromophenyl)benzoic acid (15.5 g, 0.0559 moles, preparation 59), 3-0 dichloromethane (78 mL), and dimethylformamide (0.5 grams, 0.0068 moles) to a 250 mL 3-neck round-bottom flask equipped with a condenser, magnetic stirrer, internal temperature probe, heating mantle, and addition funnel. Add thionyl chloride (8.64 grams, 0.0727 moles) to the reaction mixture via the addition funnel over 3 minutes. Stir the mixture at 40° C. for 45 minutes.

Add concentrated ammonium hydroxide (38 ml, 0.559 moles) and dichloromethane (10 mL) to a 1000 mL 3-neck round-bottom flask equipped with an overhead stirrer, internal temperature probe, cooling bath, and nitrogen inlet. Transfer the contents of the 250 mL flask to the addition funnel. Add one-half of the contents of the addition funnel to 1000 mL flask while stirring and cooling to maintain 3-10° C. Add concentrated ammonium hydroxide (20 mL, 0.30 moles) to the 1000 mL flask. Add the remainder of the contents of the addition funnel while stirring and cooling to maintain 3-10° C. Stir the mixture at 3° C. for 5 minutes then add tetrahydrofuran (150 mL) and brine (30 mL) and warm the mixture to 12° C. Transfer the resulting biphasic solution to a separatory funnel and separate the phases. Discard the aqueous phase. Concentrate the organic phase to a solid under reduced pressure (15-25 mm). Suspend the solid in water (100 mL) and stir the suspension at 23° C. for 15 minutes. Filter the suspension and rinse the filter cake with water (20 mL) three times. Suspend the filter cake in methyl-tert-butyl ether (45 mL) and stir at 23° C. for 10 minutes. Filter the suspension and air-dry the filter cake for 5 minutes. Vacuum (15-25 mm) dry the filter cake at 45° C. to provide the title compound (12.9 g, 0.0467 moles) in 83.6% yield. $^1$H NMR (DMSO-$d_6$, 500.0 MHz): δ 7.72 (br. s, 1H); 7.62 (app. d, 2H, J=8); 7.53-7.42 (m, 3H); 7.39 (dt, 1H, J=1, 8); 7.34 (br, s, 1H).

Preparation 61

Preparation of 2-(4-bromophenyl)benzenecarbonitrile

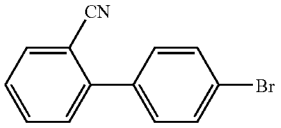

Add 2-(4-bromophenyl)benzamide (12.0 g, 0.04345 moles, preparation 60), acetonitrile (120 mL), and triethylamine (9.23 grams, 0.0912 moles) to a 250 mL 3-neck round-bottom flask equipped with a magnetic stirrer, internal temperature probe, ice-water bath, and addition funnel. Cool the contents of the 250 mL 3-neck round-bottom flask to 3° C. Add trifluoroacetic anhydride (9.6 grams, 0.0456 moles) to the reaction mixture via the addition funnel over 5 minutes. The reaction mixture warms to 12-15° C. Remove the ice-water bath, and allow the reaction mixture to warm to 20° C. and stir the mixture for 45 minutes. Add additional trifluoroacetic anhydride (0.8 g, 0.0038 moles) and stir the reaction mixture at 22° C. for 75 minutes. Add water (120 mL) and cool the resulting suspension to 3° C. Stir the suspension at 3° C. for 15 minutes. Collect the precipitate by filtration and rinse the filter cake three times with 15 mL of 30% acetonitrile and 70% water. Vacuum (15-25 mm) dry the filter cake at 45° C. to provide the title compound (10.6 g, 0.041 moles) in 94.5% yield. $^1$H NMR ($CDCl_3$, 500.0 MHz): δ 7.75 (app. d, 1H, J=8); 7.64 (td, 1H, J=1.5, 7.5); 7.61 (app. d, 2H, J=8.5); 7.5-7.4 (m, 4H).

Additional Preparation of 2-(4-bromophenyl)benzenecarbonitrile

A mixture of the 2-iodobenzenecarbonitrile, triphenylphosphine, $C_6$PyCl (2 mL) and solvent (16 mL) is degassed three times by alternating house vacuum (15 seconds) and nitrogen. The mixture is heated to 80-90° C. under nitrogen and then allowed to cool to rt (or under 35° C.). 2M sodium carbonate is added, followed by addition of 4-bromophenylboronic acid. The mixture is heated at 79° C. (heptane), 80° C. (DME), or 90° C. (toluene and 1-propanol). Periodically, an aliquot of the reaction mixture is syringed out and processed with aqueous HCl/MTBE for HPLC (Hitachi 7000 series, SB phenyl column, 218 nm, 75% MeCN/25% water with 0.05% TFA, 1 mL/min). The reaction is stopped when the boronic acid is consumed and further heating does not increase the amount of product (see Table for time). Upon cooling to rt the mixture is diluted with ~30 mL MTBE to dissolve the product; 1-propanol reaction is first concentrated before adding MTBE. The mixture is washed twice with water and once with brine. The dried (sodium sulfate) organic solution is concentrated on the rotovap. The residual solid is dissolved with heating in 25 mL of pre-boiled heptane. Undissolved brown material is removed by filtering the hot solution through a hot glass funnel/warm filter paper into a hot Erlenmeyer, rinsing the filter paper several times with a total of 5 mL of hot heptane. Filtration is done hot to prevent the product from crashing out on the filter paper.

Preparation 62

Preparation of propane-2-sulfonic acid {(2-[4-iodo-phenyl —(S,S-cyclopentyl}-amide

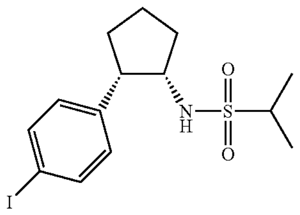

The title compound can be prepared by one of ordinary skill in the art as disclosed in WO 01/42203, example 17B [note: the structure of example 17B in WO 01/42203, drawn as the R,R isomer, is incorrect. The correct structure is provided above as the S,S isomer.).

Preparation 63

Preparation of phenyl-sulfonic acid {2-[4-(4,4,5,5-tetramethyl-[1,3,2]dioxaborolan-2-yl)-phenyl]-ethyl}-amide

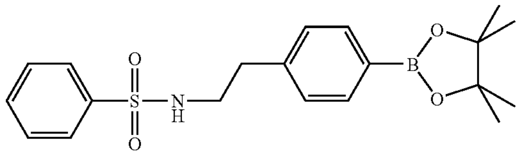

Prepare the title compound in a manner analogous to the procedure set forth in Preparation 62, using 2-[4-(4,4,5,5-tetramethyl-[1,3,2]dioxaborolan-2-yl)-phenyl]-ethylamine (567 mg, 2 mmol), DBU (0.9 mL, 6 mmol) and benzene sulfonyl chloride (0.306 mL, 2.4 mmol). Mass spectrum=386.1 (M−1).

Preparation 64

Preparation of 4'-cyanophenyl-sulfonic acid {2-[4-(4,4,5,5-tetramethyl-[1,3,2]dioxaborolan-2-yl)-phenyl]-ethyl}-amide

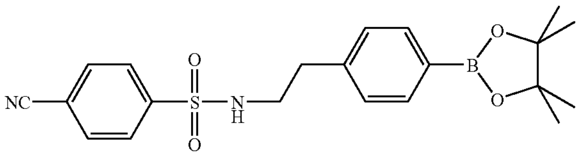

Add 2-[4-(4,4,5,5-tetramethyl-[1,3,2]dioxaborolan-2-yl)-phenyl]-ethylamine (567 mg, 2 mmol) and triethylamine (0.836 mL, 6 mmol) to tetrahydrofuran (10 mL). Next add 4-cyanobenzene sulfonyl chloride (484 mg, 2.4 mmol) and let the reaction stirred at room temperature. After 3 hours, pour the reaction mixture into HCl (1N) and extract organic with EtOAc (3×30 ml), wash the combined organic layer with water (30 mL), and brine (50 mL), dry over magnesium sulfate, filter and concentrate under reduced pressure. Recrystallize the crude product from EtOAc:Hexanes to provide the crystalline title compound (714 mg, 87%). Mass spectrum (ES+)=411.0 (M−1).

Preparation 65

Preparation of 3'-cyanophenyl-sulfonic acid {2-[4-(4,4,5,5-tetramethyl-[1,3,2]dioxaborolan-2-yl)-phenyl]-ethyl}-amide

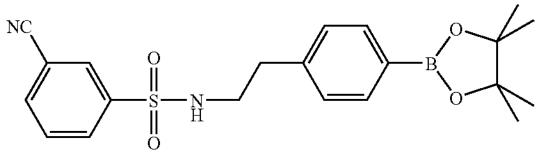

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.836 mL, 6 mmol) and 3-cyanobenzene sulfonyl chloride (484 mg, 2.4 mmol). Mass spectrum (ES+)=411.1 (M−1).

Preparation 66

Preparation of 2'-cyanophenyl-sulfonic acid {2-[4-(4,4,5,5-tetramethyl-[1,3,2]dioxaborolan-2-yl)-phenyl] ethyl}-amide

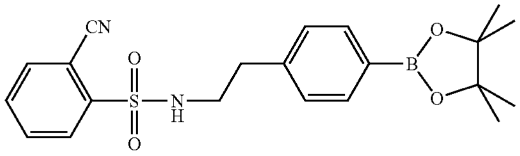

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.836 mL, 6 mmol) and 3-cyanobenzene sulfonyl chloride (484 mg, 2.4 mmol). Mass spectrum (ES+)=411.0 (M−1).

Preparation 67

Preparation of 2'-fluorophenyl-sulfonic acid {2-[4-(4,4,5,5-tetramethyl-1,3,2]dioxaborolan-2-yl)-phenyl-ethyl}-amide

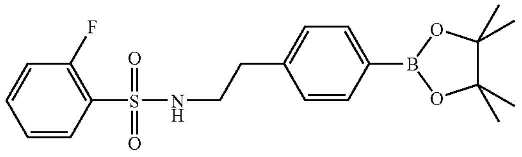

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.836 mL, 6 mmol) and 2-fluorobenzene sulfonyl chloride (467 mg, 2.4 mmol). Mass spectrum (ES+)=406.0 (M+1).

Preparation 68

Preparation of 3'-fluorophenyl-sulfonic acid {2-[4-(4,4,5,5-tetramethyl-[1,3,2]dioxaborolan-2-yl)-phenyl]-ethyl}-amide

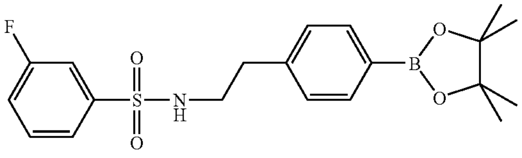

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.836 mL, 6 mmol) and 2-fluorobenzene sulfonyl chloride (467 mg, 2.4 mmol). Mass spectrum (ES+)=406.0 (M+1).

Preparation 69

Preparation of 4'-fluorophenyl-sulfonic acid {2-[4-(4,4,5,5-tetramethyl-[1,3,2]dioxaborolan-2-yl)-phenyl]-ethyl}-amide

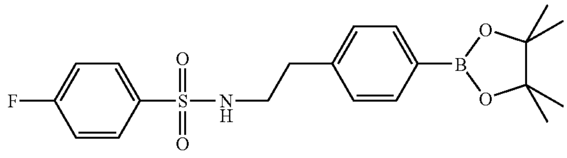

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.0.836 mL, 6 mmol) and 2-fluorobenzene sulfonyl chloride (467 mg, 2.4 mmol). Mass spectrum (ES+)=406.0 (M+1).

Preparation 70

Preparation of 4'-chlorophenyl-sulfonic acid {2-[4-(4,4,5,5-tetramethyl-[1,3,2]dioxaborolan-2-yl)-phenyl]-ethyl}-amide

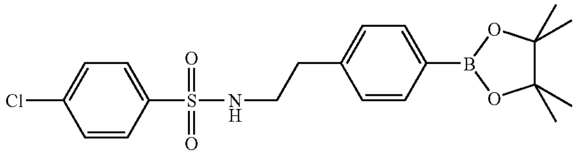

Prepare the title compound in a manner analogous to the procedure set forth in Preparation 62, using 2-[4-(4,4,5,5-tetramethyl-[1,3,2]dioxaborolan-2-yl)-phenyl]-ethylamine (567 mg, 2 mmol), DBU (0.9 mL, 6 mmol) and 2-fluorobenzene sulfonyl chloride (506 mg, 2.4 mmol). Mass spectrum=420.0 (M−1).

Preparation 71

Preparation of 3'-chlorophenyl-sulfonic acid {2-[4-(4,4,5,5-tetramethyl-[1,3,2]dioxaborolan-2-yl)-phenyl]-ethyl}-amide

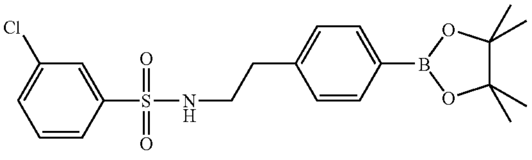

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.0.836 mL, 6 mmol) and 2-fluorobenzene sulfonyl chloride (506 mg, 2.4 mmol). Mass spectrum=422.0 (M+1).

Preparation 72

Preparation of 2'-chlorophenyl-sulfonic acid {2-[4-(4,4,5,5-tetramethyl-[1,3,2]dioxaborolan-2-yl)-phenyl]-ethyl}-amide

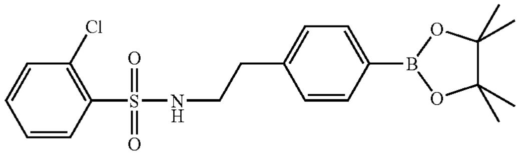

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.836 mL, 6 mmol) and 2-fluorobenzene sulfonyl chloride (506 mg, 2.4 mmol). Mass spectrum=422.0 (M+1).

Preparation 73

Preparation of N,N-dimethylamino-sulfonic acid {2-[4-(4,4,5,5-tetramethyl-[1,3,2]dioxaborolan-2-yl)-phenyl]-ethyl}-amide

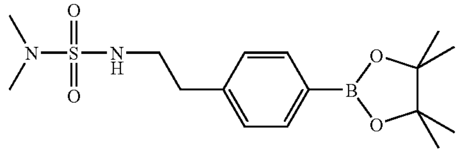

Prepare the title compound in a manner analogous to the procedure set forth in Preparation 64, using 2-[4-(4,4,5,5-tetramethyl-[1,3,2]dioxaborolan-2-yl)-phenyl]-ethylamine (567 mg, 2 mmol), triethylamine (0.837 mL, 6 mmol) and dimethylsulfamoyl chloride chloride (0.256 mL, 2.4 mmol). Mass spectrum=355.1 (M+1).

Preparation 74

Preparation of trifluoromethane-2-sulfonic acid {2-[4-(4,4,5,5-tetramethyl-[1,3,2]dioxaborolan-2-yl)-phenyl]-ethyl}-amide

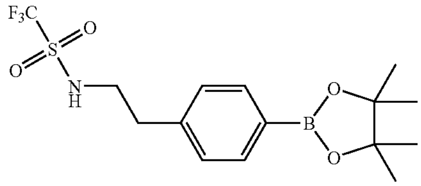

Prepare the title compound in a manner analogous to the procedure set forth in Preparation 64, using 2-[4-(4,4,5,5-tetramethyl-[1,3,2]dioxaborolan-2-yl)-phenyl]-ethylamine (1.1 g, 4 mmol), triethylamine (1.67 mL, 12 mmol) and trifluoromethylsulfamoyl chloride chloride (0.511 mL, 4.8 mmol). Mass spectrum=378.1 (M−1).

Preparation 75

Preparation of 4-tolulyl-sulfonic acid {2-[4-(4,4,5,5-tetramethyl-[1,3,2]dioxaborolan-2-yl)-phenyl]-ethyl}-amide

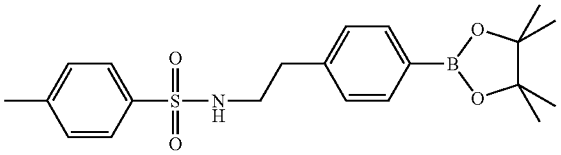

Prepare the title compound in a manner analogous to the procedure set forth in Preparation 62, using 2-[4-(4,4,5,5-tetramethyl-[1,3,2]dioxaborolan-2-yl)-phenyl]-ethylamine (500 mg, 1.76 mmol), DBU (0.79 mL, 5.28 mmol) and p-toluenesulfonylchloride (503 mg, 2.64 mmol). Mass spectrum=402.0 (M+1).

Preparation 76

Preparation of 4-methoxyphenyl-sulfonic acid {2-[4-(4,4,5,5-tetramethyl-[1,3,2]dioxaborolan-2-yl)-phenyl]-ethyl}-amide

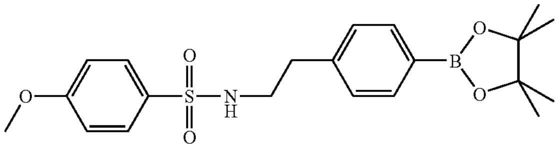

Prepare the title compound in a manner analogous to the procedure set forth in Preparation 62, using 2-[4-(4,4,5,5-tetramethyl-[1,3,2]dioxaborolan-2-yl)-phenyl]-ethylamine (500 mg, 1.76 mmol), DBU (0.79 mL, 5.28 mmol) and 4-methoxybenzenesulfonylchloride (545 mg, 2.64 mmol). Mass spectrum=418.1 (M+1).

Preparation 77

Preparation of 4-acetylphenyl-sulfonic acid {2-[4-(4,4,5,5-tetramethyl-[1,3,2]dioxaborolan-2-yl)-phenyl]-ethyl}-amide

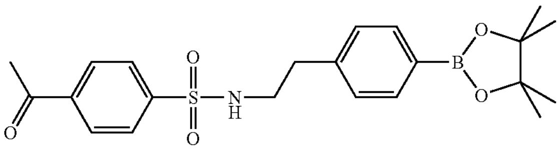

Prepare the title compound in a manner analogous to the procedure set forth in Preparation 62, using 2-[4-(4,4,5,5-tetramethyl-[1,3,2]dioxaborolan-2-yl)-phenyl]-ethylamine (500 mg, 1.76 mmol), DBU (0.79 mL, 5.28 mmol) and 4-acetylbenzenesulfonylchloride (577 mg, 2.64 mmol). Mass spectrum=430.0 (M+1).

Preparation 78

Preparation of 2-thiophyl-sulfonic acid{2-[4-(4,4,5,5-tetramethyl-[1,3,2]dioxaborolan-2-yl)-phenyl]-ethyl}-amide

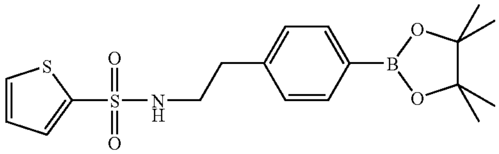

Prepare the title compound in a manner analogous to the procedure set forth in Preparation 62, using 2-[4-(4,4,5,5-tetramethyl-[1,3,2]dioxaborolan-2-yl)-phenyl]-ethylamine (500 mg, 1.76 mmol), DBU (0.79 mL, 5.28 mmol) and 2-thiophenesulfonylchloride (482 mg, 2.64 mmol). Mass spectrum=392.0 (M−1).

Preparation 79

Preparation of N-[2-(4-Bromo-phenyl sulfanyl)-ethyl]-methanesulfonamide

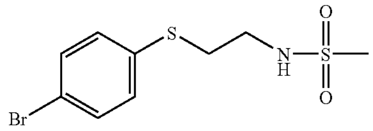

Step A: Add 4-bromothiophenol (12.35 g, 65.3 mmol) and potassium carbonate (27.0 g, 195.9 mmol) in acetone (300 mL). Next, add N-(2-bromoethyl)phthalimide and stir the reaction at room temperature. After 24 hours, concentrate the reaction and pour into water. Extract with ethyl acetate (3×100 mL). Wash the combined organics with HCl (1N), water (1×150 mL), and brine (1×150 mL), dry over magnesium sulfate, filter and concentrate under reduced pressure to provide product in a quantitative yield which is used in step B.

Step B: Add the product of step A (2-(4-bromo-phenylsulfanyl)-ethylamine, 23.6 g, 65.1 mmol) and hydrazine (6.1 mL, 195.4 mmol) in methanol:THF (300 mL, 1:1) and stir the reaction at room temperature. After 8 hours, filter off the precipitate and concentrate the crude product. Add EtOH to the product, filter off the impurity and concentrate the crude product. Add MeOH:dichloromethane to the product, filter off the impurity and concentrate the crude product to yield 11.5 g of the product that is used as is in step C.

Step C: Prepare the title compound in a manner analogous to the procedure set forth in Preparation 62, using N-2-(4-bromo-thiophenyl)ethylamine (1 g, 4.3 mmol), DBU (1.9 mL, 12.9 mmol) and methanesulfonyl chloride (0.4 mL, 5.2 mmol). Mass spectrum =309.9 (M−1).

Preparation 80

Preparation of N-[2-(4-Bromo-phenyl sulfanyl)-ethyl]-i-propanesulfonamide

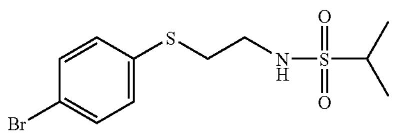

Prepare the title compound in a manner analogous to the procedure set forth in Preparation 79, using 2-(4-bromo-phenylsulfanyl)-ethylamine) (465 mg, 2.0 mmol), triethylamine (0.836 mL, 6.0 mmol) and i-propylsulfonylchloride (2.51 mL, 2.4 mmol). Mass spectrum=337.9 (M−1).

Preparation 81

Preparation of i-propyl-sulfonic acid {2-[4-bromophenyl]-ethyl}-amide

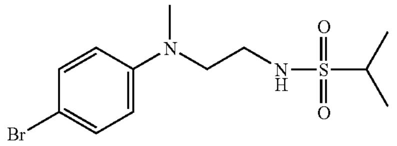

Step A: Add 4-bromoaniline (5 g, 29 mmol) and sodium cyanide (1.42 g, 29 mmol) in methanol (20 mL). The mixture is cooled to 0° C. Next, add HCl (5.8, 5N) and formaldehyde (2.35 mL, 29 mmol, 30%) and stir the reaction at 0° C. for 3 hours and at room temperature for 12 hours. Pour into water. Extract with methylene chloride (3×75). Combine the organic extracts, dry over anhydrous magnesium sulfate, filter, and concentrate under reduced pressure. Purify the residue by flash chromatography (silica gel), eluting with ethyl acetate: hexanes (25%) to provide 3.8 g (62%) of the title compound that is used as is in step B.

Step B: Add the product of step B (3.8 g, 18 mmol) formaldehyde (15 mL, excess mmol) and formic acid (15 mL, Xs mmol) and stir the reaction at reflux. After 3 hours, pour into water. Extract with ethyl acetate (3×100). Combine the organic extracts, dry over anhydrous magnesium sulfate, filter, and concentrate under reduced pressure. Purify the residue by flash chromatography (silica gel), eluting with ethyl acetate:hexanes (25%, isocratic) to provide 580 mg (14%) of the title compound that is used as is in step C.

Step C. Add the product of step B (580 mg, 2.57 mmol) and borane dimethylsulfide (0.31 mL, 3.09 mmol) in THF and stir the reaction at reflux. After 12 hours, pour into water cool and concentrate. Add saturated solution of HCl in methanol dropwise. Collect the precipitate by concentration. Triturate with diethyl ether to provide 667 mg (98%) of the desired amine that is used in step D.

Step D: Prepare the title compound in a manner analogous to the procedure set forth in Preparation 62, using the product from step C (A-05235-50) (667 mg, 2.5 mmol), DBU (1.1 mL, 7.5 mmol) and i-propylsulfonylchloride (0.338 mL, 3 mmol). Mass spectrum=336.9 (M+1).

Preparation 82

Preparation of N-[2-(4-Bromo-phenoxy)-ethyl]-i-propanesulfonamide

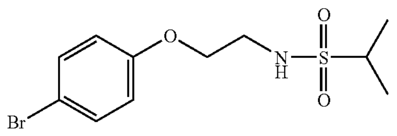

Step A: Add 4-bromophenol (5.0 g, 28.9 mmol) and potassium carbonate (12.0 g, 86.3 mmol) in acetone (100 mL) and stir for 10 minutes. Next, add bromoacetonitrile (2.4 mL, 34.7 mmol) and stir the reaction at room temperature. After 12 hours, concentrate the reaction and pour into water. Extract with ethyl acetate (3×100 mL). Wash with water (1×150 mL), and brine (1×150 mL), dry over magnesium sulfate, filter and concentrate under reduced pressure to provide crude product Purify the residue by flash chromatography (silica gel), eluting with 20% ethyl acetate:hexanes (isocratic) to provide 6 g (98%) of the desired product that is used in step B.

Step B: Add the product of step A (6.0 g, 28.3 mmol) and boron dimethyl sulfide (3.1 mL, 31.1 mmol) in THF (100 mL) and stir the reaction at reflux temperature. After 12 hours, cool and concentrate the reaction. Add saturated solution of HCl in methanol to the crude residue slowly and concentrate the solution to get the HCl salt of the corresponding amine. Triturate with diethyl ether and dry the product to provide quantitative yield of the desired product, N-2-(4-bromo-phenoxy)ethylamine, used in step C.

Step C: Prepare the title compound in a manner analogous to the procedure set forth in Preparation 62, using N-2-(4-bromo-phenoxy)ethylamine (1 g, 3.9 mmol), DBU (1.7 mL, 11.7 mmol) and i-propylsulfonylchloride (0.535 mL, 4.75 mmol). Mass spectrum=323.9 (M+1).

Preparation 83

Preparation of N-[2-((4(4,4,5,5-tetramethyl)-[1,3,2] dioxaborolan-2-yl) phenyl sulfanyl) -ethyl]-i-propanesulfonamide

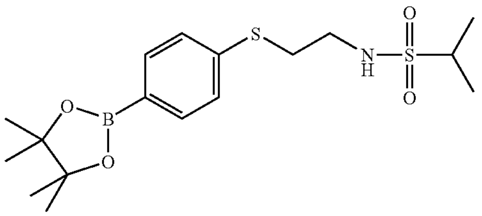

Add bis(pinacolate) diborane (412 mg, 1.62 mmol), product of preparation X-2 (A-05235-134) (500 mg, 1.48 mmol, [1,1'-bis(diphenylphosphino)ferrocene]dichloro-palladium(II) complex with methylene chloride (1:1) (0.036 g, 0.44 mmol), and potassium acetate (726 mg, 7.4 mmol) in dimethylformamide and heat to 80° C. After 3 hours, cool and pour into water. Extract with ethyl acetate. Wash the combined organics with water (3×30 mL) and brine (2×50 mL), dry over magnesium sulfate, filter and concentrate under reduced pressure. Purify the residue by flash chromatography (silica gel), eluting with ethyl 25% acetate:hexanes (isocratic) to provide 490 mg (86%) of the title compound.

Method A

Scheme I, step A: Combine the corresponding substituted benzaldehyde (1.0 mmol, structure 1), 4-toluenesulfonylacetonitrile (1.0 mmol, structure 2), a catalytic amount of piperidine (0.05 mmol) and acetic acid (0.2 mmol) in toluene, and heat to 110° C. with stirring. After 1-18 hours, cool the reaction mixture to room temperature and collect the solid by vacuum filtration. Rinse the solid with toluene and dry by vacuum filtration to provide the acrylonitrile of structure (3).

Scheme I, step B: Add the acrylonitrile (1.0 mmol, structure 3, prepared directly above) to DBU (4.0 mol) in THF and stir at room temperature. After ten minutes, add ethyl isocyanoacetate (2.0 mmol, structure 4, Y represents ethyl). After stirring for 3 to 18 hours, add water to the reaction mixture, and extract with ethyl acetate. Combine the organic layers and wash with 1N HCl, water and brine. Dry the organic phase over anhydrous magnesium sulfate, filter, and concentrate under reduced pressure. Recrystallize the residue with ethyl acetate:hexanes to provide the pyrrole of Formula Ia wherein Y represents ethyl.

Scheme I, step C: Add the pyrrole (1.0 mol, Formula IIa, prepared directly above) to potassium carbonate (1.1 mmol) in DMSO and stir at room temperature. After 10 minutes, add the alkylating agent (1.2 mmol, structure 5, wherein Hal is iodide, such as methyl iodide, ethyl iodide and n-propyl iodide). After stirring the reaction mixture for 6-18 hours, add water and extract with ethyl acetate. Combine the organic extracts and wash with 1N HCl, water and brine. Dry the organic phase over anhydrous magnesium sulfate, filter, and concentrate under reduced pressure. Recrystallize the residue from ethyl acetate:hexanes to provide the pyrrole of Formula IIb.

Prepare the following compounds listed in Table E-1 in a manner analogous to the procedure set forth in Method A.

TABLE E-1

| Ex. | Structure | Data | S.M. |
|---|---|---|---|
| E-1 | 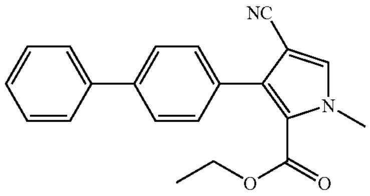 | mass spectrum (m/e): 331.2 (M + 1). | 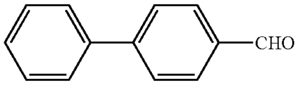 |
| E-2 | 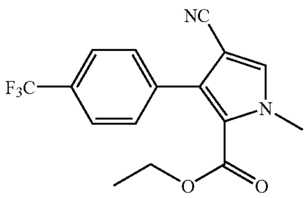 | | 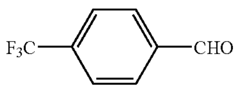 |

TABLE E-1-continued
| Ex. | Structure | Data | S.M. |
|---|---|---|---|
| E-3a (See also E-3b infra) | 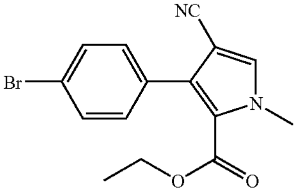 | mass spectrum (m/e): 333.1 (MS EI+). | 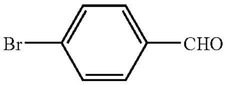 |
| E-4 | 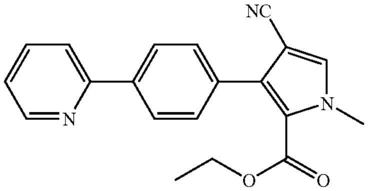 | $^1$H NMR (400 Mhz; $CDCl_3$) δ 8.72(d, 1H), 8.03(d, 2H), 7.78(m, 2H), 7.46(d, 2H), 7.27(s, 1H), 7.22-7.26(m, 1H), 4.12(q, 2H), 4.02(s, 3H), 1.04(t, 3H). | 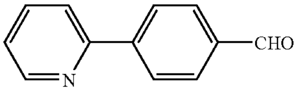 |
| E-5 | 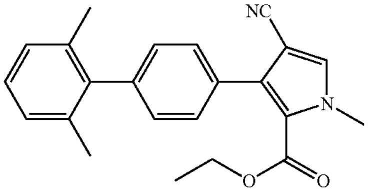 | mass spectrum (m/e): 359.3 (M − 1). | 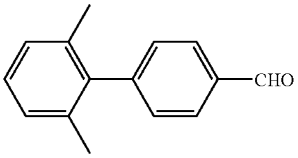 |
| E-6a (See also E-6b infra) | 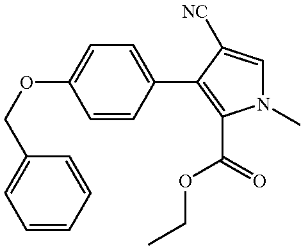 | mass spectrum (m/e): 361.1 (M + 1). | 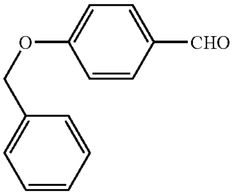 |
| E-7 | 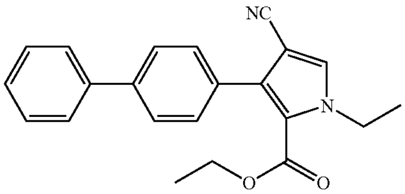 | mass spectrum (m/e): 345.4 (M + 1). | 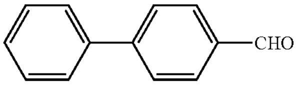 |
| E-8 | 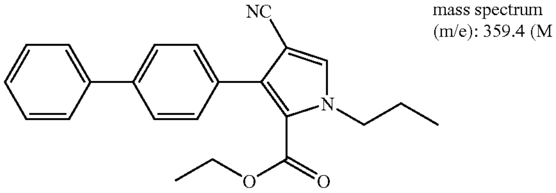 | mass spectrum (m/e): 359.4 (M + 1). | 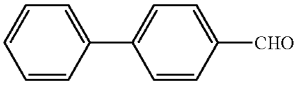 |
| E-9 | 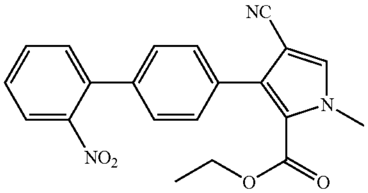 | Mass spectrum (m/e): 379.3 (M + 18). | 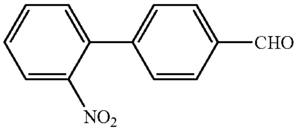 |

TABLE E-1-continued

| Ex. | Structure | Data | S.M. |
| --- | --- | --- | --- |
| E-10 | 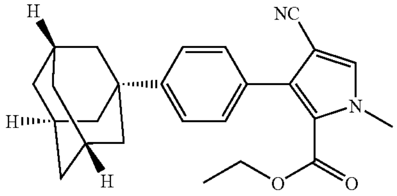 | Mass spectrum (m/e): 389.2 (M + 1) | 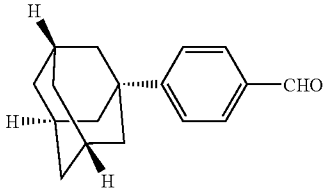 |

EXAMPLE E-3b

Additional Preparation of 3-(4-bromo-phenyl)-4-cyano-1-methyl-1H-pyrrole-2-carboxylic acid ethyl ester

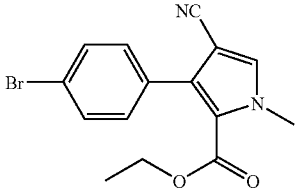

Preparation of 3-(4-bromo-phenyl)-2-(toluene-4-sulfonyl)-acrylonitrile

Scheme I, step A: A solution of 4-bromobenzaldehyde (100.00 g, 0.54 mol), p-toluenesulphonylacetonitrile (105.52 g, 0.54 mol), piperidine (2.70 mL, 0.027 mol), and acetic acid (9.30 mL, 0.162 mol) in toluene (1,000 mL) is heated at reflux for 1 hour, using a Dean-Stark trap to remove water. As the reaction mixture cools to room temperature, a yellow solid crashes out of solution. The solid is collected by vacuum filtration, washed with fresh toluene, and dried under vacuum filtration to afford the title compound (142.26 g, 72% yield) as a yellow solid: $^1$H NMR (500 MHz; $CDCl_3$) δ 2.47 (s, 3H), 7.41 (d, 2H), 7.64 (d, 2H), 7.76 (d, 2H), 7.88 (d, 2H), 8.14 (s, 1H).

Preparation of 3-(4-bromo-phenyl)-4-cyano-1H-pyrrole-2-carboxylic acid ethyl ester Scheme I, step B: A solution of 3-(4-bromo-phenyl)-2-(toluene-4-sulfonyl)-acrylonitrile (38.76 g, 0.107 mol, prepared directly above) in anhydrous THF (500 mL) is treated with DBU (65.00 mL, 0.434 mol), followed by ethyl isocyanoacetate (25.00 g, 0.214 mol). The resulting dark-brown reaction mixture is allowed to stir at room temperature for 3 hours. The reaction mixture is poured into water (1,000 mL) and extracted with EtOAc (3×250 mL each). The combined organics are washed with 1 N HCl (250 mL), water (250 mL), brine (250 mL), dried over anhydrous $Na_2SO_4$, filtered, then concentrated in vacuo to afford an off-white solid. The solid is dissolved in a minimum amount of EtOAc, then treated with excess hexanes, causing a solid to crash out. The solid is recovered by vacuum filtration, washed with hexanes, and dried under vacuum filtration to afford the title compound (23.90 g, 69.9% crude yield) as a off-white solid: $^1$H NMR (500 MHz; $CDCl_3$) δ 1.22 (t, 3H), 4.26 (q, 2H), 7.39 (d, 2H), 7.45 (d, 1H), 7.55 (d, 2H), 9.70 (bs, 1H).

Preparation of Final Title Compound

Scheme I, step C: A solution of 3-(4-bromo-phenyl)-4-cyano-1H-pyrrole-2-carboxylic acid ethyl ester (41.59 g, 0.130 mol) in DMSO (400 mL) is treated with $K_2CO_3$ (19.76 g, 0.143 mol). The resulting solution is allowed to stir at room temperature for several minutes, and then treated with iodomethane (9.75 mL, 0.156 mol). The resulting reaction mixture is allowed to stir under nitrogen at room temperature overnight, then poured into water (2,000 mL) and extracted with EtOAc (4×500 mL each). The combined organics are washed with water (2×1,000 mL each), brine (700 mL), dried over anhydrous $MgSO_4$, filtered, then concentrated in vacuo to afford an off-white solid. The solid is dissolved in a minimum amount of EtOAc, then treated with excess hexanes, causing a solid to crash out. The solid is recovered by vacuum filtration, washed with hexanes, and dried under vacuum filtration to afford the final title compound, 3-(4-bromo-phenyl)-4-cyano-1-methyl-1H-pyrrole-2-carboxylic acid ethyl ester, (33.45 g, 77% yield) as a off-white solid: $^1$H NMR (500 MHz; $CDCl_3$) δ 1.07 (t, 3H), 3.97 (s, 3H), 4.13 (q, 2H), 7.23 (s, 1H), 7.26 (d, 2H), 7.52 (d, 2H); MS(ES): m/z 333.1 ($M+H^+$). Anal. Calcd. for $C_{15}H_{13}BrN_2O_2$: C 54.07; H 3.93; N 8.40; Br 23.98. Found C 53.91; H 3.93; N 8.35; Br 24.06.

EXAMPLE E-6b

Additional Preparation of 3-(4-benzyloxy-phenyl)-4-cyano--methyl-1H-pyrrole-2-carboxylic acid ethyl ester

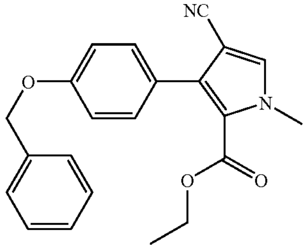

Preparation of 3-(4-benzyloxy-phenyl)-2-(toluene-4-sulfonyl)-acrylonitrile

Scheme I, step A: A solution of 4-benzyloxybenzaldehyde (174.37 g, 0.821 mol), p-toluenesulphonylacetonitrile (160.40 g, 0.821 mol), piperidine (4.10 mL, 0.041 mol), and acetic acid (14.10 mL, 0.246 mol) in toluene (1,500 mL) is heated at reflux for 2 hours, using a Dean-Stark trap to remove water. The resulting reaction mixture is then allowed to cool to room temperature, and then concentrated in vacuo to afford a solid residue. The solid is swirled in excess hexanes, then collected by vacuum filtration, drying under vacuum filtration overnight to afford the title compound (305.30 g, 95% yield) as a light yellow solid: $^1$H NMR (500 MHz; $CDCl_3$) δ 8.11 (s, 1H), 7.89 (dd, 4H), 7.42-7.37 (m, 7H), 7.04 (d, 2H), 5.14 (s, 2H), 2.45 (s, 3H); MS(FS) m/z 390.1 ($M^+$+H).

Preparation of 3-(4-benzyloxy-phenyl)-4-cyano-1H-pyrrole-2-carboxylic acid ethyl ester Scheme I, step B: A solution of 3-(4-benzyloxy-phenyl)-2-(toluene-4-sulfonyl)-acrylonitrile (250.43 g, 0.643 mol, prepared directly above) in anhydrous THF (2,500 mL) is treated with DBU (385.00 mL, 2.574 mol), followed by ethyl isocyanoacetate (150.00 g, 1.286 mol). The resulting reaction mixture is allowed to stir at room temperature for 2 hours. The reaction mixture is poured into water (4,000 mL) and the resulting solution is separated into 2 equal parts. Each part is extracted with EtOAc (3×800 mL each), then the combined organics are washed with 1N HCl (1,000 mL), water (1,000 mL), and brine (1,000 mL), dried over anhydrous $MgSO_4$, filtered, then concentrated in vacuo to afford an off-white solid. The solid is slurried in EtOAc (200 mL), then treated with excess hexanes, causing a solid to precipitate. The solid is recovered by vacuum filtration, washing with hexanes, and drying under vacuum filtration to afford the title compound (204.21 g, 91% yield) as an off-white solid: $^1$H NMR (500 MHz; $CDCl_3$) δ 9.44 (bs, 1H), 7.48-7.45 (m, 4H), 7.42-7.38 (m, 3H), 7.36-7.32 (m, 1H), 7.03 (d, 2H), 5.11 (s, 2H), 4.25 (q, 2H), 1.22 (t, 3H); MS(ES) m/z 347.1 ($M^+$+H).

Preparation of Final Title Compound

Scheme I, step C: A solution of 3-(4-benzyloxy-phenyl)-4-cyano-1H-pyrrole-2-carboxylic acid ethyl ester (266.70 g, 0.770 mol) in DMSO (2,000 mL) is treated with $K_2CO_3$ (117.06 g, 0.847 mol). The resulting solution is allowed to stir at room temperature for several minutes, then treated with iodomethane (58.00 mL, 0.931 mol). The resulting reaction mixture is allowed to stir at room temperature overnight. An additional 0.5 eq of iodomethane (24.00 mL, 0.385 mol) and 0.6 eq of $K_2CO_3$ (63.85 g, 0.462 mol) are added to the reaction. The reaction mixture is allowed to stir at room temperature for 2 hours. The reaction mixture is divided into 2 equal portions and each portion is poured into water (2,000 mL) and extracted with EtOAc (3×700 mL each). The combined organics are washed with $H_2O$ (2×1000 mL each), dried over anhydrous $MgSO_4$, filtered, then concentrated in vacuo to afford a residue. The residue is slurried in EtOAc (300 mL), then treated with excess hexanes, causing a solid to precipitate. The solid is recovered by vacuum filtration, washing with hexanes, and drying under vacuum filtration to afford the title compound, 3-(4-benzyloxy-phenyl)-4-cyano-1-methyl-1H-pyrrole-2-carboxylic acid ethyl ester, (184.73 g, 66% yield) as a light-brown solid: $^1$H NMR (500 MHz; $CDCl_3$) δ 7.46 (d, 2H), 7.39 (m, 2H), 7.32 (m, 3H), 7.24 (s, 1H), 7.00 (d, 2H), 5.10 (s, 2H), 4.13 (q, 2H), 3.95 (s, 3H), 1.06 (t, 3H); MS(ES): m/z 361.1 ($M^+$+H).

EXAMPLE E-11

Preparation of 4-cyano-3-(4-hydroxyphenyl)-1-methyl-1H-pyrrole-2-carboxylic acid ethyl ester

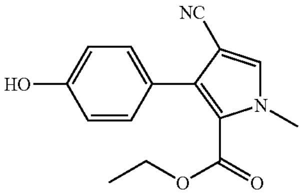

Scheme II, step A: Add a 1:2 ethanol:THF mixture to 20% palladium hydroxide on carbon (catalytic, 29.4 g) followed by 3-(4-benzyloxy-phenyl)-4-cyano-1-methyl-1H-pyrrole-2-carboxylic acid ethyl ester (97.93 g, 0.271 mol, prepared in examples E-6a or E-6b). Subject the reaction to 344.74 kPa (50 psi) of hydrogen gas. After 18 hours, filter and concentrate under reduced pressure. Purify the residue by flash chromatography eluting with ethyl acetate:hexanes to provide the title compound. Mass spectrum (m/e): 271.1 (M+1).

Method B

Scheme II, step B: Add sodium hydride (1.2 mmol) to 4-cyano-3-(4-hydroxyphenyl)-1-methyl-1H-pyrrole-2-carboxylic acid ethyl ester (1.0 mmol, prepared in example E-11) in DMF at room temperature with stirring. After 30 minutes, add alkylating agent (1.5 phenol, structure 6). After 1-18 hours, pour the reaction mixture into water and extract with ethyl acetate. Combine the organics and wash with water and brine, dry over anhydrous magnesium sulfate, filter, and concentrate under reduced pressure. Purify the residue by flash chromatography eluting with ethyl acetate:hexanes to provide the compound of Formula IIe.

Prepare the following compound listed in Table E-2 in a manner analogous to the procedure set forth in Method B from 4-cyano-3-(4-hydroxyphenyl)-1-methyl-1H-pyrrole-2-carboxylic acid ethyl ester (prepared in example E-11).

TABLE E-2

| Ex. | Structure | Data: |
|---|---|---|
| E-12 | 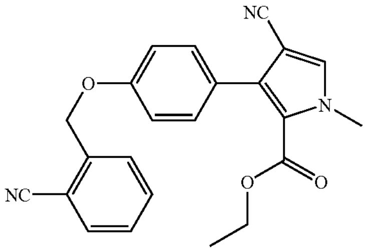 | $^1$H NMR (400 MHz; $CDCl_3$) δ -7.71(d, 2H), 7.62(t, 1H), 7.43(t, 1H), 7.33(d, 2H), 7.23(s, 1H), 7.02(d, 2H), 5.36(s, 2H), 4.10(q, 2H), 3.99(s, 3H), 1.05(t, 3H). |

Method CI

Scheme III: Add 3-(4-bromo-phenyl)-4-cyano-1-methyl-1H-pyrrole-2-carboxylic acid ethyl ester (1.0 mmol, prepared in example E-3a or E-3b), the corresponding aryl boronic acid (1.1 mmol, structure 7), tetrakis(triphenylphosphine)palladium (0.03-0.10 mmol), and 2M sodium carbonate (3-5 mmol) into 1,4-dioxane and heat to 60-100° C. with stirring. After 1-18 hours, cool the reaction mixture to room temperature and add water. Extract the quenched reaction with ethyl acetate. Combine the organic extracts, wash with water and brine, dry over anhydrous magnesium sulfate, filter and concentrate under reduced pressure. Purify the residue by flash chromatography eluting with ethyl acetate:hexanes to provide the aryl coupled compound of Formula IIg.

Method CII

Scheme IIIa: Add 4-cyano-5-ethyl-1-methyl-3-(4-trifluoromethanesulfonyloxyphenyl)-1H-pyrrole-2-carboxylic acid ethyl ester (1.0 mmol, prepared in example E-97a or E-97b), the corresponding aryl boronic acid (1.1 mmol, structure 7), tetrakis(triphenylphosphine)palladium (0.03-0.10 mmol), and 2M sodium carbonate (3-5 mmol) into 1,4-dioxane and heat to 60-100° C. with stirring. After 1-18 hours, cool the reaction mixture to room temperature and add water. Extract the quenched reaction with ethyl acetate. Combine the organic extracts, wash with water and brine, dry over anhydrous magnesium sulfate, filter and concentrate under reduced pressure. Purify the residue by flash chromatography eluting with ethyl acetate:hexanes to provide the aryl coupled compound of Formula IIg.

Alternative Method CII

Scheme IIIa: Add 4-cyano-5-ethyl-1-methyl-3-(4-trifluoromethanesulfonyloxyphenyl)-1H-pyrrole-2-carboxylic acid ethyl ester (1.0 mmol, prepared in example E-97a or E-97b), the corresponding aryl boronic acid (1.5 mmol, structure 7), tetrakis(triphenylphosphine)palladium (0.03-0.10 mmol), and 2M cesium carbonate (3-5 mmol) into tetrahydrofuran and heat to 65-70° C. with stirring. After 1-18 hours, cool the reaction mixture to room temperature and add water. Extract the quenched reaction with ethyl acetate. Combine the organic extracts, wash with water and brine, dry over anhydrous magnesium sulfate, filter and concentrate under reduced pressure. Purify the residue by flash chromatography eluting with ethyl acetate:hexanes to provide the aryl coupled compound of Formula IIg.

Prepare the following compounds listed in Table E-3 in a manner analogous to the procedure set forth in Method CI from 3-(4-bromo-phenyl)-4-cyano-1-methyl-1H-pyrrole-2-carboxylic acid ethyl ester and the corresponding aryl boronic acid.

TABLE E-3

| Ex. | Structure | Data | S.M. |
|---|---|---|---|
| E-13 | 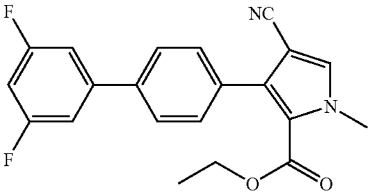 | mass spectrum (m/e): 367.1 (M + 1). | 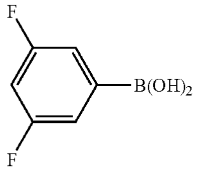 |
| E-14 | 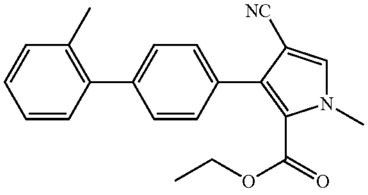 | mass spectrum (m/e): 344.1 (MS EI+). | 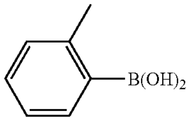 |
| E-15 | 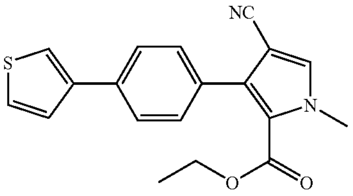 | mass spectrum (m/e): 337.1 (M + 1). | 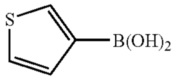 |
| E-16 | 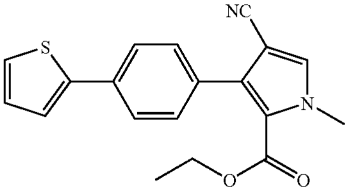 | mass spectrum (m/e): 337.1 (M + 1). | 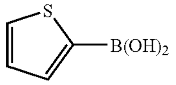 |

TABLE E-3-continued
| Ex. | Structure | Data | S.M. |
|---|---|---|---|
| E-17 | 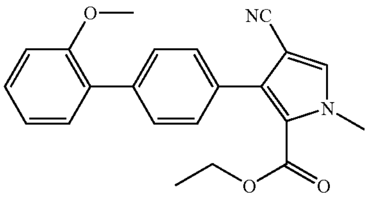 | mass spectrum (m/e): 378.3 (M + 18). | 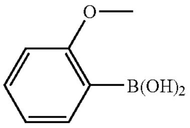 |
| E-18 | 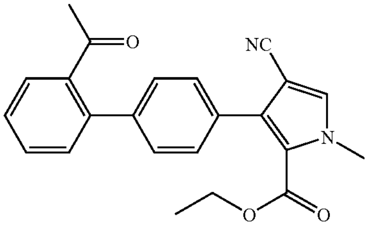 | mass spectrum (m/e): 373.3 (M + 1). | 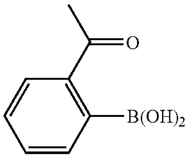 |
| E-19 | 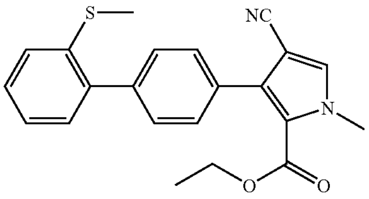 | mass spectrum (m/e): 377.1 (M + 1). | 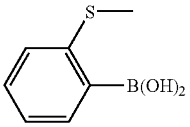 |
| E-20 | 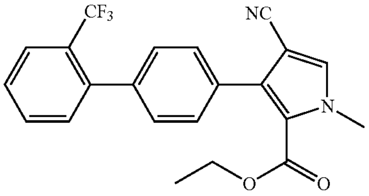 | $^1$H NMR (400 MHz; $CDCl_3$) δ 7.76(d, 1H), 7.57(t, 1H), 7.46(t, 1H), 7.35 7.42(m, 5H), 7.28(s, 1H), 4.10(q, 2H), 4.01(s, 3H), 1.05(t, 3H). | 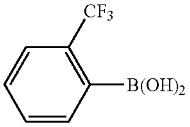 |
| E-21 | 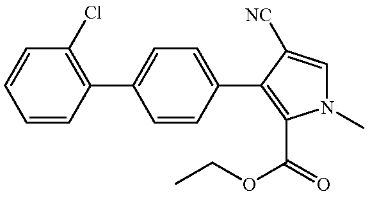 | mass spectrum (m/e): 365.1 (M + 1). | 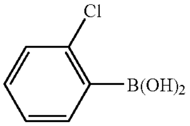 |
| E-22 | 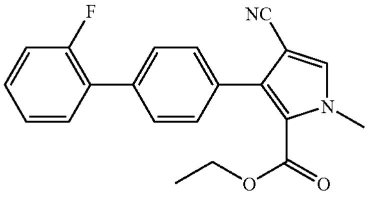 | mass spectrum (m/e): 349.1 (M + 1). | 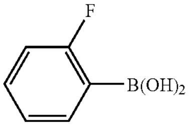 |
| E-23 | 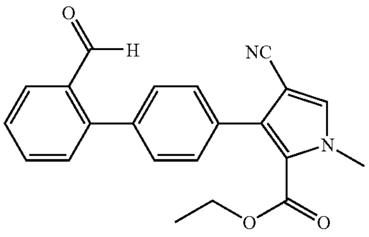 | $^1$H NMR (400 MHz; $CDCl_3$) δ 10.04(s, 1H), 8.03(d, 1H), 7.65(t, 1H), 7.48-7.57(m, 4H), 7.42(d, 2H), 7.31(s, 1H), 4.10(q, 2H), 4.12(s, 3H), 1.05(t, 3H). | 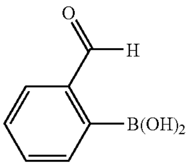 |

TABLE E-3-continued

| Ex. | Structure | Data | S.M. |
|---|---|---|---|
| E-24 | 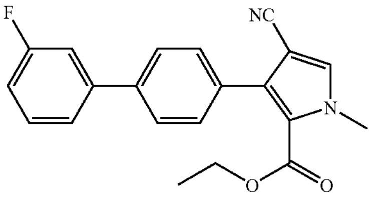 | mass spectrum (m/e): 349.2 (M + 1). | 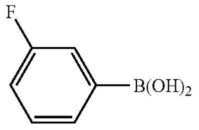 |
| E-25 | 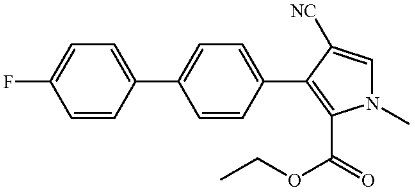 | mass spectrum (m/e): 349.2 (M + 1). | 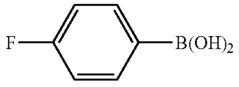 |
| E-26 | 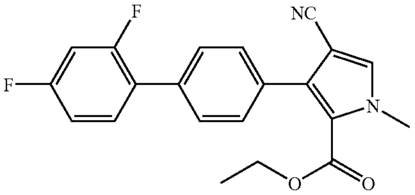 | mass spectrum (m/e): 367.1 (M + 1). | 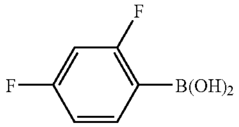 |
| E-27 | 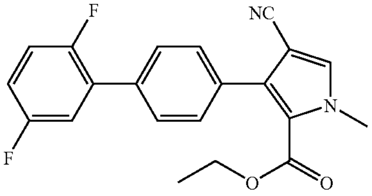 | mass spectrum (m/e): 367.1 (M + 1). | 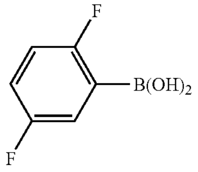 |
| E-28 | 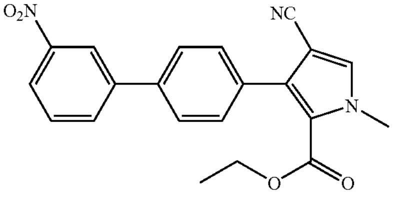 | mass spectrum (m/e): 376.1 ($FAB^+$). | 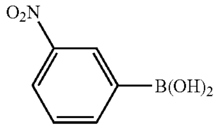 |
| E-29 | 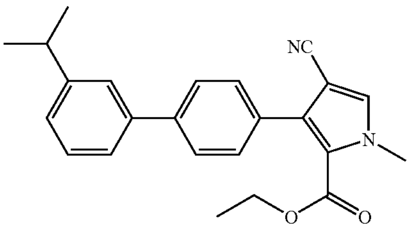 | mass spectrum (m/e): 359.2 (M + 1). | 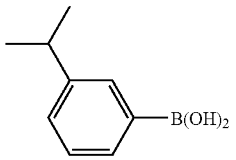 |

Method DI

Scheme IV: Add the corresponding aryl halide or aryl triflate (1.1 mmol, structure 8) to bis(pinacolato)diboron (1.2 mmol) and $PdCl_2$(dppf) (0.03 mmol) and potassium acetate (3 mmol) in DMF and heat to 80° C. with stirring. After 1-4 hours, cool the reaction mixture to room temperature. Add 3-(4-bromo-phenyl)-4-cyano-1-methyl-1H-pyrrole-2-carboxylic acid ethyl ester (1.0 mmol, prepared in example E-3a or E-3b), [1,1-bis(diphenylphospino)ferrocene]dichloropalladium(II) (0.03 mmol) and aqueous sodium carbonate (2M, 5 mmol), and heat to 80° C. After 1-18 hours at 80° C., cool the reaction mixture to room temperature and add water. Extract quenched reaction mixture with ethyl acetate. Combine the organic extracts and wash with water and brine, dry over anhydrous magnesium sulfate, filter, and concentrate under reduced pressure. Purify the residue by flash chromatography eluting with ethyl acetate:hexanes to provide the aryl coupled compound of Formula IIg.

Prepare the following compounds listed in Table E-4 in a manner analogous to the procedure set forth in Method DI from 3-(4-bromo-phenyl)-4-cyano-1-methyl-1H-pyrrole-2-carboxylic acid ethyl ester (Example E-3a or E-3b) and the corresponding aryl bromide or aryl triflate.

TABLE E-4
| Ex. | Structure | Data | S.M. |
|---|---|---|---|
| E-30 | 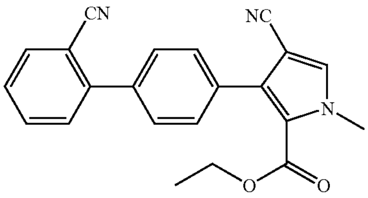 | $^{1}H$ NMR (400 MHz; $CDCl_3$) δ 7.78(d, 1H), 7.52-7.60(m, 3H), 7.41-7.49(m, 3H), 7.33(d, 2H), 7.29(s, 1H), 7.02(d, 2H), 4.10(q, 2H), 4.10(s, 3H), 1.05(t, 3H). | 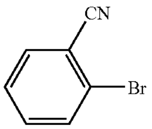 or 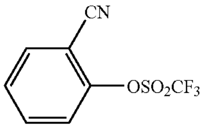 |
| E-31 | 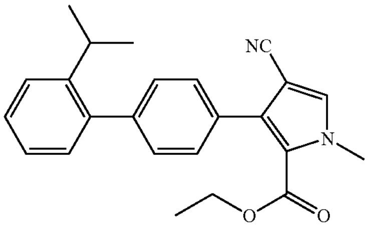 | mass spectrum (m/e): 373.2 (M + 1). | 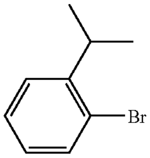 or 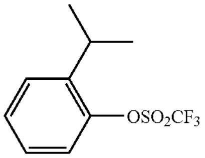 |
| E-32 | 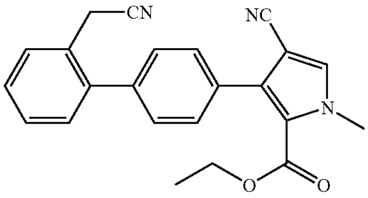 | mass spectrum (m/e): 387.2 (M + 18). | 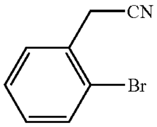 or 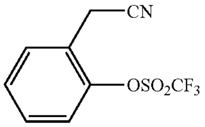 |
| E-33 | 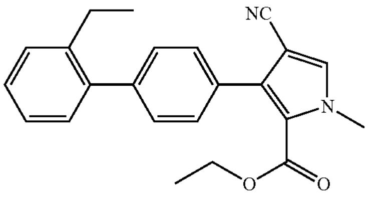 | mass spectrum (m/e): 359.2 (M + 1). | 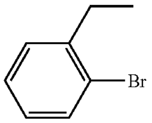 or 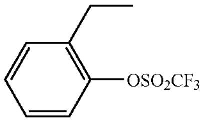 |
| E-34 | 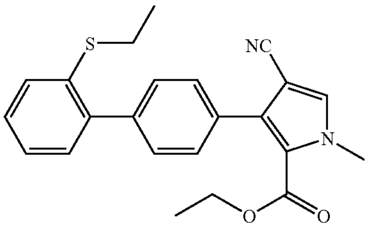 | $^{1}H$ NMR (400 MHz; $CDCl_3$) δ 7.39-7.46(m, 5H), 7.25-7.37(m, 4H), 4.10(q, 2H), 4.01(s, 1H), 2.80(d, 2H), 1.22(t, 3H), 1.05(t, 3H). | 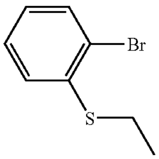 |

TABLE E-4-continued

| Ex. | Structure | Data | S.M. |
|---|---|---|---|
| E-35 | 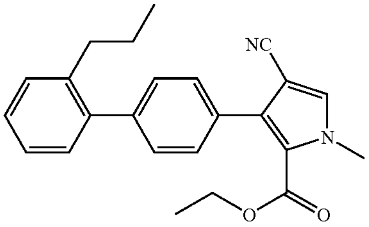 | Mass spectrum (m/e): 373.3 (M + 1). | 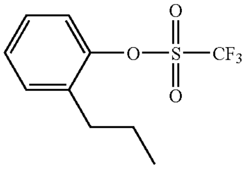 |

Method DII

Scheme III: Dissolve 3-(4-bromo-phenyl)-4-cyano-1-methyl-1H-pyrrole-2-carboxylic acid ethyl ester (0.331 mmol, prepared in example E-3a or E-3b) and aryl boronic acid (0.397 mmol, structure 7) in DME (3.0 mL). Add anhydrous cesium fluoride (1.16 mmol) to the mixture. Degas the mixture under reduced pressure for 20 minutes until no bubbles are produced. Recharge the reaction atmosphere with nitrogen. Add $PdCl_2$(dppf) (0.066 mmol). Seal the flask and heat the reaction mixture at 100° C. for 16 h. Add $H_2O$ (20 mL) and methylene chloride (20 mL) into the reaction mixture. Extract the aqueous layer with methylene chloride (3×30 mL). Combine the organic layers, dry over anhydrous magnesium sulfate, filter, and concentrate under reduced pressure. Purify the residue by flash chromatography to provide the compound of Formula IIg.

Prepare the following compounds listed in Table E-5 in a manner analogous to the procedure set forth in Method DII.

TABLE E-5

| Ex. | Structure | Data | S.M. |
|---|---|---|---|
| E-37 | 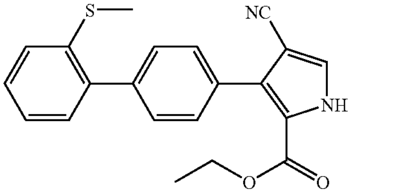 | mass spectrum (m/e): 363.1 (M + 1). $R_f$ = 0.1 (50% $Et_2O$ in hexanes). | 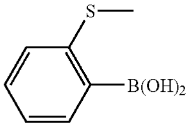 |
| E-38 | 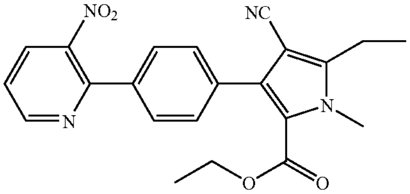 | mass spectrum (m/e): 405.2 (M + 1). $R_f$ = 0.1 (50% $Et_2O$ in hexanes). | 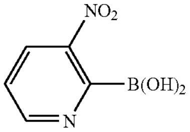 |
| E-39 | 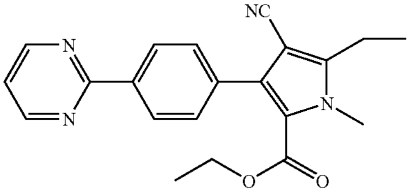 | mass spectrum (m/e): 361.1 (M + 1). $R_f$ = 0.1 (33% EtOAc in hexanes). | 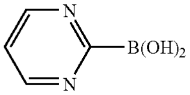 |
| E-40 | 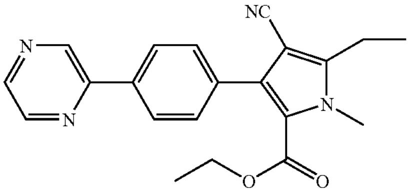 | mass spectrum (m/e): 361.1 (M + 1). $R_f$ = (50% EtOAc in hexanes). | 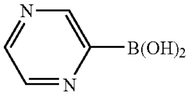 |

TABLE E-5-continued

| Ex. | Structure | Data | S.M. |
|---|---|---|---|
| E-41 | 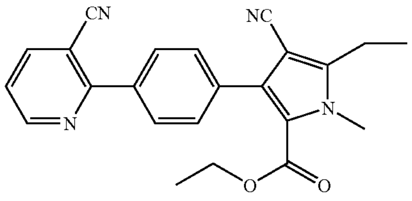 | mass spectrum (m/e): 385.1 (M + 1). $R_f$ = (50% acetone in hexanes). | 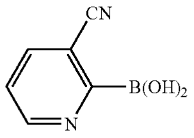 |
| E-42 | 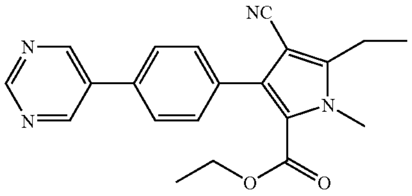 | mass spectrum (m/e): 361.1 (M + 1). $R_f$ = 0.2 (50% $Et_2O$ in hexanes). | 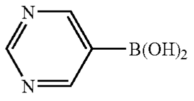 |

Method DIII

Scheme IIIa: Mix 4-cyano-5-ethyl-1-methyl-3-(4-trifluoromethanesulfonyloxyphenyl)-1H-pyrrole-2-carboxylic acid ethyl ester, (0.399 g, 0.927 mmol, prepared in example E-97a or E-97b), the corresponding aryl boronic acid (1.442 mmol), [1,1' bis(diphenylphosphino)ferrocene]dichloropalladium (II) complexed with methylene chloride (0.094 g, 0.115 mmol), 2N $Na_2CO_3$ (4 ml, 8 mmol) and dioxane then heat at 70° C. for 6 hours. Dilute the reaction with ethyl acetate and wash with $H_2O$, brine, dry with $Na_2SO_4$, filter, and concentrate under reduced pressure. Purify the residue 110 by flash chromatography (silica gel), eluting with first hexanes then up to 15% EtOAc/Hexanes to provide the compound of Formula IIg.

Prepare the following compounds listed in Table E-6 in a manner analogous to the procedure set forth in Method DIII.

EXAMPLE E-46

Preparation of 3(2'-amino-biphenyl-4-yl)-4-cyano-1-methyl-1H-pyrrole-2-carboxylic acid ethyl ester

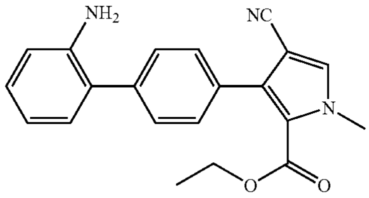

Add a 1:1 ethanol:ethyl acetate mixture to palladium on carbon (catalytic, 0.30 g) followed by 3(2'-nitro-biphenyl-4-yl)-4-cyano-1-methyl-1H-pyrrole-2-carboxylic acid ethyl ester (3.00 g, 8.30 mmol, prepared in example E-9) with stirring. Subject the reaction to an atmosphere of hydrogen gas. After 18 hours, filter and concentrate under reduced

TABLE E-6

| Ex. | Structure | Data | S.M. |
|---|---|---|---|
| E-44 | 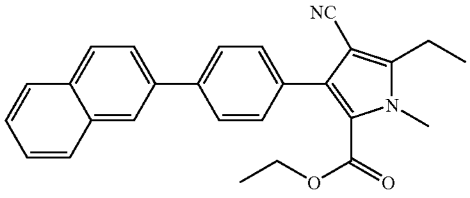 | mass spectrum (m/e): 409.2 (M + 1). | 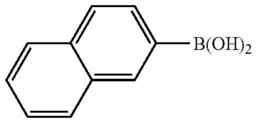 |
| E-45 | 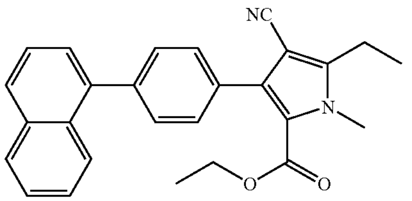 | mass spectrum (m/e): 409.2 (M + 1). | 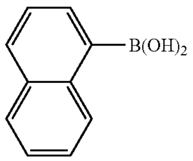 |

pressure. Purify the residue by flash chromatography eluting with ethyl acetate:hexanes to provide the title compound. Mass spectrum (m/e): 332.1 (M+1).

EXAMPLE E-47

Preparation of 4-cyano-3(2'-methanesulfinyl-biphenyl-4-yl)-1-methyl-1H-pyrrole-2-carboxylic acid ethyl ester

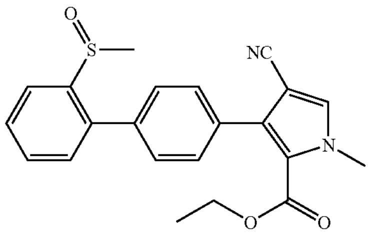

Add 3-chloroperoxybenzoic acid (0.33 g, 0.96 mmol) to 4-cyano-3(2'-methanesulfanyl-biphenyl-4-yl)-1-methyl-1H-pyrrole-2-carboxylic acid ethyl ester (0.40 g, 1.06 mmol, prepared in example E-19) in chloroform with stirring. After 18 hours, pour the reaction mixture into water and extract with methylene chloride. Combine the organic extracts, wash with saturated sodium bicarbonate, water and brine, dry over anhydrous magnesium sulfate, filter, and concentrate under reduced pressure. Purify the residue by flash chromatography eluting with acetonitrile:methylene chloride to provide the title compound. Mass spectrum (m/e): 393.9 (M+1).

EXAMPLE E-48

Preparation of 4-cyano-3(2'-methanesulfonyl-biphenyl-4-yl)-1-methyl-1H-pyrrole-2-carboxylic acid ethyl ester

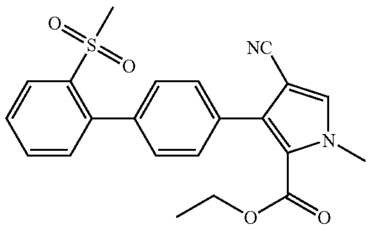

Add 3-chloroperoxybenzoic acid (0.69 g, 2.00 mmol) to 4-cyano-3(2'-methanesulfanyl-biphenyl-4-yl)-1-methyl-1H-pyrrole-2-carboxylic acid ethyl ester (0.40 g, 1.06 mmol, prepared in example E-19) in chloroform with stirring. After 18 hours, pour the reaction mixture into water and extract with methylene chloride. Combine the organic extracts, wash with saturated sodium bicarbonate, water and brine, dry over anhydrous magnesium sulfate, filter, and concentrate under reduced pressure. Purify the residue by flash chromatography eluting with acetonitrile:methylene chloride to provide the title compound. Mass spectrum (m/e): 426.9 (M+18).

EXAMPLE E-49

Preparation of 4-cyano-3(2'-hydroxy-biphenyl-4-yl)-1-methyl-1H-pyrrole-2-carboxylic acid ethyl ester

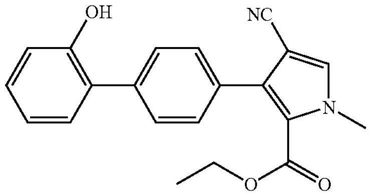

Add boron tribromide (1.60 g, 6.39 mmol) to 4-cyano-3-(2'-methoxy-biphenyl-4-yl)-1-methyl-1H-pyrrole-2-carboxylic acid ethyl ester (2.10 g, 5.81 mmol, prepared in example E-17) in methylene chloride at 0° C. with stirring. The reaction is gradually allowed to warm to ambient temperature. After 18 hours, pour the reaction mixture into ice-water and extract with methylene chloride. Combine the organic extracts, wash with water and brine, dry over anhydrous magnesium sulfate, filter and concentrate under reduced pressure. Purify the residue by flash chromatography eluting with acetonitrile:methylene chloride to provide the title compound. Mass spectrum (m/e): 345.1 (M−1).

Prepare the following compounds listed in Table E-7 in a manner analogous to the O-alkylation procedure set forth in Method B using 4-cyano-3(2'-hydroxy-biphenyl-4-yl)-1-methyl-1H-pyrrole-2-carboxylic acid ethyl ester prepared in example E-49, and the corresponding alkyl halide, such as ethyl bromide, n-propyl bromide, or isopropyl bromide, respectively.

TABLE E-7

| Ex. | Structure | Data |
| --- | --- | --- |
| E-50 | 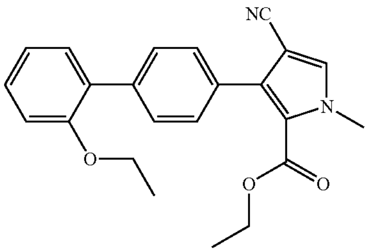 | mass spectrum (m/e): 375.2 (M + 1). |

TABLE E-7-continued

| Ex. | Structure | Data |
|---|---|---|
| E-51 | 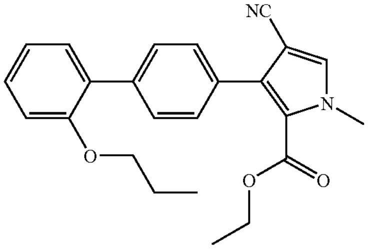 | $^1$H NMR (400 MHz; $CDCl_3$) δ -7.60(d, 2H), 7.37-7.42(m, 3H), 7.28(t, 1H), 7.25(s, 1H), 6.93-7.05 (m, 2H), 4.35(q, 2H), 4.10(q, 2H), 3.98(s, 3H), 1.70(m, 2H), 1.15(t, 3H), 1.05(t, 3H). |
| E-52 | 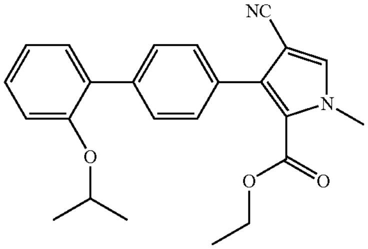 | $^1$H NMR (400 MHz; $CDCl_3$) δ -7.59(d, 2H), 7.37-7.42(m, 3H), 7.25-7.28(m, 3H), 7.00-7.04 (m, 2H), 4.44(m, 1H), 4.10(q, 2H), 4.01(s, 3H), 1.15(m, 9H), 1.05(t, 3H). |

EXAMPLE E-53

Preparation of 4-cyano-3(2'-hydroxy methyl-biphenyl-4-yl)-1-methyl-1H-pyrrole-2-carboxylic acid ethyl ester

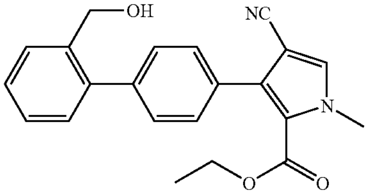

Add sodium borohydride (0.79 g, 2.1 mmol) to 4-cyano-3-(2'-formyl-biphenyl-4-yl)-1-methyl-1H-pyrrole-2-carboxylic acid ethyl ester (0.50 g, 1.40 mmol, prepared in example E-23) in methanol at 0° C. with stirring. After 1 hour, allow the reaction mixture to warm to ambient temperature. After 2 hours, pour the reaction mixture into water and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexane to provide the title compound. Mass spectrum: $EI^+$=360.2

EXAMPLE E-54

Preparation of 4-cyano-3(2'-methoxymethyl-biphenyl-4-yl)-1-methyl-1H-pyrrole-2-carboxylic acid ethyl ester

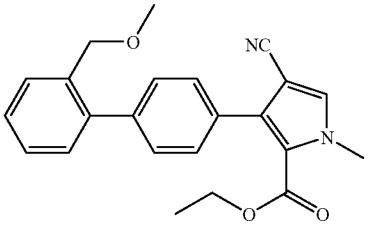

Prepare the title compound in a manner analogous to the O-alkylation procedure set forth in Method B using iodomethane and 4-cyano-3(2'-hydroxymethyl-biphenyl-4-yl)-1-methyl-1H-pyrrole-2-carboxylic acid ethyl ester (prepared in example E-53). Mass spectrum (m/e): 375.2 (M+1).

EXAMPLE E-55

Preparation of 4-cyano-3-(4-cyclopentyl-phenyl)-1-methyl-1H-pyrrole-2-carboxylic acid ethyl ester

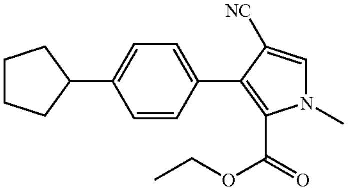

Add cyclopentylzinc bromide (0.5M, 7.2 mL, 3.6 mmol) to 3-(4-bromo-phenyl)-4-cyano-1-methyl-1H-pyrrole-2-carboxylic acid ethyl ester (0.50 g, 1.80 mmol, prepared in example E-3a or E-3b), tris(dibenzylideneacetone)palladium (0) (0.06 g, 0.07 mmol), and triphenylphosphine (0.07 g, 0.27 mmol) in dioxane and heat to 80° C. with stirring. After 18 hours, cool the reaction mixture, and pour into water. Extract the quenched reaction mixture with ethyl acetate. Combine the organic extracts, wash with water and brine, dry over anhydrous magnesium sulfate, filter, and concentrate under reduced pressure. Purify the residue by flash chromatography eluting with ethyl acetate:hexane to provide the title compound. Mass spectrum (m/e): 323.3 (M+1).

Method EI

Scheme V: Add 4-cyano-3-iodo-1-methyl-1H-pyrrole-2-carboxylic acid ethyl ester (1.0 mmol, prepared in preparation 34), the corresponding aryl boronic acid or ester (1.5 mmol, structure 7), [1,1-bis(diphenylphospino)ferrocene]dichloropalladium(II) (0.1 mmol) and cesium fluoride (5.0 mmol) in DME and heat to 80° C. with stirring. After 1-18 hours, cool and pour the reaction mixture into water. Extract the reaction mixture with ethyl acetate. Combine the organic extracts, wash with water and brine, dry over anhydrous magnesium sulfate, filter, and concentrate under reduced pressure. Purify the residue by flash chromatography eluting with ethyl acetate:hexane to provide the aryl coupled compound of Formula IIg'.

Method EII

Scheme V: Dissolve 4-cyano-3-iodo-1-methyl-1H-pyrrole-2-carboxylic acid ethyl ester or 4-cyano-5-ethyl-3-iodo-1-methyl-1H-pyrrole-2-carboxylic acid ethyl ester (0.331 mmol, prepared in preparations 34 and 38 respectively) and corresponding substituted thiophene-phenyl-boronate (0.397 mmol) in DME (3.0 mL). Add anhydrous cesium fluoride (176 mg, 1.16 mmol) to the mixture. Degas under reduced pressure (−29 inches) for 20 minutes till no bubbles are produced. Recharge with nitrogen. Add $PdCl_2$(dppf) (0.066 mmol). Well seal the flask and heat the mixture at 100° C. for 16 h. Add $H_2O$ (20 mL) and methylene chloride (20 mL) into the reaction mixture. Extract with methylene chloride (3×30 mL). Combine the organic layers and dry over magnesium sulfate, filter, and concentrate under reduced pressure. Purify the residue by flash chromatography to provide the aryl coupled compound of Formula IIg'.

Prepare the following compound listed in Table E-8 in a manner analogous to the procedure set forth in Method EII.

EXAMPLE E-58

Preparation of 4-cyano-1-methyl-3-[4-(3-methylsulfanyl-thiophen-2-yl)-phenyl]-1H-pyrrole-2-carboxylic acid ethyl ester

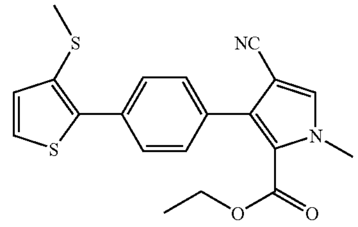

Prepare the title compound in a manner analogous to the procedure set forth in Method EI using 4-cyano-3-iodo-1-methyl-1H-pyrrole-2-carboxylic acid ethyl ester (prepared in preparation 34) and 4,4,5,5-tetramethyl-2-[4-(3-methylsulfanyl-thiophen-2-yl)-phenyl]-[1,3,2]dioxaborolane (prepared in preparation 4). Mass spectrum (m/e): 382.9. (M+1).

TABLE E-8

| Ex. | Structure | Data | S.M. |
|---|---|---|---|
| E-56 | 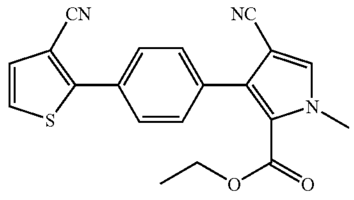 | mass spectrum (m/e): 362.1 (M + 1). | Prep 25 and Prep 34 |

EXAMPLE E-57

Preparation of 4-cyano-1-methyl-3-[2'(propane-2-sulfonylamino)-biphenyl-4-yl]-1H-pyrrole-2-carboxylic acid ethyl ester

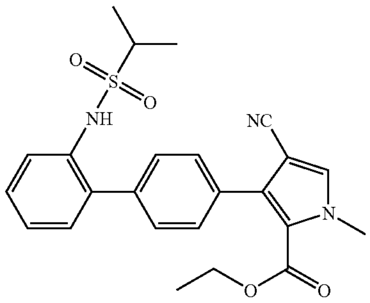

Prepare the title compound in a manner analogous to procedure set forth in Method EI from 4-cyano-3-iodo-1-methyl-1H-pyrrole-2-carboxylic acid ethyl ester (prepared in preparation 34) and propane-2-sulfonic acid [4'-(4,4,5,5-tetramethyl-[1,3,2]dioxaborolane-2-yl)-biphenyl-2yl]-amide (prepared in preparation 30). Mass spectrum (m/e): 350.1 (M−1).

Method FI

Scheme VIII: Add N-bromosuccinimide (1.5-3.0 mmol) to the ethyl ester (1.0 mmol, Formula IIb) in THF at room temperature with stirring. After 18 hours, add water to the reaction mixture and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula IIj.

Method FII

Scheme VIII: Dissolve the ethyl ester (3.00 mmol, compound of Formula IIb) in THF (10 mL) and DMF (2.5 mL). Add N-bromosuccinimide (4.50 mmol) to the mixture. Stir the mixture at room temperature for 16 h. Add $H_2O$ (30 mL) and methylene chloride (30 mL) into the reaction mixture. Extract with methylene chloride (3×30 mL). Combine the organic layers, dry over magnesium sulfate, filter, and concentrate under reduced pressure. Purify the residue by flash chromatography to provide the compound of Formula IIj.

Prepare the following compounds listed in Table E-9 in a manner analogous to the procedure set forth in Method FI.

TABLE E-9
| Ex. | Strucutre | Data | S.M. |
|---|---|---|---|
| E-59 | 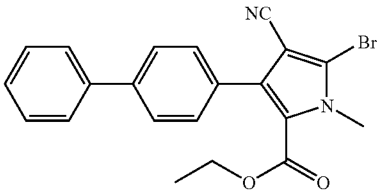 | mass spectrum (m/e): 408.0 (M − 1). | E-1 |
| E-60 | 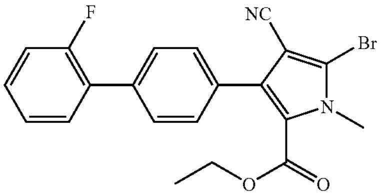 | mass spectrum (m/e): 427.1 (M + 1). | E-22 |
| E-61 | 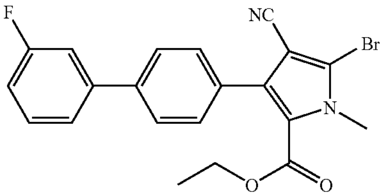 | mass spectrum (m/e): 429.1 (M + 1). | E-24 |
| E-62 | 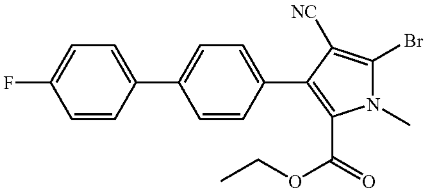 | mass spectrum (m/e): 427.1 (M + 1). | E-25 |
| E-63 | 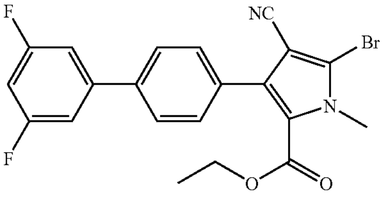 | mass spectrum (m/e): 447.1 (M + 1). | E-13 |
| E-64 | 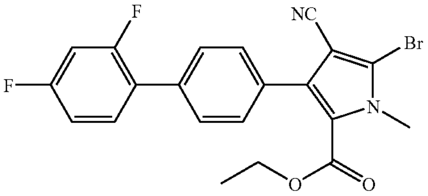 | mass spectrum (m/e): 445.1 (M + 1). | E-26 |
| E-65 | 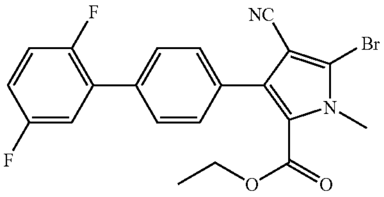 | $^1$H NMR (400 MHz; $CDCl_3$) δ 7.57(d, 2H), 7.42(d, 2H), 7.21-7.10(m, 2H), 6.98(m, 1H), 4.10(q, 2H), 4.03(s, 3H), 1.05(t, 3H). | E-27 |

TABLE E-9-continued

| Ex. | Strucutre | Data | S.M. |
|---|---|---|---|
| E-66 | 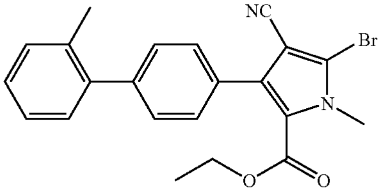 | mass spectrum (m/e): 423.1 (M + 1). | E-14 |
| E-67 | 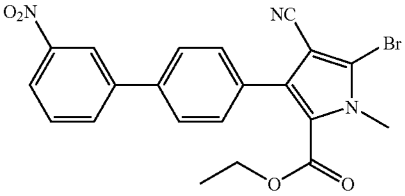 | No physical data. | E-28 |
| E-68 | 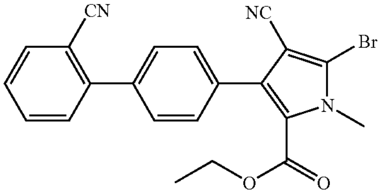 | mass spectrum (m/e): 453.2 (M + 18). | E-30 |
| E-69 | 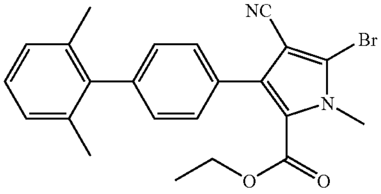 | mass spectrum (m/e): 437.2 (M + 1). | E-5 |
| E-70a | 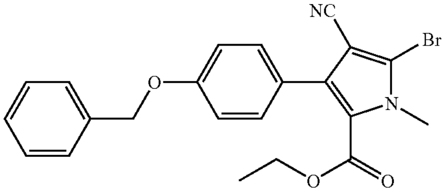 | mass spectrum (m/e): 440.1 (M + 1). | E-6a or E-6b |

EXAMPLE E-70b

Additional Preparation of 3-(4-benzyloxy-phenyl)-5-bromo-4-cyano-1-methyl-1H-pyrrole-2-carboxylic acid ethyl ester

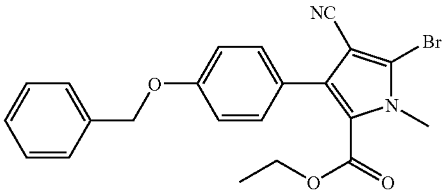

A solution of 3-(4-benzyloxy-phenyl)-4-cyano-1-methyl-1H-pyrrole-2-carboxylic acid ethyl ester. (184.73 g, 0.512 mol, prepared in example E-6a or E-6b) in anhydrous THF (2,000 mL) is treated with NBS (109.47 g, 0.615 mol). The resulting reaction mixture is allowed to stir at room temperature overnight. The reaction mixture is poured into water (2,000 mL). The resulting solution is divided into 2 equal parts, and each is extracted with EtOAc (3×800 mL each). The combined organics are dried over anhydrous $MgSO_4$, filtered, then concentrated in vacuo to afford a yellow solid. The yellow solid is purified by column chromatography (silica gel, EtOAc/Hexanes 1/3) to afford the title compound (133.99 g, ~60% yield) as a white solid: $^1H$ NMR (500 MHz; $CDCl_3$) δ 7.46-7.44 (m, 2H), 7.41-7.38 (m, 2H), 7.36-7.32 (m, 1H), 7.29-7.26 (m, 2H), 7.01-6.99 (m, 2H), 5.10 (s, 2H), 4.11 (q, 2H), 3.98 (s, 3H), 1.02 (t, 31); MS(ES): m/z 438.9.

Method HI

Scheme IX: Add tetraethyltin (2.0 mmol) to the bromo derivative (1.0 mmol, compound of Formula IIj) and tetrakis (triphenylphosphine)-palladium(0) (0.1 mmol) in HMPA and heat the reaction mixture to 100° C. with stirring. After 18 hours, cool the reaction mixture and pour into water. Extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula IIk.

Method HII

A solution of the corresponding 5-bromo-4-cyano-1-methyl-1H-pyrrole-2-carboxylic acid ethyl ester (54.30 mmol) in anhydrous THF (620 mL) is treated with $Pd(OAc)_2$ (0.609 g, 2.71 mmol) and Hartwig's Ligand (3.85 g, 5.41 mmol). A 1.0 M hexanes solution of $Et_2Zn$ (108.60 mL, 108.60 mmol) is slowly added via an addition funnel. Upon complete addition of $Et_2Zn$, the resulting reaction mixture is allowed to stir for 1 hour. The reaction is then quenched with saturated $NH_4Cl$ solution and the THF is removed under vacuum to afford a residue. The resulting residue is dissolved in methylene chloride and filtered to remove zinc, dried over anhydrous $MgSO_4$, filtered, and the organics are combined and concentrated in vacuo. The crude residue is purified by column chromatography (silica gel, methylene chloride to EtOAc/Hexanes 1/3 to EtOAc/Hexanes 1/2 to EtOAc/Hexanes 1/1) to afford the title compound.

Prepare the following ethyl derivatives listed in Table E-10 from the corresponding bromo derivatives in a manner analogous to the procedure set forth in Method HII.

TABLE E-10

| Ex | Structure | Data | S.M. |
|---|---|---|---|
| E-71 | 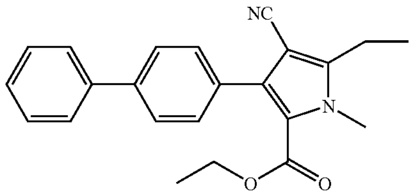 | mass spectrum (m/e): 359.1 (M + 1). | E-59 |
| E-72 | 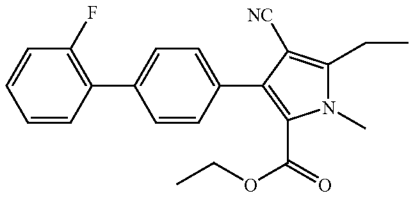 | mass spectrum (m/e): 394.2 (M + 18). | E-60 |
| E-73 | 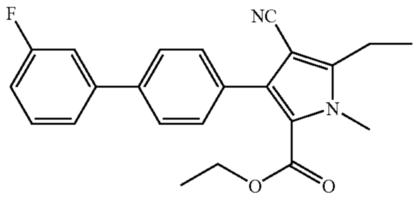 | mass spectrum (m/e): 399.2 (M + 23). | E-61 |
| E-74 | 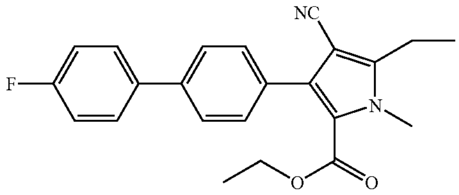 | $^1$H NMR (400 MHz; $CDCl_3$) δ 7.61-7.57(m, 4H), 7.42(d, 2H), 7.17-7.12(m, 2H), 4.10(q, 2H), 3.93(s, 3H), 2.83(q, 2H), 1.30(t, 3H), 1.05(t, 3H). | E-62 |
| E-75 | 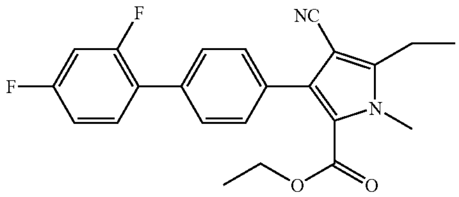 | mass spectrum (m/e): 395.1 (M + 1). | E-64 |
| E-76 | 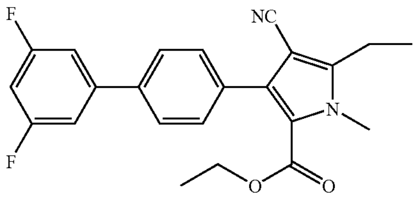 | $^1$H NMR (400 MHz; $CDCl_3$) δ 7.57(d, 2H), 7.42(d, 2H), 7.17-7.12(m, 2H), 6.84-6.78(m, 1H), 4.10(q, 2H), 3.93(s, 3H), 2.84(q, 2H), 1.30(t, 3H), 1.02(t, 3H). | E-63 |

TABLE E-10-continued

| Ex | Structure | Data | S.M. |
|---|---|---|---|
| E-77 | 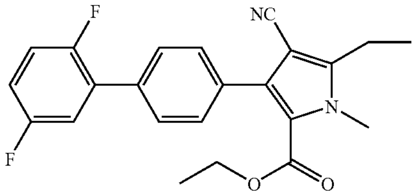 | $^1$H NMR (400 MHz; $CDCl_3$) δ 7.57(d, 2H), 7.42(d, 2H), 7.17(m, 1H), 7.10(m, 1H), 6.97(m, 1H), 4.10(q, 2H), 3.93(s, 3H), 2.84(q, 2H), 1.30(t, 3H), 1.02(t, 3H). | E-65 |
| E-78 | 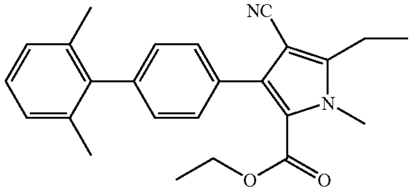 | mass spectrum (m/e): 387.3 (M + 1). | E-69 |
| E-79 | 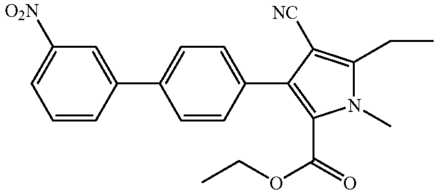 | mass spectrum (m/e): 404.3 (M + 1). | E-67 |
| E-80a (See also E-80b infra) | 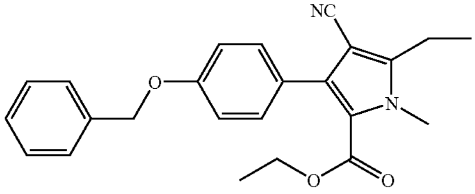 | mass spectrum (m/e): 389.3 (M + 1). | E-70a or E-70b |

EXAMPLE E-80b

Additional Preparation of 3-(4-benzyloxy-phenyl)-4-cyano-5-ethyl-1-methyl-1H-pyrrole-2-carboxylic acid ethyl ester

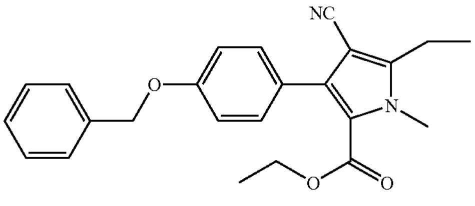

A solution of 3-(4-benzyloxy-phenyl)-5-bromo-4-cyano-1-methyl-1H-pyrrole-2-carboxylic acid ethyl ester (23.80 g, 54.30 mmol, prepared in example E-70a or E-70b) in anhydrous THF (620 mL) is treated with $Pd(OAc)_2$ (0.609 g, 2.71 mmol) and Hartwig's Ligand (3.85 g, 5.41 mmol). A 1.0 M hexanes solution of $Et_2Zn$ (108.60 mL, 108.60 mmol) is slowly added via an addition funnel. Upon complete addition of $Et_2Zn$, the resulting reaction mixture is allowed to stir for 1 hour. The reaction is then quenched with saturated $NH_4Cl$ solution and the THF is removed under vacuum to afford a residue. The resulting residue is dissolved in methylene chloride and filtered to remove zinc, dried over anhydrous $MgSO_4$, filtered, and all organics are combined and concentrated in vacuo to afford a red solid (72.90 g). The crude red solid (72.90 g) is purified by column chromatography (silica gel, methylene chloride to EtOAc/Hexanes 1/3 to EtOAc/Hexanes 1/2 to EtOAc/Hexanes 1/1) to afford the title compound (46.38 g, 73% yield) as a white solid: $^1$H NMR (500 MHz; $CDCl_3$) δ 7.46-7.44 (m, 2H), 7.41-7.38 (m, 2H), 7.36-7.32 (m, 1H), 7.30-7.28 (m, 2H), 6.99 (d, 2H), 5.10 (s, 2H), 4.09 (q, 2H), 3.87 (s, 3H), 2.84 (q, 2H), 1.29 (t, 3H), 1.02 (t, 3H).

EXAMPLE E-81

Preparation of 4-cyano-5-ethyl-3-(4-hydroxyphenyl)-1-methyl-1H-pyrrole-2-carboxylic acid ethyl ester

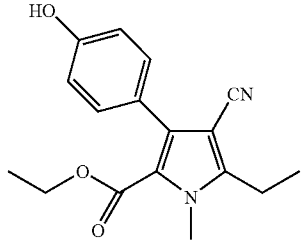

A solution of 20% $Pd(OH)_2/C$ (6.95 g) and 3-(4-benzyloxy-phenyl)-4-cyano-5-ethyl-1-methyl-1H-pyrrole-2-carboxylic acid ethyl ester (23.173 g, 59.65 mmol, prepared in example E-80a or E-80b) in a 1/2 EtOH/THF solution (300 mL) is placed under 50 PSI of $H_2$ at room temperature for 3.5 hours. The reaction mixture is combined with another reaction mixture of the same scale, and the combined reaction mixtures are filtered through Hyflo, washing with EtOAc. The filtrate is concentrated in vacuo to afford a white residue. The white residue is dissolved in a minimal amount of EtOAc, then treated with excess hexanes, causing a precipitate to form. The resulting white solid is recovered by vacuum filtration, washing with hexanes and drying under vacuum to afford the title compound (35.01 g, 98% yield) as a white solid: $^1H$ NMR (500 MHz; $CDCl_3$) δ 7.23 (d, 2H), 6.83 (d, 2H), 5.46 (s, 1H), 4.11 (q, 2H), 3.87 (s, 3H), 2.84 (q, 2H), 1.30 (t, 3H), 1.06 (t, 3H); MS(ES): m/z 299.1 ($M^+$+H), 297.1 (M−$H^-$). Anal. Calcd. For $C_{17}H_{18}N_2O_3$: C, 68.44; H, 6.08; N, 9.38. Found C, 68.18, H, 6.06; N, 9.34.

Prepare the following O-alkylated compounds listed in Table E-11 from 4-cyano-5-ethyl-3-(4-hydroxyphenyl)-1-methyl-1H-pyrrole-2-carboxylic acid ethyl ester, prepared in example E-81, and the corresponding halide, in a manner analogous to the procedure set forth in Method B.

TABLE E-11

| Ex. | Structure | Data | S.M. (halide) |
|---|---|---|---|
| E-82 | 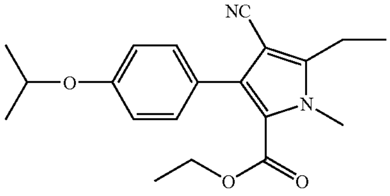 | mass spectrum (m/e): 341.1 (M + 1). | 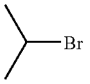 |
| E-83 | 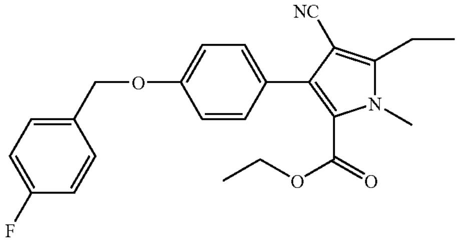 | mass spectrum (m/e): 407.1 (M + 1). | 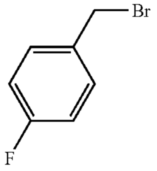 |
| E-84 | 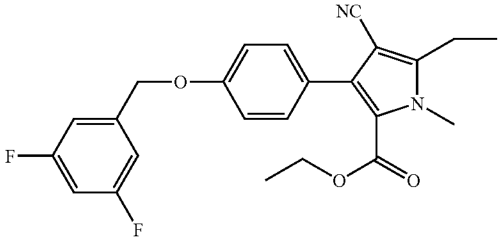 | mass spectrum (m/e): 425.1 (M + 1). | 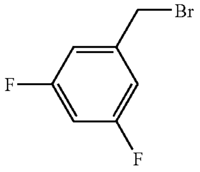 |
| E-85 | 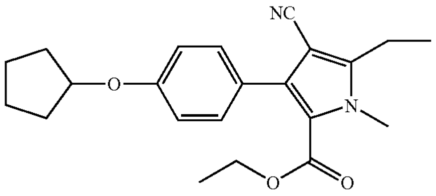 | mass spectrum (m/e): 376.1 (M + 1). | 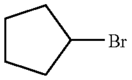 |
| E-86 | 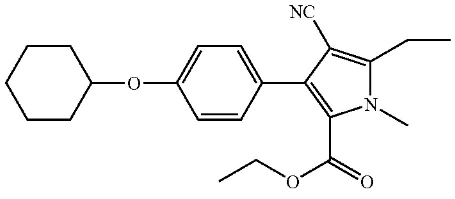 | | 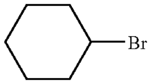 |

TABLE E-11-continued

| Ex. | Structure | Data | S.M. (halide) |
|---|---|---|---|
| E-87 | 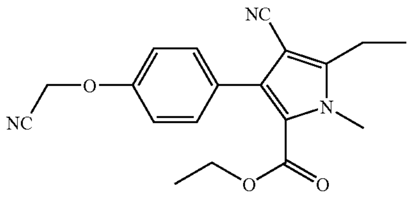 | $^{1}$H NMR (400 MHz; $CDCl_3$) δ 7.32(d, 2H), 6.98(d, 2H), 4.80(s, 2H), 4.10(q, 2H), 3.90(s, 3H), 2.83(q, 2H), 1.30(t, 3H), 1.05(t, 3H). | 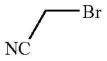 |

Method JI

Scheme X: Add 4-cyano-5-ethyl-3-(4-hydroxyphenyl)-1-methyl-1H-pyrrole-2-carboxylic acid ethyl ester (1.0 mmol, prepared in example E-81), an aryl boronic acid (2.0 mmol, structure 7), copper(II)acetate (2.0 mmol) and triethylamine (5.0 mmol) into methylene chloride at room temperature with stirring. After 18 hours, filter the reaction mixture through celite and pour the filtrate into water. Extract the filtrate/water mixture with methylene chloride. Combine the organic extracts, wash with 1N HCl, water and brine, dry over anhydrous magnesium sulfate, filter, and concentrate under reduced pressure. Purify the residue by flash chromatography eluting with ethyl acetate:hexanes to provide the compound of Formula IIn.

Prepare the following O-arylated compounds listed in Table E-12 from 4-cyano-5-ethyl-3-(4-hydroxyphenyl)-1-methyl-1H-pyrrole-2-carboxylic acid ethyl ester, prepared in example E-81, or 4-cyano-3-(4-hydroxyphenyl)-1-methyl-1H-pyrrole-2-carboxylic acid ethyl ester, prepared in example E-11, and the corresponding boronic-acid in a manner analogous to the procedure set forth in Method JI.

TABLE E-12

| Ex. | Structure | Data | S.M. |
|---|---|---|---|
| E-88 | 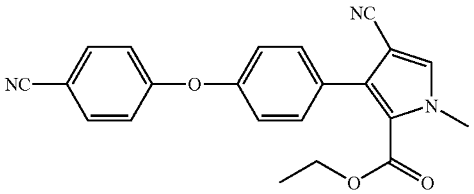 | mass spectrum (m/e): 372.0 (M + 1). | 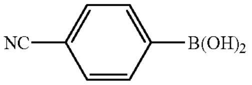 |
| E-89 | 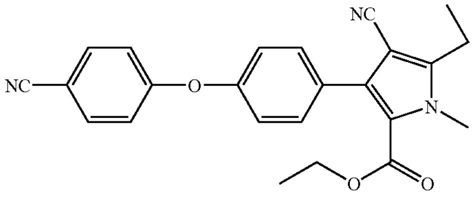 | mass spectrum (m/e): 400.0 (M + 1). | 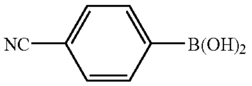 |
| E-90 | 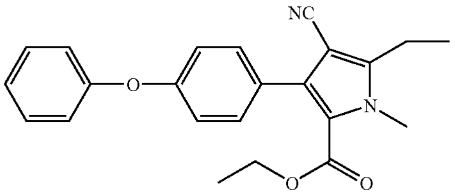 | mass spectrum (m/e): 375.0 (M + 1). | 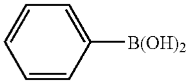 |

TABLE E-12-continued

| Ex. | Structure | Data | S.M. |
|---|---|---|---|
| E-91 | 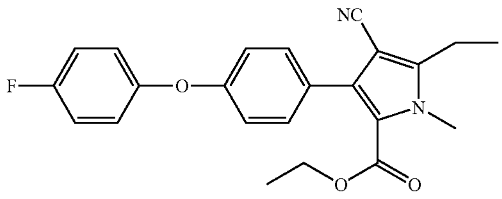 | mass spectrum (m/e): 393.0 (M + 1). | 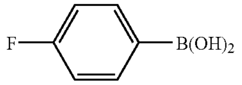 |
| E-92 | 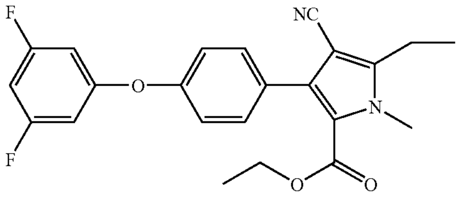 | mass spectrum (m/e): 411.0 (M + 1). | 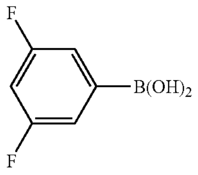 |

Method JII

Scheme X, alternative procedure: Add 4-cyano-5-ethyl-3-(4-hydroxyphenyl)-1-methyl-1H-pyrrole-2-carboxylic acid ethyl ester (1.0 mmol, prepared in example E-81), the corresponding substituted fluorobenzene (1.0 mmol), potassium fluoride on alumina (5.0 mmol) and 18-crown-6 (0.1 mmol) into acetonitrile at reflux with stirring. After 18 hours, pour the reaction mixture into water and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula IIn.

Prepare the following O-arylated compounds listed in Table E-13 from 4-cyano-5-ethyl-3-(4-hydroxyphenyl)-1-methyl-1H-pyrrole-2-carboxylic acid ethyl ester, prepared in example E-81, and the corresponding fluoro derivative, in a manner analogous to the procedure set forth in Method JII.

TABLE E-13

| Ex. | Structure | Data: | S.M. |
|---|---|---|---|
| E-93 | 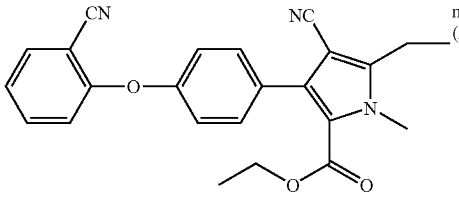 | mass spectrum (m/e): 400.4 (M + 1). | 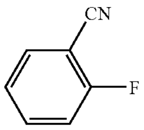 |
| E-94 | 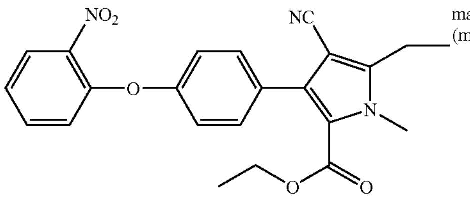 | mass spectrum (m/e): 420.2 (M + 1). | 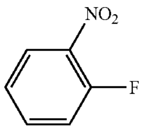 |

EXAMPLE E-95

Preparation of 3-[4-(2-amino-phenoxy)-phenyl]-4-cyano-5-ethyl-1-methyl-1H-pyrrole-2-carboxylic acid ethyl ester

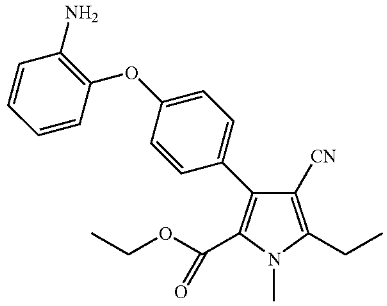

Prepare the title compound in a manner analogous to the procedure set forth in Example E-46 using 4-cyano-5-ethyl-1-methyl-3-[4-(2-nitro-phenoxy)-phenyl]-1H-pyrrole-2-carboxylic acid ethyl ester, prepared in example E-94. Mass spectrum (m/e): 390.9 (M+1).

EXAMPLE F-96

Preparation of 4-cyano-5-ethyl-1-methyl-3-{4-[2-(propane-2-sulfonylamino)-phenoxy]-phenyl}-1H-pyrrole-2-carboxylic acid ethyl ester

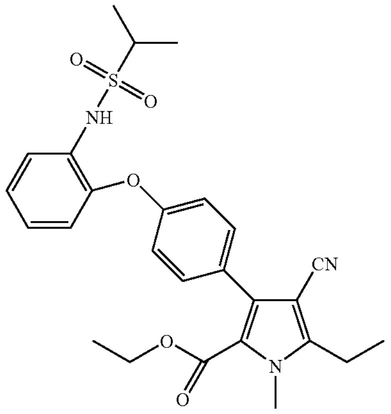

Add DBU (0.29 mL, 1.92 mmol) to 3-[4-(2-amino-phenoxy)-phenyl]-4-cyano-5-ethyl-1-methyl-1H-pyrrole-2-carboxylic acid ethyl ester (0.25 g, 0.64 mmol, prepared in example E-95) in methylene chloride at room temperature with stirring. After 10 minutes, cool to 0° C. and add isopropyl-sulfonylchloride (0.11 mL, 0.96 mmol). Stir the reaction mixture at 0° C. for 30 minutes and then at room temperature for 2-6 hours. Then pour the reaction mixture into water and extract with methylene chloride. Combine the organic extracts, wash with 1N HCl, water and brine, dry over anhydrous magnesium sulfate, filter, and concentrate under reduced pressure. Purify the residue by flash chromatography eluting with acetonitrile:methylene chloride to provide the title compound.

$^1$H NMR (400 MHz; $CDCl_3$) δ 7.67(d, 1H), 7.32(d, 2H), 7.10-7.01(m, 2H), 6.97(d, 2H), 6.93(d, 1H), 6.76(bs, 1H), 4.10(q, 2H), 3.90(s, 3H), 3.25(m, 1H), 2.83(q, 2H), 1.39(d, 6H), 1.30(t, 3H), 1.05(t, 3H).

EXAMPLE E-97a

Preparation of 4-cyano-5-ethyl-1-methyl-3-(4-trifluoromethanesulfonyloxyphenyl)-1H-pyrrole-2-carboxylic acid ethyl ester

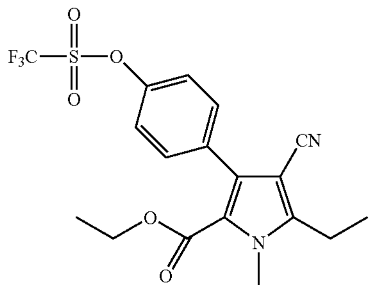

Prepare the title compound in a manner analogous to the procedures set forth in preparation 13 using 4-cyano-5-ethyl-3-(4-hydroxyphenyl)-1-methyl-1H-pyrrole-2-carboxylic acid ethyl ester (prepared in example E-81). Mass spectrum (m/e): 431.1 (MS $ES^+$).

EXAMPLE E-97b

Additional Preparation of 4-cyano-5-ethyl-1-methyl-3-(4-trifluoromethanesulfonyloxyphenyl)-1H-pyrrole-2-carboxylic acid ethyl ester A solution of 4-cyano-5-ethyl-3-(4-hydroxyphenyl)-1-methyl-1H-pyrrole-2-carboxylic acid ethyl ester (24.62 g, 82.52 mmol, prepared in example E-81) in methylene chloride (400 mL) is treated with pyridine (10.00 mL, 123.64 mmol). The resulting solution is cooled to ~0° C., is then treated with a dropwise addition of trifluoromethanesulfonic anhydride (16.70 mL, 99.26 mmol). The resulting reaction mixture is allowed to warm to room temperature. The reaction mixture is poured into water (1000 mL) and extracted with methylene chloride (3×300 mL each). The combined organics are washed with water (2×500 mL each), dried over anhydrous $MgSO_4$, filtered, and then concentrated in vacuo to afford a yellow solid. The yellow solid is slurried in EtOAc (~50 mL) and hexanes (~1000 mL), then recovered by vacuum filtration, washed with hexanes and is dried under vacuum filtration to afford the title compound (31.38 g, 88% yield) as a light yellow solid: $^1$H NMR (500 MHz, $CDCl_3$) δ 7.43 (d, 2H), 7.30 (d, 2H), 4.07 (q, 2H), 3.90 (s, 3H), 2.86 (q, 2H), 1.31 (t, 3H), 0.96 (t, 3H); MS (ES): m/z 431.1 ($M^+$+H). Anal. Calcd. For $C_{18}H_{17}F_3N_2O_5S$: C 50.23; H 3.98; N 6.50; S, 7.44. Found C 50.14; H 4.02; N 6.43; S 7.43.

Prepare the aryl coupled compounds listed in Table E-14 from 4-cyano-5-ethyl-1-methyl-3-(4-trifluoromethanesulfonyloxy-phenyl)-1H-pyrrole-2-carboxylic acid ethyl ester (prepared in example E-97a or E-97b) and the corresponding aryl boronic acid, in a manner analogous to the procedure set forth in Method CII.

TABLE E-14

| Ex. | Structure | Data | S.M. |
|---|---|---|---|
| E-98 | 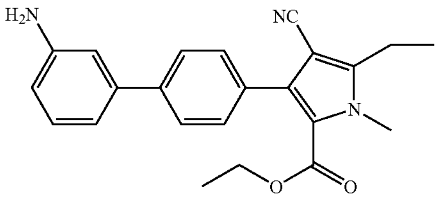 | mass spectrum (m/e): 374.1 (M + 1). | 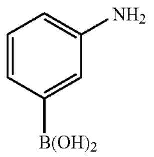 |

TABLE E-14-continued
| Ex. | Structure | Data | S.M. |
|---|---|---|---|
| E-99 | 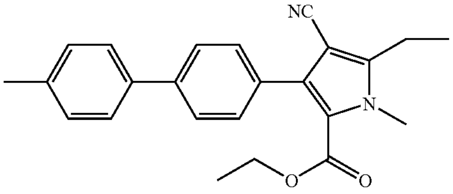 | mass spectrum (m/e): 373.1 (M + 1). | 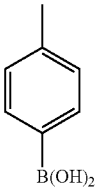 |
| E-100 | 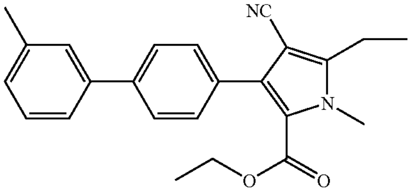 | mass spectrum (m/e): 373.1 (M + 1). | 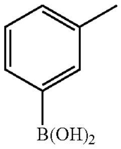 |
| E-101 | 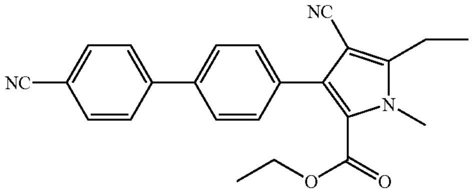 | mass spectrum (m/e): 384.1 (M + 1). | 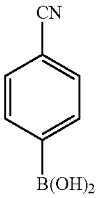 |
| E-102 | 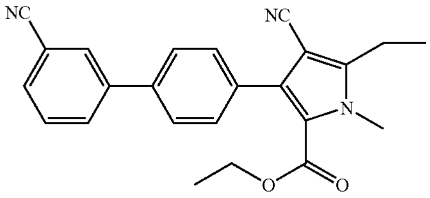 | mass spectrum (m/e): 384.1 (M + 1). | 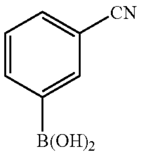 |
| E-103 | 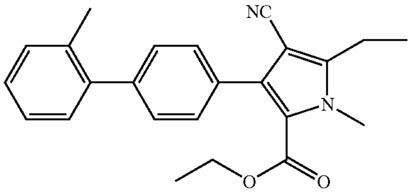 | mass spectrum (m/e): 373.1 (M + 1). | 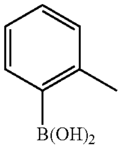 |
| E-104 | 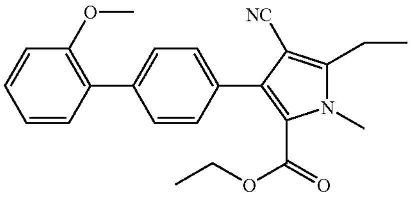 | mass spectrum (m/e): 389.1 (M + 1). | 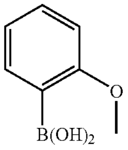 |
| E-105 | 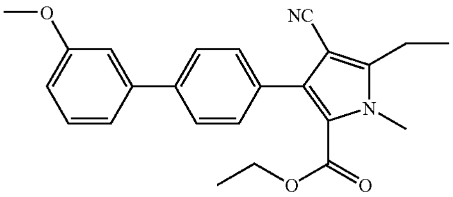 | mass spectrum (m/e): 389.1 (M + 1). | 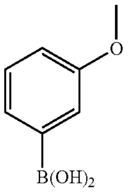 |

TABLE E-14-continued
| Ex. | Structure | Data | S.M. |
| --- | --- | --- | --- |
| E-106 | 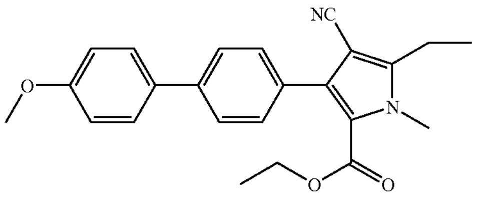 | $^1$H NMR(400 MHz; $CDCl_3$) δ 7.60-7.56(m, 4H), 7.40(d, 2H), 6.98(d, 2H), 4.10(q, 2H), 3.90(s, 3H), 3.87(s, 3H), 2.83(q, 2H), 1.30(t, 3H), 1.05(t, 3H). | 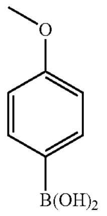 |
| E-107 | 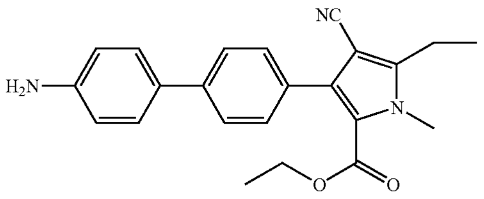 | $^1$H NMR(400 MHz; $CDCl_3$) δ 7.56(d, 2H), 7.45(d, 2H), 6.98(d, 2H), 6.78(d, 2H), 4.10(q, 2H), 3.90(s, 3H), 2.83(q, 2H), 1.30(t, 3H), 1.05(t, 3H). | 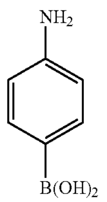 |
| E-108 | 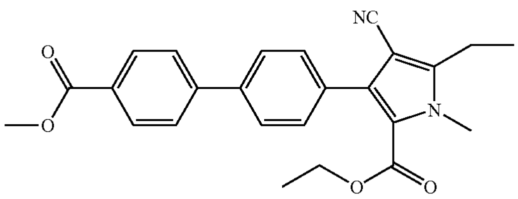 | mass spectrum (m/e): 417.1 (M + 1). | 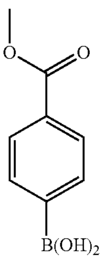 |
| E-109 | 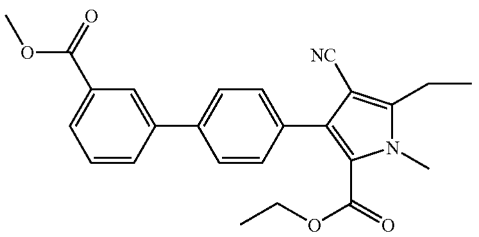 | mass spectrum (m/e): 417.1 (M + 1). | 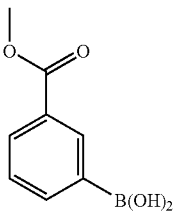 |
| E-110 | 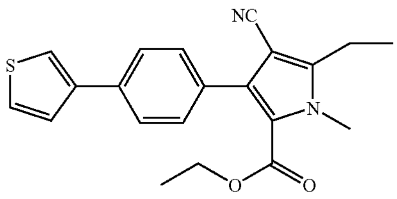 | mass spectrum (m/e): 365.1 (M + 1). | 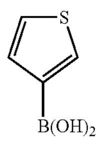 |
| E-111 | 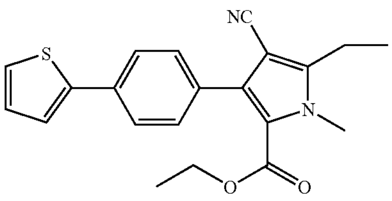 | mass spectrum (m/e): 365.1 (M + 1). | 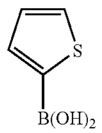 |

TABLE E-14-continued
| Ex. | Structure | Data | S.M. |
| --- | --- | --- | --- |
| E-112 | 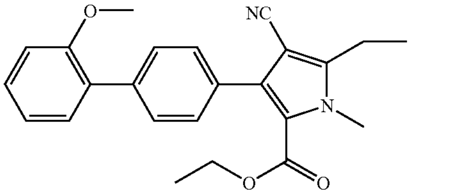 | mass spectrum (m/e): 405.0 (M + 1). | 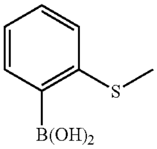 |
| E-113 | 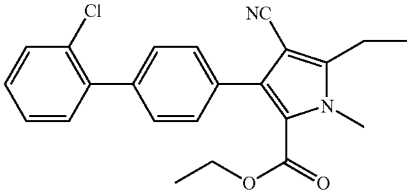 | mass spectrum (m/e): 393.0 (M + 1). | 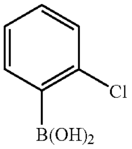 |
| E-114 | 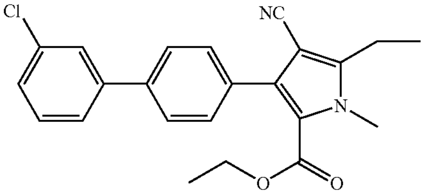 | mass spectrum (m/e): 393.0 (M + 1). | 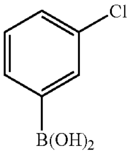 |
| E-115 | 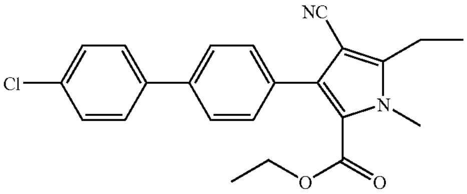 | mass spectrum (m/e): 393.2 (M + 1). | 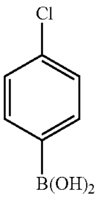 |
| E-116 | 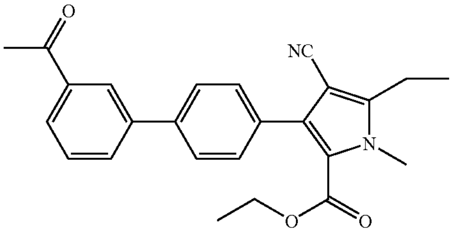 | mass spectrum (m/e): 401.1 (M + 1). | 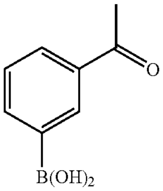 |
| E-117 | 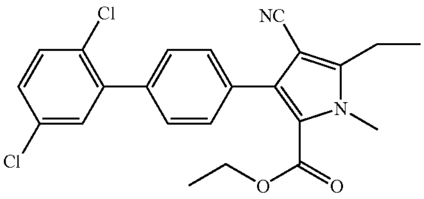 | mass spectrum (m/e): 445.9 (M + 1). | 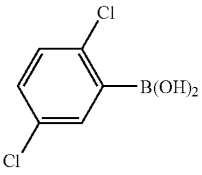 |
| E-118 | 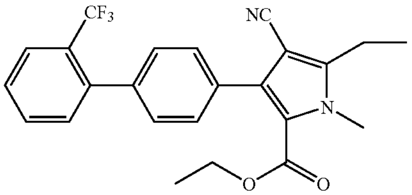 | mass spectrum (m/e): 427.0 (M + 1). | 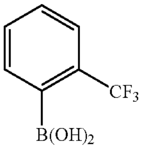 |

TABLE E-14-continued

| Ex. | Structure | Data | S.M. |
|---|---|---|---|
| E-119 | 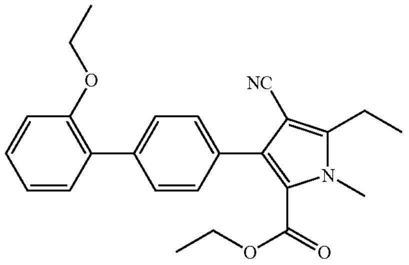 | mass spectrum (m/e): 403.16 (M + 1). | 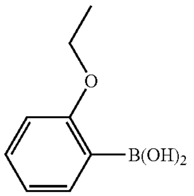 |

Prepare the aryl coupled compounds listed in Table E-15 from 4-cyano-5-ethyl-1-methyl-3-(4-trifluoromethanesulfonyloxy-phenyl)-1H-pyrrole-2-carboxylic acid ethyl ester (prepared in example E-97a or E-97b) and the corresponding halide in a manner analogous to the procedure set forth in Method DI.

TABLE E-15

| Ex. | Structure | Data | S.M. |
|---|---|---|---|
| E-120 | 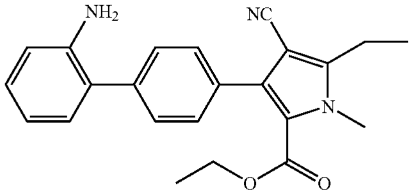 | $^1$H NMR(400 MHz; $CDCl_3$) δ 7.50-7.42(m, 4H), 7.17(d, 2H), 6.88-6.80(m, 2H), 4.10(q, 2H), 3.91(s, 3H), 2.83(q, 2H), 1.30(t, 3H), 1.05(t, 3H). | 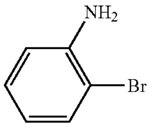 |
| E-121a (see also E-121b and E-121c infra) | 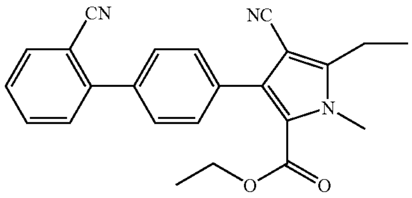 | mass spectrum (m/e): 384.1 (M + 1). | 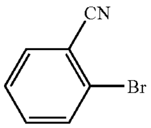 alternatively follow Method CII and start with 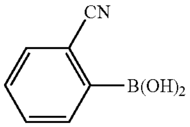 |
| E-122 | 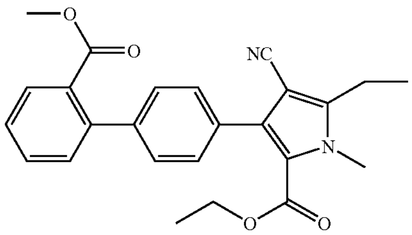 | mass spectrum (m/e): 434.1 (M + 18). | 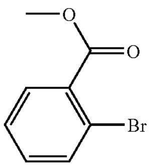 |

EXAMPLE E-121b

Additional Preparation of ethyl 4-cyano-3-[4-(2-cyanophenyl)phenyl]-5-ethyl-1-methylpyrrole-2-carboxylate

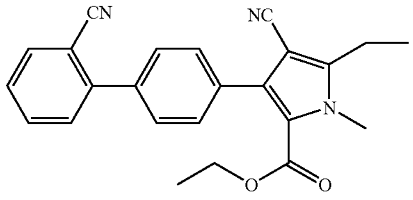

Add 2-[4-(4,4,5,5-tetramethyl-1,3,2-dioxaborolan-2-yl) phenyl]benzenecarbonitrile (0.916 grams, 0.003 moles, prepared in preparation 58), 4-cyano-5-ethyl-3-iodo-1-methyl-1H-pyrrole-2-carboxylic acid ethyl ester (0.996 grams, 0.003 moles, prepared in preparation 38), isopropyl acetate (14 mL) and ethanol (6 mL) to a 100 mL 3-neck flask. Stir the mixture under a nitrogen atmosphere and add palladium black (0.0319 grams, 0.0003 moles). Add a solution of potassium carbonate (0.663 grams, 0.0048 moles) in water (6 mL). Heat the mixture to reflux at 75° C. for 135 minutes. Add bis(acetato)bis (triphenylphosphine)palladium (II) (0.045 grams, 0.00006 moles) and continue heating at reflux for an additional 105 minutes. Add a solution of potassium carbonate (0.16 grams, 0.00116 moles) in water and continue heating at reflux for an additional 195 minutes. Cool the mixture to room temperature and stir for about 16 hours. Warm the mixture to 75° C. and filter to remove palladium black. Transfer the filtrate to a separatory funnel and add acetone (20 mL) to redissolve a precipitate and then separate the phases. Discard the aqueous phase. Concentrate the organic phase to a solid under reduced pressure (15-25 mm) and suspend the solid in ethanol (3 mL) and water (7 mL). Filter the suspension to recover the solid, and transfer the solid to a 20 mL vial. Add ethanol (12 mL) and warm to reflux. Slowly cool the resulting solution to about 23° C. and filter the resulting suspension to recover the precipitate. Dry the solid at 45° C. under reduced pressure (15-25 mm) to provide the title compound (0.72 g, 0.00188 moles) in 62.6% yield. $^1$H NMR ($CDCl_3$, 500 MHz): δ 7.77 (app d, 2H, J=8); 7.66 (app. td, 1H. J=117.5): 7.57 (m, 3H), 7.49-7.43 (m,3H); 4.10 (q, 2H, J=6.5); 3.91 (s, 3H); 2.87 (q, 2H, J=8); 1.32 (t, 3H, J=7.5); 1.04 (t, 3H, J=7).

EXAMPLE E-121c

Additional Preparation of ethyl 4-cyano-3-[4-(2-cyanophenyl)phenyl]-5-ethyl-1-methylpyrrole-2-carboxylate Preparation of 2'-cyanobiphenyl-4-carboxylic acid

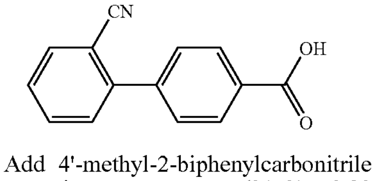

Step A: Add 4'-methyl-2-biphenylcarbonitrile (9.66 g, 0.050 mol), potassium permanganate (31.61 g, 0.20 mol), and a 1:1 solution of pyridine in water (193 mL) to 500 mL flask equipped with thermocouple, condenser, and magnetic stir bar. Heat the mixture for five hours at 100° C. Filter the reaction mixture through Hyflo and rinse the glassware and filter cake with 100 ml of 1N NaOH solution. Combine filtrates and wash with diethyl ether (1×100 mL) to afford three layers. Combine the lowest two layers and concentrate to ½ volume. Adjust pH to 1 using 5N HCl. Filter the resulting white precipitate. Dry the white precipitate at 40° C. to afford 9.41 g (84.3%) of title compound. $^1$H NMR (d6-DMSO, 400 MHz) δ 8.10 (d, 2H, J=7.9), 8.00 (d, 1H, J=7.9), 7.84 (apparent t, 1H, J=7.5), 3.36 (bs, 1H).

Preparation of 4-(2'-cyanobiphenyl)-cyanomethyl ketone

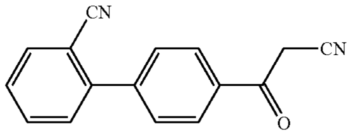

Step B: Add to a 500 mL flask with nitrogen inlet, 2'-cyanobiphenyl-4-carboxylic acid (5.00 g, 0.0224 mol, prepared in Step A above), methylene chloride (125 mL), oxalyl chloride (2.84 g, 0.0224 mol), and 5 drops of DMF to form a white slurry. Observe gas evolution from the reaction. Stir the reaction 16 hours at room temperature. Introduce additional oxalyl chloride (1.42 g, 0.0112 mol) and three drops of DMF with continued stirring to afford initially a thin white slurry that becomes a solution over three hours. Introduce additional oxalyl chloride (1.42 g, 0.0112 mol) and three drops of DMF to drive the reaction to completion, and to afford the intermediate acid chloride derivative that is taken on directly into the next reaction. Add a 1.0 M solution of cyanoacetic acid in THF (16 mL, 0.016 mol) to a 100-mL three-necked flask equipped with nitrogen inlet and thermocouple. Cool the flask contents to −10° C. Add a 32 mL solution of 1.0 M lithium bis(trimethylsilyl)amide in THF dropwise to the reactor contents over 30 minutes. Stir the reaction mixture for 30 minutes at −10° C. then add the acid chloride (1.93 g 0.00800 mol). Observe an exotherm to −3° C. and stir for ½ hour at −10° C. Pour the reaction mixture into 100 mL of 1 N HCl. Stir for ½ hour and observe gas evolution. Extract with ethyl acetate (3×50 mL), combine the ethyl acetate layers and add 10 g of silica gel. Concentrate to dryness and purify by applying the residue to a pad of silica gel. Elute with 1,2-dichloroethane to afford 1.62 g of technical grade material that is recrystallized from heptane/ethyl acetate to yield 1.175 g (59.6%) of title compound. H NMR (d6-DMSO, 400 MHz) δ 8.11 (d, 2H, J=7.9); 8.02 (d, 1H, J=7.9); 7.90-7.76 (m, 3H); 7.70 (m, 2H); 4.84 (s, 2H).

Preparation of 4'-(2-Cyano-3-ethoxy-pent-2-enoyl)-biphenyl-2-carbonitrile

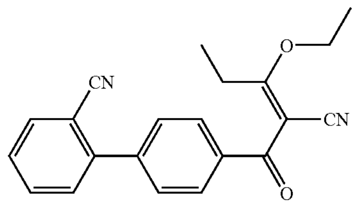

Step C: Charge 4-(2'-cyanobiphenyl)-cyanomethyl ketone (1.0 g, 4.1 mmoles, prepared in Step B above), triethylorthopropionate (0.75 g, 4.3 mmoles), and toluene (10 mL) to a 25 mL three-neck round-bottom flask fitted with a Dean-Stark trap and an internal temperature probe. Heat the resulting heterogeneous white mixture to 115° C. with azeotropic removal of ethanol. The reaction mixture becomes a homogeneous golden brown solution. Add a crystal of para-toluenesulfonic acid and stir the reaction mixture at reflux for an additional 90 minutes. Concentrate the reaction mixture to a dark red oil under a flow of nitrogen while allowing the reaction vessel to cool slowly. The reactor contents solidify at room temperature to afford the title compound as a dark red solid (1.26 g) that is used directly in the next reaction. M/z: 329 (M–H); 301 (M-Et), 206 (M-$C_7H_{11}NO$).

Preparation of Final Title Compound

Step D: Charge 4'-(2-Cyano-3-ethoxy-pent-2-enoyl)-biphenyl-2-carbonitrile (1.3 g, 3.8 mmoles, prepared in Step C) and absolute ethanol (10 mL) into a reaction vessel to produce a yellow heterogeneous mixture. Add sarcosine ethyl ester hydrochloride (0.61 g, 4.0 mmoles) and cool the resulting slightly heterogeneous mixture to 0° C. Add a solution of sodium ethoxide in ethanol (21 wt %, 1.5 mL, 4.0 mmoles) and stir the reaction mixture for 30 min to neutralize the HCl salt. Add another portion of sodium ethoxide in ethanol (21 wt %, 1.5 mL, 4.0 mmoles) and stir the reaction mixture at 0° C. for another 70 min. Add 1N hydrochloric acid (8 mL) and stir the reaction mixture for 30 min. Add water (10 mL) and filter the suspension through a glass-fritted funnel. Rinse the collected solids with water (to remove NaCl), and dry the yellow solid under vacuum at to 50° C. to afford 0.94 g of technical grade product. Slurry the technical grade in absolute ethanol and filter through a glass-fritted funnel. Rinse the collected solids with ethanol and dry to afford 0.21 g of the final title compound as an off-white solid. M/z: 383 (M); 311 (M-$CO_2$Et); 296 (M-$CO_2$Et-Me).

EXAMPLE E-123

Preparation of 4-cyano-3-(5'-cyano-2'-ethoxy-biphenyl-4-yl)-5-ethyl-1-methyl-1H-pyrrole-2-carboxylic acid ethyl ester

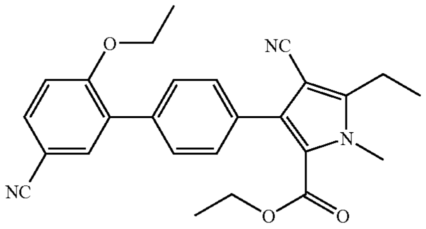

Prepare the title compound in a manner analogous to the procedure set forth in Method DI using 3-(4-bromo-phenyl)-4-cyano-5-ethyl-1-methyl-1H-pyrrole-2-carboxylic acid ethyl ester (prepared in example E-247a or E-247b) and 3-bromo-4-ethoxy-benzonitrile (prepared in preparation 18). Mass spectrum (m/e): 428.1 (M+1).

EXAMPLE E-124

Preparation of 4-cyano-3-[2'-ethoxy-5'-(2-methoxy-carbonyl-ethyl)-biphenyl-4-yl]-5-ethyl-1-methyl-1H-pyrrole-2-carboxylic acid ethyl ester

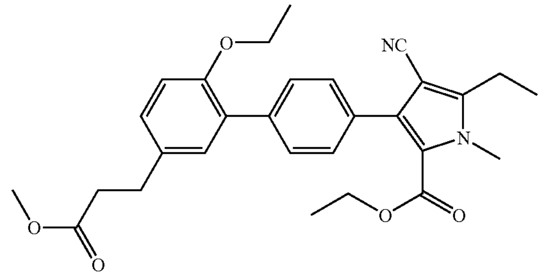

Prepare the title compound in a manner analogous to the procedure set forth in Method DI using 3-(4-bromo-phenyl)-4-cyano-5-ethyl-1-methyl-1H-pyrrole-2-carboxylic acid ethyl ester (prepared in example E-247a or E-247b) and 3-(3-bromo-4-ethoxy-phenyl)-propionic acid methyl ester (prepared in preparation 20). Mass spectrum (m/e): 489.1 (M+1).

Method K

Scheme XI: Add triethylamine (3.0 mmol) to the corresponding (amino-biphenyl-4-yl)-4-cyano-5-ethyl-1-methyl-1H-pyrrole-2-carboxylic acid ethyl ester (compound of Formula If) in THF at room temperature with stirring. After 15 minutes, add the corresponding alkyl acid chloride (1.2 mmol, structure 9) to the reaction mixture. After 2-8 hours, pour the reaction mixture into water and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula Ig.

Prepare the amides listed in Table E-16 from the corresponding (amino-biphenyl-4-yl)-4-cyano-5-ethyl-1-methyl-1H-pyrrole-2-carboxylic acid ethyl esters in a manner analogous to the procedure set forth in Method K.

TABLE E-16

| Ex. | Structure | Data | S.M. |
|---|---|---|---|
| E-125 | 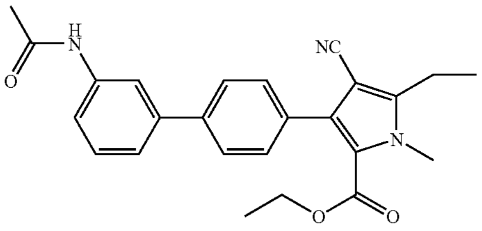 | mass spectrum (m/e): 416.1 (M + 1). | E-98 and acetyl chloride |

TABLE E-16-continued

| Ex. | Structure | Data | S.M. |
|---|---|---|---|
| E-126 | 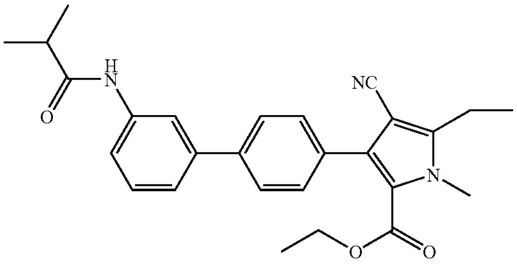 | $^1H$ NMR (400 MHz; $CDCl_3$) δ 7.82(s, 1H), 7.59(d, 2H), 7.45(d, 1H), 7.42-7.38(m, 4H), 7.24(bs, 1H), 4.10(q, 2H), 3.90(s, 3H), 2.83(q, 2H), 2.60-2.53(m, 1H), 1.39-1.30(m, 9H), 1.05(t, 3H). | E-98 and isobutyryl chloride |
| E-127 | 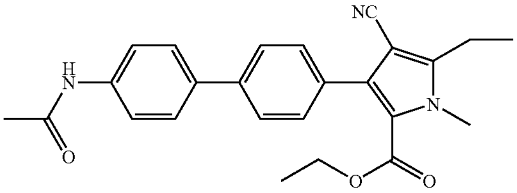 | mass spectrum (m/e): 416.1 (M + 1). | E-107 and acetyl chloride |
| E-128 | 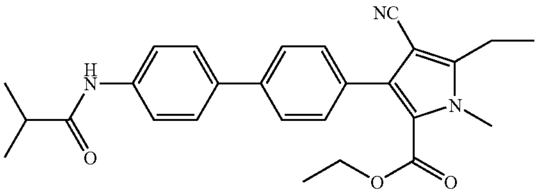 | mass spectrum (m/e): 444.1 (M + 1). | E-107 and isobutyryl chloride |
| E-129 | 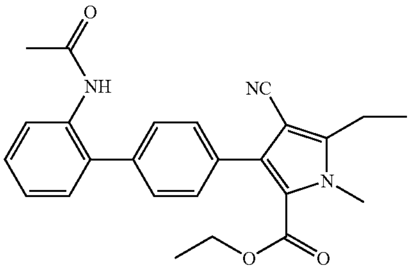 | $^1H$ NMR(400 MHz; $CDCl_3$) δ 8.23(d, 1H), 7.45(d, 2H), 7.41-7.37(m, 3H), 7.24(bs, 1H), 7.21-7.15(m, 2H), 4.10(q, 2H), 3.90(s, 3H), 2.83(q, 2H), 2.03(s, 3H), 1.30(t, 3H), 1.05(t, 3H). | E-120 and acetyl chloride |
| E-130 | 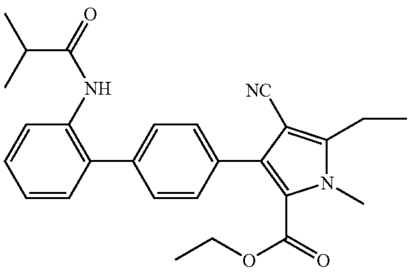 | $^1H$ NMR(400 MHz; $CDCl_3$) δ 8.33(d, 1H), 7.59(d, 2H), 7.45(d, 1H), 7.42-7.38(m, 4H), 7.24(bs, 1H), 4.10(q, 2H), 3.90(s, 3H), 2.83(q, 2H), 2.42-2.36(m, 1H), 1.30(t, 3H), 1.10(d, 6H), 1.05(t, 3H). | E-120 and isobutyryl chloride |

Prepare the compounds listed in Table E-17 from the corresponding (amino-biphenyl-4-yl)-4-cyano-5-ethyl-1-methyl-1H-pyrrole-2-carboxylic acid ethyl esters and isopropylsulfonyl chloride in a manner analogous to the procedure set forth in example E-96.

TABLE E-17

| Ex. | Structure | Data | S.M. |
|---|---|---|---|
| E-131 | 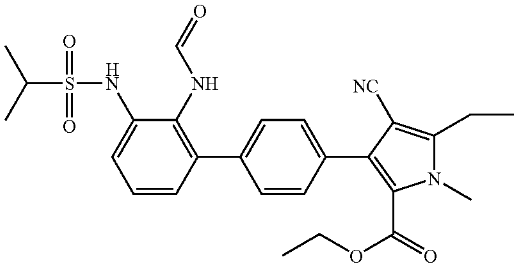 | $^{1}$H NMR (400 MHz; $CDCl_3$) δ 7.70-7.67(m, 2H), 7.57(d, 2H), 7.45-7.55(m, 4H), 6.75(bs, 1H), 4.10(q, 2H), 4.01-3.93(m, 1H), 3.90(s, 3H), 2.83(q, 2H), 1.49(d, 6H), 1.30(t, 3H), 1.05(t, 3H). | E-98 |
| E-132 | 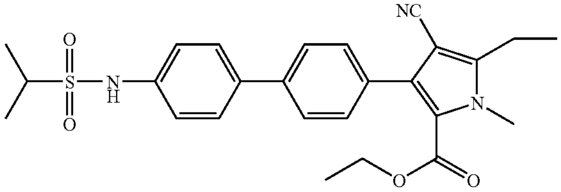 | $^{1}$H NMR (400 MHz; $CDCl_3$) δ 7.60-7.55(m, 4H), 7.42(d, 2H), 7.25(d, 2H), 6.75(bs, 1H), 4.10(q, 2H), 3.90(s, 3H), 3.39-3.34(m, 1H), 2.83(q, 2H), 1.42(d, 6H), 1.30(t, 3H), 1.05(t, 3H). | E-107 |
| E-133 | 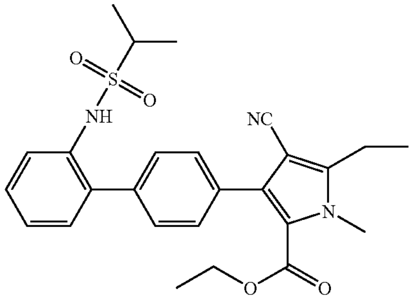 | $^{1}$H NMR (400 MHz; $CDCl_3$) δ 7.70(d, 1H), 7.50(d, 2H), 7.41-7.36(m, 3H), 7.25(d, 1H), 7.21-7.18(m, 1H), 6.75(bs, 1H), 4.10(q, 2H), 3.90(s, 3H), 3.24-3.19(m, 1H), 2.83(q, 2H), 1.30(t, 3H), 1.20(d, 6H), 1.05(t, 3H). | E-120 |

Prepare the compounds listed in Table E-18 from 4-cyano-5-ethyl-1-methyl-3-(4-trifluoromethanesulfonyloxyphenyl)-1H-pyrrole-2-carboxylic acid ethyl ester (prepared in example E-97a or E-97b) and the corresponding zinc bromide, in a manner analogous to the procedure set forth in Example E-55.

TABLE E-18

| Ex. | Structure | Data | S.M. |
|---|---|---|---|
| E-134 | 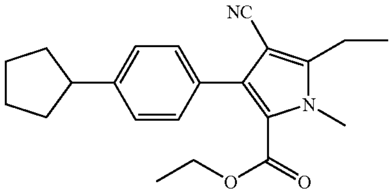 | mass spectrum (m/e): 351.2 (M + 1). | 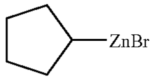 |
| E-135 | 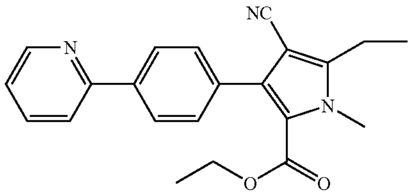 | mass spectrum (m/e): 360.2 (M + 1). | 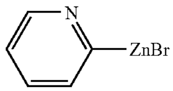 |

TABLE E-18-continued
| Ex. | Structure | Data | S.M. |
|---|---|---|---|
| E-136 | 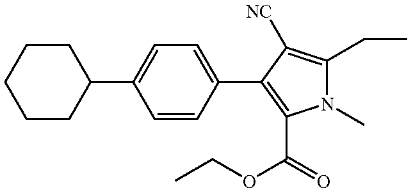 | $^1$H NMR (400 MHz; $CDCl_3$) δ 7.26(d, 2H), 7.20(d, 2H), 4.10(q, 2H), 3.90(s, 3H), 2.83(q, 2H), 2.62-2.57(m, 1H), 1.99-1.84(m, 4H), 1.81-1.75(m, 1H), 1.52-1.40(m, 3H) 1.38-1.25(m, 5H), 1.05(t, 3H). | 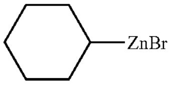 |
| E-137 | 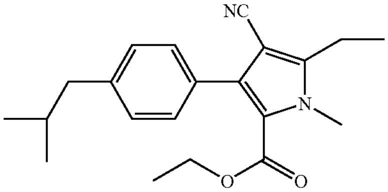 | $^1$H NMR (400 MHz; $CDCl_3$) δ 7.26(d, 2H), 7.14(d, 2H), 4.10(q, 2H), 3.90(s, 3H), 2.83(q, 2H), 2.50(d, 2H), 1.95-1.85(m, 1H), 1.30(t, 3H), 1.05(t, 3H), 0.90(d, 6H). | 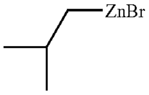 |
| E-138 | 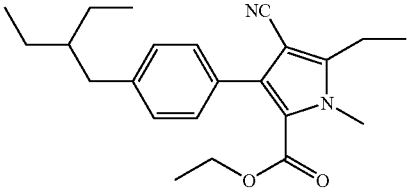 | mass spectrum (m/e): 367.4 (M + 1). | 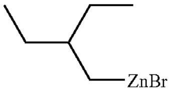 |
| E-139 | 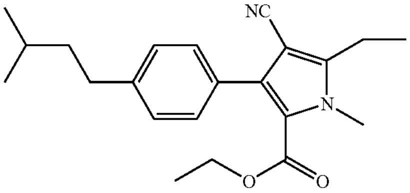 | mass spectrum (m/e): 353.3 (M + 1). | 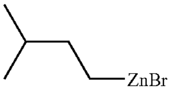 |
| E-140 | 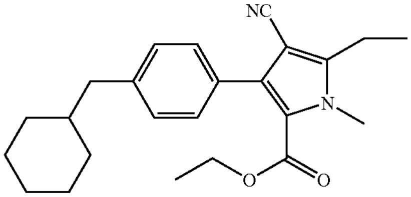 | mass spectrum (m/e): 379.3 (M + 1). | 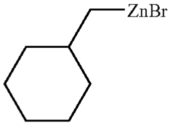 |
| E-141 | 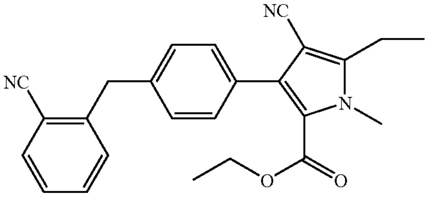 | mass spectrum (m/e): 415.2 (M + 18). | 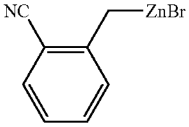 |
| E-142 | 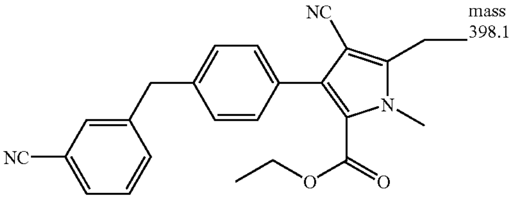 | mass spectrum (m/e): 398.1 (M + 1). | 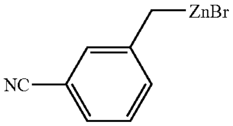 |

TABLE E-18-continued

| Ex. | Structure | Data | S.M. |
|---|---|---|---|
| E-143 | 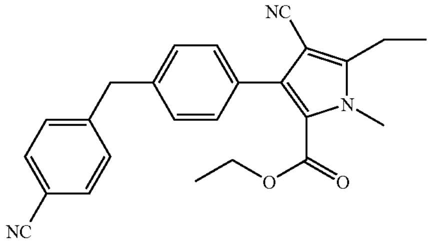 | mass spectrum (m/e): 398.1 (M + 1). | 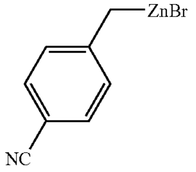 |
| E-144 | 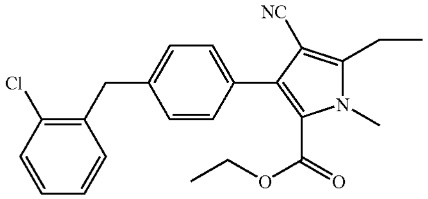 | mass spectrum (m/e): 407.0 (M + 1). | 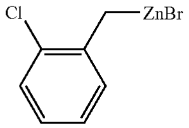 |
| E-145 | 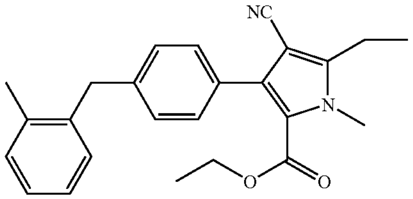 | mass spectrum (m/e): 387.1 (M + 1). | 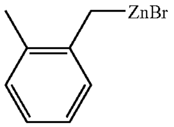 |
| E-146 | 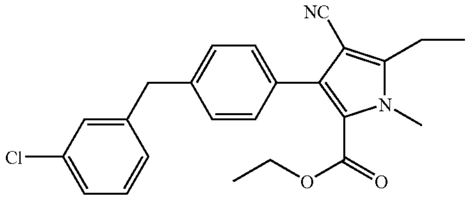 | mass spectrum (m/e): 407.0 (M + 1). | 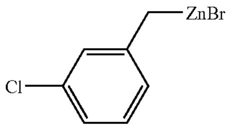 |
| E-147 | 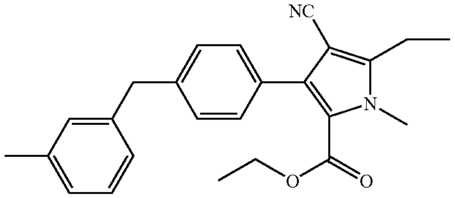 | mass spectrum (m/e): 387.1 (M + 1). | 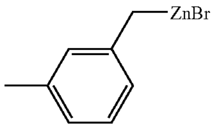 |

Prepare the compounds listed in Table E-19 from 4-cyano-5-ethyl-3-iodo-1-methyl-1H-pyrrole-2-carboxylic acid ethyl ester (prepared in preparation 38) and the corresponding boronic acid or ester in a manner analogous to the procedure set forth in Method EI.

TABLE E-19

| Ex. | Structure | Data | S.M. |
|---|---|---|---|
| E-148 | 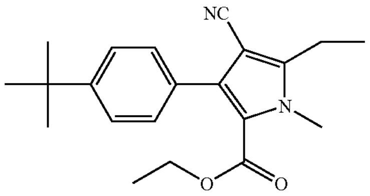 | mass spectrum (m/e): 339.3 (M + 1). | 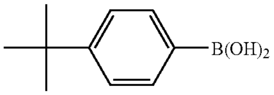 |

TABLE E-19-continued
| Ex. | Structure | Data | S.M. |
| --- | --- | --- | --- |
| E-149 | 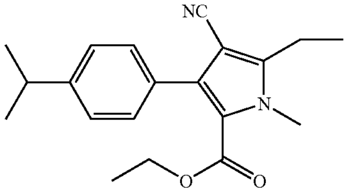 | mass spectrum (m/e): 325.3 (M + 1). | 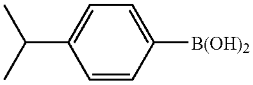 |
| E-150 | 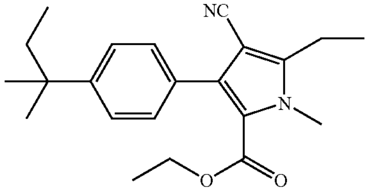 | | 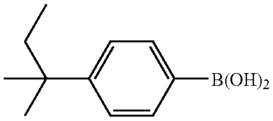 |
| E-151 | 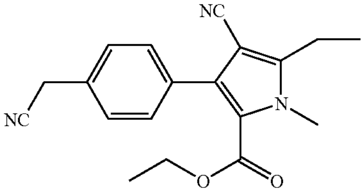 | $^1$H NMR (400 MHz; $CDCl_3$) δ 7.40-7.30 (m, 4H), 4.10(q, 2H), 3.90(s, 3H), 3.80(s, 2H), 2.83(q, 2H), 1.30(t, 3H), 1.05(t, 3H). | 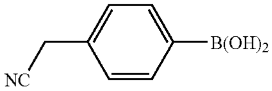 |
| E-152 | 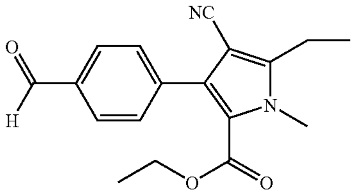 | mass spectrum (m/e): 311.1 (M + 1). | 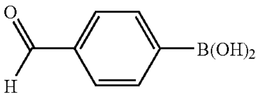 |
| E-153 | 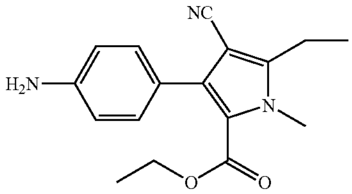 | mass spectrum (m/e): 298.0 (M + 1). | 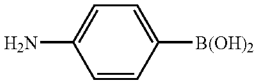 |

EXAMPLE E-154

Preparation of 4-cyano-3-[4-cyano-dimethyl-methyl-phenyl]-5-ethyl-1-methyl-1H-pyrrole-2-carboxylic acid ethyl ester

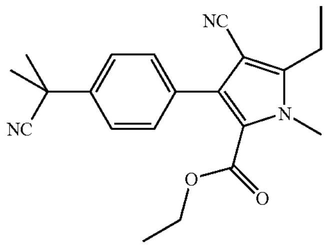

Add lithium bis(trimethylsilyl)amide (1.5 mL, 1.5 mmol) to 4-cyano-3-(4-cyanomethyl-phenyl)-5-ethyl-1-methyl-1H-pyrrole-2-carboxylic acid ethyl ester (0.20 g, 0.62 mmol, prepared in example E-151) in THF at −78° C. with stirring. After 20 minutes, add iodomethane (0.12 mL, 1.85 mmol) and allow the reaction to warm to ambient temperature. After 2-3 hours, pour the reaction mixture into water and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the title compound.

Mass spectrum (m/e): 350.3 (M+1).

EXAMPLE E-155

Preparation of 4-cyano-5-ethyl-1-methyl-3(2'-propyl-biphenyl-4-yl)-1H-pyrrole-2-carboxylic acid ethyl ester

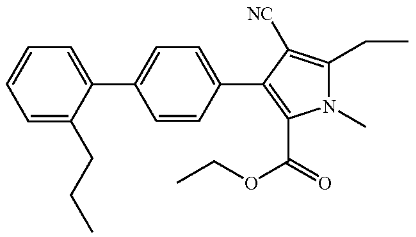

Prepare the title compound in a manner analogous to the procedure set forth in Method EI using 4-cyano-5-ethyl-3-iodo-1-methyl-1H-pyrrole-2-carboxylic acid ethyl ester (prepared in preparation 38) and 4,4,5,5-tetramethyl-2-(2'-propyl-biphenyl-4-yl) -[1,3,2]dioxaborolane (prepared in preparation 42). Mass spectrum (m/e): 401.3 (M+1).

EXAMPLE E-156

Preparation of 4-cyano-5-ethyl-1-methyl-3-[4-(3-methylsulfanyl-thiophen-2-yl)-phenyl]-1H-pyrrole-2-carboxylic acid ethyl ester

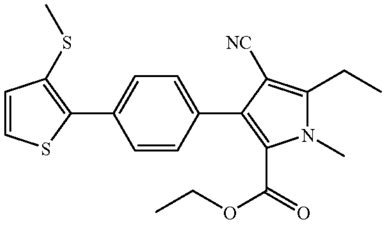

Prepare the title compound in a manner analogous to the procedure set forth in Method EI using 4-cyano-3-iodo-5-methyl-1-methyl-1H-pyrrole-2-carboxylic acid ethyl ester (prepared in preparation 38) and 4,4,5,5-tetramethyl-2-[4-(3-methylsulfanyl-thiophen-2-yl)-phenyl]-[1,3,2]dioxaborolane (prepared in preparation 4). Mass spectrum (m/e): 428.0 (M+1).

EXAMPLE E-157

Preparation of 3-(4-carboxy-phenyl)-4-cyano-5-ethyl-1-methyl-1H-pyrrole-2-carboxylic acid ethyl ester

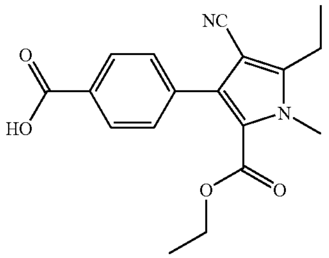

Add 30% hydrogen peroxide (0.66 mL, 5.8 mmol) and selenium dioxide (0.016 g, 0.15 mmol) to 4-cyano-5-ethyl-3-(4-formyl-phenyl)-1-methyl-1H-pyrrole-2-carboxylic acid ethyl ester (prepared in example E-152), and heat to reflux with stirring. After 18 hours, cool the reaction mixture and pour into 1N HCl. Extract the quenched reaction with methylene chloride. Combine the organic extracts, wash with water and brine, dry over anhydrous magnesium sulfate, filter, and concentrate under reduced pressure. Recrystallize the residue from ethyl acetate:hexanes to provide the title compound. Mass spectrum (m/e): 325.1 (M−1).

Method L

Scheme XII: Add 3-(4-carboxy-phenyl)-4-cyano-5-ethyl-1-methyl-1H-pyrrole-2-carboxylic acid ethyl ester (1.0 mmol, prepared in example E-157, compound of Formula IIo) in THF to oxalyl chloride (1.2 mmol) in THF followed by 1 drop of DMF and stir the reaction mixture at room temperature. After 2 hours, concentrate to a residue. Next, add the residue in THF to the corresponding aryl boronic acid (1.2 mmol), tetrakis(triphenylphosphine)-palladium(0) (0.1 mmol), and cesium carbonate (3.0 mmol) in toluene and heat to reflux with stirring. After 18 hours, cool the reaction mixture and pour into water. Extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula IIp.

Prepare the compounds listed in Table E-20 from 3-(4-carboxy-phenyl)-4-cyano-5-ethyl-1-methyl-1H-pyrrole-2-carboxylic acid ethyl ester (prepared in example E-157) and the corresponding boronic acid, in a manner analogous to the procedure set forth in Method L.

TABLE E-20

| Ex. | Structure | Data | S.M. |
|---|---|---|---|
| E-158 | 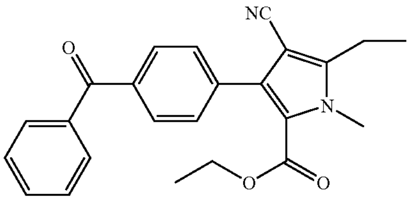 | mass spectrum (m/e): 387.1 (M + 1). | 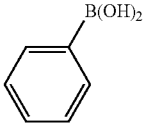 |
| E-159 | 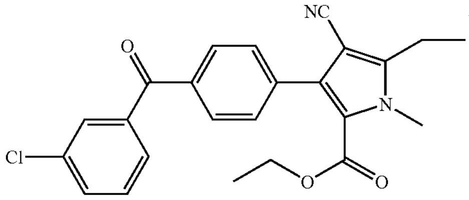 | mass spectrum (m/e): 422.9 (M + 1). | 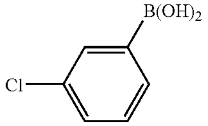 |

EXAMPLE E-160

Preparation of 4-cyano-5-ethyl-1-methyl-3-(4-phenylacetyl-phenyl)-1H-1H-pyrrole-2-carboxylic acid ethyl ester

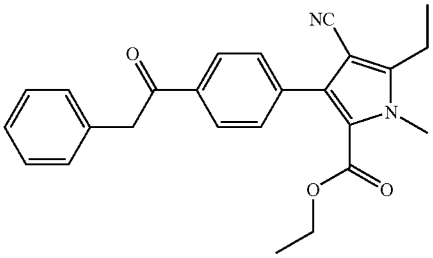

Add n-butyllithium (1.3 mL, 2.1 mmol) to phenylacetic acid (0.14 g, 1.05 mmol) in THF at −78° C. with stirring. After 30 minutes, add 4-cyano-5-ethyl-3-[4-(methoxy-methyl-carbamoyl)-phenyl]-1-methyl-1H-pyrrole-2-carboxylic acid ethyl ester 0.35 g, 0.95 mmol, prepared in preparation 43) and allow the reaction to gradually warm to ambient temperature. After 2 hours, pour the reaction mixture into water and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the title compound. Mass spectrum (m/e): 401.0 (M+1).

Method M

Scheme XIII: Add 3-(4-carboxy-phenyl)-4-cyano-5-ethyl-1-methyl-1H-pyrrole-2-carboxylic acid ethyl ester (1.0 mmol, prepared in example E-157, compound of Formula IIo) in THF to oxalyl chloride (1.2 mmol) in THF followed by 1 drop of DMF and stir at room temperature. After 2 hours, concentrate the reaction mixture to a residue. Next, add the residue in THF to copper cyanide (0.14 mmol), lithium bromide (0.14 mmol) and $R^{25}ZnBr$ (1.4 mmol), wherein $R^{25}$ represents (1-4C)alkyl, in THF at −30° C. with stirring. Allow the reaction mixture to gradually warm to room temperature. After 4 hours, pour into water and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula IIq.

Prepare the compound listed in Table E-21 from 3-(4-carboxy-phenyl)-4-cyano-5-ethyl-1-methyl-1H-pyrrole-2-carboxylic acid ethyl ester, prepared in example E-157, in a manner analogous to the procedure set forth in Method M.

TABLE E-21

| Ex. | Structure | Data |
|---|---|---|
| E-161 | 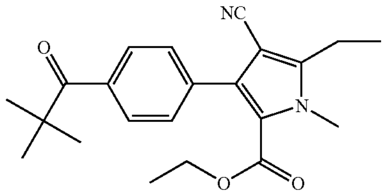 | mass spectrum (m/e): 384.1 (M + 18). |

EXAMPLE E-162

Preparation of 4-cyano-5-ethyl-3-[4-(hydroxy-phenyl-methyl)-phenyl]-1-methyl-1H-pyrrole-2-carboxylic acid ethyl ester

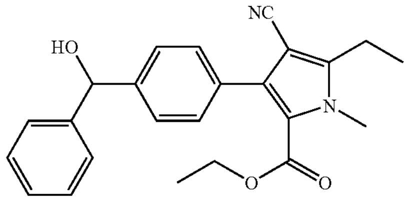

Add phenyl magnesium bromide (192 uL, 0.58 mmol) to 4-cyano-5-ethyl-3-(4-formyl-phenyl)-1-methyl-1H-pyrrole-2-carboxylic acid ethyl ester [(0.020 g, 0.64 mmol, prepared in example E-152] in THF with stirring at −78° C. After 30 minutes, gradually allow the reaction mixture to warm to ambient temperature. After 2 hours, pour the reaction mixture into water and extract with EtOAc. Combine the organic extracts, wash with water and brine, dry over anhydrous magnesium sulfate, filter, and concentrate under reduced pressure. Purify the residue by flash chromatography eluting with ethyl acetate:hexanes to provide the title compound. Mass spectrum (m/e): 406.1 (M+18).

EXAMPLE E-163

Preparation of 4-cyano-3-{4-[2-(3-cyano-phenyl)-1-hydroxy-ethyl]-phenyl}-5-ethyl-1-methyl-1H-pyrrole-2-carboxylic acid ethyl ester

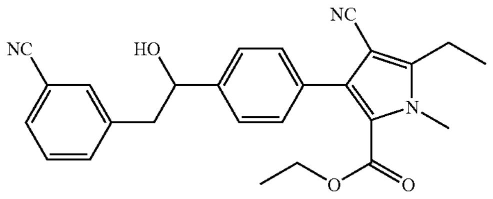

Prepare the title compound in a manner analogous to the procedure set forth in example E-162 using 4-cyano-5-ethyl-3-(4-formyl-phenyl)-1-methyl-1H-pyrrole-2-carboxylic acid ethyl ester (prepared in example E-152) and 3-cyanobenzylzinc bromide at 0° C. to room temperature. Mass spectrum (m/e): 428.0 (M+1).

EXAMPLE E-164

Preparation of 4-cyano-3-{4-[2-(3-cyano-phenyl)-1-fluoro-ethyl]-phenyl}-5-ethyl-1-methyl-1H-pyrrole-2-carboxylic acid ethyl ester

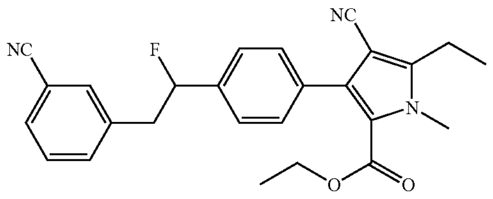

Add (diethylamino)sulfur trifluoride (145 uL, 1.1 mmol) to 4-cyano-3-{4-[2-(3-cyano-phenyl)-1-hydroxy-ethyl]-phenyl}-5-ethyl-1-methyl-1H-pyrrole-2-carboxylic acid ethyl ester (0.427 g, 1.0 mmol, prepared in example E-163) in methylene chloride with stirring at −78° C. After 30 minutes, gradually allow the reaction mixture to warm to ambient temperature. After 2 hours, pour the reaction mixture into water and extract with methylene chloride. Combine the organic extracts, wash with water and brine, dry over anhydrous magnesium sulfate, filter, and concentrate under reduced pressure. Purify the residue by flash chromatography eluting with ethyl acetate:hexanes to provide the title compound. Mass spectrum (m/e): 430.0 (M+1).

EXAMPLE E-165

Preparation of 4-cyano-5-ethyl-3-(4-phenylcarbamoyl-phenyl)-1-methyl-1H-pyrrole-2-carboxylic acid ethyl ester

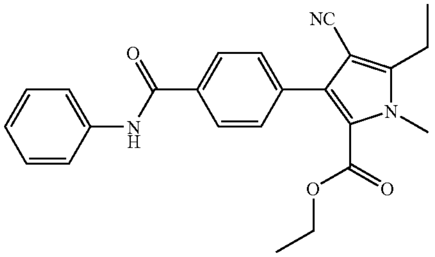

Add N-chlorosuccinimide (0.13 g, 1.0 mmol) to 3-(4-carboxy-phenyl)-4-cyano-5-ethyl-1-methyl-1H-pyrrole-2-carboxylic acid ethyl ester (0.33 g, 11.0 mmol, prepared in example E-157) and triphenyl-phosphine (0.26 g, 1.0 mmol) in methylene chloride at 0° C. with stirring. Allow the reaction to warm to room temperature. After 30 minutes, add aniline (0.18 mL, 2.0 mmol). After 2-3 hours, pour the reaction mixture into water and extract with methylene chloride. Combine the organic extracts, wash with water and brine, dry over anhydrous magnesium sulfate, filter, and concentrate under reduced pressure. Purify the residue by flash chromatography eluting with ethyl acetate:hexanes to provide the title compound. Mass spectrum (m/e): 402.0 (M+1).

EXAMPLE E-166

Preparation of 4-cyano-5-ethyl-1-methyl-3-[4-(methyl-phenyl-carbamoyl)-phenyl]-1H-pyrrole-2-carboxylic acid ethyl ester

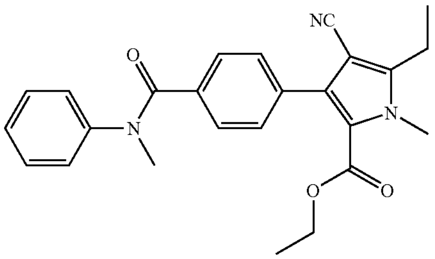

Prepare the title compound in a manner analogous to the procedures set forth in example E-165 using N-methylaniline. Mass spectrum (m/e): 416.01 (M+1).

EXAMPLE E-167

Preparation of 3-(4-benzylamino-phenyl)-4-cyano-5-ethyl-1-methyl-1H-pyrrole-2-carboxylic acid ethyl ester

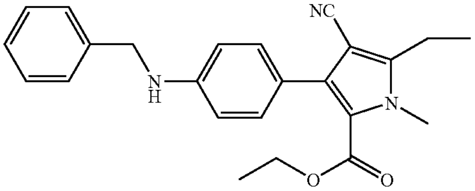

Add 3-(4-amino-phenyl)-4-cyano-5-ethyl-1-methyl-1H-pyrrole-2-carboxylic acid ethyl ester (0.297 g, 1.0 mmol, prepared in example E-153), benzaldehyde (0.106 g, 1.0 mmol), and one drop of acetic acid in methanol with stirring at room temperature. After 4 hours, add sodium borohydride (0.075 g, 2.0 mmol) portionwise and continue stirring at room temperature. After 18 hours, pour the reaction mixture into water and extract with EtOAc. Combine the organic extracts, wash with water and brine, dry over anhydrous magnesium sulfate, filter, and concentrate under reduced pressure. Purify the residue by flash chromatography eluting with ethyl acetate:hexanes to provide the title compound. Mass spectrum (m/e): 388.1 (M+1).

EXAMPLE E-168

Preparation of 3-[(4-(2-chloro-benzylamino)-phenyl]-4-cyano-5-ethyl-1-methyl-1H-pyrrole-2-carboxylic acid ethyl ester

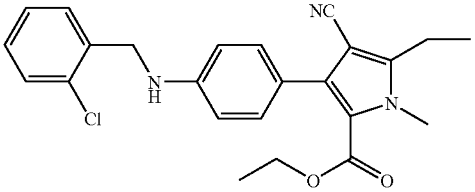

Prepare the title compound in a manner analogous to the procedure set forth in example E-167 using 3-(4-amino-phenyl)-4-cyano-5-ethyl-1-methyl-1H-pyrrole-2-carboxylic acid ethyl ester (prepared in example E-153) and 2-chlorobenzaldehyde. Mass spectrum (m/e): 422.0 (M+1).

EXAMPLE E-169

Preparation of 4-cyano-5-ethyl-3-(4-iodo-phenyl)-1-methyl-1H-pyrrole-2-carboxylic acid ethyl ester

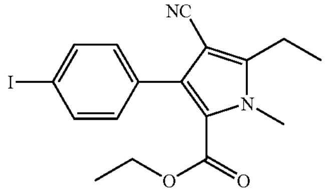

Prepare the title compound in a manner analogous to the procedure set forth in preparation 34 using 3-(4-amino-phenyl)-4-cyano-5-ethyl-1-methyl-1H-pyrrole-2-carboxylic acid ethyl ester (prepared in example E-153). Mass spectrum (m/e): 408.9 (M+1).

EXAMPLE E-170

Preparation of 4-cyano-5-ethyl-3-[4-(2-fluoro-phenylsulfanyl)-phenyl]-1H-methyl-1H-pyrrole-2-carboxylic acid isopropyl ester

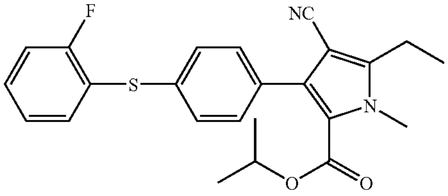

Add 4-cyano-5-ethyl-3-(4-iodo-phenyl)-1-methyl-1H-pyrrole-2-carboxylic acid ethyl ester (0.20 g, 0.49 mmol, prepared in example E-169), 2-fluorothiophenol (0.063 g, 0.49 mmol), copper (I) iodide (0.005 g, catalytic), potassium carbonate (0.135 g, 0.98 mmol), and ethylene glycol (0.061 g, 0.98 mmol) in isopropanol with stirring. Heat the reaction mixture to 80° C. After 18 hours, cool to room temperature, pour the reaction mixture into water and extract with EtOAc. Combine the organic extracts, wash with water and brine, dry over anhydrous magnesium sulfate, filter, and concentrate under reduced pressure. Purify the residue by flash chromatography eluting with ethyl acetate:hexanes to provide the title compound. Mass spectrum (m/e): 423.0 (M+1).

EXAMPLE E-171

Preparation of 4-cyano-5-ethyl-1-methyl-3-[4-(thiophene-2-yl sulfanyl)-phenyl]-1H-pyrrole-2-carboxylic acid ethyl ester

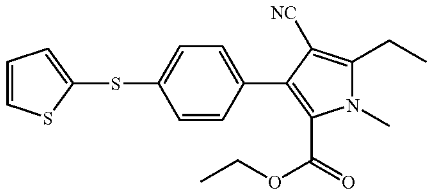

Prepare the title compound in a manner analogous to the procedure set forth in example E-170 using 4-cyano-5-ethyl-3-(4-iodo-phenyl)-1-methyl-1H-pyrrole-2-carboxylic acid ethyl ester prepared in example E-169) and thiophene-2-thiol. Mass spectrum (m/e): 469.9 (M+1).

EXAMPLE E-172

Preparation of 4-cyano-5-ethyl-3-[4-(2-ethyl-phenylsulfanyl)-phenyl]-1-methyl-1H-pyrrole-2-carboxylic acid ethyl ester

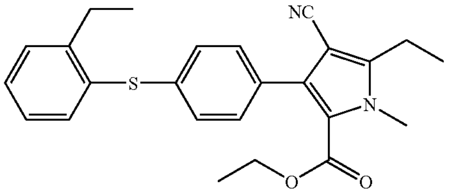

Prepare the title compound in a manner analogous to the procedure set forth in example E-170 using 4-cyano-5-ethyl-3-(4-iodo-phenyl)-1-methyl-1H-pyrrole-2-carboxylic acid ethyl ester (prepared in example E-169) and 2-ethylbenzenethiol. $^1H$ NMR (400 MHz; $CDCl_3$) δ 7.38 (d, 1H), 7.32-7.10 (m, 7H), 4.10(q, 2H), 3.89 (s, 3H), 2.91-2.80 (m, 4H), 1.30 (t, 3H) 1.10 (t, 3H), 1.00 (t, 3H).

EXAMPLE E-173

Preparation of 3-biphenyl-4-yl-5-bromo-4-cyano-1H-pyrrole-2-carboxylic acid ethyl ester

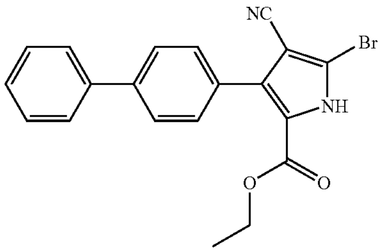

Prepare the title compound in a manner analogous to the procedures set forth in Method FI from ethyl 4-cyano-3-(4-phenylphenyl)pyrrole-2-carboxylate (prepared in a manner analogous to the procedure set forth in Method A, for the intermediate in the preparation of example 1). Mass spectrum (m/e): 393.1 (M−1).

Method N

Scheme XV: Add tributyl(1-ethoxyvinyl)tin (1.5 mmol) and dichlorobis(triphenylphosphine) palladium(II) (0.1 mmol) to bromo derivative of Formula IIj (1.0 mmol) in THF and heat to reflux with stirring. After 18 hours, cool the reaction mixture to room temperature and quench with 5N HCl with stirring. After 1 hour, pour the reaction mixture into water and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula IIr.

Prepare the methyl ketones listed in Table E-22 from the corresponding bromo derivatives in a manner analogous to the procedure set forth in Method N.

TABLE E-22

| Ex. | Structure | Data | S.M. |
| --- | --- | --- | --- |
| E-174 | 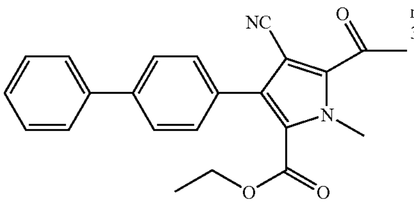 | mass spectrum (m/e): 373.3 (M + 1). | E-59 |
| E-175 | 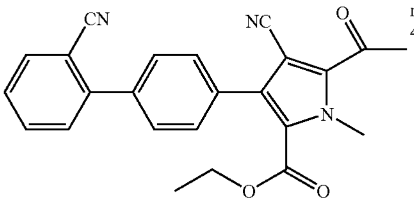 | mass spectrum (m/e): 401.2 (M + 18). | E-68 |
| E-176 | 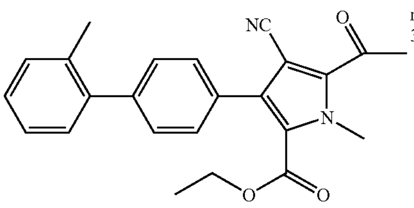 | mass spectrum (m/e): 387.2 (M + 1). | E-66 |

EXAMPLE E-177

Preparation of 3-(4-acetyl-phenyl)-4-cyano-5-ethyl-1-methyl-1H-pyrrole-2-carboxylic acid ethyl ester

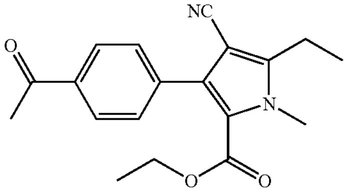

Prepare the title compound from 4-cyano-5-ethyl-1-methyl-3-(4-trifluoromethanesulfonyloxy-phenyl)-1H-pyrrole-2-carboxylic acid ethyl ester (prepared in example E-97a or E-97b) in a manner analogous to the procedure set forth in Method N.

Method P

Scheme XVI: Add N-chlorosuccinimide (1.5-3.0 mmol) to the compound of Formula IIb (1.0 mmol) in THF at room temperature with stirring. After 18 hours, add water to the reaction mixture and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the compound of Formula IIs.

Prepare the chloro derivatives listed in Table E-23 in a manner analogous to the procedure set forth in Method P.

TABLE E-23

| Ex. | Structure | Data | S.M. |
|---|---|---|---|
| E-178 | 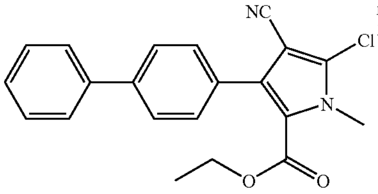 | mass spectrum (m/e): 365.2 (M + 1). | 1 |
| E-179 | 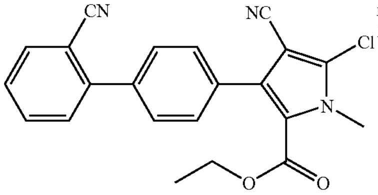 | mass spectrum (m/e): 393.3 (M + 18). | E-30 |
| E-180 | 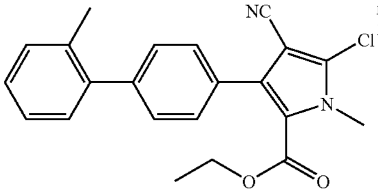 | mass spectrum (m/e): 379.2 (M + 1). | E-14 |
| E-181 | 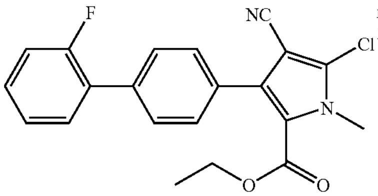 | mass spectrum (m/e): 383.0 (M + 1). | E-22 |

Method Q

Scheme XVII, step A: Add sodium hydride (2.4 mmol) to the corresponding benzoylacetonitrile (1.0 mmol, structure 11) and carbon disulfide (1.0 mmol) in DMSO at −15° C. with stirring. Allow the reaction to gradually warm to room temperature. After 2.5 hours, cool the reaction to −15° C. and add iodomethane (2.0 mmol). Allow the reaction to gradually warm to room temperature. After 18 hours, add water to the reaction and extract with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the bis-methylsulfanyl of structure 12.

Method R

Scheme XVII, step B: Add sarcosine ethyl ester hydrochloride (1.1 mmol, structure 13) and triethylamine (3.0 mmol) to the bis-methylsulfanyl (1.0 mmol, structure 12, prepared in Method Q) in ethanol and heat the reaction mixture to reflux with stirring. After 0.5 to 2 hours at reflux, cool the reaction mixture and pour into water. Extract the quenched reaction with ethyl acetate. Combine the organic extracts, wash with water and brine, dry over anhydrous magnesium sulfate, filter and concentrate under reduced pressure. Purify the residue by flash chromatography eluting with ethyl acetate:hexanes to provide the compound of Formula IIt.

Prepare the thiomethyl compounds listed in Table E-24 in a manner analogous to the procedures set forth in the sequence of Method Q and Method R.

TABLE E-24

| Ex. | Structure | Data | S.M. |
|---|---|---|---|
| E-183 | 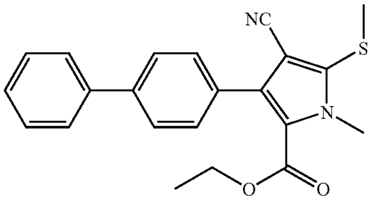 | $^1$H NMR (400MHz; $CDCl_3$)δ7.61-7.61(m, 4H), 7.42-7.50(m, 4H), 7.39-7.37(m, 1H), 4.10(q, 2H), 4.05(s, 3H), 2.55(s, 3H), 1.05(t, 3H). | 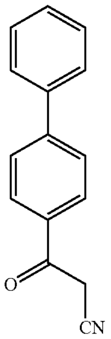 |
| E-184 | 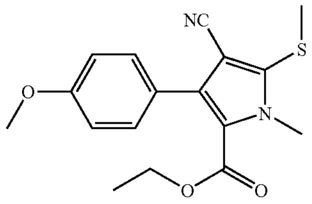 | mass spectrum (m/e): 331.0(M + 1). | 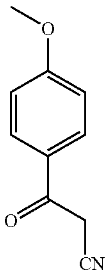 |
| E-185 | 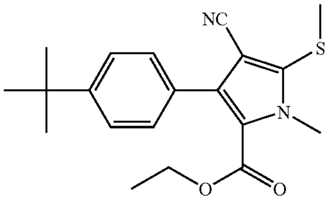 | mass spectrum (m/e): 357.1(M + 1); H-NMR(CDC13)δ 0.98(3H, t, J=7.0Hz); 1.33(9H, s); 2.50(3H, s); 4.10(c, 2H, J= 7.0Hz); 4.02(3H, s); 7.42-7.25(4H, AA'BB') | |

Method S

Scheme XVIII: Add lithium bis(trimethylsilyl)amide (1.1 mmol) to the compound of Formula IIb (1.0 mmol) in THF at −78° C. After 30 minutes, add the corresponding (1-4C)alkyl-disulfide (1.2 mmol) and allow the reaction to gradually warm to ambient temperature. After 2-6 hours, add water and extract the quenched reaction with ethyl acetate. Combine the organic extracts, wash with water and brine, dry over anhydrous magnesium sulfate, filter, and concentrate under reduced pressure. Purify the residue by flash chromatography eluting with ethyl acetate:hexanes to provide the corresponding compound of Formula IIu.

Prepare the following thioalkyl compounds listed in Table E-25 in a manner analogous to the procedure set forth in Method S.

TABLE E-25

| Ex. | Structure | Data | S.M. |
|---|---|---|---|
| E-186 | 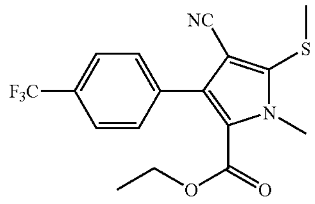 | mass spectrum (m/e): 369.0 (M + 1). | E-2 and methyl disulfide |
| E-187 | 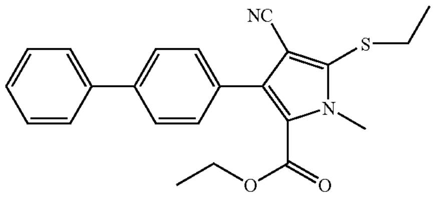 | mass spectrum (m/e): 408.1 (M + 18). | E-1 and ethyl disulfide |
| E-188 | 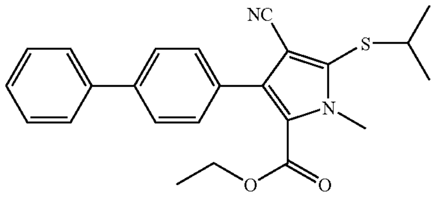 | mass spectrum (m/e): 405.1 (M + 1). | E-1 and isopropyl disulfide |
| E-189 | 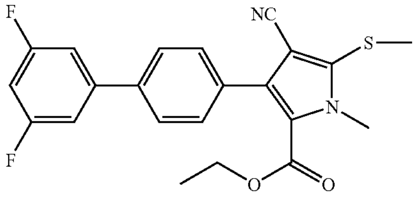 | mass spectrum (m/e): 413.2 (M + 1). | E-13 and methyl disulfide |
| E-190 | 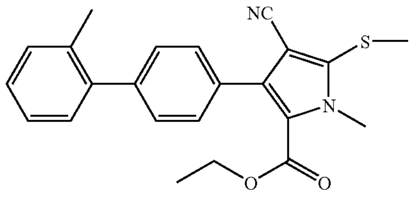 | mass spectrum (m/e): 391.1 (M + 1). | E-14 and methyl disulfide |
| E-191 | 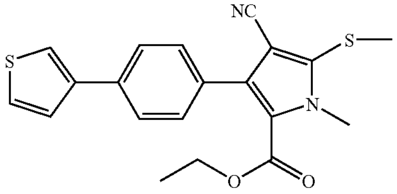 | mass spectrum (m/e): 383.1 (M + 1). | E-15 and methyl disulfide |

TABLE E-25-continued
| Ex. | Structure | Data | S.M. |
|---|---|---|---|
| E-192 | 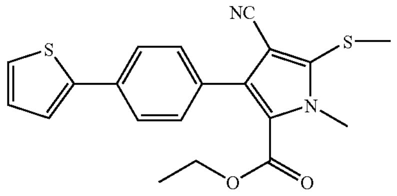 | mass spectrum (m/e): 405.1 (M + 23). | E-16 and methyl disulfide |
| E-193 | 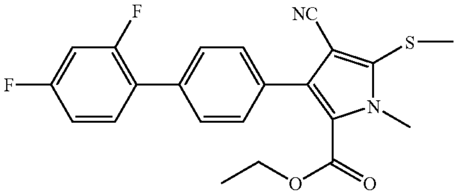 | mass spectrum (m/e): 413.1 (M + 1). | E-26 and methyl disulfide |
| E-194 | 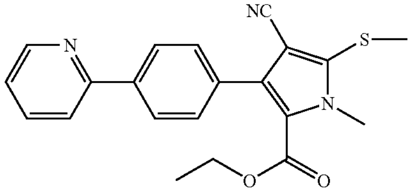 | mass spectrum (m/e): 378.3 (M + 1). | E-4 and methyl disulfide |
| E-195 | 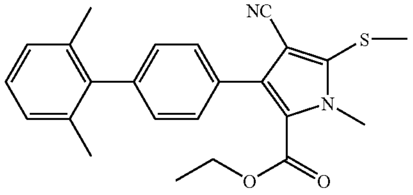 | mass spectrum (m/e): 405.2 (M + 1). | E-5 and methyl disulfide |
| E-196 | 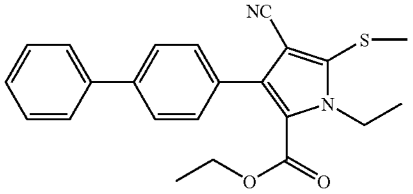 | mass spectrum (m/e): 391.4 (M + 1). | E-7 and methyl disulfide |
| E-197 | 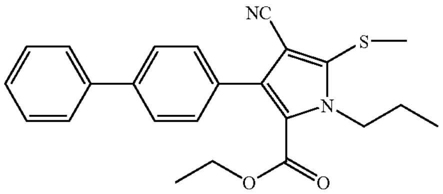 | mass spectrum (m/e): 405.4 (M + 1). | E-8 and methyl disulfide |
| E-198 | 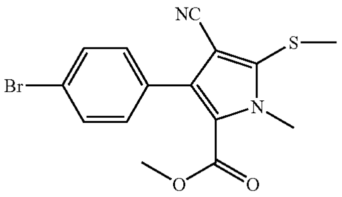 | mass spectrum (m/e): 367.0 (M + 1). | E-3a or E-3b and methyl disulfide |

TABLE E-25-continued

| Ex. | Structure | Data | S.M. |
|---|---|---|---|
| E-200 | 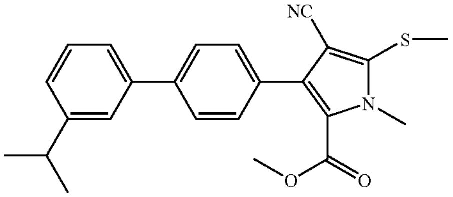 | mass spectrum (m/e): 405.2 (M + 1). | E-29 and methyl disulfide |
| E-201 | 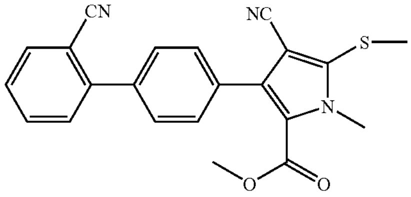 | mass spectrum (m/e): 405.2 (M + 18). | E-30 and methyl disulfide |
| E-202 | 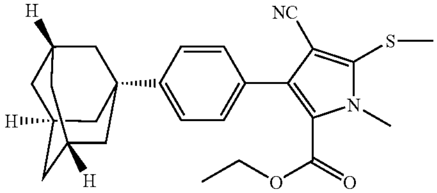 | mass spectrum (m/e): 435.1 (M + 1). | E-10 and methyl disulfide |

EXAMPLE E-203

Preparation of 3-biphenyl-4-yl-4-cyano-1-methyl-5-methanesulfinyl-1H-pyrrole-2-carboxylic acid ethyl ester

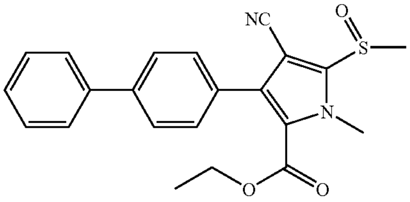

Prepare the title compound in a manner analogous to the procedure set forth in example E-47 using 3-biphenyl-4-yl-4-cyano-1-methyl-5-methanesulfanyl-1H-pyrrole-2-carboxylic acid ethyl ester (prepared in example E-183). Mass spectrum (m/e): 393.0 (M+1).

EXAMPLE E-204

Preparation of 3-biphenyl-4-yl-4-cyano-1-methyl-5-methanesulfonyl-1H-pyrrole-2-carboxylic acid ethyl ester

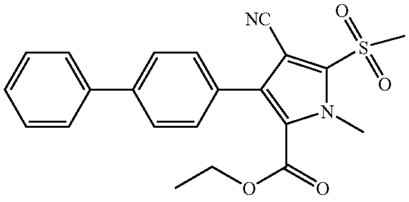

Prepare the title compound in a manner analogous to the procedure set forth in example E-48 using 3-biphenyl-4-yl-4-cyano-1-methyl-5-methanesulfanyl-1H-pyrrole-2-carboxylic acid ethyl ester (prepared in example E-183). Mass spectrum (m/e): 409.0 (M+1).

EXAMPLE E-205

Preparation of 3-[4-(3-amino-pyridin-2-yl)-phenyl]-4-cyano-5-ethyl-1-methyl-1H-pyrrole-2-carboxylic acid ethyl ester

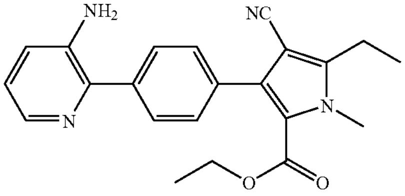

Add tin (II) chloride dihydrate (669 mg, 3.54 mmol) into a solution of 3-[4-(3-nitro-pyridin-2-yl)-phenyl]-4-cyano-5-ethyl-1-methyl-1H-pyrrole-2-carboxylic acid ethyl ester (275 mg, 0.681 mmol, prepared in example E-38) in ethanol. Heat the mixture at 90° C. for 3 hours. Concentrate the reaction to remove ethanol. Dilute the residue with methylene chloride and $H_2O$. Adjust the pH to 8 by adding saturated aqueous $NaHCO_3$ solution. Extract with methylene chloride (2×30 mL) and EtOAc (2×30 mL). Combine the organic extracts, dry over anhydrous magnesium sulfate, filter, and concentrate under reduced pressure. Purify the residue by flash chromatography (elution with 17% acetone in hexanes) to provide the title compound as yellow solid (153 mg, 0.409 mmol, 60%). Mass spectrum (m/e): 375.1 (M+1). $R_f$=0.1 (17% of acetone in hexanes).

EXAMPLE E-206

Preparation of ethyl 4-cyano-5-ethyl-1-methyl-3-[4-(3-{[(methylethyl)sulfonyl]amino}(2-pyridyl)phenyl]pyrrole-2-carboxylate

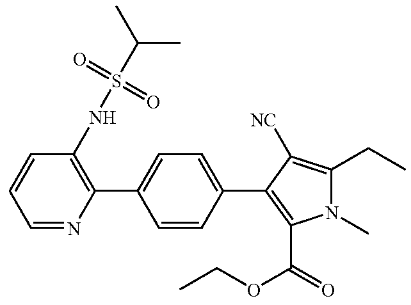

Add isopropyl sulfonyl chloride (13.8 mmol) and DBU (28.7 mmol) into a solution of 3-[4-(3-mino-pyridin-2-yl)-phenyl]-4-cyano-5-ethyl-1-methyl-1H-pyrrole-2-carboxylic acid ethyl ester (6.89 mmol, prepared in example E-205) in methylene chloride (65.6 mL) at 0° C. Warm the mixture to room temperature and stir for 5 hours. Dilute methylene chloride (30 mL) and wash with $H_2O$ (5×30 mL). Combine the organic layers, dry over anhydrous magnesium sulfate, filter, and concentrate under reduced pressure. Purify the residue by flash chromatography to provide the title compound, $R_f$=0.1 (50% ethyl acetate:hexane); MS(M+1): 481.1.

EXAMPLE E-207

4-Cyano-3-[4-(2-fluoro-benzyloxy)-phenyl]1-methyl-1H-pyrrole-2-carboxylic acid ethyl ester

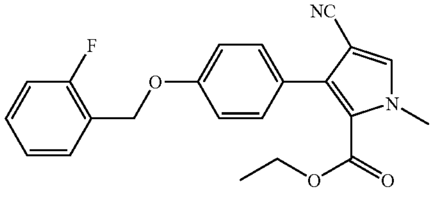

Scheme XIX: Combine 4-cyano-3-(4-hydroxyphenyl)-1-methyl-1H-pyrrole-2-carboxylic acid ethyl ester (1.0 mmol, prepared in example E-11), 2-fluorobenzyl bromide (1.2 Eq.), and potassium carbonate (1.5 Eq.) in acetone (25 mL) and stir overnight at room temperature under a nitrogen atmosphere. Filter the solution and concentrate under reduced vacuum. Purify the residue by silica gel chromatography (Chromatotron™) eluting with methylene chloride to provide the title compound as a white solid: Mass spectrum (m/e): 379.2 (M*+1): (Bruker 300) $^1$H NMR ($CDCl_3$) 7.47-7.57 (1H, t), 6.90-7.35 (8H, m), 5,15-5.20 (2H, s), 4.05-4.20 (2H, dd), 3.90-4.00 (3H, s), 1.00-1.10 (3H, t).

EXAMPLE E-208

4-Cyano-3-[4-(2-chloro-benzyloxy)-phenyl]1-methyl-1H-pyrrole-2-carboxylic acid ethyl ester

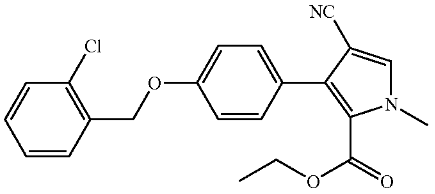

Scheme XIX: Prepare the title compound in the manner analogous to the procedure set fourth in example E-207 using 4-cyano-3-(4-hydroxyphenyl)-1-methyl-1H-pyrrole-2-carboxylic acid ethyl ester (prepared in example E-11) and 2-chlorobenzyl bromide. Purify the material by silica gel chromatography (Chromatotron™) eluting with methylene chloride/ethyl acetate 9:1 to provide the title compound as a white solid. Mass spectrum (m/e): 395.3 (M*+1): (Bruker 300) $^1$H NMR ($CDCl_3$) 7.55-7.60 (1H, m), 7.22-7.44 (6H, m), 6.97-7.05 (2H, d), 5,15-5.20 (2H, s), 4.05-4.20 (2H, dd), 3.90-4.00 (3H, s), 1.00-1.10 (3H, t).

EXAMPLE E-209

4-Cyano-5-ethyl-3-[4-(2-fluoro-benzyloxy)-phenyl]-1-methyl-1H-pyrrole-2-carboxylic acid ethyl ester

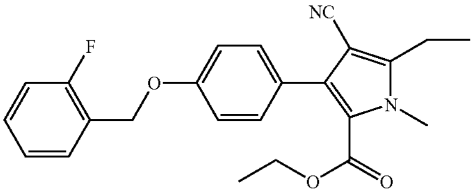

Scheme XIX: Prepare the title compound in the manner analogous to the procedure set fourth in example E-207 using 4-cyano-5-ethyl-3-(4-hydroxyphenyl)-1-methyl-1H-pyrrole-2-carboxylic acid ethyl ester (prepared in example E-81) and 2-fluorobenzyl bromide. Purify the material by silica gel chromatography (Chromatotron™) eluting with methylene chloride/ethyl acetate 9:1 to provide the title compound as a viscous oil.

EXAMPLE E-210

4-Cyano-5-ethyl-3-[4-(2-chloro-benzyloxy)-phenyl]-1-methyl-1H-pyrrole-2-carboxylic acid ethyl ester

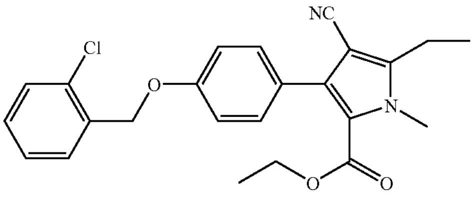

Scheme XIX: Prepare the title compound in the manner analogous to the procedure set fourth in example E-207 using 4-cyano-5-ethyl-3-(4-hydroxyphenyl)-1-methyl-1H-pyrrole-2-carboxylic acid ethyl ester prepared in example E-81) and 2-chlorobenzyl bromide. Purify the material by silica gel chromatography (Chromatotron™) eluting with methylene chloride/ethyl acetate 4:1 to provide the title compound as a slowly crystallizing oil.

EXAMPLE E-211

4-Cyano-5-ethyl-3-[4-(2-cyano-benzyloxy)-phenyl]-1-methyl-1H-pyrrole-2-carboxylic acid ethyl ester

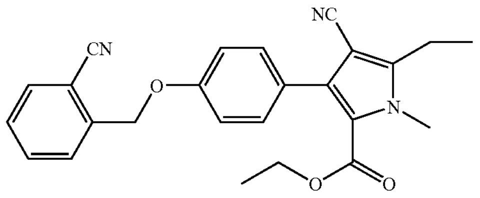

Scheme XIX: Prepare the title compound in the manner analogous to the procedure set fourth in example E-207 using 4-cyano-5-ethyl-3-(4-hydroxyphenyl)-1-methyl-1H-pyrrole-2-carboxylic acid ethyl ester (prepared in example E-81) and 2-cyanobenzyl bromide. Purify the material by silica gel chromatography (Chromatotron™) eluting with methylene chloride/ethyl acetate 4:1 to provide the title compound as a slowly crystallizing oil.

EXAMPLE E-212

4-Cyano-1-methyl-3-(4-henoxy-phenyl)-1H-pyrrole-2-carboxylic acid ethyl ester

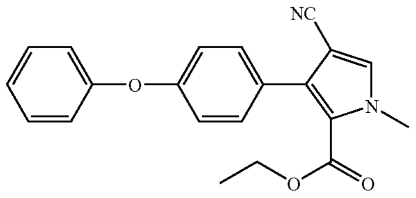

Scheme XX: Combine 4-cyano-3-(4-hydroxyphenyl)-1-methyl-1H-pyrrole-2-carboxylic acid ethyl ester (300 mg, 1.11 mmol, prepared in example E-11), phenylboronic acid (203 mg, 1.5 Eq.), copper(II) acetate (182 mg, 1.0 Eq.), and triethylamine (506 mg, 5.0 Eq.) in methylene chloride (10 mL) and stir for 22 hours at room temperature leaving the reaction mixture open to the atmosphere. Filter the reaction over a mat of diatomaceous earth, and wash the organic layer once with water, dry over potassium carbonate, filter, and concentrate under reduced vacuum to give 344 mg as an oil. Purify the material by silica gel chromatography (Chromatotron™) eluting with methylene chloride to provide 100 mg of the title compound as a white solid. Mass spectrum (m/e): 347.2 (M*+1): (Bruker 300) $^1$H NMR ($CDCl_3$) δ 7.30-7.40 (4H, t), 7.00-7.16 (6H, m), 4.05-4.20 (2H, dd), 3.95-4.10 (3H, s), 1.00-1.10 (3H, t).

EXAMPLE E-213

4-Cyano-3-[4(4-fluoro-phenoxy)-phenyl]-1-methyl-1H-pyrole-2-carboxylic acid ethyl ester

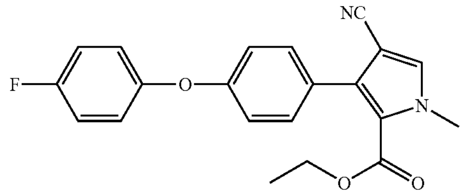

Scheme XX: Prepare the title compound in the manner analogous to the procedure set fourth in example E-212 using 4-cyano-3-(4-hydroxyphenyl)-1-methyl-1H-pyrrole-2-carboxylic acid ethyl ester (prepared in example E-11) and 4-fluoro phenylboronic acid. Purify the material by silica gel chromatography (Chromatotron™) eluting with methylene chloride to provide the title compound as a viscous oil: mass spectrum (m/e): 365.2 (M*+1): (Bruker 300) $^1$H NMR ($CDCl_3$) δ 7.30-7.40 (2H, d), 6.93-7.10 (7H, m), 4.05-4.20 (2H, dd), 3.90-4.00 (3H, s), 1.00-1.10 (3H, t).

EXAMPLE E-214

4-Cyano-3-[4(3-fluoro-phenoxy)-phenyl]-1-methyl-1H-pyrrole-2-carboxylic acid ethyl ester

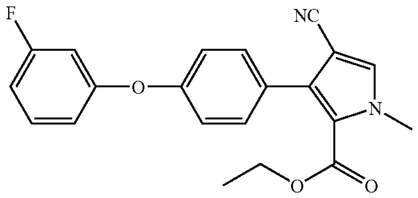

Scheme XX: Prepare the title compound in the manner analogous to the procedure set fourth in example E-212 using 4-cyano-3-(4-hydroxyphenyl)-1-methyl-1H-pyrrole-2-carboxylic acid ethyl ester (prepared in example E-11) and 3-fluoro phenylboronic acid. Purify the material by silica gel chromatography (Chromatotron™) eluting with methylene chloride to provide the title compound as a white solid. mass spectrum (m/e): 365.1 (M*+1): (Bruker 300) $^1$H NMR ($CDCl_3$) δ 7.23-7.40 (4H, d), 7.01-7.08 (2H, d), 6.70-6.85 (3H, m), 4.05-4.20 (2H, dd), 3.90-4.00 (3H, s), 1.00-1.10 (3H, t).

EXAMPLE E-215

4-cyano-3-[4(3,5-difluoro-phenoxy)-phenyl]-1-methyl-1H-pyrole-2-carboxylic acid ethyl ester

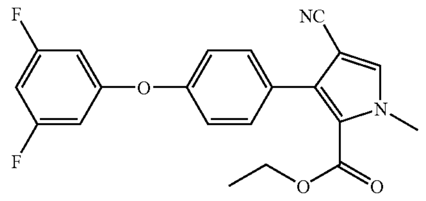

Scheme XX: Prepare the title compound in the manner analogous to the procedure set fourth in example E-212 using 4-cyano-3-(4-hydroxyphenyl)-1-methyl-1H-pyrrole-2-carboxylic acid ethyl ester (prepared in example E-11) and 3,5-difluoro phenylboronic acid. Purify the material by silica gel chromatography (Chromatotron™) eluting with methylene chloride to provide the title compound as a white solid. mass spectrum (m/e): 383.0 (M*+1): (Bruker 300) $^1$H NMR ($CDCl_3$) δ 7.35-7.43 (2H, d), 7.23-7.29 (2H, d), 7.03-7.10 (2H, d), 6.47-6.58 (2H, m), 4.05-4.20 (2H, dd), 3.90-4.00 (3H, s), 1.00-1.10 (3H, t).

EXAMPLE E-216

4-Cyano-3-[4(3,-cyano-phenoxy)-phenyl]-1-methyl-1H-pyrole-2-carboxylic acid ethyl ester

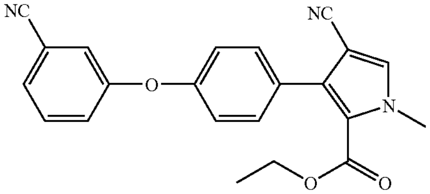

Scheme XX: Prepare the title compound in the manner analogous to the procedure set fourth in example E-212 using 4-cyano-3-(4-hydroxyphenyl)-1-methyl-1H-pyrrole-2-carboxylic acid ethyl ester (prepared in example E-11) and 3-cyano-phenylboronic acid. Purify the material by silica gel chromatography (Chromatotron™) eluting with methylene chloride to provide the title compound as a white solid: (Bruker 300) $^1$H NMR ($CDCl_3$) δ 7.35-7.48 (4H, m), 7.23-7.29 (3H, m), 7.01-7.08 (2H, d), 4.05-4.20 (2H, dd), 3.90-4.00 (3H, s), 1.00-1.10 (3H, t).

EXAMPLE E-217

4-Cyano-5-ethyl-3-[4-(3-fluoro-phenoxy)-phenyl]-1-methyl-1H-pyrole-2-carboxylic acid ethyl ester

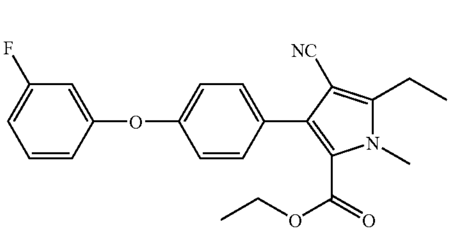

Scheme XX: Prepare the title compound in the manner analogous to the procedure set fourth in example E-212 using 4-cyano-5-ethyl-3-(4-hydroxyphenyl)-1-methyl-1H-pyrrole-2-carboxylic acid ethyl ester (prepared in example E-81) and 3-fluoro-phenylboronic acid. Purify the material by silica gel chromatography (Chromatotron™) eluting with methylene chloride to provide the title compound as a white solid. Mass spectrum (m/e): 393.1 (M*+1): (Bruker 300) $^1$H NMR ($CDCl_3$) δ 7.23-7.38 (3H, m), 7.01-7.08 (2H, d), 6.70-6.86 (3H, m), 4.06-4.16 (2H, dd), 3.85-3.900 (3H, s), 2.80-2.90 (2H, dd), 1.25-1.35 (3H, t), 1.00-1.10 (3H, t).

EXAMPLE E-218

4-Cyano-5-ethyl-3-[4-(3-cyano-phenoxy)-phenyl]-1-methyl-1H-pyrole-2-carboxylic acid ethyl ester

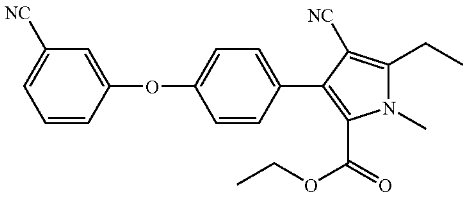

Scheme XX: Prepare the title compound in the manner analogous to the procedure set fourth in example E-212 using 4-cyano-5-ethyl-3-(4-hydroxyphenyl)-1-methyl-1H-pyrrole-2-carboxylic acid ethyl ester (prepared in example E-81) and 3-cyano-phenylboronic acid. Purify the material by silica gel chromatography (Chromatotron™) eluting with methylene chloride/ethyl acetate 1:1 to provide the title compound as a semi-solid. Mass spectrum (m/e): 400.2 (M*+1): (Bruker 300) $^1$H NMR ($CDCl_3$) δ 7.35-7.47 (3H, m), 7.23-7.30 (3H, m), 7.01-7.07 (2H, d), 4.06-4.16 (2H, dd), 3.85-3.90 (3H, s), 2.80-2.90 (2H, dd), 1.25-1.35 (3H, t), 1.00-1.10 (3H, t).

EXAMPLE E-219

4-Cyano-5-ethyl-1-methyl-3-[4-(2-methanesulfanyl-phenoxy)-phenyl]-1H-pyrole-2-carboxylic acid ethyl ester

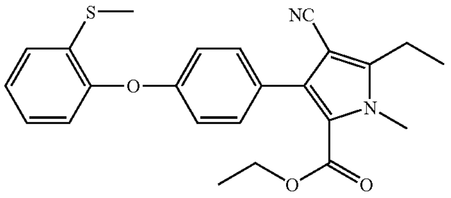

Scheme XX: Prepare the title compound in the manner analogous to the procedure set fourth in example E-212 using 4-cyano-5-ethyl-3-(4-hydroxyphenyl)-1-methyl-1H-pyrrole-2-carboxylic acid ethyl ester (prepared in example E-81) and 2-methyl-thio-phenylboronic acid. Purify the material by silica gel chromatography (Chromatotron™) eluting with methylene chloride/ethyl acetate 1:1 to provide the title compound as an oil. Mass spectrum (m/e): 420.2 (M*): (Bruker 300) $^1$H NMR δ ($CDCl_3$) 7.24-7.34 (3H, m), 7.10-7.17 (2H, m), 6.90-7.00 (3H, m), 4.06-4.16 (2H, dd), 3.85-3.90 (3H, s), 2.80-2.90 (2H, dd), 2.41-2.47 (3H, s), 1.21-1.35 (3H, t), 1.00-1.10 (3H, t).

EXAMPLE E-220

4-Cyano-1-methyl-3-[4-(2-nitro-phenoxy)-phenyl]-1H-pyrrole-2-carboxylic acid ethyl ester

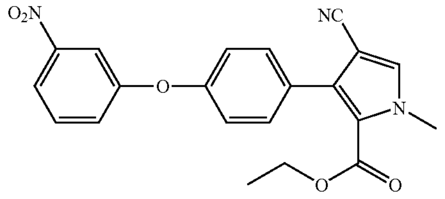

Add together 4-cyano-3-(4-hydroxyphenyl)-1-methyl-1H-pyrrole-2-carboxylic acid ethyl ester (prepared in example E-11) (600 mg, 2.22 mmol), 1-fluoro-2-nitrobenzene (313 mg, 1.0 Eq.), potassium fluoride/alumina (322 mg, 2.5 Eq.), and 18-crown-6 (60 mg, 0.1 Eq.) in acetonitrile (25 mL) and stir at reflux for 18 hours under a nitrogen atmosphere. Cool mixture and add water and methylene chloride (50 mL each) and stir vigorously. Separate layers and wash the organic layer once with water, dry over potassium carbonate, filter, and concentrate under reduced vacuum to give 762 mg as a dark solid. Purify the material by silica gel chromatography (Chromatotron™) eluting with methylene chloride to provide 602 mg of the title compound as a yellow solid. Mass spectrum (m/e): 392.2 (M*+1): (Bruker 300) $^{1}$NMR δ ($CDCl_3$) 7.93-8.00 (1H, d), 7.50-7.57 (1H, t), 7.35-7.40 (2H, d), 7.19-7.29 (2H, m), 7.03-7.13 (2H, m), 4.05-4.20 (2H, dd), 3.95-4.10 (3H, s), 1.00-1.10 (3H, t).

EXAMPLE E-221

4-Cyano-3-[4-(3-cyano-propoxy)-phenyl]-5-ethyl-1-methyl-1H-pyrrole-2-carboxylic acid ethyl ester

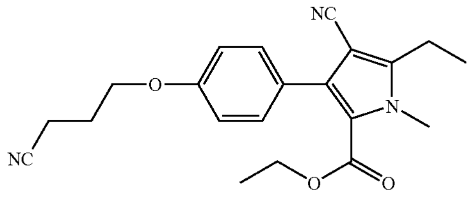

Add dropwise, 4-cyano-5-ethyl-3-(4-hydroxyphenyl)-1-methyl-1H-pyrrole-2-carboxylic acid ethyl ester (prepared in example E-81) (300 mg, 1.0 mmol) in DMF (10 mL) to a stirring solution of 60% sodium hydride (60 mg, 1.5 Eq.) in DMF (30 mL) at room temperature under a nitrogen atmosphere. After 30 minutes, add dropwise, 4-bromobutryonitrile (179 mg, 1.2Eq.) in DMF (10 mL) to the reaction mixture while continuing to stir at room temperature. After 2 hours, pour mixture into water and extract the desired ether into ethyl acetate. Wash the organic layer once with water, dry over potassium carbonate, filter, and concentrate under reduced vacuum to give 500 mg as an oil. Purify the material by silica gel chromatography (Chromatotron™) eluting with methylene chloride to provide 333 mg of the title compound as an oil. Mass spectrum (m/e): 366.2 (M*+1): (Bruker 300) $^{1}$H NMR δ ($CDCl_3$) 7.27-7.32 (2H, d), 6.87-6.94 (2H , d) 4.03-4.16 (3H, m), 3.85-3.95 (3H, s), 2.78-2.88 (2H, dd), 2.54-2.64 (2H, t), 2.10-2.20 (2H, dd), 1.22-1.33 (4H, m), 1.00-1.10 (3H, t).

EXAMPLE E-222

3-(4-Benzofuran-7-yl-phenyl)-4-cyano-1-methyl-1H-pyrrole-2-carboxylic acid ethyl ester

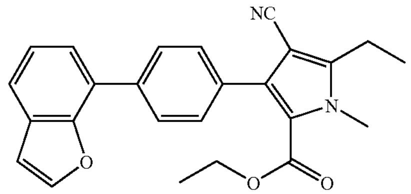

Add together 7-bromo-benzofuran (300 mg, 1.50 mmol), potassium acetate (431 mg, 2 Eq.), and bis(pinacolato)diboron (390 mg, 1.6 Eq.) in DMF (30 mL) and stir for 10 minutes while degassing with nitrogen. Add [11'bis(diphenylphosphino) ferrocene]dichloro-palladium(II) (30 mg) to the reaction mixture and stir at 80° C. for 2 hours under a nitrogen atmosphere. Cool mixture to room temperature and add 4-cyano-5-ethyl-1-methyl-3-(4-trifluoromethanesulfonyloxyphenyl)-1H-pyrrole-2-carboxylic acid ethyl ester (prepared in example E-97a or E-97b) (1.3 g, 2 Eq.), 2.0M sodium carbonate/water (3.6 mL ), and [11'bis(diphenylphosphino) ferrocene]dichloro-palladium(II) (30 mg) to the mixture and heat at 80° C. overnight. Cool to room temperature and pour into water and extract the desired product into ethyl acetate. Separate layers, and wash the organic layer once with water, dry over potassium carbonate, filter, and concentrate under reduced vacuum to give 1.08 g as a dark solid. Purify the material by silica gel chromatography (Chromatotron™) eluting with hexane/ethyl acetate 7:3 to provide 275 mg of the title compound as a white solid. Mass spectrum (m/e): 399.2 (M*+1).

EXAMPLE E-223

3-(4-Benzo(b)thiophene-7-yl-phenyl)-4-cyano-1-methyl-1H-pyrrole-2-carboxylic acid ethyl ester

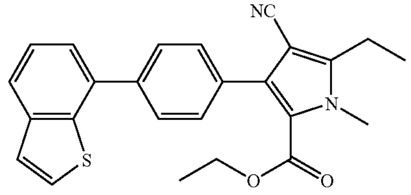

Prepare the title compound in the manner analogous to the procedure set fourth in example E-222 using 4-cyano-5-ethyl-1-methyl-3-(4-trifluoromethanesulfonyloxyphenyl)-1H-pyrrole-2-carboxylic acid ethyl ester (prepared in example E-97a or 97b) and 7-bromo-benzo(b)thiophene. Purify the material by silica gel chromatography (Chromatotron™ eluting with methylene chloride/ethyl acetate 4:1 to provide the title compound a white solid. Mass spectrum (m/e): 413.2 (M*−1).

EXAMPLE E-224

Preparation of 3-(4-Indole-7-yl-phenyl)-4-cyano-1-methyl-1H-pyrrole-2-carboxylic acid ethyl ester

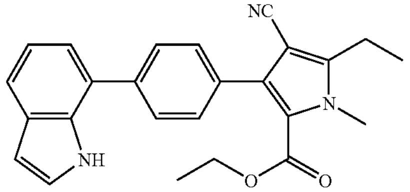

Prepare the title compound in the manner analogous to the procedure set fourth in example E-222 using 4-cyano-5-ethyl-1-methyl-3-(4-trifluoromethanesulfonyloxyphenyl)-1H-pyrrole-2-carboxylic acid ethyl ester (prepared in example E-97a or 97b) and 7-bromo-indole. Purify the material by silica gel chromatography eluting with hexanes/ethyl acetate 4:1 to provide the title compound as a white solid. Mass spectrum (m/e): 398.25 (M*+1).

EXAMPLE E-225

3-(4-Benzo(b)thiophene-4-yl-phenyl)-4-cyano-1-methyl-1H-pyrrole-2-carboxylic acid ethyl ester

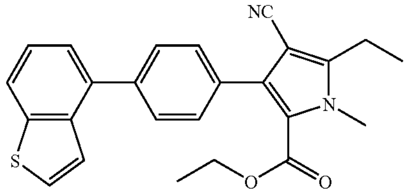

Prepare the title compound in the manner analogous to the procedure set fourth in example E-222 using 4-cyano-5-ethyl-1-methyl-3-(4-trifluoromethanesulfonyloxyphenyl)—1H-pyrrole-2-carboxylic acid ethyl ester (prepared in example E-97a or 97b) and 4-bromo-benzo(b)thiophene. Purify the material by silica gel chromatography (Chromatotron™) eluting with methylene chloride to provide the title compound a white solid. Mass spectrum (m/e): 415.2 (M*+1).

EXAMPLE E-226

Preparation of 3-(4-Indole-4-yl-phenyl)-4-cyano-1-methyl-1H-pyrrole-2-carboxylic acid ethyl ester

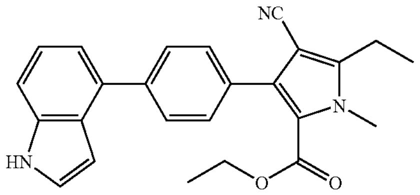

Prepare the title compound in the manner analogous to the procedure set fourth in example E-222 using 4-cyano-5-ethyl-1-methyl-3-(4-trifluoromethanesulfonyloxyphenyl)-1H-pyrrole-2-carboxylic acid ethyl ester (prepared in example E-97a or 97b) and 4-bromo-indole. Purify the material by silica gel chromatography eluting with eluting with hexanes/ethyl acetate 4:1 to provide the title compound which is triturated with methylene chloride and hexanes to provide the title compound as a white solid. Mass spectrum (m/e): 398.2 (M*+1).

EXAMPLE E-227

Preparation of 4-Cyano-5-ethyl-3-[4-(2-fluoro-phenoxy)-phenyl]-1-methyl-1H-pyrrole-2-carboxylic acid ethyl ester

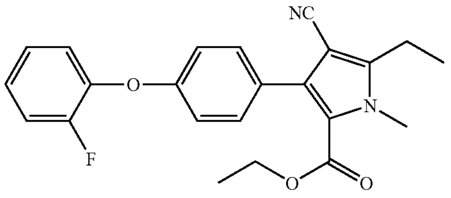

Preparation of 4-(2-Fluoro-phenoxy)-nitrobenzene

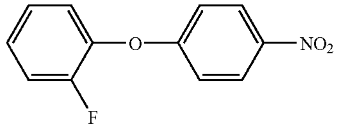

Prepare the title compound in the manner analogous to the procedure set fourth in example E-221 using 4-fluoro-nitrobenzene and 2-fluorophenol (heat 2 hours at 60° C.). Purify the material by silica gel chromatography (Prep. 2000) eluting with methylene chloride/hexane 1:1 to provide the title compound as a yellow solid. Mass spectrum (m/e): 233.1 (M*). (Bruker 300) $^1$H NMR ($CDCl_3$) 8.17-8.22 (2H, d), 7.14-7.28 (4H, m), 6.96-700 (2H, d).

Preparation of 4-(2-Fluoro-phenoxy)-phenylamine

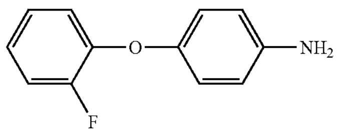

Add together 4-(2-fluoro-phenoxy)-nitrobenzene (3.18 g, 13.6 mmol) and Tin(II) chloride dihydrate (12.89 g, 5 Eq.) in absolute ethanol (20 mL) and heat to reflux while stirring under a nitrogen atmosphere for 3 hours. Cool to room temperature and dilute with ethyl acetate (50 mL). Wash this organic layer once with water, dry over potassium carbonate, filter, and concentrate under reduced vacuum to give 2.90 g as a dark oil. Purify the material by silica gel chromatography (Prep. 2000) eluting with methylene chloride to provide 1.74 g of the title compound as a tan solid. Mass spectrum (m/e):

204.2 (M*+1): (Bruker 300) $^{1}H$ NMR ($CDCl_3$) δ 7.08-7.15 (2H, m), 6.95-7.02 (3H, m), 6.81-6.92 (4H, m), 6.63-6.67 (2H, d).

Preparation of 4-(2-Fluoro-phenoxy)-iodobenzene

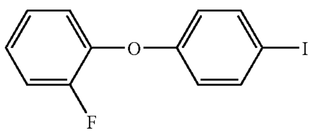

Add isoamylnitrite (2.45 g, 2.5 Eq.) to 4-(2-fluoro-phenoxy)-phenylamine (1.70 g, 8.37 mmol) and diiodomethane (7.84 g, 3.5 Eq.) in acetonitrile (10 mL) while stirring at 55° C. under a nitrogen atmosphere. Slowly heat mixture to 75° C. and heat at this temperature for 3 hours. Cool to room temperature and pour into water, and extract the desired material into ethyl acetate. Wash this organic layer once with water, dry over potassium carbonate, filter, and concentrate under reduced vacuum to give 2.41 g of an oil. Purify the material by silica gel chromatography (Prep. 2000) eluting with hexane/methylene chloride 9:1 to provide 1.60 g of the title compound as a thin oil. Mass spectrum (m/e): 314.0 (M*): (Bruker 300) $^{1}H$ NMR ($CDCl_3$) δ 7.55-7.60 (2H, d), 7.02-7.20 (4H, m), 6.69-6.72 (2H, d).

Preparation of 2-[4-(2-Fluoro-phenoxy)-phenyl]-4,4,5,5-tetramethyl-[1,3,2]-dioxaborolane

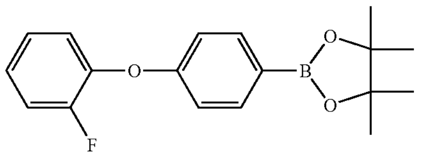

Add together 4-(2-fluoro-phenoxy)-iodobenzene (800 mg, 2.55 mmol), potassium acetate (751 mg, 3Eq.), and bis(pinacolato)diboron (971 mg, 1.5 Eq.) and [11'bis(diphenylphosphino) ferrocene]dichloro-palladium(II) (400 mg) in DMF (20 mL) and stir at 80° C. overnight under a nitrogen atmosphere. Cool to room temperature and pour into water and extract the desired product into ethyl acetate. Separate layers, and wash the organic layer once with water, dry over potassium carbonate, filter, and concentrate under reduced vacuum to give 721 mg as a dark oil. Purify the material by silica gel chromatography (Chromatotron™) eluting with methylene chloride to provide 235 mg of the title compound as an oil. Mass spectrum (m/e): 3.14.0 (M*): (Bruker 300) $^{1}H$ NMR ($CDCl_3$) δ 7.73-7.77 (2H, d), 7.04-7.20 (4H, m), 6.91-6.95 (2H, d), 1.31-1.34 (12H, s).

Preparation of Final Title Compound

Combine 4-cyano-5-ethyl-3-iodo-1-methyl-1H-pyrrole-2-carboxylic acid ethyl ester (prepared in preparation 38, 0.46 mmol), 2-[4-(2-fluoro-phenoxy)-phenyl]-4,4,5,5-tetramethyl-[1,3,2]-dioxaborolane (1.3 Eq), tetrakis(triphenylphosphine)-palladium(0) (0.1 Eq) and 2.0 M sodium carbonate/water (6.5 Eq) in 1,4-dioxane (10 mL) and heat at –80° C. to 90° C. overnight. Let the reaction cool to room temperature and pour into water. Extract the quenched reaction mixture with ethyl acetate. Combine the organic extracts, wash with water, dry over potassium carbonate, filter, and concentrate under reduced vacuum. Purify the residue by silica gel chromatography (Chromatotron™) eluting with hexane/ethyl acetate 4:1 to provide the final title compound, 4-cyano-5-ethyl-3-[4-(2-fluoro-phenoxy)-phenyl]-1-methyl-1H-pyrole-2-carboxylic acid ethyl ester, as a tan solid. Mass spectrum (m/e): 393.1 (M*+1): (Bruker 300) $^{1}H$ NMR ($CDCl_3$) δ 7.27-7.31 (3H, d), 7.07-7.20 (3H, m), 6.95-6.99 (2H, d), 4.04-4.11 (2H, dd), 3.84-3.88 (3H, s), 2.74-2.86 (2H, dd), 1.23-1.34 (3H, t), 1.00-1.06 (3H, t).

EXAMPLE E-228

Preparation of 4-Cyano-5-ethyl-3-[4-(2,4-difluoro-phenoxy)-phenyl]-1-methyl-1H-pyrole-2-carboxylic acid ethyl ester

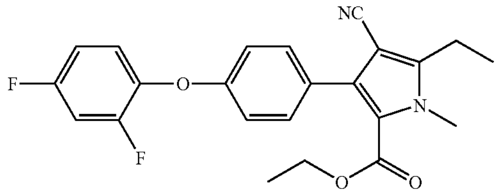

Preparation of 4-(2,4-Difluoro-phenoxy)-nitrobenzene

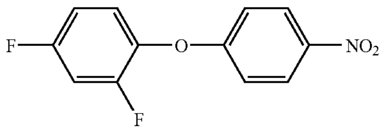

Prepare the title compound in the manner analogous to the procedure set fourth in example E-227 using 4-fluoro-nitrobenzene and 2,4-difluorophenol (heat 2 hours at 50° C.). Purify the material by silica gel chromatography (Prep.2000) eluting with methylene chloride/hexane 1:1 to provide the title compound as a slowly crystallizing oil. Mass spectrum (m/e): 251.1 (M*). (Bruker 300) $^{1}H$ NMR ($CDCl_3$) δ 8.17-8.22 (2H, d), 7.14-7.21 (1H, m), 6.90-703 (4H, m).

Preparation of 4-(2,4-Difluoro-phenoxy)-phenylamine

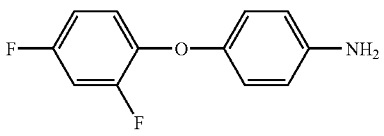

Prepare the title compound in the manner analogous to the procedure set fourth in example E-227 using 4-(2,4-fluorophenoxy)-nitrobenzene. Purify the material by silica gel chromatography (Prep.2000) eluting with methylene chloride to provide the title compound as a tan solid. Mass spectrum (m/e): 221.9 (M*). (Bruker 300) $^1$H NMR ($CDCl_3$) δ 6.86-6.94 (2H, m), 6.72-6.82 (3H, m), 6.62-6.66 (2H, d).

Preparation of 4-(2,4-Difluoro-phenoxy)-iodobenzene

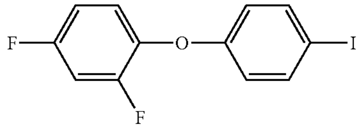

Prepare the title compound in the manner analogous to the procedure set fourth in example E-227 using 4-(2,4-fluorophenoxy)-phenylamine. Purify the material by silica gel chromatography (Prep.2000) eluting with hexane/methylene chloride 9:1 to provide the title compound as a light oil. Mass spectrum (m/e): 332.0 (M*). (Bruker 300) $^1$H NMR ($CDCl_3$) δ 7.55-7.59 (2H, d), 7.02-7.08 (1H, m), 6.90-6.97 (1H, m), 6.81-6.88 (1H, m), 6.66-6.71 (2H, d).

Preparation of 2-[4-(2,4-Difluoro-phenoxy)-phenyl]-4,4,5,5-tetramethyl-[1,3,2]-dioxaborolane

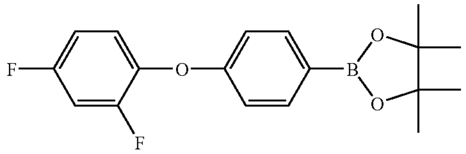

Prepare the title compound in the manner analogous to the procedure set fourth in example E-227 using 4-(2,4-fluorophenoxy)-iodobenzene. Purify the material by silica gel chromatography (Chromatotron™) eluting with hexane/methylene chloride 1:1 to provide the title compound as a tan solid. Mass spectrum (m/e): 332.0 (M*). (Bruker 300) $^1$H NMR ($CDCl_3$) δ 7.73-7.76 (2H, d), 6.81-7.10 (5H, m), 1.25-1.32 (12H, s).

Preparation of the Final Title Compound

Prepare the title compound in the manner analogous to the procedure set fourth in the final step of example E-227 using 4-cyano-5-ethyl-3-iodo-1-methyl-1H-pyrrole-2-carboxylic acid ethyl ester (prepared in preparation 38) and 2-[4-(2,4-difluoro-phenoxy)-phenyl]-4,4,5,5-tetramethyl-[1,3,2]-dioxaborolane. Purify the material by silica gel chromatography (Chromatotron™) eluting with hexane/ethyl acetate 4:1 to provide the final title compound, 4-cyano-5-ethyl-3-[4-(2,4-difluoro-phenoxy)-phenyl]-1-methyl-1H-pyrole-2-carboxylic acid ethyl ester, as a tan solid. Mass spectrum (m/e): 411.1 (M*+1): (Bruker 300) $^1$H NMR ($CDCl_3$) δ 7.27-7.31 (2H, d), 7.07-7.14 (1H, m), 6.74-6.97 (4H, m), 4.04-4.11 (2H, dd), 3.84-3.88 (3H, s), 2.78-2.89 (2H, dd), 1.23-1.34 (3H, t), 1.00-1.06 (3H, t).

EXAMPLE E-229

Preparation of 4-Cyano-5-ethyl-3-(4-cyclohexyloxy-phenyl)-1-methyl-1H-pyrrole-2-carboxylic acid ethyl ester

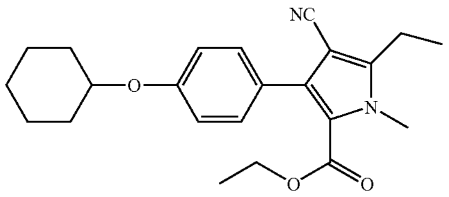

Preparation of 1-Cyclohexyloxy-4-nitrobenzene

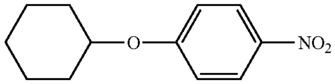

Prepare the title compound in the manner analogous to the procedure set fourth in example E-227 using 4-fluoro-nitrobenzene and cyclohexanol (heat 1.5 hours at 55° C.). Purify the material by silica gel chromatography (Prep.2000) eluting with methylene chloride/hexane 1:1 to provide the title compound as an oil. Mass spectrum (m/e): 221.1 (M*). (Bruker 300) $^1$H NMR ($CDCl_3$) δ 8.13-8.18 (2H, d), 6.90-6.93 (2H, d), 4.31-4.39 (1H, m), 1.92-2.02 (2H, m), 1.75-1.85 (2H, m), 1.50-1.62 (3H, m), 1.28-1.44 (3H, m).

Preparation of 1-Cyclohexyloxy-4-phenylamine

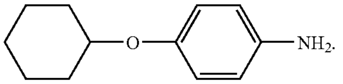

Combine 1-Cyclohexyloxy-4-nitrobenzene (2.3 g, 10.4 mmol) and 5% palladium on carbon (368 mg, excess) in 3A ethanol (80 mL) and subject to hydrogen atmosphere at 60 psi and shake at room temperature overnight. Filter the catalyst over a Celite® pad and concentrate the filtrate under reduced vacuum to give 1.63 g of an oil. Purify the material by silica gel chromatography (Chromatotron™) eluting with methylene chloride to provide 1.34 g of the title compound as an oil. Mass spectrum (m/e): 192.1 (M*+1). (Bruker 300) $^1$H NMR ($CDCl_3$) δ 6.71-6.76 (2H, d), 6.58-6.63 (2H, d), 3.96-4.07 (2H, m), 1.89-2.00 (2H, m), 1.70-1.82 (2H, m), 1.19-1.59 (5H, m).

Preparation of cyclohexyloxy-4-iodobenzene

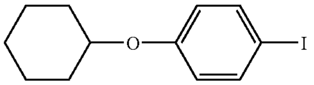

Prepare the title compound in the manner analogous to the procedure set fourth in example E-227 using 1-cyclohexyloxy-4-phenylamine. Purify the material by silica gel chromatography (Prep.2000) eluting with hexane/methylene chloride 9:1 to provide the title compound as a light yellow oil. Mass spectrum (m/e): 302.0 (M*). (Bruker 300) $^1$H NMR ($CDCl_3$) δ 7.48-7.53 (2H, d), 6.63-6.68 (2H, d), 4.13-4.21 (1H, m), 1.88-1.98 (2H, m), 1.71-1.82 (2H, m). 1.43-1.59 (3H, m), 1.22-1.40 (3H, m).

Preparation of 4-(Cyclohexyloxy)-4,4,5,5-tetramethyl-[1,3,2]-dioxaborolane

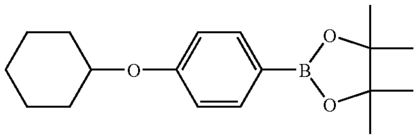

Prepare the title compound in the manner analogous to the procedure set fourth in example E-227 using cyclohexyloxy-4-iodobenzene. Purify the material by silica gel chromatography (Chromatotron™) eluting with methylene chloride to provide the title compound as a tan oil. Mass spectrum (m/e): 302.0 (M*). (Bruker 300) $^1$H NMR ($CDCl_3$) δ 7.68-7.72 (2H, d), 6.84-6.88 (2H, d), 4.24-4.32 (1H, m), 1.91-1.99 (2H, m), 1.75-1.83 (2H, m), 1.46-1.57 (3H, m), 1.24-1.40 (15H, m).

Preparation of Final Title Compound

Prepare the final title compound in the manner analogous to the procedure set fourth in the final step of example E-227 using 4-cyano-5-ethyl-3-iodo-1-methyl-1H-pyrrole-2-carboxylic acid ethyl ester (prepared in preparation 38) and 4-(cyclohexyloxy)-4,4,5,5-tetramethyl-[1,3,2]-dioxaborolane. Purify the material by silica gel chromatography (Chromatotron™) eluting with hexane/ethyl acetate 4:1 to provide the final title compound, 4-cyano-5-ethyl-3-(4-cyclohexyloxy-phenyl)-1-methyl-1H-pyrole-2-carboxylic acid ethyl ester, as an oil. Mass spectrum (m/e): 381.3 (M*+1).

EXAMPLE E-230

Preparation of 4-cyano-5-ethyl-3-[4-(2-nitro-phenoxy)-phenyl]-1-methyl-1H-pyrole-2-carboxylic acid ethyl ester

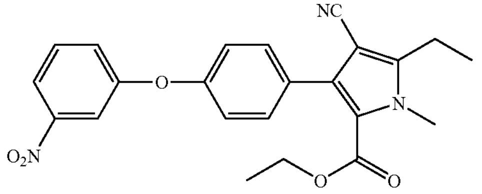

Scheme XX: Prepare the title compound in the manner analogous to the procedure set fourth in example E-212 using 4-cyano-5-ethyl-3-(4-hydroxy-phenyl)-1-methyl-1H-pyrrole-2-carboxylic acid ethyl ester (prepared in example E-81) and 3-nitro-phenylboronic acid. Purify the material by silica gel chromatography (Chromatotron™) eluting with methylene chloride to provide the title compound as a white solid. Mass spectrum (m/e): 418.2 (M*−1): (Bruker 300) $^1$H NMR ($CDCl_3$) δ 7.91-7.96 (1H, d), 7.81-7.84 (1H, t), 7.46-7.51 (1H, t), 7.31-7.41 (3H, m), 7.03-7.09 (2H, d), 4.06-4.16 (2H, dd), 3.85-3.90 (3H, s), 2.80-2.90 (2H, dd), 1.25-1.35 (3H, t), 1.00-1.10 (3H, t).

EXAMPLE E-231

Preparation of 4-cyano-5-ethyl-3-[4-(2-amino-phenoxy)-phenyl]-1-methyl-1H-pyrrole-2-carboxylic acid ethyl ester

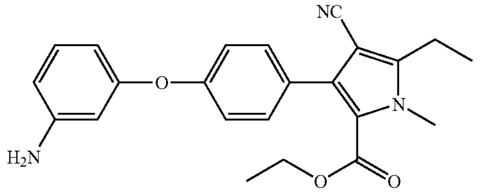

Combine 4-cyano-5-ethyl-3-[4-(2-nitro-phenoxy)-phenyl]-1-methyl-1H-pyrole-2-carboxylic acid ethyl ester (prepared in example E-230) and tin(II) chloride dihydrate (5 Eq.) in absolute ethanol (20 mL), and heat at reflux with stirring under a nitrogen atmosphere for 3 hours. Cool the reaction mixture to room temperature and dilute with ethyl acetate. Wash the organic layer with water, dry over potassium carbonate, filter, and concentrate under reduced vacuum. Purify the material by silica gel chromatography eluting with methylene chloride to provide the title compound.

EXAMPLE E-232

Preparation of 4-Cyano-5-ethyl-1-methyl-3-{4-[3-(propane-2-sulfonylamino)-phenoxy]-phenyl}-1H-pyrole-2-carboxylic acid ethyl ester

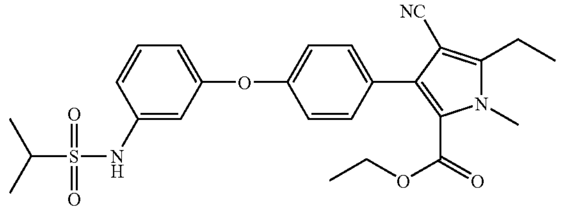

Add triethylamine (43 mg, 1.5 Eq.) dropwise to 4-cyano-5-ethyl-1-methyl-3-[4-(2-amino-phenoxy)-phenyl]-1H-pyrole-2-carboxylic acid ethyl ester (110 mg, 0.28 mmol, prepared in example E-231) in methylene chloride (25 mL) while stirring at 0° C. under a nitrogen atmosphere. Immediately add isopropylsulfonyl chloride (48 mg, 1.2Eq.) dropwise and allow the reaction to warm to room temperature and stir overnight. Add water to the mixture and separate layers. Wash the organic layer once with water, dry over potassium carbonate, filter, and concentrate under reduced vacuum to give 156 mg of a solid. Purity the material by silica gel chromatography (Chromatotron™) eluting with methylene chloride/ethyl acetate 19:1 to provide 23 mg of the title compound as a viscous oil. (Bruker 300) $^1$H NMR ($CDCl_3$) δ 7.30-7.35 (2H, d), 7.22-7.28 (1H, m), 6.99-7.03 (2H, d), 6.89-6.97 (2H, m), 6.75-6.79 (1H, d), 4.06-4.14 (2H, dd), 3.85-3.88 (3H, s), 3.29-3.36 (1H, m), 2.81-2.87 (2H, dd), 1.36-1.42 (6H, d), 1.25-1.32 (3H, t), 1.02-1.09 (3H, t).

EXAMPLE E-233

Preparation of 3-Biphenyl-4-yl-4-cyano-1,5-dimethyl-1H-pyrrole-2-carboxylic acid ethyl ester

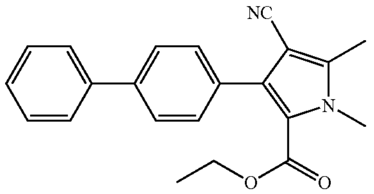

Prepare the title compound in the manner analogous to the procedure set fourth in the final step of example E-227 using 4-cyano-3-iodo-1,5-dimethyl-1H-pyrrole-2-carboxylic acid ethyl ester (prepared in preparation 45) and 4-diphenylboronic acid. Purify the material by silica gel chromatography (Chromatotron™) eluting with hexane/ethyl acetate 4:1 to provide the title compound as a white solid. mass spectrum (fd): 344.0 (M*).

EXAMPLE E-234

Preparation of 3-(4-Bromo-phenyl)-4-cyano-1,5-dimethyl-1H-pyrrole-2-carboxylic acid ethyl ester

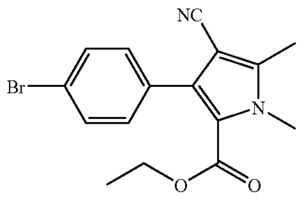

Prepare the title compound in the manner analogous to the procedure set fourth in the last step of example E-227 using 4-cyano-3-iodo-1,5-dimethyl-1H-pyrrole-2-carboxylic acid ethyl ester (prepared in preparation 45) and 4 bromo-phenylboronic acid. Purify the material by silica gel chromatography (Chromatotron™) eluting with hexane/ethyl acetate 7:3 to provide the title compound as a viscous oil. Mass spectrum (fd): 347.0 (M*): (Bruker 300) $^1$H NMR ($CDCl_3$) δ 7.47-7.52 (2H, d), 7.18-7.23 (2H, d), 4.06-4.13 (2H, dd), 3.84-3.88 (3H, s), 2.41-2.44 (3H, s), 1.00-1.05 (3H, t).

EXAMPLE E-235

Preparation of 4-Cyano-1,5-dimethyl-3-(2'-methylsulfanyl-biphenyl-4-yl)-1H-pyrrole-2-carboxylic acid ethyl ester

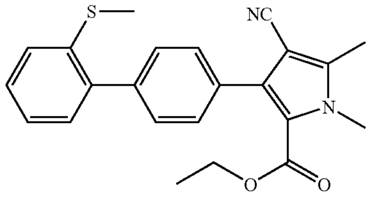

Prepare the title compound in the manner analogous to the procedure set fourth in the last step of example E-227 using 3-(4-bromo-phenyl)-4-cyano-1,5-dimethyl-1H-pyrrole-2-carboxylic acid ethyl ester (prepared in example E-234) and 2-thiomethyl-phenylboronic acid. Purify the material by silica gel chromatography (Chromatotron™) eluting with methylene chloride to provide the title compound as a clear oil. Mass spectrum (fd): 391.1 (M*+1): (Bruker 300) $^1$NMR ($CDCl_3$) δ 7.36-7.45 (2H, dd), 7.17-7.35 (5H, m), 4.06-4.13 (2H, dd), 3.87-3.89 (3H, s), 2.44-2.47 (3H, s), 2.35-2.37 (3H, s), 1.02-1.07 (3H, t).

EXAMPLE E-236

Preparation of 4-cyano-1,5-dimethyl-3-(2'-amino-biphenyl-4-yl)-1H-pyrrole-2-carboxylic acid ethyl ester

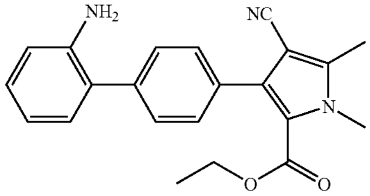

Prepare the title compound in the manner analogous to the procedure set fourth in the last step of example E-227 using 3-(4-bromo-phenyl)-4-cyano-1,5-dimethyl-1H-pyrrole-2-carboxylic acid ethyl ester (example E-234) and 2 amino-phenylboronic acid. Purify the material by silica gel chromatography (Chromatotron™) eluting with methylene chloride/ethyl acetate 9:1 to provide the title compound as a foam. Mass spectrum (fd): 360.1 (M*+1): (Bruker 300) $^1$NMR ($CDCl_3$) δ 7.39-7.48 (4H, dd), 7.11-7.16 (2H, d), 6.74-6.84 (2H, m), 4.06-4.13 (2H, dd), 3.87-3.89 (3H, s), 2.44-2.47 (3H, s), 1.02-1.07 (3H, t).

EXAMPLE E-237

Preparation of 4-cyano-1,5-dimethyl-3-[2'-(propane-2-sulfonylamino)-biphenyl-4-yl)-1H-pyrrole-2-carboxylic acid ethyl ester

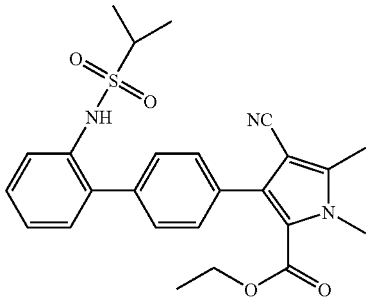

Prepare the title compound in the manner analogous to the procedure set fourth in example E-232 using 4-cyano-1,5-dimethyl-3-(2'-amino-biphenyl-4-yl)-1H-pyrrole-2-carboxylic acid ethyl ester (prepared in example E-236). Purify the material by silica gel chromatography (Chromatotron™) eluting with methylene chloride/ethyl acetate 9:1 to provide the title compound as an oil.

EXAMPLE E-238

Preparation of 4-cyano-3-(4-hydroxy-phenyl)-1,5-dimethyl-1H-pyrrole-2-carboxylic acid ethyl ester

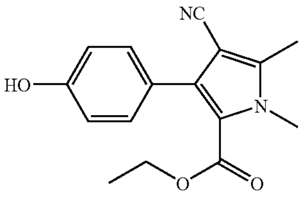

Prepare the title compound in the manner analogous to the procedure set fourth in the last step of example E-227 using 4-cyano-3-iodo-1,5-dimethyl-1H-pyrrole-2-carboxylic acid ethyl ester (prepared in preparation 45) and 4-(4,4,5,5,-Tetramethyl-[1,3,2,]dioxaborolan-2-yl)-phenol. Purify the material by silica gel chromatography (Chromatotron™) eluting with methylene chloride/ethyl acetate 1:1 to provide the title compound as a tan solid. Mass spectrum (fd): 285.1 (*+1): (Bruker 300) $^1$H NMR ($CDCl_3$) δ 7.20-7.28 (2H, d), 6.80-6.88 (2H, d), 4.06-4.13 (2H, dd), 3.82-3.87 (3H, s), 2.40-2.47 (3H, s), 1.00-1.07 (3H, t).

EXAMPLE E-239

Preparation of 4-cyano-1,5-dimethyl-3-(4-trifluoromethanesulfonyloxy-phenyl)-1H-pyrrole-2-carboxylic acid ethyl ester

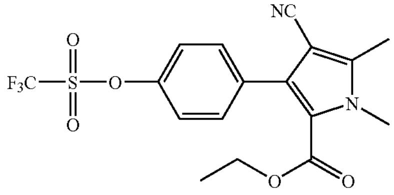

Add trifluoromethanesulfonic anhydride (1.2 Eq.) to 4-cyano-3-(4-hydroxy-phenyl)-1,5-dimethyl-1H-pyrrole-2-carboxylic acid ethyl ester (prepared in example E-238) and pyridine (1.5 Eq) in methylene chloride dropwise with stirring at 0° C. Stir the reaction mixture for 2 hours and then allow the reaction to warm to room temperature. Wash the organic layer with 1.0 N HCl, water, dry over potassium carbonate, filter, and concentrate under reduced vacuum. Purify the residue by silica gel chromatography (Chromatotron™) eluting with methylene chloride to provide the title compound as a yellow solid. Mass spectrum (m/e): 417.1 (M*+1): (Bruker 300) $^1$H NMR ($CDCl_3$) δ 7.29-7.32 (2H, d), 7.27-7.29 (2H, d), 4.01-4.11 (2H, dd), 3.85-3.89 (3H, s), 2.43-2.47 (3H, s), 0.90-1.00 (3H, t).

EXAMPLE E-240

Preparation of 4-cyano-1,5-dimethyl-3-(2'-cyano-biphenyl-4-yl)-1H-pyrrole-2-carboxylic acid ethyl ester

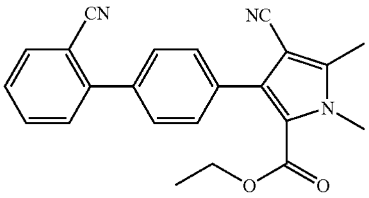

Prepare the title compound in the manner analogous to the procedure set fourth in the last step of example E-227 using 4-cyano-1,5-dimethyl-3-(4-trifluoromethanesulfonyoxy-phenyl)-1H-pyrrole-2-carboxylic acid ethyl ester (prepared in example E-239) and 2-cyano-phenylboronic acid. Purify the material by silica gel chromatography (Chromatotron™) eluting with methylene chloride to provide the title compound as a white solid. Mass spectrum (fd): 370.1 (M*+1): (Bruker 300) $^1$H NMR (DMSO) δ 8.00-8.04 (1H, d), 7.84-7.88 (1H, t), 7.63-7.75 (4H, m), 7.51-7.55 (2H, d), 4.06-4.13 (2H, dd), 3.82-3.87 (3H, s), 2.47-2.52 (3H, s), 0.99-1.01 (3H, t).

EXAMPLE E-241

Preparation of 4-cyano-5-ethyl-3-{4-[1-(4-methoxy-benzyl)-1H-tetrazol-5-yl]-phenyl}-1-methyl-1H-pyrrole-2-carboxylic acid ethyl ester

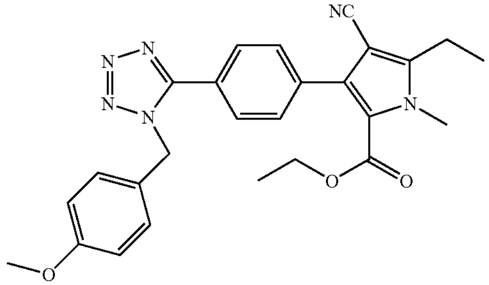

At room temperature, to a stirred mixture of 5-(4-bromophenyl)-1H-tetrazole (2.15 g, 9.55 mmol) in $CH_3CN$, add 4-methoxybenzyl chloride (1.42 mL, 10.50 mmol) followed by $Et_3N$ (1.46 mL, 10.50 mmol) and stir over night. Concentrate the mixture to half the volume and add water (100 mL). Filter the white precipitate and wash with water (100 mL). Dry the material to give 5-(4-bromophenyl)-1-(4-methoxybenzyl)-1H-tetrazole as white flocculent crystals (1.37 g).

Alternately evacuate and charge (3 times) with nitrogen, a round bottom containing 5-(4-bromophenyl)-1-(4-methoxybenzyl)-1H-tetrazole (0.500 g, 1.44 mmol, prepared directly above), bis(pinacolato)diboron (0.45 g, 1.59 mmol), potassium acetate (0.59 g, 4.34 mmol) and $Pd(dppf)_2Cl_2$ (0.23 g, 0.29 mmol). Into the flask add DMF (8 mL) and heat at 100° C. over night under nitrogen positive pressure. Dilute the mixture with brine (50 mL) and extract with ethyl acetate (3×50 mL), dry the organics with anhydrous sodium sulfate, filter, and concentrate under reduced pressure. Pass the material through silica gel, eluting with 50% diethyl ether in hexanes to give 1-(4-methoxybenzyl)-5-[4-(4,4,5,5-tetramethyl-[1,3,2]dioxaborolan-2-yl)-phenyl]-1H-tetrazole as white crystals (0.29 g).

Alternately evacuate and charge (3 times) with nitrogen, a round bottom containing 1-(4-methoxybenzyl)-5-[4-(4,4,5,5-tetramethyl-[1,3,2]dioxaborolan-2-yl)-phenyl]-1H-tetrazole (0.282 g, 0.719 mmol, prepared directly above), 4-cyano-5-ethyl-3-iodo-1-methyl-1H-pyrrole-2-carboxylic acid ethyl ester (0.28 g, 0.86 mmol, prepared in preparation 38), cesium fluoride (0.54 g, 3.59 mmol) and $Pd(dppf)_2Cl_2$ (0.11 g, 0.14 mmol). Charge the flask with DME (3.5 mL) and heat at 80° C. over night under nitrogen positive pressure. Dilute the mixture with brine (25 mL) and extract with ethyl acetate (3×50 mL). Combine the organic extracts, dry over anhydrous sodium sulfate, filter, and concentrate under reduced pressure. Purify the residue by flash chromatography (silica gel), eluting with 25-60% diethyl ether in Hexanes. Combine the purified fractions and concentrate under reduced pressure to provide the title compound as a yellow tar (0.20 g);

mass spectrum (m/e): 471.2 (M+1).

EXAMPLE E-242

Preparation of 4-Cyano-5-ethyl-1-methyl-3-[4-(1H-tetrazol-5-yl)-phenyl]-1H-pyrrole-2-carboxylic acid ethyl ester

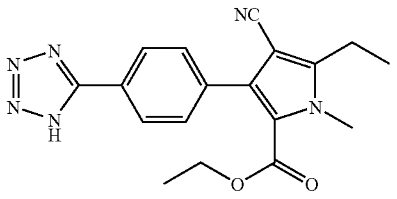

Into a round bottom flask containing 4-cyano-5-ethyl-3-{4-[1-(4-methoxybenzyl)-1H-tetrazol-5-yl]-phenyl}-1-methyl-1H-pyrrole-2-carboxylic acid ethyl ester (0.15 g, 0.33 mmol, prepared in example E-241) add TFA (2 mL) and stir over night. Concentrate the mixture and azeotrope the residue with a mixture of methylene chloride/hexanes. Dilute the mixture with 0.500 N HCl (20 mL) and extract with ethyl acetate (3x30 mL). Combine the organic extracts, dry over anhydrous sodium sulfate, filter, and concentrate under reduced pressure. Purify the residue by silica gel chromatography (eluent: 0 to 5% MeOH/ethyl acetate). Concentrate the purified fractions under reduced pressure and place under vacuum to provide the title compound as a tan solid (0.105 g); mass spectrum (m/e): 351.05 (M+H)

EXAMPLE E-243

Preparation of 4-Cyano-5-ethyl-1-methyl-3-[4-(1-methyl-1H-tetrazol-5-yl)-phenyl]-1H-pyrrole-2-carboxylic acid ethyl ester

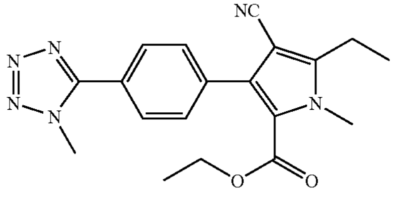

Into a round bottom flask containing a solution of 4-cyano-5-ethyl-1-methyl-3-[4-(1H-tetrazol-5-yl)-phenyl]-1H-pyrrole-2-carboxylic acid ethyl ester (0.116 g, 0.331 mmol, prepared in example E-242) in DMF (2 mL) cooled to 0° C. while stirring add NaH (0.015 g, 0.364 mmol, 60% in mineral oil). Let stir for 20 min, then add methyl iodide (0.022 mL, 0.364 mmol) and let stir for 3 h. Dilute the mixture with brine (20 mL) and extract the mixture with EtOAc (3x30 mL). Combine the organic layers and wash with brine (2x30 mL), aqueous $NH_4Cl$ (1x30 mL), aqueous $NaHCO_3$ (1x30 mL) and water (1x30 mL). Dry the organic layer over anhydrous $Na_2SO_4$, filter and concentrate under reduced pressure. Separate the two regioisomeric products via silica gel chromatography (eluent: 20 to 98% EtOAc in hexanes) and concentrate under reduced pressure the purified fractions. Place the residue under vacuum to give the title compound as a white solid (0.055 g); mass spectrum (m/e): 365.07 (M+H)

EXAMPLE E-244

Preparation of 4-Cyano-5-ethyl-1-methyl-3-[4-(2-methyl-1H-tetrazol-5-yl)-phenyl]-1H-pyrrole-2-carboxylic acid ethyl ester

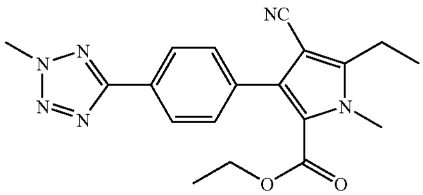

Into a round bottom flask containing a solution of 4-cyano-5-ethyl-1-methyl-3-[4-(1H-tetrazol-5-yl)-phenyl]-1H-pyrrole-2-carboxylic acid ethyl ester (0.116 g, 0.331 mmol, prepared in example E-242 in DMF (2 mL) cooled to 0° C. while stirring add NaH (0.015 g, 0.364 mmol, 60% in mineral oil). Let stir for 20 min, then add methyl iodide (0.022 mL, 0.364 mmol) and let stir for 3 h. Dilute the mixture with brine (20 mL) and extract the mixture with EtOAc (3x30 mL). Combine the organic layers and wash with brine (2x30 mL), aqueous $NH_4Cl$ (1x30 mL), aqueous $NaHCO_3$ (1x30 mL) and water (1x30 mL). Dry the organic layer over anhydrous $Na_2SO_4$, filter, and concentrate under reduced pressure. Separate the two regioisomeric products via silica gel chromatography (eluent: 20 to 98% EtOAc in hexanes) and concentrate under reduced pressure the purified fractions. Place the residue under vacuum to provide the title compound as a white solid (0.015 g); mass spectrum (m/e): 365.09 (M+H)

EXAMPLE E-245

Preparation of 3-[4-(1-Butyl-1H-tetrazol-5-yl)-phenyl]-4-cyano-5-ethyl-1-methyl-1H-pyrrole-2-carboxylic acid ethyl ester

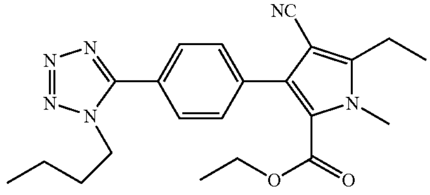

Into a round bottom flask containing a solution of 4-cyano-5-ethyl-1-methyl-3-[4-(1H-tetrazol-5-yl)-phenyl]-1H-pyrrole-2-carboxylic acid ethyl ester (0.150 g, 0.428 mmol, prepared in example E-242) in DMF (2 mL) cooled to 0° C. while stirring add NaH (0.019 g, 0.479 mmol, 60% in mineral oil). Let stir for 1 h, then add butyl iodide (0.054 mL, 0.479 mmol) and let stir for 2.5 h. Dilute the mixture with brine (20 mL) and extract the mixture with EtOAc (3x15 mL). Combine the organic layers and wash with brine (2x20 mL), aqueous $NH_4Cl$ (1x20 mL), aqueous $NaHCO_3$ (1x20 mL) and water (1x20 mL). Dry the organic layer over anhydrous $Na_{2\ SO4}$, filter, and concentrate under reduced pressure. Purify the residue via silica gel chromatography (eluent: 20 to 98%

EtOAc in hexanes). Concentrate under reduced pressure the purified fractions and place under vacuum to provide the title compound as a colorless oil (0.059 g); mass spectrum (m/e): 407.4 (M+H)

EXAMPLE E-246

Preparation of 4-Cyano-5-ethyl-3-[4-(1-isobutyl-1H-tetrazol-5-yl)-phenyl]-1-methyl-1H-pyrrole-2-carboxylic acid ethyl ester

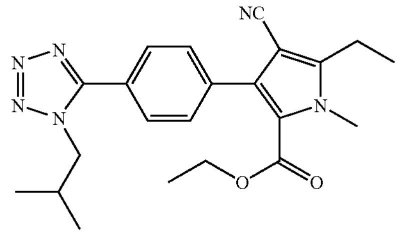

Into a round bottom flask containing a solution of 4-cyano-5-ethyl-1-methyl-3-[4-(1H-tetrazol-5-yl)-phenyl]-1H-pyrrole-2-carboxylic acid ethyl ester (0.150 g, 0.428 mmol, prepared in example E-242) in DMF (2 mL) cooled to 0° C. while stirring add NaH (0.019 g, 0.479 mmol, 60% in mineral oil). Let stir for 1 h, then add 1-bromo-2-methylpropane (0.052 mL, 0.479 mmol) and let stir overnight. Dilute the mixture with brine (20 mL) and extract the mixture with EtOAc (3×15 mL). Combine the organic layers and wash with brine (2×20 mL), aqueous $NH_4Cl$ (1×20 mL), aqueous $NaHCO_3$ (1×20 mL) and water (1×20 mL). Dry the organic layer over anhydrous $Na_2SO_4$, filter, and concentrate under reduced pressure. Purify the residue via silica gel chromatography (eluent: 20 to 98% EtOAc in hexanes). Concentrate under reduced pressure the purified fractions and azeotroped with methylene chloride/hexanes. Place the residue under vacuum to provide the title compound as a colorless tar (0.011 g); mass spectrum (m/e): 407.3 (M+H)

EXAMPLE E-247a

Preparation of 3-(4-bromo-phenyl)-4-cyano-5-ethyl-1-methyl-1H-pyrrole-2-carboxylic acid ethyl ester

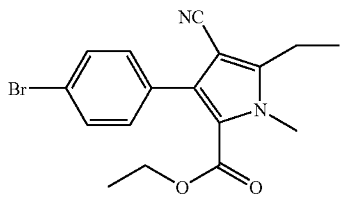

A 10 mL round bottom flask is charged with 4-cyano-5-ethyl-3-iodo-1-methyl-1H-pyrrole-2-carboxylic acid ethyl ester (200 mg, 0.602 mmol, prepared in preparation 38) and absolute ethanol (4.0 mL). To this solution is added 4-bromophenylboronic acid (242 mg, 1.20 mmol) and 2M aqueous $Na_2CO_3$ solution (0.90 mL). This mixture is degassed under house vacuum for about 20 min until no bubbles produced. Nitrogen gas is recharged into the flask and $Pd(PPh_3)_4$ (56 mg, 0.048 mmol) is quickly added. The septum cap is well sealed with copper wire and teflon tape. The mixture in this sealed flask is then heated in oil bath at 80° C. for 18-20 hours. The mixture is cooled to room temperature. It is diluted in methylene chloride (20 mL) and poured into 0.1 M HCl solution (30 mL), pH is adjusted to 7-8 with sat. aq. $NaHCO_3$ solution. The mixture is extracted with methylene chloride (2×30 mL), and diethyl ether (2×30 mL), the combined extracts are dried over anhydrous $MgSO_4$, filtered, and concentrated in vacuo. The residue is then purified by flash chromatography (silica gel, elution with 20% $Et_2O$ in hexanes) to provide the title compound (170 mg, 77%) as a light brown oil. Mass spectrum (m/e): 360.9 (M+1). $R_f$=0.4 (50% of $Et_2O$ in hexanes).

EXAMPLE E-247b

Additional Preparation of 3-(4-bromo-phenyl)-4-cyano-5-ethyl-1-methyl-1H-pyrrole-2-carboxylic acid ethyl ester Preparation of ethyl 2-cyano-3-oxopentanoate

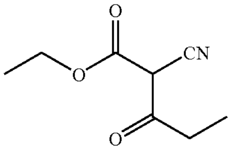

Into a 500-mL round-bottomed flask containing anhydrous acetonitrile (60 mL) at 23° C. is slowly added anhydrous $MgCl_2$ (10.0 g, 0.0795 mol, 0.76 eq, ampoules) under nitrogen. The heat of solvation causes a temperature rise to about 53° C. The mixture is allowed to cool to 29° C., ethyl cyanoacetate (11.8 g, 0.105 mol, 1 eq) is added dropwise over about 5 minutes to the mixture, followed by an acetonitrile rinse (5 mL). Anhydrous triethylamine (21.2 g, 0.209 mol, 2 eq) is added dropwise to the 25° C. reaction mixture, followed by an acetonitrile rinse (5 mL). The reaction mixture is cooled to 1° C., and propionyl chloride (9.68 g, 0.105 mol, 1 eq.) is added dropwise at such a rate as to maintain a reaction temperature below 13° C. (addition is stopped periodically), followed by an acetonitrile rinse (5 mL). The contents of the cooled reaction flask are allowed to warm to 23° C. overnight.

The mixture is re-cooled to about 0° C., and aqueous HCl (18 mL conc. HCl diluted with 52 mL water) is added dropwise with stirring. MTBE (100 mL) is added to the 0° C. mixture forming a two phase mixture that is allowed to warm to 23° C. with stirring. The organic phase (top) is isolated and the aqueous phase is extracted with MTBE (100 mL). The combined organic phases are extracted with water (2×50 mL), then saturated aq. NaCl (50 mL). The organic phase is isolated, dried over anhydrous $Na_2SO_4$, and filtered to afford a yellow filtrate. The filtrate is concentrated by Rotovap to afford 17.3 g (97.7%) of the title compound as a yellow oil.

In-Situ Preparation of 3-oxopentanenitrile

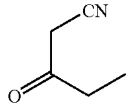

Into a 50 mL round-bottom flask is placed a solution of ethyl 2-cyano-3-oxopentanoate (5.5 g, 0.0325 mol) in DMSO (12.5 mL) at 23° C. under nitrogen. Water (1.25 mL) is added, and the stirred mixture is heated to 110° C., and held there for about 1 h. An HPLC sample is removed and the DMSO solution of 3-oxo-pentanenitrile is allowed to cool back to 23° C. in preparation for the Knorr cyclization. The HPLC sample (218 nm, area %) shows essentially complete consumption of the starting ethyl 2-cyano-3-oxopentanoate (13 minutes), and the production of new product at 11.6 min (DMSO is apparent in the chromatogram at about 2.4 minutes). This DMSO solution of 3-oxo-pentanenitrile (containing in theory 2 eq. of ketone) is used directly in the Knorr cyclization step.

Preparation of ethyl 3-(4-bromophenyl)-3-oxopropanoate

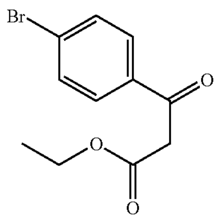

A mixture of diethyl carbonate (24.1 g, 0.204 mol, 2.03 eq.), ethanol (0.14 g, 0.003 mol, 0.03 eq.), and MTBE (50 mL) is added to a 23° C. suspension of 60% sodium hydride (8.44 g, 0.211 mol, 2.1 eq.; in mineral oil) in MTBE (150 mL). This mixture is heated to about 35° C., and a solution of 4-bromoacetophenone (20.0 g, 0.101 mol, 1 eq.) in MTBE (100 mL) is added dropwise with stirring over a period of about 1 h and 20 minutes (35 to 37° C.), followed by a about 20 mL MTBE rinse. The reaction is left to stir overnight at 36° C., and HPLC analysis confirms consumption (<1.2 area %, 218 nm) of starting 4-bromoacetophenone.

The reaction mixture is cooled to 23° C. after 14 hours at 36° C. The mixture is slowly poured into a stirred mixture of acetic acid (40 mL) in water (160 mL), followed by an MTBE rinse to afford a two-phase mixture. The organic phase is separated and washed with water (200 mL), saturated $NaHCO_3$ (2×200 mL), and dried over anhydrous $Na_2SO_4$. Filtration and concentration by Rotovap, affords 35.8 g of crude title compound as a yellow oil. This oil is dissolved in methanol (250 mL) and is extracted with heptane (2×100 mL) to remove residual mineral oil. The methanol phase is concentrated by Rotovap to afford 24.5 g of title compound that is carried on to the next step.

Preparation of ethyl 3-(4-bromophenyl)-2-(hydroxyimino)-3-oxopropanoate

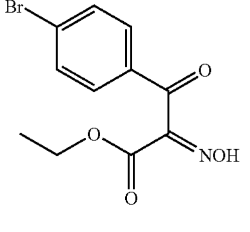

Crude ethyl 3-(4-bromophenyl)-3-oxopropanoate (24.5 g, 0.0884 mol) is dissolved in acetic acid (250 mL) at 23° C. under nitrogen, and water (60 mL) is added. The mixture is cooled to 1° C., and a solution of sodium nitrite (7.63 g, 0.111 mol) in water (60 mL) is added dropwise while maintaining the reaction temperature between 1 to 3° C. The mixture is allowed to stir at 1° C. for 3 hours. Water (100 mL) is added dropwise to the cooled reaction mixture to precipitate the product. The cold (about 5° C.) mixture is suction filtered and the collected solids are rinsed with cold 1:1 (v/v) HOAc/water (50 mL), followed by water (2×50 mL). The solids are suction dried overnight to give 18.3 g of crude title compound.

A suspension of crude title compound in toluene (90 mL) at 23° C. is heated to about 70° C. with stirring under nitrogen. Upon reaching 70° C., the heating mantle is removed and the suspension is allowed to cool back to 23° C. At about 25-26° C., heptane (90 mL) is added dropwise with stirring at 23° C. After 1 h, the solids are suction filtered at 23° C. and rinsed with 1:1 (v/v) toluene/heptane (20 mL), followed by pure heptane (2×20 mL). Suction drying affords 14.5 g of title compound as a white solid; mp 149° C.

Preparation of ethyl 3-(4-bromophenyl)-4-cyano-5-ethylpyrrole-2-carboxylate

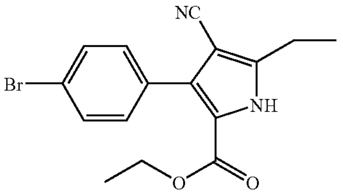

Into an ice-bath cooled 250 mL round-bottom flask containing pre-chilled ethanol (50 mL) is placed ethyl 3-(4-bromophenyl)-2-(hydroxyimino)-3-oxopropanoate (4.88 g, 0.0163 mol, 1 eq) and zinc dust (3.36 g, 0.0514 (3.2 eq). The aqueous DMSO solution (13.8 mL) of freshly prepared 3-oxo-pentanenitrile (in theory: 0.0325 mol, prepared above) is added to the reaction mixture dropwise with stirring and cooling, followed by an ethanol (2-3 mL) rinse. Glacial acetic acid (5.86 g, 0.0976 mol, 6 eq) is diluted to 12 mL with ethanol (~6 mL) and placed in an addition funnel. From the addition funnel, about 1 mL HOAc/EtOH is added dropwise with stirring at 1-2° C. The ice-bath is removed and the mixture is allowed to warm to 9° C. to initiate the reaction. The ice-bath is replaced and another 1 mL portion of HOAc/EtOH is added dropwise with stirring at 9 to 11° C. The final portion of HOAc/EtOH is added dropwise while maintaining the reaction temperature between 9 and 10° C. The residual HOAc/EtOH is rinsed in with ethanol (2-3 mL). The ice-bath is removed and the mixture is allowed to warm to 23° C. with stirring. After 3 h, HPLC indicates complete consumption of hydroximino starting material.

After 3.45 h, ethyl acetate (50 mL) is added to the reaction mixture at 23° C. and stirring is continued for 10-15 min. The mixture is suction filtered through a whatman GF/F filter (90 mm) to remove $Zn(OAc)_2$, followed by an EtOAc rinse (2×25 mL). The resulting yellow filtrate is concentrated by Rotovap to afford 25.8 g of a thick yellow oil. The oil is taken up in isopropyl alcohol (50 mL), and a yellow solid begins to precipitate. Water (50 mL) is added dropwise to the suspension at 23° C. over 1 h. The solids are suction filtered, and the filter cake is rinsed with water (2×10 mL). The solids are dried in a vacuum oven (23° C.) overnight. This process affords 3.46 g (61%) of title compound as a pale yellow crystalline solid.

Preparation of Final Title Compound

Ethyl 3-(4-bromophenyl)-4-cyano-5-ethylpyrrole-2-carboxylate (1.50 g, 4.32 mmoles, 1 eq.), and powdered potassium carbonate (1.19 g, 8.64 mmoles, 2 eq) are suspended in acetone (10 mL) and stirred at 23° C. under nitrogen. Iodomethane (1.23 g, 8.64 mmoles, 2 eq) is added via an addition funnel, followed by a 5 mL acetone rinse. The mixture is stirred at 23° C. overnight. After about 20 h of stirring, HPLC analysis (218 nm, area %) shows complete consumption of starting material (14.99 min) to give the title compound at (15.7 min). Water (7-8 mL) is added dropwise to the reaction suspension, inducing dissolution of the solids to afford a cloudy solution. The mixture is seeded with authentic product, and additional water (12 mL) is added at 23° C., which causes a yellow precipitate to form. The mixture is cooled to 2° C., stirred for 30 min, and suction filtered to afford a yellow solid that is rinsed with water (2×5 mL). The wet cake (1.43 g) is further dried in a vacuum oven (23° C.) to give 1.41 g (90%) of final title compound as a yellow solid.

EXAMPLE E-247c

Additional Preparation of 3-(4-bromo-phenyl)-4-cyano-5-ethyl-1-methyl-1H-pyrrole-2-carboxylic acid ethyl ester A mixture of 4-cyano-5-ethyl-3-iodo-1-methyl-1H-pyrrole-2-carboxylic acid ethyl ester (2.0 g, 6.0 mmol, prepared in preparation 38), 4-bromophenyl boronic acid (1.32 g, 6.6 mmol), 10 mL of $Na_2CO_3$ (2M) and 20 mL of dioxane is degassed under reduced pressure (−29 inches) for 30 minutes till no bubbles. Recharge with nitrogen. Add $PdCl_2$ $(PPh)_4$ (0.24 mmol). Well seal the flask and heat the mixture at 80° C. overnight. After cooling, water and methylene chloride are added to the reaction mixture. It is then extracted with methylene chloride. The organic layers are combined, dried over magnesium sulfate, filtered, and concentrated under reduced pressure. The residue is purified by flash chromatography to provide the title compound (1.71 g, 78%). MS(ES, m/e) 361.1 (M+1), 380.1(M+18). $R_f$=0.35 (50% ether in hexanes).

EXAMPLE E-247d

Additional Preparation of 3-(4-bromo-phenyl)-4-cyano-5-ethyl-1-methyl-1H-pyrrole-2-carboxylic acid ethyl ester Preparation of 4-bromobenzoylacetonitrile

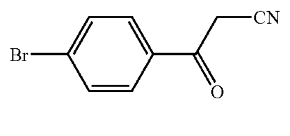

Step A: Cool a solution of cyanoacetic acid (8.72 g, 103 mmoles) in THF (300 mL) to −78° C. in a dry ice-acetone bath. Add a 2.5 M solution of butyllithium in hexanes (82 mL, 205 mmoles) at the rate such that the reaction mixture does not rise above 60° C. Stir the reaction mixture at −78° C. for approximately 45 minutes. Add the solution of 4-bromobenzoyl chloride (15.0 g, 68.3 mmoles) in THF (75 mL) at such a rate such that the reaction mixture does not rise above -60° C. After the addition is complete, cool the reaction mixture to −78° C. Slowly warm the reaction mixture to ambient temperature while stirring under nitrogen for 20 hours. Quench the reaction mixture with a 1N HCl solution (400 mL) to afford a bright yellow heterogeneous mixture. Stir the mixture at ambient temperature for approximately 60 minutes. Transfer the reaction mixture to a separatory funnel and separate the organic and aqueous layers. Extract the aqueous layer with 3×100 mL of EtOAc. Combine the organic extracts, wash with brine and dry over magnesium sulfate. Filter and evaporate the solution to afford a yellow solid. Dissolve the yellow solid into a minimum volume of acetone and add hexanes. Collect the resulting precipitate and rinse with hexane. Dissolve the product in acetone and adsorb onto silica gel. Rinse the silica gel with 1 L of hexane and then elute with a 1:1 solution of hexanes and EtOAc. Evaporate the eluant to afford 7.55 g (49%) of title compound as an off-white crystalline solid. $^1$H NMR (DMSO, 400 MHz) δ 7.89 (d, 2H, J=8.8), 7.81 (d, 2H, J=8.8), 4.76 (s, 2H).

Preparation of 2-(4-Bromo-benzoyl)-3-ethoxy-pent-2-enenitrile

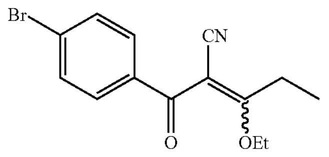

Step B: Prepare the title compound in a manner analogous to Step C of the procedure set forth in example E-121c, starting with p-bromobenzoylacetonitrile (prepared in Step A above), to provide the title compound as a semi-solid mixture of geometric isomers. Mass spectrum: 307 (M*), 309 (M*+2).

Preparation of the Final Title Compound

Step C: Prepare the final title compound in the manner analogous to Step D of the procedure set forth in example E-121c, starting with 2-(4-bromo-benzoyl)-3-ethoxy-pent-2-enenitrile (prepared in Step B above), to provide the final title compound as an off-white solid. Mass spectrum: 360 (M*), 362 (M*+2), 288 (M-$CO_2$Et).

EXAMPLE E-248

Preparation of 4-cyano-5-ethyl-1-methyl-3-(4-pyridin-3-yl-phenyl)-1H-pyrrole-2-carboxylic acid ethyl ester

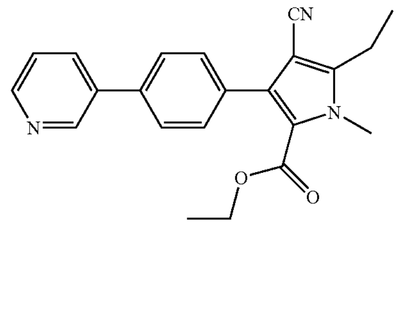

Prepare the title compound in a manner analogous to the procedure set forth in Method CII from 4-cyano-5-ethyl-1-methyl-3-(4-trifluoromethanesulfonyloxy-phenyl)-1H-pyrrole-2-carboxylic acid ethyl ester (prepared in example E-97a or E-97b) and the corresponding aryl boronic acid. Mass spectrum (m/e): 360.2 (M+1)

EXAMPLE E-249

Preparation of 3-[4'-(2-carboxy-ethyl-biphenyl-4-yl]-4-cyano-5-ethyl-1-methyl-1-H pyrrole-2-carboxylic acid ethyl ester

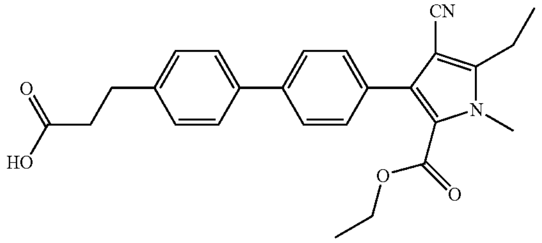

Prepare the title compound in a manner analogous to the procedure set forth in Method CII from 4-cyano-5-ethyl-1-methyl-3-(4-trifluoromethanesulfonyloxy-phenyl)-1H-pyrrole-2-carboxylic acid ethyl ester (prepared in example E-247a or E-247b) and the corresponding aryl boronic acid. Mass spectrum (m/e): 431.2 (M+1)

EXAMPLE E-250

Preparation of 4-cyano-5-ethyl-1-methyl-3-(4-pyridin-4-yl-phenyl)-1H-pyrrole-2-carboxylic acid ethyl ester

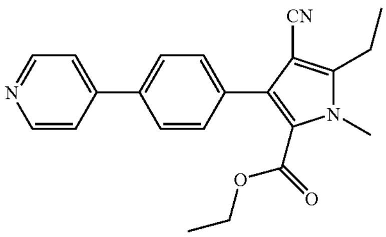

Add 4-cyano-5-ethyl-1-methyl-3-(4-trifluoromethanesulfonyloxy-phenyl)-1H-pyrrole-2-carboxylic acid ethyl ester (0.204 g, 0.474 mmol, prepared in example E-97a or E-97b), 4-pyridyl boronic acid (0.116 g, 0.948 mmol), $Pd_2(dba)_3$ (13.02 mg, 0.01422 mmol), triphenyl phosphine (14.92 mg, 0.0569 mmol), 2M aqueous potassium carbonate (2 mL, 4.0 mmol) in 3 ml of dioxane, and heat to reflux with stirring. After 2.5 hours, cool the reaction mixture and pour into water. Extract the quenched reaction with ethyl acetate. Combine the organic extracts, dry over anhydrous sodium sulfate, filter, and concentrate under reduced pressure. Purify the residue by flash chromatography eluting with 1:1 ethyl acetate:hexanes to ethyl acetate to provide the title compound. Mass spectrum (m/e) 360.1 (M+1).

EXAMPLE E-251

Preparation of 4-cyano-5-ethyl-1-methyl-3-(4-thiazol-2-yl-phenyl)-1H-pyrrole-2-carboxylic acid ethyl ester

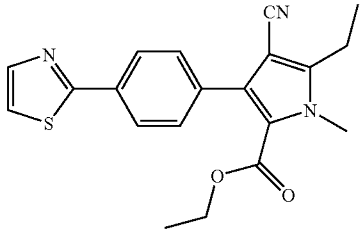

Prepare the title compound in a manner analogous to the procedure set forth in Example E-55 from 4-cyano-5-ethyl-1-methyl-3-(4-trifluoromethanesulfonyloxy-phenyl)-1H-pyrrole-2-carboxylic acid ethyl ester (prepared in example E-97a or E-97b) and the corresponding aryl zinc bromide. Mass spectrum (m/e) 366.2 (M+1).

EXAMPLE E-252

Preparation of 4-cyano-5-ethyl-1-methyl-3-(4-pyrrolidin-1-yl-phenyl)-1H-pyrrole-2-carboxylic acid ethyl ester

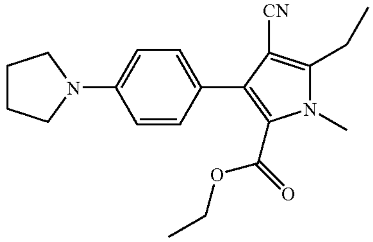

Add 4-cyano-5-ethyl-1-methyl-3-(4-trifluoromethanesulfonyloxy-phenyl)-1H-pyrrole-2-carboxylic acid ethyl ester (0.3 g, 0.697 mmol, 1.0 eq, prepared in example E-97b or 97b), pyrrolidine (0.069 ml, 0.836 mmol, 1.2 eq), $Pd(OAc)_2$ (4.69 mg, 0.0209 mmol, 0.03 eq), BINAP (19.53 mg, 0.0314 mmol, 0.045 eq) and cesium carbonate (0.318 g, 0.976 mmol, 1.4 eq) in toluene and heat at 100° C. with stirring. After 4 hours, stop reaction and let it cool down to room temperature. Partition the mixture between water and ethyl acetate. Separate the aqueous layer and extract it with ethyl acetate three times. Combine organic solution, dry over anhydrous sodium sulfate, filter, and concentrate under reduced pressure. Purify the crude with flash chromatography eluting with 1:3 EtOAc/Hexane to provide 0.176 g (72%) of desired product as light yellow solid. Mass spectrum (m/e) 352.3 (M+1)

EXAMPLE E-253

Preparation of 4-cyano-5-ethyl-1-methyl-3-(4-oxazol-5-yl-phenyl)-1H-pyrrole-2-carboxylic acid ethyl ester

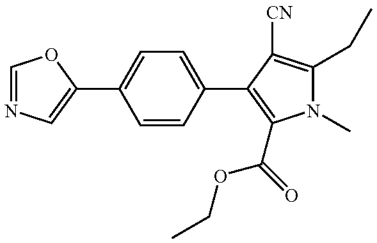

Preparation of 5-[4-(4,4,5,5-tetramethyl-[1,3,2]dioxaborolan-2-yl)-phenyl]-oxazole

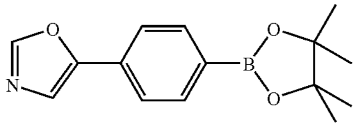

Add 5-(4-bromo-phenyl)-oxazole (0.25 g, 1.116 mmol), bis(pinacolato)diboron (0.312 g, 1.227 mmol), [1,1-bis(diphenylphosphino)-ferrocene]dichloropalladium(II) (0.182 g, 0.223 mmol), potassium acetate (0.329 g, 3.348 mmol) in 3 ml of DMF, and heat at 100° C. under nitrogen for over night. Stop reaction and let the mixture cool down to room temperature. Partition the mixture between ethyl acetate and brine. Separate the aqueous layer, extract with ethyl acetate once. Combine organic and wash with brine three times, dry over sodium sulfate, filter, and concentrate under reduced pressure. Purify the crude residue using flash chromatography eluting with 30% ethyl acetate in hexane to give 0.276 g title compound (91%). Mass spectrum (m/e) 272.3 (M+1).

Preparation of Final Title Compound

Add 4-cyano-5-ethyl-3-iodo-1-methyl-1-H-pyrrole-2-carboxylic acid ethyl ester (0.338 g, 1.018 mmol, 1.0 eq, prepared in preparation 38), 5-[4-(4,4,5,5-tetramethyl-[1,3,2]dioxaborolan-2-yl)-phenyl]-oxazole (0.276 g, 1.018 mmol, 1.0 eq, prepared directly above), $PdCl_2(dppf)$ (0.166 g, 0.204 mmol, 0.2 eq), CsF (0.464 g, 3.054 mmol, 3.0 eq) in 12 ml of DME, heat at 80° C. with stirring for 18 hours. Stop reaction and let it cool down to room temperature. Partition the reaction mixture between ethyl acetate and brine. Separate the aqueous layer and extract with ethyl acetate twice. Combine the organic solution and dry over sodium sulfate, filter, and concentrate under reduced pressure. Purify the crude residue by flash chromatography eluting with 30% ethyl acetate in hexane to give 0.266 g (75%) of final title compound. Mass spectrum (m/e) 350.3 (M+1).

EXAMPLE E-254

Preparation of 4-cyano-5-ethyl-1-methyl-3-(4-[1,2,4]thiadiazol-3-yl-phenyl)-1H-pyrrole-2-carboxylic acid ethyl ester

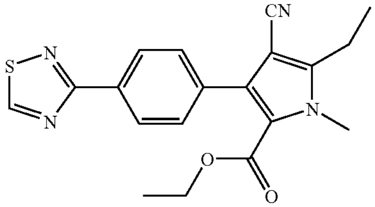

Preparation of 3-[4-(4,4,545-tetramethyl-[1,3,2]dioxaborolan-2-yl)-phenyl]-[1,2,4]thiadiazole

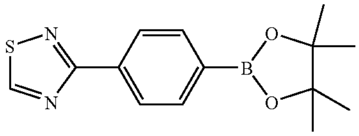

Prepare the title compound in a manner analogous to the procedure set forth for the preparation of 5-[4-(4,4,5,5-tetramethyl-[1,3,2]dioxaborolan-2-yl)-phenyl]-oxazole in Example E-253. Mass spectrum (m/e) 289.3 (M+1).

Preparation of Final Title Compound

Prepare the final title compound in a manner analogous to the procedure set forth in Example E-253 from 4-cyano-5-ethyl-3-iodo-1-methyl-1-H-pyrrole-2-carboxylic acid ethyl ester (prepared in preparation 38) and 3-[4-(4,4,5,5-tetramethyl-[1,3,2]dioxaborolan-2-yl)-phenyl]-[1,2,4]thiadiazole (prepared above). Mass spectrum (m/e) 367.3 (M+1)

EXAMPLE E-255

Preparation of 4-cyano-5-ethyl-3-(4-imidazol-1-yl-phenyl)-1-methyl-1H-pyrrole-2-carboxylic acid ethyl ester

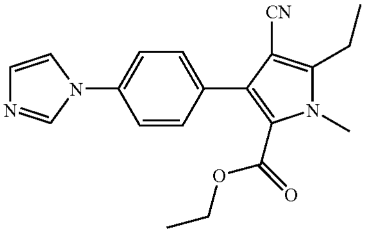

Preparation of 1-[4-(4,4,5,5-tetramethyl-[1,3,2]dioxaborolan-2-yl)-phenyl]-1H-imidazole

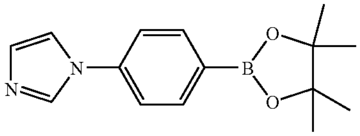

Prepare the title compound in a manner analogous to the procedure set forth in Example E-253. Mass spectrum (m/e) 271.3 (M+1).

Preparation of Final Title Compound

Prepare the final title compound in a manner analogous to the procedure set forth in Example E-253 from 4-cyano-5-ethyl-3-iodo-1-methyl-1-H-pyrrole-2-carboxylic acid ethyl ester (prepared in preparation 38) and 1-[4-(4,4,5,5-tetramethyl-[1,3,2]dioxaborolan-2-yl)-phenyl]-1H-imidazole (prepared above). Mass spectrum (m/e) 349.07 (M+1).

EXAMPLE E-256

Preparation of 4-cyano-3-[4-(5-dimethylamino-[1,3,4]thiadiazol-2-yl-phenyl)-5-ethyl-1-methyl-1H-pyrrole-2-carboxylic acid ethyl ester

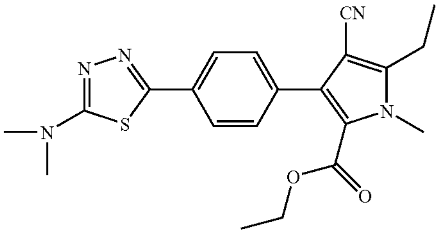

Preparation of dimethyl-{5-[4-(4,4,5,5-tetramethyl-[1,3,2]dioxaborolan-2-yl)-phenyl]-[1,3,4]thiadiazole-2-yl}-amine

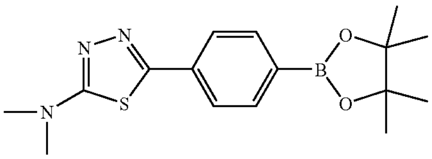

Prepare the title compound in a manner analogous to the procedure set forth for the preparation of 5-[4-(4,4,5,5-tetramethyl-[1,3,2]dioxaborolan-2-yl)-phenyl]-oxazole in Example E-253. Mass spectrum (m/e) 332.06 (M+1).

Preparation of Final Title Compound

Prepare the final title compound in a manner analogous to the procedure set forth in Example E-253 from dimethyl-{5-[4-(4,4,5,5-tetramethyl-[1,3,2]dioxaborolan-2-yl)-phenyl]-[1,3,4]thiadiazole-2-yl}-amine (prepared above) and 4-cyano-5-ethyl-3-iodo-1-methyl-1-H-pyrrole-2-carboxylic acid ethyl ester (prepared in preparation 38). Mass spectrum (m/e) 410.07 (M+1).

EXAMPLE E-257

Preparation of ethyl 3-(4-bromophenyl)-4-cyano-5-fluoro-1-methylpyrrole-2-carboxylate

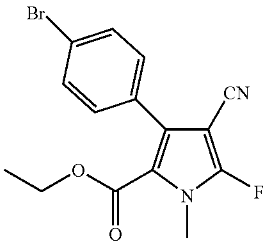

Prepare the title compound in a manner analogous to the procedure set forth in preparation 49 from 3-(4-bromo-phenyl)-4-cyano-1-methyl-1H-pyrrole-2-carboxylic acid ethyl ester (prepared in examples E-3a or E-3b) using SELECTFLUOR®. Mass spectrum (m/e): 350.0 (M). $R_f$=0.4 (50% $Et_2O$ in hexanes).

Prepare the following compounds listed in Table E-26 in a manner analogous to the procedure set forth in Method DII from appropriate halo-substituted ethyl ester derivative and the corresponding boronic acid or boronate.

TABLE E-26

| Ex. | Structure | Data | S.M. |
|---|---|---|---|
| E-259 | 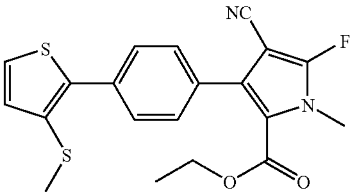 | mass spectrum (m/e): 418.1 (M + 18). $R_f$=0.5(50%$Et_2O$ in hexanes). | E-257 and 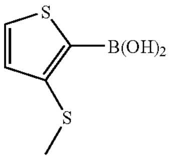 |
| E-260 | 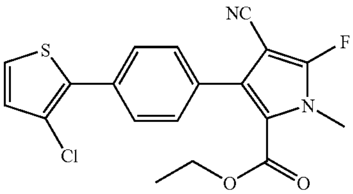 | mass spectrum (m/e): 389.0 (M + 1). $R_f$=0.5(50%$Et_2O$ in hexanes). | E-257 and 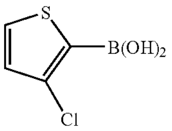 |

TABLE E-26-continued

| Ex. | Structure | Data | S.M. |
|---|---|---|---|
| E-261 | 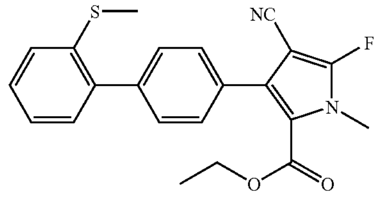 | mass spectrum (m/e): (M + 1). $R_f$=0.4(50%$Et_2O$ in hexanes). | E-257 and 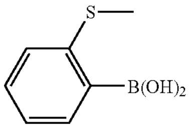 |
| E-262 | 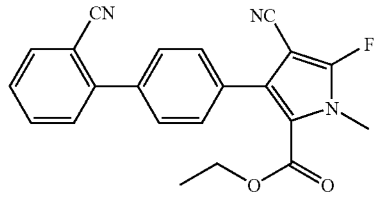 | mass spectrum (m/e): 391.1 (M + 18). $R_f$=0.3(50%$Et_2O$ in hexanes). | E-257 and 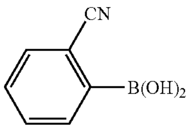 |
| E-263 | 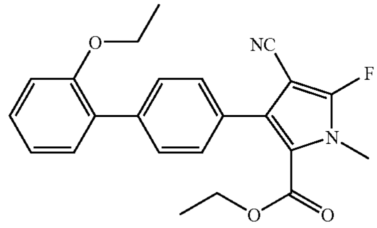 | mass spectrum (m/e): 392.0 (M). $R_f$=0.3(50% $Et_2O$ in hexanes). | E-257 and 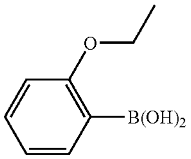 |
| E-264 | 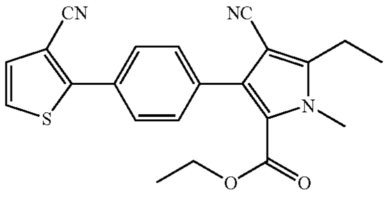 | mass spectrum (m/e): 407.1 (M + 18). $R_f$=0.2(50%$Et_2O$ in hexanes). | Prep. 38 and 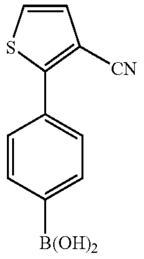 |

Prepare the following compounds listed in Table E-27 in a manner analogous to the procedure set forth in Method FII.

TABLE E-27

| Ex. | Structure | Data | S.M. |
|---|---|---|---|
| E-265 | 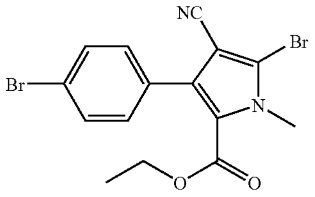 | mass spectrum (m/e): 410.9 (M + 1). $R_f$=0.4(50%$Et_2O$ in hexanes). | E-3a or E-3b |
| E-266 | 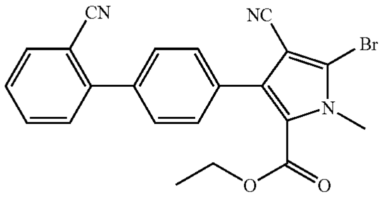 | mass spectrum (m/e): 451.0 (M + 18). $R_f$=0.3(50%$Et_2O$ in hexanes). | E-30 |

EXAMPLE E-267

Preparation of 3-(4-Bromo-phenyl)-4,5-dicyano-1-methyl-1H-pyrrole-2-carboxylic acid ethyl ester

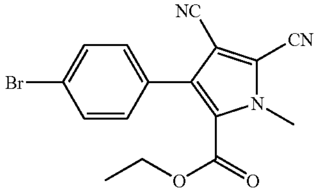

Dissolve 5-bromo-3-(4-bromo-phenyl)-4-cyano-1-methyl-1H-pyrrole-2-carboxylic acid ethyl ester (205 mg, 0.500 mmol, prepared in example E-265) in DMSO (2.5 mL). Add potassium cyanide (325 mg, 5.0 mmol) to the mixture. Heat the mixture at 80° C. for 16 h. Add $H_2O$ (30 mL) and methylene chloride (30 mL) into the reaction mixture. Extract with $H_2O$ (5×30 mL). Combine the organic layers, dry over magnesium sulfate, filter, and concentrate under reduced pressure. Purify by flash chromatography (elution with 33% $Et_2O$ in hexanes) to provide the title compound (161 mg, 0.450 mmol, 90%). Mass spectrum (m/e): 375.0 (M+18). $R_f$=0.2 (50% $Et_2O$ in hexanes).

EXAMPLE E-268

Preparation of ethyl 4-cyano-3-[4-(2-cyanophenyl) phenyl]-5 ethylthio-1-methylpyrrole-2-carboxylate

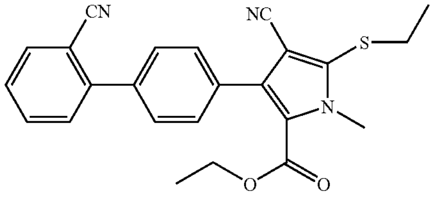

Dissolve 5-bromo-4-cyano-3-(2'-cyano-biphenyl-4-yl)-1-methyl-1H-pyrrole-2-carboxylic acid ethyl ester (100 mg, 0.231 mmol, prepared in example E-266) in DME (2.0 mL). Add sodium ethylthiolate (0.462 mmol) to the mixture. Heat the mixture at 80° C. for 16 h. Add $H_2O$ (30 mL) and methylene chloride (30 mL) into the reaction mixture. Extract with methylene chloride (3×30 mL). Combine the organic layers, dry over magnesium sulfate, filter, and concentrate under reduced pressure. Purify the residue by flash chromatography to provide the title compound. Mass spectrum (m/e): 433.1 (M+18). $R_f$=0.2 (50% $Et_2O$ in hexanes)

EXAMPLE E-269

Preparation of ethyl 4-cyano-3-[4-(2-cyanophenyl) phenyl]1-methyl-5-phenylthiopyrrole-2-carboxylate

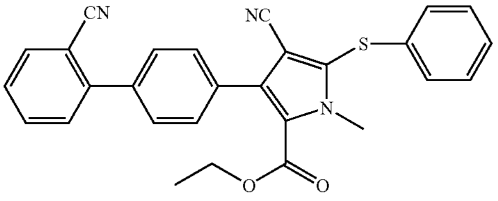

Dissolve 5-bromo-4-cyano-3-(2'-cyano-biphenyl-4-yl)-1-methyl-1H-pyrrole-2-carboxylic acid ethyl ester (100 mg, 0.231 mmol, prepared in example E-266) in DME (2.0 mL). Add sodium phenylthiolate (0.462 mmol) to the mixture. Heat the mixture at 80° C. for 16 h. Add $H_2O$ (30 mL) and methylene chloride (30 mL) into the reaction mixture. Extract with methylene chloride (3×30 mL). Combine the organic layers, dry over magnesium sulfate, filter, and concentrate under reduced pressure. Purify the residue by flash chromatography to provide the title compound. Mass spectrum (m/e): 481.1 (M+18). $R_f$=0.25 (50% $Et_2O$ in hexanes)

EXAMPLE E-270

Preparation of ethyl 4,5-dicyano-1-methyl-3-[4-(2-methylthiophenyl)phenyl]pyrrole-2-carboxylate

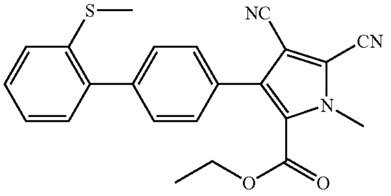

The title compound is prepared in a manner analogous to the procedure set forth in Method DII from 3-(4-bromo-phenyl)-4,5-dicyano-1-methyl-1H-pyrrole-2-carboxylic acid ethyl ester (prepared in example E-267) and the corresponding aryl boronate. Mass spectrum (m/e): 402.1 (M+1). $R_f$=0.4 (50% $Et_2O$ in hexanes).

EXAMPLE E-271

Preparation of ethyl 4,5-dicyano-3-[4-(2-cyanophenyl)phenyl]-1-methylpyrrole-2-carboxylate

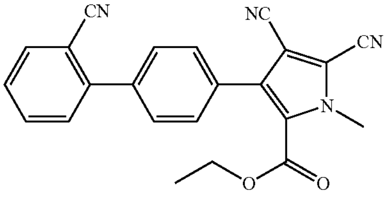

The title compound is prepared in a manner analogous to the procedure set forth in Method DII from 3-(4-bromo-phenyl)-4,5-dicyano-1-methyl-1H-pyrrole-2-carboxylic acid ethyl ester (prepared in example E-267) and the corresponding aryl boronate. Mass spectrum (m/e): 398.1 (M+18). $R_f$=0.3 (50% $Et_2O$ in hexanes).

EXAMPLE E-272

Preparation of 4-cyano-5-ethyl-1-methyl-3-(tert-amylphen-4-yl)-1H-pyrrole-2-carboxylic acid ethyl ester

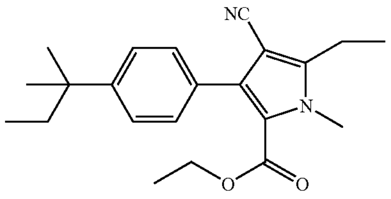

Prepare the title compound in a manner analogous to the procedure set forth in Method EI using 4-cyano-5 ethyl-1-methyl-3-iodo-1H-pyrrole-2-carboxylic acid ethyl ester (prepared in preparation 38) and 4,4,5,5-tetramethyl-2-(tert-amylphen-4-yl)-[1,3,2]dioxaborolane (prepared in preparation 15). $^{1}$H NMR (400 MHz, CDCL3) δ 7.33(dd, J=2.20, 6.61 Hz, 2H), 7.26-7.29 (m, 2H), 4.07 (q, J=7.49 Hz, 2H), 3.88 (s, 3), 2.86 (q, J=7.49 Hz, 2H), 1.66 (q, J=7.49 Hz, 2H), 1.28-1.34 (m, 9H), 0.97 (t, J=7.49 Hz, 3H), 0.7 (t, J=7.49 Hz, 3H).

EXAMPLE E-273

Preparation of 4-Cyano-1,5-dimethyl-3-(2'-thiophene-4-phenyl-4-yl)-1H-pyrrole-2-carboxylic acid ethyl ester

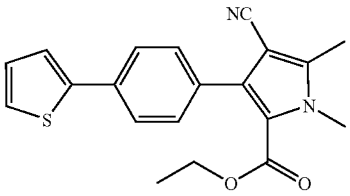

Prepare the title compound in the manner analogous to the procedure set fourth in the last step of example E-227 using 3-(4-bromo-phenyl)-4-cyano-1,5-dimethyl-1H-pyrrole-2-carboxylic acid ethyl ester (prepared in example E-234) and 2-thiophene-boronic acid. Purify the material by silica gel chromatography (Chromatotron™) eluting with methylene chloride to provide the title compound as a yellow wax. Mass spectrum (fd): 351.1 (M*+1): (Bruker 300) $^{1}$H NMR ($CDCl_3$) 7.43-7.61 (3H, m), 7.21-7.39 (3H, m), 7.06-7.12 (1H, m), 4.06-4.13 (2H, dd), 3.87-3.91 (3H,S), 2.44-2.48 (3H, s), 1.00-1.12 (3H, t).

EXAMPLE E-274

Preparation of 4-cyano-1,5-dimethyl-3-(2'-chloro-biphenyl-4-yl)-1H-pyrrole-2-carboxylic acid ethyl ester

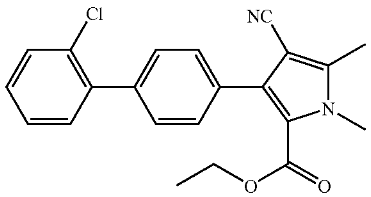

Prepare the title compound in the manner analogous to the last step of example E-227 using 4-cyano-1,5-dimethyl-3-(4-trifluoromethanesulfonyoxy-phenyl)-1H-pyrrole-2-carboxylic acid ethyl ester (prepared in example E-239) and 2-chloro-phenylboronic acid. Purify the material by silica gel chromatography (Chromatotron™) eluting with hexane/ethyl acetate 7:3 to provide the title compound as an oil. Mass spectrum (fd): 379.1 (M*+1): (Bruker 300) $^{1}$H NMR ($CDCl_3$) 7.43-7.50 (3H, m), 7.37-7.43 (3H, m), 7.27-7.36 (2H, m), 4.06-4.13 (2H, dd), 3.87-3.91 (3H, s), 2.44-2.48 (3H, s), 0.99-1.04 (3H, t).

EXAMPLE E-275

Preparation of 4-cyano-1,5-diethyl-3-(2'-methylsulfonamide-biphenyl-4-yl)-1H-pyrrole-2-carboxylic acid ethyl ester

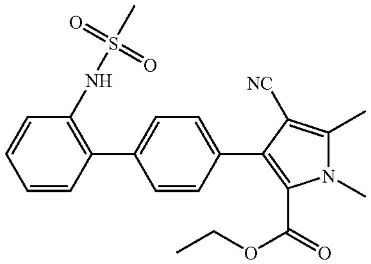

Prepare the title compound in a manner analogous to the last step of example E-227 using 4-cyano-1,5-dimethyl-3-(4-trifluoromethanesulfonyoxy-phenyl)-1H-pyrrole-2-carboxylic acid ethyl ester (prepared in example E-239) and (methylsulfonyl)[3-(4,4,5,5-tetramethyl(1,3,2-dioxaborolan-2-yl))phenyl]amine. Purify the material by silica gel chromatography (Chromatotron™) eluting with a gradient solvent of methylene chloride to methylene chloride/ethyl acetate 9:1 to provide the title compound as a white foam.

Mass spectrum (fd): 436.1 (M*−1): (Bruker 300) $^{1}$H NMR ($CDCl_3$) 7.57-7.63 (2H, d), 7.41-7.49 (4H, m), 7.19-7.28 (2H, m), 4.06-4.15 (2H, dd), 3.84-3.91 (3H,S), 2.44-2.48 (3H, s), 1.00-1.08 (3H, t).

EXAMPLE E-276

Preparation of ethyl 4-cyano-3-(4-hydroxyphenyl)-1-methyl-5-(trifluoromethyl)pyrrole-2-carboxylate

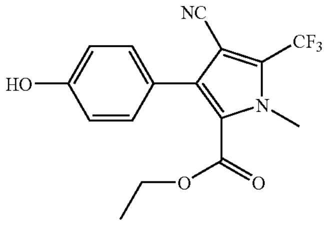

In a manner analogous to the procedure set forth in Scheme II, step A, hydrogenate ethyl 4-cyano-1-methyl-3-[4-(phenylmethoxy)phenyl]-5-(trifluoromethyl)pyrrole-2-carboxylate, (intermediate prepared in example A-237) using Pearlman's catalyst and 60 psi of hydrogen gas in 1:1 ethanol/THF for 11 hours. Filter the reaction through diatomaceous earth and concentrate in vacuo. Purify the residue via radial chromatography eluting with ethyl acetate and hexane to provide the title compound. MS (m/e): 337.0 (M−1) $^1$H NMR: 7.20 (d, 2H, J=8.3 Hz), 6.84 (d, 2H, J=8.8 Hz), 5.85 (s, 1H), 4.16 (q, 2H, J=7.0 Hz), 4.05 (s, 3H), 1.07 (t, 3H, J=7.0 Hz)

EXAMPLE E-277

Preparation of ethyl 4-cyano-1-methyl-5-(trifluoromethyl)-3-{4-[(trifluoromethyl)sulfonyloxy]phenyl}pyrrole-2-carboxylate

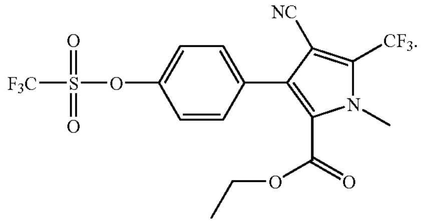

To a solution of ethyl 4-cyano-3-(4-hydroxyphenyl)-1-methyl-5-(trifluoromethyl)pyrrole-2-carboxylate (1.0 mmol, prepared in example E-276) in methylene chloride and pyridine (1.25 mmol) in an ice bath, add trifluoroacetic anhydride (1.0 mmol) and stir for 2 hours at 0° C. Allow the reaction to warm to room temperature and stir for 18 hours. Then wash the reaction with water while extracting with methylene chloride. Dry the organic layer with sodium sulfate, filter, and concentrate in vacuo. Purify the residue via radial chromatography eluting with ethyl acetate and hexane to provide the title compound. MS (m/e): 488.0 (M+18); $^1$H NMR: 7.43 (d, 2H, J=8.8 Hz), 7.35 (d, 2H, J=8.8 Hz), 4.16-4.08 (m, 5H), 0.98 (t, 3H, J=7.0 Hz)

EXAMPLE E-278

Preparation of 4-cyano-3-(2'-cyano-biphenyl-4-yl)-1-methyl-5-trifluoromethyl-1H-pyrrole-2-carboxylic acid ethyl ester

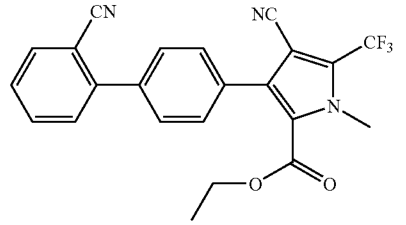

Prepare the title compound in a manner analogous to the procedure described in Scheme IIIa. For example, place ethyl 4-cyano-1-methyl-5-(trifluoromethyl)-3-{4-[(trifluoromethyl)sulfonyloxy]phenyl}pyrrole-2-carboxylate (11.0 mmol, prepared in example E-277), 2-cyano-phenyl boronic acid (1.5 mmol), palladium (II) acetate (0.12 mmol), triphenylphosphate (0.24 mmol), and tribasic potassium phosphate (3.6 mmol) in a round bottom flask and add dioxane. Heat reaction to reflux for 18 hours, remove the heat and wash with water while extracting with ethyl acetate. Dry organics with sodium sulfate, filter, and concentrate in vacuo. Purify the residue via radial chromatography eluting with methylene chloride, ethyl acetate and hexane to provide the title compound.

MS (m/e): 441.1 (M+18); $^1$H NMR: 7.86-7.72 (m, 2H), 7.69-7.55 (m, 3H), 7.51-7.44 (m, 3H), 4.19-4.12 (m, 2H), 4.11 (s, 3H), 1.05 (t, 3H, J=7.0 Hz).

EXAMPLE E-279

Preparation of ethyl 3-[4-(3-amino(2-thienyl))phenyl]-4-cyano-1-methyl-5-(trifluoromethyl)pyrrole-2-carboxylate

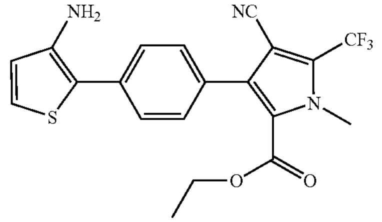

Preparation of ethyl 4-cyano-1-methyl-3-[4-(3-nitro(2-thienyl))phenyl]pyrrole-2-carboxylate

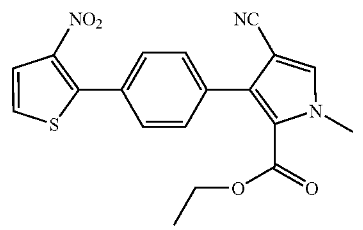

Scheme I, step C: To a solution of ethyl 4-cyano-3-[4-(3-nitro(2-thienyl))phenyl]pyrrole-2-carboxylate (prepared in a manner analogous to the synthetic sequence set forth in example A-239 from 2-chloro-3-nitro-thiophene and 4-formylphenyl boronic acid) (1.0 mmol) in dimethylformamide, add sodium hydride (1.1 mmol) and stir for ten minutes at room temperature. Add methyl iodide to the reaction and stir at room temperature for 1 hour. Then wash the reaction with water while extracting with ethyl acetate. Dry organic layer with sodium sulfate, filter, and concentrate in vacuo. Purify the residue via radial chromatography eluting with ethyl acetate and hexane to provide the title compound. MS (m/e): 399.1 (M+18).

Preparation of ethyl 5-bromo-4-cyano-1-methyl-3-[4-(3-nitro(2-thienyl))phenyl]pyrrole-2-carboxylate

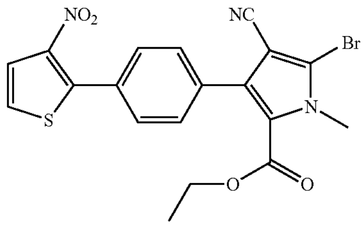

The title compound is prepared in a manner analogous to the procedure set forth in Scheme XXIII, step A wherein the starting pyrrole nitrogen is already methylated. For example, to a solution of ethyl 4-cyano-1-methyl-3-[4-(3-nitro(2-thienyl))phenyl]pyrrole-2-carboxylate, prepared directly above (1.0 mmol) in methylene chloride in an ice bath add N-bromo-succinamide (1.5 mmol). Allow the reaction to warm to room temperature and stir for 18 hours. After this time, wash reaction with water while extracting with ethyl acetate. Dry organic layer with sodium sulfate, filter and concentrate in vacuo to provide the title compound. Use as crude in the next step.

MS (m/e): 479.0 (M+18)

Preparation of ethyl 4-cyano-1-methyl-3-[4-(3-nitro(2-thienyl))phenyl]-5-(trifluoromethyl)pyrrole-2-carboxylate

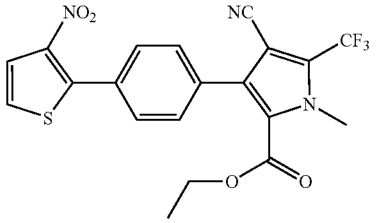

Scheme XXIII, step B: In a manner analogous to the procedure set forth in example A-237, ethyl 5-bromo-4-cyano-1-methyl-3-[4-(3-nitro(2-thienyl))phenyl]pyrrole-2-carboxylate, prepared directly above, is treated with copper bromide and methyl 2,2-difluoro-2-(fluorosulfonyl)acetate (2.0 mmol) in DMF to provide the title compound. MS (m/e): 467.1 (M+18); $^{1}$H NMR: 7.68 (d, 1H, J=5.7 Hz), 7.54 (d, 2H, J=8.4 Hz), 7.41 (d, 2H, J=8.8 Hz), 7.31 (d, 1H, J=5.7 Hz), 4.14 (q, 2H, J=5.3 Hz), 4.09 (s, 3H), 1.05 (t, 3H, J=7.3 Hz)

Preparation of Final Title Compound

To a solution of ethyl 4-cyano-1-methyl-3-[4-(3-nitro(2-thienyl))phenyl]-5-(trifluoromethyl)pyrrole-2-carboxylate (1.0 mmol) in ethanol, add tin (II) chloride (5.2 mmol). Heat reaction to reflux for two hours, remove the heat, and filter reaction through diatomaceous earth. Wash the filtrate with saturated aqueous sodium bicarbonate while extracting with methylene chloride. Dry organics with sodium sulfate, filter, and concentrate in vacuo. Purify the residue via radial chromatography eluting with methanol:methylene chloride. Crash out remaining impurities with ether:hexane and concentrate the mother liquor in vacuo to provide the final title compound. MS (m/e): 420.1 (M+1) 419.1 (M−1); $^{1}$H NMR: 7.58 (d, 2H, J=8.4 Hz), 7.38 (d, 2H, J=8.4 Hz), 7.14 (d, 1H, J=5.3 Hz), 6.67 (d, 1H, J=5.3 Hz), 4.16 (q, 2H, J=7.0 Hz), 4.07 (d, 3H, J=0.9 Hz), 3.99-3.88 (m, 2H), 1.04 (t, 3H, J=7.0 Hz)

EXAMPLE E-280

Preparation of 4-cyano-3-(5'-cyanomethyl-2'-ethoxy-biphenyl-4-yl)-5-ethyl-1-methyl-1H-pyrrole-2-carboxylic acid ethyl ester

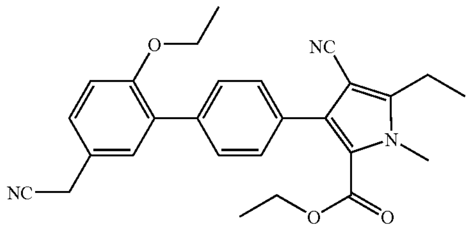

Prepare the title compound in a manner analogous to the procedure set forth in Method DI using 3-(4-bromo-phenyl)-4-cyano-5-ethyl-1-methyl-1H-pyrrole-2-carboxylic acid ethyl ester (prepared in example E-247a or E-247b) and (3-bromo-4-ethoxy-phenyl)-acetonitrile (prepared in preparation 22). Mass spectrum (m/e): 442.1 (M+1).

EXAMPLE E-281

Preparation of 4-cyano-5-ethyl-1-methyl-3-{4-[1-methyl-2-(propane-2-sulfonylamino)-ethyl]-phenyl}-1H-pyrrole-2-carboxylic acid ethyl ester

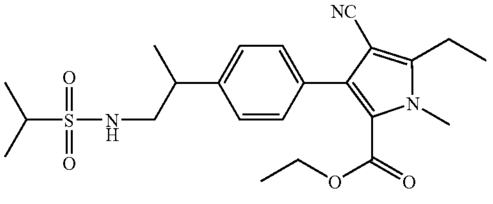

Add 4-cyano-5-ethyl-1-methyl-3-(4,4,5,5-tetramethyl-[1,3,2]dioxaborolan-2-yl)-1H-pyrrole-2-carboxylic acid ethyl ester (0.22 g, 0.65 mmol, prepared in preparation 50), to propane-2-sulfonic acid [2-(4-iodo-phenyl)-propyl]-amide (0.20 g, 0.65 mmol, can be prepared as in *J. Med. Chem.*, 43, 4354 (2000)), [1,1'-bis(diphenyl-phosphino)-ferrocene] dichloropalladium(1H) complex with methylene chloride (1:1) (0.013 g, 0.016 mmol), and 2M aqueous sodium carbonate (1.35 mL, 2.7 mmol) in DMF and heat to 80° C. After 3 hours, cool and pour into water. Extract with ethyl acetate.

Wash the combined organics with water, and brine, dry over magnesium sulfate, filter and concentrate under reduced pressure. Purify the residue by flash chromatography (silica gel), eluting with ethyl acetate:hexanes to provide the title compound. Mass spectrum (ES+)=446.3 (M+1).

EXAMPLE E-282

Preparation of 4-cyano-5-ethyl-1-methyl-3-{4-[2-(propane-2-sulfonylamino)-ethyl]-phenyl}-1H-pyrrole-2-carboxylic acid ethyl ester

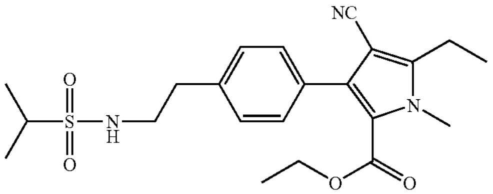

Prepare the title compound in a manner analogous to the procedure set forth in Method EI using propane-2-sulfonic acid {2-[4-(4,4,5,5-tetramethyl-[1,3,2]dioxaborolan-2-yl)-phenyl]-ethyl}-amide, prepared in preparation 51) and 4-cyano-5-ethyl-3-iodo-1-methyl-1H-pyrrole-2-carboxylic acid ethyl ester (prepared in preparation 38). Mass spectrum (ES+) =432.3 (M+1).

EXAMPLE E-283

Preparation of ethyl 3-[4-(2,4-dichlorophenyl)phenyl]-4-cyano-5-ethyl-1-methylpyrrole-2-carboxylate

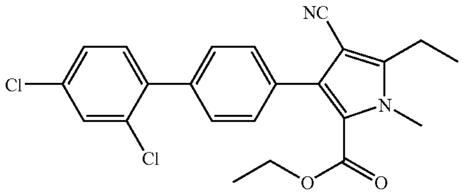

Prepare the title compound in a manner analogous to the procedure set forth in Method CI using 3-(4-bromo-phenyl)-4-cyano-5-ethyl-1-methyl-1H-pyrrole-2-carboxylic acid ethyl ester, (prepared in example E-247a or b) and 2,4-dichlorobenzene boronic acid.

Mass spectrum (ES+)=428.9 (M+1).

EXAMPLE E-284

Preparation of 4-cyano-5-ethyl-1-methyl-3-{4-(methane-2-sulfonylamino)-ethyl]-phenyl}-1H-pyrrole-2-carboxylic acid ethyl ester

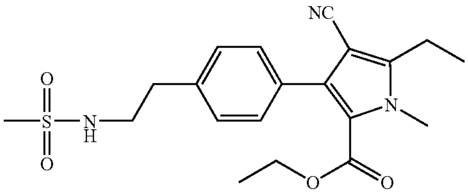

Prepare the title compound in a manner analogous to the procedure set forth in Example E-282, using methane-2-sulfonic acid {2-(4-phenyl boronic acid)]-ethyl}-amide (291 mg, 1.2 mmol) and 4-cyano-5-ethyl-3-iodo-1-methyl-1H-pyrrole-2-carboxylic acid ethyl ester (200 mg, 0.6 mmol, prepared in preparation 38), [1,1'-bis(diphenyl-phosphino)-ferrocene]dichloropalladium(II) complex with methylene chloride (1:1) (0.049 g, 0.069 mmol), and cesium fluoride (456 mg, 3 mmol). Mass spectrum (ES+)=404.0 (M+1).

EXAMPLE E-285

Preparation of 4-cyano-5-ethyl-1-methyl-3-{4-(ethane-2-sulfonylamino)-ethyl]-phenyl}-1H-pyrrole-2-carboxylic acid ethyl ester

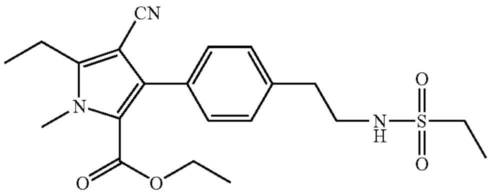

Prepare the title compound in a manner analogous to the procedure set forth in Example E-282, using ethane-2-sulfonic acid {2-[4-(4,4,5,5-tetramethyl-[1,3,2]dioxaborolan-2-yl)-phenyl]-ethyl}-amide (1000 mg, 2.95 mmol) and 4-cyano-5-ethyl-3-iodo-1-methyl-1H-pyrrole-2-carboxylic acid ethyl ester (816 mg, 2.45 mmol, prepared in preparation 38), [1,1'-bis(diphenyl-phosphino)-ferrocene]dichloropalladium (II) complex with methylene chloride (1:1) (0.245 g, 0.3 mmol), and cesium fluoride (2.2 g, 14.75 mmol). Mass spectrum (ES+)=416.1 (M−1).

EXAMPLE E-286

Preparation of 4-cyano-5-ethyl-1-methyl-3-{4-[2-propane-2-sulfonylamino)-(S,S)-cyclopentyl]-phenyl}-1H-pyrrole-2-carboxylic acid ethyl ester

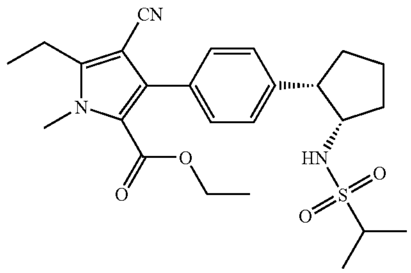

Prepare the title compound in a manner analogous to the procedure set forth in Example E-281, using 4-cyano-5-ethyl-1-methyl-3-(4,4,5,5-tetramethyl-[1,3,2]dioxaborolan-2-yl)-1H-pyrrole-2-carboxylic acid ethyl ester (1010 mg, 3.05 mmol, prepared in preparation 50), propane-2-sulfonic acid [2-(4-iodo-phenyl]-cyclopentyl-amide (1000 mg, 2.5 mmol, prepared in preparation 62), and [1,1'-bis(diphenyl-phosphino)-ferrocene]dichloropalladium(II) complex with methylene chloride (1:1) (204 mg, 0.25 mmol) and cesium fluoride (1.9 g, 12.5 mmol) to give quantitative yield of the corresponding product. Mass spectrum (ES+)=472.1 (M+1).

EXAMPLE E-287

Preparation of 4-cyano-5-ethyl-1-methyl-3-{4-((phenyl)-2-sulfonylamino)-ethyl]-phenyl}-1H-pyrrole-2-carboxylic acid ethyl ester

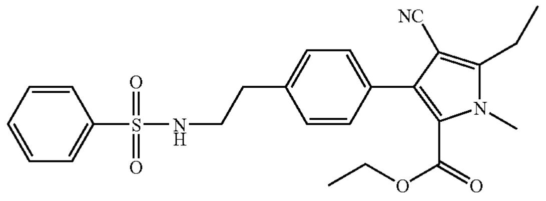

Prepare the title compound in a manner analogous to the procedure set forth in Example E-282, using phenyl-2-sulfonic acid {2-[4-(4,4,5,5-tetramethyl-[1,3,2]dioxaborolan-2-yl)-phenyl]-ethyl}-amide (392 mg, 1.0 mmol, prepared in preparation 63) and 4-cyano-5-ethyl-3-iodo-1-methyl-1H-pyrrole-2-carboxylic acid ethyl ester (222 mg, 0.67 mmol, prepared in preparation 38), [1,1'-bis(diphenyl-phosphino)-ferrocene]dichloropalladium(II) complex with methylene chloride (1:1) (57 mg, 0.07 mmol), and cesium fluoride (501 mg, 3.3 mmol) to give the desired product (quantitative). Mass spectrum (ES+)=464.0 (M−1).

EXAMPLE E-288

Preparation of 4-cyano-5-ethyl-1-methyl-3-{4-(4-cyanophenyl)-2-sulfonylamino)-ethyl]-phenyl}-1H-pyrrole-2-carboxylic acid ethyl ester

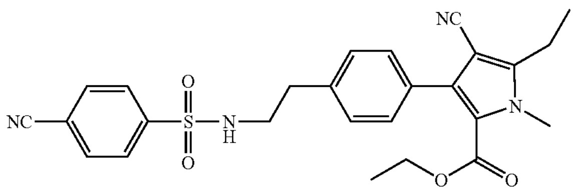

Prepare the title compound in a manner analogous to the procedure set forth in Example E-282, using 4-(cyanophenyl)-2-sulfonic acid {2-[4-(4,4,5,5-tetramethyl-[1,3,2]dioxaborolan-2-yl)-phenyl]-ethyl}-amide (495 mg, 1.2 mmol, prepared in preparation 64) and 4-cyano-5-ethyl-3-iodo-1-methyl-1H-pyrrole-2-carboxylic acid ethyl ester (332 mg, 1.0 mmol, prepared in preparation 38), [1,1'-bis(diphenyl-phosphino)-ferrocene]dichloropalladium(II) complex with methylene chloride (1:1) (82 mg, 0.1 mmol), and cesium fluoride (760 mg, 5 mmol) to give the desired product (275 mg, 56%).

Mass spectrum (ES+)=489.0 (M−1).

EXAMPLE E-289

Preparation of 4-cyano-5-methyl-1-methyl-3-{4-(3-cyanophenyl-2-sulfonylamino)-ethyl]-phenyl}-1H-pyrrole-2-carboxylic acid ethyl ester

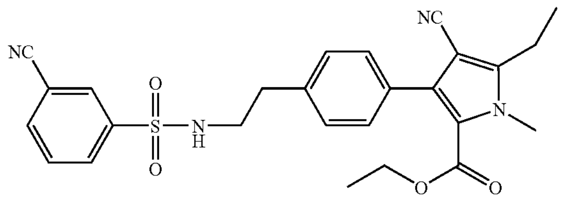

Prepare the title compound in a manner analogous to the procedure set forth in Example E-282, using 3-(cyanophenyl)-2-sulfonic acid {2-[4-(4,4,5,5-tetramethyl-[1,3,2]dioxaborolan-2-yl)-phenyl]-ethyl}-amide (500 mg, 1.2 mmol, prepared in preparation 65) and 4-cyano-5-ethyl-3-iodo-1-methyl-1H-pyrrole-2-carboxylic acid ethyl ester (332 mg, 1.0 mmol, prepared in preparation 38), [1,1'-bis(diphenyl-phosphino)-ferrocene]dichloropalladium(II) complex with methylene chloride (1:1) (82 mg, 0.1 mmol), and cesium fluoride (760 mg, 5 mmol) to give the desired product (220 mg, 45%).

Mass spectrum (ES+)=489.0 (M−1).

EXAMPLE E-290

Preparation of 2-cyano-5-ethyl-1-methyl-3-{4-(2-cyanophenyl)-2-sulfonylamino)-ethyl]-phenyl}-1H-pyrrole-2-carboxylic acid ethyl ester

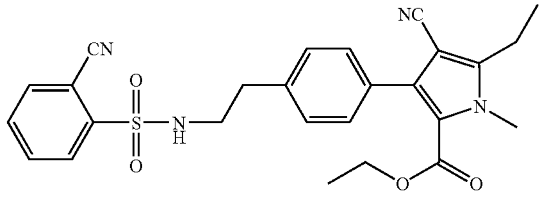

Prepare the title compound in a manner analogous to the procedure set forth in Example E-282, using 2-(cyanophenyl)-2-sulfonic acid {2-[4-(4,4,5,5-tetramethyl-[1,3,2]dioxaborolan-2-yl)-phenyl]-ethyl}-amide (195 mg, 0.47 mmol, prepared in preparation 66) and 4-cyano-5-ethyl-3-iodo-1-methyl-1H-pyrrole-2-carboxylic acid ethyl ester (78 mg, 0.24 mmol, prepared in preparation 38), [1,1'-bis(diphenyl-phosphino)-ferrocene]dichloropalladium(II) complex with methylene chloride (1:1) (75 mg, 0.09 mmol), and cesium fluoride (182 mg, 1.2 mmol) to give the desired product in a quantitative yield. Mass spectrum (ES+)=489.1 (M−1).

EXAMPLE E-291

Preparation of 4-cyano-5-ethyl-1-methyl-3-{4-(2-fluorophenyl)-2-sulfonylamino)-ethyl]-phenyl}-1H-pyrrole-2-carboxylic acid ethyl ester

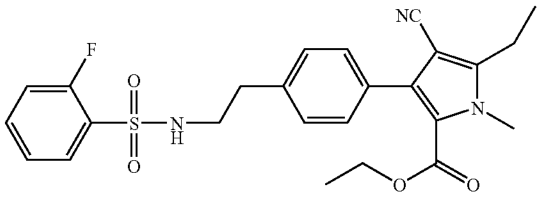

Prepare the title compound in a manner analogous to the procedure set forth in Example E-282, using 2-(fluorophenyl)-2-sulfonic acid {2-[4-(4,4,5,5-tetramethyl-[1,3,2]dioxaborolan-2-yl)-phenyl]-ethyl}-amide (750 mg, 1.85 mmol, prepared in preparation 67) and 4-cyano-5-ethyl-3-iodo-1-methyl-1H-pyrrole-2-carboxylic acid ethyl ester (307 mg, 0.92 mmol, prepared in preparation 38), [1,1'-bis(diphenylphosphino)-ferrocene]dichloropalladium(II) complex with methylene chloride (1:1) (75 mg, 0.09 mmol), and cesium fluoride (699 mg, 4.6 mmol) to give the desired product (quantitative). Mass spectrum (ES+)=482.0 (M−1).

EXAMPLE E-292

Preparation of 4-cyano-5-ethyl-1-methyl-3-{4-(3-fluorophenyl)-2-sulfonylamino)-ethyl]-phenyl}-1H-pyrrole-2-carboxylic acid ethyl ester

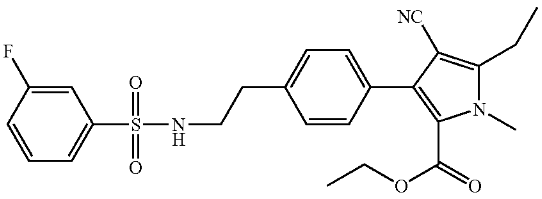

Prepare the title compound in a manner analogous to the procedure set forth in Example E-282, using 3-(fluorophenyl)-2-sulfonic acid {2-[4-(4,4,5,5-tetramethyl-[1,3,2]dioxaborolan-2-yl)-phenyl]-ethyl}-amide (750 mg, 1.85 mmol, prepared in preparation 68) and 4-cyano-5-ethyl-3-iodo-1-methyl-1H-pyrrole-2-carboxylic acid ethyl ester (307 mg, 0.92 mmol, prepared in preparation 38), [1,1'-bis(diphenylphosphino)-ferrocene]dichloropalladium(II) complex with methylene chloride (1:1) (75 mg, 0.09 mmol), and cesium fluoride (699 mg, 4.6 mmol) to give the desired product (414 mg, 93%). Mass spectrum (ES+)=482.0 (M−1).

EXAMPLE E-293

Preparation of 4-cyano-5-ethyl-1-methyl-3-{4-(4-fluorophenyl-2-sulfonylamino)-ethyl]-phenyl}-1H-pyrrole-2-carboxylic acid ethyl ester

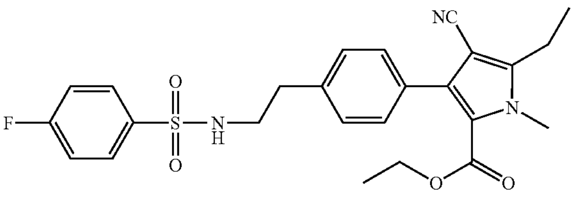

Prepare the title compound in a manner analogous to the procedure set forth in Example E-282, using 4-(fluorophenyl)-2-sulfonic acid {2-[4-(4,4,5,5-tetramethyl-[1,3,2]dioxaborolan-2-yl)-phenyl]-ethyl}-amide (750 mg, 1.85 mmol, prepared in preparation 69) and 4-cyano-5-ethyl-3-iodo-1-methyl-1H-pyrrole-2-carboxylic acid ethyl ester (307 mg, 0.92 mmol, prepared in preparation 38), [1,1'-bis(diphenylphosphino)-ferrocene]dichloropalladium(II) complex with methylene chloride (1:1) (75 mg, 0.09 mmol), and cesium fluoride (699 mg, 4.6 mmol) to give the desired product (444 mg, 99%). Mass spectrum (ES+)=482.0 (M−1).

EXAMPLE E-294

Preparation of 4-cyano-5-ethyl-1-methyl-3-{4-(4-chlorophenyl)-2-sulfonylamino)-ethyl]-phenyl}-1H-pyrrole-2-carboxylic acid ethyl ester

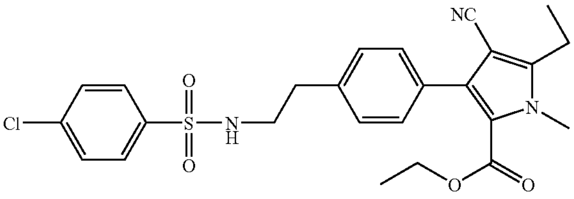

Prepare the title compound in a manner analogous to the procedure set forth in Example E-282, using 4-(chlorophenyl)-2-sulfonic acid {2-[4-(4,4,5,5-tetramethyl-[1,3,2]dioxaborolan-2-yl)-phenyl]-ethyl}-amide (452 mg, 1.07 mmol, prepared in preparation 70) and 4-cyano-5-ethyl-3-iodo-1-methyl-1H-pyrrole-2-carboxylic acid ethyl ester (237 mg, 0.71 mmol, prepared in preparation 38), [1,1'-bis(diphenylphosphino)-ferrocene]dichloropalladium(II) complex with methylene chloride (1:1) (57 mg, 0.07 mmol), and cesium fluoride (539 mg, 3.55 mmol) to give the desired product (quantitative). Mass spectrum (ES+)=497.98 (M−1).

EXAMPLE E-295

Preparation of 4-cyano-5-ethyl-1-methyl-3-{4-(3-chlorophenyl)-2-sulfonylamino)-ethyl]-phenyl}-1H-pyrrole-2-carboxylic acid ethyl ester

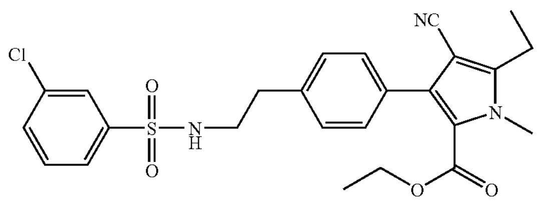

Prepare the title compound in a manner analogous to the procedure set forth in Example E-282, using 3-(chlorophenyl)-2-sulfonic acid {2-[4-(4,4,5,5-tetramethyl-[1,3,2]dioxaborolan-2-yl)-phenyl]-ethyl}-amide (385 mg, 0.91 mmol, prepared in preparation 71) and 4-cyano-5-ethyl-3-iodo-1-methyl-1H-pyrrole-2-carboxylic acid ethyl ester (202 mg, 0.61 mmol, prepared in preparation 38), [1,1'-bis(diphenyl-phosphino)-ferrocene]dichloropalladium(II) complex with methylene chloride (1:1) (50 mg, 0.06 mmol), and cesium fluoride (463 mg, 3.0 mmol) to give the desired product (320 mg, 71%). Mass spectrum (ES+)=498-0 (M−1).

EXAMPLE E-296

Preparation of 4-cyano-5-ethyl-1-methyl-3-{4-(2-chlorophenyl)-2-sulfonylamino)-ethyl]-phenyl}-1H-pyrrole-2-carboxylic acid ethyl ester

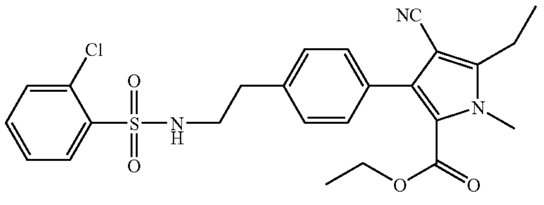

Prepare the title compound in a manner analogous to the procedure set forth in Example E-282, using 2-(chlorophenyl)-2-sulfonic acid {2-[4-(4,4,5,5-tetramethyl-[1,3,2]dioxaborolan-2-yl)-phenyl]-ethyl}-amide (539 mg, 1.3 mmol, prepared in preparation 72) and 4-cyano-5-ethyl-3-iodo-1-methyl-1H-pyrrole-2-carboxylic acid ethyl ester (289 mg, 0.87 mmol, prepared in preparation 38), [1,1'-bis(diphenyl-phosphino)-ferrocene]dichloropalladium(II) complex with methylene chloride (1:1) (71 mg, 0.09 mmol), and cesium fluoride (660 mg, 4.3 mmol) to give the desired product (375 mg, 86%). Mass spectrum (ES+)=498.0 (M−1).

EXAMPLE E-297

Preparation of 4-cyano-5-ethyl-1-methyl-3-{4-[2-toluene-4-sulfonylamino)-ethyl]-phenyl}-1H-pyrrole-2-carboxylic acid ethyl ester

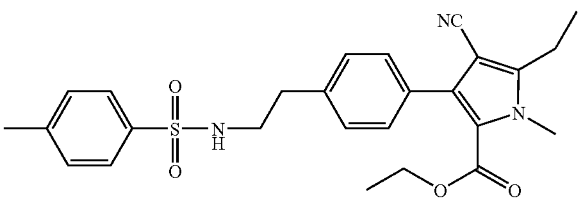

Prepare the title compound in a manner analogous to the procedure set forth in Example E-282, using 4-tolulyl-sulfonic acid {2-[4-(4,4,5,5-tetramethyl-[1,3,2]dioxaborolan-2-yl)-phenyl]-ethyl}-amide (400 mg, 1.0 mmol prepared in preparation 75) and 4-cyano-5-ethyl-3-iodo-1-methyl-1H-pyrrole-2-carboxylic acid ethyl ester (277 mg, 0.83 mmol, prepared in preparation 38), [1,1'-bis(diphenyl-phosphino)-ferrocene]dichloropalladium(II) complex with methylene chloride (1:1) (65 mg, 0.08 mmol), and cesium fluoride (630 mg, 4.1 mmol) to give the desired product (quantitative). Mass spectrum (ES+)=478.0 (M−1).

EXAMPLE E-298

Preparation of 4-cyano-5-ethyl-1-methyl-3-{4-(2-(4-methoxyphenyl)-2-sulfonylamino)-ethyl]-phenyl}-1H-pyrrole-2-carboxylic acid ethyl ester

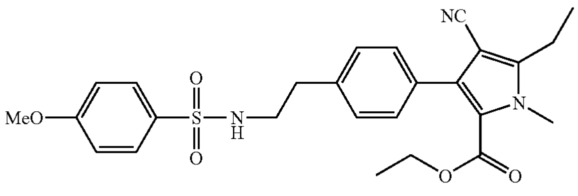

Prepare the title compound in a manner analogous to the procedure set forth in Example E-282, using 4-methoxyphenyl-sulfonic acid {2-[4-(4,4,5,5-tetramethyl-[1,3,2]dioxaborolan-2-yl)-phenyl]-ethyl}-amide (375 mg, 0.9 mmol, prepared in preparation 76) and 4-cyano-5-ethyl-3-iodo-1-methyl-1H-pyrrole-2-carboxylic acid ethyl ester (249 mg, 0.75 mmol, prepared in preparation 38), [1,1'-bis(diphenyl-phosphino)-ferrocene]dichloropalladium(ID) complex with methylene chloride (1:1) (61 mg, 0.075 mmol), and cesium fluoride (570 mg, 3.75 mmol) to give the desired product (quantitative). Mass spectrum (ES+)=496.0 (M+1).

EXAMPLE E-299

Preparation of 4-cyano-5-ethyl-1-methyl-3-{4-(2-(4-acetohenyl)-2-sulfonylamino)-ethyl]-phenyl}-1H-pyrrole-2-carboxylic acid ethyl ester

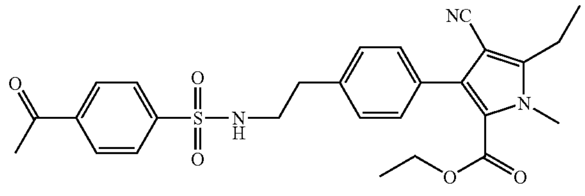

Prepare the title compound in a manner analogous to the procedure set forth in Example E-282, using 2-(4-acetophenyl)-2-sulfonic acid {2-[4-(4,4,5,5-tetramethyl-[1,3,2]dioxaborolan-2-yl)-phenyl]-ethyl}-amide (314 g, 0.73 mol, prepared in preparation 77) and 4-cyano-5-ethyl-3-iodo-1-methyl-1H-pyrrole-2-carboxylic acid ethyl ester (202 g, 0.61 mol, prepared in preparation 38), [1,1'-bis(diphenyl-phosphino)-ferrocene]dichloropalladium(II) complex with methylene chloride (1:1) (50 mg, 0.61 mmol), and cesium fluoride (463 mg, 3.1 mmol) to give the desired product (141 mg, 45%). Mass spectrum (ES+)=506.5 (M−1).

EXAMPLE E-300

Preparation of 4-cyano-5-ethyl-1-methyl-3-{4-(2-(thiophyl)-2-sulfonylamino)-ethyl]-phenyl}-1H-pyrrole-2-carboxylic acid ethyl ester

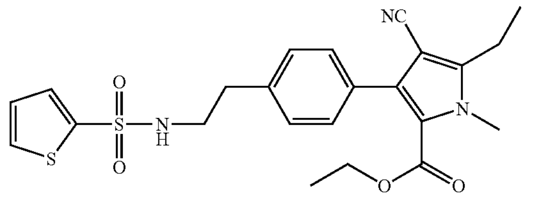

Prepare the title compound in a manner analogous to the procedure set forth in Example E-282, using 2-thiophyl-sulfonic acid {2-[4-(4,4,5,5-tetramethyl-[1,3,2]dioxaborolan-2-yl)-phenyl]-ethyl}-amide (400 mg, 1.0 mmol, prepared in preparation 78) and 4-cyano-5-ethyl-3-iodo-1-methyl-1H-pyrrole-2-carboxylic acid ethyl ester (281 mg, 0.85 mmol, prepared in preparation 38), [1,1'-bis(diphenyl-phosphino)-ferrocene]dichloropalladium(II) complex with methylene chloride (1:1) (69 mg, 0.085 mmol), and cesium fluoride (645 mg, 4.25 mmol) to give the desired product (321 mg, 80%). Mass spectrum (ES+)=470.1 (M−1)

EXAMPLE E-301

Preparation of 4-cyano-5-ethyl-1-methyl-3-{4-[2-(propane-2-sulfonylamino)-ethoxy]-phenyl}-1H-pyrrole-2-carboxylic acid ethyl ester

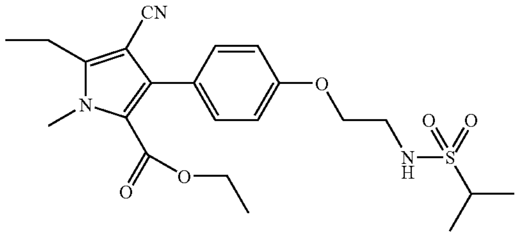

Prepare the title compound in a manner analogous to the procedure set forth in Example E-281, using 4-cyano-5-ethyl-1-methyl-3-(4,4,5,5-tetramethyl-[1,3,2]dioxaborolan-2-yl)-1H-pyrrole-2-carboxylic acid ethyl ester (478 mg, 1.4 mmol, prepared in preparation 50), N-[2-(bromo-phenoxy)-ethyl]-i-propanesulfonamide (385 mg, 1.2 mmol, prepared in preparation 82), aqueous sodium carbonate (3.0 mL, 6.0 mmol, 2N), and [1,1'-bis(diphenyl-phosphino)-ferrocene]dichloropalladium(II) complex with methylene chloride (1:1) (30 mg, 0.04 mmol) to give 533 mg (99%) of the title compound. Mass spectrum (ES+)=446.1 (M−1).

EXAMPLE E-302

Preparation of 4-cyano-5-ethyl-1-methyl-3{-4-[2-(methane-2-sulfonylamino)-ethoxy]-phenyl}-1H-pyrrole-2-carboxylic acid ethyl ester

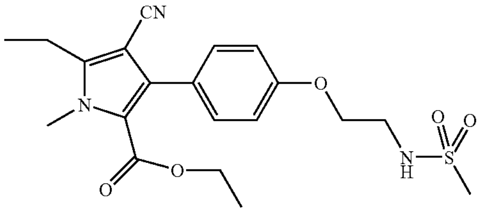

Prepare the title compound in a manner analogous to the procedure set forth in Example E-281, using 4-cyano-5-ethyl-1-methyl-3-(4,4,5,5-tetramethyl-[1,3,2]dioxaborolan-2-yl)-1H-pyrrole-2-carboxylic acid ethyl ester (398 mg, 1.2 mmol, prepared in preparation 50), N-[2-(bromo-phenoxy)-ethyl]-methanesulfonamide (294 mg, 1 mmol, prepared in a manner analogous to the procedure set forth in preparation 82 using methanesulfonyl chloride), aqueous sodium carbonate (2.5 mL, 5 mmol, 2N), and [1,1'-bis(diphenyl-phosphino)-ferrocene]dichloropalladium(II) complex with methylene chloride (1:1) (0.024 g, 0.03 mmol) to give quantitative yield of the desired product. Mass spectrum (ES+)=418.1 (M−1).

EXAMPLE E-303

Preparation of 4-cyano-5-ethyl-1-methyl-3-{4-[2-(phenol-2-sulfonylamino)-ethoxy]-phenyl}-1H-pyrrole-2-carboxylic acid ethyl ester

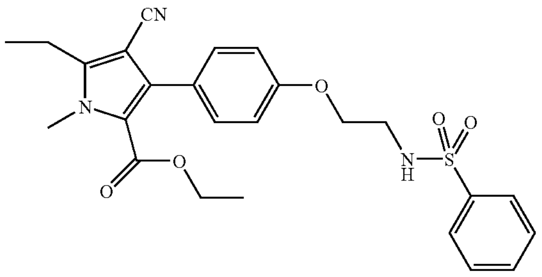

Prepare the title compound in a manner analogous to the procedure set forth in Example E-281, using 4-cyano-5-ethyl-1-methyl-3-(4,4,5,5-tetramethyl-[1,3,2]dioxaborolan-2-yl)-1H-pyrrole-2-carboxylic acid ethyl ester (447 mg, 1.34 mmol, prepared in preparation 50), N-[2-(bromo-phenoxy)-ethyl]-phenylsulfonamide (400 mg, 1.2 mmol, prepared in a manner analogous to the procedure set forth in preparation 82 from phenylsulfonyl chloride), aqueous sodium carbonate (2.8 mL, 5.6 mmol, 2N), and [1,1'-bis(diphenyl-phosphino)-ferrocene]dichloropalladium(II) complex with methylene chloride (1:1) (27 mg, 0.033 mmol) to give the desired product. Mass spectrum (ES+)=480.1 (M−1).

EXAMPLE E-304

Preparation of 4-cyano-5-ethyl-1-methyl-3-(4-{methyl-[2-(propane-2-sulfonylamino)-ethyl]-amino}-phenyl)-1H-pyrrole-2-carboxylic acid ethyl ester

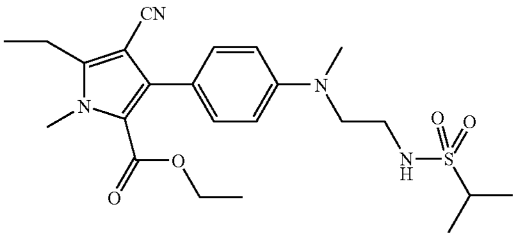

Prepare the title compound in a manner analogous to the procedure set forth in Example E-281, using 4-cyano-5-ethyl-1-methyl-3-(4,4,5,5-tetramethyl-[1,3,2]dioxaborolan-2-yl)-1H-pyrrole-2-carboxylic acid ethyl ester (817 mg, 2-4 mmol, prepared in preparation 50), propane-2-sulfonic acid {2-[(4-bromo-phenyl)-methyl-amino]-ethyl}-amide (550 mg, 1.6 mmol, prepared in preparation 81), aqueous sodium carbonate (4.0 mL, 8.0 mmol, 2N), and [1,1'-bis(diphenyl-phosphino)-ferrocene]dichloropalladium(II) complex with methylene chloride (1:1) (39 mg, 0.05 mmol) to give 404 mg (55%) of the title compound. Mass spectrum (ES+)=461.1 (M+1).

EXAMPLE E-305

Preparation of 4-cyano-5-ethyl-1-methyl-3-{4-[2-(methane-2-sulfonylamino)-ethyl sulfanyl]-phenyl}-1H-pyrrole-2-carboxylic acid ethyl ester

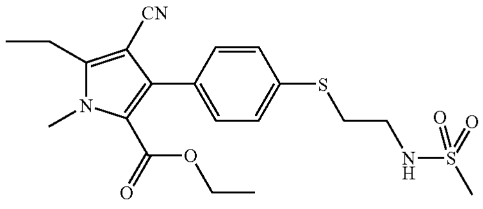

Prepare the title compound in a manner analogous to the procedure set forth in Example E-281, using 4-cyano-5-ethyl-1-methyl-3-(4,4,5,5-tetramethyl-[1,3,2]dioxaborolan-2-yl)-1H-pyrrole-2-carboxylic acid ethyl ester (398 mg, 1.2 mmol, prepared in preparation 50), N-[2-(bromo-phenyl sulfanyl)-ethyl]-methanesulfonamide (294 mg, 1.0 mmol, prepared in preparation 79), aqueous sodium carbonate (2.5 mL, 5 mmol, 2N), and [1,1'-bis(diphenyl-phosphino)-ferrocene]dichloropalladium(II) complex with methylene chloride (1:1) (0.024 g, 0.03 mmol) to give 425 mg (80%) of the desired product. Mass spectrum (ES+)=434.0 (M−1).

EXAMPLE E-306

Preparation of 4-cyano-5-ethyl-1-methyl-3-{4-[2-(methane-2-sulfonylamino)-ethylsulfanyl]-phenyl}-1H-pyrrole-2-carboxylic acid ethyl ester

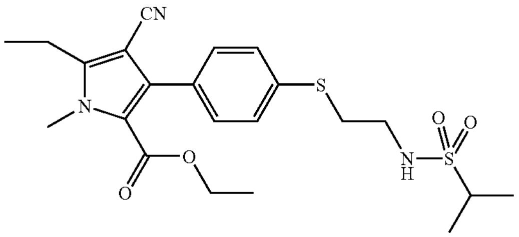

Prepare the title compound in a manner analogous to the procedure set forth in Example E-281, using 4-cyano-5-ethyl-1-methyl-3-(4,4,5,5-tetramethyl-[1,3,2]dioxaborolan-2-yl)-1H-pyrrole-2-carboxylic acid ethyl ester (498 mg, 1.5 mmol, prepared in preparation 50), N-[2-(bromo-phenyl sulfanyl)-ethyl]-methanesulfonamide (338.3 mg, 1.0 mmol, prepared in preparation 80), aqueous sodium carbonate (2.5 mL, 5 mmol, 2N), and [1,1'-bis(diphenyl-phosphino)-ferrocene] dichloropalladium(II) complex with methylene chloride (1:1) (0.025 g, 0.03 mmol) to give quantitative yield of the desired product. Mass spectrum (ES+)=464.2 (M+1).

EXAMPLE E-307

Preparation of 4-cyano-5-ethyl-1-methyl-3-{4-[2-N,N-dimethylamino-2-sulfonylamino)-phenyl}-1H-pyrrole-2-carboxylic acid ethyl ester

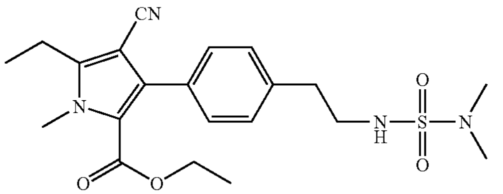

Prepare the title compound in a manner analogous to the procedure set forth in Example E-282, using N,N-dimethylamine-2-sulfonic acid {2-[4-(4,4,5,5-tetramethyl-[1,3,2]dioxaborolan-2-yl)-phenyl]-ethyl}-amide (530 mg, 1.5 mmol, prepared in preparation 73) and 4-cyano-5-ethyl-3-iodo-1-methyl-1H-pyrrole-2-carboxylic acid ethyl ester (415 mg, 1.25 mmol, prepared in preparation 38), [1,1'-bis(diphenyl-phosphino)-ferrocene]dichloropalladium(II) complex with methylene chloride (1:1) (0.102 g, 0.12 mmol), and cesium fluoride (950 mg, 6.25 mmol) to give 230 mg (42%) of the title compound

EXAMPLE E-308

Preparation of 4-cyano-5-ethyl-1-methyl-3-{4-[2-N N-dimethylamino-2-sulfonylamino)-phenyl}-1H-pyrrole-2-carboxylic acid ethyl ester

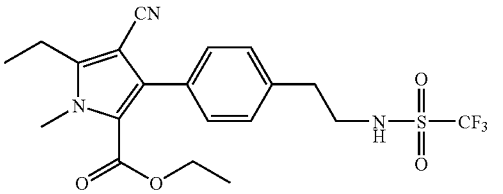

Prepare the title compound in a manner analogous to the procedure set forth in Example E-282, using trifluoromethane-2-sulfonic acid {2-[4-(4,4,5,5-tetramethyl-[1,3,2]dioxaborolan-2-yl)-phenyl]-ethyl}-amide (690 mg, 1.8 mmol, prepared in preparation 74) and 4-cyano-5-ethyl-3-iodo-1-methyl-1H-pyrrole-2-carboxylic acid ethyl ester (465 mg, 1.4 mmol, prepared in preparation 38), [1,1'-bis(diphenyl-phosphino)-ferrocene]dichloropalladium(II) complex with methylene chloride (1:1) (0.114 g, 0.14 mmol), and cesium fluoride (1069 mg, 7 mmol) to give 313 mg (49%) of the title compound. Mass spectrum (ES+)=358.0 (M+1).

Method TI

Scheme VI: Add lithium hydroxide (0.072 g, 3.0 mmol) to the ester (1.0 mmol, Formula II) in a 3:2:1 mixture of THF:MeOH:$H_2O$ and heat to 60° C. with stirring. After 3 hours cool the reaction mixture to room temperature and pour into 1N HCl. Extract with methylene chloride. Combine the organic extracts, dry over anhydrous magnesium sulfate, filter, and concentrate under reduced pressure. Recrystallize the residue from hexanes:ethyl acetate to provide the corresponding compound of Formula Ia.

Mass spectrum (m/e): 323.3 (M+1).

Method TII

Scheme VIa: Add lithium hydroxide (1.45 mmol) to the ester (0.291 mmol, Formula IIh) in THF (2.0 mL) and $H_2O$ (1.0 mL). Add 1.0 mL of methanol, ethanol, n-propanol or n-butanol. Stir at room temperature. After 16 hours cool to room temperature and concentrate in vacuo. Dilute the residue in water (20 mL), wash with methylene chloride (2×20 mL). Treat the aqueous layer with 1N HCl to pH 3-4. Extract with methylene chloride and $Et_2O$. Combine the organic layers, dry over magnesium sulfate, filter, and concentrate under reduced pressure to provide the compound of Formula Ib.

Method TIII

Scheme VI: Combine the ester (0.178 mmol, Formula II) with 1N NaOH (1 mmol) in methanol in a flask and heat the reaction mixture to 65° C. After 1 hour, cool to room temperature, then cool in ice bath, and add 0.2N HCl (0.8 mmol) to neutralize the base (pH 7). Filter the reaction to provide the corresponding acid of Formula Ia.

Method TIV

Add lithium hydroxide (1.45 mmol) to the ester (0.291 mmol, Formula II) in a 2:1:1 mixture of THF:MeOH:$H_2O$ (4.0 mL) and heat to 60° C. with stirring. After 3 hours cool to room temperature and concentrate in vacuo. Dilute the residue in water (20 mL), wash with methylene chloride (2×20 mL). Treat the aqueous layer with 1N HCl to pH 4-5. Extract with methylene chloride and $Et_2O$. Combine the organic layers and dry over magnesium sulfate, filter, and concentrate under reduced pressure to provide the corresponding acid of Formula Ia.

Prepare the following carboxylic acids listed in Table A-1 in a manner analogous to the procedure set forth in Method TI.

TABLE A-1

| Ex. | Structure | Data | S.M. |
|---|---|---|---|
| A-1 | 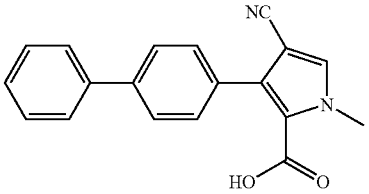 | mass spectrum (m/e): 303.1 (M + 1); analysis for $C_{19}H_{14}N_2O_2$: calcd: C, 75.48; H, 4.67; N, 9.27; found: C, 75.48; H, 4.77; N, 9.18. | E-1 |

TABLE A-1-continued
| Ex. | Structure | Data | S.M. |
|---|---|---|---|
| A-2 | 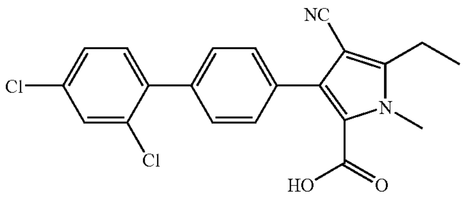 | mass spectrum (ES−): 297.0 (M − 1); analysis for $C_{21}H_{16}Cl_2N_2O_2$: calcd: C, 63.17; H, 4.04; N, 7.02; found: C, 63.30; H, 4.20; N, 6.82. | E-283 |
| A-3 | 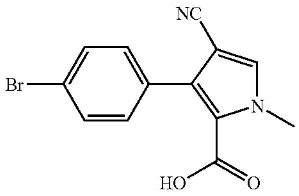 | mass spectrum (m/e): 307.1 (M + 1); analysis for $C_{13}H_{19}BrN_2O_2$: calcd: C, 51.17; H, 2.97; N, 9.18; found: C, 51.05; H, 2.93; N, 8.98. | E-3a or E-3b |
| A-4 | 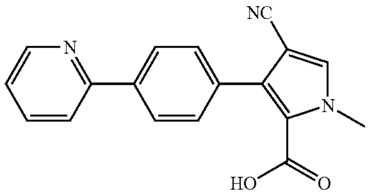 | mass spectrum (m/e): 304.2 (M + 1). | E-4 |
| A-6 | 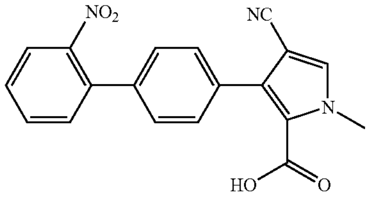 | mass spectrum (m/e): 359.2 (M + 1). | E-9 |
| A-7 | 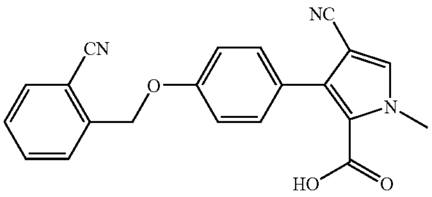 | mass spectrum (m/e): 356.1 (M − 1). | E-12 |
| A-8 | 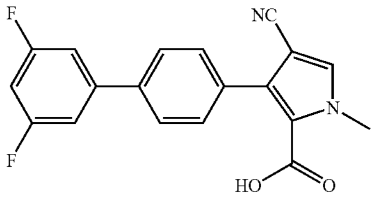 | mass spectrum (m/e): 337.1 (M − 1). | E-13 |
| A-9 | 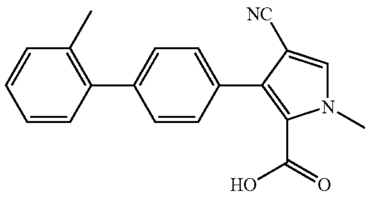 | mass spectrum (m/e): 315.1 (M − 1). | E-14 |

TABLE A-1-continued
| Ex. | Structure | Data | S.M. |
| --- | --- | --- | --- |
| A-10 | 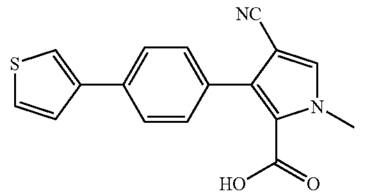 | mass spectrum (m/e): 309.1 (M + 1). | E-15 |
| A-11 | 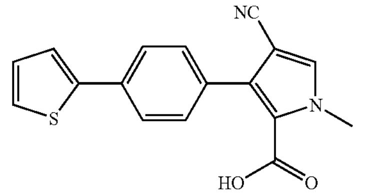 | mass spectrum (m/e): 309.1 (M + 1). | E-16 |
| A-12 | 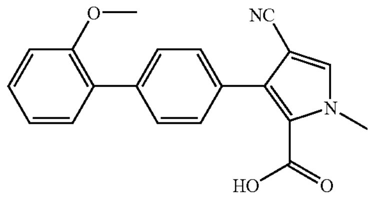 | mass spectrum (m/e): 331.2 (M − 1). | E-17 |
| A-13 | 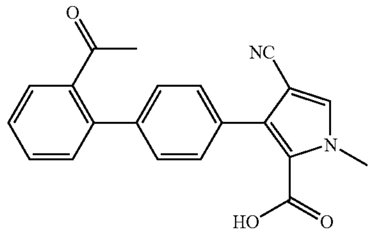 | mass spectrum (m/e): 343.1 (M − 1). | E-18 |
| A-14 | 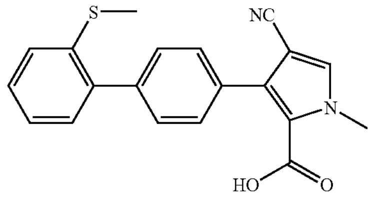 | mass spectrum (m/e): 349.1 (M + 1). | E-19 |
| A-15 | 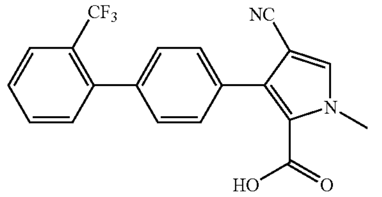 | mass spectrum (m/e): 369.1 (M − 1). | E-20 |
| A-16 | 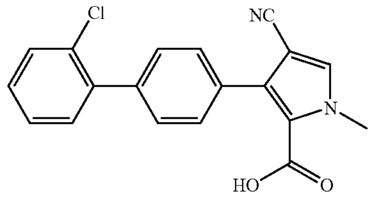 | mass spectrum (m/e): 335.1 (M − 1); analysis for $C_{19}H_{13}ClN_2O_2$: calcd: C, 67.76; H, 3.89; N, 8.32; found: C, 67.40; H, 3.97; N, 7.97. | E-21 |

TABLE A-1-continued
| Ex. | Structure | Data | S.M. |
|---|---|---|---|
| A-17 | 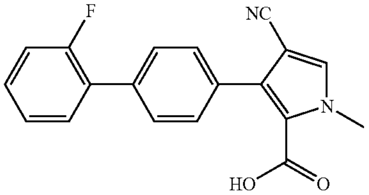 | mass spectrum (m/e): 321.1 (M + 1). | E-22 |
| A-18 | 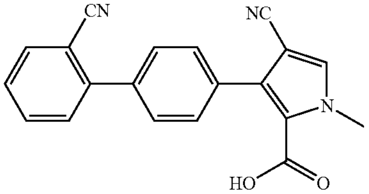 | mass spectrum (m/e): 326.1 (M − 1). | E-30 |
| A-19 | 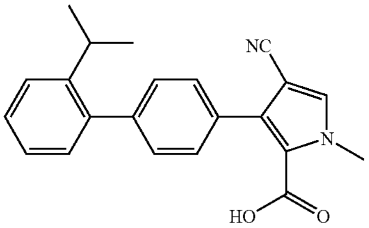 | mass spectrum (m/e): 345.1 (M + 1). | E-31 |
| A-20 | 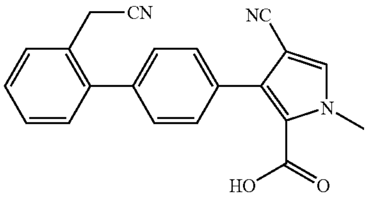 | mass spectrum (m/e): 340.1 (M − 1). | E-32 |
| A-21 | 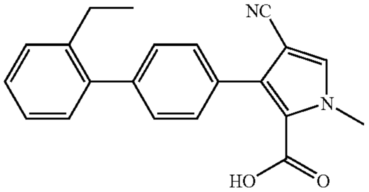 | mass spectrum (m/e): 329.1 (M − 1). | E-33 |
| A-22 | 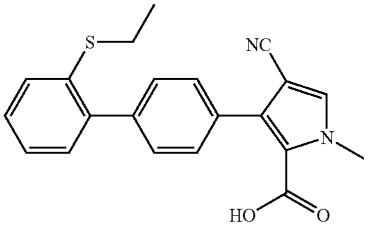 | mass spectrum (m/e): 363.2 (M + 1). | E-34 |
| A-23 | 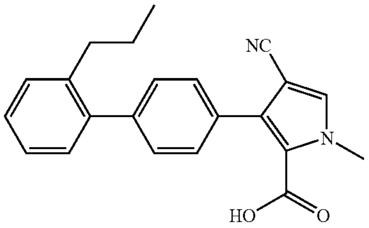 | mass spectrum (m/e): 345.2 (M + 1). | E-35 |

TABLE A-1-continued
| Ex. | Structure | Data | S.M. |
|---|---|---|---|
| A-24 | 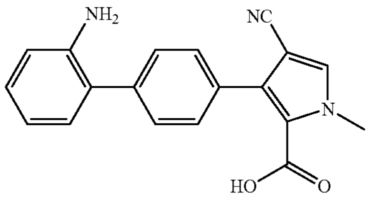 | mass spectrum (m/e): 318.1 (M + 1). | E-46 |
| A-25 | 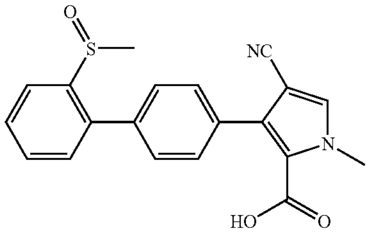 | mass spectrum (m/e): 365.1 (M + 1). | E-47 |
| A-26 | 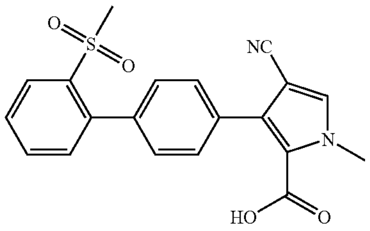 | mass spectrum (m/e): 379.1 (M − 1). | E-48 |
| A-27 | 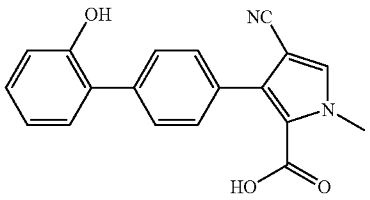 | mass spectrum (m/e): 317.1 (M − 1). | E-49 |
| A-28 | 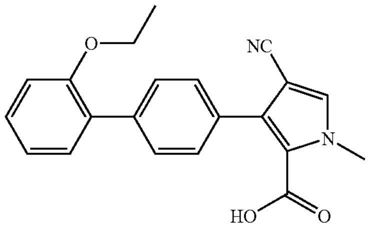 | mass spectrum (m/e): 347.1 (M + 1); analysis for $C_{21}H_{18}N_2O_3$: calcd: C, 72.81; H, 5.24; N, 8.09; found: C, 72.66; H, 5.46; N, 7.71. | E-50 |
| A-29 | 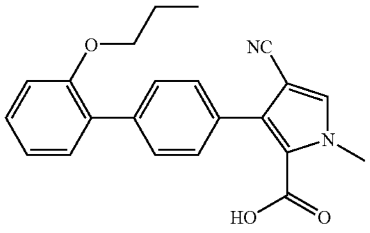 | mass spectrum (m/e): 361.1 (M + 1). | E-51 |

TABLE A-1-continued
| Ex. | Structure | Data | S.M. |
|---|---|---|---|
| A-30 | 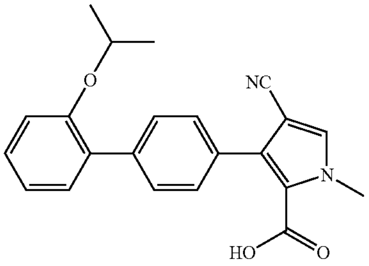 | mass spectrum (m/e): 361.1 (M + 1); analysis for $C_{22}H_{20}N_2O_3$: calcd: C, 73.32; H, 5.59; N, 7.77; found: C, 74.72; H, 5.41; N, 7.50. | E-52 |
| A-31 | 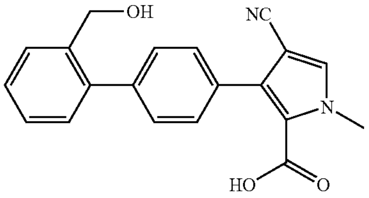 | mass spectrum (m/e): 331.1 (M − 1). | E-53 |
| A-32 | 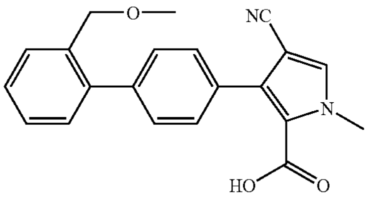 | mass spectrum (m/e): 345.1 (M − 1). | E-54 |
| A-33 | 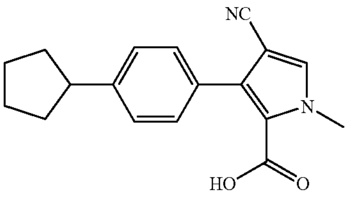 | mass spectrum (m/e): 295.2 (M + 1). | E-55 |
| A-34 | 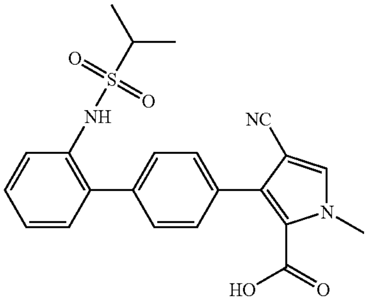 | mass spectrum (m/e): 422.1 (M − 1). | E-57 |
| A-35 | 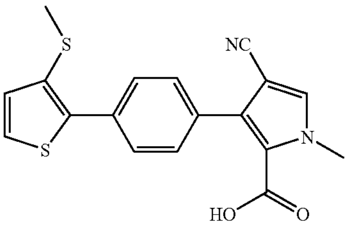 | mass spectrum (m/e): 353.0 (M − 1); analysis for $C_{18}H_{14}N_2O_2S_2$: calcd: C, 60.99; H, 3.98; N, 7.90; found: C, 60.96; H, 4.03; N, 7.70. | E-58 |

TABLE A-1-continued

| Ex. | Structure | Data | S.M. |
|---|---|---|---|
| A-36 | 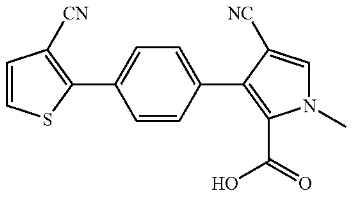 | mass spectrum (m/e): 332.0 (M − 1); | E-56 |
| A-37 | 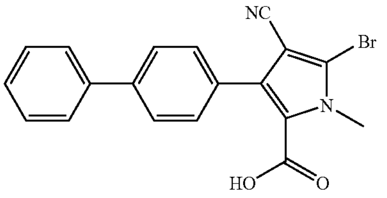 | mass spectrum (m/e): 383.1 (M + 1). | E-59 |
| A-38 | 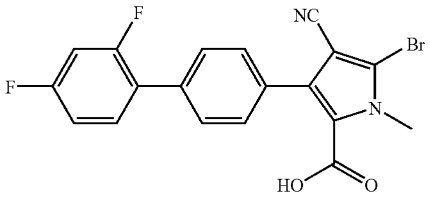 | mass spectrum (m/e): 417.1 (M + 1); analysis for $C_{19}H_{11}BrF_2N_2O_2$: calcd: C, 54.70; H, 2.66; N, 96.71; found: C, 54.62; H, 2.86; N, 6.68. | E-64 |
| A-39a (seel also example A-39b infra) | 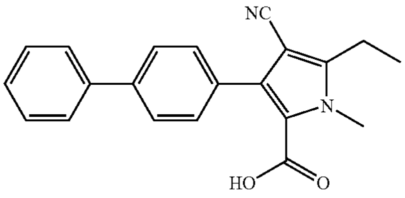 | mass spectrum (m/e): 331.2 (M + 1). | E-71 |
| A-40 | 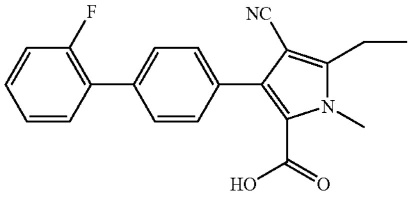 | mass spectrum (m/e): 347.3 (M − 1); analysis for $C_{21}H_{17}FN_2O_2$: calcd: C, 72.40; H, 4.92; N, 8.04; found: C, 72.21; H, 4.89; N, 8.01. | E-72 |
| A-41 | 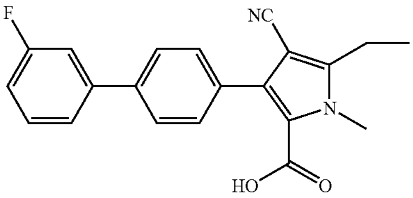 | mass spectrum (m/e): 347.3 (M − 1); analysis for $C_{21}H_{17}FN_2O_2$: calcd: C, 72.40; H, 4.92; N, 8.04; found: C, 72.77; H, 5.10; N, 7.66. | E-73 |
| A-42 | 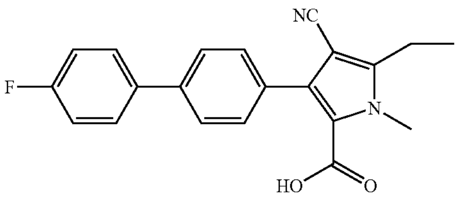 | mass spectrum (m/e): 347.3 (M − 1); analysis for $C_{21}H_{17}FN_2O_2$: calcd: C, 72.40; H, 4.92; N, 8.04; found: C, 72.28; H, 5.02; N, 7.73. | E-74 |

TABLE A-1-continued
| Ex. | Structure | Data | S.M. |
|---|---|---|---|
| A-43 | 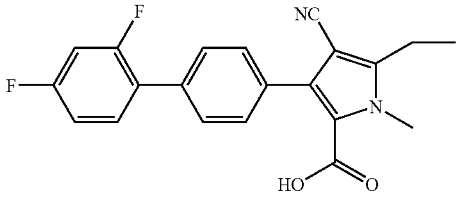 | mass spectrum (m/e): 367.3 (M + 1); analysis for $C_{21}H_{17}F_2N_2O_2$: calcd: C, 68.85; H, 4.40; N, 7.65; found: C, 68.86; H, 4.23; N, 7.59. | E-75 |
| A-44 | 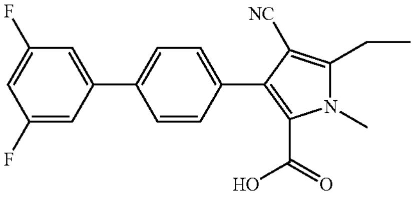 | mass spectrum (m/e): 365.1 (M − 1). | E-76 |
| A-45 | 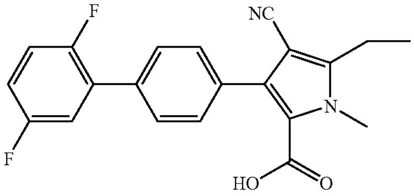 | mass spectrum (m/e): 367.4 (M + 1). | E-77 |
| A-46 | 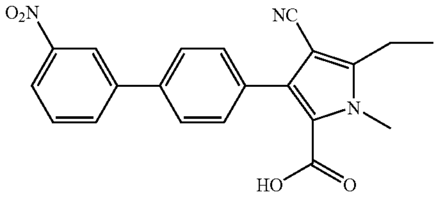 | mass spectrum (m/e): 374.3 (M − 1). | E-79 |
| A-47 | 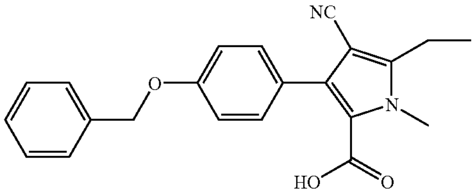 | mass spectrum (m/e): 361.3 (M + 1). | E-80a or E-80b |
| A-48 | 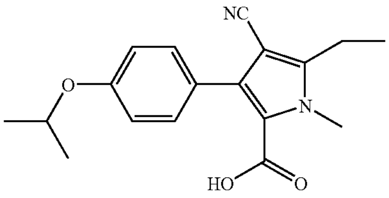 | mass spectrum (m/e): 313.2 (M + 1). | E-82 |
| A-49 | 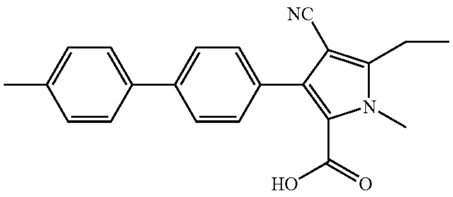 | mass spectrum (m/e): 343.2 (M − 1). | E-99 |

TABLE A-1-continued
| Ex. | Structure | Data | S.M. |
|---|---|---|---|
| A-50 | 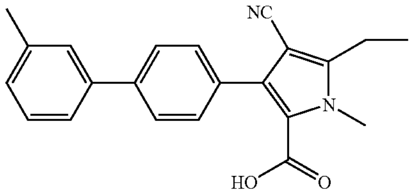 | mass spectrum (m/e): 345.2 (M + 1). | E-100 |
| A-51 | 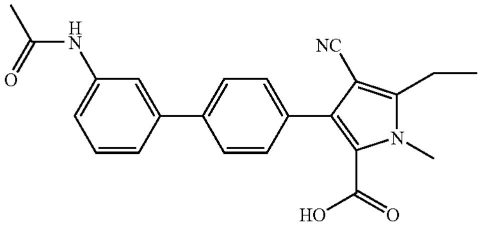 | mass spectrum (m/e): 388.2 (M + 1). | E-125 |
| A-52 | 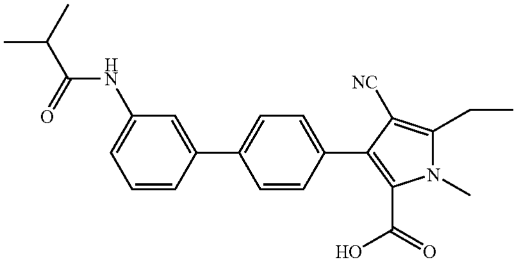 | mass spectrum (m/e): 416.2 (M + 1). | E-126 |
| A-53 | 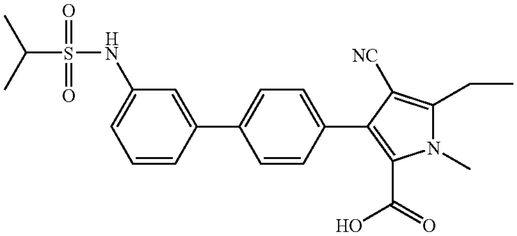 | mass spectrum (m/e): 450.2 (M − 1). | E-131 |
| A-54 | 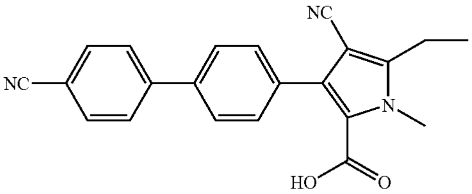 | mass spectrum (m/e): 356.1 (M + 1). | E-101 |
| A-55 | 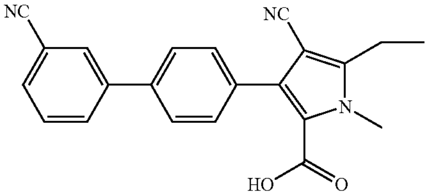 | mass spectrum (m/e): 354.2 (M − 1). | E-102 |
| A-56 | 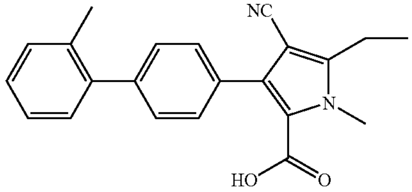 | mass spectrum (m/e): 345.2 (M + 1). | E-103 |

TABLE A-1-continued
| Ex. | Structure | Data | S.M. |
|---|---|---|---|
| A-57 | 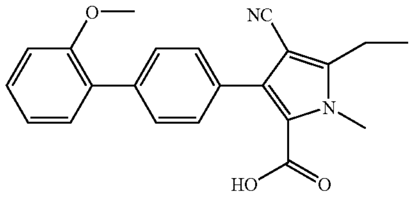 | mass spectrum (m/e): 361.2 (M + 1). | E-104 |
| A-58 | 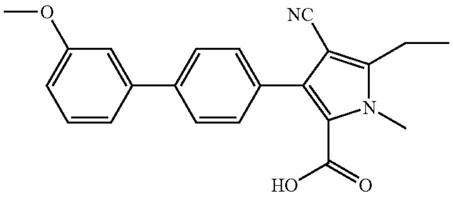 | mass spectrum (m/e): 361.2 (M + 1). | E-105 |
| A-59 | 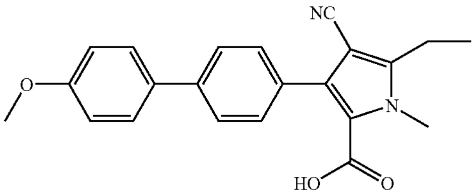 | mass spectrum (m/e): 361.2 (M + 1). | E-106 |
| A-60 | 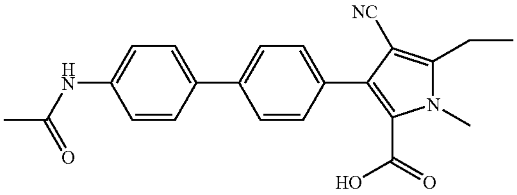 | mass spectrum (m/e): 388.1 (M + 1). | E-127 |
| A-61 | 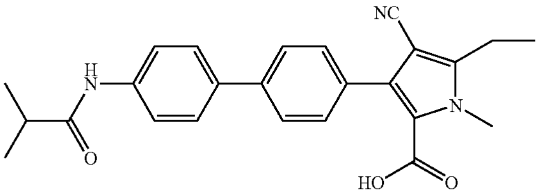 | mass spectrum (m/e): 416.1 (M + 1). | E-128 |
| A-62 | 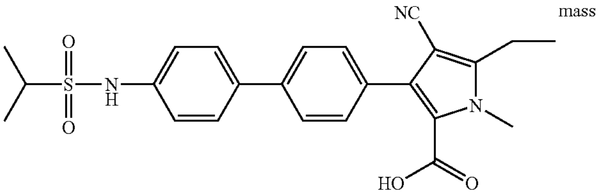 | mass spectrum (m/e): 452.1 (M + 1). | E-132 |
| A-63 | 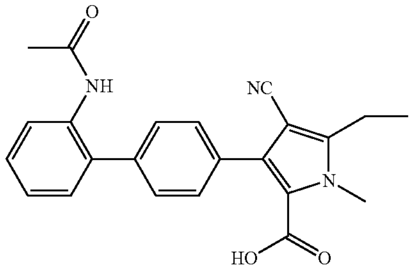 | mass spectrum (m/e): 388.2 (M + 1). | E-129 |

TABLE A-1-continued
| Ex. | Structure | Data | S.M. |
|---|---|---|---|
| A-64 | 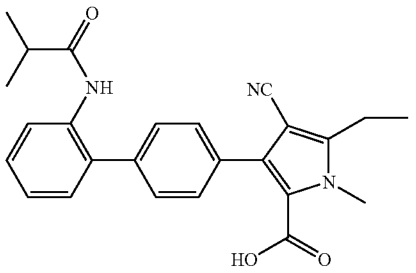 | mass spectrum (m/e): 416.2 (M + 1). | E-130 |
| A-65 | 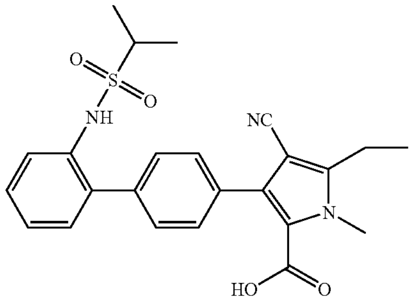 | mass spectrum (m/e): 450.1 (M − 1). | E-133 |
| A-66 | 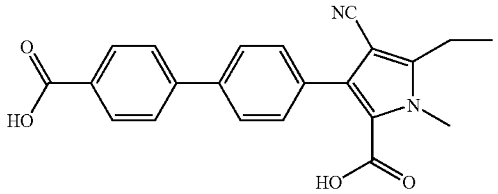 | mass spectrum (m/e): 375.1 (M + 1). | E-108 |
| A-67 | 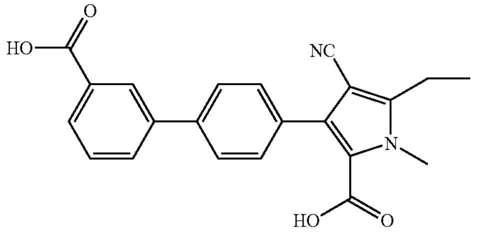 | mass spectrum (m/e): 375.0 (M + 1). | E-109 |
| A-68 | 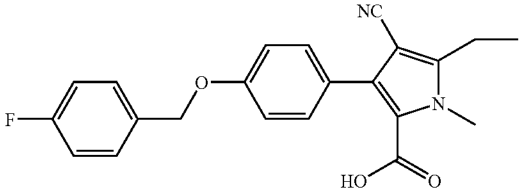 | mass spectrum (m/e): 379.1 (M + 1). | E-83 |
| A-69 | 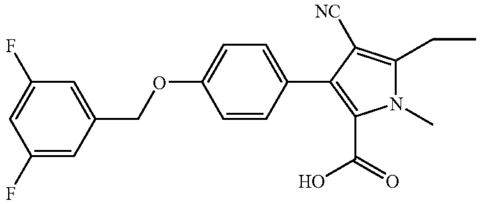 | mass spectrum (m/e): 397.2 (M + 1); analysis for $C_{22}H_{18}F_2N_2O_3$: calcd: C, 66.66; H, 4.58; N, 7.07; found: C, 66.30; H, 4.57; N, 7.02. | E-84 |

TABLE A-1-continued
| Ex. | Structure | Data | S.M. |
|---|---|---|---|
| A-70 | 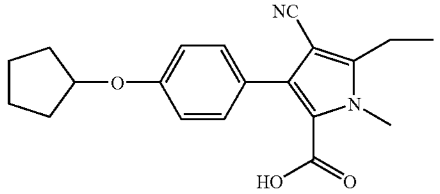 | mass spectrum (m/e): 339.2 (M + 1). | E-85 |
| A-71 | 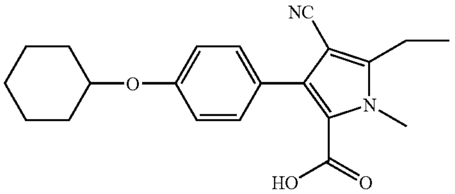 | | E-86 |
| A-72 | 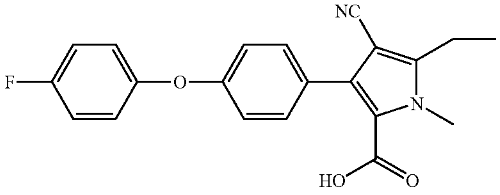 | mass spectrum (m/e): 365.2 (M + 1). | E-91 |
| A-73 | 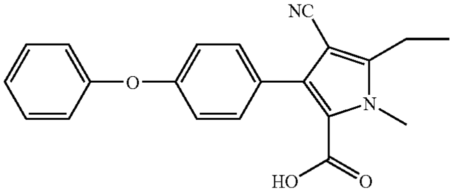 | mass spectrum (m/e): 347.3 (M + 1). | E-90 |
| A-74 | 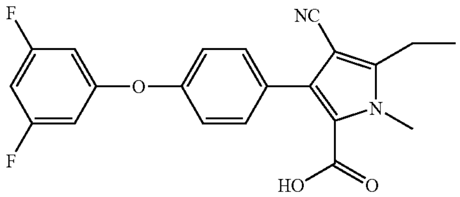 | mass spectrum (m/e): 383.2 (M + 1). | E-92 |
| A-75a (see also A-75b and A-75c infra) | 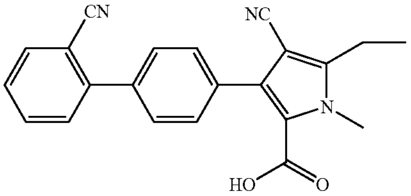 | mass spectrum (m/e): 354.2 (M − 1). | E-121a or E-121b |
| A-76 | 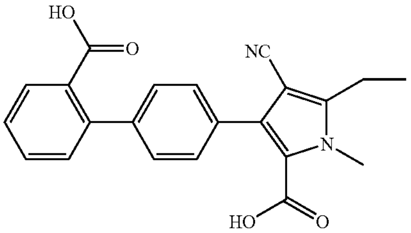 | mass spectrum (m/e): 373.1 (M − 1). | E-122 |

TABLE A-1-continued
| Ex. | Structure | Data | S.M. |
| --- | --- | --- | --- |
| A-77 | 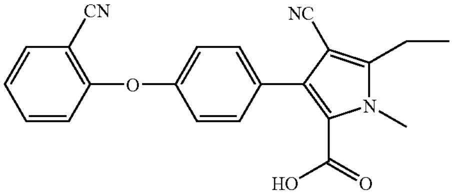 | mass spectrum (m/e): 370.2 (M − 1); analysis for $C_{22}H_{17}N_3O_3$: calcd: C, 71.15; H, 4.61; N, 11.31; found: C, 71.25; H, 4.66; N, 11.62. | E-93 |
| A-78 | 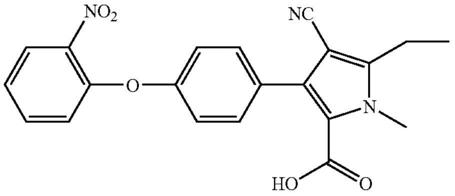 | mass spectrum (m/e): 390.2 (M − 1). | E-94 |
| A-79 | 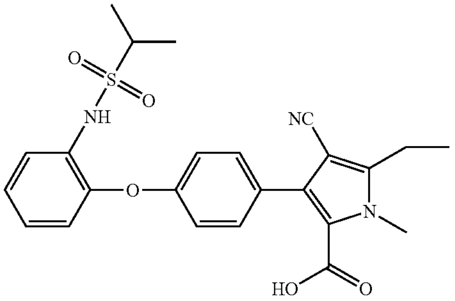 | mass spectrum (m/e): 466.1 (M − 1). | E-96 |
| A-80 | 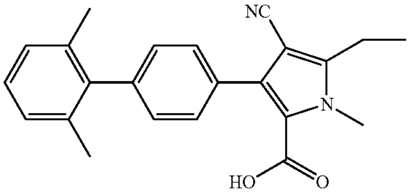 | mass spectrum (m/e): 359.2 (M + 1); analysis for $C_{23}H_{22}N_2O_2$: calcd: C, 77.07; H, 6.19; N, 7.82; found: C, 76.88; H, 6.22; N, 7.76. | E-78 |
| A-81 | 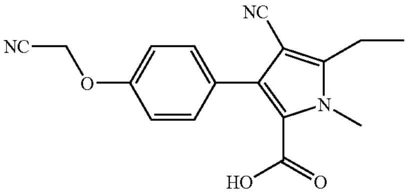 | mass spectrum (m/e): 307.2 (M − 1). | E-87 |
| A-82 | 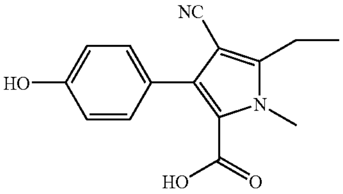 | mass spectrum (m/e): 269.1 (M + 1). | E-81 |
| A-83 | 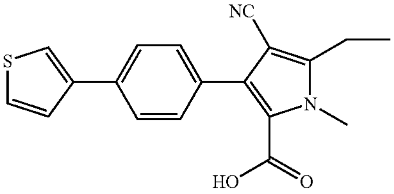 | mass spectrum (m/e): 337.1 (M + 1). | E-110 |

TABLE A-1-continued
| Ex. | Structure | Data | S.M. |
|---|---|---|---|
| A-84 | 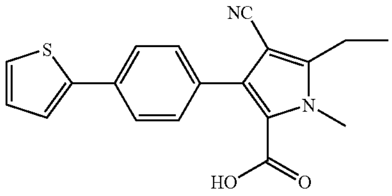 | mass spectrum (m/e): 337.1 (M + 1). | E-111 |
| A-85 | 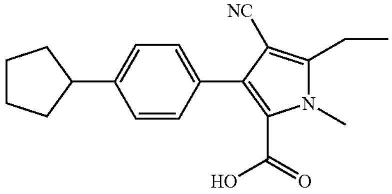 | mass spectrum (m/e): 323.2 (M + 1). | E-134 |
| A-86 | 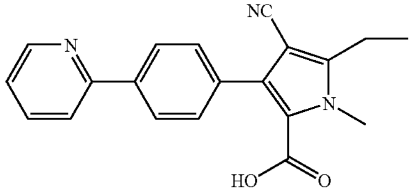 | mass spectrum (m/e): 332.3 (M + 1); analysis for $C_{20}H_{17}N_3O_2$: calcd: C, 72.49; H, 5.17; N, 12.68; found: C, 72.13; H, 5.02; N, 12.48. | E-135 |
| A-87 | 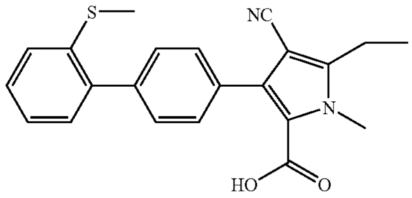 | mass spectrum (m/e): 377.3 (M + 1); analysis for $C_{22}H_{20}N_2O_2S$: calcd: C, 70.19; H, 5.35; N, 7.44; found: C, 70.15; H, 5.42; N, 7.10. | E-112 |
| A-88 | 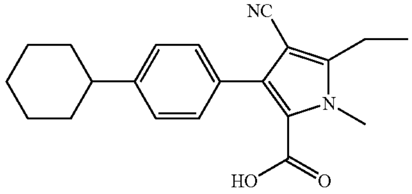 | mass spectrum (m/e): 337.3 (M + 1). | E-136 |
| A-89 | 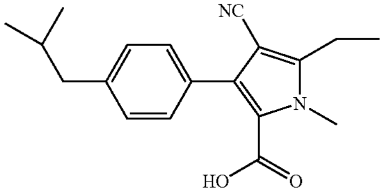 | mass spectrum (m/e): 311.3 (M + 1); analysis for $C_{19}H_{22}N_2O_2$: calcd: C, 73.52; H, 7.14; N, 9.03; found: C, 73.15; H, 7.12; N, 8.80. | E-137 |
| A-90 | 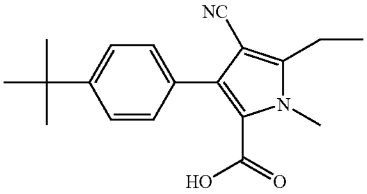 | mass spectrum (m/e): 311.3 (M + 1); analysis for $C_{19}H_{22}N_2O_2$: calcd: C, 73.52; H, 7.14; N, 9.03; found: C, 73.35; H, 7.02; N, 8.98. | E-148 |

TABLE A-1-continued
| Ex. | Structure | Data | S.M. |
|---|---|---|---|
| A-91 | 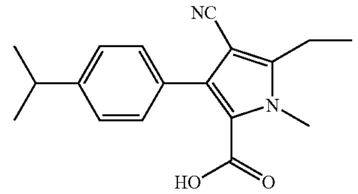 | mass spectrum (m/e): 297.2 (M + 1); analysis for $C_{18}H_{20}N_2O_2$: calcd: C, 72.95; H, 6.80; N, 9.45; found: C, 72.74; H, 6.62; N, 9.25. | E-149 |
| A-92 | 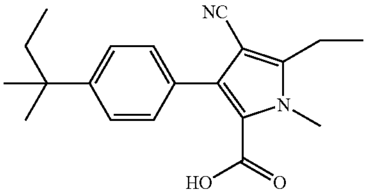 | | E-150 |
| A-93 | 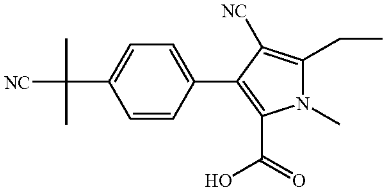 | mass spectrum (m/e): 322.3 (M + 1). | E-154 |
| A-94 | 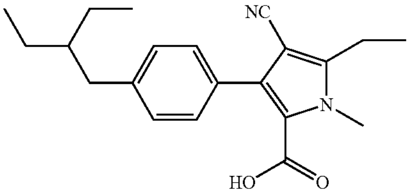 | mass spectrum (m/e): 339.3 (M + 1). | E-138 |
| A-95 | 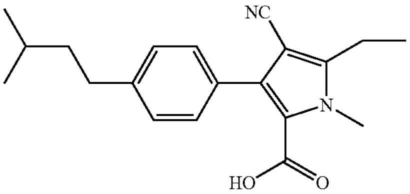 | mass spectrum (m/e): 325.3 (M + 1). | E-139 |
| A-96 | 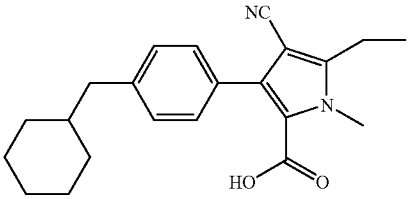 | mass spectrum (m/e): 351.3 (M + 1). | E-140 |
| A-97 | 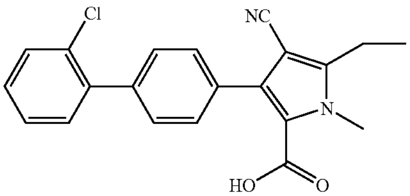 | mass spectrum (m/e): 363.1 (M − 1); analysis for $C_{21}H_{17}ClN_2O_2$: calcd: C, 69.14; H, 4.70; N, 7.68; found: C, 68.74; H, 4.77; N, 7.56. | E-113 |

TABLE A-1-continued
| Ex. | Structure | Data | S.M. |
|---|---|---|---|
| A-98 | 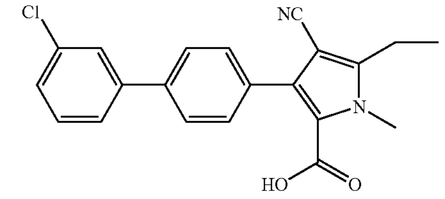 | mass spectrum (m/e): 363.1 (M − 1). | E-114 |
| A-99 | 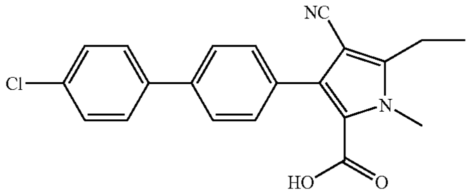 | mass spectrum (m/e): 365.2 (M + 1). | E-115 |
| A-100 | 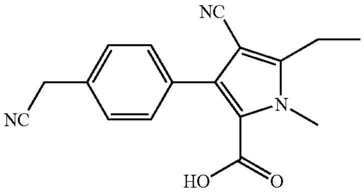 | mass spectrum (m/e): 294.0 (M + 1). | E-151 |
| A-101 | 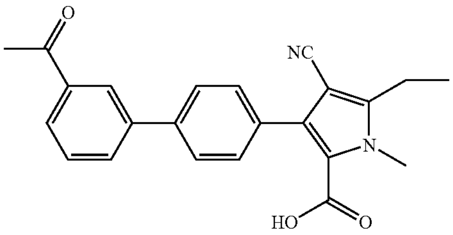 | mass spectrum (m/e): 373.0 (M + 1). | E-116 |
| A-102 | 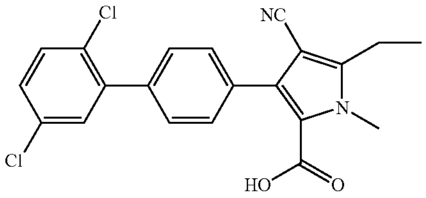 | mass spectrum (m/e): 400.9 (M + 1); analysis for $C_{21}H_{16}Cl_2N_2O_2$: calcd: C, 63.17; H, 4.04; N, 7.02; found: C, 63.26; H, 4.26; N, 6.84. | E-117 |
| A-103 | 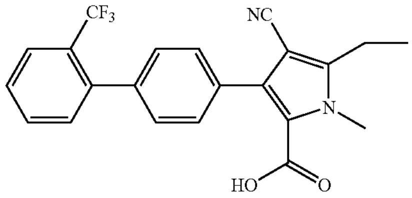 | mass spectrum (m/e): 399.0 (M + 1); analysis for $C_{22}H_{17}F_3N_2O_2$: calcd: C, 66.33; H, 4.30; N, 7.03; found: C, 66.12; H, 4.55; N, 6.84. | E-118 |
| A-104 | 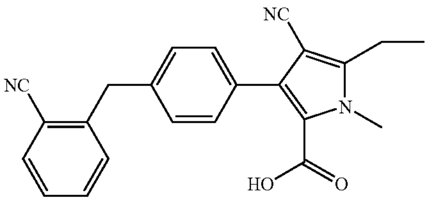 | mass spectrum (m/e): 368.1 (M − 1). | E-141 |

TABLE A-1-continued
| Ex. | Structure | Data | S.M. |
|---|---|---|---|
| A-105 | 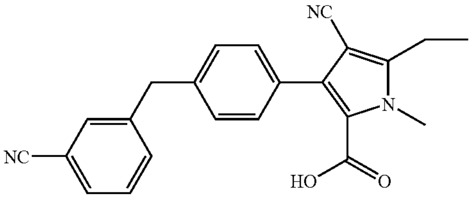 | mass spectrum (m/e): 368.3 (M − 1). | E-142 |
| A-106 | 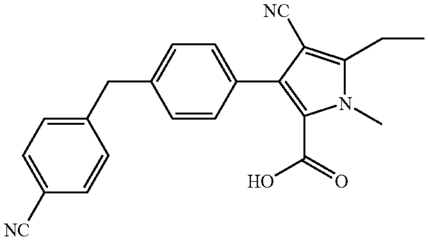 | mass spectrum (m/e): 370.1 (M + 1). | E-143 |
| A-107 | 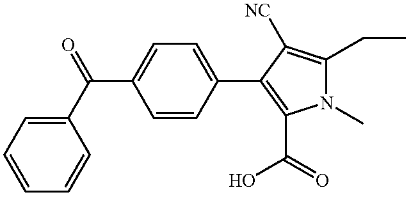 | mass spectrum (m/e): 359.3 (M + 1); analysis for $C_{22}H_{18}N_2O_3$: calcd : C, 73.73; H, 5.06; N, 7.82; found: C, 73.72; H, 5.28; N, 7.71. | E-158 |
| A-108 | 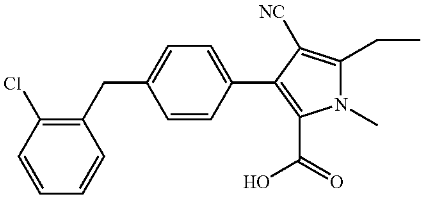 | mass spectrum (m/e): 377.1 (M − 1). | E-144 |
| A-109 | 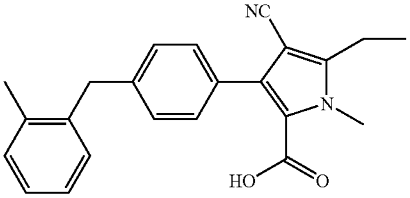 | mass spectrum (m/e): 359.0 (M + 1). | E-145 |
| A-110 | 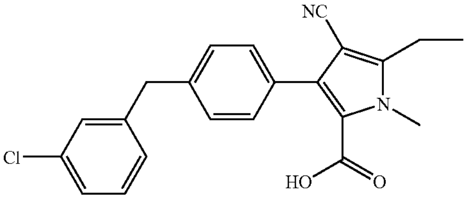 | mass spectrum (m/e): 379.2 (M + 1). | E-146 |
| A-111 | 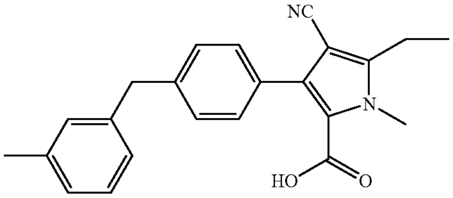 | mass spectrum (m/e): 359.3 (M + 1). | E-147 |

TABLE A-1-continued
| Ex. | Structure | Data | S.M. |
|---|---|---|---|
| A-112 | 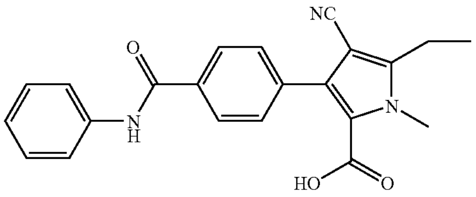 | mass spectrum (m/e): 374.0 (M + 1). | E-165 |
| A-113 | 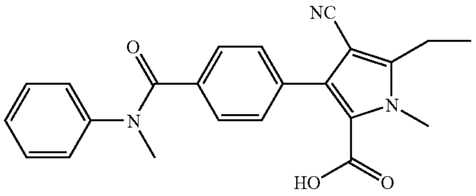 | mass spectrum (m/e): 388.0 (M + 1). | E-166 |
| A-114 | 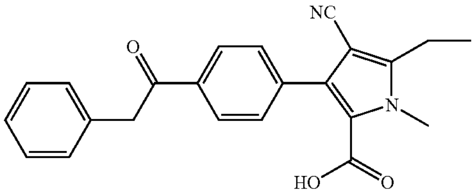 | mass spectrum (m/e): 373.0 (M + 1). | E-160 |
| A-115 | 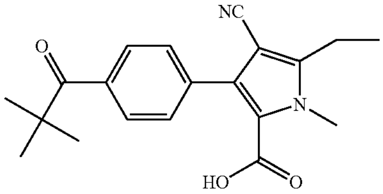 | mass spectrum (m/e): 339.0 (M + 1); analysis for $C_{20}H_{22}N_2O_3$: calcd : C, 70.98; H, 6.55; N, 8.28; found: C, 70.82; H, 6.55; N, 8.17. | E-161 |
| A-116 | 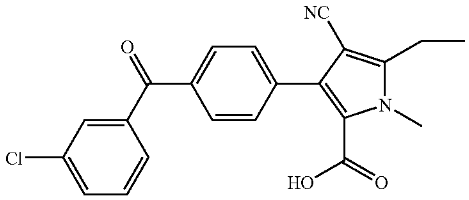 | mass spectrum (m/e): 329.9 (M + 1). | E-159 |
| A-117 | 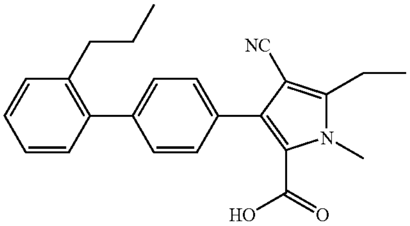 | mass spectrum (m/e): 373.1 (M + 1). | E-155 |
| A-118 | 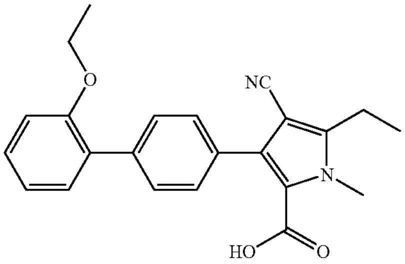 | mass spectrum (m/e): 375.19 (M + 1). | E-119 |

TABLE A-1-continued

| Ex. | Structure | Data | S.M. |
|---|---|---|---|
| A-119 | 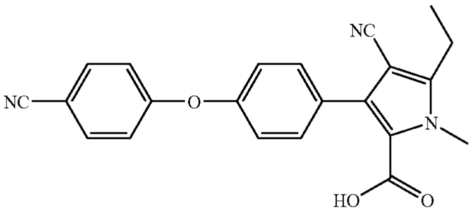 | mass spectrum (m/e): 372.0 (M + 1). | E-89 |
| A-120 | 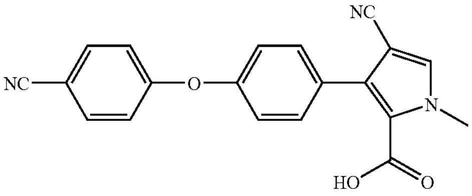 | mass spectrum (m/e): 344.0 (M + 1). | E-88 |
| A-121 | 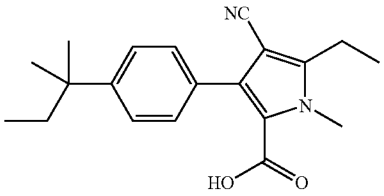 | $^1$H NMR (400 MHz, DMSO)δ7.34(d, J=7.93Hz, 2H), 7.26(d, J=8.37Hz, 2H), 3.82(s, 3H), 2.81(q, J=7.93Hz, 2H), 1.62(q, J=7.49Hz, 211), 1.26(s, 6H), 1.20(t, J=7.49Hz, 3H), 0.64(t, J=7.49Hz, 3H). mass spectrum (m/e): 323.2 (M − 1). | E-272 |
| A-122 | 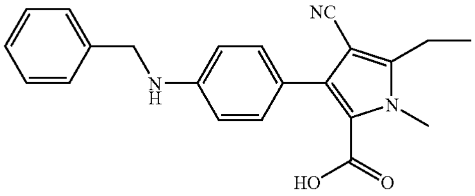 | mass spectrum (m/e): 360.0 (M + 1); analysis for $C_{22}H_{21}N_3O_2$: calcd: C, 73.52; H, 5.89; N, 11.69; found: C, 73.41; H, 5.97; N, 11.59. | E-167 |
| A-123 | 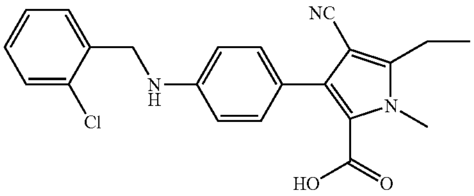 | mass spectrum (m/e): 392.1 (M − 1); analysis for $C_{22}H_{20}ClN_3O_2$: calcd: C, 67.09; H, 5.12; N, 10.67; found: C, 67.04; H, 5.15; N, 10.32. | E-168 |
| A-124 | 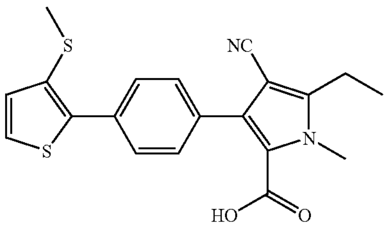 | mass spectrum (m/e): 383.0 (M + 1); analysis for $C_{20}H_{18}N_2O_2S_2$: calcd: C, 62.80; H, 4.74; N, 7.32; found: C, 62.89; H, 4.73; N, 7.31. | E-156 |
| A-125 | 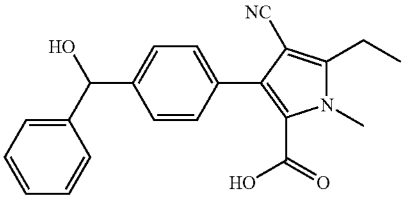 | mass spectrum (m/e): 359.1 (M − 1). | E-162 |

TABLE A-1-continued
| Ex. | Structure | Data | S.M. |
|---|---|---|---|
| A-126 | 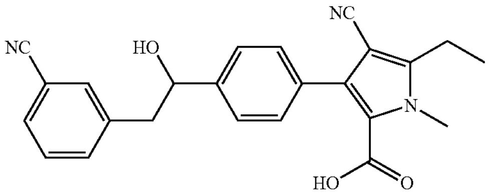 | mass spectrum (m/e): 400.0 (M + 1). | E-163 |
| A-127 | 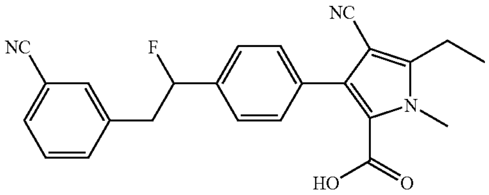 | mass spectrum (m/e): 402.0 (M + 1); analysis for $C_{24}H_{20}FN_3O_2$: calcd: C, 71.81; H, 5.02; N, 10.47; found: C, 72.02; H, 5.25; N, 10.22. | E-164 |
| A-128 | 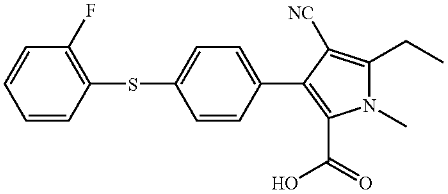 | mass spectrum (m/e): 380.9 (M + 1). | E-170 |
| A-129 | 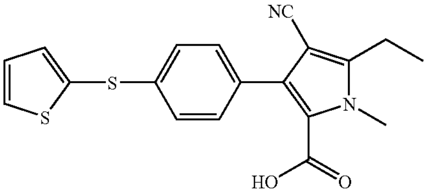 | mass spectrum (m/e): 368.9 (M + 1). | E-171 |
| A-130 | 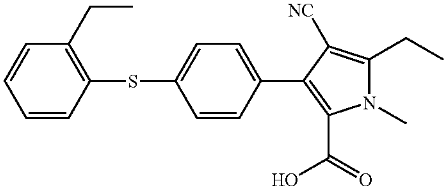 | mass spectrum (m/e): 391.1 (M + 1); analysis for $C_{23}H_{22}N_2O_2S$: calcd: C, 70.74; H, 5.68; N, 7.17; found: C, 70.48; H, 5.73; N, 7.13. | E-172 |
| A-131 | 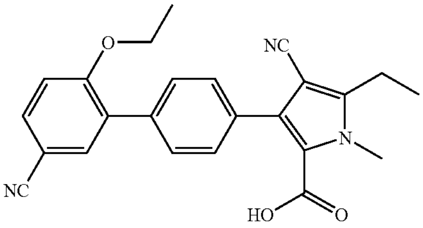 | mass spectrum (m/e): 400.0 (M + 1). | E-123 |
| A-132 | 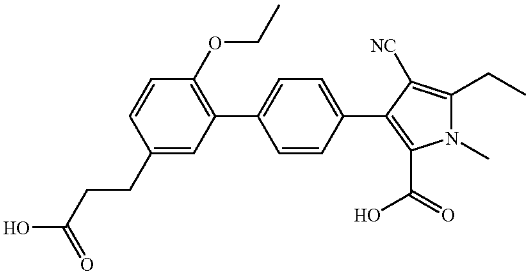 | mass spectrum (m/e): 445.1 (M + 1); analysis for $C_{26}H_{26}N_2O_5$: calcd: C, 69.94; H, 5.87; N, 6.27; found: C, 69.54; H, 6.01; N, 5.96. | E-124 |

TABLE A-1-continued
| Ex. | Structure | Data | S.M. |
|---|---|---|---|
| A-133 | 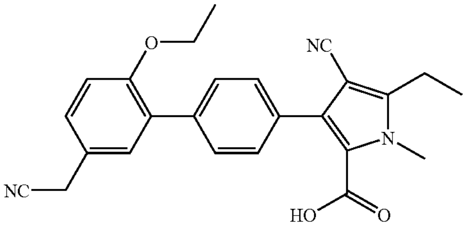 | mass spectrum (m/e): 414.1 (M + 1). | E-280 |
| A-134 | 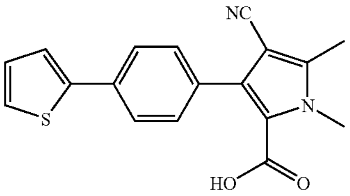 | MS (fd): 323.1 (M* + 1): (Bruker 300) $^{1}$H NMR (DMSO) 7.70-7.74(2H, d), 7.60-7.65(2H, t), 7.50-7.55 (1H, m), 7.44-7.49(1H, d), 7.21-7.24(1H, m), 3.82-3.89(3H, S), 2.44-2.48(3H, s). | E-273 |
| A-135 | 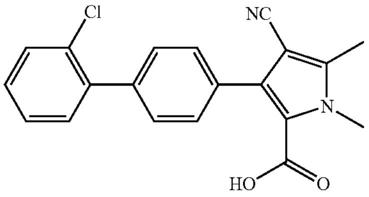 | MS (fd): 351.1 (M* + 1): (Bruker 300) $^{1}$H NMR (DMSO) 7.59-7.63(1H, dd), 7.41-7.53(7H, m), 3.82-3.87(3H, S), 2.42-2.48(3H, s). | E-274 |
| A-136 | 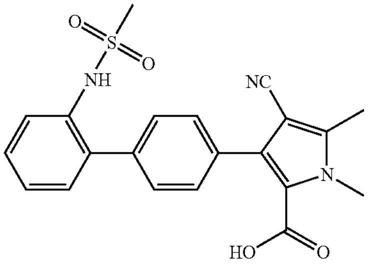 | MS (fd): 408.1 (M* − 1): (Bruker 300) $^{1}$H NMR (DMSO) 7.64-7.69(2H, d), 7.43-7.54(4H, m), 7.51-7.54(1H, s), 7.21-7.28(1H, m), 3.82-3.86(3H, s), 3.04-3.08(3H, s), 2.44-2.48(3H, s). | E-275 |
| A-137 | 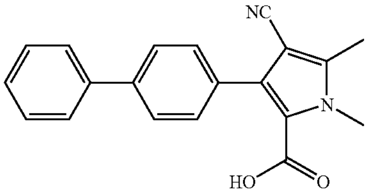 | Mass spectrum (m/e): 315.3 (M − 1) | E-233 |
| A-138 | 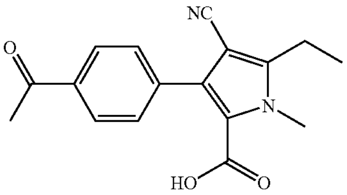 | | E-177 |
| A-139 | 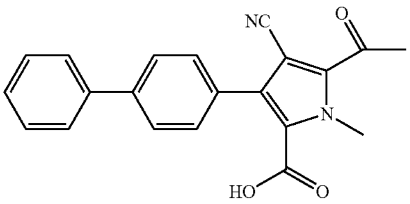 | mass spectrum (m/e): 345.4 (M + 1). | E-174 |

TABLE A-1-continued
| Ex. | Structure | Data | S.M. |
|---|---|---|---|
| A-140 | 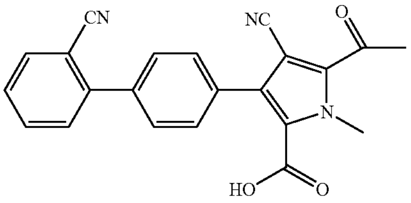 | mass spectrum (m/e): 387.2 (M + 18). | E-175 |
| A-141 | 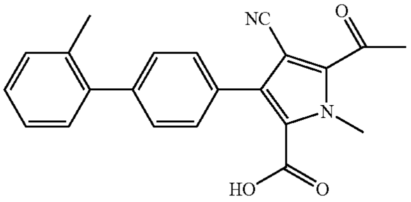 | mass spectrum (m/e): 359.2 (M + 1). | E-176 |
| A-142 | 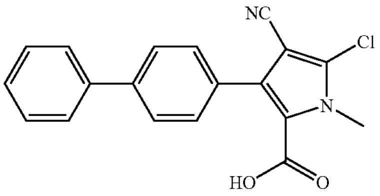 | mass spectrum (m/e): 355.1 (M − 1) ); analysis for $C_{19}H_{13}ClN_2O_2$: calcd: C, 67.76; H, 3.89; N, 8.32; found: C, 67.58; H, 4.03; N, 8.06. | E-178 |
| A-143 | 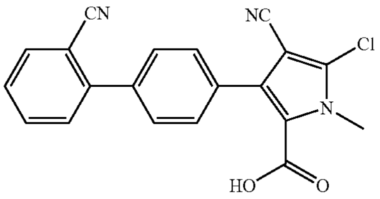 | mass spectrum (m/e): 379.2 (M + 18). | E-179 |
| A-144 | 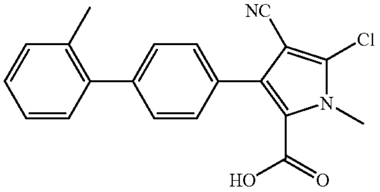 | mass spectrum (m/e): 351.2 (M + 1). | E-180 |
| A-145 | 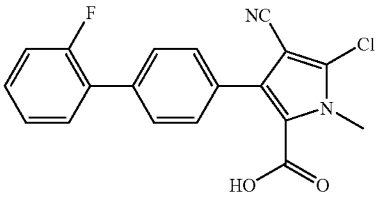 | mass spectrum (m/e): 353.1 (M − 1). | E-181 |
| A-147 | 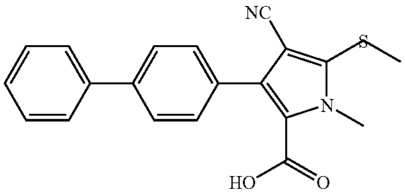 | mass spectrum (m/e): 347.0 (M − 1). | E-183 |

TABLE A-1-continued
| Ex. | Structure | Data | S.M. |
|---|---|---|---|
| A-148 | 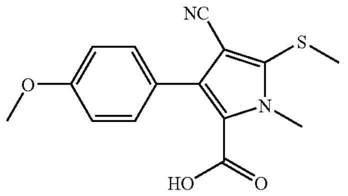 | mass spectrum (m/e): 303.0 (M + 1). | E-184 |
| A-149 | 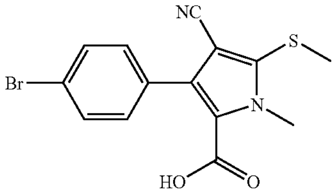 | mass spectrum (m/e): 350.8 (M − 1). | E-198 |
| A-151 | 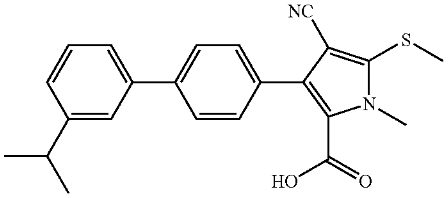 | mass spectrum (m/e): 391.2 (M − 1); analysis for $C_{23}H_{22}N_2O_2S$: calcd: C, 70.74; H, 5.67; N, 7.17; found: C, 70.99; H, 6.07; N, 6.78. | E-200 |
| A-152 | 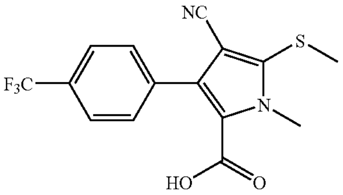 | mass spectrum (m/e): 341.1 (M + 1); analysis for $C_{15}H_{11}F_3N_2O_2S$: calcd: C, 52.94; H, 3.26; N, 8.23; found: C, 52.84; H, 3.19; N, 8.02. | E-186 |
| A-153 | 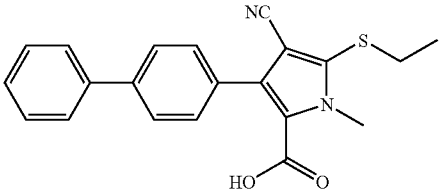 | mass spectrum (m/e): 363.1 (M + 1); analysis for $C_{21}H_{18}N_2O_2S$: calcd: C, 69.59; H, 5.01; N, 7.73; found: C, 69.37; H, 5.17; N, 7.52. | E-187 |
| A-154 | 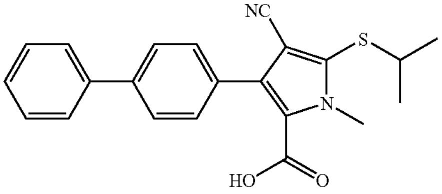 | mass spectrum (m/e): 377.1 (M + 1). | E-188 |
| A-155 | 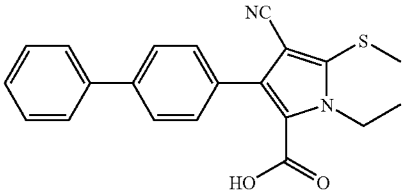 | mass spectrum (m/e): 363.3 (M + 1). | E-196 |

TABLE A-1-continued

| Ex. | Structure | Data | S.M. |
|---|---|---|---|
| A-156 | 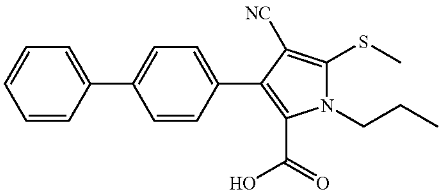 | mass spectrum (m/e): 377.3 (M + 1); analysis for $C_{22}H_{20}N_2O_2S$: calcd: C, 70.19; H, 5.35; N, 7.44; found: C, 70.34; H, 5.24; N, 7.34. | E-197 |
| A-157 | 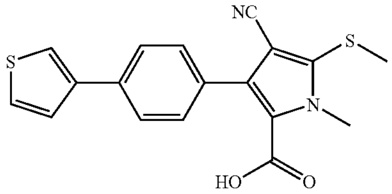 | mass spectrum (m/e): 355.1 (M + 1); analysis for $C_{18}H_{14}N_2O_2S_2$: calcd: C, 60.99; H, 3.98; N, 7.90; found: C, 61.13; H, 4.05; N, 7.73. | E-191 |
| A-158 | 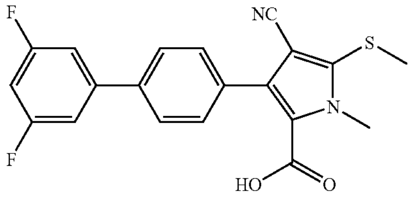 | mass spectrum (m/e): 383.0 (M − 1). | E-189 |
| A-159 | 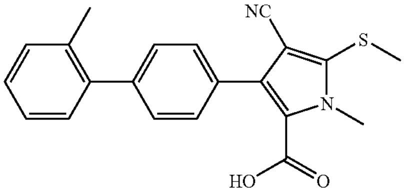 | mass spectrum (m/e): 361.2 (M − 1). | E-190 |
| A-160 | 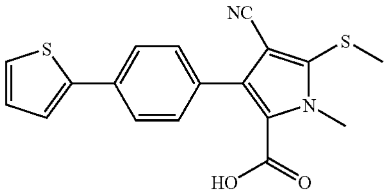 | mass spectrum (m/e): 355.1 (M + 1); analysis for $C_{18}H_{14}N_2O_2S_2$: calcd: C, 60.99; H, 3.98; N, 7.90; found: C, 60.96; H, 4.20; N, 7.72. | E-192 |
| A-161 | 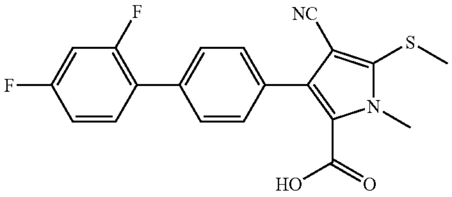 | mass spectrum (m/e): 385.3 (M + 1); analysis for $C_{20}H_{14}F_2N_2O_2S$: calcd: C, 62.49; H, 3.67; N, 7.29; found: C, 62.10; H, 3.94; N, 6.99. | E-193 |
| A-162 | 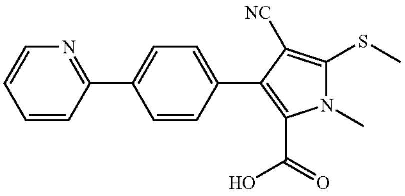 | mass spectrum (m/e): 350.2 (M + 1); analysis for $C_{19}H_{15}N_3O_2S$: calcd: C, 65.31; H, 4.33; N, 12.03; found: C, 65.02; H, 4.50; N, 11.69. | E-194 |

TABLE A-1-continued
| Ex. | Structure | Data | S.M. |
|---|---|---|---|
| A-163 | 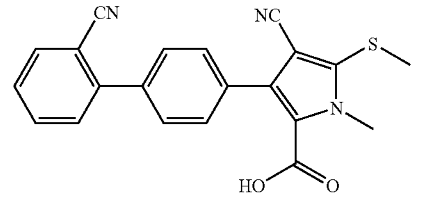 | mass spectrum (m/e): 372.1 (M − 1). | E-201 |
| A-164 | 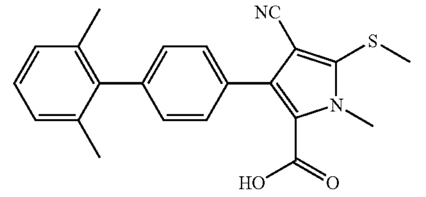 | mass spectrum (m/e): 377.2 (M + 1); analysis for $C_{22}H_{20}N_2O_2S$: calcd: C, 70.19; H, 5.35; N, 7.44; found: C, 70.12; H, 5.36; N, 7.46. | E-195 |
| A-165 | 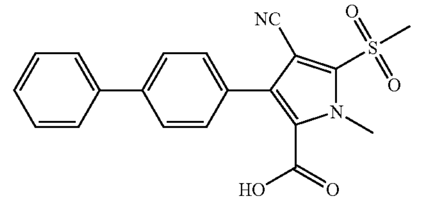 | mass spectrum (m/e): 398.2 (M + 18). | E-204 |
| A-166 | 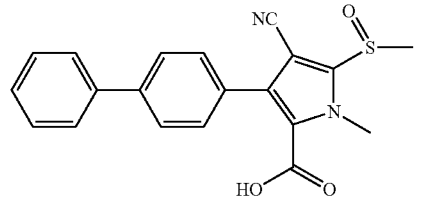 | Mass spectrum (m/e): 365.2 (M + 1). | E-203 |
| A-167 | 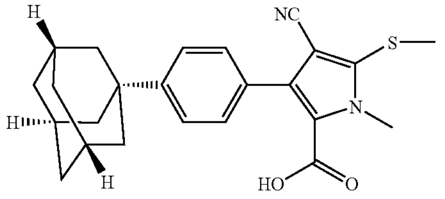 | mass spectrum (m/e): 407.2 (M + 1). | E-202 |
| A-168 | 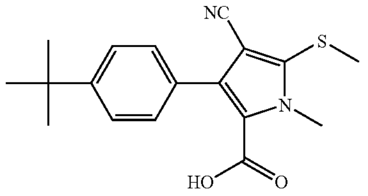 | mass spectrum (m/e): 329.2 (M + 1); H-NMR (MeOH-d-4): 1.35(9H, s); 2.49(3H, s); 4.05(3H, s); 7.46-7.27(4H, AA'BB') | E-185 |
| A-169 | 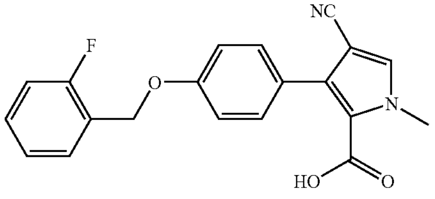 | white solid: mass spectrum (m/e): 351.1 (M* + 1): (Bruker 300) $^1$H NMR (DMSO) 7.83-7.90(1H, s), 7.53-7.63(1H, t), 7.40-7.50(1H, dd), 7.20-7.35(4H, m), 7.00-7.15(2H, d), 5.05-5.20(2H, s), 3.75-3.95(3H, s). | E-207 |

TABLE A-1-continued

| Ex. | Structure | Data | S.M. |
|---|---|---|---|
| A-170 | 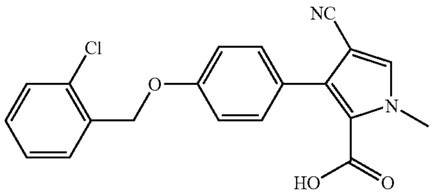 | white crystals: mass spectrum (m/e): 365.0 (M* + 1): (Bruker 300) $^{1}$H NMR (DMSO) 7.83-7.93(1H, s), 7.60-7.67(1H, m), 7.48-7.56(1H, m), 7.36-7.45(2H, m), 7.25-7.35(2H, d), 7.00-7.10(2H, d), 5.05-5.20 (2H, s), 3.75-3.95(3H, s). | E-208 |
| A-171 | 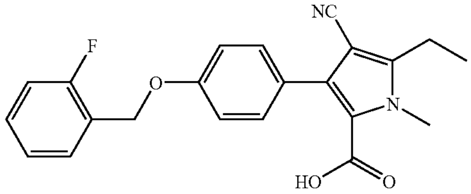 | white crystals: mass spectrum (m/e): 379.3 (M* + 1): (Bruker 300) $^{1}$NMR (DMSO) 7.54-7.64(1H, t), 7.40-7.50(1H, m), 7.28-7.35(4H, m), 7.00-7.10(2H, d), 5.05-5.20(2H, s), 3.70-3.90(3H, s), 2.65-2.85(2H, dd), 1.05-1.30(3H, t). | E-209 |
| A-172 | 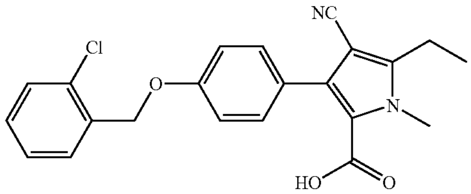 | white crystals: mass spectrum (m/e): 395.3 (M* + 1): (Bruker 300) $^{1}$H NMR (DMSO) 7.60-7.65(1H, m), 7.50-7.55(1H, m), 7.38-7.44(2H, m), 7.25-7.31(2H, d), 7.00-7.10(2H, d), 5.05-5.20(2H, s), 3.75-3.85(3H, s), 2.70-2.85(2H, dd), 1.05-1.30(3H, t). | E-210 |
| A-173 | 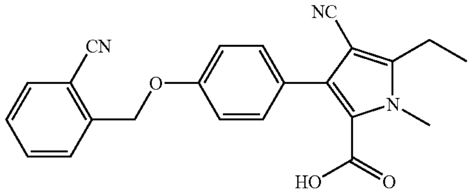 | tan solid: mass spectrum (m/e): 384.2 (M* − 1): (Bruker 300) $^{1}$H NMR (DMSO) 7.85-7.95(1H, d), 7.70-7.80 (2H, m), 7.54-7.62(1H, m), 7.35-7.45(2H, m), 6.95-7.05(2H, d), 5.15-5.25(2H, s), 3.60-3.80(3H, s), 2.60-2.80(2H, dd), 1.05-1.23(3H, t). | E-211 |
| A-174 | 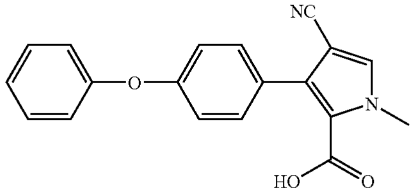 | white solid: mass spectrum (m/e): 319.1 (M* + 1): (Bruker 300) $^{1}$H NMR (DMSO) 7.90-7.92(1H, s), 7.30-7.50(4H, m), 7.15-7.22(1H, t), 7.04-7.12(2H, d), 6.90-7.05(2H, d), 3.78-3.95(3H, s) | E-212 |
| A-175 | 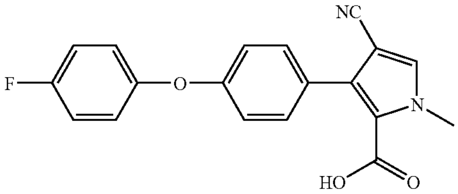 | white solid: mass spectrum (m/e): 337.2 (M* + 1): (Bruker 300) $^{1}$H NMR (DMSO) 7.85-7.92(1H, s), 7.09-7.40(6H, m), 6.93-7.05(2H, d), 3.78-3.95(3H, s) | E-213 |
| A-176 | 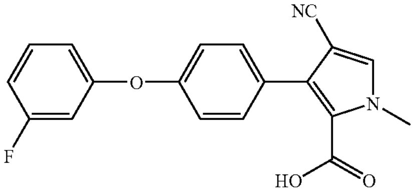 | white crystals: mass spectrum (m/e): 337.2 (M* + 1): (Bruker 300) $^{1}$H NMR (DMSO) 7.88-7.94(1H, s), 7.35-7.51(3H, m), 6.85-7.15(5H, m), 3.81-3.98(3H, s) | E-214 |

TABLE A-1-continued

| Ex. | Structure | Data | S.M. |
| --- | --- | --- | --- |
| A-177 | 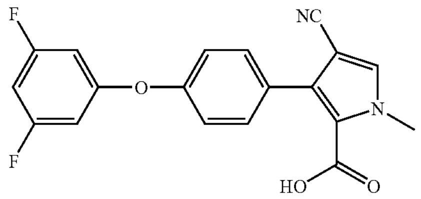 | white crystals: mass spectrum (m/e): 355.3 (M* + 1): (Bruker 300) $^{1}$H NMR (DMSO) 7.88-7.91(1H, s), 7.38-7.45(2H, d), 7.11-7.18(2H, d), 6.96-7.07(1H, t), 6.72-6.81(2H, d), 3.81-3.98(3H, s) | E-215 |
| A-178 | 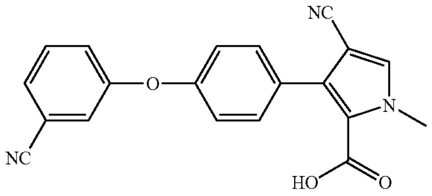 | white solid: mass spectrum (m/e): 342.1 (M* − 1): (Bruker 300) $^{1}$H NMR (DMSO) 7.90-7.94(1H, s), 7.55-7.66(3H, m), 7.36-7.45(3H, d), 7.02-7.08(2H, d), 3.83-3.93(3H, s) | E-216 |
| A-179 | 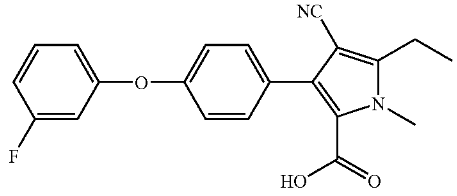 | mass spectrum (m/e): 321.2 (M* + 1): (Bruker 300) $^{1}$H NMR (DMSO) 7.37-7.52(2H, m), 6.82-7.08(6H, m), 3.53-3.63(3H, s), 2.70-2.84(2H, dd), 1.13-1.25 (3H, t) | E-217 |
| A-180 | 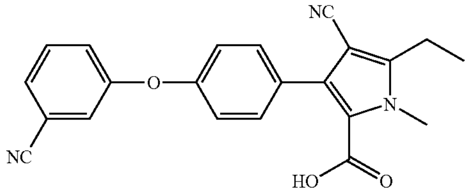 | white solid: mass spectrum (m/e): 370.2 (M* − 1): (Bruker 300) $^{1}$H NMR (DMSO) 7.54-7.68(3H, m), 7.31-7.45(3H, m), 7.04-7.12(2H, d), 3.78-3.88(3H, s), 2.74-2.87(2H, dd), 1.13-1.25(3H, t) | E-218 |
| A-181 | 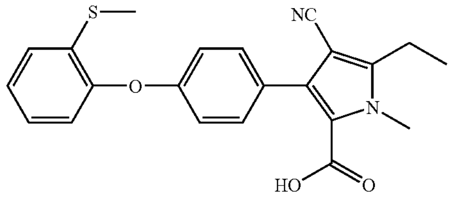 | mass spectrum (m/e): 391.1 (M* − 1): (Bruker 300) $^{1}$H NMR (DMSO) 7.24-7.35(4H, m), 7.08-7.16(2H, m), 6.90-6.98(2H, d), 3.80-3.85(3H, s), 2.74-2.87 (2H, dd), 2.39-2.44(3H, s), 1.23-1.31(3H, t) | E-219 |
| A-182 | 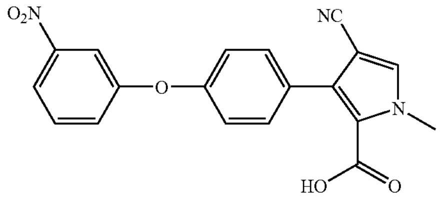 | white solid: mass spectrum (m/e): 362.1 (M* − 1): (Bruker 300) $^{1}$H NMR (DMSO) 8.06-8.15(1H, d), 7.91-7.98(1H, s), 7.70-7.80(1H, t), 7.36-7.48(3H, m), 7.22-7.30(1H, d), 7.05-7.15(2H, d), 3.80-3.90(3H, s) | E-220 |
| A-183 | 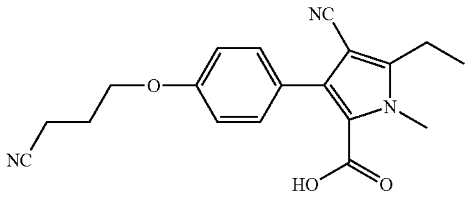 | white crystals: mass spectrum (m/e): 336.1 (M* − 1): (Bruker 300) $^{1}$H NMR (DMSO) 7.22-7.28(2H, d), 6.93-6.98(2H, d), 4,00-4.10(2H, m), 3.80-3.85(3H, s), 2.75-2.84(2H, dd), 2.61-2.69(2H, m), 1.98-2.06(2H, dd), 1.14-1.25(3H, t) | E-221 |

TABLE A-1-continued

| Ex. | Structure | Data | S.M. |
|---|---|---|---|
| A-184 | 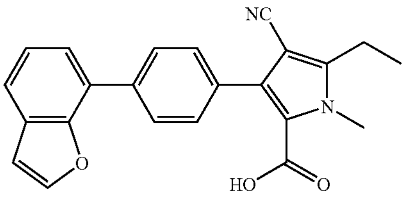 | white solid: mass spectrum (m/e): 369.1 (M* − 1): (Bruker 300) $^{1}$H NMR (DMSO) 8.03-8.07(1H, s), 7.79-7.84(2H, d), 7.62-7.67(2H, d), 7.50-7.59(2H, m), 7.31-7.37(2H, t), 7.02-7.04(1H, s), 4,00-4.10(2H, m), 3.80-3.85(3H, s), 2.75-2.84(2H, dd), 1.14-1.25 (3H, t) | E-222 |
| A-185 | 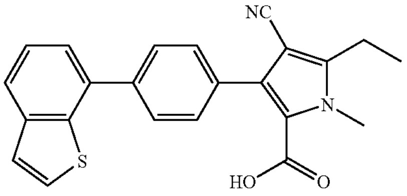 | white solid: mass spectrum (m/e): 385.1 (M* − 1): (Bruker 300) $^{1}$H NMR (DMSO) 8.03-8.07(1H, s), 7.73-7.82(3H, m), 7.50-7.57(2H, m), 7.37-7.47(4H, m), 3.85-3.90(3H, s), 2.82-2.90(2H, dd), 1.26-1.35 (3H, t) | E-223 |
| A-186 | 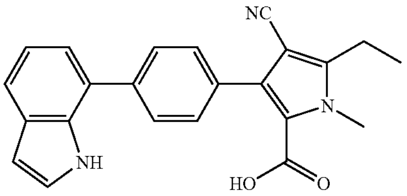 | white solid: mass spectrum (m/e): 370.24 (M* − 1) | E-224 |
| A-187 | 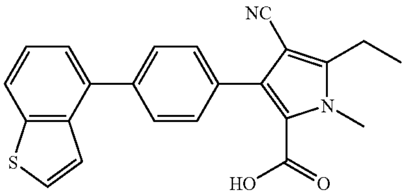 | light solid. mass spectrum (m/e): 385.1 (M* − 1) | E-225 |
| A-188 | 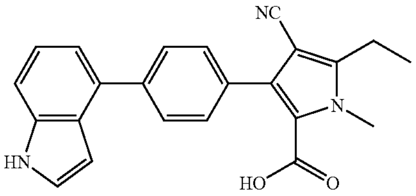 | light solid. mass spectrum (m/e): 370.24 (M* − 1) | E-226 |
| A-189 | 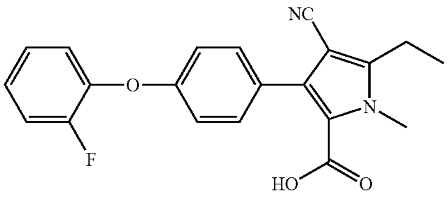 | tan solid. mass spectrum (m/e): 363.1 (M* − 1): (Bruker 300) $^{1}$H NMR (DMSO) 7.40-7.50(3H, m), 7.24-7.34(3H, m), 6.94-7.00(2H, d), 3.78-3.88(3H, s), 2.78-2.88(2H, dd), 1.20-1.32(3H, t) | E-227 |
| A-190 | 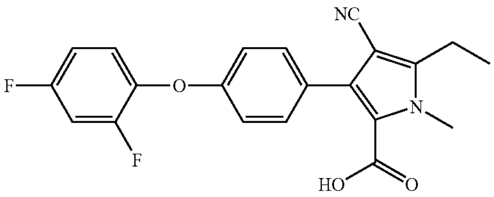 | tan solid: mass spectrum (m/e): 381.1 (M* − 1): (Bruker 300) $^{1}$NMR (DMSO) 7.51-7.59(1H, t), 7.34-7.46(3H, m), 7.17-7.24(1H, t), 6.98-7.03(2H, d), 3.86-3.90(3H, s), 2.82-2.90(2H, dd), 1.22-1.30(3H, t) | E-228 |

TABLE A-1-continued

| Ex. | Structure | Data | S.M. |
|---|---|---|---|
| A-191 | 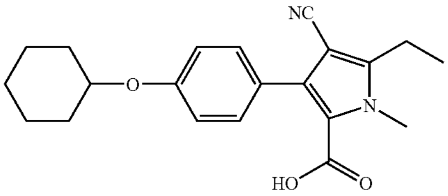 | mass spectrum (m/e): 351.2 (M* − 1): (Bruker 300) $^1$H NMR (DMSO) 7.35-7.40(1H, d), 7.25-7.30(1H, d), 6.95-7.02(2H, t), 4.35-4.43(1H, m), 3.86-3.90(3H, s), 2.82-2.90(2H, dd), 1.93-2.04(2H, m), 1.73-1.81 (2H, m), 1.31-1.63(6H, m), 1.22-1.30(3H, t) | E-229 |
| A-192 | 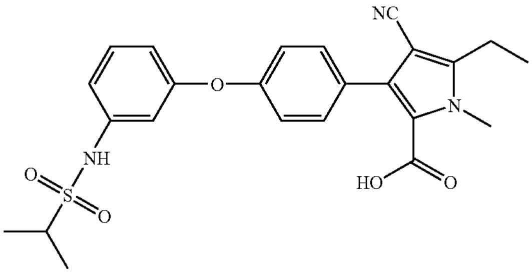 | mass spectrum (m/e): 466.1 (M* − 1): (Bruker 300) $^1$H NMR ($CDCl_3$) 7.34-7.56(2H, d), 6.96-7.1(1H, m), 6.75-6.80(2H, d), 6.39-6.43(1H, d), 6.30-6.32(1H, t), 6.21-6.26(1H, d), 4.06-4.14(2H, dd), 3.75-3.85(3H, s), 3.29-3.36(1H, m), 2.75-2.88(1H, m)1.17-1.34(9H, m) | E-232 |
| A-193 | 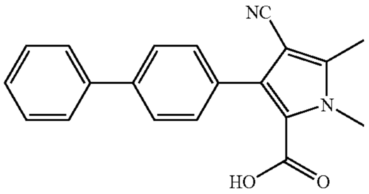 | mass spectrum (m/e): 315.1 (M* − 1): (Bruker 300) $^1$H NMR (DMSO) 7.67-7.71(3H, m), 7.34-7.49(6H, m), 3.80-3.84(3H, s), 2.40-2.43(3H, s). | E-233 |
| A-194 | 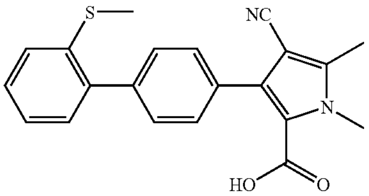 | tan oil: mass spectrum (m/e): 361.1 (M* − 1): (Bruker 300) $^1$H NMR (DMSO) 7.42-7.48(2H, d), 7.29-7.37 (4H, m), 7.18-7.22(2H, d), 3.70-3.79(3H, s), 2.46-2.50 (3H, s), 2.34-2.40(3H, s) | E-235 |
| A-195 | 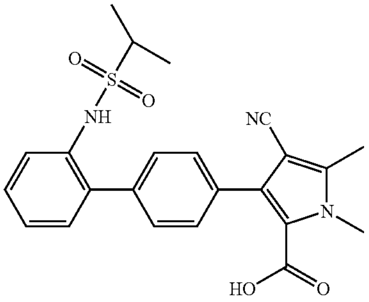 | tan solid: mass spectrum (m/e): 436.1 (M* − 1): (Bruker 300) $^1$H NMR ($CDCL_3$) 7.61-7.67(1H, d), 7.44-7.50 (2H, m), 7.18-7.38(5H, m), 3.82-3.86(3H, s), 3.04-3.10(1H, m), 2.42-2.47(3H, s), 1.07-1.17(6H, d) | E-237 |
| A-196 | 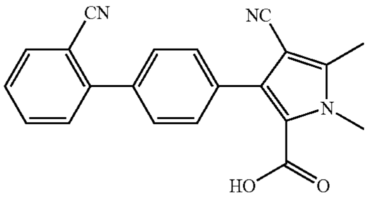 | mass spectrum (m/e): 340.1 (M* − 1): (Bruker 300) $^1$NMR (DMSO) 7.91-7.94(2H, d), 7.75-7.80(2H, t), 7.51-7.65(4H, m), 3.28-3.33(3H, s), 2.42-2.47(3H, s). | E-240 |

TABLE A-1-continued
| Ex. | Structure | Data | S.M. |
|---|---|---|---|
| A-197 | 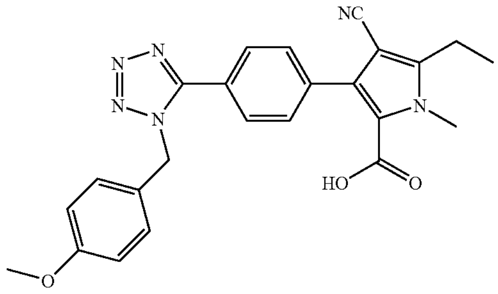 | mass spectrum (m/e): 443.3 (M + H) | E-241 |
| A-198 | 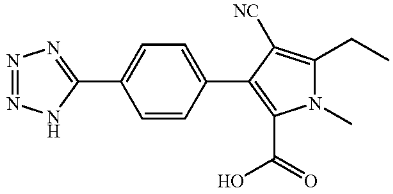 | mass spectrum (m/e): 321.36 (M − H) | E-242 |
| A-199 | 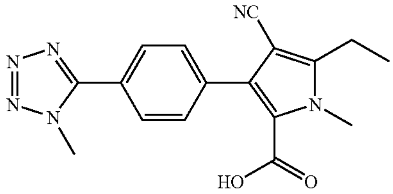 | mass spectrum (m/e): 337.04 (M + H) | E-243 |
| A-200 | 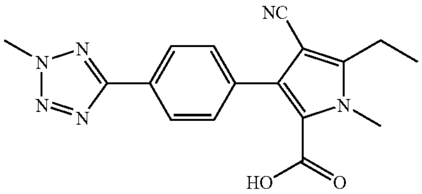 | mass spectrum (m/e): 337.04 (M + H) | E-244 |
| A-201 | 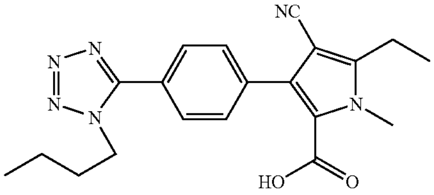 | mass spectrum (m/e): 379.05 (M + H) | E-245 |
| A-202 | 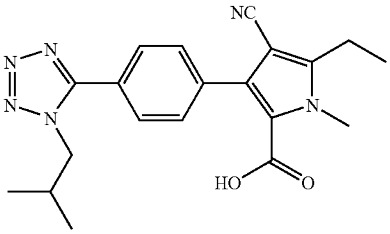 | mass spectrum (m/e): 379.05 (M + H) | E-246 |
| A-203 | 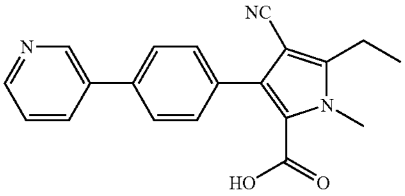 | Mass spectrum (m/e): 332.1 (M + 1) | E-248 |

TABLE A-1-continued
| Ex. | Structure | Data | S.M. |
|---|---|---|---|
| A-204 | 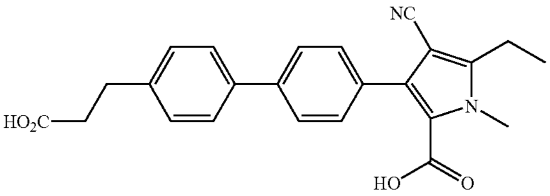 | Mass spectrum (m/e): 403.2 (M + 1) | E-249 |
| A-205 | 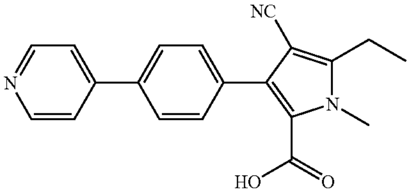 | Mass spectrum (m/e): 332.1 (M + 1) | E-250 |
| A-206 | 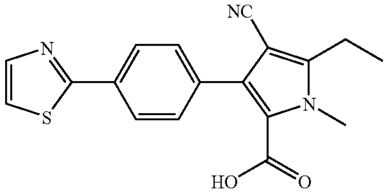 | Mass spectrum (m/e): 338.3 (M + 1) | E-251 |
| A-207 | 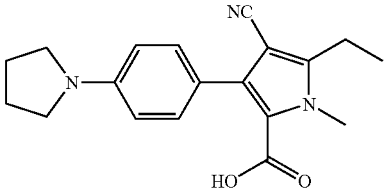 | Mass spectrum (m/e): 324.3 (M + 1) | E-252 |
| A-208 | 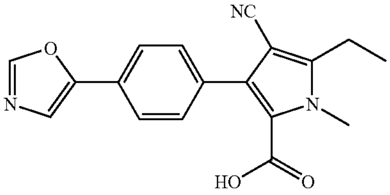 | Mass spectrum (m/e): 322.09 (M + 1) | E-253 |
| A-209 | 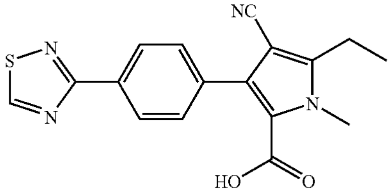 | Mass spectrum (m/e): 339.02 (M + 1) | E-254 |
| A-210 | 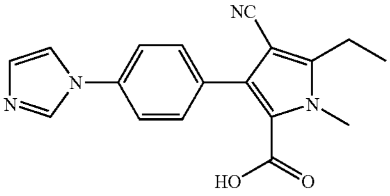 | Mass spectrum (m/e): 321.04 (M + 1) | E-255 |

TABLE A-1-continued

| Ex. | Structure | Data | S.M. |
|---|---|---|---|
| A-211 | 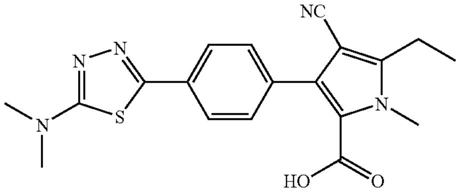 | Mass spectrum (m/e): 382.01 (M + 1) | E-256 |

EXAMPLE A-39b

Additional procedure for preparing 4-cyano-3-(4-biphenyl)-5-ethyl-1-methylpyrrole-2-carboxylic acid (see Example A-39a)

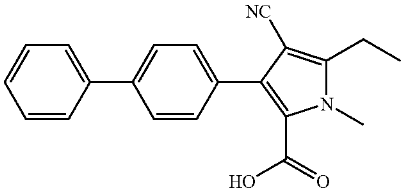

Preparation of 3-biphenyl-4-yl-4-cyano-1-methyl-5-ethyl-1H-pyrrole-2-carboxylic acid ethyl ester (see also Example E-71)

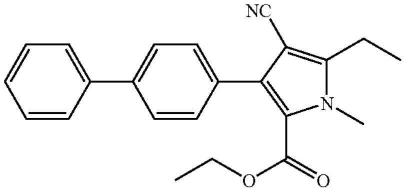

Charge deionized water (0.50 L), potassium carbonate (66.3 grams, 0.48 mol), and 4-biphenyl boronic acid (62.4 grams, 0.315 mol) and ethanol (1.4 L) to a 3 L 3-neck reaction flask equipped with a mechanical stirrer, condenser, heating mantle, thermocouple, and nitrogen inlet. Stir the mixture to dissolve the solids. Add 4-cyano-5-ethyl-3-iodo-1-methyl-1H-pyrrole-2-carboxylic acid ethyl ester (Preparation 38), additional ethanol (0.90 L) and stir the mixture while the flask is inerted with nitrogen. Add palladium black to the reaction mixture and heat the mixture to reflux at 80° C. Stir the reaction mixture at reflux for 70 minutes. Add ethyl acetate (0.50 L) and filter the mixture through Whatman® GF/F to remove palladium black. Concentrate the filtrate to about 0.6 L by distillation and filter the resulting suspension to collect the precipitate. Rinse the filter cake with ethanol (0.441 L) and vacuum-dry to afford 95.6 grams of the title compound in 88.7% yield.

Preparation of Final Title Compound

Charge 3-biphenyl-4-yl-4-cyano-1-methyl-5-ethyl-1H-pyrrole-2-carboxylic acid ethyl ester, (140 g, 0.39 mol, prepared directly above), acetone (0.84 L), and methanol (0.28 L) to a 3 L 3-neck reaction flask equipped with a mechanical stirrer, condenser, heating mantle, thermocouple, nitrogen inlet, and addition funnel. Warm the mixture to 45° C., and add 2N sodium hydroxide (0.244 L, 0.488 mol) via addition funnel in a steady stream while the reaction mixture is further warmed to 55° C. Stir the reaction mixture at 55° C. for 1 hour. Warm the mixture to 65° C. and add deionized water (0.30 L). Adjust the pH to 2.3 by adding 1 N HCl. Cool the mixture to 50° C. and add deionized water (0.365 L). Cool the mixture to 10° C. over 2 hours and collect the precipitate by filtration. Rinse the filter cake with deionized water (0.60 L) and vacuum-dry at 55° C. to afford 125.8 grams of the final title compound as a technical grade in 97.6% yield.

Charge the above technical grade of the final title compound (242.0 grams) and acetone (2.42 L) to a 3 L 3-neck reaction flask equipped with a mechanical stirrer, condenser, heating mantle, thermocouple, and nitrogen inlet. Stir the mixture until the solids dissolve and filter the resulting solution through a Whatman® GF/F filter to clarify the solution. Charge the filtrate to a 5 L 3-neck reaction flask equipped with a mechanical stirrer, condenser, heating mantle, thermocouple, and nitrogen inlet. Charge deionized water (2.7 L) to a 3 L 3-neck reaction flask equipped with a mechanical stirrer, condenser, heating mantle, thermocouple, and nitrogen inlet and warm to 75° C. Filter the hot water through a Whatman® GF/F filter, and slowly add 2.4 Liters of the resulting filtered water to the 5 L reaction flask containing the solution of the technical grade of the title compound. Reduce the temperature of the resulting mixture to 50° C. over 1.5 hours, and stir the suspension at 50° C. for 2.5 hours. Slowly cool the suspension to room temperature with stirring at room temperature overnight. Filter the suspension to collect the precipitate. Air-dry the filter cake on the filter. Vacuum-dry the filter cake at 55° C. to constant weight to afford 231.9 grams of the final title compound in 95.8% yield.

Additional procedures for preparing 4-cyano-3-[4-(2-cyanophenyl)phenyl]-5-ethyl-1-methylpyrrole-2-carboxylic acid of Example A-75a are set forth below in Example A-75b and Example A-75c.

EXAMPLE A-75b

Additional Preparation of 4-cyano-3-[4-(2-cyanophenyl)phenyl]-5-ethyl-1-methylpyrrole-2-carboxylic acid

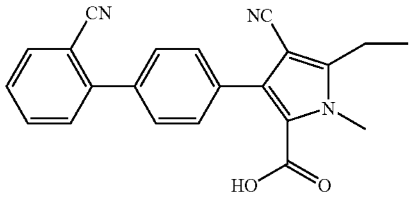

A 2 L round bottom flask equipped with mechanical stirring and a reflux condenser is charged with ethyl 4-cyano-3-[4-(2-cyanophenyl)phenyl]-5-ethyl-1-methylpyrrole-2-carboxylate (67.0 g, 175 mmol, 1.00 eq., prepared in example E-121a or E-121b), ethanol (670 mL) and 1N aqueous NaOH (215 mL, 215 mmol, 1.23 eq.). The resulting slurry is heated to reflux and is maintained at reflux for 50 min. To the clear homogeneous solution is added 670 mL water and 13.3 g Darco (activated carbon) and the mixture is stirred for 20 min. The mixture is filtered through a glass fiber filter with a ¾" bed of Hyflo filter aid. The cake is rinsed with water (2×100 mL) and the combined filtrate is acidified to pH 2 with 5 N aqueous HCl (~75 mL). The resulting slurry is stirred for about 1 hr, then the white solids are collected by filtration. The material is air dried under vacuum for 3 hr, then slurried in a mixture of 670 mL water and 67 mL acetone at 40° C. After 15 hr, the heat is removed and the solution is allowed to cool slowly to ambient temperature (~3 hr). The slurry is filtered to provide 186 g of wet material. The wet material is placed in a vacuum oven at 50° C. for approximately 24 hr to provide the title compound (58.3 g, 164 mmol, 93.8% yield, 97.6% purity by HPLC area %). Melting temperature (onset-maximum)= 191.97-194.18° C.; Enthalpy of fusion: 94.32 J/g; Elemental Analysis: Theoretical; C: 74.3516 H, 4.8215 N: 11.8233. Found: C: 74.19 H: 4.74 N: 11.77.

EXAMPLE A-75c

Additional Preparation of 4-cyano-3-[4-(2-cyanophenyl)phenyl]-5-ethyl-1-methylpyrrole-2-carboxylic acid

Preparation of ethyl 3-(4-bromophenyl)-3-oxopropanoate

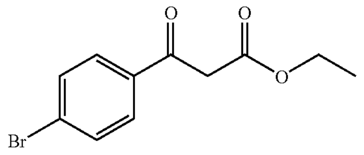

Step A: Under inert an atmosphere, charge a 400 L vessel with 4-bromoacetophenone (14.625 kg, 73.48 mol, 1 eq) at an internal temperature of 20° C. Add THF (4 L) and stir the resulting solution overnight at internal temperature of 15° C. Transfer the solution into a barrel. Charge the emptied vessel with potassium tert-butoxide (18.13 kg, 161.66 mol, 2.2 eq) and THF (116 L) at an internal temperature of 18° C. To this solution, add diethyl carbonate (18 L, 154.31 mol, 2.1 eq) at an internal temperature of 15 to 21° C. during 30 min. Heat the resulting mixture to an internal temperature of 38° C. Add the bromoacetophenone solution during 35 min and stir the mixture for additional 3 h. Then cool the reaction mixture to an internal temperature of 1° C. over 30 min and quench by the addition of 50% aqueous acetic acid (25 L) within 1 h. Heat the reaction mixture to an internal temperature of 20° C. and add water (51 L) and MTBE (60 L). Extract the aqueous layer with MTBE (44 L) and combine the organic layers. Wash the combined organic layers with saturated aqueous sodium bicarbonate solution (73 L) and then with semi saturated brine (74 L). Reduce the volume of the organic solution by distillation (jacket temperature=50° C., pressure<220 mbar) to 27% of starting volume. Add THF (44 L) and distill the volume.

Preparation of ethyl 3-(4-bromophenyl)-2-(hydroxyamino)-3-oxopropanoate

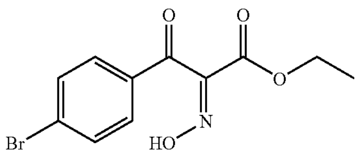

Step B: To the solution of ethyl 3-(4-bromophenyl)-3-oxopropanoate in THF (prepared in step A above), add acetic acid (160 L) and water (73 L) at an internal temperature of 8° C. To this mixture, add a solution of sodium nitrite (6.35 kg, 92.00 mol, 1.25 eq) in water (30 L) at an internal temperature of 6 to 9° C. during 90 min and stir at this temperature for 90 min. At an internal temperature of 4 to 7° C., add water (147 L) over 30 min to the reaction mixture and stir the resulting suspension for 30 min. Filter the suspension and wash the filter cake with water (59 L) and heptane (60 L). Dry the filter cake under a constant flow of nitrogen for 13 h to obtain the title compound: 18.731 kg according to loss of drying (23.044 kg wet); white powder; $^1H$ NMR (DMSO-$d_6$, 500.0 MHz): δ 1.22 (t, J=7.1 Hz, 3H), 4.27 (q, J=7.1 Hz, 2H), 7.75 (d, J=8.8 Hz, 2H, 7.83 (d, J=8.8 Hz, 2H), 13.18 (s, 1H); $^{13}C$ NMR (DMSO-$d_6$, 125.7 MHz): δ 14.36, 62.27, 129.68, 131.09, 133.08, 133.36, 148.44, 161.17, 191.08; Anal. Calcd for $C_{11}H_{10}BrNO_4$: C, 44.02; H, 3.36; Br, 26.63; N, 4.67; O, 21.32. Found: C, 43.98; H, 3.31; Br, 26.65; N, 4.59; MS (ES−) 299; IR (KBr): 3281, 3219, 3049, 2983, 2870, 1728, 1680, 1586, 1446, 1400, 1302, 1262, 1029, 944 $cm^{-1}$.

Preparation of Potassium Enolate

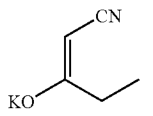

Step C': Dissolve potassium tert-butoxide (13.097 kg, 117.29 mol, 2.75 eq) in THF in a 100-L vessel. Add a mixture of ethyl propionate (12.2 L, 106.63 mol, 2.5 eq) and acetonitrile (6.68 L) over 45 min at an internal temperature of 18 to 21° C. and stir for 1 h at this temperature to provide the corresponding potassium enolate.

Preparation of ethyl 2-amino-3-(4-bromophenyl)-3-oxopropanoate

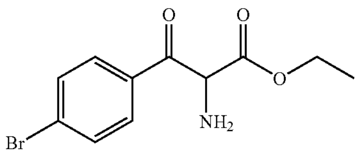

Step C'': Dissolve ethyl 3-(4-bromophenyl)-2-(hydroxyimino)-3-oxopropanoate (12.8 kg dry mass (15.75 kg wet), 42.65 mol, 1 eq, prepared in step B above) in ethanol (110 L) in a 400-L vessel at an internal temperature of 20° C. Cool the solution to an internal temperature of 1° C. over 20 min and add zinc dust (6.429 kg, 98.01 mol, 2.3 eq) portion-wise over 30 min at an internal temperature of 2 to 3° C. Prepare a solution of acetic acid (19.5 L), water (2.5 L), and ethanol (11.5 L) in a feeder. Add about 1 to 2% of the solution to the zinc suspension at 0° C. After 5 min, no exotherm is observed. Add another 1 to 2% of the solution. A rise of temperature could be observed. Add the rest of the solution, slowly in the beginning but continuously over 95 min at an internal temperature of −2 to 2° C. Cool the suspension to an internal temperature of −5° C. and stir for 15 min. to provide the title compound.

Preparation of ethyl 3-(4-bromophenyl)-4-cyano-5-ethylpyrrole-2-carboxylate

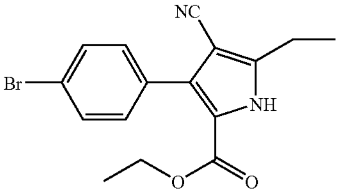

Step C: Transfer the potassium enolate suspension (prepared in step C' above) via a tube from the 100-L vessel and add into the 400-L vessel of the zinc suspension (prepared in step C" prepared above) during 35 min at an internal temperature of −9 to −2° C. Stir the reaction mixture at −4° C. for an 3 additional h. Warm it to an internal temperature of 20° C. during 10 h and stir at an internal temperature of 20° C. for an additional 3 h. Filter the suspension and wash the filter cake with ethanol (6 L). Clean the vessel from zinc traces using dilute aqueous hydrochloric acid. Concentrate the mother liquor by distillation (Jacket temp=55° C., pressure, 130 mbar) to 28% of its original volume. At an internal temperature of 35 to 38° C., add 2-propanol (66 L) over 10 min, followed by water (128 L) over 18 min. Stir the suspension for 10 min at this temperature, then cool to 25° C. over 4.5 h and then to 10° C. over 1.5 h. Stir at this temperature for 6 h. Filter the suspension and wash the filter cake with water (51 L). Dry the filter cake under a constant flow of nitrogen for 48 h to provide 12.48 kg of title compound according to LOD (20.264 kg wet); yellow crystals (LOD: 61.6%); yield 84% uncorrected. Dry a part of the wet material (5.82 kg) in a rotovap at a jacket temperature of 50° C. (pressure<80 mbar) for 7.5 h to obtain 3.641 kg of title compound as yellow crystals; melting point 209 to 211° C.; $^1$H NMR (DMSO-$d_6$, 500.0 MHz): δ 1.15 (t, J=7.1 Hz, 3H), 1.27 (t, J=7.7 Hz, 3H), 2.77 (q, J=7.1 Hz, 2H), 4.17 (q, J=7.7 Hz, 2H), 7.40 (d, J=8.8 Hz, 2H), 7.64 (d, J=8.8 Hz, 2H), 12.66 (bs, 1H); $^{13}$C NMR (DMSO-$d_6$, 125.7 MHz): δ13.65, 13.88, 60.16, 92.44, 115.41, 117.88, 121.25, 130.67, 131.25, 131.39, 131.84, 146.98, 159.41; Anal. Calcd for $C_{16}H_{15}BrN_2O_2$: C, 55.35; H, 4.35; Br, 23.01; N, 8.07; 0, 9.22. Found: C, 55.51; H, 4.37; Br, 22.99; N, 8.08; MS (ES+) 347; IR (KBr): 3283, 2217, 1659, 1519, 1484, 1424, 1282, 1187, 1010, 773 $^{cm-1}$ Preparation of ethyl 3-(4-bromophenyl)-4-cyano-5-ethyl-1-methylpyrrole-2-carboxylate

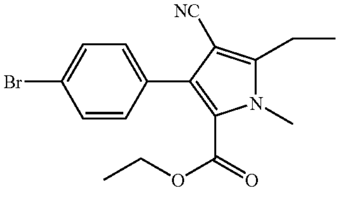

Step DI: Suspend ethyl 3-(4-bromophenyl)-4-cyano-5-ethylpyrrole-2-carboxylate (7.0 kg, 20.17 mol, 1 eq, prepared in step C above) in acetone (70 L) in a 100-L reactor. Add water (0.7 L), iodomethane (3.153 kg, 1.38 L, 22.21 mol, 1.1 eq), and potassium carbonate (5.58 kg, 40.37 mol, 2 eq). Stir the mixture at 30° C. for 14 h. Concentrate the reaction mixture by removing 41 L of solvent by distillation at 50° C. under reduced pressure. Add water (55 L) slowly over 45 min at 20-22° C. Cool the suspension to 0° C. within 1 h and stir for an additional h at this temperature. Collect the precipitate by filtration and wash with a cold (0-5° C.) mixture of acetone/water (1.2+3 L.) and then with water (4.2 L). Dry the product in 100-L rotary evaporator under reduced pressure at 60° C. for 66 h to obtain 7.133 kg of title compound as a beige powder (98% yield). $^1$H NMR ($CDCl_3$, 500.0 MHz): δ 1.08 (t, J=7.1 Hz, 3H), 1.34 (t, J=7.1 Hz, 3H), 2.88 (q, J 2 0=7.1 Hz, 2H), 3.92 (s, 3H), 4.13 (q, J=7.1 Hz, 2H), 7.26 (d, J=8.8 Hz, 2H), 7.54 (d, J=8.8 Hz, 2H); $^{13}$C NMR DMSO-$d_6$, 125.7 MHz): δ 12.96, 13.44, 18.79, 60.16, 92.04, 115.22, 119.96, 121.12, 130.73, 131.58, 131.86, 132.05, 147.87, 159.82; Anal. Calcd for $C_{17}H_{17}BrN_2O_2$: C, 56.52; H, 4.74; Br, 22.12; N, 7.75; 0, 8.86. Found: C, 56.32; H, 4.72; N, 7.73; IR (KBr): 3347, 2979, 2938, 2216, 1698, 1441, 1510, 1476, 1400, 1379, 1258, 1212, 1110, 771 $^{cm-1.}$ Additional Preparation of ethyl 3-(4-bromophenyl)-4-cyano-5-ethyl-1-methylpyrrole-2-carboxylate Step DII: In a 500 mL round bottom flask, a mixture of 4-cyano-5-ethyl-3-iodo-1-methyl-1H-pyrrole-2-carboxylic acid ethyl ester (20.00 g, 60.2 mmol, preparation 38), $Pd(OAc)_2$ (202 mg, 0.901 mmol, 0.0150 equiv)), $Ph_3P$ (479 mg, 1.83 mmol, 0.0304 equiv) and 1-hexylpyridinium chloride ($C_6$PyCl, 10.0 mL) is degassed 3 times by alternating house vacuum (15 seconds) and nitrogen. Degassed heptane (200 mL) is added and the mixture is kept under nitrogen and heated to ~80° C. (nearly to reflux). The resulting brown solution is allowed to cool to rt. 4-Bromophenylboronic acid (13.60 g, 67.66 mmol, 1.12 equiv) and degassed 2M $Na_2CO_3$ (60.0 mL, 120 mmol, 2.00 equiv) are added. The mixture is heated at 84.5° C. (reflux) for 5.5 h under nitrogen. Upon cooling to rt, water (200 mL) and EtOAc (50 mL) are added and stirred for 15 min. until the layers separate. The aqueous phase is extracted 3 times with EtOAc (100 mL each). The combined organic extracts are washed with water (100 mL) and brine (100 mL), dried $Na_2SO_4$), filtered and concentrated on the rotovap. This provides 21.3 g of crude title compound. 42 mL EtOH and 4 mL THF are added to this solid and the mixture is heated to 60° C. at which point everything dissolves. Eight mL water is added at 60° C. and the solution is allowed to slowly cool. At ~40° C. solids start to form. The mixture is cooled to 28° C. then placed in an ice bath to cool to 8° C. The solids are collected by filtration and rinsed three times with cold EtOH (25 mL each). The wet material is dried in a vacuum oven at 40° C. to provide 13.78 g of title compound (63% yield).

Preparation of ethyl 4-cyano-3-[4-(2-cyanophenyl)phenyl]-5-ethyl-1-methylpyrrole-2-carboxylate

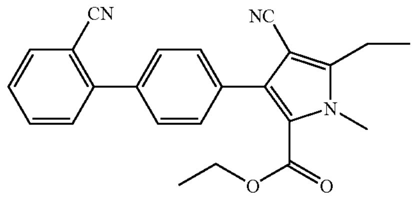

Step E: Charge a 100-L reactor with ethyl 3-(4-bromophenyl)-4-cyano-5-ethyl-1-methylpyrrole-2-carboxylate (6.0 kg, 16.61 mol, 1 eq, prepared in step DI above), potassium carbonate powder (5.050 kg, 36.54 mol, 2.2 eq), THF (63 L, peroxide test: <0.5 mg/L) and water (23 L). Degas the mixture by sparging with nitrogen for 20 min (oxygen sensor: 0.01 ppm). Continue sparging with argon for 24 min (oxygen sensor: 0.01 ppm). Heat the mixture to 30° C. and add 2-cyanophenylboronic acid (2.7 kg, 18.37 mol, 1.1 eq, prepared in preparation 53). Degas the mixture by continuing to sparging with argon for additional 10 min (oxygen sensor: 0.00 ppm). Add tri-t-butylphosphonium tetrafluoroborate (25.33 g, 0.087 mol, 0.005 eq) and tris(dibenzylideneacetone)dipalladium(0) (40.13 g, 0.044 mol, 0.0025 eq) at 30° C. Stir the resulting mixture for 50 min at 30° C. (an exotherm to 45° C. is observed). Separate the aqueous layer and extract with THF (17 L). Combine the organic layers (green) and filter through THF-wet (9 L) Celite® (2.21 kg). Wash the filter cake with THF (2×8.5 L). Filter the combined organic solution through a charcoal inline filter element. Change the filter element after the first half of the solution. Rinse the filter elements twice with THF (9 L and 11 L). Concentrate the resulting clear orange solution (133 L). Concentrate at reduced pressure (50° C. jacket temperature) to remove 50 L of the solvent. Add a solution of potassium carbonate powder (233.9 g) in water (23 L) to the residual mixture. Continue distillation until the THF is removed and the distillation ceases at 50° C. jacket temperature, 80 mbar pressure. Cool the suspension to 20-22° C. in 15 min and stir for additional 25 min. Collect the product by filtration, wash with water (2×8.5 L), and dry at 50° C. under reduced pressure to obtain 6.112 kg of crude title compound. Suspend the crude title compound in ethyl acetate (29 L). Heat the suspension to reflux for 1 h. Add heptane (30 L) over a period of 35 min at reflux temperature. Cool the suspension in 90 min to 0° C. and stir at that temperature for 30 min. Collect the product by filtration. Wash with a cold (0° C.) mixture of ethyl acetate (6 L) and heptane (6 L). Dry at 50° C. in a rotary evaporator under reduced pressure for 9 h to obtain 5.862 kg of title compound as a slightly yellow powder (92% yield). $^1$H NMR ($CDCl_3$, 500.0 MHz): δ 1.08 (t, J=7.1 Hz, 3H), 1.37 (t, J=7.7 Hz, 3H), 2.91 (q, J=7.1 Hz, 2H), 3.96 (s, 3H), 4.16 (q, J=7.7 Hz, 2H), 7.48-7.53 (m, 3H), 7.60-7.64 (m, 3H), 7.69-7.73 (td, 1H), 7.81-7.83 (dd, 1H); $^{13}$C NMR (DMSO-$d_6$, 125.7 MHz): δ 12.99, 13.79, 18.81, 33.47, 60.21, 92.04, 110.15, 115.40, 118.44, 120.15, 128.09, 128.25, 129.78, 130.09, 132.33, 133.21, 133.51, 133.90, 137.11, 144.03, 147.90, 159.99. Anal Calcd for $C_{24}H_{21}N_3O_2$: C, 75.17; H, 5.52; N, 10.96. Found: C, 75.26; H, 5.48; N, 11.08. IR (KBr): 3067, 2978, 2901, 2232, 2218, 1693, 1486, 1476, 1396, 1385, 1268, 1249, 1211, 1160, 1104, 756 $^{cm-1.}$ Preparation of Final Title Compound Step F: Charge a 100-L reactor with lithium hydroxide.x$H_2O$ (0.755 kg, 17.99 mol, 1.2 eq) and water (9 L). Add THF (23 L), methanol (6 L), and ethyl 4-cyano-3-[4-(2-cyanophenyl)phenyl]-5-ethyl-1-methylpyrrole-2-carboxylate (5.722 kg, 15.05 mol, 1 eq, prepared in step E above). Stir the suspension for 24 h at 23° C. to obtain a homogeneous solution. Filter the reaction mixture through a charcoal inline filter element. Rinse the reactor and the filter element with water (2×6 L). Cool the mother liquor to 16° C. and slowly acidify with 1M HCl (27 L, 1.8 eq) over 5 h. Filter the white suspension. Wash the filter cake with water (4×29 L)—slurry the filter cake each time to remove lithium salts. Dry the product at 35° C. under reduced pressure on the rotary evaporator for 9 h. to obtain 4.988 kg of final title compound, 4-cyano-3-[4-(2-cyanophenyl)phenyl]-5-ethyl-1-methylpyrrole-2-carboxylic acid, as a white powder; XRPD reveals mostly preferred polymorph Form I and a trace of polymorph Form II.

Two polymorphs of 4-cyano-3-[4-(2-cyanophenyl)phenyl]-5-ethyl-1-methylpyrrole-2-carboxylic acid, as referred to above, are designated as Form I and Form II. These two polymorphs are enantiotropically related with a transition temperature of approximately 45° C. below which Form I is thermodynamically more stable and above which Form II is thermodynamically more stable.

To ensure that pure phases of each form are obtained, addition of slurry steps are recommended for quantitative conversion to the desired polymorphic form (slurrying below the transition temperature for quantitative conversion to Form I and above the transition temperature for quantitative conversion to Form II). For example, for quantitative conversion to Form I, Form I (50 mg) and Form II (50 mg) are physically mixed and slurried in acetone-water (5 mL, 2:1 v/v) at 40° C. for approximately 4 days. For quantitative conversion to Form II, Form I (115 mg) and Form I (115 mg) are physically mixed and slurried in acetone-water (5 mL, 2:1 v/v) at 50° C. for approximately 4 days.

Polymorph control of the final title compound: Suspend the 4-cyano-3-[4-(2-cyanophenyl)phenyl]-5-ethyl-1-methylpyrrole-2-carboxylic acid prepared directly above in acetone (45 L) and water (5 L). Heat the suspension to 40° C. and stir at this temperature for 63 h. Add water (41 L) to the suspension slowly over 8 h at an inner temperature of 38-39° C. After the addition, cool the suspension to 20° C. over 90 min and stir for additional 20 min at this temperature. Collect the crystals by filtration and pre-dry on the nutsch in a flow of nitrogen for 14 h. Perform final drying on a 100-L rotary evaporator at 35° C. and 1 mbar for 5 h to obtain 4.852 kg of the final title compound as off-white powder; (91% yield) as substantially pure Form I polymorph.

Particle size control of the final title compound: Jet Mill 4.774 kg of the final title compound, Form I polymorph, prepared directly above, using a setting that gives a particle size (D90) of less than 12 microns. After micronization, homogenize by drum rolling overnight for 10 h to obtain 4.568 kg of final title compound with particle size: bimodal distribution with D90 of 20.1 μm. Repeat micronization using the same settings to obtain 4.072 kg of final title compound with particle size: unimodal distribution with D90 of 9.74 μm. $^1$H NMR (DMSO-$d_6$, 500.0 MHz): δ 1.26 (t, J=7.7 Hz, 3H), 2.87 (q, J=7.7 Hz, 2H), 3.88 (s, 3H), 7.52 (d, J=8.2 Hz, 2H), 7.62 (t, 7.7 Hz, 1H), 7.65 (d, J=7.7 Hz, 2H), 7.71 (d, J=7.6 Hz, 1H), 7.83 (t, J=7.7 Hz, 1H), 7.99 (d, J=7.6 Hz, 1H), 12.85 (s, 1H); $^{13}$C NMR (DMSO-$d_6$, 125.7 MHz): δ 13.01, 18.83, 92.03, 110.00, 115.58, 118.57, 120.85, 128.05, 128.22, 129.90, 130.16, 131.82, 133.45, 133.53, 133.98, 136.85, 143.95, 147.58, 161.44. Anal Calcd for $C_{22}H_{17}N_3O_2$: C, 74.35; H, 4.82; N, 11.82. Found: C, 74.10; H, 4.88; N, 11.75. IR (KBr): 2938, 2225, 1654, 1476, 1440, 1356, 1280, 1252, 1166, 763 $^{cm-1.}$ EXAMPLE A-75d Preparation of 4-cyano-3-[4-(2-cyanophenyl phenyl]-5-ethyl-1-methylpyrrole-2-carboxylic acid, diethanolamine salt 4-Cyano-3-[4-(2-cyanophenyl)phenyl]-5-ethyl-1-methylpyrrole-2-carboxylic acid (109 mg) is weighed into a scintillation vial. The sample is heated to about 60° C. with stirring in 2 mL of acetone. With a suspension present, a 1 molar equivalence of diethanolamine in 1 mL of methanol is added. Immediately the batch becomes clear. The clear solution is allowed to cool to room temperature. After overnight stirring, the suspension is then isolated by vacuum filtration and the solid is allowed to air dry to provide the title compound.

EXAMPLE A-75e

Preparation of 4-cyano-3-[4-(2-cyanophenyl)phenyl]-5-ethyl-1-methylpyrrole-2-carboxylic acid, diethylamine salt 4-Cyano-3-[4-(2-cyanophenyl)phenyl]-5-ethyl-1-methylpyrrole-2-carboxylic acid (103 mg) is weighed into a scintillation vial. The sample is heated to about 60° C. with stirring in 2 mL of acetone. With a suspension present, a 1 molar equivalence of diethylamine in 1 mL of methanol is added. Immediately the batch becomes clear. After a few minutes, precipitation occurs. The suspension is allowed to stir at temperature for a few hours and then cooled to room temperature. After overnight stirring, the suspension is isolated by vacuum filtration and the solid is allowed to air dry to provide the title compound.

EXAMPLE A-75f

Preparation of 4-cyano-3-[4-(2-cyanophenyl)phenyl]-5-ethyl-1-methylpyrrole-2-carboxylic acids, calcium salt 4-Cyano-3-[4-(2-cyanophenyl)phenyl]-5-ethyl-1-methylpyrrole-2-carboxylic acid (116 mg) is weighed into a scintillation vial. The sample is heated to about 60° C. with stirring in 3 mL of methanol. A 1 molar equivalence of NaOH is added, followed by a 0.5 molar equivalence of calcium acetate to provide an ion exchange. Water is added drop wise until a nice suspension is observed. The solvent system is allowed to stir at temperature for a few hours and then cooled to room temperature. After overnight stirring, the suspension is isolated by vacuum filtration and the solid is allowed to air dry to provide the title compound.

More specifically, procedures for preparing various polymorphs and solvates of 4-cyano-3-[4-(2-cyanophenyl)phenyl]-5-ethyl-1-methylpyrrole-2-carboxylic acid are set forth below in Examples A-75I through A-75XI.

EXAMPLE A-75I

Preparation of Form I of 4-cyano-3-[4-(2-cyanophenyl)phenyl]-5-ethyl-1-methylpyrrole-2-carboxylic acid Add ethyl 4-cyano-3-[4-(2-cyanophenyl)phenyl]-5-ethyl-1-methylpyrrole-2-carboxylate to a round bottom flask with a nitrogen inlet, thermocouple and magnetic stirring. Add THF (4.0 volumes). MeOH (1.0 volume) and 1.20 equiv. of 2N LiOH and stir the reaction mixture at RT. After stirring for 24 h no starting material remains. Add Darco (40 w %) and stir the slurry for 30 min. Then filter the reaction mixture through a plug of Hyflo Super Cel® (about ½" thick) and rinse 2 times with 1 volume of water. Filter this initial filtrate again through a Whatman® GF/F filter to collect small black particulates that escape through the first filtration. Acidify the filtrate slowly with 1 N HCl (1.5 equiv as compared to the LiOH added) {slow addition is very important for polymorph control—about 90 min. addition on 100 g scale}. Stir the milky suspension for 15 min. Filter the thick suspension through a glass frit to obtain a wet solid. Wash this wet solid 4 times with 5 volumes of water (breaking vacuum and stirring the solids with the water each time). Place the wet solid in a vacuum oven at 40° C. overnight (~15 h) to provide the title compound (92.2% yield).

EXAMPLE A-75II

Preparation of Form I of 4-cyano-3-[4-(2-cyanophenyl)phenyl]-5-ethyl-1-methylpyrrole-2-carboxylic acid Add 4-cyano-3-[4-(2-cyanophenyl)phenyl]-5-ethyl-1-methylpyrrole-2-carboxylic acid to a round bottom flask with a nitrogen inlet, thermocouple and magnetic stirring. Add acetone (9 volumes) and water (1 volume) and heat the mixture to 40° C. If the initially isolated solid is not pure Form I, hold the slurry at 40° C. until only Form I is present, as detected by XRPD. At 40° C., add water (8 volumes) slowly (0.77 mL/min) to keep the temperature at 40° C. Water addition must be slow to ensure that only Form I comes out of solution. After the water addition is complete, remove the heat and allow the slurry to slowly cool to ambient temperature. Once the slurry reaches ambient temperature, collect the solid by filtration to provide the title compound (90-95% recovery). It is important not to rinse the solids because this can induce Form II formation if any solids are crashed out of trap solvent.

EXAMPLE A-75III

Preparation of Form II of 4-cyano-3-[4-(2-cyanophenyl)phenyl]-5-ethyl-1-methylpyrrole-2-carboxylic acid Form II of 4-cyano-3-[4-(2-cyanophenyl)phenyl]-5-ethyl-1-methylpyrrole-2-carboxylic acid can be crystallized directly at high temperatures (~above 70° C.) from solvents like isopropanol/heptane and acetonitrile/water. For example, Form II of 4-cyano-3-[4-(2-cyanophenyl)phenyl]-5-ethyl-1-methylpyrrole-2-carboxylic acid can be prepared as follows: Form I of 4-cyano-3-[4-(2-cyanophenyl)phenyl]-5-ethyl-1-methylpyrrole-2-carboxylic acid (200 mg) is dissolved in isopropanol (8 mL) at approximately 73° C. At 81° C., heptane (15 mL) is added gradually. Crystallization occurs with the addition of heptane (approximately 3 mL) at approximately 79° C. The title compound is isolated from the hot slurry by vacuum filtration.

EXAMPLE A-75IV

Preparation of Form II of 4-cyano-3-[4-(2-cyanophenyl)phenyl]-5-ethyl-1-methylpyrrole-2-carboxylic acid Form I of 4-cyano-3-[4-(2-cyanophenyl)phenyl]-5-ethyl-1-methylpyrrole-2-carboxylic acid (200 mg) is dissolved in acetonitrile (4 mL) at approximately 79° C. At 81° C., water (15 mL) is added gradually. Crystallization occurs with the addition of approximately 6 mL of water at approximately 79° C. The title compound is isolated from the hot slurry by vacuum filtration.

EXAMPLE A-75V

Preparation of Form II of 4-cyano-3-[4-(2-cyanophenyl)phenyl]-5-ethyl-1-methylpyrrole-2-carboxylic acid Form I of 4-cyano-3-[4-(2-cyanophenyl)phenyl]-5-ethyl-1-methylpyrrole-2-carboxylic acid (400 mg) is dissolved in isopropanol (16 mL) at approximately 73° C. At 82° C. heptane (20 mL) is added gradually. Crystallization occurs with the addition of approximately 20 mL heptane at approximately 76° C. The title compound is isolated from the hot slurry by vacuum filtration.

EXAMPLE A-75I

Preparation of Form II of 4-cyano-3-[4-(2-cyanophenyl)phenyl]-5-ethyl-1-methylpyrrole-2-carboxylic acid Combine 4-cyano-3-[4-(2-cyanophenyl)phenyl]-5-ethyl-1-methylpyrrole-2-carboxylic acid (3.1144 g) with n-propanol (25 mL) and heat the mixture to reflux. Add more n-propanol to obtain a solution at reflux (6 mL additional n-propanol is added, with a total of 31 mL n-propanol being used). Cool the reaction to below reflux, and allow crystallization occur. Cool the mixture slowly to rt, then to 0° C. and hold at that temperature for 1 h. Filter and rinse with cold (0° C.) n-propanol, and dry in vacuo at 60° C. to afford the title compound as a crystalline solid (2.9286 g, 94%).

EXAMPLE A-75VII

Preparation of Form III of 4-cyano-3-[4-(2-cyanophenyl)phenyl]-5-ethyl-1-methylpyrrole-2-carboxylic acid Ethyl 4-cyano-3-[4-(2-cyanophenyl)phenyl]-5-ethyl-1-methylpyrrole-2-carboxylate is hydrolyzed using LiOH (1.2eqs) in THF (10 vols), methanol (2 vols) and water (3 vols). After the starting ethyl ester and intermediate methyl ester (from transesterification with the methanol) are consumed, the reaction mixture is treated with Darco (20% wt. load) and stirred at room temperature for 0.5 h. The mixture is filtered over a pad of Hi-Flo and the filtrate refiltered across GFF paper to ensure complete Darco removal. The filtrate is concentrated in vacuo to remove the THF, methanol and ethanol, leaving an aqueous slurry of the carboxylate. This lithium carboxylate is dissolved in ethanol (6 vols) and treated with acetic acid (1.5 eqs). The resulting slurry is stirred at room temperature for 0.5 h. and then filtered. The solids are rinsed with 4×10 vols. water and vacuum dried at room temperature to provide the title compound.

EXAMPLE A-75VIII

Preparation of Form IV of 4-cyano-3-[4-(2-cyanophenyl)phenyl]-5-ethyl-1-methylpyrrole-2-carboxylic acid 4-Cyano-3-[4-(2-cyanophenyl)phenyl]-5-ethyl-1-methylpyrrole-2-carboxylic acid (2.0 g) is dissolved in a mixture of acetone (300 mL) and water (200 mL) at RT and lyophilized to produce a fluffy, fairly static solid of title compound.

EXAMPLE A-75IX

Preparation of 4-cyano-3-[4-(2-cyanophenyl)phenyl]-5-ethyl-1-methylpyrrole-2-carboxylic acid monodimethylformamide solvate 4-Cyano-3-[4-(2-cyanophenyl)phenyl]-5-ethyl-1-methylpyrrole-2-carboxylic acid (279 mg) is dissolved in a 1:1:1 v/v/v mixture (6 mL) of DMF/MIPK/acetone at RT. Heptane (12 mL) is added to the clear solution. After the solution is stirred for about 24 hours, the solid is isolated by vacuum filtration to provide the title compound.

Alternatively, 4-cyano-3-[4-(2-cyanophenyl)phenyl]-5-ethyl-1-methylpyrrole-2-carboxylic acid (200 mg) is dissolved in a 1:1 v/v mixture (2 mL) of DMF/MIPK at RT. Addition of heptane (2 mL) causes phase separation. A homogenous solution is formed with the addition of acetone (1 mL). Crystallization occurs with the addition of heptane (0.5 mL). A total of about 18 mL of heptane is then added to increase the yield, and the title compound is isolated as a granular solid.

EXAMPLE A-75X

Preparation of 4-cyano-3-[4-(2-cyanophenyl)phenyl]-5-ethyl-1-methylpyrrole-2-carboxylic acid dimethylsulfoxide solvate 4-Cyano-3-[4-(2-cyanophenyl)phenyl]-5-ethyl-1-methylpyrrole-2-carboxylic acid, Form I (300 mg) is slurried at RT in a 1:1 v/v mixture (8 mL) of DMSO-$H_2O$ for approximately 22 hours, yielding the title compound as a clumpy, granular solid.

EXAMPLE A-75XI

Preparation of 4-cyano-3-[4-(2-cyanophenyl)phenyl]-5-ethyl-1-methylpyrrole-2-carboxylic acid hemidimethylsulfoxide solvate 4-Cyano-3-[4-(2-cyanophenyl)phenyl]-5-ethyl-1-methylpyrrole-2-carboxylic acid (200 mg) is dissolved in DMSO (1 mL) at RT. Crystallization is observed with the addition of $H_2O$ (~1 mL). A total of 10 mL of $H_2O$ are added. Vacuum filtration provides the title compound as a clumpy solid.

X-Ray Powder Diffraction (XRPD) Data and Solid State NMR (ss NMR) Data for 4-Cyano-3-[4-(2-cyanophenyl)phenyl]-5-ethyl-1-methylpyrrole-2-carboxylic acid, Forms I and II Two polymorphs of 4-cyano-3-[4-(2-cyanophenyl)phenyl]-5-ethyl-1-methylpyrrole-2-carboxylic acid, designated Form I and Form II, are characterized below.

Using XRPD, Form I of 4-cyano-3-[4-(2-cyanophenyl)phenyl]-5-ethyl-1-methylpyrrole-2-carboxylic acid may be characterized by the presence of diagnostic peaks at 11.0° and 28.8° in 2-theta. Additionally, the presence of peaks at 7.6°, 12.2°, 22.5° and 25.7° in 2-theta are also characteristic of Form I. The above patterns are obtained from a copper radiation source ($\lambda$=1.54056 Å) at ambient temperature. The following table provides additional diagnostic peaks in 2-theta and relative intensities for Form I.

XRPD data for Form I of 4-cyano-3-[4-(2-cyanophenyl)phenyl]-5-ethyl-1-methylpyrrole-2-carboxylic acid

| Angle (°2-theta) | $I/I_0$ (%) |
|---|---|
| 7.6 | 87.0 |
| 11.0 | 96.3 |
| 12.2 | 82.5 |
| 14.2 | 11.8 |
| 15.3 | 5.1 |

-continued

| Angle (°2-theta) | $I/I_0$ (%) |
|---|---|
| 16.1 | 14.1 |
| 16.6 | 4.8 |
| 17.9 | 18.2 |
| 19.3 | 6.3 |
| 20.0 | 4.0 |
| 20.6 | 8.4 |
| 21.6 | 14.0 |
| 22.5 | 45.0 |
| 24.3 | 4.9 |
| 25.7 | 100.0 |
| 27.3 | 13.8 |
| 27.8 | 8.2 |
| 28.8 | 28.5 |

Using XRPD, Form II may be identified by the presence of diagnostic peaks at 8.3°, 10.0°, 16.4°, and 29.4° in 2-theta. Additionally, the presence of peaks at 7.5°, 12.3° and 22.7° in 2-theta are also characteristic of Form II. The above patterns are obtained from a copper radiation source (λ=1.54056 Å) at ambient temperature. The following table provides additional diagnostic peaks in 2-theta and relative intensities for Form II.

XRPD data for form II of 4-cyano-3-[4-(2-cyanophenyl)phenyl]-5-ethyl-1-methylpyrrole-2-carboxylic acid

| Angle (°2-theta) | $I/I_0$ (%) |
|---|---|
| 7.5 | 19.8 |
| 8.3 | 9.4 |
| 10.0 | 16.7 |
| 12.3 | 82.5 |
| 14.5 | 5.3 |
| 15.1 | 11.2 |
| 15.5 | 5.7 |
| 15.7 | 5.6 |
| 16.4 | 23.3 |
| 17.3 | 5.7 |
| 20.3 | 13.0 |
| 21.9 | 13.3 |
| 22.7 | 100.0 |
| 25.2 | 9.7 |
| 25.8 | 9.4 |
| 29.4 | 20.7 |

For reference to the ±0.1° in 2-theta error in the XRPD data, see e.g., The United States Pharmacopeia No. 23, National Formulary No. 18, pages 1843-1844, 1995. This reference also provides information regarding the effects of preferred orientation, i.e. while relative peak intensities may vary due to changes in crystal habit; the characteristic peak positions of the polymorph remain unchanged.

The above XRPD patterns are obtained on a Siemens D5000 X-ray powder diffractometer, equipped with a CuKα source (λ=1.54056 Å) and a Kevex solid-state Si (Li) detector, operating at 50 kV and 40 mA. Each sample is scanned between 3° and 40° in 2-theta, with a step size of 0.02 in 2-theta and a minimum scan rate of 9.0 seconds/step, with 1 mm divergence and receiving slits and a 0.1 mm detector slit. The dry powder is packed onto a low background sample holder and a smooth surface is obtained using a glass slide. Two patterns are collected, the first as received, and the second with NIST standard mica 675 to calculate actual d-values.

Forms I and II of 4-cyano-3-[4-(2-cyanophenyl)phenyl]-5-ethyl-1-methylpyrrole-2-carboxylic acid are also analyzed by solid-state $^{13}C$ nuclear magnetic resonance (ss NMR) spectroscopy.

The spectrum for Form I of 4-cyano-3-[4-(2-cyanophenyl)phenyl]-5-ethyl-1-methylpyrrole-2-carboxylic acid is comprised of isotropic diagnostic peaks at the following chemical shifts: 113.3, 125.6, 132.7, 139.1 and 147.2 ppm. Additionally, isotropic peaks at the following chemical shifts (118.1, 129.5, 136.9 and 144.0 ppm) are also characteristic of Form I.

The spectrum for Form II of 4-cyano-3-[4-(2-cyanophenyl)phenyl]-5-ethyl-1-methylpyrrole-2-carboxylic acid is comprised of isotropic diagnostic peaks at the following chemical shifts: 110.6, 134.1 and 150.8 ppm. Additionally, isotropic peaks at the following chemical shifts (118.3, 129.8, 130.8, 137.3 and 144.0 ppm) are also characteristic of Form II.

$^{13}C$ Cross polarization/magic angle spinning (CP/MAS) NMR (solid-state NMR or SSNMR) spectra are obtained using a Varian Unity Inova 400 MHz NMR spectrometer operating at a carbon frequency of 100.578 MHz and equipped with a complete solids accessory and a Chemagnetics 4.0 mm T3 probe. Ramped-amplitude cross polarization (RAMP-CP) at 62 kHz and TPPM decoupling at 70 kHz are used. Acquisition parameters are as follows: 90° proton r.f. pulse width 4.0 μs, contact time 3.0 ms, pulse repetition time 10 s, MAS frequency 10 kHz, spectral width 50 kHz, and acquisition time 50 ms. Chemical shifts are referenced to the methyl group of hexamethylbenzene (δ=17.3 ppm) by sample replacement.

Prepare the following carboxylic acids listed in Table A-2 in a manner analogous to the procedure set forth in Method TII.

TABLE A-2

| Ex. | Structure | Data | S.M. |
|---|---|---|---|
| A-212 | 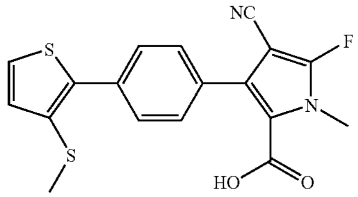 | mass spectrum (m/e) 373.0 (M + 1) | E-259 |

TABLE A-2-continued
| Ex. | Structure | Data | S.M. |
|---|---|---|---|
| A-213 | 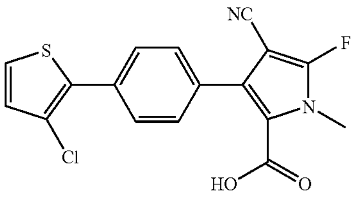 | mass spectrum (m/e): 378.0 (M + 18) | E-260 |
| A-214 | 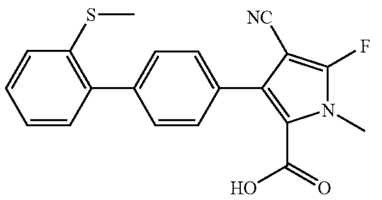 | mass spectrum (m/e): 365.0 (M − 1) | E-261 |
| A-215 | 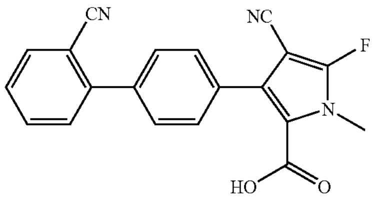 | mass spectrum (m/e): 344.0 (M − 1) | E-262 |
| A-216 | 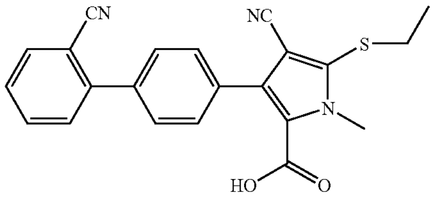 | mass spectrum (m/e): 386.0 (M − 1) | E-268 |
| A-217 | 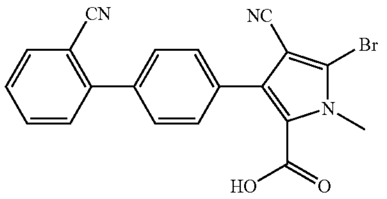 | mass spectrum (m/e): 404.0 (M − 1) | E-266 |
| A-218 | 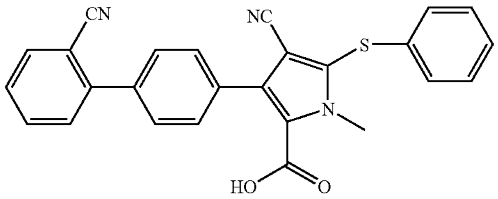 | mass spectrum (m/e): 436.1 (M) | E-269 |
| A-219 | 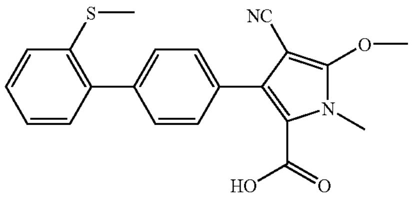 | mass spectrum (m/e): 377.2 (M − 1) | E-261 |

TABLE A-2-continued
| Ex. | Structure | Data | S.M. |
|---|---|---|---|
| A-220 | 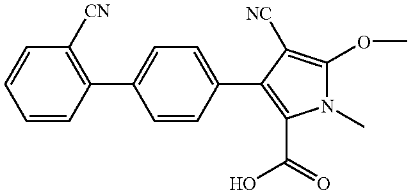 | mass spectrum (m/e): 356.1 (M − 1) | E-262 |
| A-221 | 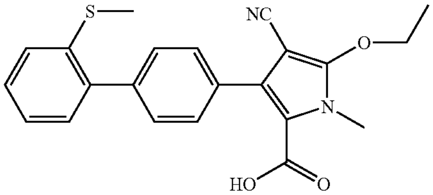 | mass spectrum (m/e): 393.1 (M − 1). $R_f$=0.2(10% MeOH in methylene chloride). | E-261 |
| A-222 | 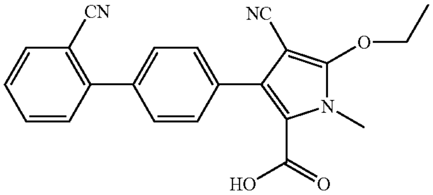 | mass spectrum (m/e): 370.0 (M − 1). $R_f$=0.2(10% MeOH in methylene chloride). | E-262 |
| A-223 | 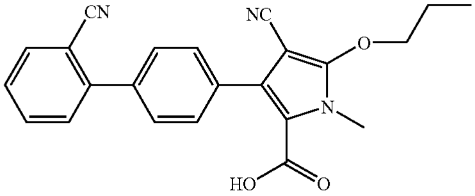 | mass spectrum (m/e): 384.1 (M − 1). $R_f$=0.3(10% MeOH in methylene chloride). | E-262 |
| A-224 | 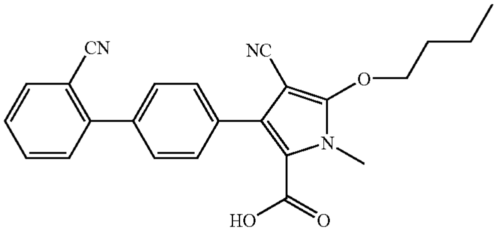 | mass spectrum (m/e): 398.1 (M − 1). $R_f$=0.4(10% MeOH in methylene chloride). | E-262 |
| A-225 | 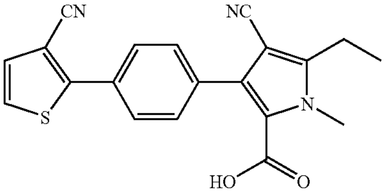 | mass spectrum (m/e): 360.0 (M − 1) | E-264 |
| A-226 | 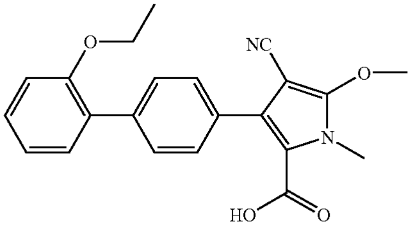 | mass spectrum (m/e): 375.2 (M − 1) | E-263 |

TABLE A-2-continued

| Ex. | Structure | Data | S.M. |
|---|---|---|---|
| A-228 | 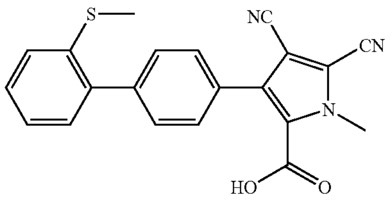 | Mass spectrum (m/e): 374.0 (M + 1). | E-270 |
| A-229 | 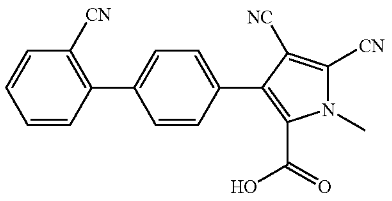 | Mass spectrum (m/e): 351.0 (M − 1). | E-271 |

Prepare the following carboxylic acids listed in Table A-3 in a manner analogous to the procedure set forth in Method TIII.

TABLE A-3

| Ex. | Structure | Data | S.M. |
|---|---|---|---|
| A-230 | 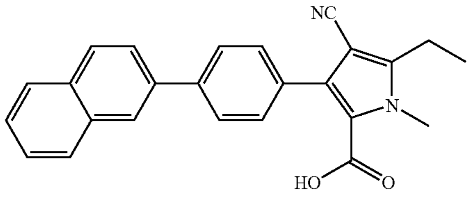 | MS (m/e): 379 (M − 1) | E-44 |
| A-231 | 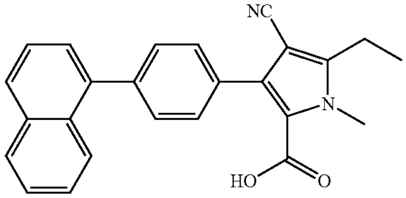 | MS (m/e): 381 (M + 1) | E-45 |

Prepare the following carboxylic acids listed in Table A-4 in a manner analogous to the procedure set forth in Method TIV.

TABLE A-4

| Ex. | Structure | Data | S.M. |
|---|---|---|---|
| A-232 | 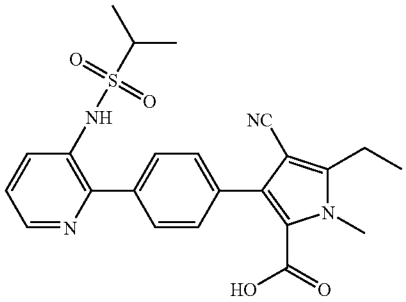 | MS (m/e): 453.1 (M + 1) | E-206 |

TABLE A-4-continued

| Ex. | Structure | Data | S.M. |
|---|---|---|---|
| A-233 | 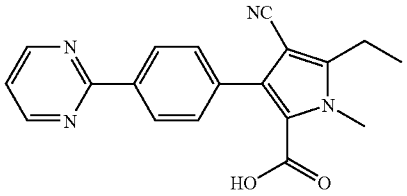 | MS (m/e): 333.1 (M + 1) | E-39 |
| A-234 | 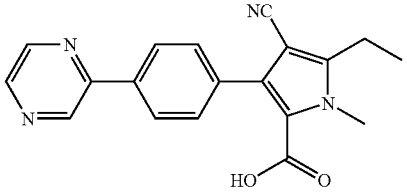 | MS (m/e): 333.1 (M + 1) | E-40 |
| A-235 | 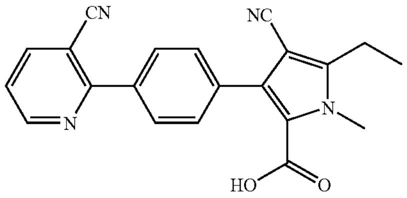 | MS (m/e): 357.1 (M + 1) | E-41 |
| A-236 | 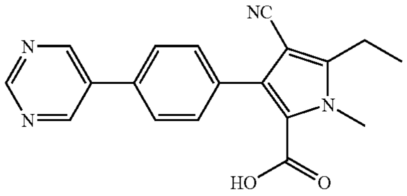 | MS (m/e): 333.1 (M + 1) | E-42 |

EXAMPLE A-237

Preparation of 4-cyano-1-methyl-3-[4-(phenylmethoxy)phenyl]-5-(trifluoromethyl)pyrrole-2-carboxylic acid

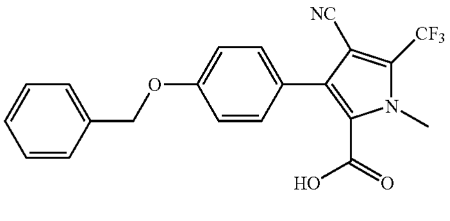

Preparation of ethyl 4-cyano-5-iodo-1-methyl-3-[4-(phenylmethoxy)phenyl]pyrrole-2-carboxylate

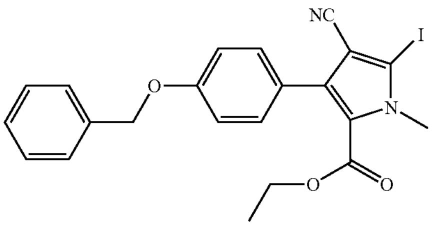

Scheme XXIII, step D: Prepare the title compound in a manner analogous to the procedures set forth in Schemes VIII or XVI: To a solution of -(4-benzyloxy-phenyl)-4-cyano-1-methyl-1H-pyrrole-2-carboxylic acid ethyl ester (11.0 mmol, prepared in example E-6a or E-6b) in methylene chloride in an ice bath, add N-iodo-succinamide (11.0 mmol). Allow the reaction to warm to room temperature and stir for 18 hours. Then wash reaction with water while extracting with methylene chloride. Dry the organic layer with sodium sulfate, filter, and concentrate in vacuo. Purify the residue on a prepacked silica column eluting with ethyl acetate and hexane to provide the title compound.

Preparation of ethyl 4-cyano-1-methyl-3-[4-(phenylmethoxy)phenyl]-5-(trifluoromethyl)pyrrole-2-carboxylate

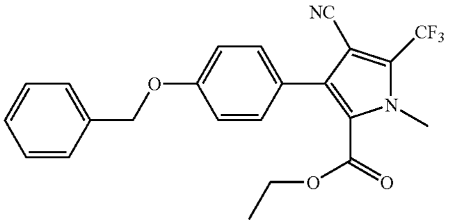

Scheme XXIII, step E: Place ethyl 4-cyano-5-iodo-1-methyl-3-[4-(phenylmethoxy)phenyl]pyrrole-2-carboxylate (10 mmol, prepared directly above), copper bromide (0.2 mmol), and methyl 2,2-difluoro-2-(fluorosulfonyl)acetate (2.0 mmol) in a round bottom flask and add dimethylformamide. Quickly heat the stirring reaction to reflux for 45 minutes after which time remove the heat and wash with water while extracting with ethyl acetate. Dry the organic extracts with sodium sulfate, filter, and concentrate in vacuo. Purify the residue via radial chromatography eluting with methylene chloride, ethyl acetate and hexane to provide the title compound.

Preparation of Final Title Compound

Scheme VI: To a solution of ethyl 4-cyano-1-methyl-3-[4-(phenylmethoxy)phenyl]-5-(trifluoromethyl)pyrrole-2-carboxylate, prepared directly above, (1.0 mmol) in 1:1 ethanol/THF, add 2N NaOH (4.0 mmol). Stir at room temperature for 1 hour before diluting in methylene chloride and washing with 1N hydrochloric acid. Concentrate the organic layer in vacuo. Purify the residue via radial chromatography eluting with acetic acid, ethyl acetate and hexane to provide the final title compound. MS (m/e): 418.1 (M+18) 399.0 (M−1); $^{1}$H NMR δ 13.59 (s, 1H), 7.47 (d, 2H, J=7.0 Hz), 7.39 (t, 2H, J=7.3 Hz), 7.35-7.28(m, 3H), 7.06 (d, 2H, J=8.8 Hz), 5.12 (s, 2H), 3.98 (s, 3H)

EXAMPLE A-238

Preparation of 4-cyano-1-methyl-3-[4-(2-methylthiophenyl)phenyl]-5-(trifluoromethyl)pyrrole-2-carboxylic acid

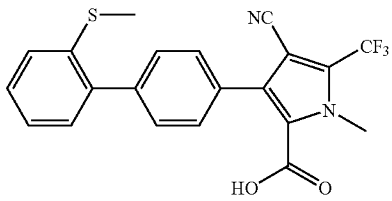

Preparation of ethyl 4-cyano-5-iodo-1-methyl-3-[4-(2-methylthiophenyl)phenyl]pyrrole-2-carboxylate

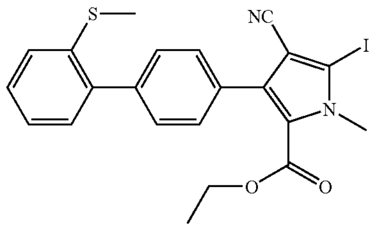

Scheme XXIII, step D: In a manner analogous to the procedure set forth in example A-237, the title compound is prepared by iodinating ethyl 4-cyano-1-methyl-3-[4-(2-methylthiophenyl)phenyl]pyrrole-2-carboxylate (prepared in example E-19) with N-iodo-succinamide.

Preparation of ethyl 4-cyano-1-methyl-3-[4-(2-methylthiophenyl)phenyl]-5-(trifluoromethyl)pyrrole-2-carboxylate

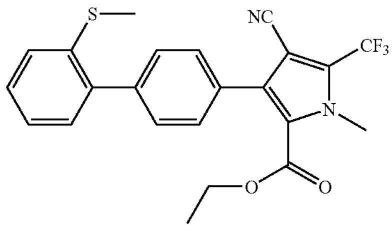

Scheme XXII, step E: In a manner analogous to the procedure set forth in example A-237, ethyl 4-cyano-5-iodo-1-methyl-3-[4-(2-methylthiophenyl)phenyl]pyrrole-2-carboxylate, prepared directly above, is treated with copper bromide and methyl 2,2-difluoro-2-(fluorosulfonyl)acetate (2.0 mmol) in DMF to provide the title compound.

Preparation of Final Title Compound

Scheme VI: In a manner analogous to the last step of example A-237, ethyl 4-cyano-1-methyl-3-[4-(2-methylthiophenyl)phenyl]-5-(trifluoromethyl)pyrrole-2-carboxylate, prepared directly above, is hydrolyzed to provide the final title compound.

MS (m/e): 417.0 (M+1) 434.0 (M+1) 415 (M−1); $^{1}$H NMR δ 7.36 (s, 4H), 7.31-7.25 (m, 2H), 7.15 (d, 2H, J=3.1 Hz), 3.92 (s, 3H), 2.29 (s, 3H).

EXAMPLE A-239

Preparation of 4-cyano-1-methyl-3-[4-(3-methylthio(2-thienyl))phenyl]-5-(trifluoromethyl)pyrrole-2-carboxylic acid

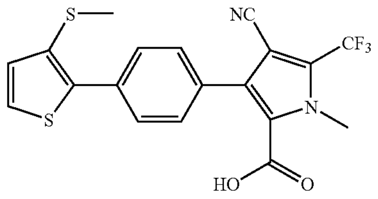

Preparation of 4-(3-methylthio-2-thienyl)benzaldehyde

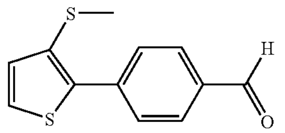

To a stirring solution of 2-iodo-3-thiomethyl-thiophene (1.0 mmol, prepared in preparation 2) and 4-formylphenyl boronic acid (1.5 mmol) in dioxane, add tetrakis(triphenylphosphine)palladium (0.044 mmol) and 2M aqueous sodium carbonate (5.0 mmol). Heat the reaction to 90° C. for 18 hours. After this time, remove heat and wash the reaction with water while extracting with ethyl acetate. Dry the organic layer with sodium sulfate, filter, and concentrate in vacuo. Purify the residue via radial chromatography eluting with ethyl acetate and hexane to provide the title compound.

Preparation of 2-[(4-methylphenyl)sulfonyl]-3-[4-(3-methylthio(2-thienyl))phenyl]prop-2-enenitrile

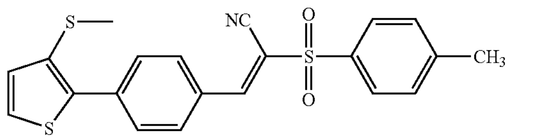

Scheme I, Step A: To a stirring solution of 4-(3-methylthio-2-thienyl)benzaldehyde (1.0 mmol, prepared directly above) and p-toluenesulphonylacetonitrile (1.0 mmol) in toluene, add piperidine (0.05 mmol) and acetic acid (0.3 mmol). Heat the reaction mixture to reflux for 2 hours while using a Dean-Stark trap, remove the heat and concentrate the reaction in vacuo. The crude material can be carried on to the next step without further purification.

Preparation of ethyl 4-cyano-3-[4-(3-methylthio(2-thienyl))phenyl]pyrrole-2-carboxylate

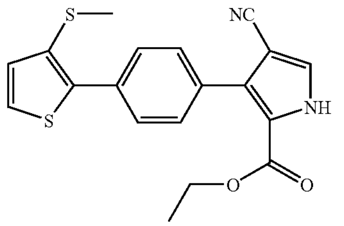

Scheme I, Step B: To a solution of ethyl 4-cyano-3-[4-(3-methylthio(2-thienyl))phenyl]pyrrole-2-carboxylate (10 mmol, prepared directly above) in THF, add ethyl cyanoacetate (1.0 mmol) and 1,8-diazabicyclo[5.4.0]undec-7-ene (1.0 mmol). Stir the reaction at room temperature for two hours. Then wash the reaction with water while extracting with ethyl acetate. Dry the organics with sodium sulfate, decant, and concentrate in vacuo to provide the title compound.

Preparation of ethyl 4-cyano-5-iodo-3-[4-(3-methylthio(2-thienyl))phenyl]pyrrole-2-carboxylate

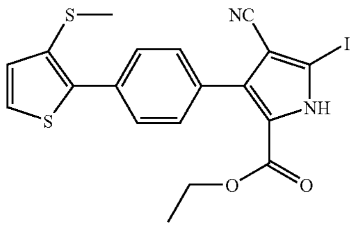

Scheme XXIII, step A: In a manner analogous to the procedure set forth in example A-237, the title compound is prepared by iodinating ethyl 4-cyano-3-[4-(3 methylthio(2-thienyl))phenyl]pyrrole-2-carboxylate, prepared directly above, with N-iodo-succinamide.

Preparation of ethyl 4-cyano-1-methyl-3-[4-(3-methylthio(2-thienyl))phenyl]-5-(trifluoromethyl)pyrrole-2-carboxylate

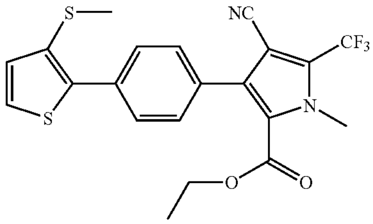

Scheme XXIII, step B: In a manner analogous to the procedure set forth in example A-237, ethyl 4-cyano-5-iodo-3-[4-(3-methylthio(2-thienyl))phenyl]pyrrole-2-carboxylate, prepared directly above, is treated with copper bromide and methyl 2,2-difluoro-2-(fluorosulfonyl)acetate (2.0 mmol) in DME to provide the title compound. MS (m/e): 468.0 (M+18); $^{1}$H NMR δ 7.70 (d, 2H, J=8.3 Hz), 7.38 (d, 2H, J=8.3 Hz), 7.32 (d, 1H, J=5.3 Hz), 7.10 (d, 1H, J=5.3 Hz), 4.16 (q, 2H, J=7.0 Hz), 4.08 (s, 3H), 2.43 (s, 3H), 1.05 (t, 3H, J=7.3 Hz).

Preparation of Final Title Compound

Scheme VI: In a manner analogous to the last step of example A-237, ethyl 4-cyano-1-methyl-3-[4-(3-methylthio(2-thienyl))phenyl]-5-(trifluoromethyl)pyrrole-2-carboxylate, prepared directly above, is hydrolyzed to provide the final title compound.

MS (m/e): 440.0 (M+18) 421.0 (M−1); $^{1}$H NMR δ 7.68 (d, 1H, J=5.3 Hz), 7.62 (d, 2H, J=8.4 Hz), 7.46 (d, 2H, J=8.4 Hz), 7.24 (d, 1H, J=5.3 Hz), 4.00 (s, 3H), 2.47 (s, 3H).

EXAMPLE A-240

Preparation of 4-cyano-3-[4-(3-cyano(2-thienyl))phenyl]-1-methyl-5-(trifluoromethyl)pyrrole-2-carboxylic acid

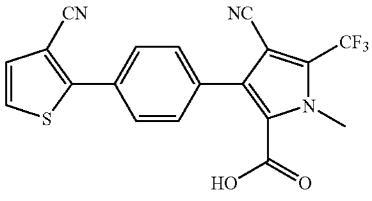

Preparation of 2-(4-formylphenyl)thiophene-3-carbonitrile

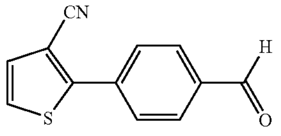

In a manner analogous to the procedure set forth in example A-239, the title compound is prepared from 2-iodo-3-cyano-thiophene and 4-formylphenyl boronic acid.

Preparation of 2-(4-{2-cyano-2-[(4-methylphenyl)sulfonyl]vinyl}phenyl)thiophene-3-carbonitrile

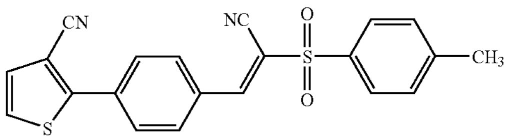

Scheme I, step A: In a manner analogous to the procedure set forth in example A-239, the title compound is prepared from 2-(4-formylphenyl)thiophene-3-carbonitrile, prepared directly above, and p-toluenesulphonylacetonitrile.

Preparation of ethyl 4-cyano-3-[4-(3-cyano(2-thienyl))phenyl]pyrrole-2-carboxylate

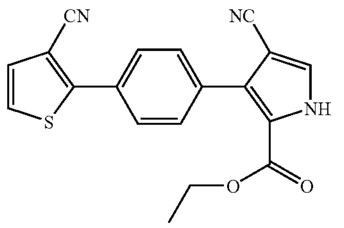

Scheme I, Step B: In a manner analogous to the procedure set forth in example A-239, the title compound is prepared from 2-(4-{2-cyano-2-[(4-methylphenyl)sulfonyl]vinyl}phenyl)thiophene-3-carbonitrile, prepared directly above, ethyl cyanoacetate and 1,8-diazabicyclo[5.4.0]undec-7-ene.

Preparation of ethyl 4-cyano-3-[4-(3-cyano(2-thienyl)phenyl]-5-iodopyrrole-2-carboxylate

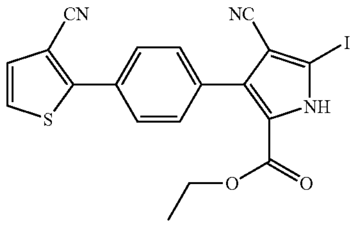

Scheme XXII, step A: In a manner analogous to the procedure set forth in example A-237, the title compound is prepared by iodinating ethyl 4-cyano-3-[4-(3-cyano(2-thienyl))phenyl]pyrrole-2-carboxylate, prepared directly above, with N-iodo-succinamide.

Preparation of ethyl 4-cyano-3-[4-(3-cyano(2-thienyl))phenyl]-1-methyl-5-(trifluoromethyl)pyrrole-2-carboxylate

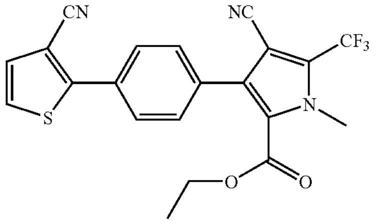

Scheme XXII, step B: In a manner analogous to the procedure set forth in example A-237, ethyl 4-cyano-3-[4-(3-cyano(2-thienyl))phenyl]-5-iodopyrrole-2-carboxylate, prepared directly above, is treated with copper bromide and methyl 2,2-difluoro-2-(fluorosulfonyl)acetate (2.0 mmol) in DMF to provide the title compound.

Preparation of Final Title Compound

Scheme VI: In a manner analogous to the last step of example A-237, ethyl 4-cyano-3-[4-(3-cyano(2-thienyl))phenyl]-1-methyl-5-(trifluoromethyl)pyrrole-2-carboxylate, prepared directly above, is hydrolyzed to provide the final title compound.

MS (m/e): 419.0 (M+1) 400.0 (M−1); $^1$H NMR δ 7.84 (d, 2H, J=7.9 Hz), 7.62 (d, 1H, J=5.7 Hz), 7.56 (d, 2H, J=8.3 Hz), 7.40 (d, 1H, J=5.3 Hz), 4.11 (s, 3H).

EXAMPLE A-241

Preparation of 4-Cyano-3-(2'-cyano-biphenyl-4-yl)-1-methyl-5-trifluoromethyl-1H-pyrrole-2-carboxylic acid

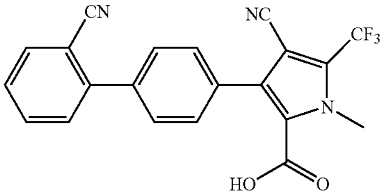

Scheme VI: In a manner analogous to the last step of example A-237, 4-cyano-3-(2'-cyano-biphenyl-4-yl)-1-methyl-5-trifluoromethyl-1H-pyrrole-2-carboxylic acid ethyl ester, prepared in example E-278, is hydrolyzed to provide the title compound. MS (m/e): 413.0 (M+18); $^1$H NMR δ 7.96 (s, 1H), 7.80 (s, 1H), 7.71-7.52 (m, 6H), 4.01 (s, 3H).

EXAMPLE A-242

Preparation of 4-cyano-5-ethyl-1-methyl-3-{4-[1-methyl-2-(propane-2-sulfonylamino)-ethyl]-phenyl}-1H-pyrrole-2-carboxylic acid

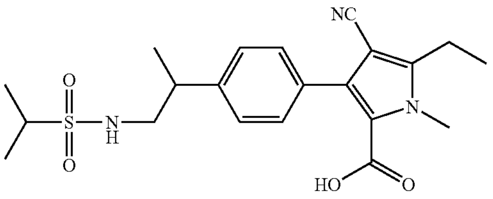

Prepare the title compound in a manner analogous to the procedure set forth in Method TI using 4-cyano-5-ethyl-1-methyl-3-{4-[1-methyl-2-(propane-2-sulfonylamino)-ethyl]-phenyl}-1H-pyrrole-2-carboxylic acid ethyl ester, prepared in Example E-281.

Mass spectrum (ES−)=416.4 (M−1).

EXAMPLE A-243

Preparation of 4-cyano-5-ethyl-1-methyl-3-{4-[2-(propane-2-sulfonylamino)-ethyl]-phenyl}-1H-pyrrole-2-carboxylic acid

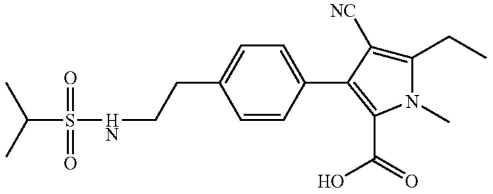

Prepare the title compound in a manner analogous to the procedure set forth in Method TI using 4-cyano-5-ethyl-1-methyl-3-{4-[2-(propane-2-sulfonylamino)-ethyl]-phenyl}-1H-pyrrole-2-carboxylic acid ethyl ester (prepared in example E-282). Mass spectrum (ES−)=402.4 (M−1).

Prepare the following carboxylic acids listed in Table A-5 in a manner analogous to the procedure set forth in Method TIV from the corresponding esters.

TABLE A-5

| Ex. | Structure | | S.M. |
|---|---|---|---|
| A-244 | 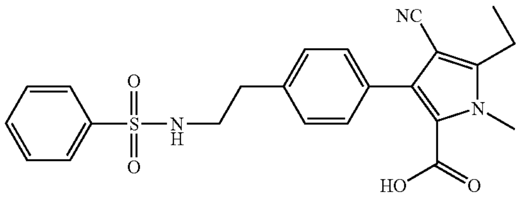 | mass spectrum(m/e): 436.0 (M − 1). | E-287 |
| A-245 | 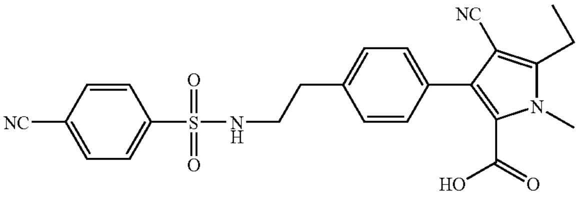 | mass spectrum(m/e): 461.0 (M − 1). | E-288 |
| A-246 | 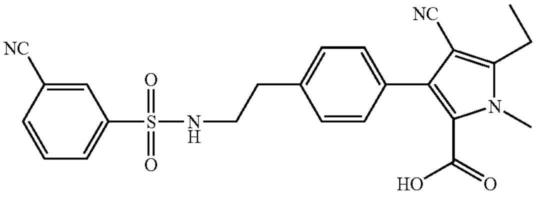 | mass spectrum(m/e): 461.0 (M − 1). | E-289 |
| A-247 | 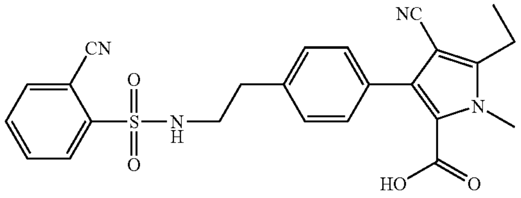 | mass spectrum(m/e): 463.0 (M + 1). | E-290 |
| A-248 | 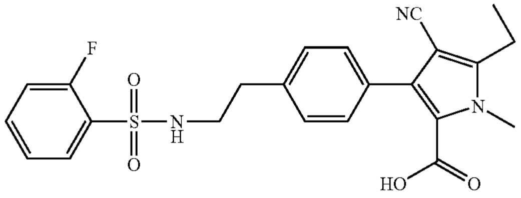 | mass spectrum(m/e): 454.0 (M − 1). | E-291 |

TABLE A-5-continued
| Ex. | Structure | | S.M. |
|---|---|---|---|
| A-249 | 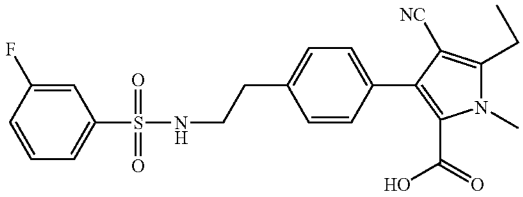 | mass spectrum(m/e): 454.0 (M − 1). | E-292 |
| A-250 | 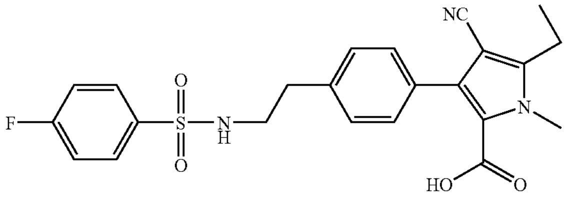 | mass spectrum(m/e): 454.0 (M − 1). | E-293 |
| A-251 | 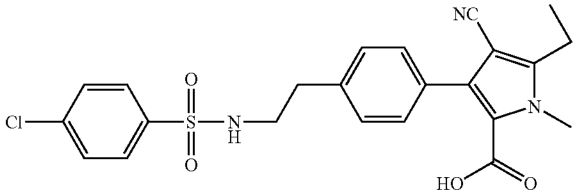 | mass spectrum(m/e): 470.0 (M − 1). | E-294 |
| A-252 | 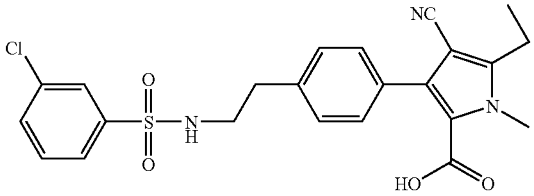 | mass spectrum(m/e): 470.0 (M − 1). | E-295 |
| A-253 | 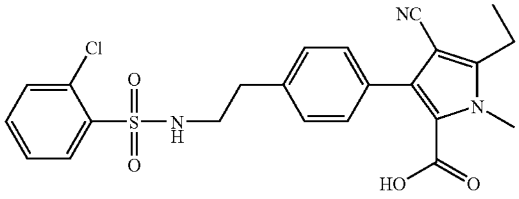 | mass spectrum(m/e): 470.0 (M − 1). | E-296 |
| A-254 | 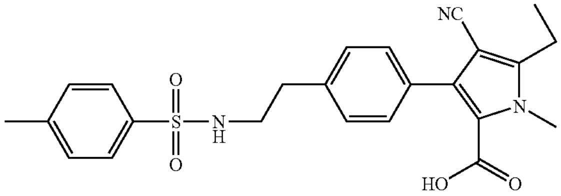 | mass spectrum(m/e): 450.0 (M − 1). | E-297 |
| A-255 | 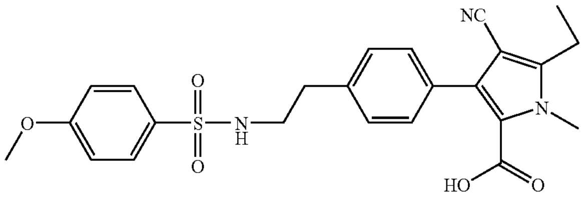 | mass spectrum(m/e): 466.5 (M − 1). | E-298 |

TABLE A-5-continued
| Ex. | Structure | | S.M. |
|---|---|---|---|
| A-256 | 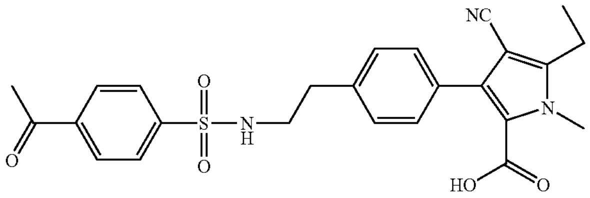 | mass spectrum(m/e): 478.5 (M − 1). | E-299 |
| A-257 | 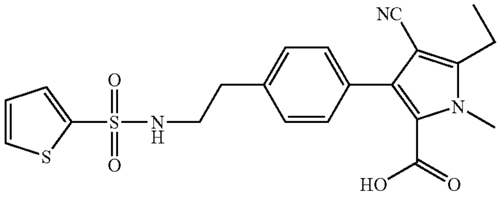 | mass spectrum(m/e): 442.0 (M − 1). | E-300 |
| A-258 | 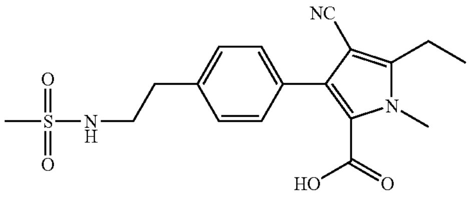 | mass spectrum(m/e): 374.0 (M − 1). | E-284 |
| A-259 | 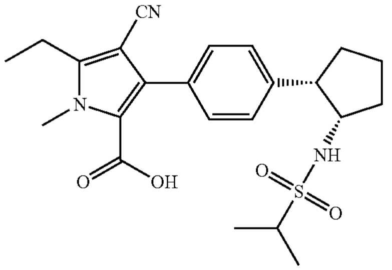 | mass spectrum(m/e): 442.2 (M − 1). | E-286 |
| A-260 | 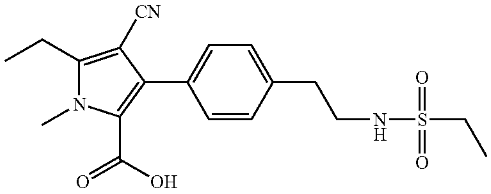 | Mass spectrum(m/e): 388.1 (M − 1). | E-285 |
| A-261 | 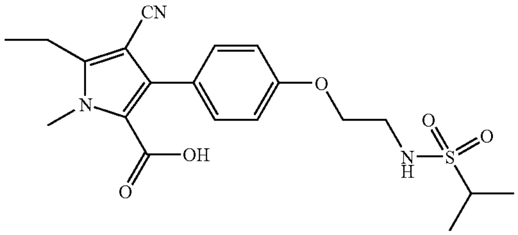 | Mass spectrum(m/e): 418.1(M − 1). | E-301 |
| A-262 | 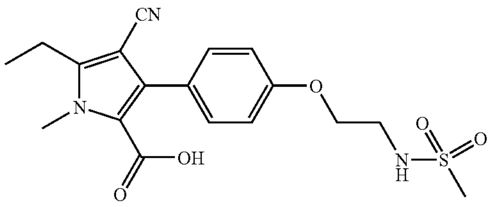 | Mass spectrum(m/e): 390.1(M − 1). | E-302 |

TABLE A-5-continued
| Ex. | Structure | | S.M. |
|---|---|---|---|
| A-263 | 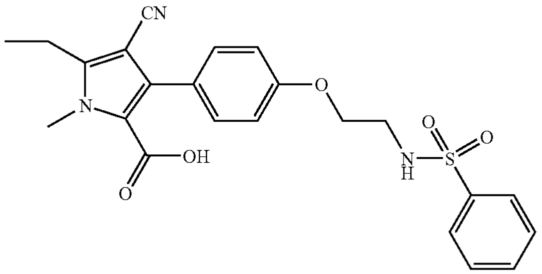 | Mass spectrum(m/e): 452.1(M − 1). | E-303 |
| A-264 | 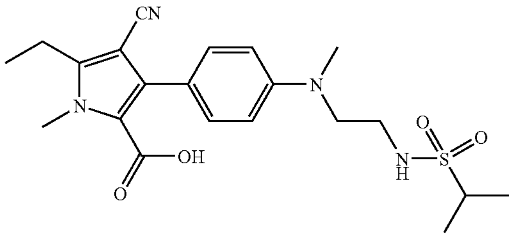 | Mass spectrum(m/e): 433.1(M + 1). | E-304 |
| A-265 | 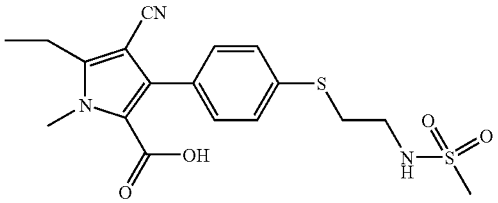 | Mass spectrum(m/e): 406.0 (M − 1). | E-305 |
| A-266 | 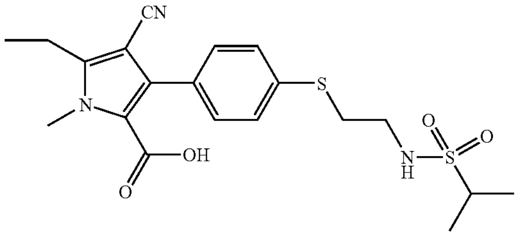 | mass spectrum(m/e): 434.01 (M − 1). | E-306 |
| A-267 | 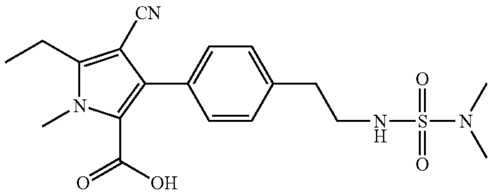 | mass spectrum(m/e): 405.4 (M + 1). | E-307 |
| A-268 | 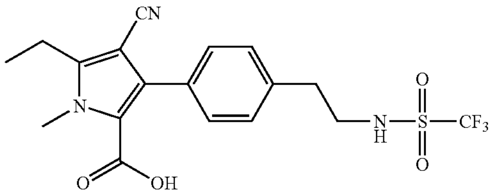 | mass spectrum(m/e): 430.0 (M + 1). | E-308 |

EXAMPLE A-269

Preparation of 4-cyano-3-[4-(1,1-dioxo-1λ$^6$-[1,2,5]thiadiazolidin-2-ylmethyl)-phenyl]-5-ethyl-1-methyl-1H-pyrrole-2-carboxylic acid

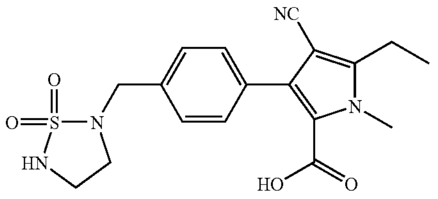

Preparation of 4-cyano-5-ethyl-3(4-hydroxymethyl-phenyl)-1-methyl-1H-pyrrole-2-carboxylic acid ethyl ester

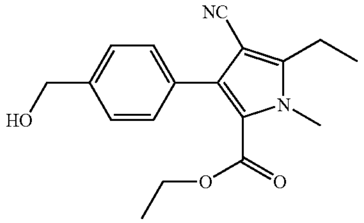

Step 1: Add 4-bromobenzyl alcohol (0.224 g, 1.2 mmol) to a mixture of 4-cyano-5-ethyl-1-methyl-3-(4,4,5,5-tetramethyl-[1,3,2]dioxaborolan-2-yl)-1H-pyrrole-2-carboxylic acid ethyl ester (preparation 50, 0.332 g, 1.0 mmol), bis(diphenylphosphino)ferrocene palladium(II) dichloride (1:1) dichloromethane complex (0.041 g, 0.05 mmol) and cesium fluoride (0.456 g, 3.0 mmol) in dimethoxyethane (5 mL) under an argon atmosphere in a reaction tube. Close the tube and warm to 90° C. for 5 min. Add more dimethoxyethane (5 mL) and warm to 90° C. for 1.5 h. Cool down, add acetone and filter through an Isolute® silica gel cartridge eluting with acetone. Collect all fractions with the desired product and purify by Strata® silica gel cartridge eluting with hexane-ethyl acetate to give the title compound as a colorless thick oil (0.245 g). $^1$H NMR ($CDCl_3$, δ (ppm)): 7.40-7.33 (m, 4H); 4.73 (s, 2H), 4.09 (q, J=7.1 Hz, 2H); 3.87 (s, 3H); 2.85 (q, J=7.7 Hz, 2H); 1.30 (t, J=7.7 Hz, 3H); 1.01 (t, J=7.1 Hz, 3H).

Preparation of 4-cyano-5-ethyl-3(4-methanesulfonyloxymethyl-phenyl)-1-methyl-1H-pyrrole-2-carboxylic acid ethyl ester

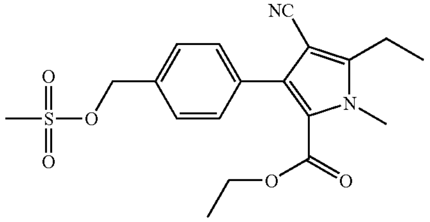

Step 2: Add triethyl amine (0.053 g, 0.53 mmol) to a solution of 4-cyano-5-ethyl-3(4-hydroxymethyl-phenyl)-1-methyl-1H-pyrrole-2-carboxylic acid ethyl ester (0.15 g, 0.48 mmol, prepared directly above) in dichloromethane (5 mL) at 0° C. under nitrogen, followed by drop-wise addition of methanesulfonyl chloride (0.06 g, 0.53 mmol). Stir at 0° C. for 1.5 h. Add ice-water and dichloromethane. Separate phases and wash organics with water. Combine aqueous layers and back-extract aqueous phase with more dichloromethane. Combine organic phases, wash with brine, dry (sodium sulfate), filter and concentrate in vacuo, to give 0.181 g of title compound for use without further purification. $^1$H NMR ($CDCl_3$, δ (ppm)): 7.46-7.38 (m, 4H); 5.28 (s, 2H), 4.09 (q, J=7.1 Hz, 2H); 3.89 (s, 3H); 2.93 (s, 3H); 2.85 (q, J=7.5 Hz, 2H); 1.30 (t, J=7.7 Hz, 3H); 1.00 (t, J=7.1 Hz, 3H).

Preparation of 4-cyano-3-[4-(1,1-dioxo-1λ$^6$-[1,2,5]thiazolidin-2-ylmethyl)-phenyl]-5-ethyl-1-methyl-1H-pyrrole-2-carboxylic acid ethyl ester

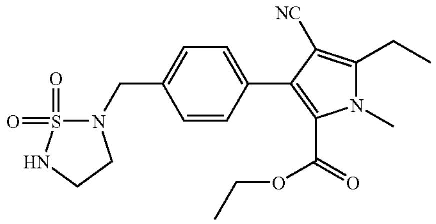

Step 3: Add potassium carbonate (0.032 g) and [1,2,5]thiadiazolidine 1,1-dioxide (0.028 g) to a solution of 4-cyano-5-ethyl-3(4-methanesulfonyloxymethyl-phenyl)-1-methyl-1H-pyrrole-2-carboxylic acid ethyl ester (0.23 mmol, prepared directly above) in anhydrous DMF under nitrogen and stir at room temperature overnight and then at 70° C. for 5 h. Add more [1,2,5]thiadiazolidine 1,1-dioxide (0.028 g) and continue stirring at 70° C. overnight. Cool down and add ethyl acetate and 1.2 M aqueous HCl. Separate phases and wash organics with more 1.2 M aqueous HCl (×2). Back-extract aqueous with ethyl acetate. Wash combined organics with brine, dry (sodium sulfate) and concentrate in vacuo. Purify the residue by Strata® silica gel cartridge and further with ISCO eluting with hexane-ethyl acetate to give 0.035 g of title compound for use in the next step without further purification. Mass spectrum ESI negative (m/z): 415 (M−1).

Preparation of Final Title Compound

Step 4: Add lithium hydroxide (2.5 M aqueous solution, 0.25 mL) to 4-cyano-3-[4-(1,1-dioxo-1λ$^6$-[1,2,5]thiadiazolidin-2-ylmethyl)-phenyl]-5-ethyl-1-methyl-1H-pyrrole-2-carboxylic acid ethyl ester (material-prepared directly above) in EtOH (1.0 mL) and warm at 60° C. for 30 min. Remove EtOH under reduced pressure and acidify with 1.2 M aqueous HCl. Add acetone until clear solution and concentrate in vacuo over Celite®. Purify using Strata® silica gel cartridge eluting with hexane-EtOAc and finally with EtOAc-TFA (1%) to give the final title compound (0.009 g). Mass spectrum ESI negative (m/z): 387 (M−1).

EXAMPLE A-270

Preparation of 4-cyano-3-{4-[2-(1,1-dioxo-1λ$^6$-[1,2,5]thiadiazolidin-2-yl)ethyl]-phenyl}-5-ethyl-1-methyl-1H-pyrrole-2-carboxylic acid

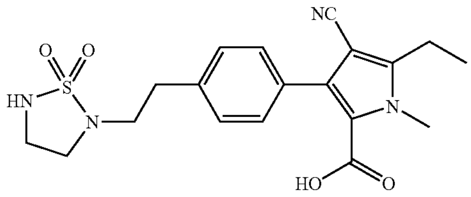

Preparation of 4-cyano-5-ethyl-3-[4-(2-hydroxy-ethyl)-phenyl]-1-methyl-1H-pyrrole-2-carboxylic acid ethyl ester

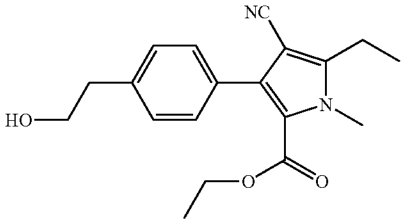

Step 1: Prepare the title compound in a manner analogous to the procedure set forth in preparation of Example A-269, step 1, using 0.261 g of 4-bromophenethyl alcohol to provide the title compound as a colorless thick oil (0.230 g). $^1$H NMR ($CDCl_3$, δ(ppm)): 7.33-7.22 (m, 4H); 4.09 (q, J=7.1 Hz, 2H); 3.88 (t, J 36.4 Hz, 2H); 3.87 (s, 3H); 2.90 (t, J=6.4 Hz, 2H); 2.85 (q, J=7.5 Hz, 2H); 1.30 (t, J=7.7 Hz, 3H); 1.01 (t, J=7.3 Hz, 3H).

Preparation of 4-cyano-5-ethyl-3-[4-(2-methanesulfonyloxy-ethyl)-phenyl]-1-methyl-1H-pyrrole-2-carboxylic acid ethyl ester

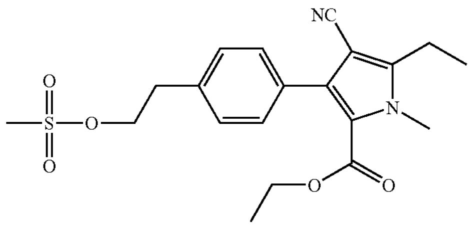

Step 2: Prepare the title compound in a manner analogous to the procedure set forth in preparation of Example A-269, step 2, using 0.15 g of 4-cyano-5-ethyl-3-[4-(2-hydroxy-ethyl)-phenyl]-1-methyl-1H-pyrrole-2-carboxylic acid ethyl ester, prepared directly above, to give 0.2 g of title compound for use without further purification. $^1$H NMR ($CDCl_3$, δ(ppm)): 7.33-7.24 (m, 4H); 4.44 (t, J=6.9 Hz, 2H), 4.06(q, J=7.1 Hz, 2H); 3.87 (s, 3H); 3.08 (t, J=6.7 Hz, 2H); 2.83 (s, 3H); 2.85 (q, J=7.5 Hz, 2H); 1.30 (t, J=7.7 Hz, 3H); 1.01 (t, J=7.1 Hz, 3H).

Preparation of 4-cyano-3-{4-[2-(1,1-dioxo-1λ$^6$-[1,2,5]thiadiazolidin-2-yl)ethyl]-phenyl}-5-ethyl-1-methyl-1H-pyrrole-2-carboxylic acid ethyl ester

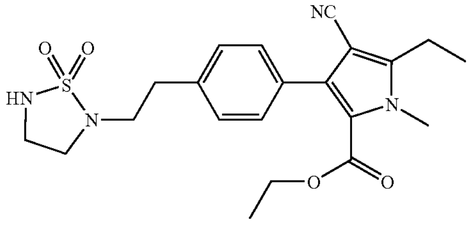

Step 3: Prepare the title compound in a manner analogous to the procedure set forth in preparation of Example A-269, step 3, using approximately 0.2 mmol of 4-cyano-5-ethyl-3-[4-(2-methanesulfonyloxy-ethyl)-phenyl]-1-methyl-1H-pyrrole-2-carboxylic acid ethyl ester, prepared directly above to give 0.017 g of title compound. Mass spectrum ESI positive (m/z): 431 (M+1).

Preparation of Final Title Compound

Step 4: Prepare the final title compound in a manner analogous to the procedure set forth in preparation of Example A-269, step 4, using 4-cyano-3-{4-[2-(1,1-dioxo-1λ$^6$-[1,2,5]thiadiazolidin-2-yl)ethyl]-phenyl}-5-ethyl-1-methyl-1H-pyrrole-2-carboxylic acid ethyl ester, prepared directly above. Purify the crude material by HPLC to give 0.004 g of the final title compound. Mass spectrum ESI positive (m/z): 403 (M+1).

EXAMPLE Pz-1

Preparation of 4-(2'-Cyano-biphenyl-4-yl)-1-methyl-1H-pyrazole-3-carbonitrile

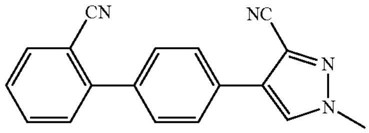

Preparation of the Final Title Compound

Scheme XXI, step A: Prepare a solution of 2'-carbonitrile-biphenyl-boronic acid (550 mg, 2.47 mmol), 4-bromo-1-methyl-1H-pyrazole-3-carbonitrile (300 mg, 1.61 mmol, prepared in preparation 46), 2M aqueous $Na_2CO_3$ (10.8 mmol) and tetrakis(triphenylphosphine)-palladium(0) (0.18 mmol) in 27 mL of dioxane and heat to 80° C. under nitrogen. After 3 hours cool to room temperature, dilute with 50 mL of EtOAc and wash with water (2×10 mL) and brine (1×10 mL). Dry the organics over anhydrous $Na_2SO_4$, filter, and evaporate. Chromatograph on silica gel (100/0 to 3/1 toluene/EtOAc) to give the final title compound. Yield=101 mg (18%).

EXAMPLE Pz-2

Preparation of 5-Cyano-4-(2'-cyano-biphenyl-4-yl)-2-methyl-2H-pyrazole-3-carboxylic acid ethyl ester

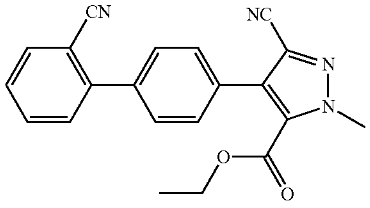

Scheme XXI, step B: Prepare a solution of 4-(2'-cyano-biphenyl-4-yl)-1-methyl-1H-pyrazole-3-carbonitrile (101 mg, 0.355 mmol, prepared in preparation 46) in 3 mL of anhydrous THF and cool to −70° C. Add n-butyl lithium (1.6M in hexanes, 0.2 mL, 0.32 mmol) dropwise, keeping the internal temperature less than −65° C. Stir the orange solution for 30 minutes at −70° C. Next, add ethyl chloroformate (0.1 mL, 1.02 mmol) and allow the reaction to warm to room temperature over one hour. Quench with 2 mL of saturated $NH_4Cl$ and dilute with 50 mL of EtOAc. Wash the organic layer with water (1×10 mL) and brine (1×10 mL) and dry over anhydrous $Na_2SO_4$. Filter, evaporate and chromatograph over silica gel (100/0-7/3 toluene/EtOAc) to give the title compound, 37 mg (29%) along with 38 mg of recovered starting material.

EXAMPLE Pz-3

Preparation of 5-Cyano-4-(2'-cyano-biphenyl-4-yl)-2-methyl-2H-pyrazole-3-carboxylic acid

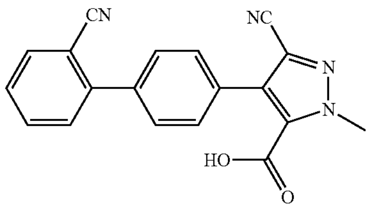

Dissolve the 5-cyano-4-(2'-cyano-biphenyl-4-yl)-2-methyl-2H-pyrazole-3-carboxylic acid ethyl ester (37 mg, 0.10 mmol, prepared in example Pz-2) in 2 mL of EtOH, add 1 mL of 2N aqueous NaOH and heat to reflux. After 20 minutes cool the reaction mixture in an ice-bath and add 2 mL of 1N aqueous HCl. Stir 10 minutes and filter, rinsing with 1 mL of EtOH followed by 2 mL of water. Vacuum-dry at 50° C. overnight to give the title compound. Yield=7.0 mg (21%). MS(ES−, m/e)=283 ($M^+$−COOH).

EXAMPLE Pz-4

Preparation of Propane-2-sulfonic acid [4'-(3-cyano-1-methyl-1H-pyrazol-4-yl)-biphenyl-2-yl]-amide

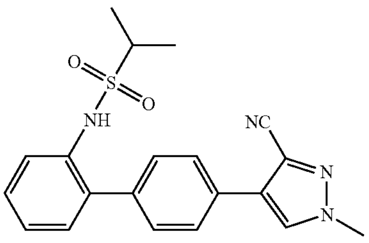

Scheme XXI, step A: Prepare the title compound in a manner analogous to the procedure set forth in example Pz-1 using 4-bromo-1-methyl-1H-pyrazole-3-carbonitrile (150 mg, 0.81 mmol) and propane-2-sulfonic acid [4'-(4,4,5,5-tetramethyl-[1,3,2]dioxaborolan-2-yl)-biphenyl-2-yl]-amide (400 mg, 1.0 mmol) to give the title compound as an off-white solid. Yield=115 mg (37%). MS(ES−, m/e)=379 ($M^+$−1).

EXAMPLE Pz-5

Preparation of 5-Cyano-2-methyl-4-[2'-(propane-2-sulfonylamino)-biphenyl-4-yl]-2H-pyrazole-3-carboxylic acid

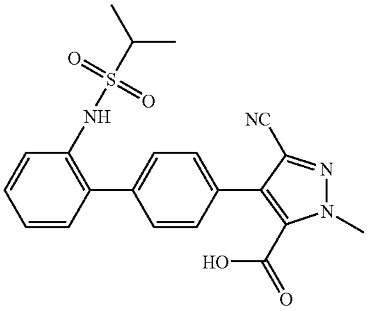

Dissolve propane-2-sulfonic acid [4'-(3-cyano-1-methyl-1H-pyrazol-4-yl)-biphenyl-2-yl]-amide (115 mg, 0.302 mmol, prepared in example Pz-4) in 5 mL of anhydrous THF and cool to −70° C. under nitrogen. Add n-butyl lithium in hexanes (1.6M, 0.5 mL, 0.8 mmol), warm to 0° C. and cool back to −70° C. over thirty minutes. After 1 hour, bubble in $CO_2$ gas until the reaction is saturated. Allow the reaction to warm to room temperature over 30 minutes. Cool the reaction to 0° C. and add 10 mL of 1N aqueous HCl. Extract with methylene chloride (3×20 mL) and evaporate the combined organic extracts. Dissolve the residue in 5 mL of 1N aqueous NaOH and 20 mL of water and stir ten minutes. Filter through a pad of diatomaceous earth and cool the filtrate to 0° C. Add 5 mL of 1N aqueous HCl and extract again with (3×20 mL). Evaporate the organic layers and chromatograph the residue over silica gel (1/9-3/7 MeOH/methylene chloride) to give the title compound as a tan solid, 39 mg (30%). MS(ES−, m/e)=423 ($M^+$−1), 379($M^+$−COOH).

EXAMPLE Pz-6

Preparation of 4-(4-Hydroxy-phenyl)-1-methyl-1H-pyrazole-3-carbonitrile

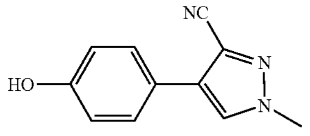

Scheme XXI, step A: Prepare the title compound in a manner analogous to the procedure set forth in example Pz-1 using 4-bromo-1-methyl-1H-pyrazole-3-carbonitrile (1.5 g, 8.06 mmol, prepared in example Pz-1) and 4-(4,4,5,5-tetramethyl-[1,3,2]dioxaborolan-2-yl)-phenol (2.8 g, 12.3 mmol). Yield=1.5 g (94%) of the product as a tan solid. MS(ES−, m/e)=198 ($M^+$−1).

EXAMPLE Pz-7

Preparation of Trifluoro-methanesulfonic acid 4-(3-cyano-1-methyl-1H-pyrazol-4-yl)-phenyl ester

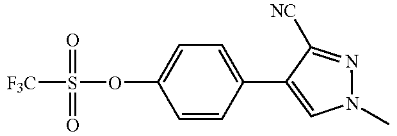

Add dry pyridine (14.7 mmol) to a solution of 4-(4-hydroxy-phenyl)-1-methyl-1H-pyrazole-3-carbonitrile (1.0 g, 5.0 mmol, prepared in example Pz-6) in 30 mL of methylene chloride and cool to −70° C. under nitrogen. Add trifluoromethanesulfonic anhydride (6.2 mmol) dropwise and remove the cooling bath and allow the reaction to warm to room temperature. Ninety minutes later pour the mixture into 50 mL cold 1N HCl. Shake and separate the layers; wash the organics with ice-water (1×20 mL) and saturated aqueous $NaHCO_3$ (1×20 mL) and dry over anhydrous $Na_2SO_4$. Filter and evaporate to provide the title compound (1.6 g, 96% yield) which is used without further purification.

EXAMPLE Pz-8

Preparation of 1-Methyl-4-(2'-methylsulfanyl-biphenyl-4-yl)-1H-pyrazole-3-carbonitrile

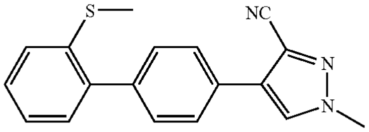

Scheme XXI, step A: Prepare the title compound in a manner analogous to the procedure set forth in Example Pz-1 using trifluoro-methanesulfonic acid 4-(3-cyano-1-methyl-1H-pyrazol-4-yl)-phenyl ester (600 mg, 1.81 mmol, prepared in example Pz-7) and 2-(methylthio)benzeneboronic acid (560 mg, 3.3 mmol). Yield=350 mg (63%).

EXAMPLE Pz-9

Preparation of 5-Cyano-2-methyl-4-(2'-methylsulfanyl-biphenyl-4-yl)-2H-pyrazole-3-carboxylic acid

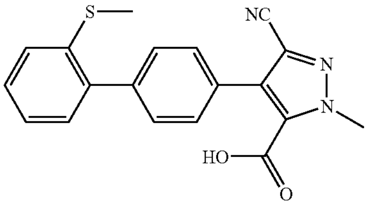

Prepare the title compound in a manner analogous to the procedure set forth in example Pz-5 using 1-methyl-4-(2'-methylsulfanyl-biphenyl-4-yl)-1H-pyrazole-3-carbonitrile (350 mg, 1.15 mmol, prepared in example Pz-8). Yield=206 mg (52%). MS (ES−, m/e)=348 ($M^+$−1).

EXAMPLE Pz-10

Preparation of 4-(2'-Ethoxy-biphenyl-4-yl)-1-methyl-1H-pyrazole-3-carbonitrile

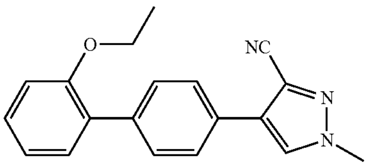

Scheme XXI, step A: Prepare the title compound in a manner analogous to the procedure set forth in example Pz-1 using trifluoro-methanesulfonic acid 4-(3-cyano-1-methyl-1H-pyrazol-4-yl)-phenyl ester (500 mg, 1.51 mmol, prepared in example Pz-7) and 2-ethoxyphenylboronic acid (450 mg, 2.71 mmol). Yield=321 mg (70%).

EXAMPLE Pz-11

Preparation of 5-Cyano-4-(2'-ethoxy-biphenyl-4-yl)-2-methyl-2H-pyrazole-3-carboxylic acid

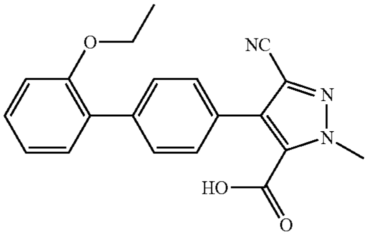

Prepare the title compound in a manner analogous to the procedure set forth in example Pz-5 using 4-(2'-ethoxy-biphenyl-4-yl)-1-methyl-1H-pyrazole-3-carbonitrile (321 mg, 1.06 mmol, prepared in example Pz-10). Yield=291 mg (79%). MS (ES−, m/e)=346 ($M^+$−1), 302 ($M^+$−COOH).

EXAMPLE Pz-12

Preparation of 5-Cyano-4-(2'-ethoxy-biphenyl-4-yl)-2-methyl-2H-pyrazole-3-carboxylic acid (1H-tetrazol-5-yl)-amide

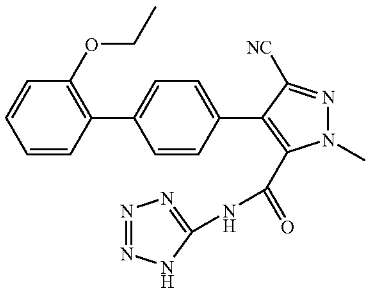

Prepare the title compound in a manner analogous to the procedure set forth in example Am-8 using 5-cyano-4-(2'-ethoxy-biphenyl-4-yl)-2-methyl-2H-pyrazole-3-carboxylic acid (180 mg, 0.52 mmol, prepared in example Pz-11) and 5-aminotetrazole (3.5 mmol). Yield=68 mg (32%). MS (ES−, m/e)=347 ($M^+$−1).

Method U

Scheme VII, step A: Add the corresponding carboxylic acid (1.0 mmol, compound of Formula Ia) in THF to oxalyl chloride (1.2 mmol) in THF followed by 1 drop of DMF at room temperature with stirring. After 2 hours, concentrate the reaction mixture under reduced pressure. Next, add the resulting residue in THF to ammonia/methanol (5 mmol) at room temperature with stirring. After 1-4 hours, concentrate the reaction mixture under reduced pressure. Purify the residue by flash chromatography eluting with methanol:methylene chloride to provide the compound of Formula Ic.

Prepare the following compound listed in Table Am-1 in a manner analogous to the procedure set forth in Method U.

TABLE Am-1

| Ex. | Structure | Data: | S.M. |
|---|---|---|---|
| Am-1 | 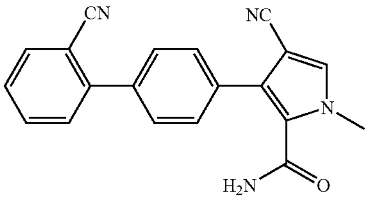 | mass spectrum (m/e): 325.1 (M − 1). | A-18 |
| Am-2 | 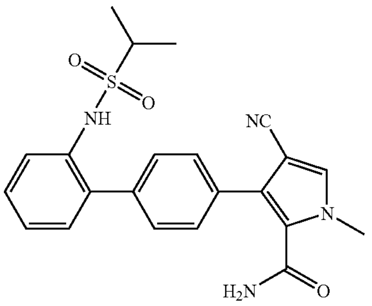 | mass spectrum (m/e): 423.1 (M + 1). | A-34 |
| Am-3 | 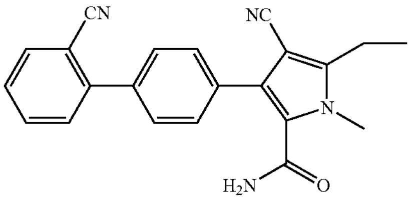 | mass spectrum (m/e): 355.2 (M + 1). | A-75 |
| Am-4 | 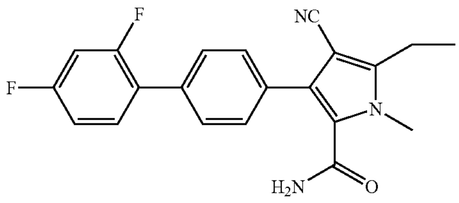 | mass spectrum (m/e): 366.1 (M + 1); analysis for $C_{21}H_{17}F_2N_3O$ calcd: C, 69.03; H, 4.69; N, 11.50; found: C, 68.70; H, 4.89; N, 11.26. | A-43 |

TABLE Am-1-continued

| Ex. | Structure | Data: | S.M. |
|---|---|---|---|
| Am-5 | 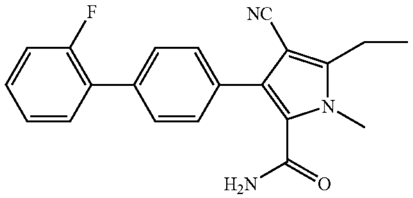 | mass spectrum (m/e): 348.1 (M + 1). | A-40 |
| Am-6 | 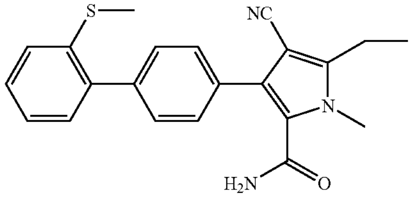 | mass spectrum (m/e): 376.3 (M + 1). | A-87 |

EXAMPLE Am-7

Preparation of 4-cyano-3-(2'cyano-biphenyl-4-yl)-5-ethyl-1-methyl-1H-pyrrole-2-carboxylic acid methylamide

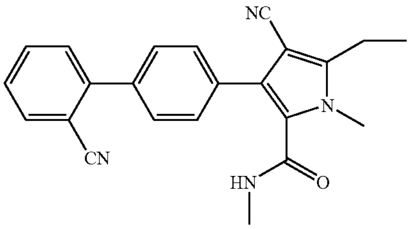

Prepare the title compound in a manner analogous to the procedure set forth in Method U using methylamine in place of ammonia and the carboxylic acid prepared in example A-75. Mass spectrum (m/e): 369.1 (M+1).

EXAMPLE Am-8

Preparation of 4-Cyano-3-(2'-cyano-biphenyl-4-yl)-5-ethyl-1-methyl-1H-pyrrole-2-carboxylic acid (1H-[1,2,4]triazol-3-yl)-amide

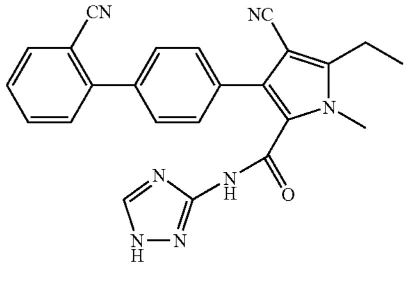

Scheme VII, step C: prepare a solution of 4-cyano-3-(2'-cyano-biphenyl-4-yl)-5-ethyl-1-methyl-1H-pyrrole-2-carboxylic acid (200 mg, 0.57 mmol, prepared in example A-75) in 5 mL of methylene chloride and stir under nitrogen. Add 2 drops of dry DMF and cool the mixture to 0° C. Next, add oxalyl chloride (1.10 mmol) dropwise over five minutes. Remove the icebath and stir the reaction for one hour. Add another 1.10 mmol of oxalyl chloride and continue stirring for one hour. Then concentrate the reaction mixture under vacuum to provide the crude acid chloride. Dissolve the crude acid chloride in 3.5 mL of dry pyridine and add 2-amino-1,3,4-triazole (5.9 mmol) and stir overnight at room temperature. Pour into 100 mL of ice-water and extract with methylene chloride (3×50 mL). Dry the combined organic layers over anhydrous $Na_2SO_4$, filter and evaporate. Chromatograph the residue over silica gel (100/0-3/1 toluene/EtOAc) to give the title compound (110 mg, 46% yield). MS(ES+, m/e)=422 ($M^+$+1).

Method W

Scheme VII, step A: Dissolve the corresponding carboxylic acid (0.567 mmol, compound of Formula Ia) in methylene chloride (8.5 mL). Add DMF (8 drops) and oxalyl chloride (293 mg, 2.31 mmol) into the above mixture at 0° C. Stir the mixture at 0° C. for 0.5 h and room temperature for 1 hour. Transfer the above mixture with THF (1.92 mL) and methylene chloride (1.92 mL) into a solution of concentrated ammonia solution (1.02 mL) at 0° C. and stir at room temperature for 1 h. Concentrate under vacuum to remove the organic solvents. Filter under reduced pressure with $H_2O$ wash to collect the compound of Formula Ic.

Prepare the following primary amides listed in Table Am-2 in a manner analogous to the procedure set forth in Method W.

TABLE Am-2

| Ex. | Structure | Data | S.M. |
|---|---|---|---|
| Am-9 | 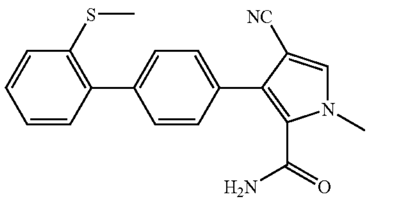 | mass spectrum (m/e): 346.2 (M − 1). | A-14 |
| Am-10 | 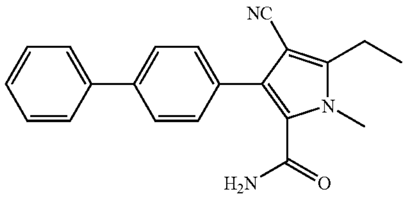 | mass spectrum (m/e): 329.1 (M − 1). | A-39 |
| Am-11 | 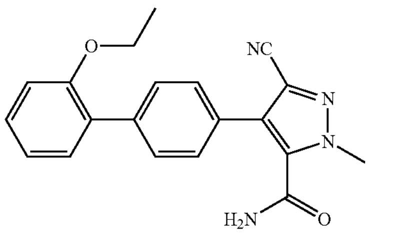 | Mass spectrum (m/e): 345.1 (M − 1). $R_f$ = 0.2 (50% EtOAc in hexane) | Pz-11 |

EXAMPLE Am-12

Preparation of 4-cyano-3-[4-(2-cyanophenyl)phenyl] 1-methyl-5-methylthiopyrrole-2-carboxamide

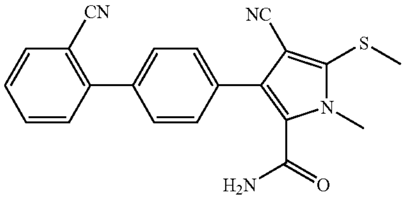

Scheme VII, step A: To a stirring solution of 4-cyano-3-[4-(2-cyanophenyl)phenyl]-1-methyl-5-methylthiopyrrole-2-carboxylic acid (11.0 mmol, prepared in example A-163) in methylene chloride, add oxalyl chloride (2.0 mmol) and catalytic DMF. Stir this solution for 20 minutes at room temperature and then concentrate in vacuo. Dissolve the residue in methylene chloride and ammonia hydroxide (2.0 mmol). Stir this reaction for one minute. The reaction becomes cloudy. Concentrate in vacuo. Purify the residue via radial chromatography and recrystallize using ether and hexanes to yield the title compound. MS (m/e): 373.1 (M+1) 371.0 (M−1); $^{1}H$ NMR δ 7.97 (d, 1H), 7.84 (s, 2H), 7.80 (t, 1H), 7.66 (m, 3H), 7.57 (m, 3H), 3.80 (s, 3H), 2.46 (s, 3H).

EXAMPLE Am-13

Preparation of 4-cyano-1,5-dimethyl-3-(2'-methylsulfonamide-biphenyl-4-yl)-1H-pyrrole-2-carboxylic amide

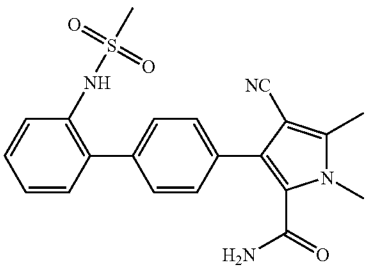

Oxalyl chloride (1.0 mL, excess) is added syringe wise to 4-cyano-1,5-dimethyl-3-(2'-methylsulfonamide-biphenyl-4-yl)-1H-pyrrole-2-carboxylic acid (200 mg, 0.46 mmol prepared in example A-136) while stirring in methylene chloride (20 mL) at room temperature under a nitrogen atmosphere. Then, 1 drop of DMF is added to initiate the reaction as the solution begins to foam. After ½ hour, the solution is concentrated under reduced vacuum. The resulting white foam is placed into 1,4 dioxane (10 mL) and added dropwise to 28% ammonium hydroxide (5 mL) while stirring at room temperature. The reaction is stirred overnight at this temperature. The solution is then concentrated under reduced vacuum and the resulting white solid is taken into methylene chloride, washed once with water, dried over potassium carbonate, filtered, and concentrated under reduced vacuum to afford 315 mg of a crude white solid. The material is purified by silica gel chromatography (Chromatotron™) eluting with a gradient solvent of methylene chloride to methylene chloride/ethyl acetate (1:1) providing 85 mg of the title compound as a white solid. Mass spectrum (fd): 407.1 (M*−1): (Bruker 300) $^{1}$H NMR (DMSO) δ 7.67-7.71 (2H, d), 7.61-7.64 (1H, s), 7.42-7.53 (4H, m), 7.20-7.25 (1H, m), 3.62-3.66 (3H,S), 3.03-3.07 (3H, s), 2.39-2.43 (3H, s).

EXAMPLE T-1

Preparation of 4-(2'-Cyano-biphenyl-4-yl)-2-ethyl-1-methyl-5-(4H-[1,2,4]triazol-3-yl)-1H-pyrrole-3-carbonitrile

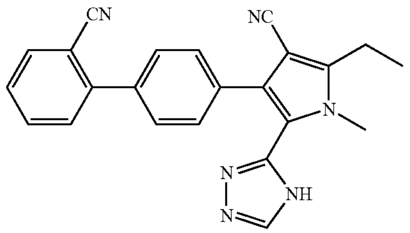

Dissolve 4-cyano-3-(2'-cyano-biphenyl-4-yl)-5-ethyl-1-methyl-1H-pyrrole-2-carboxylic acid dimethylaminomethyleneamide (183 mg, 0.45 mmol, prepared in preparation 47) in 2 mL of glacial acetic acid, add hydrazine monohydrate (0.70 mmol) and heat to 90° C. under nitrogen. After 90 minutes cool the reaction slightly, pour into 50 mL of ice-water and stir for twenty minutes. Filter off the resulting solid and rinse with 10 mL of water. Vacuum-dry overnight to give the title compound (66 mg, 39%). MS(ES+, m/e)=379 ($M^{+}$+1).

Method X

Scheme VII, step B: Add silicon tetrachloride (2.0 mmol) into a mixture of sodium azide (12 mmol) in acetonitrile (20 mL). Stir the mixture at room temperature for 20 minutes. Add the corresponding primary amide (1.0 mmol, compound of Formula Ic). Heat the mixture at 100° C. for 16 h. Add saturated aqueous $K_2CO_3$ (30 mL) and methylene chloride (30 mL) into the reaction mixture. Extract with methylene chloride (2×30 mL). Add 1.0 M HCl solution to the aqueous layer to adjust pH 3-4, then extract with methylene chloride (3×30 mL). Combine the organic layers, dry over magnesium sulfate, filter, and concentrate under reduced pressure to provide the compound of Formula Id.

Prepare the following tetrazoles listed in Table T-1 in a manner analogous to the procedure set forth in Method X.

TABLE T-1

| Ex. | Structure | Data | S.M. |
|---|---|---|---|
| T-2 | 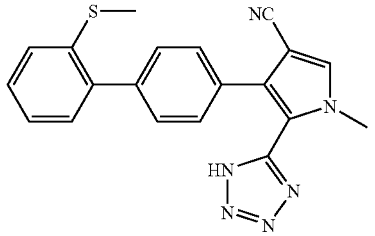 | mass spectrum (m/e): 371.3 (M − 1) | Am-9 |
| T-3 | 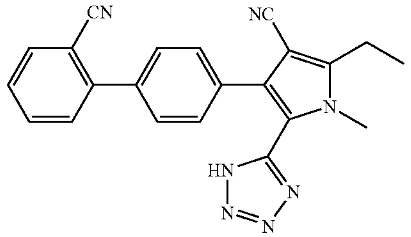 | mass spectrum (m/e): 378.3 (M − 1) | Am-3 |
| T-4 | 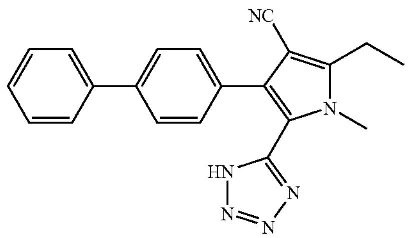 | mass spectrum (m/e): 353.1 (M − 1) | Am-10 |

TABLE T-1-continued

| Ex. | Structure | Data | S.M. |
|---|---|---|---|
| T-5 | 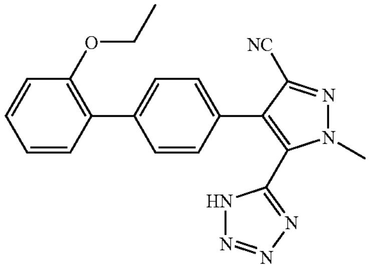 | mass spectrum (m/e): 370.1 (M − 1) | Am-11 |

Method Y

Scheme XIV: Add methane sulfonamide (1.1 mmol) to the corresponding carboxylic acid (1.0 mmol, compound of Formula Ia'), EDCI (1.2 mmol) and N,N-dimethylaminopyridine (1.1 mmol) in methylene chloride with stirring at room temperature. After 3-18 hours, pour the reaction mixture into 1N HCl and extract with methylene chloride. Combine the organic extracts, wash with water and brine, dry over anhydrous magnesium sulfate, filter, and concentrate under reduced pressure. Purify the residue by flash chromatography eluting with methylene chloride:methanol to provide the corresponding methane sulfonamide.

Prepare the methane sulfonamides listed in Table S-1 from the corresponding carboxylic acids in a manner analogous to the procedure set forth in Method Y.

TABLE S-1

| Ex. | Structure | Data: | S.M. |
|---|---|---|---|
| S-1 | 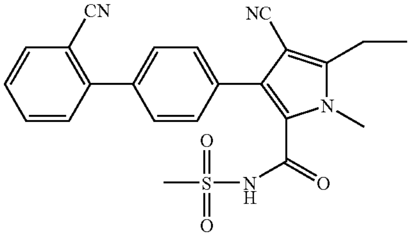 | mass spectrum (m/e): 431.1 (M − 1). | A-75 |
| S-2 | 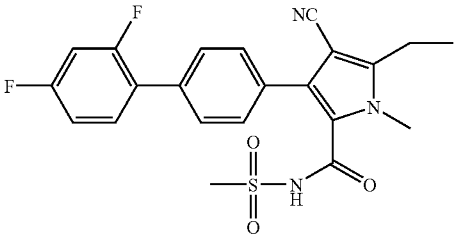 | mass spectrum (m/e): 444.1 (M + 1). | A-43 |
| S-3 | 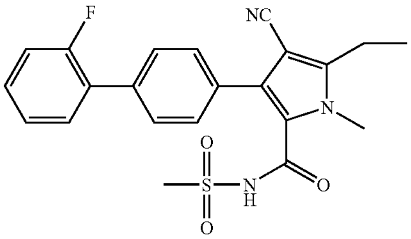 | mass spectrum (m/e): 426.1 (M + 1): analysis for $C_{22}H_{20}FN_3O_3S$: calcd: C, 62.10; H, 4.74; N, 9.88; found: C, 61.91; H, 4.41; N, 9.74. | A-40 |

TABLE S-1-continued

| Ex. | Structure | Data: | S.M. |
|---|---|---|---|
| S-4 | 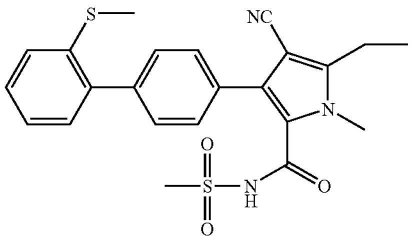 | mass spectrum (m/e): 454.0 (M + 1); analysis for $C_{23}H_{23}N_3O_3S_2$: calcd: C, 60.91; H, 5.11; N, 9.26; found: C, 61.11; H, 5.37; N, 8.99. | A-87 |

EXAMPLE S-5

Preparation of N-(1-{4-cyano-5-ethyl-3-[4-(2-fluoro-benzyloxy)-phenyl]-1-methyl-1H-pyrrole-2-yl}-vinyl)-methanesulfonamide

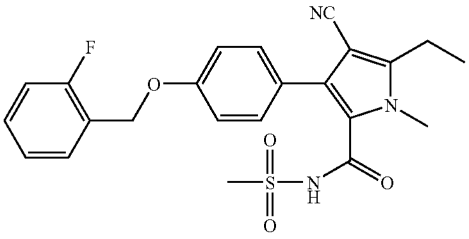

Mix together 4-cyano-5-ethyl-3-[4-(2-fluoro-benzyloxy)-phenyl]-1-methyl-1H-pyrrole-2-carboxylic acid (100 mg, 0.26 mmol, prepared in example A-171), methanesulfonamide (27 mg, 1.1 Eq.), 1-(3-dimethylaminopropyl)-3-ethyl-carbodiimide hydrochloride (60 mg, 1.2 Eq.), and 4-dimethylaminopyridine (35 mg, 1.1 Eq.) in methylene chloride (8 mL) and stir overnight at room temperature under a nitrogen atmosphere. Pour the mixture into 1N HCl and extract the desired amide into methylene chloride. Separate layers, wash the organic layer once with water, dry over anhydrous magnesium sulfate, filter, and concentrate under reduced vacuum to provide 107 mg as an oil. Purify the material by silica gel chromatography (Chromatotron™) eluting with methylene chloride/methanol 19:1 to provide 71 mg of the title compound as a tan foam: Mass spectrum (m/e): 456.2 (M*+1): (Bruker 300) $^1$H NMR (DMSO) 8.70-8.75 (1H, s), 7.50-7.65 (2H, d), 7.00-7.40 (6H, m), 5.05-5.20 (2H, s), 3.65-3.75 (3H, s), 3.45-3.60 (3H, s), 2.56-2.76 (2H, dd), 1.00-1.10 (3H, t).

Prepare the following sulfonamides listed in Table S-2 from the corresponding carboxylic acids in a manner analogous to the procedure set forth in example S-5.

TABLE S-2

| Ex. | Structure | Data | S.M. |
|---|---|---|---|
| S-6 | 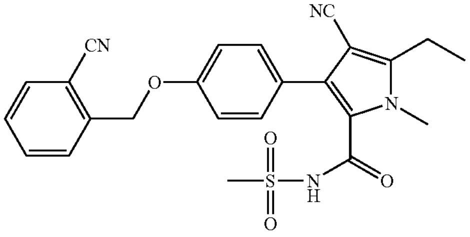 | tan solid: mass spectrum (m/e): 462.1 (M* − 1): (Bruker 300) $^1$H NMR (DMSO) 7.57-7.74(3H, m), 7.33-7.48(3H, m), 7.13-7.20 (2H, d), 5.25-5.35(2H, s), 3.80-3.95(3H, s), 3.15-3.25(3H, s), 2.75-2.90(2H, dd), 1.20-1.35 (3H, t) | A-173 |
| S-7 | 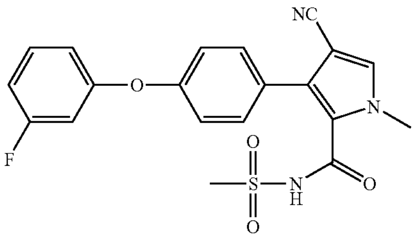 | white foam: mass spectrum (m/e): 414.1 (M* − 1): (Bruker 300) $^1$H NMR (DMSO) 7.82-7.86(1H, s), 7.43-7.55(3H, m), 7.14-7.21(2H, d), 6.90-7.09(3H, m), 3.76-3.81 (3H, s), 3.85-3.95(3H, s) | A-176 |

TABLE S-2-continued

| Ex. | Structure | Data | S.M. |
|---|---|---|---|
| S-8 | 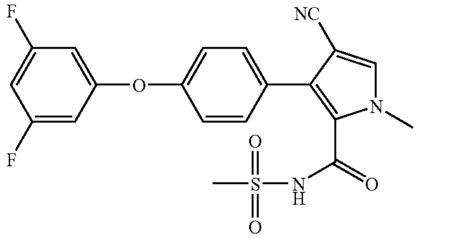 | white solid. mass spectrum (m/e): 430.1 (M* + 1): (Bruker 300) $^1$H NMR (DMSO) 7.62-7.66(1H, s), 7.44-7.52(2H, d), 7.10-7.16(2H, d), 6.92-7.02(1H, t), 6.71-6.79 (2H, d), 3.76-3.81(3H, s), 2.87-2.94(3H, s) | A-177 |
| S-9 | 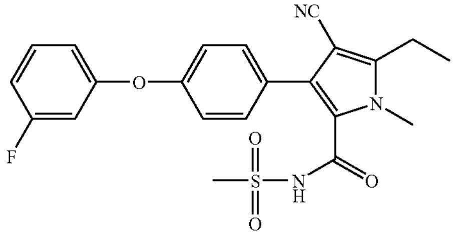 | oil: mass spectrum (m/e): 442.2 (M* + 1): (Bruker 300) $^1$NMR (DMSO) 7.35-7.47(3H, m), 7.10-7.16(2H, d), 6.83-7.03(3H, m), 3.66-3.72(3H, s), 3.14-3.24(3H, s), 2.75-2.87(2H, dd), 1.17-1.27 (3H, t). | A-179 |

The ability of compounds of Formula I to potentiate glutamate receptor-mediated response can be determined by one of ordinary skill in the art. For example, see U.S. Pat. No. 6,303,816. In particular, the following test may be utilized:

HEK293 cells stably expressing human iGluR4 (obtained as described in European Patent Application Publication No. EP-A1-0583917) are used in the electrophysiological characterization of AMPA receptor potentiators. The extracellular recording solution contains (in mM): 140 NaCl, 5 KCl, 10 HEPES, 1 $MgCl_2$, 2 $CaCl_2$, 10 glucose, pH=7.4 with NaOH, 295 mOsm kg-1. The intracellular recording solution contains (in mM): 140 CsCl, 1 $MgCl_2$, 10 HEPES, (N-[2-hydroxyethyl]piperazine-N1-[2-ethanesulfonic acid]) 10 EGTA (ethylene-bis(oxyethylene-nitrilo)tetraacetic acid), pH=7.2 with CsOH, 295 mOsm kg-1. With these solutions, recording pipettes have a resistance of 2-3 MΩ. Using the whole-cell voltage clamp technique (Hamill et al. (1981) Pflügers Arch., 391: 85-100), cells are voltage-clamped at −60 mV and control current responses to 1 mM glutamate are evoked. Responses to 1 mM glutamate are then determined in the presence of test compound. Compounds are deemed active in this test if, at a test concentration of 10 μM or less, they produce a greater than 10% increase in the value of the current evoked by 1 mM glutamate.

In order to determine the potency of test compounds, the concentration of the test compound, both in the bathing solution and co-applied with glutamate, is increased in half log units until the maximum effect is seen. Data collected in this manner are fit to the Hill equation, yielding an $EC_{50}$ value, indicative of the potency of the test compound. Reversibility of test compound activity is determined by assessing control glutamate 1 mM responses. Once the control responses to the glutamate challenge are re-established, the potentiation of these responses by 100 μM cyclothiazide is determined by its inclusion in both the bathing solution and the glutamate-containing solution. In this manner, the efficacy of the test compound relative to that of cyclothiazide can be determined.

In addition, certain behavioral despair animal models, which can be practiced by one of ordinary skill in the art to evaluate compounds of the present invention, are predictive of antidepressant activity in man, such as the Forced Swim Test and the Tail Suspension Test. For example, see "*Experimental Approaches to Anxiety and Depression*", Edited by J. M. Elliott, et al., (1992), John Wiley & Sons Ltd., Chapter 5, *Behavioural Models of Depression*, Porsolt and Lenegre, pages 73-85.

According to another aspect, the present invention provides a pharmaceutical composition, which comprises a compound of formula I or a pharmaceutically acceptable salt thereof and a pharmaceutically acceptable carrier, diluent, or excipient. In addition, the present invention provides a pharmaceutical composition, which comprises a compound of Formula II or a pharmaceutically acceptable salt thereof and a pharmaceutically acceptable carrier, diluent, or excipient.

The pharmaceutical compositions are prepared by known procedures using well-known and readily available ingredients. In making the compositions of the present invention, the active ingredient will usually be mixed with a carrier, or diluted by a carrier, or enclosed within a carrier, and may be in the form of a capsule, sachet, paper, or other container. When the carrier serves as a diluent, it may be a solid, semi-solid, or liquid material which acts as a vehicle, excipient, or medium for the active ingredient. The compositions can be in the form of tablets, pills, powders, lozenges, sachets, cachets, elixirs, suspensions, emulsions, solutions, syrups, aerosols, ointments containing, for example, up to 10% by weight of active compound, soft and hard gelatin capsules, suppositories, sterile injectable solutions, and sterile packaged powders.

Some examples of suitable carriers, excipients, and diluents include lactose, dextrose, sucrose, sorbitol, mannitol, starches, gum, acacia, calcium phosphate, alginates, tragcanth, gelatin, calcium silicate, micro-crystalline cellulose, polyvinylpyrrolidone, cellulose, water syrup, methyl cellulose, methyl and propyl hydroxybenzoates, talc, magnesium stearate, and mineral oil. The formulations can additionally include lubricating agents, wetting agents, emulsifying and suspending agents, preserving agents, sweetening agents, or flavoring agents. Compositions of the invention may be formulated so as to provide quick, sustained, or delayed release of the active ingredient after administration to the patient by employing procedures well known in the art.

The compositions are preferably formulated in a unit dosage form, each dosage containing from about 0.1 mg to about 300 mg, preferably about 0.1 mg to about 100 mg, and most preferably about 0.1 to about 50 mg of compound of Formula I or Formula II. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical carrier, diluent, or excipient.

As used herein the term "patient" refers to a mammal, such as a mouse, guinea pig, rat, dog or human. It is understood that the preferred patient is a human.

As used herein, the terms "treating" or "to treat" each mean to alleviate symptoms, eliminate the causation either on a temporary or permanent basis, or to prevent or slow the appearance of symptoms of the named disorder. As such, the methods of this invention encompass both therapeutic and prophylactic administration.

As used herein, the term "effective amount" refers to the amount of a compound of Formula I or Formula II which is effective, upon single or multiple dose administration to a patient, in treating the patient suffering from the named disorder.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compound of Formula I or Formula II can be administered by a variety of routes including oral, rectal, transdermal, subcutaneous, intravenous, intramuscular, bucal or intranasal routes. Alternatively, the compounds of Formula I or Formula II may be administered by continuous infusion. A typical daily dose will contain from about 0.005 mg/kg to about 10 mg/kg of the compound of Formula I or Formula II. Preferably, daily doses will be about 0.005 mg/kg to about 5 mg/kg, more preferably from about 0.005 mg/kg to about 1 mg/kg.

The dosages of the drugs used in the combinations set forth herein, must also, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred dosages, are provide herein. Dosage guidelines for some of the drugs will first be given separately; in order to create a guideline for any desired combination, one would choose the guidelines for each of the component drugs.

Olanzapine: from about 0.25 to 50 mg, once/day; preferred, from 1 to 30 mg, once/day; and most preferably 1 to 25 mg once/day;

Clozapine: from about 12.5 to 900 mg daily; preferred, from about 150 to 450 mg daily;

Risperidone: from about 0.25 to 16 mg daily; preferred from about 2-8 mg daily;

Sertindole: from about 0.0001 to 1.0 mg/kg daily;

Quetiapine: from about 1.0 to 40 mg/kg given once daily or in divided doses;

Ziprasidone: from about 5 to 500 mg daily; preferred from about 50 to 100 mg daily;

Aripiprazole from about 1 to about 50 mg daily, preferred from about 5 to about 30 mg daily.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 20 to about 50 mg once/day; preferred, from about 20 to about 30 mg once/day.

Sertraline: from about 20 to about 500 mg once/day; preferred, from about 50 to about 200 mg once/day;

Donepizil: from about 1 mg to about 20 mg, once/day; with from about 5 mg to about 10 mg, once/day being preferred.

Rivastigmine: from about 1 mg to about 15 mg daily; with from about 5 to 12 mg daily being preferred;

Galantamine: from about 4 mg to 64 mg daily; with from about 4 mg to about 32 mg daily being preferred;

Memantine: from about 5 mg to about 30 mg/kg daily, with about 20 mg daily being preferred.

In more general terms, one would create a combination of the present invention by choosing a dosage of first and second component compounds according to the spirit of the above guideline.

The adjunctive therapy of the present invention is carried out by administering a first component together with the second component in any manner which provides effective levels of the compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the others may be administered by the transdermal, percutaneous, intravenous, intramuscular, intranasal or intrarectal route, in particular circumstances. The route of administration may be varied in any way, limited by the physical properties of the drugs and the convenience of the patient and the caregiver.

The adjunctive combination may be administered as a single pharmaceutical composition, and so pharmaceutical compositions incorporating both compounds are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of all compounds, or may contain a fraction of the daily doses, such as one-third of the doses. Alternatively, each dosage unit may contain the entire dose of one of the compounds, and a fraction of the dose of the other compounds. In such case, the patient would daily take one of the combination dosage units, and one or more units containing only the other compounds. The amounts of each drug to be contained in each dosage unit depends on the identity of the drugs chosen for the therapy, and other factors such as the indication for which the adjunctive therapy is being given.

The inert ingredients and manner of formulation of the adjunctive pharmaceutical compositions are conventional, except for the presence of the combination of the present invention. The usual methods of formulation used in pharmaceutical science may be used here. All of the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compounds in total, depending on the desired doses and the type of composition to be used. The amount of the compounds, however, is best defined as the effective amount, that is, the amount of each compound which provides the desired dose to the patient in need of such treatment. The activity of the adjunctive combinations do not depend on the nature of the composition, so the compositions are chosen and formulated solely for convenience and economy. Any of the combinations may be formulated in any desired form of composition.

As with any group of structurally related compounds which possess a particular generic utility, certain groups and configurations are preferred for compounds of Formula I and Formula II as set forth below.

With respect to substituent R, compounds wherein R is hydrogen, methyl or ethyl are preferred, with methyl being especially preferred.

With respect to substituent $R^1$, compounds wherein $R^1$ is hydrogen, F, $-OCH_3$, $-C(=O)CH_3$, methyl, or ethyl are preferred, with hydrogen, methyl, or ethyl being especially preferred, and with ethyl being most especially preferred.

With respect to substituent $R^2$ in compounds of Formula I, compounds wherein $R^2$ is $-CO_2H$, $-CONHSO_2$(1-4C) alkyl, or

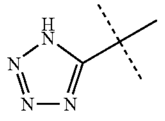

are preferred, with $-CO_2H$ being especially preferred.

With respect to substituent A, compounds wherein A is; $-(CH_2)_mNHSO_2R^{12}$, $-CH(CH_3)(CH_2)_pNHSO_2R^{12}$, $-(CH_2)_pCH(CH_3)NHSO_2R^{12}$,

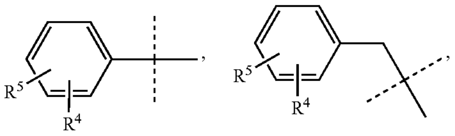

-continued

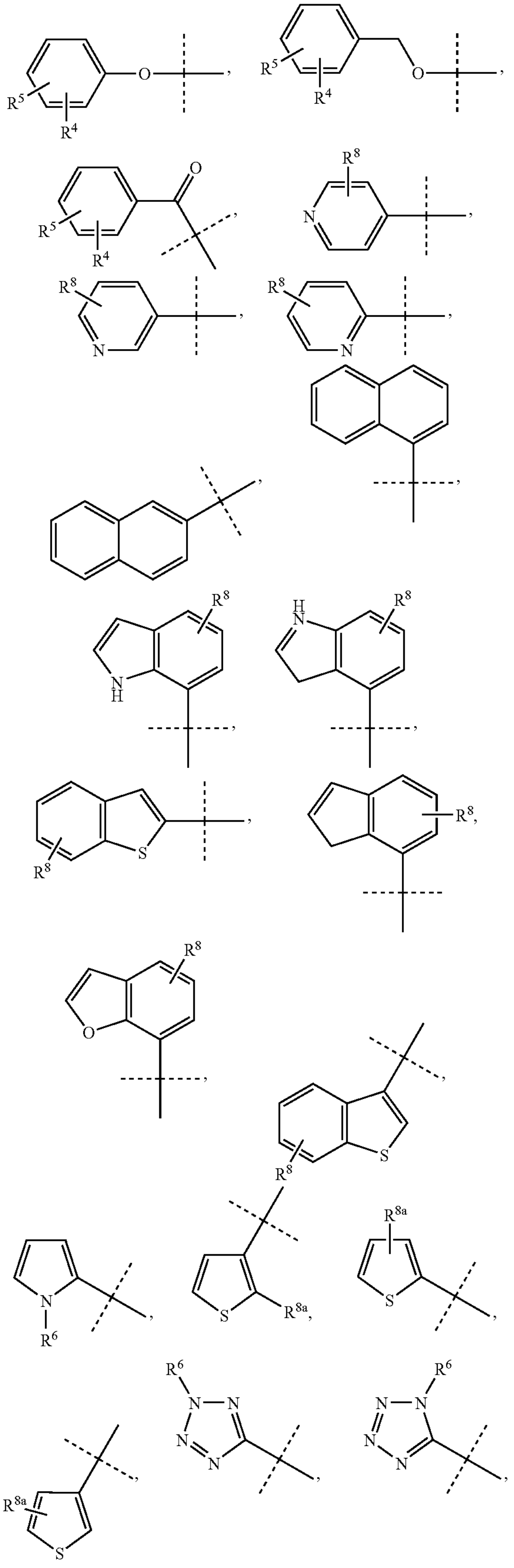

-continued

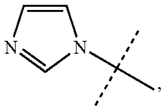,
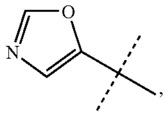,
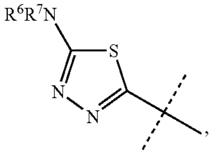,
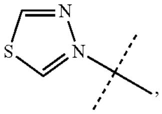,
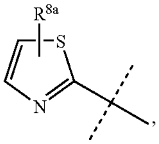,
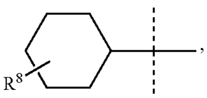,
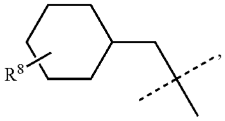,
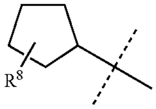
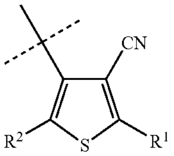
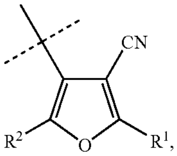
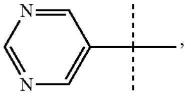,
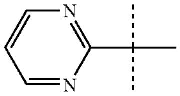

or

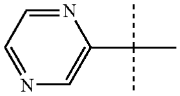

are preferred, with $-(CH_2)_2NHSO_2R^{12}$, $-CH(CH_3)(CH_2)NHSO_2R^{12}$, $-(CH_2)CH(CH_3)NHSO_2R^{12}$,

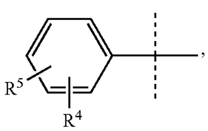,
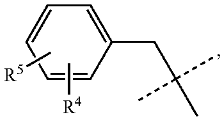
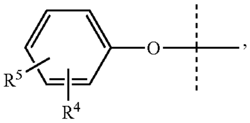,
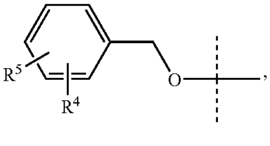,
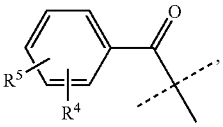,
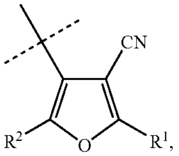
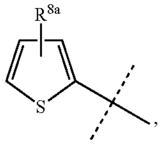,
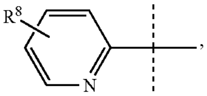, -continued

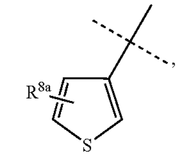,
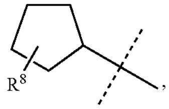,
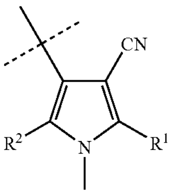

or

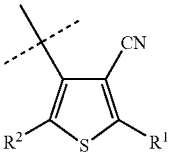

being especially preferred, and;

$-(CH_2)_2NHSO_2R^{12}$ or

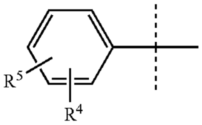

being most especially preferred.

With respect to substituent $R^4$, compounds wherein $R^4$ is hydrogen, F, —(1-4C)alkyl, -(1-4C)alkoxy, —C(═O)NH(1-4C)alkyl, —NHC(═O)(1-4C)alkyl, $-NHSO_2R^{10}$, —CN, $-CO_2H$, —C(═O)(1-4C)alkyl, or —S(1-4C)alkyl are preferred, and compounds wherein $R^4$ is hydrogen, -(1-4C) alkoxy, —CN, or —S(1-4C)alkyl are especially preferred, and compounds wherein $R^4$ is hydrogen, —CN, ethoxy, or $-SCH_3$ are most especially preferred.

With respect to substituent $R^5$, compounds wherein $R^5$ is hydrogen, F, Cl, and -(1-4C)alkyl are preferred, with hydrogen, F, and methyl being especially preferred, and hydrogen being most especially preferred.

With respect to substituent $R^6$, compounds wherein $R^6$ is hydrogen or methyl are preferred, with hydrogen being especially preferred.

With respect to substituent $R^7$, compounds wherein $R^7$ is hydrogen or methyl are preferred, with hydrogen being especially preferred.

With respect to substituent $R^8$, compounds wherein $R^8$ is hydrogen are preferred.

With respect to substituent $R^{10}$, compounds wherein $R^{10}$ is (1-4C)alkyl are preferred with methyl, ethyl, or 2-propyl being especially preferred, and with methyl being most especially preferred.

With respect to substituent $R^{11}$, compounds wherein $R^{11}$ is (1-4C)alkyl are preferred.

With respect to substituent $R^{12}$, compounds wherein $R^{12}$ is (1-4C)alkyl are preferred, with methyl, ethyl, and 2-propyl being especially preferred.

With respect to substituent $R^{13}$, compounds wherein $R^{13}$ is (1-4C)alkyl are preferred.

With respect to substituent $R^{14}$, compounds wherein $R^{14}$ is (1-4C)alkyl are preferred, with methyl, ethyl, or propyl being especially preferred.

With respect to m, compounds wherein m is 0, 1, or 2 are preferred, with 2 being especially preferred.

With respect to n, compounds wherein n is 1 or 2 are preferred, with 2 being especially preferred.

With respect to p, compounds wherein p is 1 are preferred.

With respect to substituent Z, compounds wherein Z is —O(1-6C)alkyl are preferred, with methyl, ethyl, propyl, and isopropyl being preferred, with ethyl being especially preferred.

In particular, compounds of the following formulas and their pharmaceutically acceptable salts are especially preferred:

A

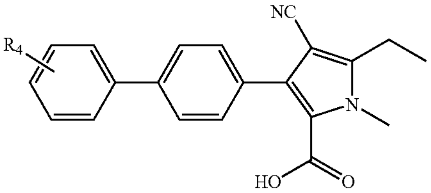

B

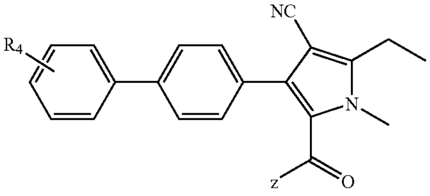

C

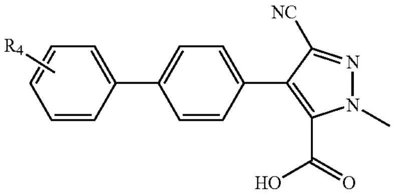

D

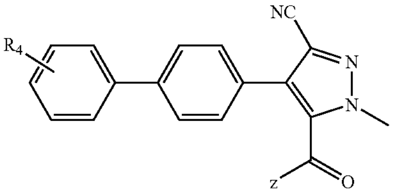

Compound of the following formulas and their pharmaceutically acceptable salts are most especially preferred:

E

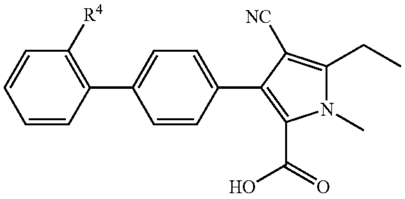

F

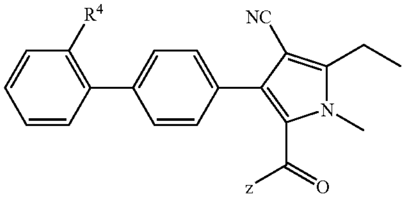

-continued

G

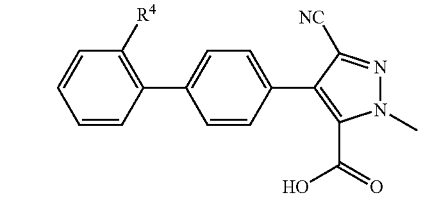

H

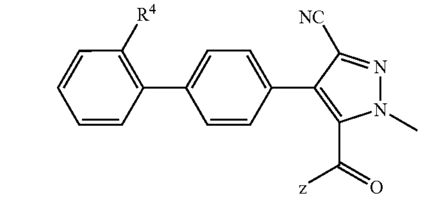

I

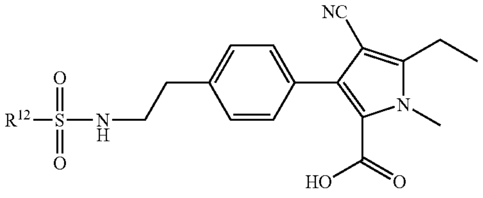

J

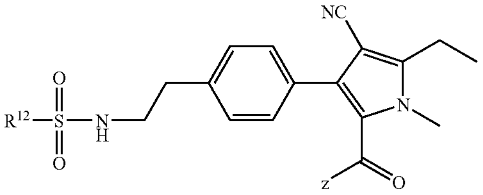

The following specific compounds are particularly preferred:

a

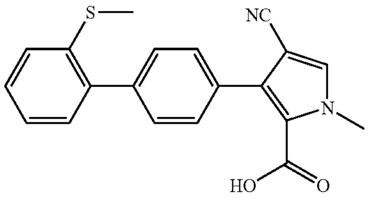

b

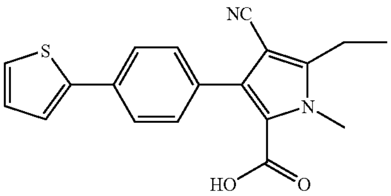

c

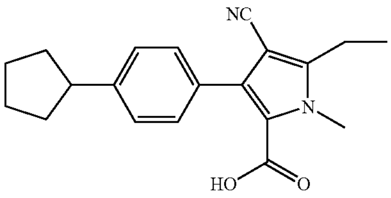

-continued
d
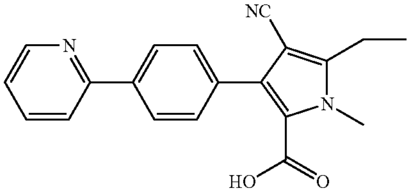
e
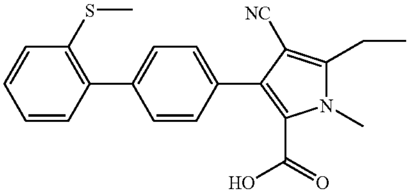
f
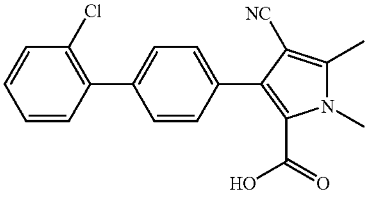
g
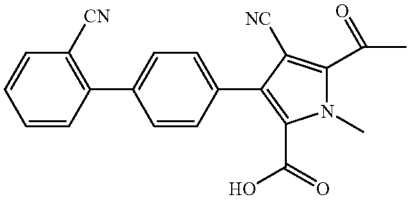
h
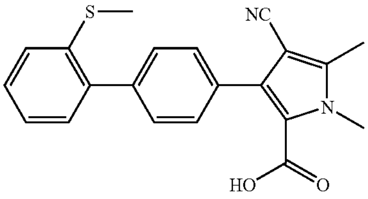
i
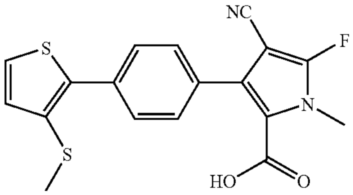
j
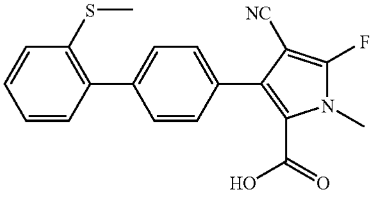
k
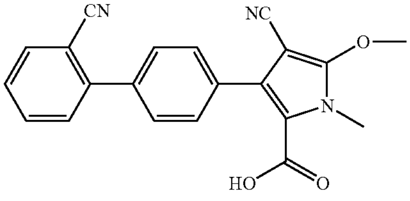
-continued
l
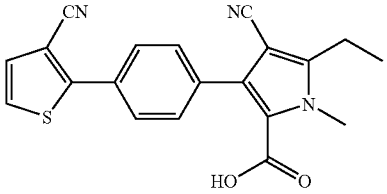
m
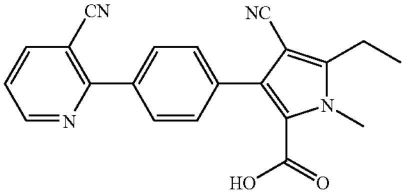
n
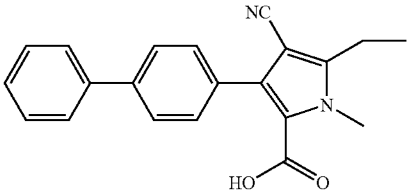
o
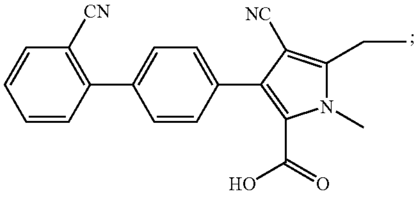
;
p
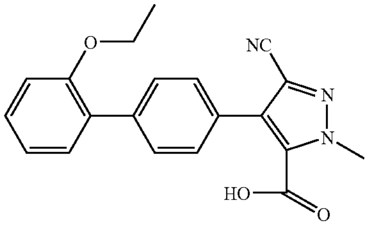
; and
q
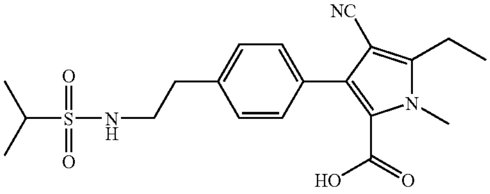
.
The following specific compounds are most particularly preferred:
aa
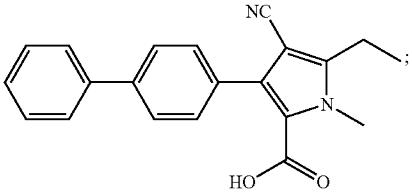
;

-continued bb

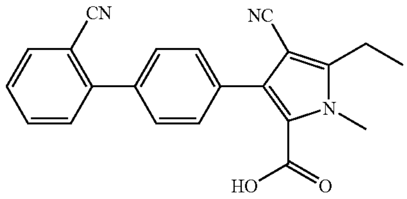;

cc

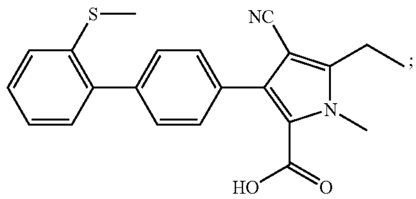;

dd

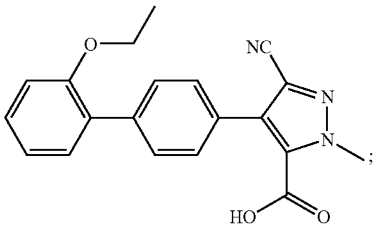; and

In addition, the Form I polymorph of the compound of formula:

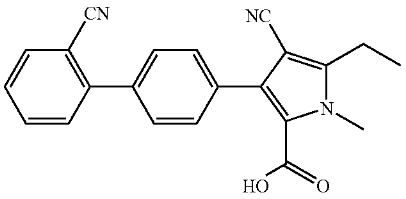

wherein the Form I polymorph is characterized by at least one of the following:

a) an X-ray powder diffraction obtained from a copper radiation source at ambient temperature containing 2-theta values at 11.0° and 28.8°; and b) a solid-state $^{13}C$ nuclear magnetic resonance spectrum with peaks at the following chemical shifts: 113.3, 125.6, 132.7, 139.1 and 147.2 ppm; is most especially preferred, and substantially pure Form I is even more preferred.

We claim:

1. A compound of Formula I:

Formula I

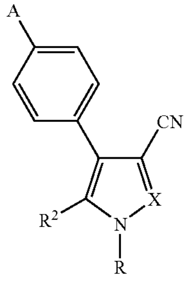

wherein

X represents N or $CR^1$;

R represents hydrogen, methyl, ethyl, n-propyl, or —$SO_2$(1-4C)alkyl;

$R^1$ represents hydrogen, F, Cl, Br, I, CHO, —CN, —S(phenyl), $CF_3$, -(1-4C)alkyl, -(1-4C)alkoxy, —S(1-4C)alkyl, —SO(1-4C)alkyl, —$SO_2$(1-4C)alkyl, —C(═O)(1-3C) alkyl, $NH_2$, —NH(1-4C)alkyl, —N[(1-4C)alkyl]$_2$, or —NH(4-7C)cycloalkyl;

$R^2$ represents —$CO_2H$, —C(═O)$NHR^{13}$; —C(═O)NHOH, and —C(═O)NHCN;

$R^4$ represents hydrogen, OH, —$CH_2OH$, —$CH_2O$(1-4C) alkyl, F, Cl, $CF_3$, $OCF_3$, —CN, $NO_2$, $NH_2$, -(1-4C) alkyl, -(1-4C)alkoxy, —C(═O)NH(1-4C)alkyl, —C(═O)$NH_2$, —NHC(═O)(1-4C)alkyl, —$(CH_2)_m$$NHSO_2R^{10}$, —$(CH_2)_n$CN, —$(CH_2)_m$$CO_2H$, —$(CH_2)_m$$CO_2$(1-6C)alkyl, —C(═O)H, —C(═O)(1-4C)alkyl, —NH(1-4C)alkyl, —N[(1-4C)alkyl]$_2$, —$SR^{10}$, —$SOR^{10}$, —$SO_2R^{10}$, or SH;

$R^5$ represents hydrogen; F, Cl, —CN, $NO_2$, $NH_2$, —$(CH_2)_m$$NHSO_2R^{10}$, -(1-4C)alkyl, or -(1-4C)alkoxy;

$R^8$ represents hydrogen, F, Cl, Br, -(1-4C)alkyl, -(1-4C) alkoxy, $NO_2$, $NH_2$, —CN, —$NHSO_2R^{11}$, or —C(═O)(1-4C)alkyl;

$R^{10}$, $R^{11}$, and $R^{12}$ each independently represent -(1-4C) alkyl, $CF_3$, N[(1-4C)alkyl]$_2$, —$(CH_2)_3$Cl, thienyl, phenyl, —$CH_2$phenyl, or —$(CH_2)_2$phenyl, wherein phenyl, as used in substituent $R^{10}$, $R^{11}$ or $R^{12}$, is unsubstituted or substituted with F, Cl, Br, —CN, $CF_3$, -(1-4C) alkyl, -(1-4)alkoxy, or acetyl;

$R^{13}$ represents hydrogen, -(1-4C)alkyl, —$CH_2CF_3$, triazole, or tetrazole;

A is selected from the group consisting of

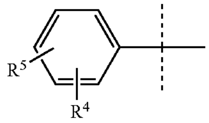, 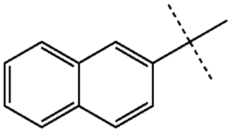, 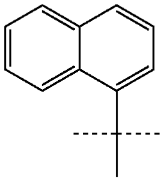, 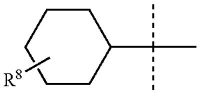, 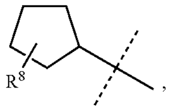, 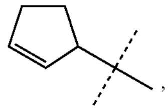, 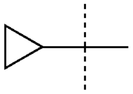, 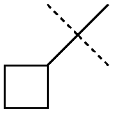, and 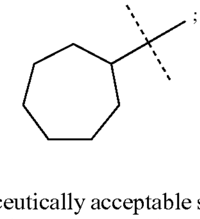;

and the pharmaceutically acceptable salts thereof, with the proviso that when R is methyl, X is $CR^1$ wherein $R^1$ is $SCH_3$, and $R^2$ is $CO_2H$, A is other than 4-tert-butylphenyl; and provided that when R is methyl, X is $CR^1$ wherein $R^1$ is hydrogen, and $R^2$ is $CO_2H$, A is other than 2,6-dimethylphenyl.

2. A compound according to claim 1 wherein $R^2$ represents $—CO_2H$.

3. A compound according to claim 2 wherein X represents $CR^1$.

4. A compound according to claim 2 or claim 3 wherein A is

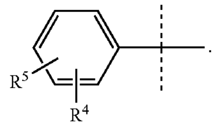

5. A compound according to claim 4 wherein $R^5$ represents hydrogen, F, Cl, or -(1-4C)alkyl.

6. A compound according to claim 5 wherein $R^4$ represents hydrogen, -(1-4C)alkoxy, —CN, or —S(1-4)alkyl.

7. A compound which is:

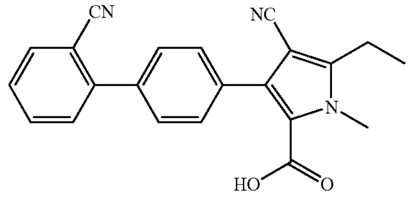

and the pharmaceutically acceptable salts thereof.

8. A composition comprising a compound according to claim 1 in combination with a pharmaceutically acceptable carrier, diluent or excipient.

9. A method of treating Alzheimer's disease in a patient comprising administering to said patient an effective amount of a compound according to claim 1.

10. A compound according to claim 1 for use as a pharmaceutical.

* * * * *